United States Patent
Altman et al.

(10) Patent No.: US 10,793,557 B2
(45) Date of Patent: Oct. 6, 2020

(54) STING AGONIST COMPOUNDS

(71) Applicant: Merck Sharp & Dohme Corp., Rahway, NJ (US)

(72) Inventors: Michael D. Altman, Needham, MA (US); Brandon D. Cash, Stoughton, MA (US); Matthew Lloyd Childers, Medfield, MA (US); Jared N. Cumming, Winchester, MA (US); Duane E. DeMong, Hanover, MA (US); Andrew Marc Haidle, Somerville, MA (US); Timothy J. Henderson, Natick, MA (US); James P. Jewell, Newton, MA (US); Matthew A. Larsen, Dedham, MA (US); Jongwon Lim, Lexington, MA (US); Min Lu, Brookline, MA (US); Ryan D. Otte, Natick, MA (US); Benjamin Wesley Trotter, Medfield, MA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 16/372,103

(22) Filed: Apr. 1, 2019

(65) Prior Publication Data
US 2019/0300513 A1 Oct. 3, 2019

Related U.S. Application Data

(60) Provisional application No. 62/809,956, filed on Feb. 25, 2019, provisional application No. 62/652,018, filed on Apr. 3, 2018.

(51) Int. Cl.
*C07D 409/12* (2006.01)
*C07D 417/10* (2006.01)
(Continued)

(52) U.S. Cl.
CPC ............ *C07D 409/12* (2013.01); *A61P 35/00* (2018.01); *C07D 277/64* (2013.01);
(Continued)

(58) Field of Classification Search
CPC .. C07D 409/12; C07D 333/56; C07D 417/12; C07D 277/64; C07D 495/04; C07D 498/04; C07D 417/10; A61P 35/00
See application file for complete search history.

(56) References Cited

U.S. PATENT DOCUMENTS

| 4,299,769 A | 11/1981 | McEvoy et al. |
| 4,342,689 A | 8/1982 | McEvoy et al. |

(Continued)

FOREIGN PATENT DOCUMENTS

| EP | 0146243 | 6/1985 |
| EP | 0350990 A1 | 1/1990 |

(Continued)

OTHER PUBLICATIONS

Ablasser et al., Cell intrinsic immunity spreads to bystander cells via the intercellular transfer of cGAMP, Nature, Nov. 28, 2013, 530-546, 503.

(Continued)

*Primary Examiner* — John M Mauro
(74) *Attorney, Agent, or Firm* — Julie M. Lake; Catherine D. Fitch

(57) ABSTRACT

Compounds of general formula (I), of general formula (II), of general formula (III), of general formula (IV), of general formula (V), of general formula (VI), and their pharmaceutically acceptable salts, wherein all variables are defined herein, that may be useful as inductors of type I interferon production, specifically as STING active agents, are provided. Also provided are compositions comprising such compounds, processes for the synthesis of such compounds, and to uses of such compounds, including administration of such compounds to induce immune response, to induce STING-dependent type I interferon production, and/or to treat a cell proliferation disorder, such as cancer.

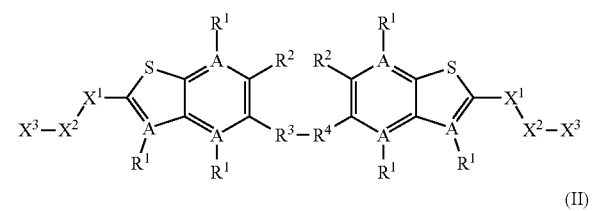

(I)

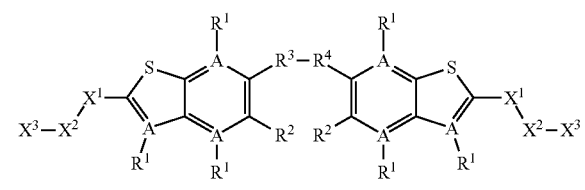

(II)

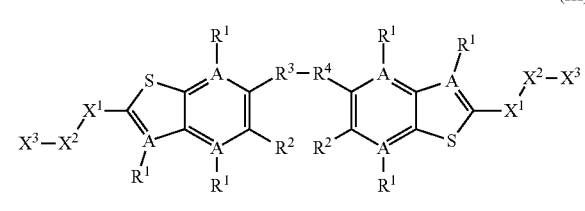

(III)

(Continued)

-continued

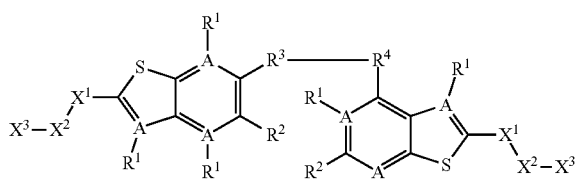
(IV)

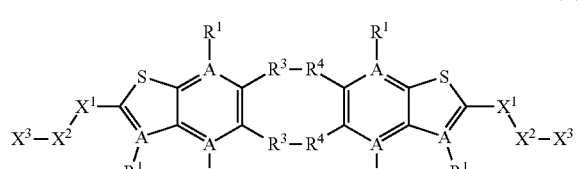

(V)

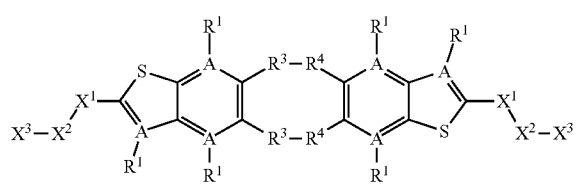

(VI)

43 Claims, No Drawings

Specification includes a Sequence Listing.

(51) Int. Cl.
*C07D 498/04* (2006.01)
*C07D 495/04* (2006.01)
*C07D 277/64* (2006.01)
*C07D 417/12* (2006.01)
*C07D 333/56* (2006.01)
*A61P 35/00* (2006.01)

(52) U.S. Cl.
CPC .......... *C07D 333/56* (2013.01); *C07D 417/10* (2013.01); *C07D 417/12* (2013.01); *C07D 495/04* (2013.01); *C07D 498/04* (2013.01)

(56) References Cited

U.S. PATENT DOCUMENTS

| | | | |
|---|---|---|---|
| 4,342,690 A | 8/1982 | McEvoy et al. | |
| 4,342,691 A | 8/1982 | McEvoy et al. | |
| 4,952,571 A | 8/1990 | Redpath et al. | |
| 5,569,655 A * | 10/1996 | Dority, Jr. ............ | C07D 471/18 514/226.8 |
| 6,262,055 B1 | 7/2001 | Young et al. | |
| 7,288,567 B2 | 10/2007 | Delorme et al. | |
| 7,488,802 B2 | 2/2009 | Collins et al. | |
| 7,521,051 B2 | 4/2009 | Collins et al. | |
| 7,595,048 B2 | 9/2009 | Honjo et al. | |
| 8,008,449 B2 | 8/2011 | Korman et al. | |
| 8,168,757 B2 | 5/2012 | Finnefroch et al. | |
| 8,354,509 B2 | 1/2013 | Carven et al. | |
| 8,383,796 B2 | 2/2013 | Korman et al. | |
| 8,664,255 B2 | 3/2014 | Freundlich et al. | |
| 9,724,408 B2 | 8/2017 | Dubensky, Jr. et al. | |
| 10,414,747 B2 | 9/2019 | Altman et al. | |
| 2002/0115826 A1 | 8/2002 | Delorme et al. | |
| 2006/0040887 A1 | 2/2006 | Karaolis | |
| 2008/0025979 A1 | 1/2008 | Honjo et al. | |
| 2008/0286296 A1 | 11/2008 | Ebensen et al. | |
| 2009/0181971 A1 | 7/2009 | Delorme et al. | |
| 2010/0113477 A1 | 5/2010 | Freundlich et al. | |
| 2011/0271358 A1 | 11/2011 | Gordon et al. | |
| 2014/0017444 A1 | 1/2014 | Shimizu et al. | |
| 2014/0206640 A1 | 7/2014 | Girijavallabhan et al. | |
| 2014/0329889 A1 | 11/2014 | Vance et al. | |
| 2014/0341976 A1 | 11/2014 | Dubensky, Jr. et al. | |
| 2015/0056224 A1 | 2/2015 | Dubensky, Jr. et al. | |
| 2015/0158886 A1 | 6/2015 | Jones et al. | |
| 2016/0287698 A1 | 10/2016 | Yan et al. | |
| 2016/0362441 A1 | 12/2016 | Vernejoul et al. | |
| 2017/0050967 A1 | 2/2017 | Burai et al. | |
| 2017/0158724 A1 | 6/2017 | Adams et al. | |
| 2019/0337917 A1 | 11/2019 | Altman et al. | |
| 2019/0337918 A1 | 11/2019 | Altman et al. | |

FOREIGN PATENT DOCUMENTS

| | | |
|---|---|---|
| EP | 0350990 B1 | 9/1995 |
| EP | 3135290 A1 | 1/2018 |
| GB | 532822 | 1/1941 |
| WO | 1994008962 | 4/1994 |
| WO | 199962897 | 12/1999 |
| WO | 2001002369 A2 | 1/2001 |
| WO | 2001002369 A3 | 1/2001 |
| WO | 2001070675 | 9/2001 |
| WO | 2002010192 | 2/2002 |
| WO | 2002068470 | 9/2002 |
| WO | 2004004771 | 2/2004 |
| WO | 2004056875 | 7/2004 |
| WO | 2004072286 | 8/2004 |
| WO | 2005020917 | 3/2005 |
| WO | 2010027827 A3 | 3/2010 |
| WO | 2010047774 | 4/2010 |
| WO | 2010077634 A1 | 7/2010 |
| WO | 2011066342 A3 | 6/2011 |
| WO | 2012068702 | 5/2012 |
| WO | 2013019906 A1 | 2/2013 |
| WO | 2013185052 A1 | 12/2013 |
| WO | 2014093936 | 6/2014 |
| WO | 2014099824 | 6/2014 |
| WO | 2014099941 | 6/2014 |
| WO | 2014139388 A1 | 9/2014 |
| WO | 201479335 A1 | 11/2014 |
| WO | 2014179760 | 11/2014 |
| WO | 2014189805 A1 | 11/2014 |
| WO | 2014189806 | 11/2014 |
| WO | 2015017652 | 2/2015 |
| WO | 2015074145 A1 | 5/2015 |
| WO | 2015077354 A1 | 5/2015 |
| WO | 2015148746 A1 | 10/2015 |
| WO | 2015161137 | 10/2015 |
| WO | 2015185565 | 12/2015 |
| WO | 2015189117 | 12/2015 |
| WO | 2016096174 | 6/2016 |
| WO | 2016096577 | 6/2016 |
| WO | 2016100261 | 6/2016 |
| WO | 2016120305 | 8/2016 |
| WO | 2016145102 | 9/2016 |
| WO | 2017011622 | 1/2017 |
| WO | 2017011920 | 1/2017 |
| WO | 2017027645 | 2/2017 |
| WO | 2017027646 | 2/2017 |
| WO | 2017075477 A1 | 5/2017 |
| WO | 2017093933 A1 | 6/2017 |
| WO | 2017100305 | 6/2017 |
| WO | 2017123657 | 7/2017 |
| WO | 2017123669 | 7/2017 |
| WO | 2017161349 A1 | 9/2017 |
| WO | 2017175147 | 10/2017 |
| WO | 2017175156 | 10/2017 |
| WO | 2017216726 | 12/2017 |
| WO | 2018009466 | 1/2018 |

(56) References Cited

FOREIGN PATENT DOCUMENTS

| | | |
|---|---|---|
| WO | 2018067423 A1 | 4/2018 |
| WO | 2019/195063 A1 | 10/2019 |

OTHER PUBLICATIONS

Ablasser et al., cGAS produces a 2'-5'-linked cyclic dinucleotide second messenger that activates STING, Nature, Jun. 20, 2013, 380-385, 498.

Ausmees et al., Genetic Data Indicate that Proteins Containing the GGDEF Domain Possess Diguanylate Cyclase Activity, FEMS Microbiology, 2001, 163-167, Letters 204.

Berge, S.M., et al.,, "Pharmaceutical Salts", J. Pharm. Sci, 1977, pp. 1-19, vol. 66, No. 1.

Bhattacharjee et al, Synthesis of heterocyclic steroids-III: An unsuccessful attempt at the Synthesis of B-Nor-6-thiaequilenin through 3-cyano-7-methoxy-4-oxo-1,2,3,4-Tetrahydrodibenzothiophene, Tetrahedron, 1960, 215-222, 10.

Bookser et al., High-Throughput Five Minute Microwave Accelerated Glycosylation Approach to the Synthesis of Nucleoside Libraries, JOC Article, 2007, 173-179, 72.

Bruno et al., N-Substituted 2-aminobiphenylpalladium Methanesulfonate Precatalysts and Their Use in C—C and C—N Cross Couplings, The Journal of Organic Chamistry, 2014, 4161-4166, 79.

Burtner, et al., Synthetic Choleretics. I. Naphthol Derivatives, Journal of the American Chemical Society, 1951, 897-900, vol. 73.

Cagniant, et al., Condensed sulfur heterocycles. III. 1,2,3,4-Tetrahydrodibenzothiophene and, Bulletin de la Societe Chimique de France, 1952, 336-343.

Cagniant, et al., Condensed sulfur heterocycles. IV. Condensation of thianaphthene with glutaric anhydride and the, Bulletin de la Societe Chimique de France, 1952, 629-633.

Cagniant, et al., Condensed sulfur heterocycles. XIX. Synthesis of some ω-thionaphthenylalkanoic acids, Bulletin de la Societe Chimique de France, 1962, 576-581.

Child, et al., A New Non-steroidal Anti-Inflammatory Analgesic: γ-Oxo.(1,1'-biphenyl)-4-butanoic Acid (Fenbufen), Arzneimittel-Forschung, 1980, 695-702, vol. 30; Issue 4A.

Dande et al., Improving RNA Interference in Mammalian Cells by 4'-Thio-Modified Small Interfering RNA (siRNA): Effect on siRNA Activity and Nuclease Stability When Used in Combination with 2'-O-Alkyl Modifications, Journal of Medicinal Chemistry, 2006, 1624-1634, 49(5).

Diner et al., The Innate Immune DNA Sensor cGAS Produces a Noncanonical Cyclic Dinucleotide that Activates Human STING, 3 Cell Reports, Cell Reports, 2013, 1355-1361, 3.

Downey et al., DMXAA Causes Tumor Site-Specific Vascular Disruption in Murine Non-Small Molecule Lung Cancer, and Like the Endogenous Non-Canonical Cyclic Dinucleotide STING Agonist, 2'3'-cGAMP, Induces M2 Macrophage Repolarization, Plos One, 2014, 1-14, 9-6-e99988.

Ertem et al., Synthesis of RNA oligomers on heterogeneous templates, Nature, 1996, 238-240, 379-18.

Fagundes et al., Building unique bonds to tight misplaced DNA, Cell Research, 2013, 1065-1066, 2-9.

Gadthula et al., Synthesis and Anti-HIV Activity of β-D-3'-Azido-2',3'-unsaturated Nucleosides and β-D-3'-Azido-3'deoxyribofuranosylnucleosides, Nucleoside, Nucleotides, Nucleic Acids, 2005, 1707-1727, 24.

Gao et al., Cyclic [G(2',5')pA(3',5")p] Is the Metazoan Second Messenger Produced by DNA-Activated Cyclic GMP-AMP Synthase, Cell, 2013, 1094-1107, 153.

Gao et al., Structure-Function Ananlysis of Sting Activation by c[G(2',5')pA(3',5')p] and Targeting by Antiviral DMXAA, Cell, 2013, 748-762, 154.

Goerlitzer, et al., 1,3-Dicarbonyl Compounds. XIX: 4-Oxo-4H-[1]benzofuro[3,2-b]pyrans, Archiv der Pharmazie, 1980, 385-398, vol. 313; Issue 5.

Gopinath et al., As many as six tandem reactions in one step! Unprecendented formation of highly functionalized enzothiophenes, Chemical Communication, Jul. 17, 2009, 7131-7133, vol. 46.

Gopinath, et al., Highly chemoselective Esterification Reactions and Boc/THP/TBDMS Discriminating Deprotections Under Samarium(III) Catalysis, Organic Letters, 2011, 1932-1935, vol. 13, Issue No. 8.

Gosselin et al., Systematic Synthesis and Biological Evaluation of α- and β-D-lyxofuranosyl Nucleosides of the Five Naturally Occurring Nucleic Acid Bases, J. Med. Chem, 1987, 982-991, 30.

Gould, Salt Selections for Basic Drugs, Intl. J. Pharmaceutics, 1986, pp. 201-217, vol. 33.

Guanghui Yi et al., Single Nucleotide Polymorphisms of Human STING Can Affect Innate Immune Response to Cyclic Dinucleotides, Plos One, 2013, 1-16, 8-10-e77846.

Hornfeldt, et al., Unsaturted γ-thiolactones II*. The Structures of 3-and 4-Methyl-2-thienols, Acta chem. Scand., 1962, 789-791, vol. 16; Issue No. 2.

Ikeuchi et al., Practical synthesis of natural plant-growth regulator 2-azahypoxanthine, its derivatives, and biotin-labeled probes, Organic & Biomolecular Chemistry, 2014, 3813, 12(23).

Joshi et al., Selectivity of montmorillonite catalyzed prebiotic reactions of D, L-nucleotides, Orig Life Evol Biosph, 2007, 3-26, 37-3.

Kim et al., A Convenient and Versatile Syntheses of 2' (and 3') amino (and azido)-2'(and 3') deoxyadenosine as Diverse Synthetic Precursors of Cyclic Adenosine Diphosphate Ribose (cADPR), Bull. Korean Chem. Soc., 2004, 243, 25-2.

Kobayashi et al., Bacterial c-di-GMP Affects Hematopoietic Stem/Progenitors and their Niches through STING, Cell Reports, 2015, 71-84, 11.

Kranzusch et al., Structure-Guided Reporgramming of Human cGAS Dinucleotide Linkage Specificity, Cell Inc., Elsevier Inc., 2014, 1011-1021, 158.

Kudo, et al., Synthesis of Monoamino and Monohydroxydibenzothiophenes, J. Heterocyclic Chem., 1985, 215218, vol. 22.

Li et al., Cyclic GMP-AMP Synthase is Activated by Double-Stranded DNA-Induced Oligomerization, Immunity, 2013, 1019-1031, 39.

Li et al., Hydrolysis of 2'3'-cGAMP by ENPPI and Design of Nonhydrolyzable Analogs, 10 Nature Chemical Biology 1043 (Dec. 2014); Li et al., Hydrolysis of 2'3'-cGAMP by ENPPI and Design of Nonhydrolyzable Analogs: ERRATUM, Nature Chemical Biology, 2014, 1043, 10.

Liu et al., Activated Sting in a Vascular and Pulmonary Syndrome, The New England Journal of Medicine, 2015, 507,371-6.

Liu et al., Hepatitis B Virus Polymerase Disrupts K63-Linked Ubiquitination of STING to Block Inate Cytosolic DNA-Sensing Pathways, Journal of Virology, 2015, 2287, 89-4.

Lolicato et al., Cyclic Dinucleotides Bind the C-Linker of HCN4 to Control Channel cGAMP Responsiveness, 10 Nature Chemical Biology 457 (Jun. 2014); Lolicato et al., Cyclic Dinucleotides Bind the C-Linker of HCN4 to Control Channel cGAMP Responsiveness, Nature Chemical Biology, 2014, 457, 10.

Mikhailov et al., Conformational Peculiarities of 5'-C-methylnucleosides, Bioorganicheskaya Khimiya, 1989, 969-975, 15(7).

Minakawa et al., Nucleosides and nucleotides. 116. Convenient syntheses of 3-deazaadenosine, 3-deazaguanosine, and 3-deazainosine via ring closure of 5-ethynyl-1-B-D-ribofuranosylimidazole-4-carboxamide or—carbonitrile, Tetrahedron, 1993, 557-570, 49(3).

Minakawa et al., Nucleosides and Nucleotides. 143. Synthesis of 5-Amino-4-imidazolecarboxamide (AICA) Deoxyribosides from Deoxyinosines and Their Conversion into 3-Deazapurine Derivatives, Chemical & Pharmaceutical Bulletin, 1996, 288-295, 44(2).

Mlochowski, et al., A Simple Route to Benzo[b]thiophenes: Sulfanylation-acylation of C—H Acids With 2-(Chlorosulfanyl)benzoyl Chloride, Phosphorus, Sulfur, and Silicon, 2009, 1115-1123, vol. 184; Issue 5.

O'Neill et al., Sensing the Dark Side of DNA, Sceince, 2013, 763, 339.

Ora et al., Hydrolytic reactions of cyclic bis(3'-5') diadenylic acid (c-di-AMP), J. Phys. Org. Chem, 2013, 218-225, 26.

(56) References Cited

OTHER PUBLICATIONS

Panne et al., Cytosolic DNA sensing unraveled, Nature Chemical Biology, 2013, 533, 9.
Patil et al., 4-aza-7,9-dideazaadenosine, a new cytotoxic synthetic C-nucleoside analogue of adenosine, Tetrahedron Letters, 1994, 5339-5342, 35(30).
Puech et al., Synthesis of 9-(3-deoxy- and 2,3-dideoxy-3-fluoro-β-D-xylofuranosyl)guanines as potential antiviral agents, Tetrahedron Letters, 1989, 3171-3174, 30-24.
Ramesh et al., A convenient synthesis of 1-(β-D-ribofuranosyl)imidazo[4,5-d]pyridazin-4(5H)-one (2-aza-3-deazainosine) and its 2'-deoxy counterpart by ring closure of imidazole nucleosides, Journal of the Chemical Society, Perkin Transaction 1, 1989, 1769-1774, 10.
Roembke et al., A cyclic dinucleotide contianing 2-aminopurine is a general fluorescent sensor for c-di-GMP and 3'-3'-cGAMP, Molecular BioSystems, 2014, 1568-1575, 10.
Sali, et al., Characterization of a Novel Human-Specific STING Agonist that Elicits Antiviral Activity Against Emerging Alphaviruses, PLOS Pathogens, 2015, 1-30.
Simm et al., Phenotypic Convergence Mediated by GGDEF-Domain-Containing Proteins, Journal of Bacteriology, 2005, 6816-6823, 187(19).
Stahl et al., Aminoquinazoline Compounds As A2A Antagonist, Handbook of Pharmaceutical Salts Properties, Selection, and Use, 2002, 330-331.
Sun et al., Cyclic GMP-AMP Synthase Is a Cytosolic DNA Sensor That Activates the Type I Interferon Pathway, Science, 2013, 786, 339.
Tang et al., Single Amino Acid change in Sting Leads to Constitutive Active Signaling, Plos One, 2015, 1-10, (10)3.
Tosolini et al., Human Monocyte Recognition of Adenosine-Based Cyclic Dinucleotides Unveils the A2a G∞s Protein-Coupled Receptor Tonic Inhibition of Mitochondrially Induced Cell Death, Molecular and Cellular Biology, 2015 179-495, 35-2.

Urata et al., Regio- and Diastereo-Selectivity of Montmorillonite-Catalyzed Oligomerization of Racemic Adenosine 5'-Phosphorimidazolide, Nucleotides and Nucleic Acids, Nucleosides, Nucleotides and Nucleic Acids, 2008, 421-430, 27.
Wang et al., Synthesis and Biological Activity of 5-Fluorotubercidin, Nucleosides, Nucleotides and Nucleic Acids, 2004, 161-170, 23(1).
Wu et al., Cyclic GMP-AMP Is an Endogenous Second Messenger in Innate Immune Signaling by Cytosolic DNA, Science 826, 2013, 826-830, 339.
Zeng et al., MAVS, cGAS, and Endogenous Retroviruses in T-Independent B Cell Responses, Science, 2014, 1486-1492, 346-6216.
Zhang et al., Cyclic GMP-AMP Containing Mixed Phosphodiester Linkages Is an Endogenous High-Affinity Ligand for STING, Molecular Cell, 2013, 226-235, 51.
Zhou et al., The ER-Associated Protein ZDHHC1 Is a Positive Regulator of DNA Virus-Triggered, MITA/STING-Dependent Innate Immune Signaling, Cell Host & Microbe, 2014, 450-461, 16.
Burdette, Dara L., Sting and the innate immune response to nucleic acids in the cytosol, Nature Immunology, Jan. 2013, 19-26, 14(1).
Burdette, Dara L., Sting is a direct innate immune sensor of cyclic di-GMP, Nature, Oct. 27, 2011, 515-519, 478.
Fu, Juan, et al., Sting agonist formulated cancer vaccines can cure established tumors resistant to PD-1 blockade, Science Translational Medicine, 2015, 1-13, 7.
Heping Shi, et al., Molecular basis for the specific recognition of the metazoan cyclic GMP-AMP by the innate immune adaptor protein Sting, PNAS, 2015, 8947-8952, vol. 112/No. 29.
Markert, Jurgen et al., Darstellung von 1,2-Benzisothiazolen und einige Folgereaktionen, Liebigs Ann. Chem., 1980, 768-778, 5.
English language translation of Markert, Jurgen et al., Darstellung von 1,2-Benzisothiazolen und einige Folgereaktionen, Liebigs Ann. Chem., 1980, 768-778, 5.
Sheridan, Cormac, Drug Developers Switch Gears to Inhibit STING, Nature Biotechnology, Mar. 4, 2019, 37 199-208, 37.

* cited by examiner

SEQUENCE LISTING

<160> NUMBER OF SEQ ID NOS: 4

<210> SEQ ID NO 1
<211> LENGTH: 414
<212> TYPE: PRT
<213> ORGANISM: Artificial Sequence
<220> FEATURE:
<223> OTHER INFORMATION: Full-Length HAQ STING
[STING(1-379)R71H,G230A,H232R,R293Q-GG-AviTag-GS-HRV3C-HIS8]Amino
Acid Sequence

<400> SEQUENCE: 1

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
            20                  25                  30

Leu Trp Gly Leu Gly Glu Pro Pro Glu His Thr Leu Arg Tyr Leu Val
        35                  40                  45

Leu His Leu Ala Ser Leu Gln Leu Gly Leu Leu Leu Asn Gly Val Cys
    50                  55                  60

Ser Leu Ala Glu Glu Leu His His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
            100                 105                 110

Val Gly Pro Pro Phe Thr Trp Met Leu Ala Leu Leu Gly Leu Ser Gln
        115                 120                 125

Ala Leu Asn Ile Leu Leu Gly Leu Lys Gly Leu Ala Pro Ala Glu Ile
    130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
            180                 185                 190

Ala Val Ser Gln Arg Leu Tyr Ile Leu Leu Pro Leu Asp Cys Gly Val
        195                 200                 205

Pro Asp Asn Leu Ser Met Ala Asp Pro Asn Ile Arg Phe Leu Asp Lys
    210                 215                 220

Leu Pro Gln Gln Thr Ala Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
            260                 265                 270

Gln Tyr Ser Gln Ala Gly Phe Ser Arg Glu Asp Arg Leu Glu Gln Ala
        275                 280                 285

Lys Leu Phe Cys Gln Thr Leu Glu Asp Ile Leu Ala Asp Ala Pro Glu
    290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335

Glu Lys Glu Glu Val Thr Val Gly Ser Leu Lys Thr Ser Ala Val Pro
            340                 345                 350
```

```
Ser Thr Ser Thr Met Ser Gln Glu Pro Glu Leu Leu Ile Ser Gly Met
        355                 360                 365

Glu Lys Pro Leu Pro Leu Arg Thr Asp Phe Ser Gly Gly Gly Leu Asn
    370                 375                 380

Asp Ile Phe Glu Ala Gln Lys Ile Glu Trp His Glu Gly Ser Leu Glu
385                 390                 395                 400

Val Leu Phe Gln Gly Pro His His His His His His His His
                405                 410

<210> SEQ ID NO 2
<211> LENGTH: 6482
<212> TYPE: DNA
<213> ORGANISM: Artificial Sequence
<220> FEATURE:
<223> OTHER INFORMATION: Full-length HAQ
      [STING(1-379)R71H,G230A,H232R,R293Q-GG-AviTag-GS-HRV3C-
      HIS8/pBAC1] Plasmid DNA Sequence

<400> SEQUENCE: 2
```

| | | | | | |
|---|---|---|---|---|---|
| ggaacggctc | cgcccactat | taatgaaatt | aaaaattcca | attttaaaaa | acgcagcaag | 60 |
| agaaacattt | gtatgaaaga | atgcgtagaa | ggaaagaaaa | atgtcgtcga | catgctgaac | 120 |
| aacaagatta | atatgcctcc | gtgtataaaa | aaaatattga | acgatttgaa | agaaaacaat | 180 |
| gtaccgcgcg | gcgtatgta | caggaagagg | tttatactaa | actgttacat | tgcaaacgtg | 240 |
| gtttcgtgtg | ccaagtgtga | aaaccgatgt | ttaatcaagg | ctctgacgca | tttctacaac | 300 |
| cacgactcca | agtgtgtggg | tgaagtcatg | catcttttaa | tcaaatccca | agatgtgtat | 360 |
| aaaccaccaa | actgccaaaa | aatgaaaact | gtcgacaagc | tctgtccgtt | tgctggcaac | 420 |
| tgcaagggtc | tcaatcctat | ttgtaattat | tgaataataa | acaattata | aatgctaaat | 480 |
| ttgtttttta | ttaacgatac | aaaccaaacg | caacaagaac | atttgtagta | ttatctataa | 540 |
| ttgaaaacgc | gtagttataa | tcgctgaggt | aatatttaaa | atcattttca | aatgattcac | 600 |
| agttaatttg | cgacaatata | attttatttt | cacataaact | agacgccttg | tcgtcttctt | 660 |
| cttcgtattc | cttctctttt | tcattttttct | cttcataaaa | attaacatag | ttattatcgt | 720 |
| atccatatat | gtatctatcg | tatagagtaa | atttttttgtt | gtcataaaata | tatatgtctt | 780 |
| ttttaatggg | gtgtatagta | ccgctgcgca | tagttttttct | gtaatttaca | acagtgctat | 840 |
| tttctggtag | ttcttcggag | tgtgttgctt | taattattaa | atttatataa | tcaatgaatt | 900 |
| tgggatcgtc | ggttttgtac | aatatgttgc | cggcatagta | cgcagcttct | tctagttcaa | 960 |
| ttacaccatt | ttttagcagc | accggattaa | cataactttc | caaaatgttg | tacgaaccgt | 1020 |
| taaacaaaaa | cagttcacct | cccttttcta | tactattgtc | tgcgagcagt | tgtttgttgt | 1080 |
| taaaaataac | agccattgta | atgagacgca | caaactaata | tcacaaactg | gaaatgtcta | 1140 |
| tcaatatata | gttgctgatc | agatctgatc | atggagataa | ttaaaatgat | aaccatctcg | 1200 |
| caaataaata | agtattttac | tgttttcgta | acagttttgt | aataaaaaaa | cctataaata | 1260 |
| taggatccat | gccccactcc | agcctgcatc | catccatccc | gtgtcccagg | ggtcacgggg | 1320 |
| cccagaaggc | agccttggtt | ctgctgagtg | cctgcctggt | gacccttttgg | gggctaggag | 1380 |
| agccaccaga | gcacactctc | cggtacctgg | tgctccacct | agcctccctg | cagctgggac | 1440 |
| tgctgttaaa | cggggtctgc | agcctggctg | aggagctgca | ccacatccac | tccaggtacc | 1500 |
| ggggcagcta | ctggaggact | gtgcgggcct | gctgggctg | ccccctccgc | cgtgggccc | 1560 |
| tgttgctgct | gtccatctat | ttctactact | ccctcccaaa | tgcggtcggc | ccgcccttca | 1620 |

```
cttggatgct tgccctcctg ggcctctcgc aggcactgaa catcctcctg ggcctcaagg    1680
gcctggcccc agctgagatc tctgcagtgt gtgaaaaagg gaatttcaac gtggcccatg    1740
ggctggcatg gtcatattac atcggatatc tgcggctgat cctgccagag ctccaggccc    1800
ggattcgaac ttacaatcag cattacaaca acctgctacg gggtgcagtg agccagcggc    1860
tgtatattct cctcccattg gactgtgggg tgcctgataa cctgagtatg gctgacccca    1920
acattcgctt cctggataaa ctgccccagc agaccgctga ccgtgctggc atcaaggatc    1980
gggtttacag caacagcatc tatgagcttc tggagaacgg gcagcgggcg ggcacctgtg    2040
tcctggagta cgccacccce ttgcagactt tgtttgccat gtcacaatac agtcaagctg    2100
gctttagccg ggaggatagg cttgagcagg ccaaactctt ctgccagaca cttgaggaca    2160
tcctggcaga tgcccctgag tctcagaaca actgccgcct cattgcctac caggaacctg    2220
cagatgacag cagcttctcg ctgtcccagg aggttctccg gcacctgcgg caggaggaaa    2280
aggaagaggt tactgtgggc agcttgaaga cctcagcggt gcccagtacc tccacgatgt    2340
cccaagagcc tgagctcctc atcagtggaa tggaaaagcc cctccctctc cgcacggatt    2400
tctctggcgg tggcctgaac gacatcttcg aagcccagaa aatcgaatgg catgaaggca    2460
gcctggaagt gctgttccag ggcccacacc accatcatca ccatcaccat taatgagcgg    2520
ccgcactcga gcaccaccac caccaccact aacctaggta gctgagcgca tgcaagctga    2580
tccgggttat tagtacattt attaagcgct agattctgtg cgttgttgat ttacagacaa    2640
ttgttgtacg tattttaata attcattaaa tttataatct ttagggtggt atgttagagc    2700
gaaaatcaaa tgattttcag cgtctttata tctgaattta aatattaaat cctcaataga    2760
tttgtaaaat aggtttcgat tagtttcaaa caagggttgt ttttccgaac cgatggctgg    2820
actatctaat ggattttcgc tcaacgccac aaaacttgcc aaatcttgta gcagcaatct    2880
agctttgtcg atattcgttt gtgttttgtt ttgtaataaa ggttcgacgt cgttcaaaat    2940
attatgcgct tttgtatttc tttcatcact gtcgttagtg tacaattgac tcgacgtaaa    3000
cacgttaaat agagcttgga catatttaac atcgggcgtg ttagctttat taggccgatt    3060
atcgtcgtcg tcccaaccct cgtcgttaga agttgcttcc gaagacgatt tgccatagc    3120 cacacgacgc ctattaattg tgtcggctaa cacgtccgcg atcaaatttg tagttgagct    3180
ttttggaatt atttctgatt gcgggcgttt tgggcgggt ttcaatctaa ctgtgcccga    3240
ttttaattca gacaacacgt tagaaagcga tggtgcaggc ggtggtaaca tttcagacgg    3300
caaatctact aatggcggcg gtggtggagc tgatgataaa tctaccatcg gtggaggcgc    3360
aggcggggct ggcggcggag gcggaggcgg aggtggtggc ggtgatgcag acggcggttt    3420
aggctcaaat gtctctttag gcaacacagt cggcacctca actattgtac tggtttcggg    3480
cgccgttttt ggtttgaccg gtctgagacg agtgcgattt ttttcgtttc taatagcttc    3540
caacaattgt tgtctgtcgt ctaaaggtgc agcgggttga ggttccgtcg gcattggtgg    3600
agcgggcggc aattcagaca tcgatggtgg tggtggtggt ggaggcgctg gaatgttagg    3660
cacgggagaa ggtggtggcg gcggtgccgc cggtataatt tgttctggtt tagtttgttc    3720
gcgcacgatt gtgggcaccg gcgcaggcgc cgctggctgc acaacggaag gtcgtctgct    3780
tcgaggcagc gcttggggtg gtggcaattc aatattataa ttggaataca aatcgtaaaa    3840
atctgctata agcattgtaa tttcgctatc gtttaccgtg ccgatattta acaaccgctc    3900
aatgtaagca attgtattgt aaagagattg tctcaagctc ggatcgatcc cgcacgccga    3960
taacaagcct tttcattttt actacagcat tgtagtggcg agacacttcg ctgtcgtcga    4020
```

```
ggtttaaacg cttcctcgct cactgactcg ctgcgctcgg tcgttcggct gcggcgagcg    4080
gtatcagctc actcaaaggc ggtaatacgg ttatccacag aatcagggga taacgcagga    4140
aagaacatgt gagcaaaagg ccagcaaaag gccaggaacc gtaaaaaggc cgcgttgctg    4200
gcgtttttcc ataggctccg ccccctgac gagcatcaca aaaatcgacg ctcaagtcag    4260
aggtggcgaa acccgacagg actataaaga taccaggcgt ttccccctgg aagctccctc    4320
gtgcgctctc ctgttccgac cctgccgctt accggatacc tgtccgcctt tctcccttcg    4380
ggaagcgtgg cgctttctca tagctcacgc tgtaggtatc tcagttcggt gtaggtcgtt    4440
cgctccaagc tgggctgtgt gcacgaaccc cccgttcagc ccgaccgctg cgccttatcc    4500
ggtaactatc gtcttgagtc caacccggta agacacgact tatcgccact ggcagcagcc    4560
actggtaaca ggattagcag agcgaggtat gtaggcggtg ctacagagtt cttgaagtgg    4620
tggcctaact acggctacac tagaaggaca gtatttggta tctgcgctct gctgaagcca    4680
gttaccttcg gaaaaagagt tggtagctct tgatccggca acaaaccac cgctggtagc    4740 ggtggttttt ttgtttgcaa gcagcagatt acgcgcagaa aaaaggatc tcaagaagat    4800 cctttgatct tttctacggg gtctgacgct cagtggaacg aaaactcacg ttaagggatt    4860
ttggtcatga gattatcaaa aaggatcttc acctagatcc ttttaaatta aaaatgaagt    4920
tttaaatcaa tctaaagtat atatgagtaa acttggtctg acagttacca atgcttaatc    4980
agtgaggcac ctatctcagc gatctgtcta tttcgttcat ccatagttgc ctgactcccc    5040
gtcgtgtaga taactacgat acgggagggc ttaccatctg gccccagtgc tgcaatgata    5100
ccgcgagacc cacgctcacc ggctccagat ttatcagcaa taaccagcc agccggaagg    5160 gccgagcgca gaagtggtcc tgcaacttta tccgcctcca tccagtctat taattgttgc    5220
cgggaagcta gagtaagtag ttcgccagtt aatagtttgc gcaacgttgt tgccattgct    5280
acaggcatcg tggtgtcacg ctcgtcgttt ggtatggctt cattcagctc cggttcccaa    5340
cgatcaaggc gagttacatg atcccccatg ttgtgcaaaa aagcggttag ctccttcggt    5400
cctccgatcg ttgtcagaag taagttggcc gcagtgttat cactcatggt tatggcagca    5460
ctgcataatt ctcttactgt catgccatcc gtaagatgct tttctgtgac tggtgagtac    5520
tcaaccaagt cattctgaga atagtgtatg cggcgaccga gttgctcttg cccggcgtca    5580
atacgggata taccgcgcc acatagcaga actttaaaag tgctcatcat tggaaaacgt    5640
tcttcggggc gaaaactctc aaggatctta ccgctgttga tccagttc gatgtaaccc    5700 actcgtgcac ccaactgatc ttcagcatct tttactttca ccagcgtttc tgggtgagca    5760
aaaacaggaa ggcaaaatgc cgcaaaaaag ggaataaggg cgacacggaa atgttgaata    5820
ctcatactct tcctttttca atattattga agcatttatc agggttattg tctcatgagc    5880
ggatacatat ttgaatgtat ttagaaaaat aaacaaatag gggttccgcg cacatttccc    5940
cgaaaagtgc cacctgacgc gccctgtagc ggcgcattaa gcgcggcggg tgtggtggtt    6000
acgcgcagcg tgaccgctac acttgccagc gccctagcgc ccgctccttt cgctttcttc    6060
ccttcctttc tcgccacgtt cgccggcttt ccccgtcaag ctctaaatcg ggggctccct    6120
ttagggttcc gatttagtgc tttacggcac ctcgacccca aaaaacttga ttagggtgat    6180
ggttcacgta gtgggccatc gccctgatag acggtttttc gccctttgac gttggagtcc    6240
acgttcttta atagtggact cttgttccaa actggaacaa cactcaaccc tatctcggtc    6300 tattctttg atttataagg gattttgccg atttcggcct attggttaaa aaatgagctg    6360
```

```
atttaacaaa aatttaacgc gaattttaac aaaatattaa cgtttacaat ttcccattcg    6420
ccattcaggc tgcgcaactg ttgggaaggg cgatcggtgc gggcctcttc gctattacgc    6480
ca                                                                   6482
```

<210> SEQ ID NO 3
<211> LENGTH: 414
<212> TYPE: PRT
<213> ORGANISM: Artificial Sequence
<220> FEATURE:
<223> OTHER INFORMATION: Full-Length STING WT [STING(1-379)H232R-gg-
      AviTag-gs-HRV3C-HIS8] Amino Acid Sequence

<400> SEQUENCE: 3

```
Met Pro His Ser Ser Leu His Pro Ser Ile Pro Cys Pro Arg Gly His
1               5                   10                  15

Gly Ala Gln Lys Ala Ala Leu Val Leu Leu Ser Ala Cys Leu Val Thr
                20                  25                  30

Leu Trp Gly Leu Gly Glu Pro Pro Glu His Thr Leu Arg Tyr Leu Val
            35                  40                  45

Leu His Leu Ala Ser Leu Gln Leu Gly Leu Leu Leu Asn Gly Val Cys
        50                  55                  60

Ser Leu Ala Glu Glu Leu Arg His Ile His Ser Arg Tyr Arg Gly Ser
65                  70                  75                  80

Tyr Trp Arg Thr Val Arg Ala Cys Leu Gly Cys Pro Leu Arg Arg Gly
                85                  90                  95

Ala Leu Leu Leu Leu Ser Ile Tyr Phe Tyr Tyr Ser Leu Pro Asn Ala
                100                 105                 110

Val Gly Pro Pro Phe Thr Trp Met Leu Ala Leu Leu Gly Leu Ser Gln
            115                 120                 125

Ala Leu Asn Ile Leu Leu Gly Leu Lys Gly Leu Ala Pro Ala Glu Ile
        130                 135                 140

Ser Ala Val Cys Glu Lys Gly Asn Phe Asn Val Ala His Gly Leu Ala
145                 150                 155                 160

Trp Ser Tyr Tyr Ile Gly Tyr Leu Arg Leu Ile Leu Pro Glu Leu Gln
                165                 170                 175

Ala Arg Ile Arg Thr Tyr Asn Gln His Tyr Asn Asn Leu Leu Arg Gly
                180                 185                 190

Ala Val Ser Gln Arg Leu Tyr Ile Leu Leu Pro Leu Asp Cys Gly Val
            195                 200                 205

Pro Asp Asn Leu Ser Met Ala Asp Pro Asn Ile Arg Phe Leu Asp Lys
        210                 215                 220

Leu Pro Gln Gln Thr Gly Asp Arg Ala Gly Ile Lys Asp Arg Val Tyr
225                 230                 235                 240

Ser Asn Ser Ile Tyr Glu Leu Leu Glu Asn Gly Gln Arg Ala Gly Thr
                245                 250                 255

Cys Val Leu Glu Tyr Ala Thr Pro Leu Gln Thr Leu Phe Ala Met Ser
                260                 265                 270

Gln Tyr Ser Gln Ala Gly Phe Ser Arg Glu Asp Arg Leu Glu Gln Ala
            275                 280                 285

Lys Leu Phe Cys Arg Thr Leu Glu Asp Ile Leu Ala Asp Ala Pro Glu
        290                 295                 300

Ser Gln Asn Asn Cys Arg Leu Ile Ala Tyr Gln Glu Pro Ala Asp Asp
305                 310                 315                 320

Ser Ser Phe Ser Leu Ser Gln Glu Val Leu Arg His Leu Arg Gln Glu
                325                 330                 335
```

Glu Lys Glu Glu Val Thr Val Gly Ser Leu Lys Thr Ser Ala Val Pro
            340                 345                 350

Ser Thr Ser Thr Met Ser Gln Glu Pro Glu Leu Leu Ile Ser Gly Met
            355                 360                 365

Glu Lys Pro Leu Pro Leu Arg Thr Asp Phe Ser Gly Gly Gly Leu Asn
370                 375                 380

Asp Ile Phe Glu Ala Gln Lys Ile Glu Trp His Glu Gly Ser Leu Glu
385                 390                 395                 400

Val Leu Phe Gln Gly Pro His His His His His His His His
            405                 410

<210> SEQ ID NO 4
<211> LENGTH: 6482
<212> TYPE: DNA
<213> ORGANISM: Artificial Sequence
<220> FEATURE:
<223> OTHER INFORMATION: Full-length WT STING
      [STING(1-379)H232R-gg-AviTag-gs-HRV3C-HIS8/pBAC1] plasmid
      sequence

<400> SEQUENCE: 4
ggaacggctc cgcccactat taatgaaatt aaaaattcca atttttaaaaa acgcagcaag      60 agaaacattt gtatgaaaga atgcgtagaa ggaaagaaaa atgtcgtcga catgctgaac     120
aacaagatta tatgcctcc gtgtataaaa aaatattga acgatttgaa agaaaacaat     180
gtaccgcgcg gcggtatgta caggaagagg tttatactaa actgttacat tgcaaacgtg     240
gtttcgtgtg ccaagtgtga aaaccgatgt ttaatcaagg ctctgacgca tttctacaac     300
cacgactcca agtgtgtggg tgaagtcatg catcttttaa tcaaatccca agatgtgtat     360
aaaccaccaa actgccaaaa aatgaaaact gtcgacaagc tctgtccgtt tgctggcaac     420
tgcaagggtc tcaatcctat ttgtaattat tgaataataa acaattata aatgtcaaat     480 ttgttttttta ttaacgatac aaaccaaacg caacaagaac atttgtagta ttatctataa     540
ttgaaaacgc gtagttataa tcgctgaggt aatatttaaa atcattttca aatgattcac     600
agttaatttg cgacaatata attttattttt cacataaact agacgccttg tcgtcttctt     660
cttcgtattc cttctctttt tcatttttct cttcataaaa attaacatag ttattatcgt     720
atccatatat gtatctatcg tatagagtaa attttttgtt gtcataaata tatatgtctt     780
ttttaatggg gtgtatagta ccgctgcgca tagttttttct gtaatttaca acagtgctat     840
tttctggtag ttcttcggag tgtgttgctt taattattaa atttatataa tcaatgaatt     900
tgggatcgtc ggttttgtac aatatgttgc cggcatagta cgcagcttct tctagttcaa     960
ttacaccatt ttttagcagc accggattaa cataactttc caaaatgttg tacgaaccgt    1020
taaacaaaaa cagttcacct cccttttcta tactattgtc tgcgagcagt tgtttgttgt    1080
taaaaataac agccattgta atgagacgca caactaata tcacaaactg gaaatgtcta    1140
tcaatatata gttgctgatc agatctgatc atggagataa ttaaaatgat aaccatctcg    1200
caaataaata agtattttac tgttttcgta acagttttgt aataaaaaaa cctataaata    1260
taggatccat gccccactcc agcctgcatc catccatccc gtgtcccagg ggtcacgggg    1320
cccagaaggc agccttggtt ctgctgagtg cctgcctggt gacccttggg gggctaggag    1380
agccaccaga gcacactctc cggtacctgg tgctccacct agcctccctg cagctgggac    1440
tgctgttaaa cggggtctgc agcctggctg aggagctgcg ccacatccac tccaggtacc    1500
ggggcagcta ctggaggact gtgcgggcct gcctgggctg cccccttcgc cgtgggggccc    1560

-continued

```
tgttgctgct gtccatctat ttctactact ccctcccaaa tgcgtcggc ccgcccttca   1620
cttggatgct tgccctcctg ggcctctcgc aggcactgaa catcctcctg ggcctcaagg   1680
gcctggcccc agctgagatc tctgcagtgt gtgaaaaagg gaatttcaac gtggcccatg   1740
ggctggcatg gtcatattac atcggatatc tgcggctgat cctgccagag ctccaggccc   1800
ggattcgaac ttacaatcag cattacaaca acctgctacg gggtgcagtg agccagcggc   1860
tgtatattct cctcccattg gactgtgggg tgcctgataa cctgagtatg ctgaccccca   1920
acattcgctt cctggataaa ctgccccagc agaccggtga ccgtgctggc atcaaggatc   1980
gggtttacag caacagcatc tatgagcttc tggagaacgg gcagcgggcg ggcacctgtg   2040
tcctggagta cgccaccccc ttgcagactt tgtttgccat gtcacaatac agtcaagctg   2100
gctttagccg ggaggatagg cttgagcagg ccaaactctt ctgccggaca cttgaggaca   2160
tcctggcaga tgcccctgag tctcagaaca actgccgcct cattgcctac caggaacctg   2220
cagatgacag cagcttctcg ctgtcccagg aggttctccg gcacctgcgg caggaggaaa   2280
aggaagaggt tactgtgggc agcttgaaga cctcagcggt gcccagtacc tccacgatgt   2340
cccaagagcc tgagctcctc atcagtggaa tggaaaagcc cctccctctc cgcacggatt   2400
tctctggcgg tggcctgaac gacatcttcg aagcccagaa aatcgaatgg catgaaggca   2460
gcctggaagt gctgttccag ggcccacacc accatcatca ccatcaccat taatgagcgg   2520
ccgcactcga gcaccaccac caccaccact aacctaggta gctgagcgca tgcaagctga   2580
tccgggttat tagtacattt attaagcgct agattctgtg cgttgttgat ttacagacaa   2640
ttgttgtacg tattttaata attcattaaa tttataatct ttagggtggt atgttagagc   2700
gaaaatcaaa tgattttcag cgtctttata tctgaattta atattaaat cctcaataga   2760
tttgtaaaat aggtttcgat tagtttcaaa caagggttgt ttttccgaac cgatggctgg   2820
actatctaat ggattttcgc tcaacgccac aaaacttgcc aaatcttgta gcagcaatct   2880
agctttgtcg atattcgttt gtgttttgtt ttgtaataaa ggttcgacgt cgttcaaaat   2940
attatgcgct tttgtatttc tttcatcact gtcgttagtg tacaattgac tcgacgtaaa   3000
cacgttaaat agagcttgga catatttaac atcgggcgtg ttagctttat taggccgatt   3060
atcgtcgtcg tcccaaccct cgtcgttaga agttgcttcc gaagacgatt ttgccatagc   3120
cacacgacgc ctattaattg tgtcggctaa cacgtccgcg atcaaatttg tagttgagct   3180
ttttggaatt atttctgatt gcgggcgttt ttgggcgggt ttcaatctaa ctgtgcccga   3240
ttttaattca gacaacacgt tagaaagcga tggtgcaggc ggtggtaaca tttcagacgg   3300
caaatctact aatggcggcg gtggtggagc tgatgataaa tctaccatcg gtggaggcgc   3360
aggcggggct ggcggcggag gcggaggcgg aggtggtggc ggtgatgcag acggcggttt   3420
aggctcaaat gtctctttag gcaacacagt cggcacctca actattgtac tggtttcggg   3480
cgccgttttt ggtttgaccg gtctgagacg agtgcgattt ttttcgtttc taatagcttc   3540
caacaattgt tgtctgtcgt ctaaaggtgc agcgggttga ggttccgtcg gcattggtgg   3600
agcgggcggc aattcagaca tcgatggtgg tggtggtggt ggaggcgctg gaatgttagg   3660
cacgggagaa ggtggtggcg gcggtgccgc cggtataatt tgttctggtt tagtttgttc   3720
gcgcacgatt gtgggcaccg gcgcaggcgc cgctggctgc acaacggaag gtcgtctgct   3780
tcgaggcagc gcttggggtg gtggcaattc aatattataa ttggaataca aatcgtaaaa   3840
atctgctata agcattgtaa tttcgctatc gtttaccgtg ccgatattta acaaccgctc   3900
```

```
aatgtaagca attgtattgt aaagagattg tctcaagctc ggatcgatcc cgcacgccga   3960
taacaagcct tttcattttt actacagcat tgtagtggcg agacacttcg ctgtcgtcga   4020
ggtttaaacg cttcctcgct cactgactcg ctgcgctcgg tcgttcggct gcggcgagcg   4080
gtatcagctc actcaaaggc ggtaatacgg ttatccacag aatcagggga taacgcagga   4140
aagaacatgt gagcaaaagg ccagcaaaag gccaggaacc gtaaaaaggc cgcgttgctg   4200
gcgtttttcc ataggctccg ccccctgac gagcatcaca aaaatcgacg ctcaagtcag   4260
aggtggcgaa acccgacagg actataaaga taccaggcgt ttccccctgg aagctccctc   4320
gtgcgctctc ctgttccgac cctgccgctt accggatacc tgtccgcctt tctcccttcg   4380
ggaagcgtgg cgctttctca tagctcacgc tgtaggtatc tcagttcggt gtaggtcgtt   4440
cgctccaagc tgggctgtgt gcacgaaccc cccgttcagc ccgaccgctg cgccttatcc   4500
ggtaactatc gtcttgagtc aacccggta agacacgact tatcgccact ggcagcagcc   4560
actggtaaca ggattagcag agcgaggtat gtaggcggtg ctacagagtt cttgaagtgg   4620
tggcctaact acggctacac tagaaggaca gtatttggta tctgcgctct gctgaagcca   4680
gttaccttcg gaaaaagagt tggtagctct tgatccggca aacaaaccac cgctggtagc   4740
ggtggttttt ttgtttgcaa gcagcagatt acgcgcagaa aaaaggatc tcaagaagat   4800
cctttgatct tttctacggg gtctgacgct cagtggaacg aaaactcacg ttaagggatt   4860
ttggtcatga gattatcaaa aaggatcttc acctagatcc ttttaaatta aaaatgaagt   4920
tttaaatcaa tctaaagtat atatgagtaa acttggtctg acagttacca atgcttaatc   4980
agtgaggcac ctatctcagc gatctgtcta tttcgttcat ccatagttgc ctgactcccc   5040
gtcgtgtaga taactacgat acgggagggc ttaccatctg gccccagtgc tgcaatgata   5100
ccgcgagacc cacgctcacc ggctccagat ttatcagcaa taaaccagcc agccggaagg   5160
gccgagcgca gaagtggtcc tgcaaacttta tccgcctcca tccagtctat taattgttgc   5220
cgggaagcta gagtaagtag ttcgccagtt aatagtttgc gcaacgttgt tgccattgct   5280
acaggcatcg tggtgtcacg ctcgtcgttt ggtatggctt cattcagctc cggttcccaa   5340
cgatcaaggc gagttacatg atcccccatg ttgtgcaaaa aagcggttag ctccttcggt   5400
cctccgatcg ttgtcagaag taagttggcc gcagtgttat cactcatggt tatggcagca   5460
ctgcataatt ctcttactgt catgccatcc gtaagatgct tttctgtgac tggtgagtac   5520
tcaaccaagt cattctgaga atagtgtatg cggcgaccga gttgctcttg cccggcgtca   5580
atacgggata taccgcgcc acatagcaga actttaaaag tgctcatcat tggaaaacgt   5640
tcttcgggc gaaaactctc aaggatctta ccgctgttga gatccagttc gatgtaaccc   5700
actcgtgcac ccaactgatc ttcagcatct tttactttca ccagcgtttc tgggtgagca   5760
aaaacaggaa ggcaaaatgc cgcaaaaaag ggaataaggg cgacacggaa atgttgaata   5820
ctcatactct tcctttttca atattattga agcatttatc agggttattg tctcatgagc   5880
ggatacatat ttgaatgtat ttagaaaaat aaacaaatag gggttccgcg cacatttccc   5940
cgaaaagtgc cacctgacgc gccctgtagc ggcgcattaa gcgcggcggg tgtggtggtt   6000
acgcgcagcg tgaccgctac acttgccagc gccctagcgc ccgctccttt cgctttcttc   6060
ccttcctttc tcgccacgtt cgccggcttt ccccgtcaag ctctaaatcg ggggctccct   6120
ttagggttcc gatttagtgc tttacggcac ctcgacccca aaaaacttga ttagggtgat   6180
ggttcacgta gtgggccatc gccctgatag acggtttttc gccctttgac gttggagtcc   6240
acgttcttta atagtggact cttgttccaa actggaacaa cactcaaccc tatctcggtc   6300
```

```
tattcttttg atttataagg gattttgccg atttcggcct attggttaaa aaatgagctg    6360
atttaacaaa aatttaacgc gaattttaac aaaatattaa cgtttacaat ttcccattcg    6420
ccattcaggc tgcgcaactg ttgggaaggg cgatcggtgc gggcctcttc gctattacgc    6480
ca                                                                   6482
```

STING AGONIST COMPOUNDS

CROSS-REFERENCE TO RELATED APPLICATIONS

This application claims the benefit of priority to U.S. Provisional Patent Application No. 62/809,956, filed Feb. 25, 2019, and to U.S. Provisional Patent Application No. 62/652,018, filed Apr. 3, 2018.

FIELD OF THE INVENTION

The present disclosure relates to compounds and derivatives thereof that may be useful as STING (Stimulator of Interferon Genes) agonists that activate the STING pathway. The present disclosure also relates to compositions comprising such compounds, processes for the synthesis of such compounds, and to uses of such compounds, including administration of such compounds to induce immune response, to induce STING-dependent type I interferon production, and/or to treat a cell proliferation disorder, such as cancer.

REFERENCE TO SEQUENCE LISTING SUBMITTED ELECTRONICALLY

The sequence listing of the present application is submitted electronically via EFS-Web as an ASCII-formatted sequence listing, with a file name of "24578_SEQLIST-FEB2019", a creation date of Mar. 1, 2019, and a size of 25 KB. This sequence listing submitted via EFS-Web is part of the specification and is herein incorporated by reference in its entirety.

BACKGROUND OF THE INVENTION

The immune system has evolved to recognize and neutralize different types of threats in order to maintain the homeostasis of the host, and it is generally broken down into two arms: adaptive and innate. The adaptive immune system is specialized to recognize as foreign those antigens not naturally expressed in the host and to mount an anti-antigen response through the coordinated actions of many leukocyte subsets. The hallmark of adaptive immune responses is the ability to provide "memory" or long-lasting immunity against the encountered antigen.

While this specific and long-lasting effect is critical to host health and survival, the adaptive immune response requires time to generate a full-blown response.

The innate immune system compensates for this time delay and is specialized to act quickly against different insults or danger signals. It provides the first line of defense against bacteria, viruses, parasites and other infectious threats, but it also responds strongly to certain danger signals associated with cellular or tissue damage. The innate immune system has no antigen specificity but does respond to a variety of effector mechanisms. Opsonization, phagocytosis, activation of the complement system, and production of soluble bioactive molecules such as cytokines or chemokines are all mechanisms by which the innate immune system mediates its response. By responding to these damage-associated molecular patterns (DAMPs) or pathogen-associated molecular patterns (PAMPs) described above, the innate immune system is able to provide broad protection against a wide range of threats to the host.

Free cytosolic DNA and RNA are among these PAMPs and DAMPs. It has recently been demonstrated that the main sensor for cytosolic DNA is cGAS (cyclic GMP-AMP synthase). Upon recognition of cytosolic DNA, cGAS catalyzes the generation of the cyclic-dinucleotide 2'3'-cGAMP, an atypical second messenger that strongly binds to the ER-transmembrane adaptor protein STING. A conformational change is undergone by cGAMP-bound STING, which translocates to a perinuclear compartment and induces the activation of critical transcription factors IRF-3 and NF-κB. This leads to a strong induction of type I interferons and production of pro-inflammatory cytokines such as IL-6, TNF-α and IFN-γ.

The importance of type I interferons and pro-inflammatory cytokines on various cells of the immune system has been very well established. In particular, these molecules strongly potentiate T-cell activation by enhancing the ability of dendritic cells and macrophages to uptake, process, present and cross-present antigens to T-cells. The T-cell stimulatory capacity of these antigen-presenting cells is augmented by the up-regulation of critical co-stimulatory molecules, such as CD80 or CD86. Finally, type I interferons can rapidly engage their cognate receptors and trigger the activation of interferon-responsive genes that can significantly contribute to adaptive immune cell activation.

From a therapeutic perspective, type I interferons are shown to have antiviral activities by directly inhibiting human hepatitis B virus and hepatitis C virus replication, and by stimulating immune responses to virally infected cells. Compounds that can induce type I interferon production are used in vaccines, where they act as adjuvants, enhancing specific immune responses to antigens and minimizing side effects by reducing dosage and broadening the immune response.

In addition, interferons, and compounds that can induce interferon production, have potential use in the treatment of human cancers. Such molecules are potentially useful as anti-cancer agents with multiple pathways of activity. Interferons can inhibit human tumor cell proliferation directly and may be synergistic with various approved chemotherapeutic agents.

Type I interferons can significantly enhance anti-tumor immune responses by inducing activation of both the adaptive and innate immune cells. Finally, tumor invasiveness may be inhibited by interferons by modulating enzyme expression related to tissue remodeling.

In view of the potential of type I interferons and type I interferon-inducing compounds as anti-viral and anti-cancer agents, there remains a need for new agents that can induce potent type I interferon production. With the growing body of data demonstrating that the cGAS-STING cytosolic DNA sensory pathway has a significant capacity to induce type I interferons, the development of STING activating agents is rapidly taking an important place in today's anti-tumor therapy landscape.

SUMMARY OF THE INVENTION

The present disclosure includes compounds of general formula (I), compounds of general formula (II), compounds of general formula (III), compounds of general formula (IV), compounds of general formula (V), compounds of general formula (VI), and pharmaceutically acceptable salts thereof. These compounds and their pharmaceutically acceptable salts may be useful as agents to induce immune responses, to induce STING-dependent type I interferon production, and/or to treat a cell proliferation disorder.

The present disclosure relates to novel compounds of general formula (I). In particular, the present disclosure relates to compounds having the general structural formula (I):

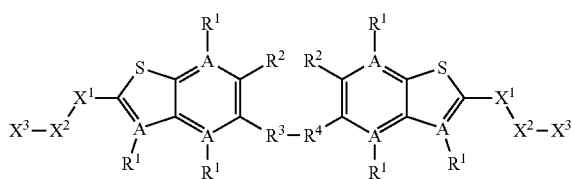

(I)

or pharmaceutically acceptable salts thereof, as described herein. Uses of compounds of general formula (I) and processes for making compounds of general formula (I) are also disclosed.

The present disclosure also relates to novel compounds of general formula (II). In particular, the present disclosure relates to compounds having the general structural formula (II):

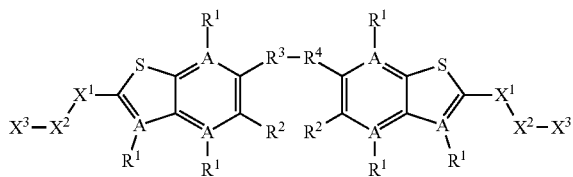

(II)

or pharmaceutically acceptable salts thereof, as described herein. Uses of compounds of general formula (II) and processes for making compounds of general formula (II) are also disclosed.

The present disclosure also relates to novel compounds of general formula (III). In particular, the present disclosure relates to compounds having the general structural formula (III):

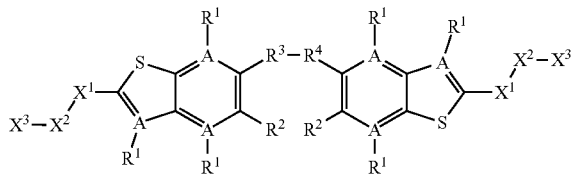

(III)

or pharmaceutically acceptable salts thereof, as described herein. Uses of compounds of general formula (III) and processes for making compounds of general formula (III) are also disclosed.

The present disclosure also relates to novel compounds of general formula (IV). In particular, the present disclosure relates to compounds having the general structural formula (IV):

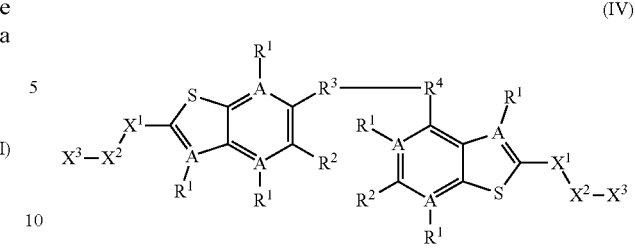

(IV)

or pharmaceutically acceptable salts thereof, as described herein. Uses of compounds of general formula (IV) and processes for making compounds of general formula (IV) are also disclosed.

The present disclosure also relates to novel compounds of general formula (V). In particular, the present disclosure relates to compounds having the general structural formula (V):

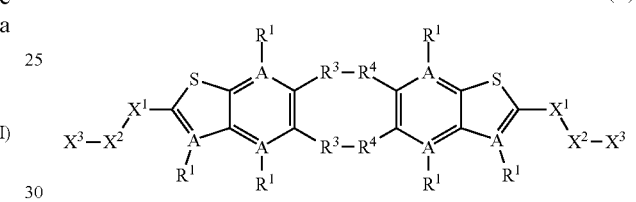

(V)

or pharmaceutically acceptable salts thereof, as described herein. Uses of compounds of general formula (V) and processes for making compounds of general formula (V) are also disclosed.

The present disclosure also relates to novel compounds of general formula (V). In particular, the present disclosure relates to compounds having the general structural formula (VI):

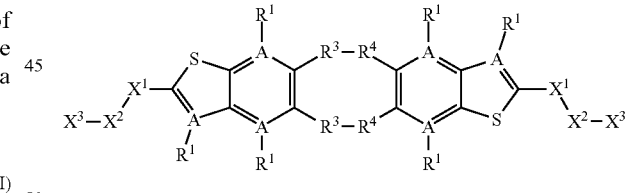

(VI)

or pharmaceutically acceptable salts thereof, as described herein. Uses of compounds of general formula (VI) and processes for making compounds of general formula (VI) are also disclosed.

Other embodiments, aspects and features of the present invention are either further described in or will be apparent from the ensuing description, examples and appended claims.

BRIEF DESCRIPTION OF THE DRAWINGS

Not Applicable.

DETAILED DESCRIPTION OF THE INVENTION

The present disclosure includes compounds of general formula (I), compounds of general formula (II), compounds of general formula (III), compounds of general formula (IV), compounds of general formula (V), compounds of general formula (VI), and pharmaceutically acceptable salts thereof. These compounds and their pharmaceutically acceptable salts may be useful as agents to induce immune responses, to induce STING-dependent type I interferon production, and/or to treat a cell proliferation disorder.

A first embodiment relates to compounds of general formula (I):

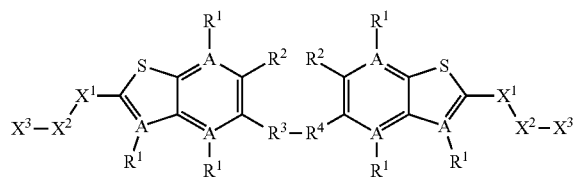

or a pharmaceutically acceptable salt thereof, wherein each A-$R^1$ is independently selected from the group consisting of C—$R^1$ and N; each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); optionally $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl; each $R^6$ is independently selected from the group consisting of H, $C_1$-$C_6$ alkyl, and $C_1$-$C_6$ haloalkyl; each $X^1$ is independently selected from the group consisting of C=O, —$CH_2$—, —CHF—, and —$CF_2$—; each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle; each $X^3$ is independently selected from the group consisting of $COOR^6$, $C(O)SR^6$, $C(S)OR^6$,

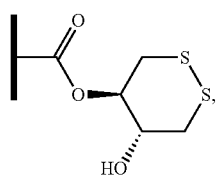

$SO_2R^6$, $C(O)N(R^9)_2$, and CN; and each $R^9$ is independently selected from the group consisting of H, $COOR^6$, and $SO_2R^6$.

In a first aspect of the first embodiment, each A-$R^1$ is independently selected from the group consisting of C—$R^1$ and N. In particular instances of this aspect, each

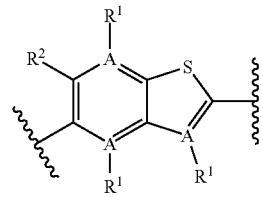

is independently selected from the group consisting of

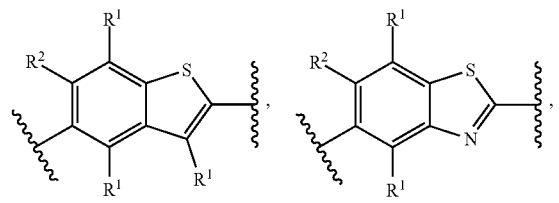

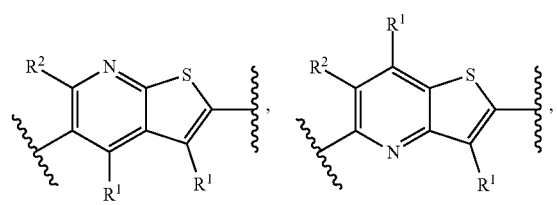

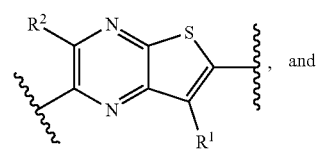, and

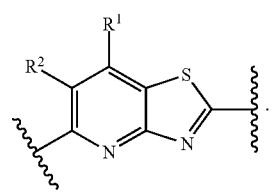.

In more particular instances of this aspect, each

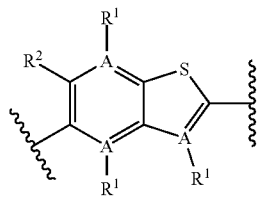

is independently selected from the group consisting of

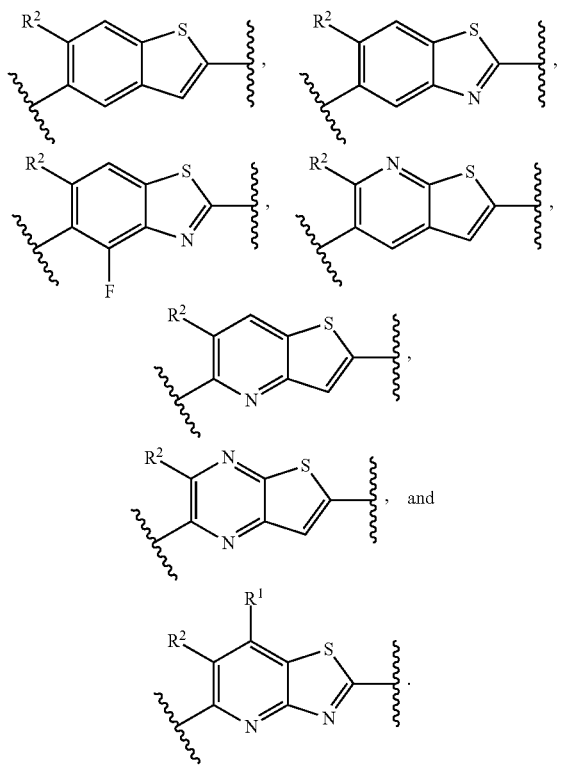

In this aspect, all other groups are as provided in the general formula (I) of the first embodiment above.

In a second aspect of the first embodiment, each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, each $R^1$ is independently selected from the group consisting of H, halogen, $C_1$-$C_3$ alkyl, and $C_1$-$C_3$ haloalkyl. In particular instances of this aspect, each $R^1$ is independently selected from the group consisting of H and halogen. In more particular instances of this aspect, each $R^1$ is independently selected from the group consisting of H and F. In this aspect, all other groups are as provided in the general formula (I) of the first embodiment above or in the first aspect above.

In a third aspect of the first embodiment, each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, each $R^2$ is independently selected from the group consisting of H, halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, each $R^2$ independently is selected from the group consisting of H, Br, Cl, $CH_3$, $CH_2CH_3$, $CH=CH_2$, $OCH_3$, $OCFH_2$, $OCF_2H$, $OCF_3$, and $N(R^6)_2$. In more particular instances of this aspect, each $R^2$ independently is selected from the group consisting of H, $CH_3$, $OCH_3$, and $OCF_2H$. In this aspect, all other groups are as provided in the general formula (I) of the first embodiment or in the first or second aspects described above.

In a fourth aspect of the first embodiment, $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); optionally $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl. In instances of this fourth aspect, $R^3$-$R^4$ is selected from the group consisting of —$(CH_2)_{2-8}$—, —$O(CH_2)_{1-7}$—, —$O(CH_2)_{1-6}O$—, —$NH(CH_2)_{1-7}$—, and —$NH(CH_2)_{1-6}O$—. In particular instances of this fourth aspect, $R^3$-$R^4$ is selected from the group consisting of —$(CH_2)_2$—, —$(CH_2)_3$—, —$(CH_2)_4$—, —$O(CH_2)_2$—, —$O(CH_2)_3$—, —$O(CH_2)_4$—, —$O(CH_2)_{20}$—, —$O(CH_2)_3O$—, —$OCH_2CH(CH_3)CH_2O$—, —$O(CH_2)_4O$—, —$O(CH_2)_5O$—, —$NH(CH_2)_2$—, —$NH(CH_2)_3$—, and —$NH(CH_2)_3O$—. In specific instances of this fourth aspect, $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl. In this instance, the structure of general formula (I) is formula (Ia):

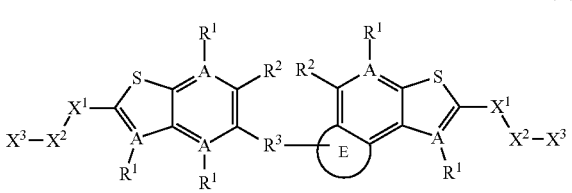

(Ia)

wherein all groups are as provided in the general formula (I). In this aspect, all other groups are as provided in the general formula (I) of the first embodiment or in the first through third aspects described above.

In a fifth aspect of the first embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H, $CH_3$, and $CHF_2$. In this aspect, all other groups are as provided in the general formula (I) of the first embodiment or in the first through fourth aspects described above.

In a sixth aspect of the first embodiment, each $X^1$ is independently selected from the group consisting of C=O, —$CH_2$—, —CHF—, and —$CF_2$—. In instances of this aspect, $X^1$ is selected from the group consisting of C=O and —$CH_2$—. In particular instances of this aspect, $X^1$ is C=O.

In this embodiment, all other groups are as provided in the general formula (I) of the first embodiment or in the first through fifth aspects described above.

In a seventh aspect of the first embodiment, each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle. In a first instance of this aspect, each $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular occurrences of this first instance, each $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, each $X^2$ is $CHR^8CHR^8$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on different carbon atoms are taken together, along with the atoms to which they are attached, to form a 3- to 6-membered fused ring. In particular occurrences of this second instance, each $X^2$ is $CHR^8CHR^8$, where each $R^8$ is independently selected from the group consisting of H and $C_1$-$C_3$ alkyl, and optionally the 2 $R^8$ on different carbon atoms are taken together, along with the atoms to which they are attached, to form a 3- to 6-membered fused ring. In a third instance of this aspect, each $X^2$ is $CH_2C(R^8)_2$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on a single carbon atom are taken together, along with the atoms to which they are attached, to form a 3- to 6-membered spirocycle. In particular occurrences of this third instance, each $X^2$ is $CH_2C(R^8)_2$, where each $R^8$ is independently selected from the group consisting of H and $C_1$-$C_3$ alkyl, and optionally the 2 $R^8$ on a single carbon atom are taken together, along with the atoms to which they are attached, to form a 3- to 6-membered spirocycle. In this aspect, all other groups are as provided in the general formula (I) of the first embodiment or in the first through sixth aspects described above.

In an eighth aspect of the first embodiment, each $X^3$ is independently selected from the group consisting of $COOR^6$, $C(O)SR^6$, $C(S)OR^6$,

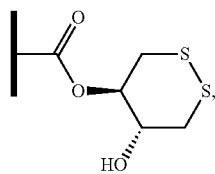

$SO_2R^6$, $C(O)N(R^9)_2$, and CN. In instances of this aspect, each $X^3$ is independently selected from the group consisting of $COOR^6$,

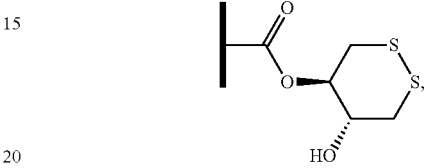

$SO_2R^6$, $C(O)N(R^9)_2$, and CN. In particular instances of this aspect, each $X^3$ is independently selected from the group consisting of $COOR^6$, $C(O)N(R^9)_2$, and CN. In even more particular instances of this aspect, each $X^3$ is independently selected from the group consisting of COOH, $COOCH_3$, $CONH_2$, and CN. In this aspect, all other groups are as provided in the general formula (I) of the first embodiment or in the first through seventh aspects described above.

In a ninth aspect of the first embodiment, each $R^9$ is independently selected from the group consisting of H, $COOR^6$, and $SO_2R^6$. In instances of this aspect, each $R^9$ is independently H. In this aspect, all other groups are as provided in the general formula (I) of the first embodiment or in the first through eighth aspects described above.

A tenth aspect of the first embodiment relates to a pharmaceutical composition, said pharmaceutical composition comprising (a) a compound according to general formula (I) above of the first embodiment or the first through ninth aspects described above or a pharmaceutically acceptable salt thereof, and (b) a pharmaceutically acceptable carrier.

An eleventh aspect of the first embodiment relates to methods of inducing an immune response in a patient in need of therapy, comprising administering a therapeutically effective amount of a compound according to general formula (I) above of the first embodiment or the first through ninth aspects described above described above or a pharmaceutically acceptable salt thereof to the patient.

A twelfth aspect of the first embodiment relates to methods of inducing an immune response in a patient in need of therapy, comprising administering a therapeutically effective amount of a composition according to the tenth aspect described above to the patient.

A thirteenth aspect of the first embodiment relates to methods of inducing a STING-dependent type I interferon production in a patient in need of therapy, comprising administering a therapeutically effective amount of a compound according to general formula (I) of the first embodiment above or the first through ninth aspects described above or a pharmaceutically acceptable salt thereof to the patient.

A fourteenth aspect of the first embodiment relates to methods of inducing STING-dependent type I interferon production in a patient in need of therapy, comprising administering a therapeutically effective amount of a composition according to the tenth aspect described above to the patient.

A fifteenth aspect of the first embodiment relates to methods of inducing STING-dependent cytokine production in a patient in need of therapy, comprising administering a therapeutically effective amount of a compound according to general formula (I) of the first embodiment above or the first through ninth aspects described above or a pharmaceutically acceptable salt thereof to the patient.

A sixteenth aspect of the first embodiment relates to methods of inducing a STING-dependent cytokine production in a patient in need of therapy, comprising administering a therapeutically effective amount of a composition according to the tenth aspect described above to the patient.

A seventeenth aspect of the first embodiment relates to methods of treating a cell proliferation disorder in a patient in need of therapy, comprising administering a therapeutically effective amount of a compound of general formula (I), or a pharmaceutically acceptable salt thereof to the patient. In instances of this seventeenth aspect of the first embodiment, the cell proliferation disorder is cancer.

An eighteenth aspect of the first embodiment relates to methods of treating a cell proliferation disorder in a patient in need of therapy, said method comprising administering a therapeutically effective amount of a composition according to the eleventh aspect described above to the patient. In instances of this eighteenth aspect of the first embodiment, the cell proliferation disorder is cancer.

In each aspect of the first embodiment described herein, variables $R^1$, $R^2$, $R^3$, $R^4$, $R^6$, $R^8$, $R^9$, A, $X^1$, $X^2$, and $X^3$ of general formula (I) of the first embodiment, and the various aspects and instances thereof, are each independently selected from each other, with the proviso that at least one of $R^1$, $R^2$, $R^3$, $R^4$, $R^6$, $R^8$, and $R^9$ is not H.

A second embodiment relates to compounds of general formula (II):

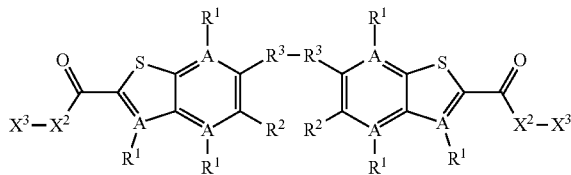

(II)

or a pharmaceutically acceptable salt thereof, wherein each A-$R^1$ is independently selected from the group consisting of C—$R^1$ and N; each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); optionally $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl; each $R^6$ is independently selected from the group consisting of H, $C_1$-$C_6$ alkyl, and $C_1$-$C_6$ haloalkyl; each $X^1$ is independently selected from the group consisting of C=O, —$CH_2$—, —CHF—, and —$CF_2$—; each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle; each $X^3$ is independently selected from the group consisting of $COOR^6$, C(O)$SR^6$, C(S)$OR^6$,

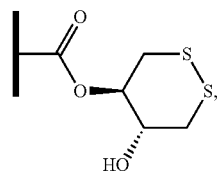

$SO_2R^6$, C(O)N($R^9$)$_2$, and CN; and each $R^9$ is independently selected from the group consisting of H, $COOR^6$, and $SO_2R^6$.

In a first aspect of the second embodiment, each A-$R^1$ is independently selected from the group consisting of C—$R^1$ and N. In particular instances of this aspect, each

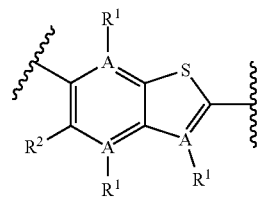

is independently selected from the group consisting of

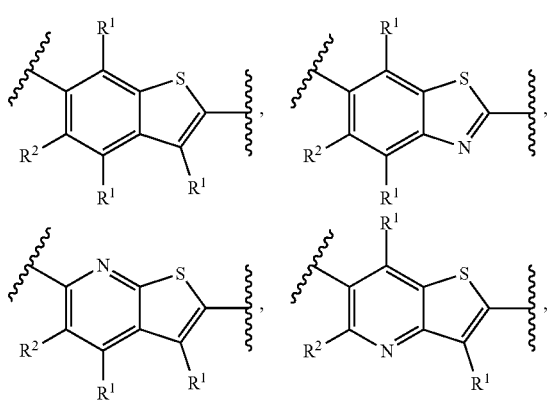

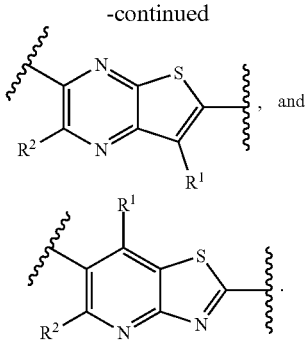

In more particular instances of this aspect, each

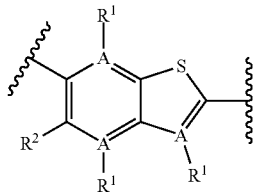

is independently selected from the group consisting of

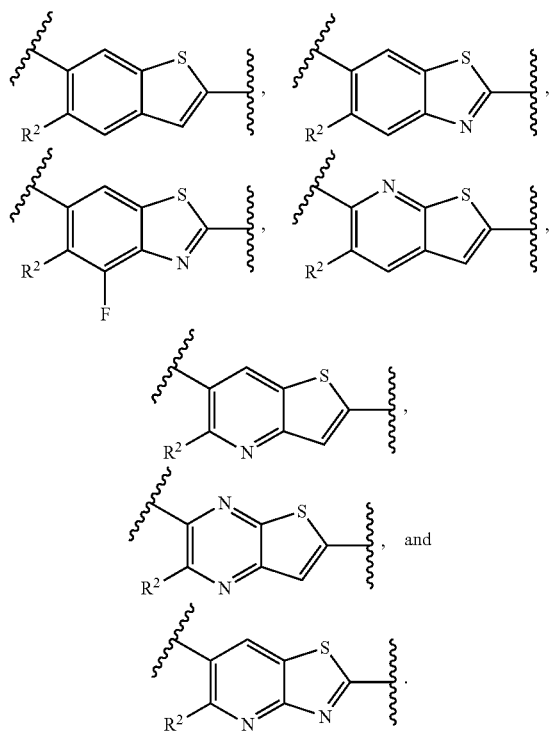

In this aspect, all other groups are as provided in the general formula (II) of the second embodiment above.

In a second aspect of the second embodiment, each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, each $R^1$ is independently selected from the group consisting of H, halogen, $C_1$-$C_3$ alkyl, and $C_1$-$C_3$ haloalkyl. In particular instances of this aspect, each $R^1$ is independently selected from the group consisting of H and halogen. In more particular instances of this aspect, each $R^1$ is independently selected from the group consisting of H and F. In this aspect, all other groups are as provided in the general formula (II) of the second embodiment above or in the first aspect above.

In a third aspect of the second embodiment, each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, each $R^2$ is independently selected from the group consisting of H, halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, each $R^2$ independently is selected from the group consisting of H, Br, Cl, $CH_3$, $CH_2CH_3$, $CH=CH_2$, $OCH_3$, $OCFH_2$, $OCF_2H$, $OCF_3$, and $N(R^6)_2$. In more particular instances of this aspect, each $R^2$ independently is selected from the group consisting of H, $CH_3$, $OCH_3$, and $OCF_2H$. In this aspect, all other groups are as provided in the general formula (II) of the second embodiment or in the first or second aspects described above.

In a fourth aspect of the second embodiment, $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); optionally $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl. In instances of this fourth aspect, $R^3$-$R^4$ is selected from the group consisting of —$(CH_2)_{2-8}$—, —$O(CH_2)_{1-7}$—, —$O(CH_2)_{1-6}O$—, —$NH(CH_2)_{1-7}$—, and —$NH(CH_2)_{1-6}O$—. In particular instances of this fourth aspect, $R^3$-$R^4$ is selected from the group consisting of —$(CH_2)_2$—, —$(CH_2)_3$—, —$(CH_2)_4$—, —$O(CH_2)_2$—, —$O(CH_2)_3$—, —$O(CH_2)_4$—, —$O(CH_2)_{20}$—, —$O(CH_2)_3O$—, —$OCH_2CH(CH_3)CH_2O$—, —$O(CH_2)_4O$—, —$O(CH_2)_5O$—, —$NH(CH_2)_2$—, —$NH(CH_2)_3$—, and —$NH(CH_2)_3O$—. In specific instances of this fourth aspect, $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl. In this instance, the structure of general formula (II) is formula (IIa):

(IIa)

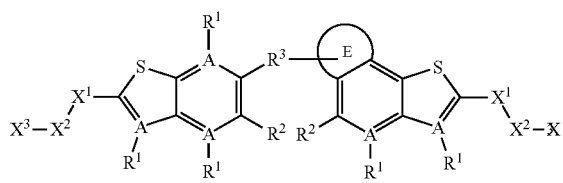

wherein all groups are as provided in the general formula (II). In this aspect, all other groups are as provided in the general formula (II) of the second embodiment or in the first through third aspects described above.

In a fifth aspect of the second embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H, $CH_3$, and $CHF_2$. In this aspect, all other groups are as provided in the general formula (II) of the second embodiment or in the first through fourth aspects described above.

In a sixth aspect of the second embodiment, each $X^1$ is independently selected from the group consisting of C=O, —$CH_2$—, —CHF—, and —$CF_2$—. In instances of this aspect, $X^1$ is selected from the group consisting of C=O and —$CH_2$—. In particular instances of this aspect, $X^1$ is C=O. In this embodiment, all other groups are as provided in the general formula (II) of the second embodiment or in the first through fifth aspects described above In a seventh aspect of the second embodiment, each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle. In a first instance of this aspect, each $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular occurrences of this first instance, each $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, each $X^2$ is $CHR^8CHR^8$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on different carbon atoms are taken together, along with the atoms to which they are attached, to form a 3- to 6-membered fused ring. In particular occurrences of this second instance, each $X^2$ is $CHR^8CHR^8$, where each $R^8$ is independently selected from the group consisting of H and $C_1$-$C_3$ alkyl, and optionally the 2 $R^8$ on different carbon atoms are taken together, along with the atoms to which they are attached, to form a 3- to 6-membered fused ring. In a third instance of this aspect, each $X^2$ is $CH_2C(R^8)_2$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on a single carbon atom are taken together, along with the atoms to which they are attached, to form a 3- to 6-membered spirocycle. In particular occurrences of this third instance, each $X^2$ is $CH_2C(R^8)_2$, where each $R^8$ is independently selected from the group consisting of H and $C_1$-$C_3$ alkyl, and optionally the 2 $R^8$ on a single carbon atom are taken together, along with the atoms to which they are attached, to form a 3- to 6-membered spirocycle. In this aspect, all other groups are as provided in the general formula (II) of the second embodiment or in the first through sixth aspects described above.

In an eighth aspect of the second embodiment, each $X^3$ is independently selected from the group consisting of $COOR^6$, $C(O)SR^6$, $C(S)OR^6$,

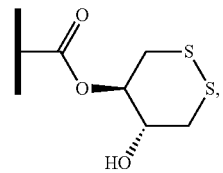

$SO_2R^6$, $C(O)N(R^9)_2$, and CN. In instances of this aspect, each $X^3$ is independently selected from the group consisting of $COOR^6$,

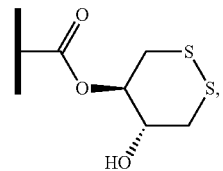

$SO_2R^6$, $C(O)N(R^9)_2$, and CN. In particular instances of this aspect, each $X^3$ is independently selected from the group consisting of $COOR^6$, $C(O)N(R^9)_2$, and CN. In even more particular instances of this aspect, each $X^3$ is independently selected from the group consisting of COOH, $COOCH_3$, $CONH_2$, and CN. In this aspect, all other groups are as provided in the general formula (II) of the second embodiment or in the first through seventh aspects described above.

In a ninth aspect of the second embodiment, each $R^9$ is independently selected from the group consisting of H, $COOR^6$, and $SO_2R^6$. In instances of this aspect, each $R^9$ is independently H. In this aspect, all other groups are as provided in the general formula (II) of the second embodiment or in the first through eighth aspects described above.

A tenth aspect of the second embodiment relates to a pharmaceutical composition, said pharmaceutical composition comprising (a) a compound according to general formula (II) above of the second embodiment or the first through ninth aspects described above or a pharmaceutically acceptable salt thereof; and (b) a pharmaceutically acceptable carrier.

An eleventh aspect of the second embodiment relates to methods of inducing an immune response in a patient in need of therapy, comprising administering a therapeutically effective amount of a compound according to general formula (II) above of the second embodiment or the first through ninth aspects described above described above or a pharmaceutically acceptable salt thereof to the patient.

A twelfth aspect of the second embodiment relates to methods of inducing an immune response in a patient in need of therapy, comprising administering a therapeutically effective amount of a composition according to the tenth aspect described above to the patient.

A thirteenth aspect of the second embodiment relates to methods of inducing a STING-dependent type I interferon production in a patient in need of therapy, comprising administering a therapeutically effective amount of a compound according to general formula (II) of the second embodiment above or the first through ninth aspects described above or a pharmaceutically acceptable salt thereof to the patient.

A fourteenth aspect of the second embodiment relates to methods of inducing STING-dependent type I interferon production in a patient in need of therapy, comprising administering a therapeutically effective amount of a composition according to the tenth aspect described above to the patient.

A fifteenth aspect of the second embodiment relates to methods of inducing STING-dependent cytokine production in a patient in need of therapy, comprising administering a therapeutically effective amount of a compound according to general formula (II) of the second embodiment above or the first through ninth aspects described above or a pharmaceutically acceptable salt thereof to the patient.

A sixteenth aspect of the second embodiment relates to methods of inducing a STING-dependent cytokine production in a patient in need of therapy, comprising administering a therapeutically effective amount of a composition according to the tenth aspect described above to the patient.

A seventeenth aspect of the second embodiment relates to methods of treating a cell proliferation disorder in a patient in need of therapy, comprising administering a therapeutically effective amount of a compound of general formula (II), or a pharmaceutically acceptable salt thereof to the patient. In instances of this seventeenth aspect of the second embodiment, the cell proliferation disorder is cancer.

An eighteenth aspect of the second embodiment relates to methods of treating a cell proliferation disorder in a patient in need of therapy, said method comprising administering a therapeutically effective amount of a composition according to the eleventh aspect described above to the patient. In instances of this eighteenth aspect of the second embodiment, the cell proliferation disorder is cancer.

In each aspect of the second embodiment described herein, variables $R^1$, $R^2$, $R^3$, $R^4$, $R^6$, $R^8$, $R^9$, A, $X^1$, $X^2$, and $X^3$ of general formula (II) of the second embodiment, and the various aspects and instances thereof, are each independently selected from each other, with the proviso that at least one of $R^1$, $R^2$, $R^3$, $R^4$, $R^6$, $R^8$, and $R^9$ is not H.

A third embodiment relates to compounds of general formula (III):

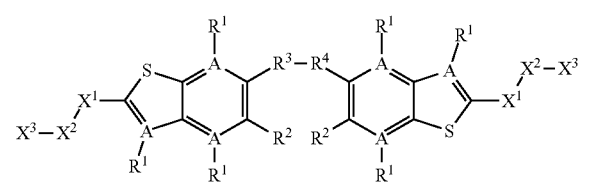

(III)

or a pharmaceutically acceptable salt thereof, wherein each A-$R^1$ is independently selected from the group consisting of C—$R^1$ and N; each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); optionally $R^3$ may be taken together with an adjacent C—$R^1$ and the atom to which they are attached to form fused ring G, which is selected from phenyl or a 5- or 6-membered heterocyclic ring including 1 to 2 ring members selected from the group consisting of O, S, N, and $N(R^6)$ wherein the bond to $R^3$ from said ring G is from an atom on said ring G with an open valence for substitution and wherein said phenyl or heterocyclic ring is optionally substituted with one or more members of the group consisting of halogen, $C_1$-$C_3$ alkyl, and $C_1$-$C_3$ haloalkyl; optionally $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^4$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl; each $R^6$ is independently selected from the group consisting of H, $C_1$-$C_6$ alkyl, and $C_1$-$C_6$ haloalkyl; each $X^1$ is independently selected from the group consisting of C=O, —$CH_2$—, —CHF—, and —$CF_2$—; each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle; each $X^3$ is independently selected from the group consisting of $COOR^6$, $C(O)SR^6$, $C(S)OR^6$,

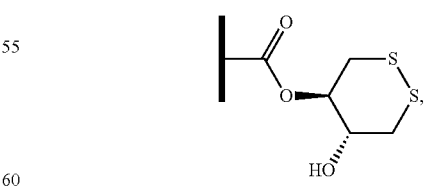

$SO_2R^6$, $C(O)N(R^9)_2$, and CN; and each $R^9$ is independently selected from the group consisting of H, $COOR^6$, and $SO_2R^6$.

In a first aspect of the third embodiment, each A-$R^1$ is independently selected from the group consisting of C—$R^1$ and N. In particular instances of this aspect, each

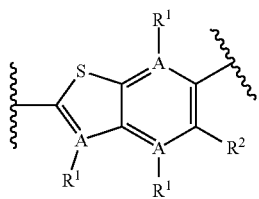
is independently selected from the group consisting of
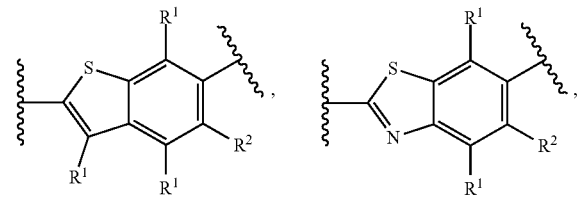
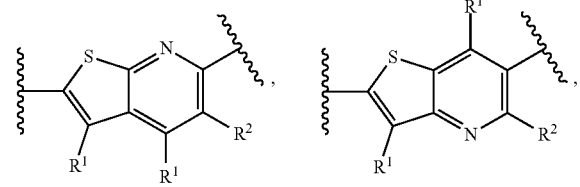
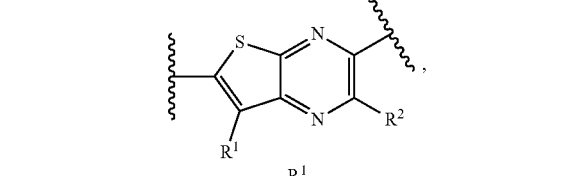
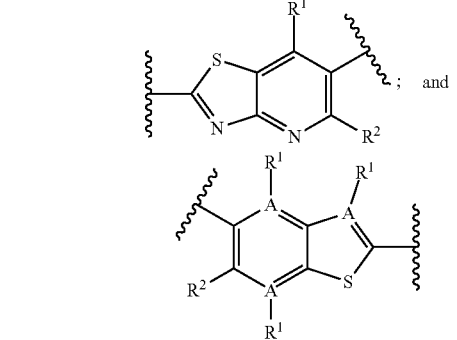
is selected from the group consisting of
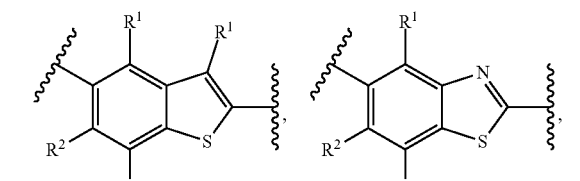
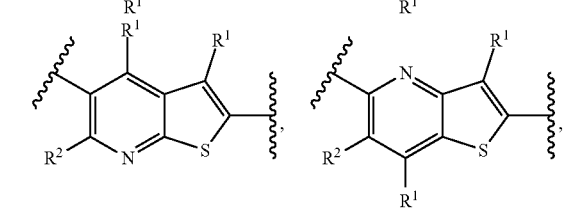
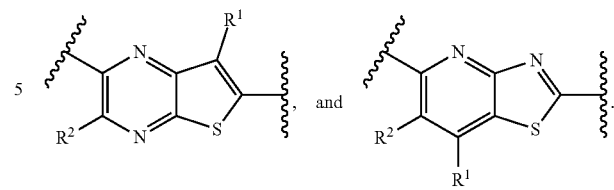, and
In more particular instances of this aspect, each
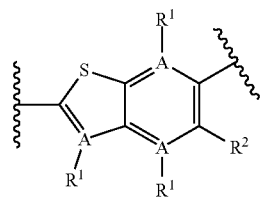
is independently selected from the group consisting of
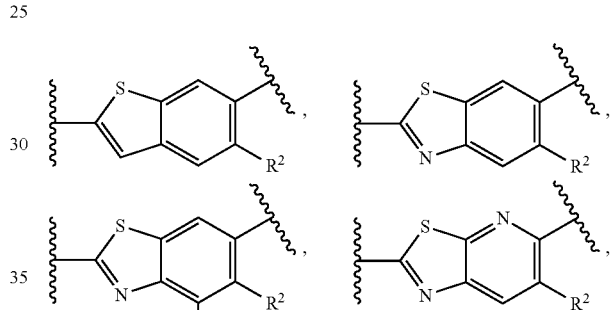
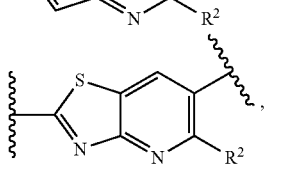, and
and each
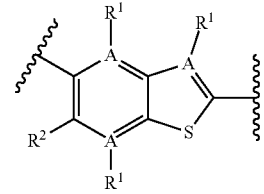

is selected from the group consisting of

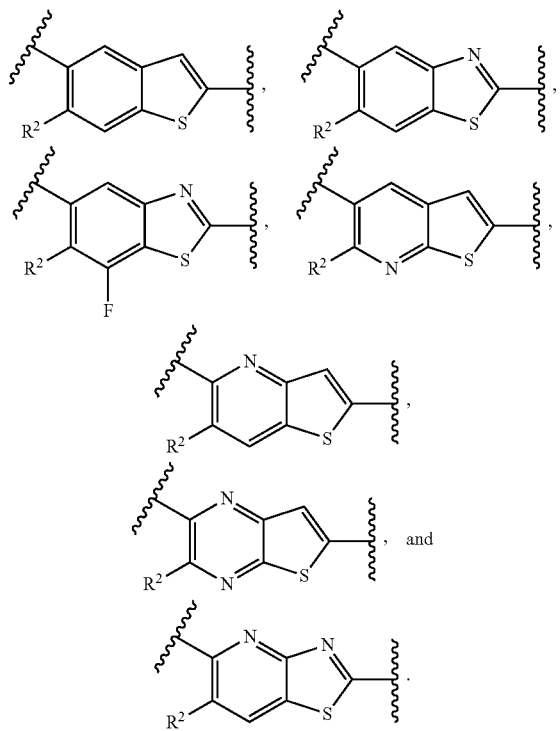

In this aspect, all other groups are as provided in the general formula (III) of the third embodiment above.

In a second aspect of the third embodiment, each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, each $R^1$ is independently selected from the group consisting of H, halogen, $C_1$-$C_3$ alkyl, and $C_1$-$C_3$ haloalkyl. In particular instances of this aspect, each $R^1$ is independently selected from the group consisting of H and halogen. In more particular instances of this aspect, each $R^1$ is independently selected from the group consisting of H and F. In this aspect, all other groups are as provided in the general formula (III) of the third embodiment above or in the first aspect above.

In a third aspect of the third embodiment, each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, each $R^2$ is independently selected from the group consisting of H, halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, each $R^2$ independently is selected from the group consisting of H, Br, Cl, $CH_3$, $CH_2CH_3$, $CH=CH_2$, $OCH_3$, $OCFH_2$, $OCF_2H$, $OCF_3$, and $N(R^6)_2$. In more particular instances of this aspect, each $R^2$ independently is selected from the group consisting of H, $CH_3$, $OCH_3$, and $OCF_2H$. In this aspect, all other groups are as provided in the general formula (III) of the third embodiment or in the first or second aspects described above.

In a fourth aspect of the third embodiment, $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); optionally $R^3$ may be taken together with an adjacent C—$R^1$ and the atom to which they are attached to form fused ring G, which is selected from phenyl or a 5- or 6-membered heterocyclic ring including 1 to 2 ring members selected from the group consisting of O, S, N, and $N(R^6)$ wherein the bond to $R^3$ from said ring G is from an atom on said ring G with an open valence for substitution and wherein said phenyl or heterocyclic ring is optionally substituted with one or more members of the group consisting of halogen, $C_1$-$C_3$ alkyl, and $C_1$-$C_3$ haloalkyl; optionally $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^4$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl. In instances of this fourth aspect, $R^3$-$R^4$ is selected from the group consisting of —$(CH_2)_{2-8}$—, —$O(CH_2)_{1-7}$—, —$O(CH_2)_{1-6}O$—, —$NH(CH_2)_{1-7}$—, and —$NH(CH_2)_{1-6}O$—. In particular instances of this fourth aspect, $R^3$-$R^4$ is selected from the group consisting of —$(CH_2)_2$—, —$(CH_2)_3$—, —$(CH_2)_4$—, —$O(CH_2)_2$—, —$O(CH_2)_3$—, —$O(CH_2)_4$—, —$O(CH_2)_{20}$—, —$O(CH_2)_3O$—, —$OCH_2CH(CH_3)CH_2O$—, —$O(CH_2)_4O$—, —$O(CH_2)_5O$—, —$NH(CH_2)_2$—, —$NH(CH_2)_3$—, and —$NH(CH_2)_3O$—. In specific instances of this fourth aspect, $R^3$ may be taken together with an adjacent C—$R^1$ and the atom to which they are attached to form fused ring G, which is selected from phenyl or a 5- or 6-membered heterocyclic ring including 1 to 2 ring members selected from the group consisting of O, S, N, and $N(R^6)$ wherein the bond to $R^4$ from said ring G is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl. In this instance, the structure of general formula (III) is formula (IIIa):

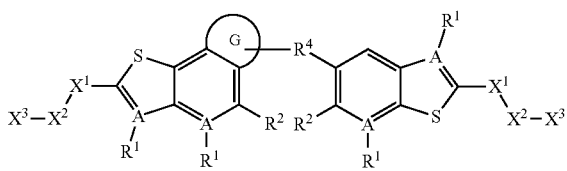

(IIIa)

wherein all groups are as provided in the general formula (III). In further specific instances of this fourth aspect, $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl.

In this instance, the structure of general formula (III) is formula (IIIb):

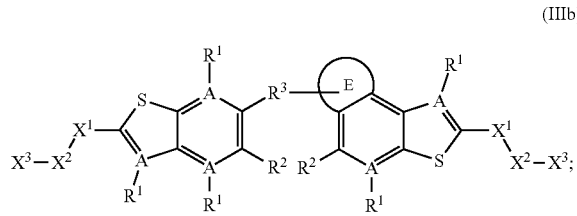

(IIIb)

wherein all groups are as provided in the general formula (III). In this aspect, all other groups are as provided in the general formula (III) of the first embodiment or in the first through third aspects described above.

In a fifth aspect of the third embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H, $CH_3$, and $CHF_2$. In this aspect, all other groups are as provided in the general formula (III) of the third embodiment or in the first through fourth aspects described above.

In a sixth aspect of the third embodiment, each $X^1$ is independently selected from the group consisting of C=O, —$CH_2$—, —CHF—, and —$CF_2$—. In instances of this aspect, $X^1$ is selected from the group consisting of C=O and —$CH_2$—. In particular instances of this aspect, $X^1$ is C=O.

In this embodiment, all other groups are as provided in the general formula (III) of the third embodiment or in the first through fifth aspects described above.

In a seventh aspect of the third embodiment, each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle. In a first instance of this aspect, each $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular occurrences of this first instance, each $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, each $X^2$ is $CHR^8CHR^8$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on different carbon atoms are taken together, along with the atoms to which they are attached, to form a 3- to 6-membered fused ring. In particular occurrences of this second instance, each $X^2$ is $CHR^8CHR^8$, where each $R^8$ is independently selected from the group consisting of H and $C_1$-$C_3$ alkyl, and optionally the 2 $R^8$ on different carbon atoms are taken together, along with the atoms to which they are attached, to form a 3- to 6-membered fused ring. In a third instance of this aspect, each $X^2$ is $CH_2C(R^8)_2$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on a single carbon atom are taken together, along with the atoms to which they are attached, to form a 3- to 6-membered spirocycle. In particular occurrences of this third instance, each $X^2$ is $CH_2C(R^8)_2$, where each $R^8$ is independently selected from the group consisting of H and $C_1$-$C_3$ alkyl, and optionally the 2 $R^8$ on a single carbon atom are taken together, along with the atoms to which they are attached, to form a 3- to 6-membered spirocycle. In this aspect, all other groups are as provided in the general formula (III) of the third embodiment or in the first through sixth aspects described above.

In an eighth aspect of the third embodiment, each $X^3$ is independently selected from the group consisting of $COOR^6$, $C(O)SR^6$, $C(S)OR^6$,

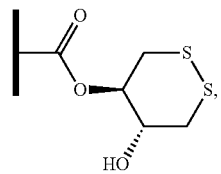

$SO_2R^6$, $C(O)N(R^9)_2$, and CN. In instances of this aspect, each $X^3$ is independently selected from the group consisting of $COOR^6$,

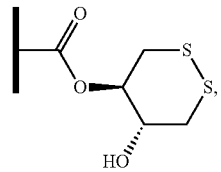

$SO_2R^6$, $C(O)N(R^9)_2$, and CN. In particular instances of this aspect, each $X^3$ is independently selected from the group consisting of $COOR^6$, $C(O)N(R^9)_2$, and CN. In even more particular instances of this aspect, each $X^3$ is independently selected from the group consisting of COOH, $COOCH_3$, $CONH_2$, and CN. In this aspect, all other groups are as provided in the general formula (III) of the third embodiment or in the first through seventh aspects described above.

In a ninth aspect of the third embodiment, each $R^9$ is independently selected from the group consisting of H, $COOR^6$, and $SO_2R^6$. In instances of this aspect, each $R^9$ is independently H. In this aspect, all other groups are as provided in the general formula (III) of the third embodiment or in the first through sixth aspects described above.

A tenth aspect of the third embodiment relates to a pharmaceutical composition, said pharmaceutical composition comprising (a) a compound according to general formula (III) of the third embodiment or the first through ninth aspects described above or a pharmaceutically acceptable salt thereof; and (b) a pharmaceutically acceptable carrier.

An eleventh aspect of the third embodiment relates to methods of inducing an immune response in a patient in need of therapy, comprising administering a therapeutically effective amount of a compound according to general formula (III) of the third embodiment or the first through ninth aspects described above described above or a pharmaceutically acceptable salt thereof to the patient.

A twelfth aspect of the third embodiment relates to methods of inducing an immune response in a patient in need of therapy, comprising administering a therapeutically effective amount of a composition according to the tenth aspect described above to the patient.

A thirteenth aspect of the third embodiment relates to methods of inducing a STING-dependent type I interferon production in a patient in need of therapy, comprising administering a therapeutically effective amount of a compound according to general formula (III) of the third embodiment above or the first through ninth aspects described above or a pharmaceutically acceptable salt thereof to the patient.

A fourteenth aspect of the third embodiment relates to methods of inducing STING-dependent type I interferon production in a patient in need of therapy, comprising administering a therapeutically effective amount of a composition according to the tenth aspect described above to the patient.

A fifteenth aspect of the third embodiment relates to methods of inducing STING-dependent cytokine production in a patient in need of therapy, comprising administering a therapeutically effective amount of a compound according to general formula (III) of the third embodiment above or the first through ninth aspects described above or a pharmaceutically acceptable salt thereof to the patient.

A sixteenth aspect of the third embodiment relates to methods of inducing a STING-dependent cytokine production in a patient in need of therapy, comprising administering a therapeutically effective amount of a composition according to the tenth aspect described above to the patient.

A seventeenth aspect of the third embodiment relates to methods of treating a cell proliferation disorder in a patient in need of therapy, comprising administering a therapeutically effective amount of a compound of general formula (III), or a pharmaceutically acceptable salt thereof to the patient. In instances of this seventeenth aspect of the third embodiment, the cell proliferation disorder is cancer.

An eighteenth aspect of the third embodiment relates to methods of treating a cell proliferation disorder in a patient in need of therapy, said method comprising administering a therapeutically effective amount of a composition according to the eleventh aspect described above to the patient. In instances of this eighteenth aspect of the third embodiment, the cell proliferation disorder is cancer.

In each aspect of the third embodiment described herein, variables $R^1$, $R^2$, $R^3$, $R^4$, $R^6$, $R^8$, $R^9$, A, $X^1$, $X^2$, and $X^3$ of general formula (III) of the third embodiment, and the various aspects and instances thereof, are each independently selected from each other, with the proviso that at least one of $R^1$, $R^2$, $R^3$, $R^4$, $R^6$, $R^8$, and $R^9$ is not H.

A fourth embodiment relates to compounds of general formula (IV):

or a pharmaceutically acceptable salt thereof, wherein each A-$R^1$ is independently selected from the group consisting of C—$R^1$ and N; each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$; $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); each $R^6$ is independently selected from the group consisting of H, $C_1$-$C_6$ alkyl, and $C_1$-$C_6$ haloalkyl; each $X^1$ is independently selected from the group consisting of C=O, —$CH_2$—, —CHF—, and —$CF_2$—; each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle; each $X^3$ is independently selected from the group consisting of $COOR^6$, $C(O)SR^6$, $C(S)OR^6$,

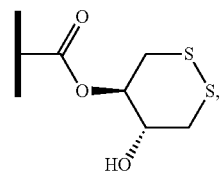

$SO_2R^6$, $C(O)N(R^9)_2$, and CN; and each $R^9$ is independently selected from the group consisting of H, $COOR^6$, and $SO_2R^6$.

In a first aspect of the fourth embodiment, each A-$R^1$ is independently selected from the group consisting of C—$R^1$ and N. In particular instances of this aspect, each (IV)

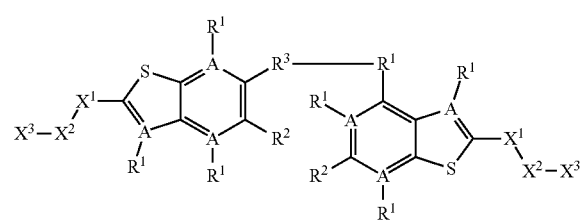

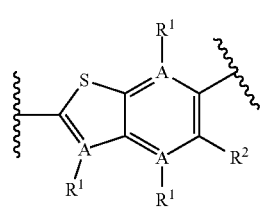

is independently selected from the group consisting of
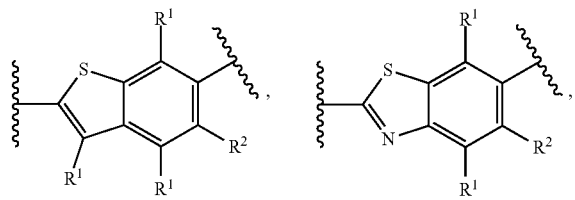
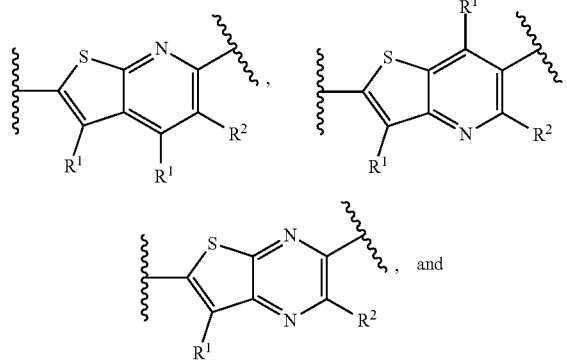
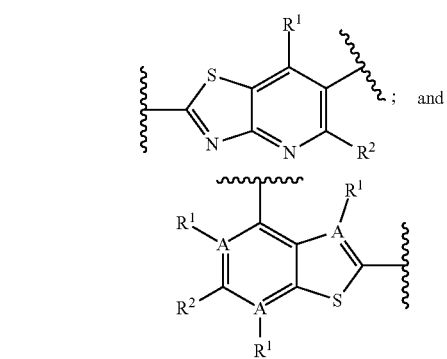
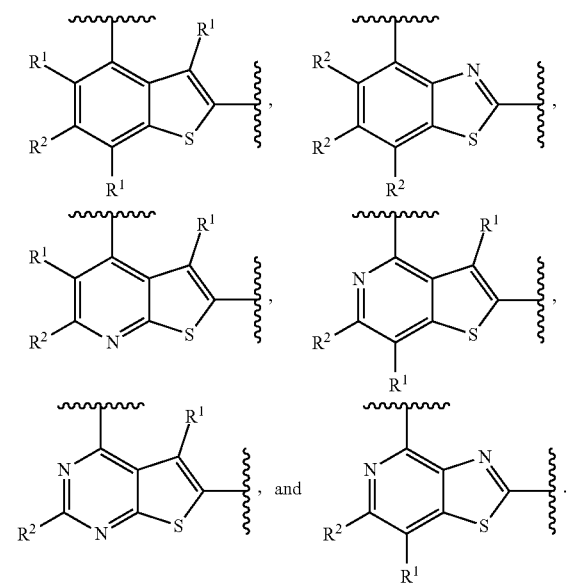
is selected from the group consisting of
In more particular instances of this aspect, each
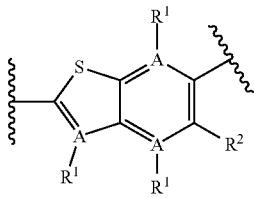
independently selected from the group consisting of
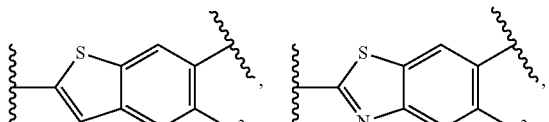
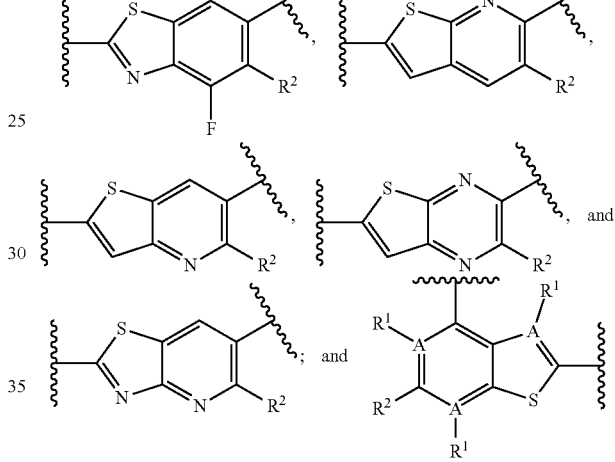
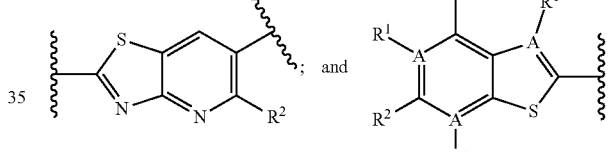
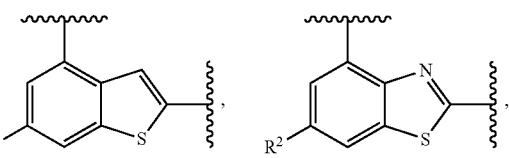
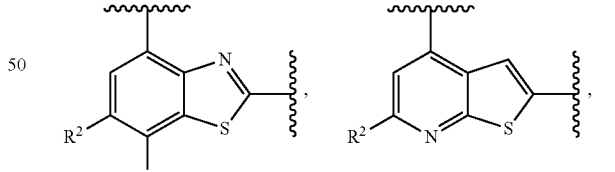
is selected from the group consisting of
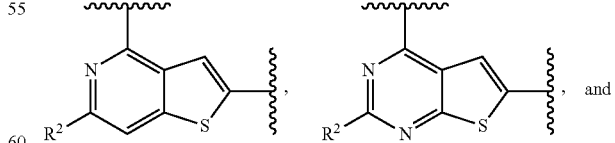
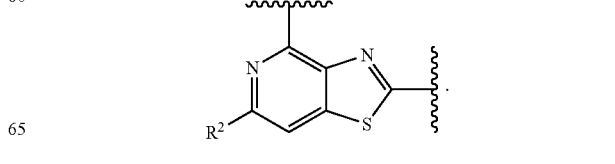

In this aspect, all other groups are as provided in the general formula (IV) of the fourth embodiment above.

In a second aspect of the fourth embodiment, each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, each $R^1$ is independently selected from the group consisting of H, halogen, $C_1$-$C_3$ alkyl, and $C_1$-$C_3$ haloalkyl. In particular instances of this aspect, each $R^1$ is independently selected from the group consisting of H and halogen. In more particular instances of this aspect, each $R^1$ is independently selected from the group consisting of H and F. In this aspect, all other groups are as provided in the general formula (IV) of the fourth embodiment above or in the first aspect above.

In a third aspect of the fourth embodiment, each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$. In instances of this aspect, each $R^2$ is independently selected from the group consisting of H, halogen, $C_1$-$C_3$ alkyl, $C_1$-$C_3$ haloalkyl, $OC_1$-$C_3$ alkyl, $C_2$-$C_3$ alkenyl, and $N(R^6)_2$. In particular instances of this aspect, each $R^2$ independently is selected from the group consisting of H, Br, Cl, $CH_3$, $CH_2CH_3$, $CH=CH_2$, $OCH_3$, $OCFH_2$, $OCF_2H$, $OCF_3$, and $N(R^6)_2$. In more particular instances of this aspect, each $R^2$ independently is selected from the group consisting of H, $CH_3$, $OCH_3$, and $OCF_2H$. In this aspect, all other groups are as provided in the general formula (IV) of the fourth embodiment or in the first or second aspects described above.

In a fourth aspect of the fourth embodiment, $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene). In instances of this fourth aspect, $R^3$-$R^4$ is selected from the group consisting of —$(CH_2)_{2-8}$—, —$O(CH_2)_{1-7}$—, —$O(CH_2)_{1-6}O$—, —$NH(CH_2)_{1-7}$—, and —$NH(CH_2)_{1-6}O$—. In particular instances of this fourth aspect, $R^3$-$R^4$ is selected from the group consisting of —$(CH_2)_2$—, —$(CH_2)_3$—, —$(CH_2)_4$—, —$O(CH_2)_2$—, —$O(CH_2)_3$—, —$O(CH_2)_4$—, —$O(CH_2)_{20}$—, —$O(CH_2)_3O$—, —$OCH_2CH(CH_3)CH_2O$—, —$O(CH_2)_4O$—, —$O(CH_2)_5O$—, —$NH(CH_2)_2$—, —$NH(CH_2)_3$—, and —$NH(CH_2)_3O$—. In this aspect, all other groups are as provided in the general formula (IV) of the fourth embodiment or in the first through third aspects described above.

In a fifth aspect of the fourth embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H, $CH_3$, and $CHF_2$. In this aspect, all other groups are as provided in the general formula (IV) of the fourth embodiment or in the first through fourth aspects described above.

In a sixth aspect of the fourth embodiment, each $X^1$ is independently selected from the group consisting of C=O, —$CH_2$—, —CHF—, and —$CF_2$—. In instances of this aspect, $X^1$ is selected from the group consisting of C=O and —$CH_2$—. In particular instances of this aspect, $X^1$ is C=O.

In this embodiment, all other groups are as provided in the general formula (IV) of the fourth embodiment or in the first through fifth aspects described above.

In a seventh aspect of the fourth embodiment, each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle. In a first instance of this aspect, each $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular occurrences of this first instance, each $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, each $X^2$ is $CHR^8CHR^8$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on different carbon atoms are taken together, along with the atoms to which they are attached, to form a 3- to 6-membered fused ring. In particular occurrences of this second instance, each $X^2$ is $CHR^8CHR^8$, where each $R^8$ is independently selected from the group consisting of H and $C_1$-$C_3$ alkyl, and optionally the 2 $R^8$ on different carbon atoms are taken together, along with the atoms to which they are attached, to form a 3- to 6-membered fused ring. In a third instance of this aspect, each $X^2$ is $CH_2C(R^8)_2$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on a single carbon atom are taken together, along with the atoms to which they are attached, to form a 3- to 6-membered spirocycle. In particular occurrences of this third instance, each $X^2$ is $CH_2C(R^8)_2$, where each $R^8$ is independently selected from the group consisting of H and $C_1$-$C_3$ alkyl, and optionally the 2 $R^8$ on a single carbon atom are taken together, along with the atoms to which they are attached, to form a 3- to 6-membered spirocycle. In this aspect, all other groups are as provided in the general formula (IV) of the fourth embodiment or in the first through sixth aspects described above.

In an eighth aspect of the fourth embodiment, each $X^3$ is independently selected from the group consisting of $COOR^6$, $C(O)SR^6$, $C(S)OR^6$,

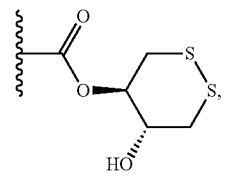 [SMILES: *C(=O)O[C@H]1CSSC[C@@H]1O]

$SO_2R^6$, $C(O)N(R^9)_2$, and CN. In instances of this aspect, each $X^3$ is independently selected from the group consisting of $COOR^6$,

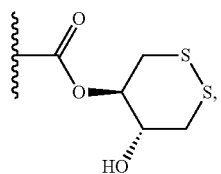 [SMILES: *C(=O)O[C@H]1CSSC[C@@H]1O]

$SO_2R^6$, $C(O)N(R^9)_2$, and CN. In particular instances of this aspect, each $X^3$ is independently selected from the group consisting of $COOR^6$, $C(O)N(R^9)_2$, and CN. In even more particular instances of this aspect, each $X^3$ is independently selected from the group consisting of COOH, $COOCH_3$, $CONH_2$, and CN. In this aspect, all other groups are as provided in the general formula (IV) of the fourth embodiment or in the first through seventh aspects described above.

In a ninth aspect of the fourth embodiment, each $R^9$ is independently selected from the group consisting of H, $COOR^6$, and $SO_2R^6$. In instances of this aspect, each $R^9$ is independently H. In this aspect, all other groups are as provided in the general formula (IV) of the fourth embodiment or in the first through eighth aspects described above.

A tenth aspect of the fourth embodiment relates to a pharmaceutical composition, said pharmaceutical composition comprising (a) a compound according to general formula (IV) of the fourth embodiment or the first through ninth aspects described above or a pharmaceutically acceptable salt thereof; and (b) a pharmaceutically acceptable carrier.

An eleventh aspect of the fourth embodiment relates to methods of inducing an immune response in a patient in need of therapy, comprising administering a therapeutically effective amount of a compound according to general formula (IV) of the fourth embodiment or the first through ninth aspects described above described above or a pharmaceutically acceptable salt thereof to the patient.

A twelfth aspect of the fourth embodiment relates to methods of inducing an immune response in a patient in need of therapy, comprising administering a therapeutically effective amount of a composition according to the tenth aspect described above to the patient.

A thirteenth aspect of the fourth embodiment relates to methods of inducing a STING-dependent type I interferon production in a patient in need of therapy, comprising administering a therapeutically effective amount of a compound according to general formula (IV) of the fourth embodiment above or the first through ninth aspects described above or a pharmaceutically acceptable salt thereof to the patient.

A fourteenth aspect of the fourth embodiment relates to methods of inducing STING-dependent type I interferon production in a patient in need of therapy, comprising administering a therapeutically effective amount of a composition according to the tenth aspect described above to the patient.

A fifteenth aspect of the fourth embodiment relates to methods of inducing STING-dependent cytokine production in a patient in need of therapy, comprising administering a therapeutically effective amount of a compound according to general formula (IV) of the fourth embodiment above or the first through ninth aspects described above or a pharmaceutically acceptable salt thereof to the patient.

A sixteenth aspect of the fourth embodiment relates to methods of inducing a STING-dependent cytokine production in a patient in need of therapy, comprising administering a therapeutically effective amount of a composition according to the tenth aspect described above to the patient.

A seventeenth aspect of the fourth embodiment relates to methods of treating a cell proliferation disorder in a patient in need of therapy, comprising administering a therapeutically effective amount of a compound of general formula (IV), or a pharmaceutically acceptable salt thereof to the patient. In instances of this seventeenth aspect of the fourth embodiment, the cell proliferation disorder is cancer.

An eighteenth aspect of the fourth embodiment relates to methods of treating a cell proliferation disorder in a patient in need of therapy, said method comprising administering a therapeutically effective amount of a composition according to the eleventh aspect described above to the patient. In instances of this eighteenth aspect of the fourth embodiment, the cell proliferation disorder is cancer.

In each aspect of the fourth embodiment described herein, variables $R^1$, $R^2$, $R^3$, $R^4$, $R^6$, $R^8$, $R^9$, A, $X^1$, $X^2$, and $X^3$ of general formula (IV) of the fourth embodiment, and the various aspects and instances thereof, are each independently selected from each other, with the proviso that at least one of $R^1$, $R^2$, $R^3$, $R^4$, $R^6$, $R^8$, and $R^9$ is not H.

A fifth embodiment relates to compounds of general formula (V):

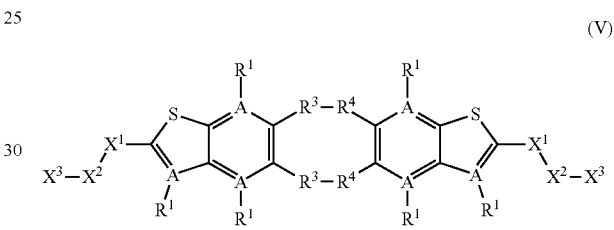

or a pharmaceutically acceptable salt thereof, wherein each $A-R^1$ is independently selected from the group consisting of $C—R^1$ and N; each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); each $X^1$ is independently selected from the group consisting of C=O, —$CH_2$—, —CHF—, and —$CF_2$—; each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle; each $X^3$ is independently selected from the group consisting of $COOR^6$, $C(O)SR^6$, $C(S)OR^6$,

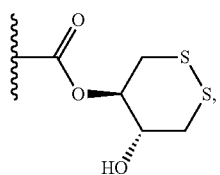

$SO_2R^6$, $C(O)N(R^9)_2$, and CN; and each $R^9$ is independently selected from the group consisting of H, $COOR^6$, and $SO_2R^6$.

In a first aspect of the fifth embodiment, each $A-R^1$ is independently selected from the group consisting of $C-R^1$ and N. In particular instances of this aspect, each

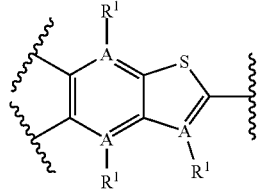

is independently selected from the group consisting of

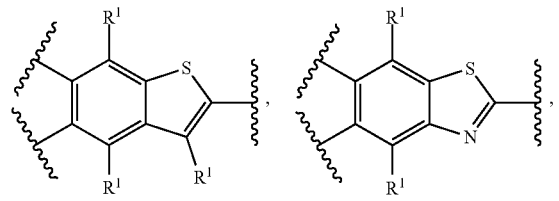

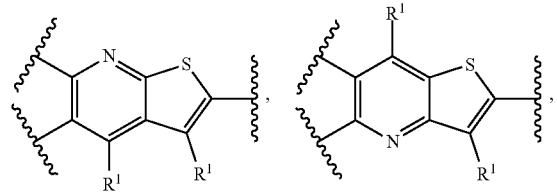

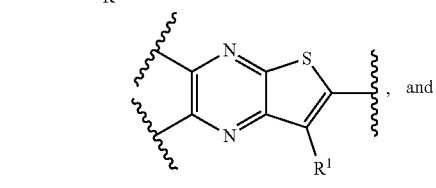

In more particular instances of this aspect, each

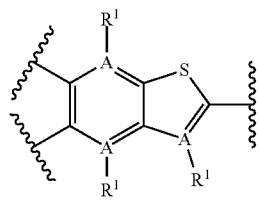

is independently selected from the group consisting of

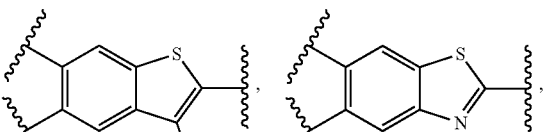

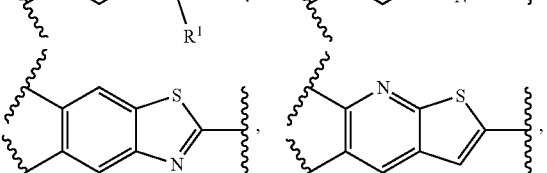

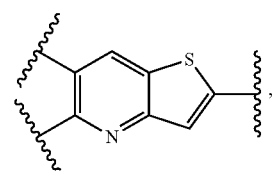

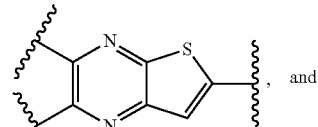, and

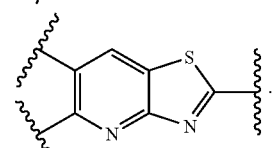.

In this aspect, all other groups are as provided in the general formula (V) of the fifth embodiment above.

In a second aspect of the fifth embodiment, each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, each $R^1$ is independently selected from the group consisting of H, halogen, $C_1$-$C_3$ alkyl, and $C_1$-$C_3$ haloalkyl. In particular instances of this aspect, each $R^1$ is independently selected from the group consisting of H and halogen. In more particular instances of this aspect, each $R^1$ is independently selected from the group consisting of H and F. In this aspect, all other groups are as provided in the general formula (V) of the fifth embodiment above or in the first aspect above.

In a third aspect of the fifth embodiment, $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene). In instances of this fourth aspect, $R^3$-$R^4$ is selected from the group consisting of —$(CH_2)_{2-8}$—, —$O(CH_2)_{1-7}$—, —$O(CH_2)_{1-6}O$—, —$NH(CH_2)_{1-7}$—, and —$NH(CH_2)_{1-6}O$—. In particular instances of this fourth aspect, $R^3$-$R^4$ is selected from the group consisting of —$(CH_2)_2$—, —$(CH_2)_3$—, —$(CH_2)_4$—, —$O(CH_2)_2$—, —$O(CH_2)_3$—, —$O(CH_2)_4$—, —$O(CH_2)_{20}$—, —$O(CH_2)_3O$—, —$OCH_2CH(CH_3)CH_2O$—, —$O(CH_2)_4O$—, —$O(CH_2)_5O$—, —$NH(CH_2)_2$—, —$NH(CH_2)_3$—, and —$NH(CH_2)_3O$—. In this aspect, all other groups are as provided in the general formula (V) of the fifth embodiment or in the first and second aspects described above.

In a fourth aspect of the fifth embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H, $CH_3$, and $CHF_2$. In this aspect, all other groups are as provided in the general formula (V) of the fifth embodiment or in the first through third aspects described above.

In a fifth aspect of the fifth embodiment, each $X^1$ is independently selected from the group consisting of C=O, —$CH_2$—, —CHF—, and —$CF_2$—. In instances of this aspect, $X^1$ is selected from the group consisting of C=O and —$CH_2$—. In particular instances of this aspect, $X^1$ is C=O.

In this embodiment, all other groups are as provided in the general formula (V) of the fifth embodiment or in the first through fourth aspects described above.

In a sixth aspect of the fifth embodiment, each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle. In a first instance of this aspect, each $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular occurrences of this first instance, each $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, each $X^2$ is $CHR^8CHR^8$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on different carbon atoms are taken together, along with the atoms to which they are attached, to form a 3- to 6-membered fused ring. In particular occurrences of this second instance, each $X^2$ is $CHR^8CHR^8$, where each $R^8$ is independently selected from the group consisting of H and $C_1$-$C_3$ alkyl, and optionally the 2 $R^8$ on different carbon atoms are taken together, along with the atoms to which they are attached, to form a 3- to 6-membered fused ring. In a third instance of this aspect, each $X^2$ is $CH_2C(R^8)_2$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on a single carbon atom are taken together, along with the atoms to which they are attached, to form a 3- to 6-membered spirocycle. In particular occurrences of this third instance, each $X^2$ is $CH_2C(R^8)_2$, where each $R^8$ is independently selected from the group consisting of H and $C_1$-$C_3$ alkyl, and optionally the 2 $R^8$ on a single carbon atom are taken together, along with the atoms to which they are attached, to form a 3- to 6-membered spirocycle. In this aspect, all other groups are as provided in the general formula (V) of the fifth embodiment or in the first through fifth aspects described above.

In a seventh aspect of the fifth embodiment, each $X^3$ is independently selected from the group consisting of $COOR^6$, $C(O)SR^6$, $C(S)OR^6$,

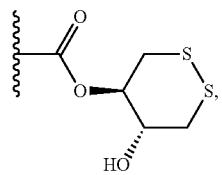 [SMILES: *C(=O)O[C@H]1CSSC[C@@H]1O]

$SO_2R^6$, $C(O)N(R^9)_2$, and CN. In instances of this aspect, each $X^3$ is independently selected from the group consisting of $COOR^6$,

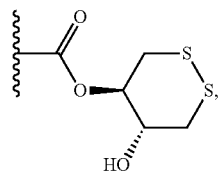 [SMILES: *C(=O)O[C@H]1CSSC[C@@H]1O]

$SO_2R^6$, $C(O)N(R^9)_2$, and CN. In particular instances of this aspect, each $X^3$ is independently selected from the group consisting of $COOR^6$, $C(O)N(R^9)_2$, and CN. In even more particular instances of this aspect, each $X^3$ is independently selected from the group consisting of COOH, $COOCH_3$, $CONH_2$, and CN. In this aspect, all other groups are as provided in the general formula (V) of the fifth embodiment or in the first through sixth aspects described above.

In an eighth aspect of the fifth embodiment, each $R^9$ is independently selected from the group consisting of H, $COOR^6$, and $SO_2R^6$. In instances of this aspect, each $R^9$ is independently H. In this aspect, all other groups are as provided in the general formula (V) of the fifth embodiment or in the first through seventh aspects described above.

A ninth aspect of the fifth embodiment relates to a pharmaceutical composition, said pharmaceutical composition comprising (a) a compound according to general formula (V) of the fifth embodiment or the first through eighth aspects described above or a pharmaceutically acceptable salt thereof; and (b) a pharmaceutically acceptable carrier.

A tenth aspect of the fifth embodiment relates to methods of inducing an immune response in a patient in need of therapy, comprising administering a therapeutically effective amount of a compound according to general formula (V) of the fifth embodiment or the first through eighth aspects described above described above or a pharmaceutically acceptable salt thereof to the patient.

An eleventh aspect of the fifth embodiment relates to methods of inducing an immune response in a patient in need of therapy, comprising administering a therapeutically effective amount of a composition according to the ninth aspect described above to the patient.

A twelfth aspect of the fifth embodiment relates to methods of inducing a STING-dependent type I interferon production in a patient in need of therapy, comprising administering a therapeutically effective amount of a compound according to general formula (V) of the fifth embodiment above or the first through eighth aspects described above or a pharmaceutically acceptable salt thereof to the patient.

A thirteenth aspect of the fifth embodiment relates to methods of inducing STING-dependent type I interferon production in a patient in need of therapy, comprising administering a therapeutically effective amount of a composition according to the ninth aspect described above to the patient.

A fourteenth aspect of the fifth embodiment relates to methods of inducing STING-dependent cytokine production in a patient in need of therapy, comprising administering a therapeutically effective amount of a compound according to general formula (V) of the fifth embodiment above or the first through eighth aspects described above or a pharmaceutically acceptable salt thereof to the patient.

A fifteenth aspect of the fifth embodiment relates to methods of inducing a STING-dependent cytokine production in a patient in need of therapy, comprising administering a therapeutically effective amount of a composition according to the ninth aspect described above to the patient.

A sixteenth aspect of the fifth embodiment relates to methods of treating a cell proliferation disorder in a patient in need of therapy, comprising administering a therapeutically effective amount of a compound according to general formula (V) of the fifth embodiment above or the first through eighth aspects described above or a pharmaceutically acceptable salt thereof to the patient. In instances of this sixteenth aspect of the fifth embodiment, the cell proliferation disorder is cancer.

A seventeenth aspect of the fifth embodiment relates to methods of treating a cell proliferation disorder in a patient in need of therapy, said method comprising administering a therapeutically effective amount of a composition according to the ninth aspect described above to the patient. In instances of this seventeenth aspect of the fifth embodiment, the cell proliferation disorder is cancer.

In each aspect of the fifth embodiment described herein, variables $R^1$, $R^2$, $R^3$, $R^4$, $R^6$, $R^8$, $R^9$, A, $X^1$, $X^2$, and $X^3$ of general formula (V) of the fifth embodiment, and the various aspects and instances thereof, are each independently selected from each other, with the proviso that at least one of $R^1$, $R^2$, $R^3$, $R^4$, $R^6$, $R^8$, and $R^9$ is not H.

A sixth embodiment relates to compounds of general formula (VI):

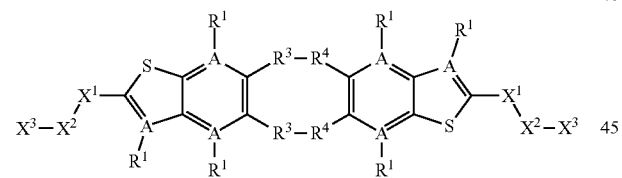
(VI)

or a pharmaceutically acceptable salt thereof, wherein each A-$R^1$ is independently selected from the group consisting of C—$R^1$ and N; each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$; $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene); each $R^6$ is independently selected from the group consisting of H, $C_1$-$C_6$ alkyl, and $C_1$-$C_6$ haloalkyl; each $X^1$ is independently selected from the group consisting of C=O, —$CH_2$—, —CHF—, and —$CF_2$—; each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle; each $X^3$ is independently selected from the group consisting of $COOR^6$, C(O)$SR^6$, C(S)$OR^6$,

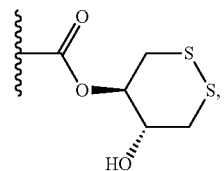 [SMILES: *C(=O)O[C@H]1CSSC[C@@H]1O]

$SO_2R^6$, C(O)N($R^9$)$_2$, and CN; and each $R^9$ is independently selected from the group consisting of H, $COOR^6$, and $SO_2R^6$.

In a first aspect of the sixth embodiment, each A-$R^1$ is independently selected from the group consisting of C—$R^1$ and N. In particular instances of this aspect, each

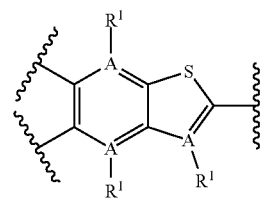

is independently selected from the group consisting of

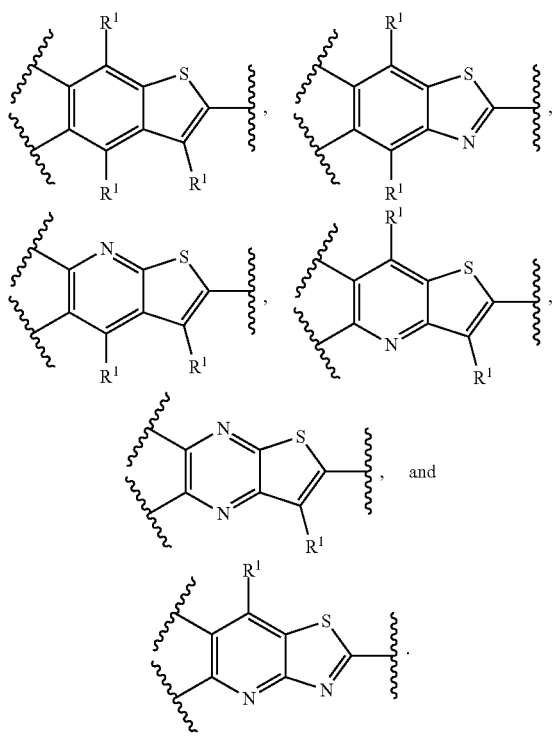

In more particular instances of this aspect, each

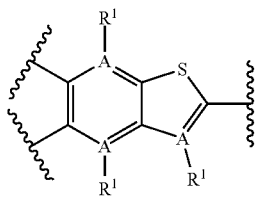

is independently selected from the group consisting of

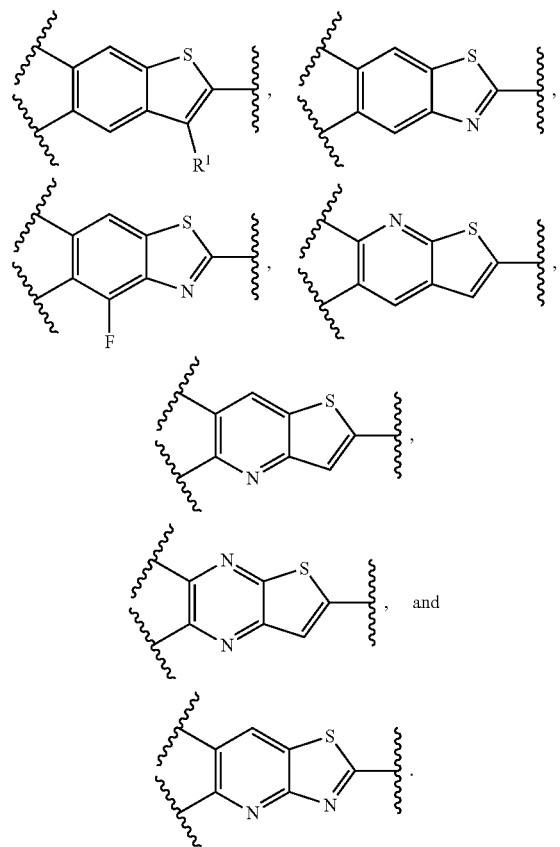

In this aspect, all other groups are as provided in the general formula (VI) of the sixth embodiment above.

In a second aspect of the sixth embodiment, each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$. In instances of this aspect, each $R^1$ is independently selected from the group consisting of H, halogen, $C_1$-$C_3$ alkyl, and $C_1$-$C_3$ haloalkyl. In particular instances of this aspect, each $R^1$ is independently selected from the group consisting of H and halogen. In more particular instances of this aspect, each $R^1$ is independently selected from the group consisting of H and F. In this aspect, all other groups are as provided in the general formula (VI) of the sixth embodiment above or in the first aspect above.

In a third aspect of the sixth embodiment, $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene). In instances of this fourth aspect, $R^3$-$R^4$ is selected from the group consisting of —$(CH_2)_{2-8}$—, —$O(CH_2)_{1-7}$—, —$O(CH_2)_{1-6}O$—, —$NH(CH_2)_{1-7}$—, and —$NH(CH_2)_{1-6}O$—. In particular instances of this fourth aspect, $R^3$-$R^4$ is selected from the group consisting of —$(CH_2)_2$—, —$(CH_2)_3$—, —$(CH_2)_4$—, —$O(CH_2)_2$—, —$O(CH_2)_3$—, —$O(CH_2)_4$—, —$O(CH_2)_{20}$—, —$O(CH_2)_3O$—, —$OCH_2CH(CH_3)CH_2O$—, —$O(CH_2)_4O$—, —$O(CH_2)_5O$—, —$NH(CH_2)_2$—, —$NH(CH_2)_3$—, and —$NH(CH_2)_3O$—. In this aspect, all other groups are as provided in the general formula (VI) of the sixth embodiment or in the first and second aspects described above.

In a fourth aspect of the sixth embodiment, each $R^6$ is independently selected from the group consisting of H, $C_1$-$C_6$ alkyl, and $C_1$-$C_6$ haloalkyl. In instances of this aspect, each $R^6$ is independently selected from the group consisting of H, $C_1$-$C_3$ alkyl, and $C_1$-$C_3$ haloalkyl. In particular instances of this aspect, each $R^6$ is independently selected from the group consisting of H, $CH_3$, and $CHF_2$. In this aspect, all other groups are as provided in the general formula (VI) of the sixth embodiment or in the first through third aspects described above.

In a fifth aspect of the sixth embodiment, each $X^1$ is independently selected from the group consisting of C=O, —$CH_2$—, —CHF—, and —$CF_2$—. In instances of this aspect, $X^1$ is selected from the group consisting of C=O and —$CH_2$—. In particular instances of this aspect, $X^1$ is C=O.

In this embodiment, all other groups are as provided in the general formula (VI) of the sixth embodiment or in the first through fourth aspects described above In a sixth aspect of the sixth embodiment, each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$; optionally 2 $R^8$ on different carbon atoms may be taken together, along with the atoms to which they are attached, to form a 3- to 6-membered fused ring; and optionally 2 $R^8$ on a single carbon atom may be taken together, along with the atom to which they are attached, to form a 3- to 6-membered spirocycle. In a first instance of this aspect, each $X^2$ is $CH_2CHR^8$, where $R^8$ is selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl. In particular occurrences of this first instance, each $X^2$ is $CH_2CHR^8$, wherein $R^8$ is selected from the group consisting of H, $CH_3$, $CH_2OH$, $CH_2CH_3$, $CH_2CH_2CH_3$, $CH(CH_3)_2$, $CH_2OCH_3$, and cyclopropyl. In a second instance of this aspect, each $X^2$ is $CHR^8CHR^8$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on different carbon atoms are taken together, along with the atoms to which they are attached, to form a 3- to 6-membered fused ring. In particular occurrences of this second instance, each $X^2$ is $CHR^8CHR^8$, where each $R^8$ is independently selected from the group consisting of H and $C_1$-$C_3$ alkyl, and optionally the 2 $R^8$ on different carbon atoms are taken together, along with the atoms to which they are attached, to form a 3- to 6-membered fused ring. In a third instance of this aspect, each $X^2$ is $CH_2C(R^8)_2$, where each $R^8$ is independently selected from the group consisting of H, $C_1$-$C_3$ alkyl, $C_1$-$C_3$ alkyl substituted by OH, $C_1$-$C_3$ alkyl substituted by $OC_1$-$C_3$ alkyl, and $C_3$-$C_6$ cycloalkyl, and optionally the 2 $R^8$ on a single carbon atom are taken together, along with the atoms to which they are attached, to form a 3- to 6-membered spirocycle. In particular occurrences of this third instance, each $X^2$ is $CH_2C(R^8)_2$, where each $R^8$ is independently selected from the group consisting of H and $C_1$-$C_3$ alkyl, and optionally the 2 $R^8$ on a single carbon atom are taken together, along with the atoms to which they are attached, to form a 3- to 6-membered spirocycle. In this aspect, all other groups are as provided in the general formula (VI) of the sixth embodiment or in the first through fifth aspects described above.

In a seventh aspect of the sixth embodiment, each $X^3$ is independently selected from the group consisting of $COOR^6$, $C(O)SR^6$, $C(S)OR^6$,

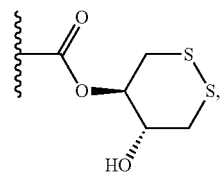 [SMILES: *C(=O)O[C@H]1CSSC[C@@H]1O]

$SO_2R^6$, $C(O)N(R^9)_2$, and CN. In instances of this aspect, each $X^3$ is independently selected from the group consisting of $COOR^6$,

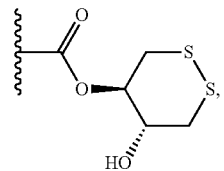 [SMILES: *C(=O)O[C@H]1CSSC[C@@H]1O]

$SO_2R^6$, $C(O)N(R^9)_2$, and CN. In particular instances of this aspect, each $X^3$ is independently selected from the group consisting of $COOR^6$, $C(O)N(R^9)_2$, and CN. In even more particular instances of this aspect, each $X^3$ is independently selected from the group consisting of COOH, $COOCH_3$, $CONH_2$, and CN. In this aspect, all other groups are as provided in the general formula (VI) of the sixth embodiment or in the first through sixth aspects described above.

In an eighth aspect of the sixth embodiment, each $R^9$ is independently selected from the group consisting of H, $COOR^6$, and $SO_2R^6$. In instances of this aspect, each $R^9$ is independently H. In this aspect, all other groups are as provided in the general formula (V) of the fifth embodiment or in the first through seventh aspects described above.

A ninth aspect of the sixth embodiment relates to a pharmaceutical composition, said pharmaceutical composition comprising (a) a compound according to general formula (VI) of the sixth embodiment or the first through eighth aspects described above or a pharmaceutically acceptable salt thereof; and (b) a pharmaceutically acceptable carrier.

A tenth aspect of the sixth embodiment relates to methods of inducing an immune response in a patient in need of therapy, comprising administering a therapeutically effective amount of a compound according to general formula (VI) of the sixth embodiment or the first through eighth aspects described above described above or a pharmaceutically acceptable salt thereof to the patient.

An eleventh aspect of the sixth embodiment relates to methods of inducing an immune response in a patient in need of therapy, comprising administering a therapeutically effective amount of a composition according to the ninth aspect described above to the patient.

A twelfth aspect of the sixth embodiment relates to methods of inducing a STING-dependent type I interferon production in a patient in need of therapy, comprising administering a therapeutically effective amount of a compound according to general formula (VI) of the sixth embodiment above or the first through eighth aspects described above or a pharmaceutically acceptable salt thereof to the patient.

A thirteenth aspect of the sixth embodiment relates to methods of inducing STING-dependent type I interferon production in a patient in need of therapy, comprising administering a therapeutically effective amount of a composition according to the ninth aspect described above to the patient.

A fourteenth aspect of the sixth embodiment relates to methods of inducing STING-dependent cytokine production in a patient in need of therapy, comprising administering a therapeutically effective amount of a compound according to general formula (VI) of the sixth embodiment above or the first through eighth aspects described above or a pharmaceutically acceptable salt thereof to the patient.

A fifteenth aspect of the sixth embodiment relates to methods of inducing a STING-dependent cytokine production in a patient in need of therapy, comprising administering a therapeutically effective amount of a composition according to the ninth aspect described above to the patient.

A sixteenth aspect of the sixth embodiment relates to methods of treating a cell proliferation disorder in a patient in need of therapy, comprising administering a therapeutically effective amount of a compound according to general formula (VI) of the sixth embodiment above or the first through eighth aspects described above or a pharmaceutically acceptable salt thereof to the patient. In instances of this sixteenth aspect of the sixth embodiment, the cell proliferation disorder is cancer.

A seventeenth aspect of the sixth embodiment relates to methods of treating a cell proliferation disorder in a patient in need of therapy, said method comprising administering a therapeutically effective amount of a composition according to the ninth aspect described above to the patient. In instances of this seventeenth aspect of the sixth embodiment, the cell proliferation disorder is cancer.

In each aspect of the sixth embodiment described herein, variables $R^1$, $R^2$, $R^3$, $R^4$, $R^6$, $R^8$, $R^9$, A, $X^1$, $X^2$, and $X^3$ of general formula (VI) of the sixth embodiment, and the various aspects and instances thereof, are each independently selected from each other, with the proviso that at least one of $R^1$, $R^2$, $R^3$, $R^4$, $R^6$, $R^8$, and $R^9$ is not H.

A seventh embodiment relates to a compound selected from the group consisting of
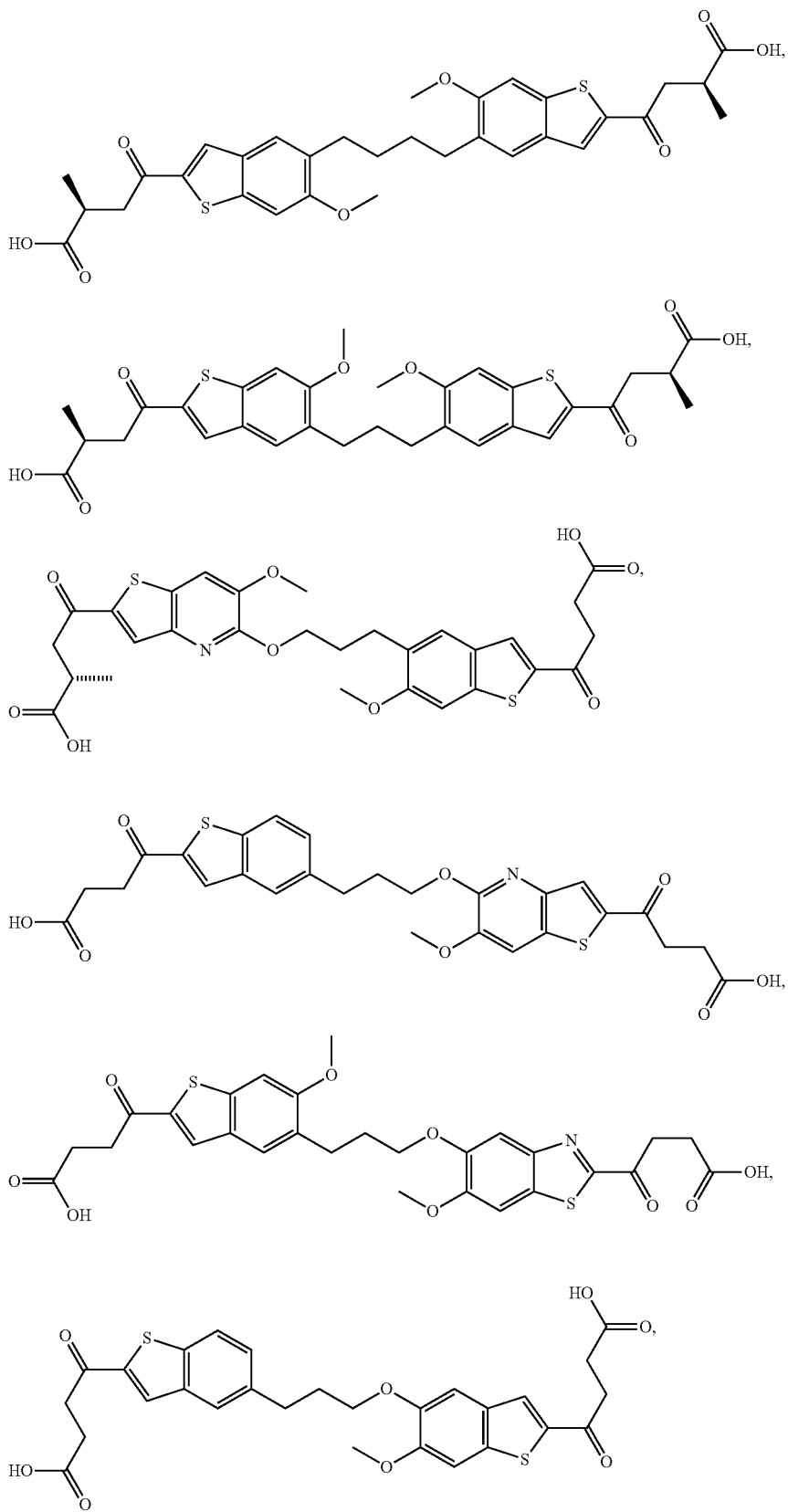

-continued
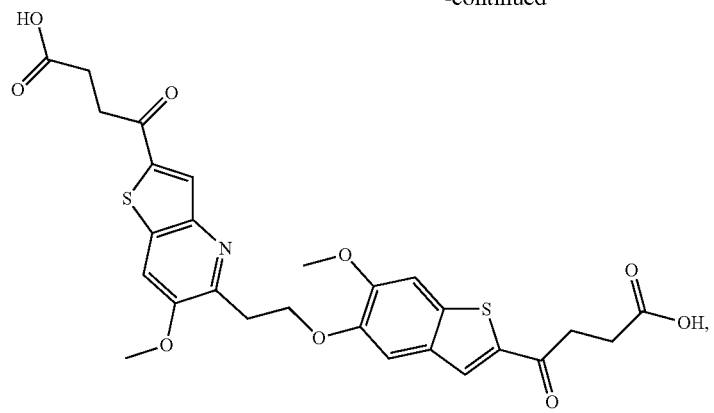
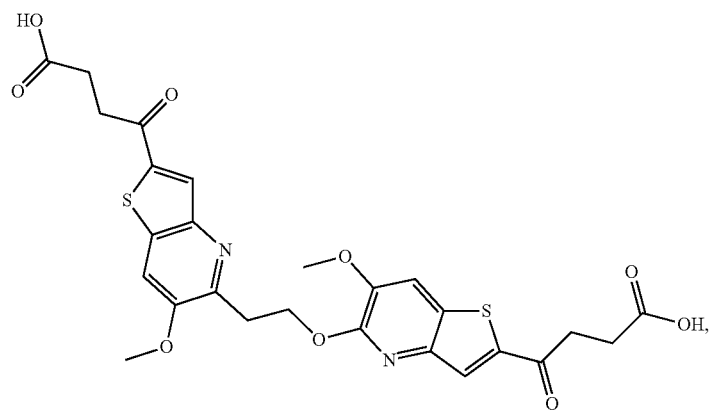
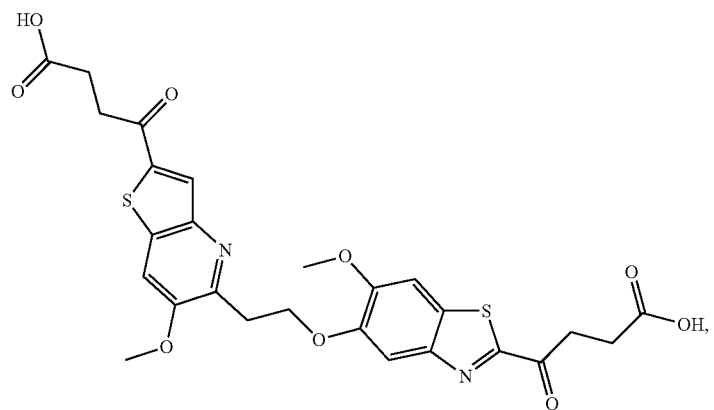
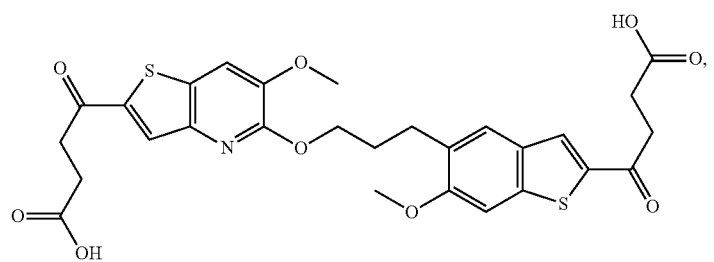

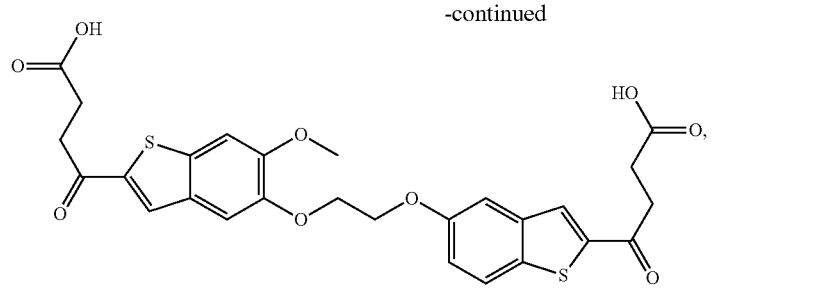
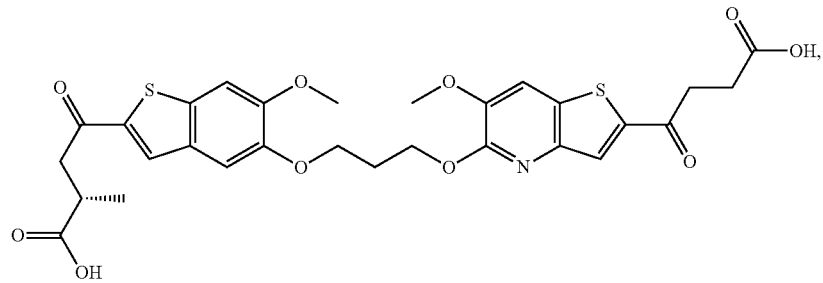
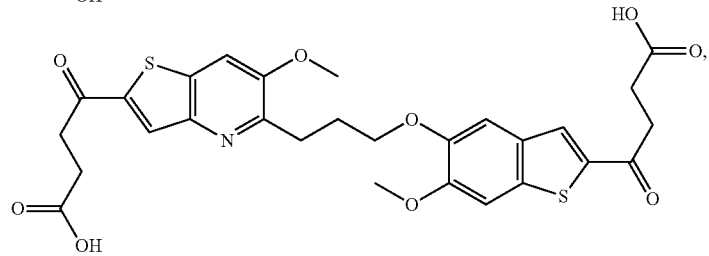
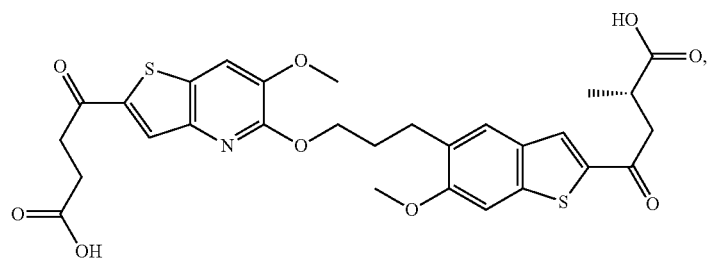
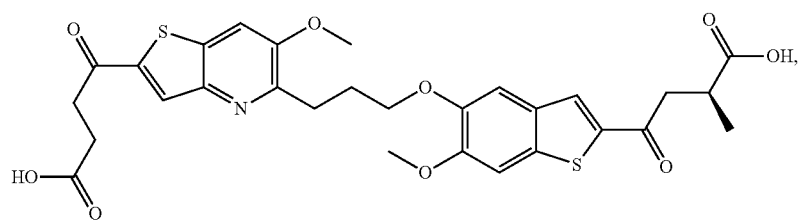
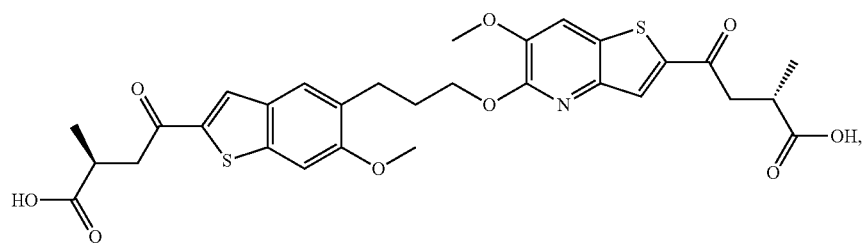

-continued
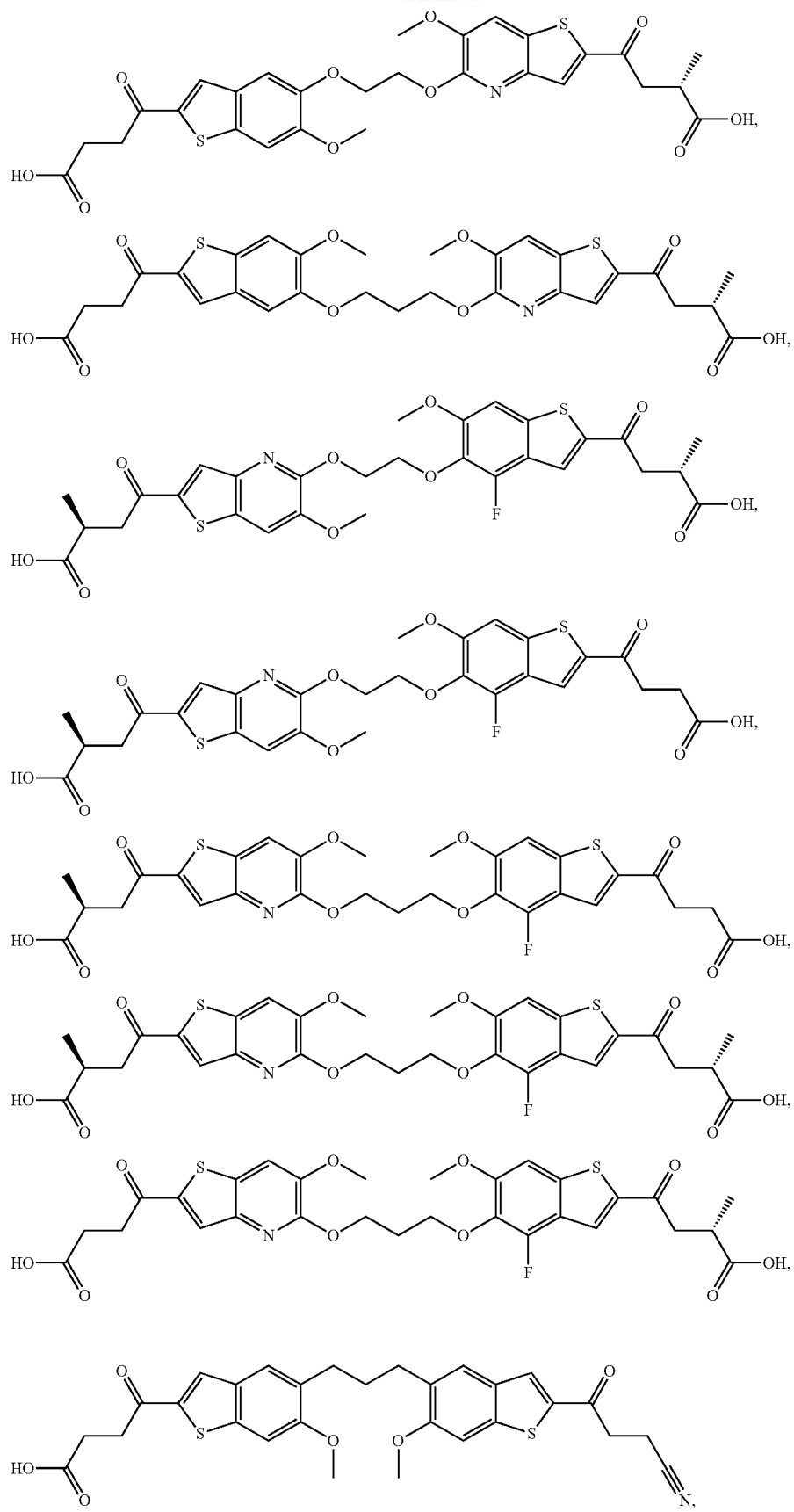

-continued
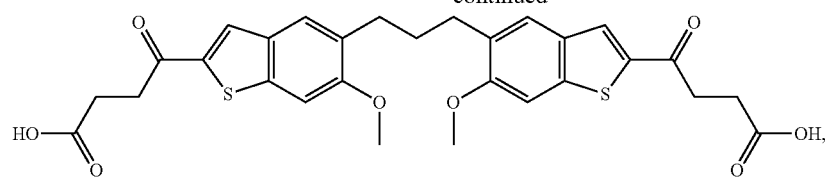
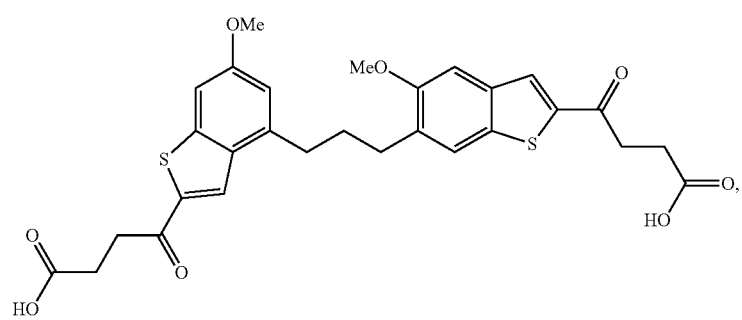
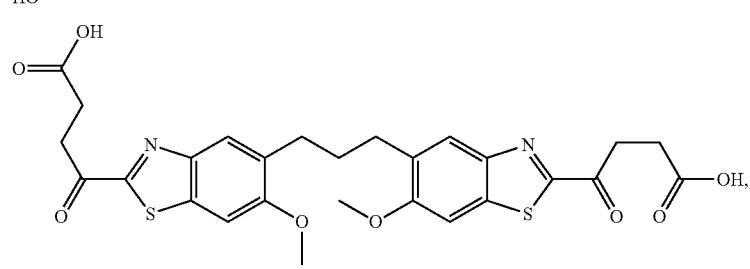
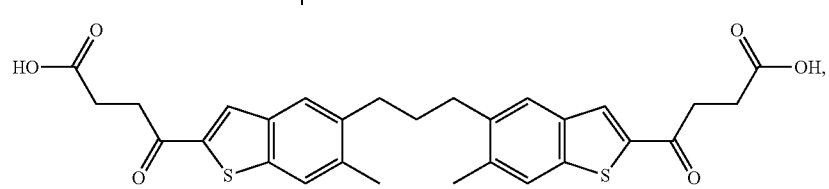
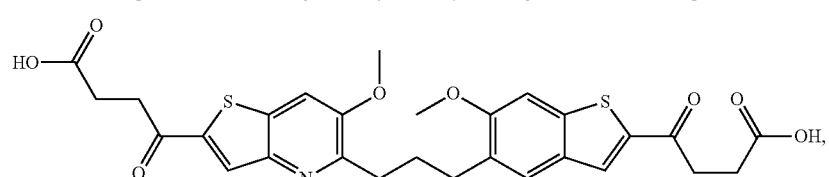
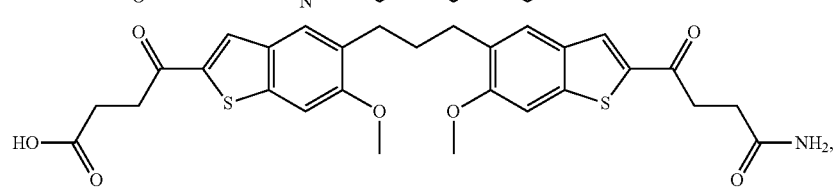
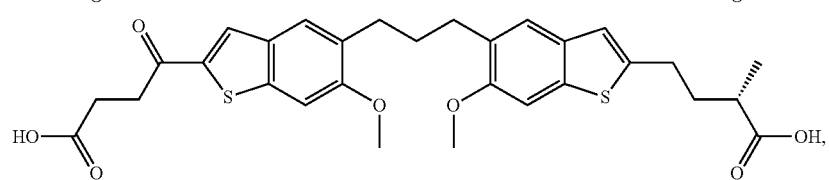
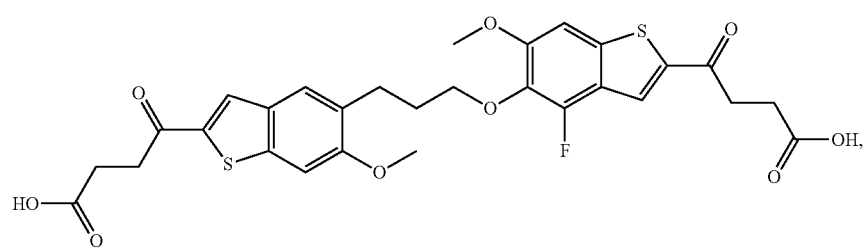

-continued
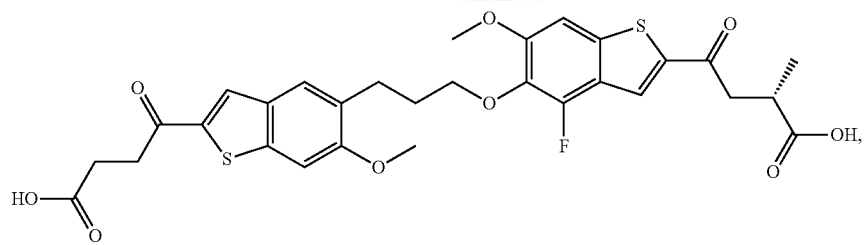
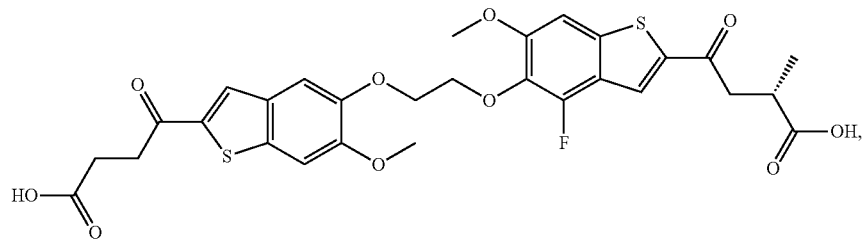
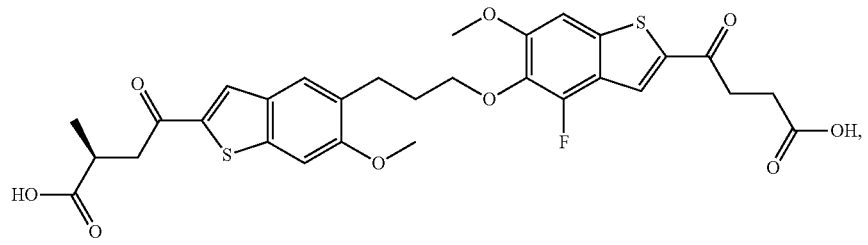
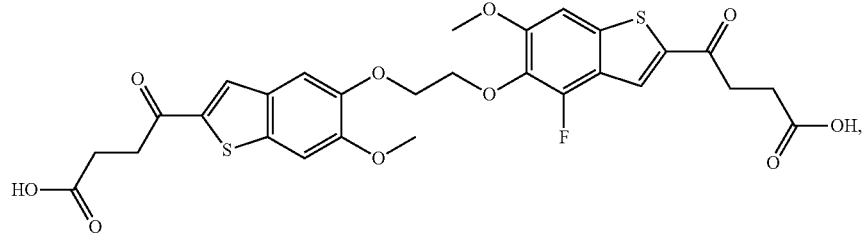
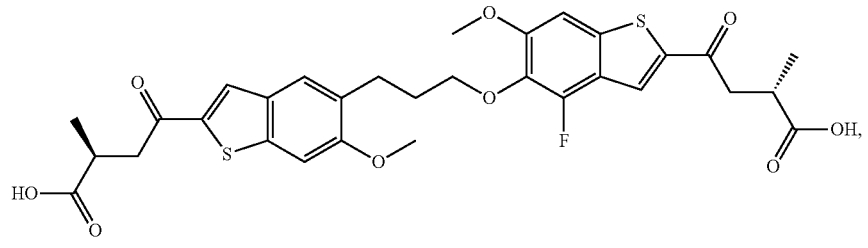
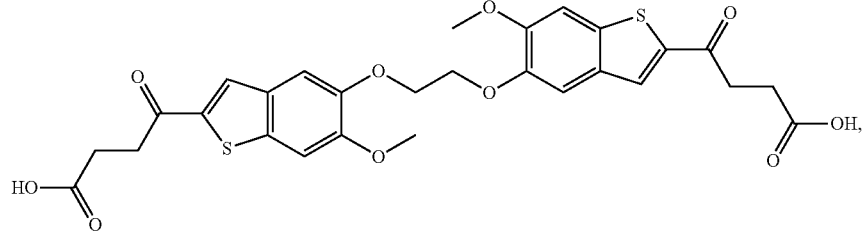
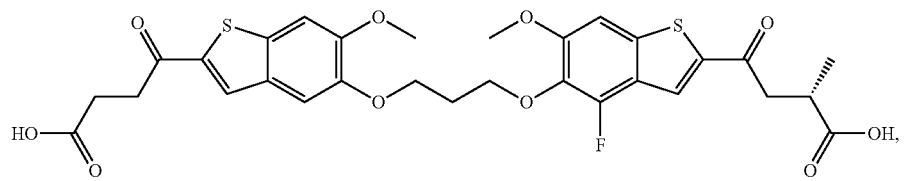

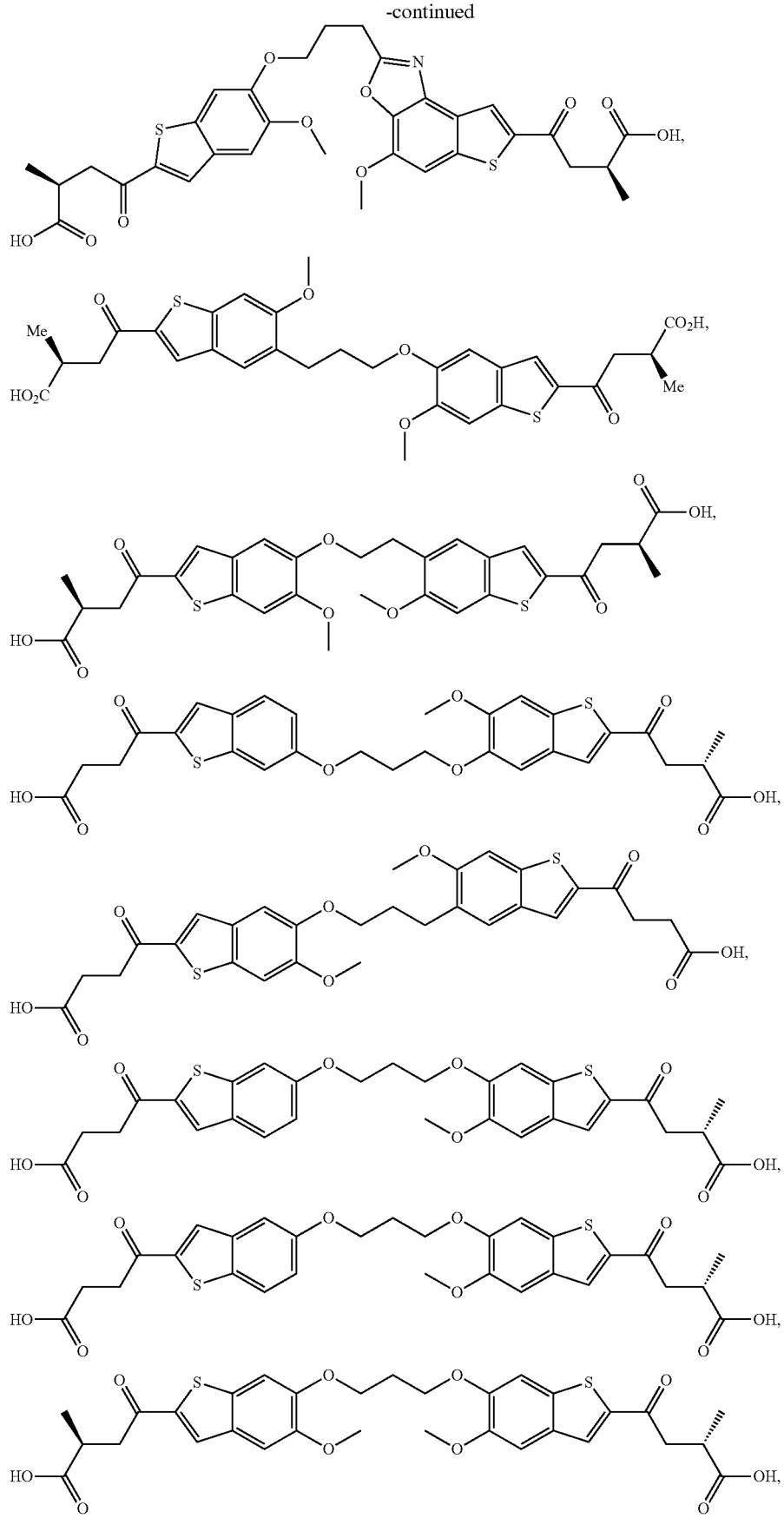

-continued
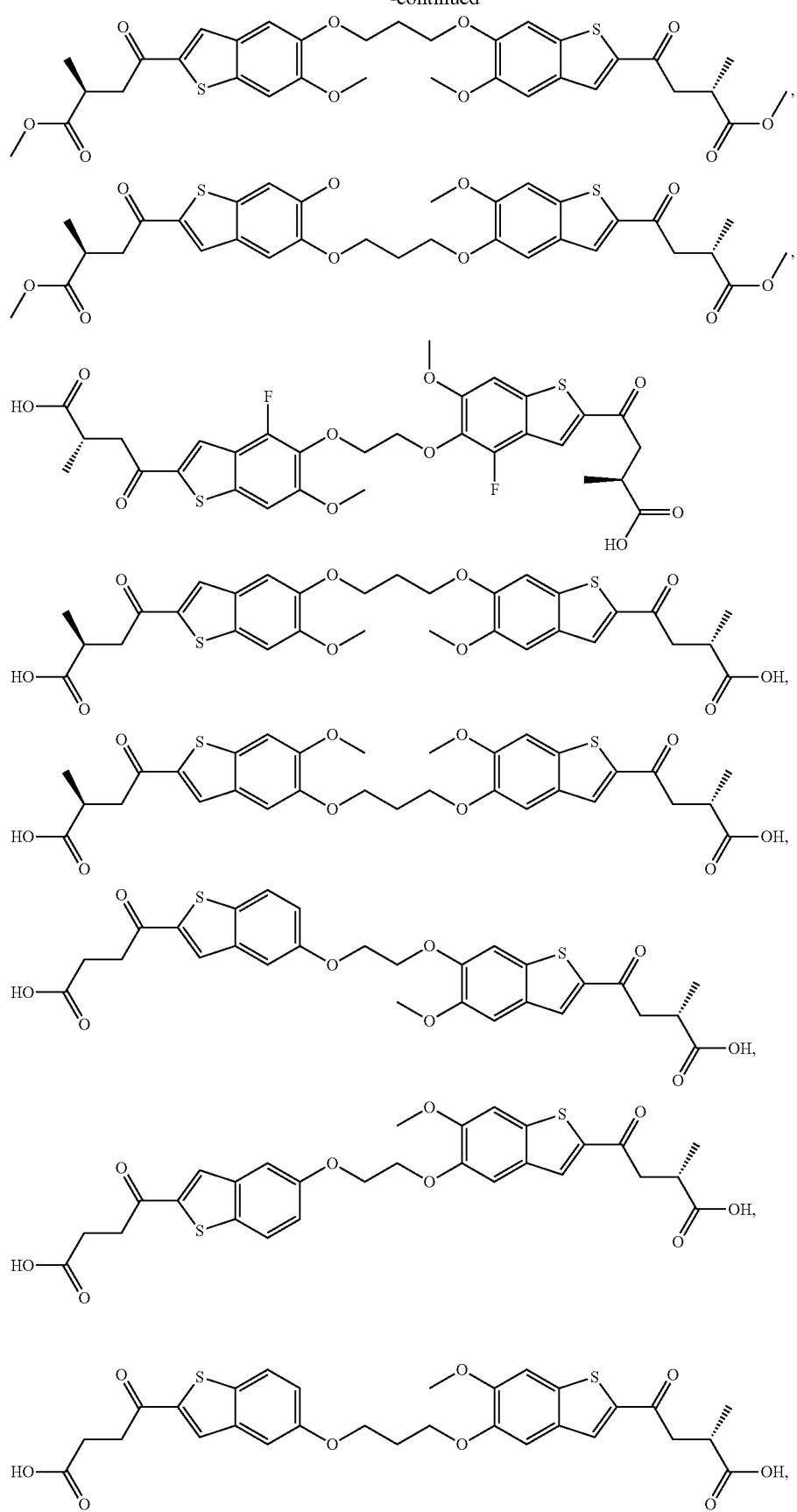

-continued
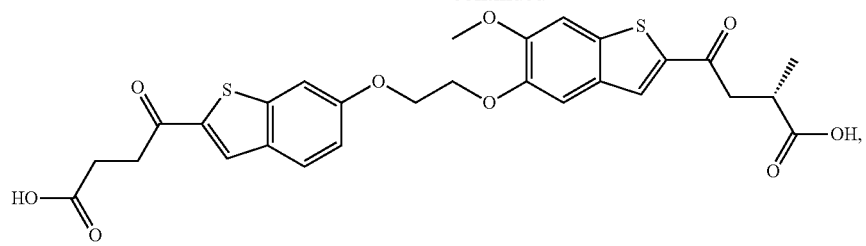
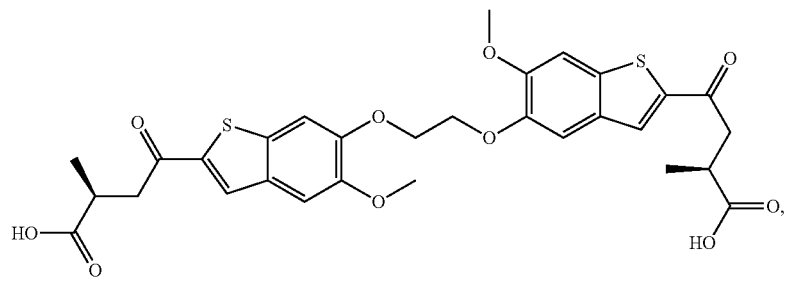
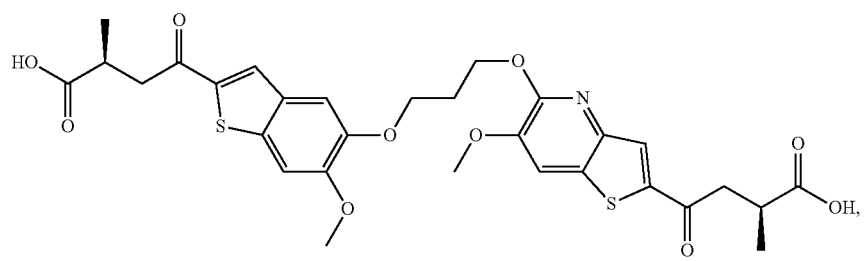
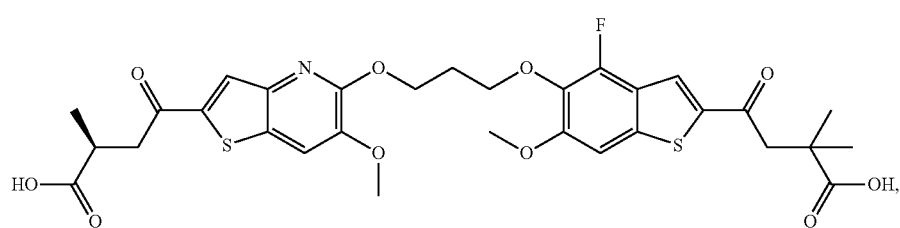
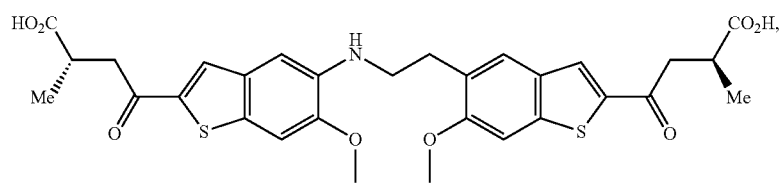
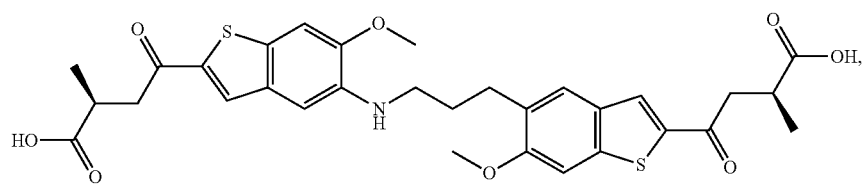
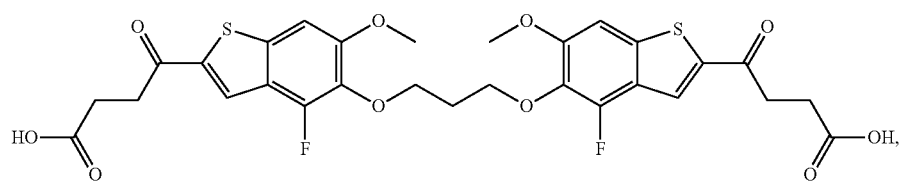

-continued
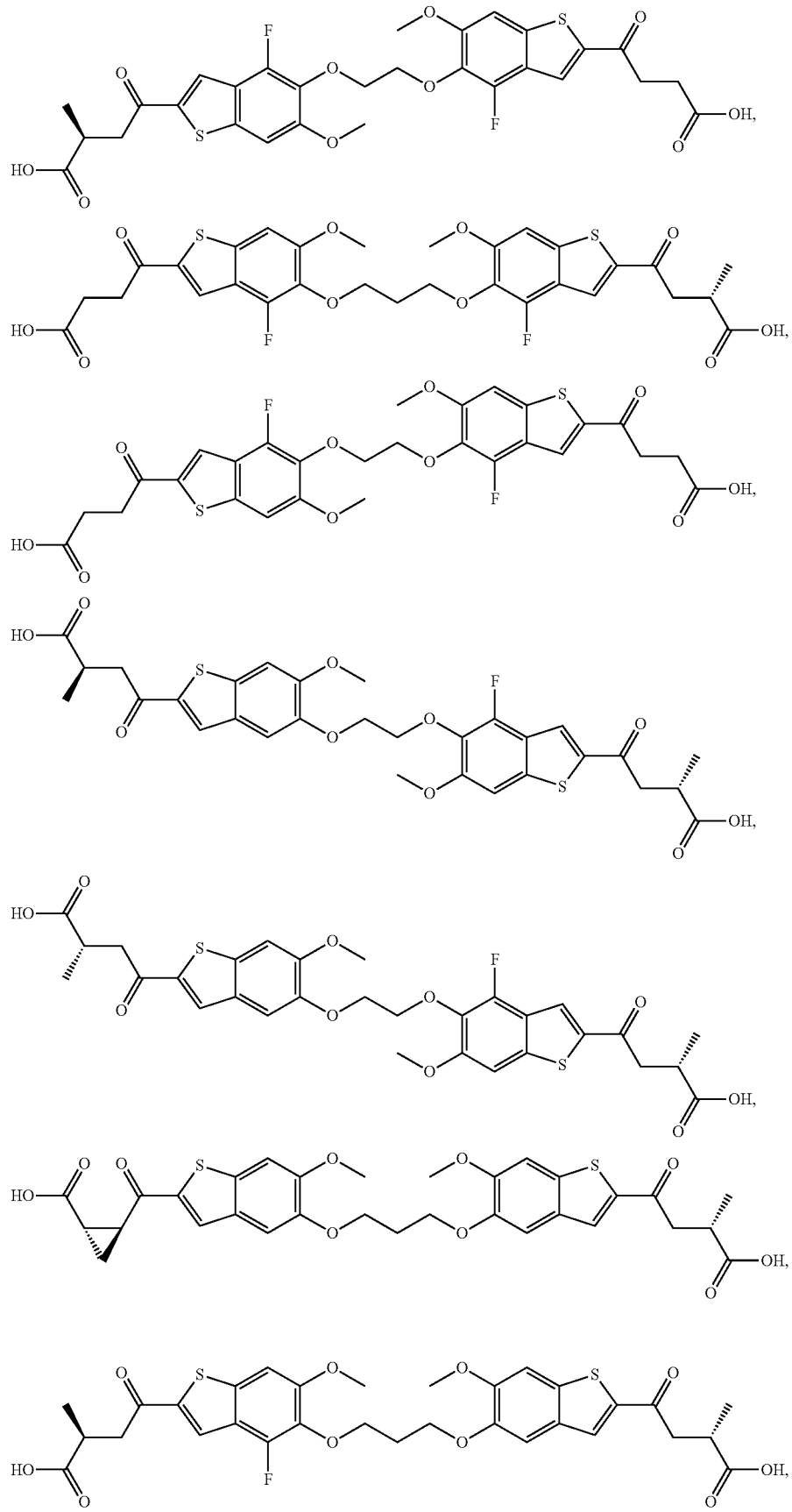

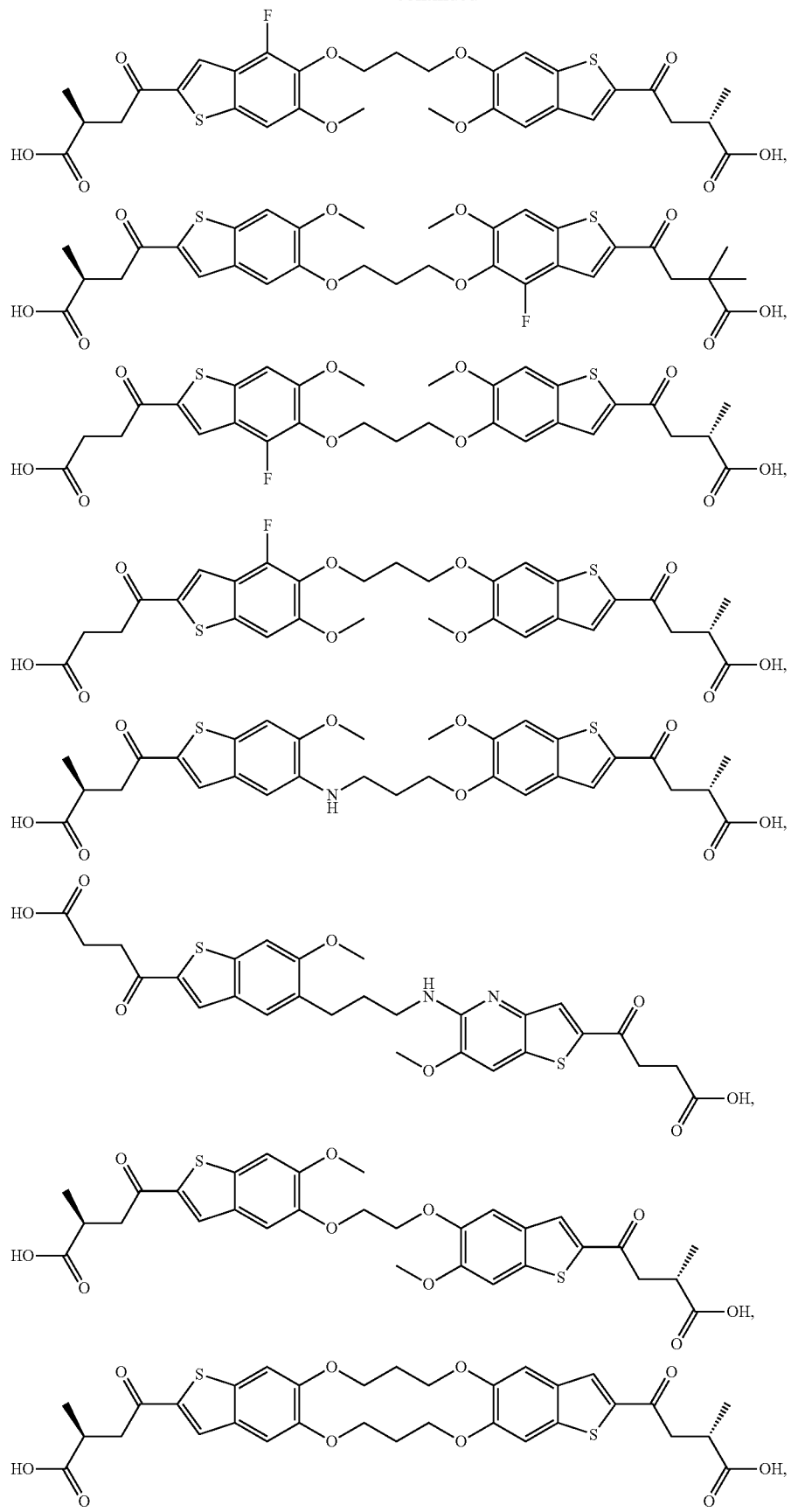

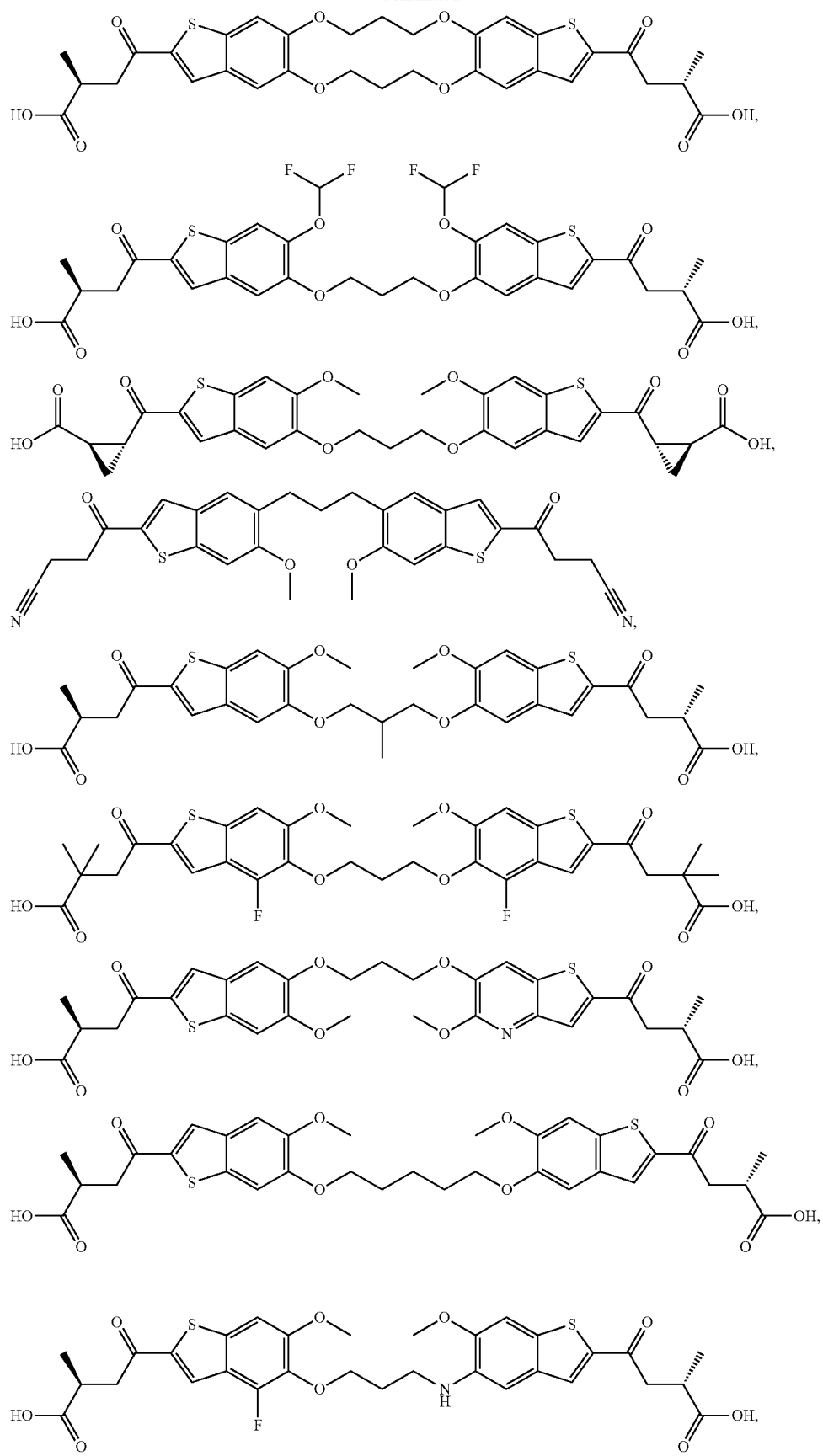

-continued
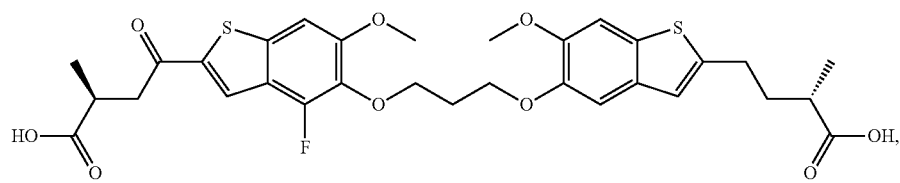
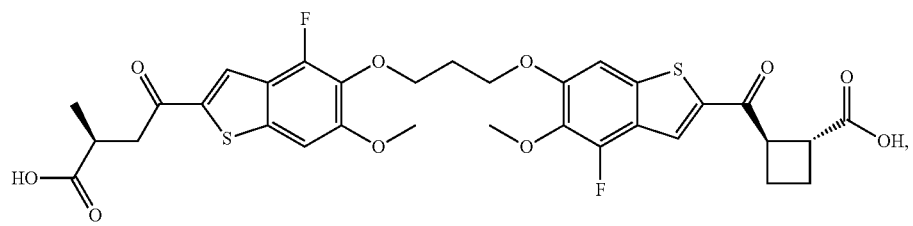
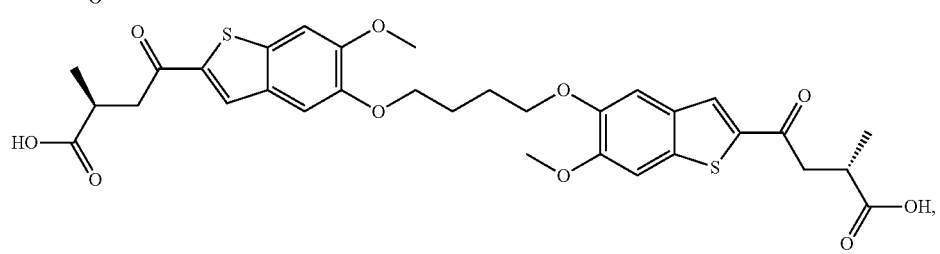
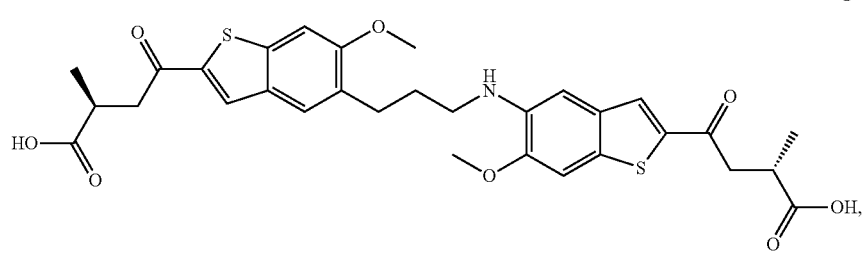
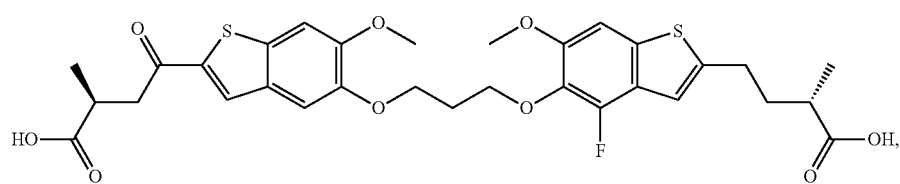
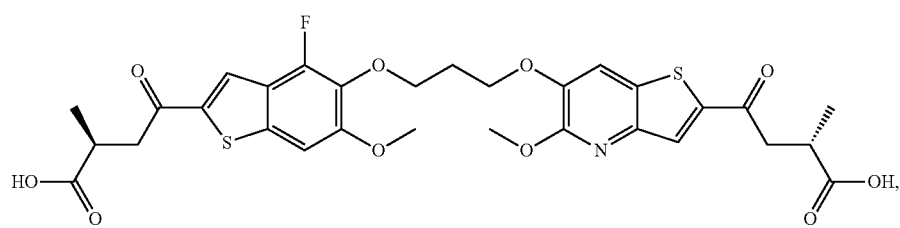
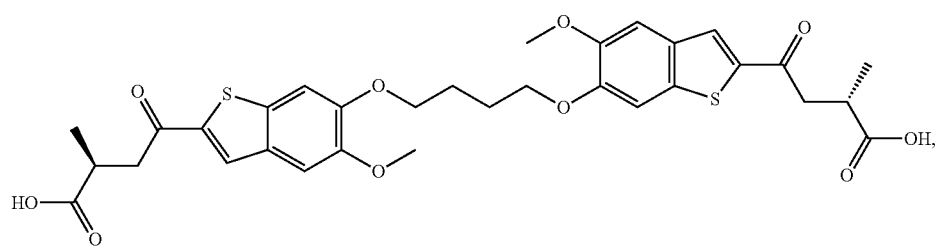

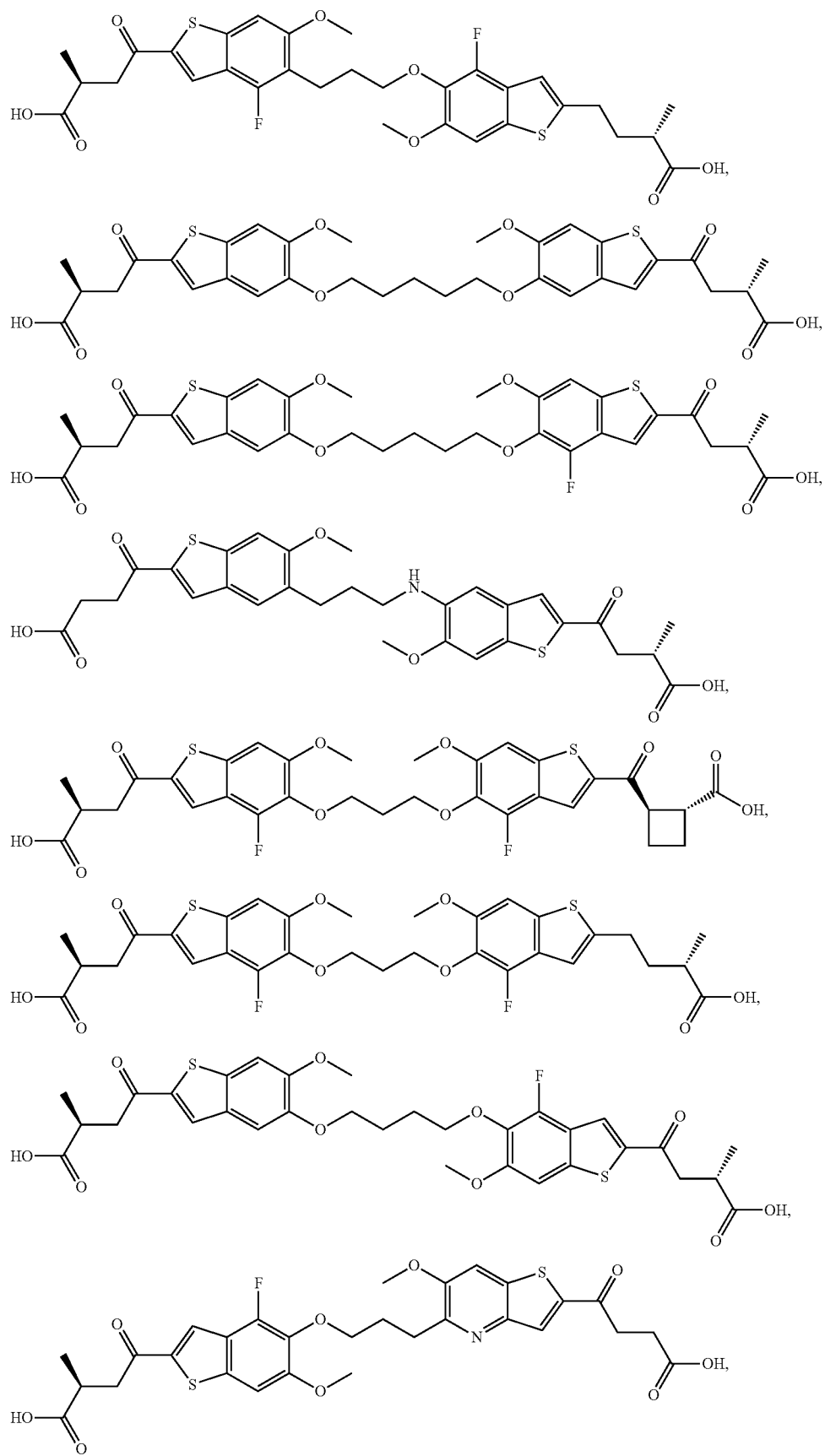

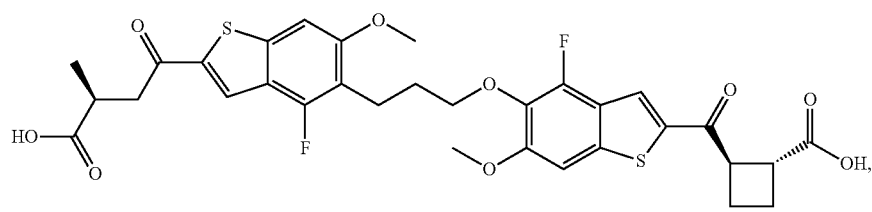
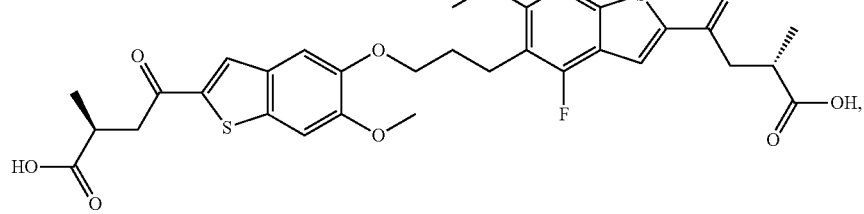
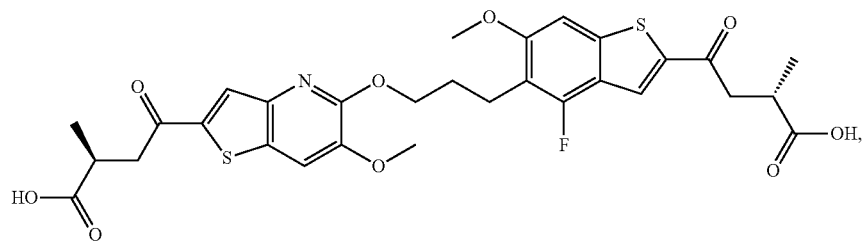
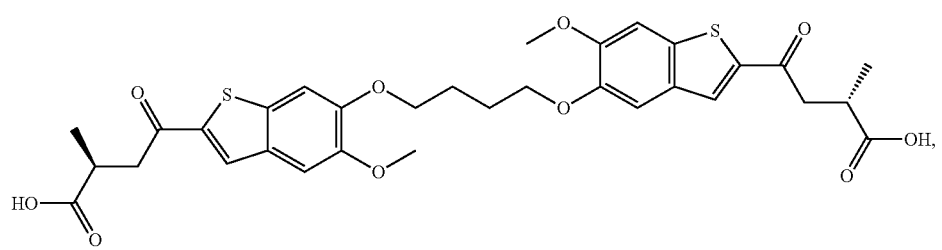
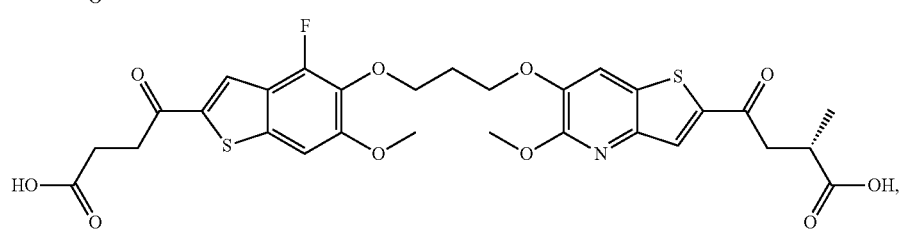
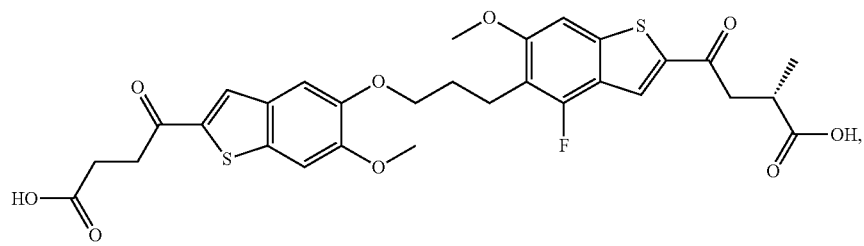
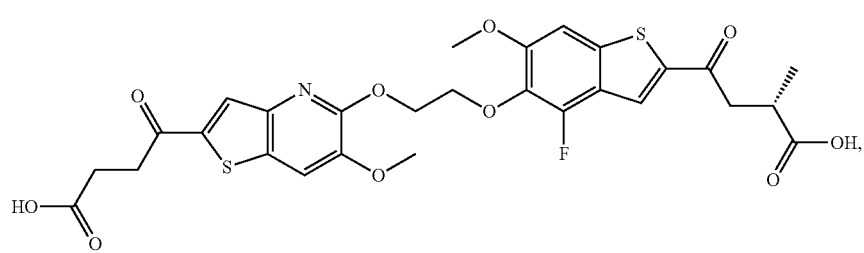

-continued
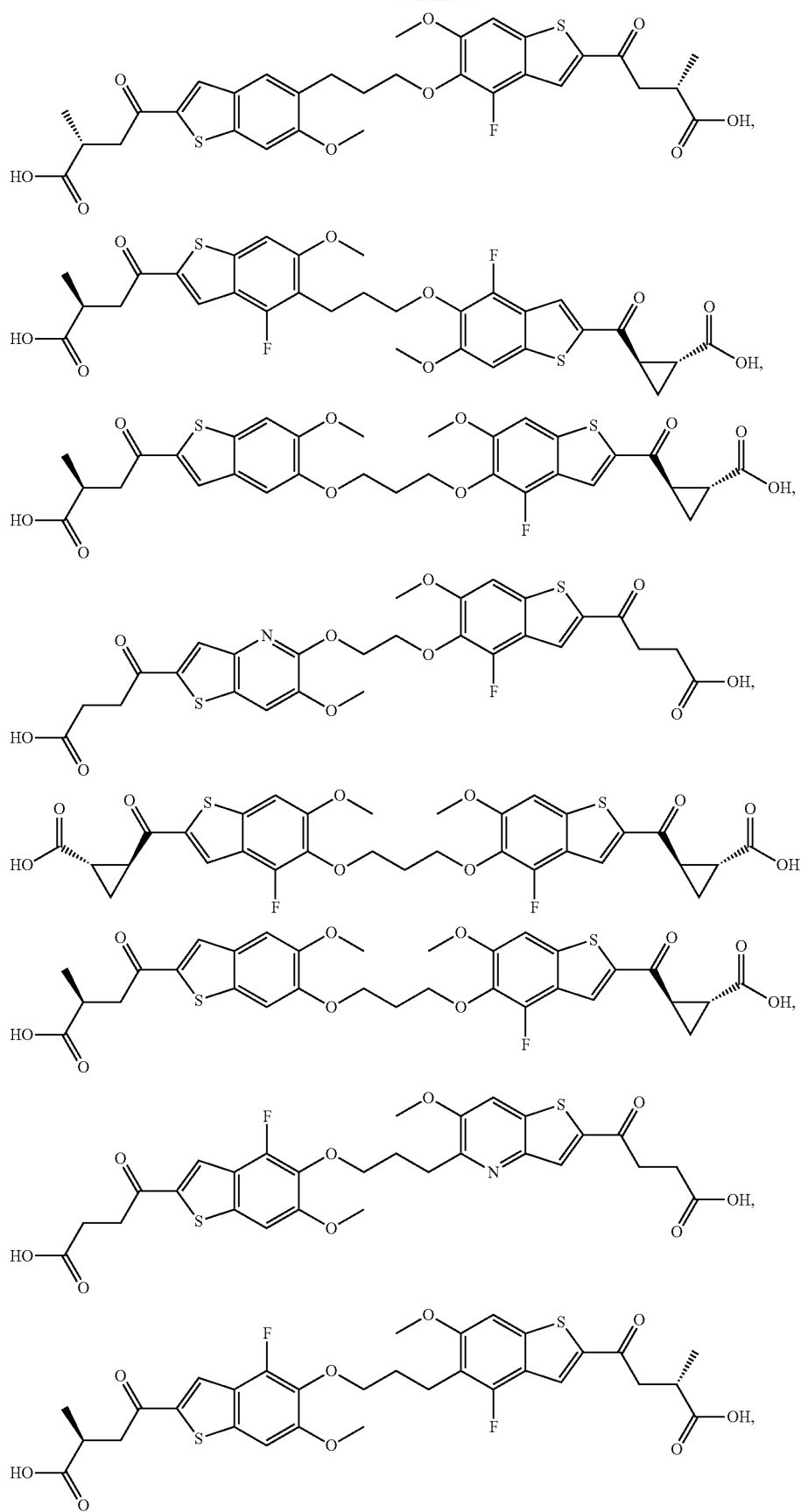

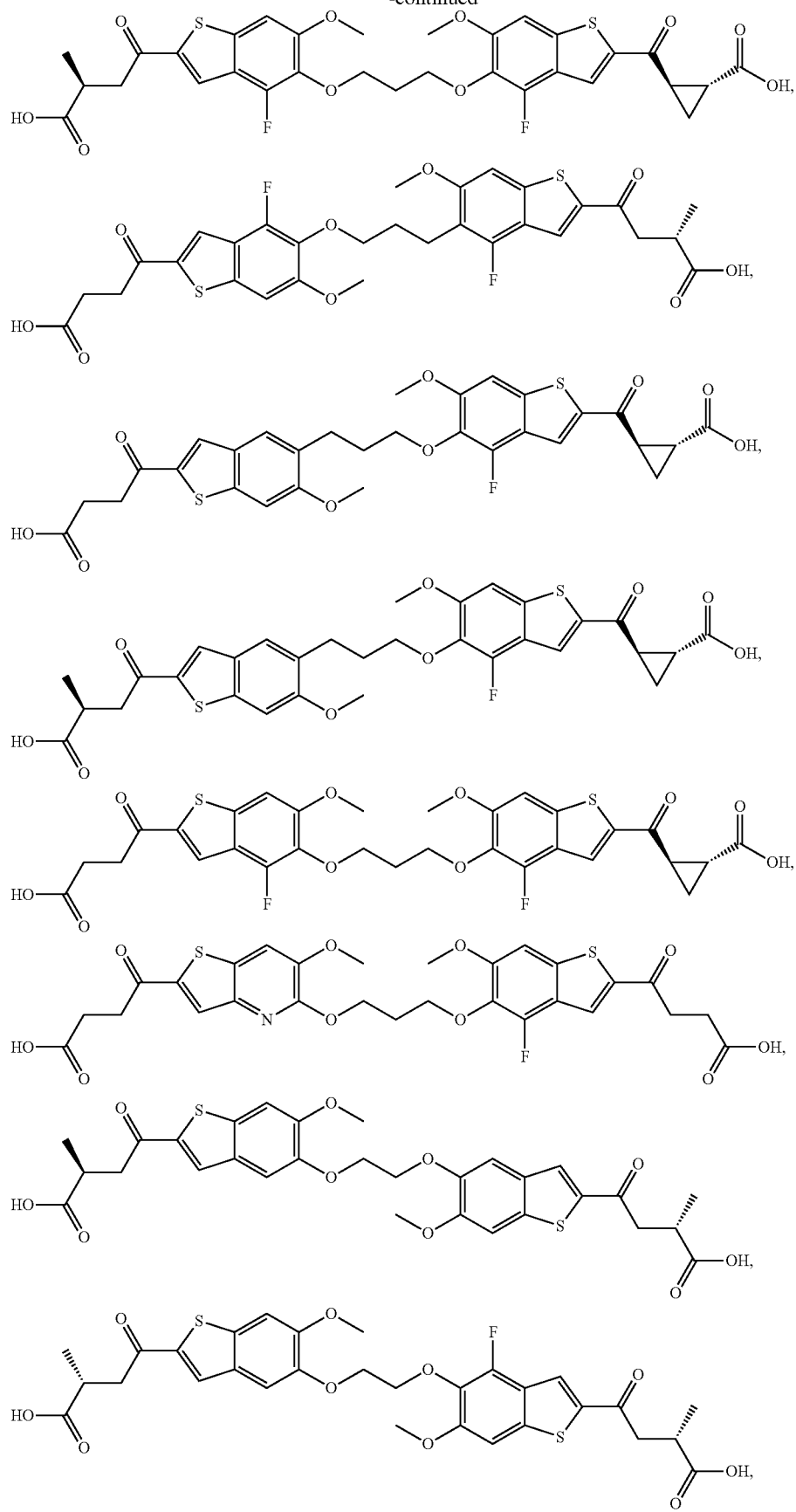

-continued
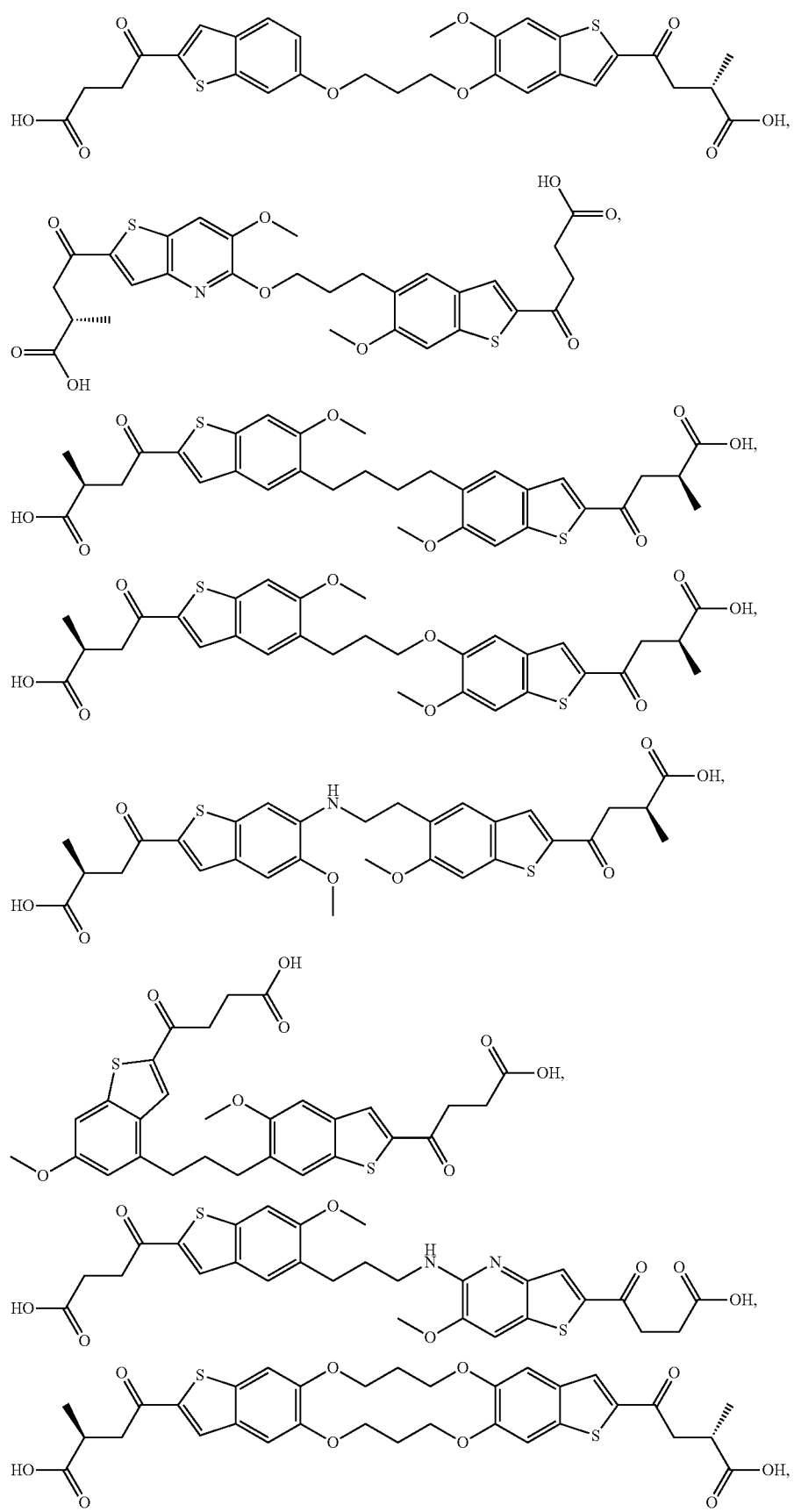

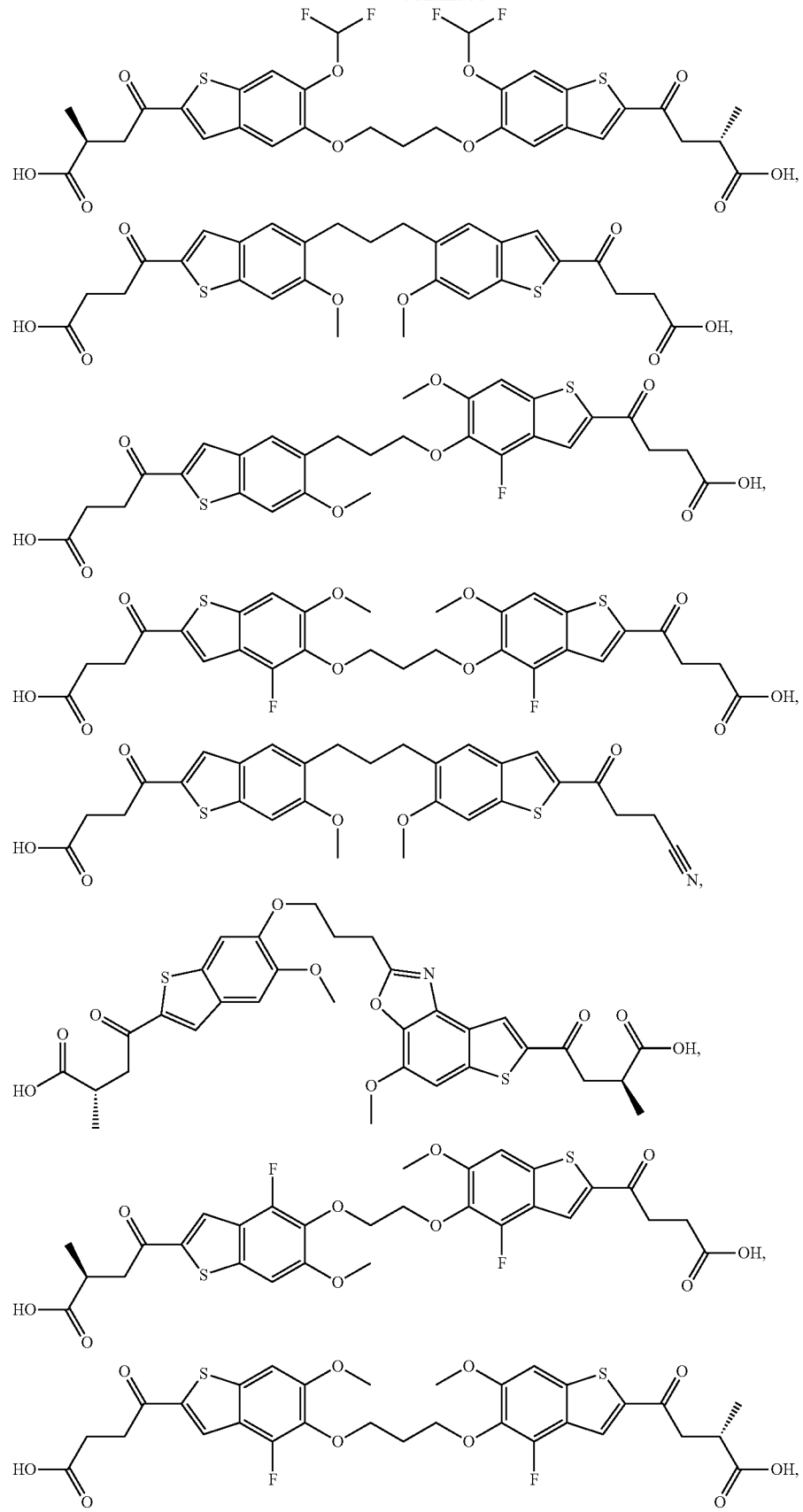

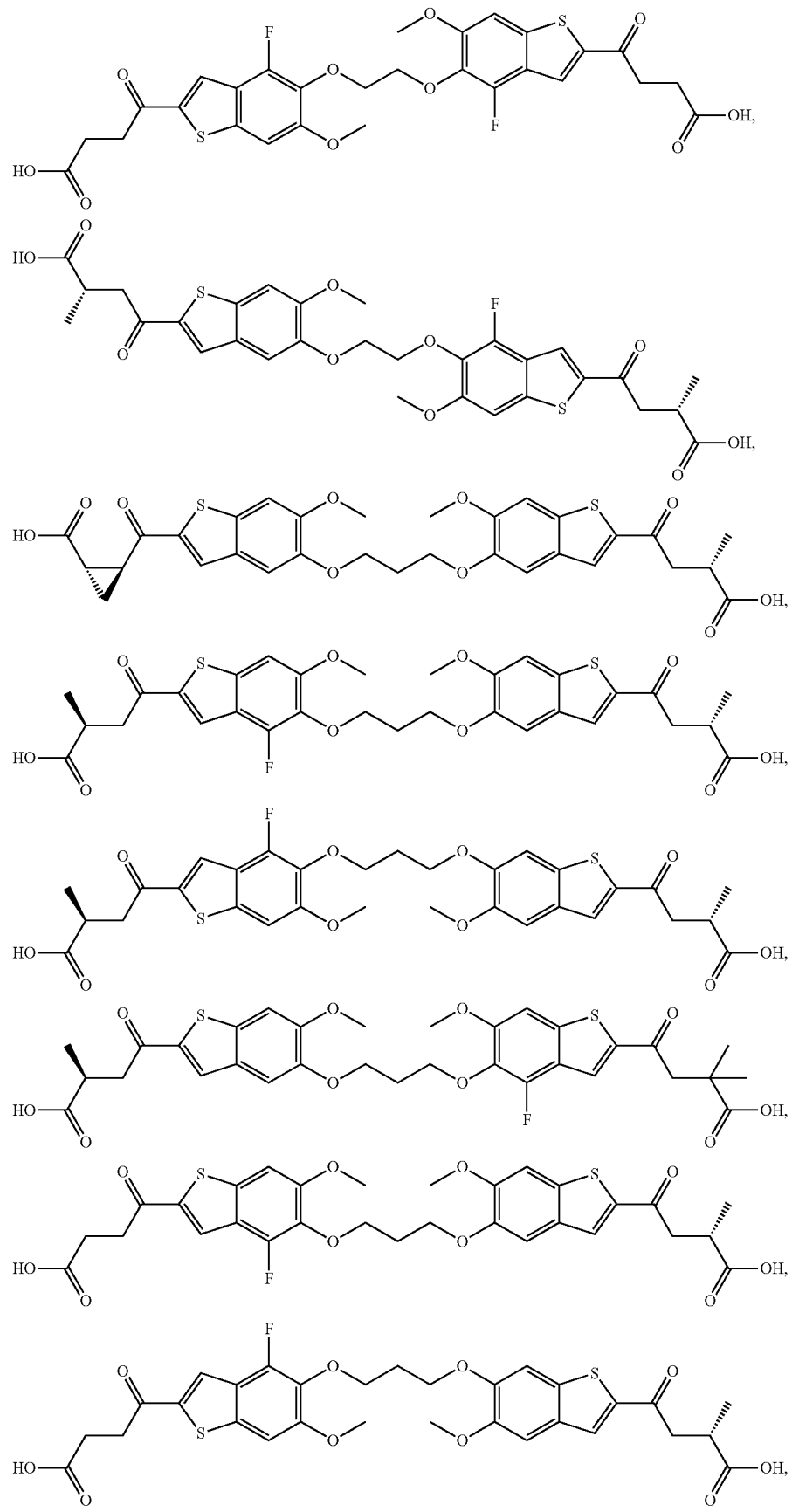

-continued
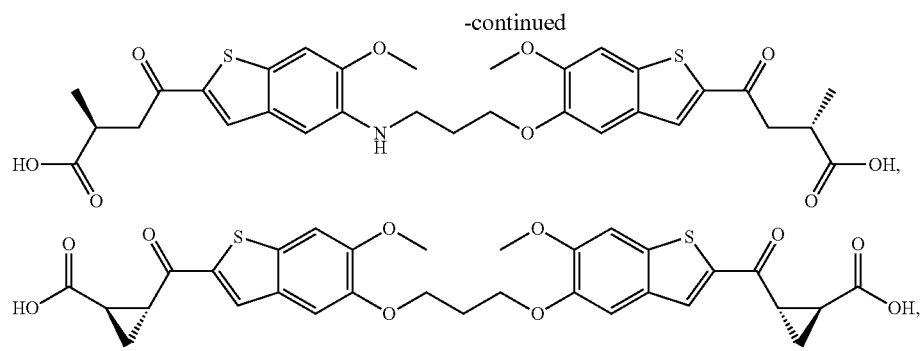
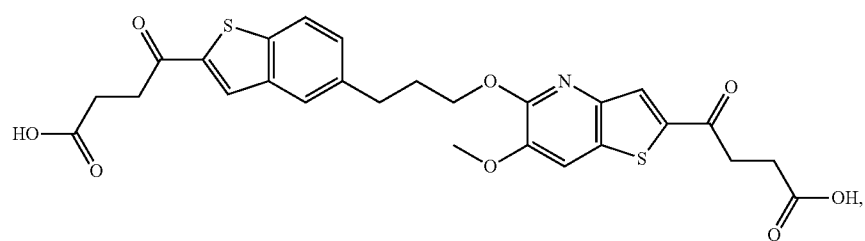
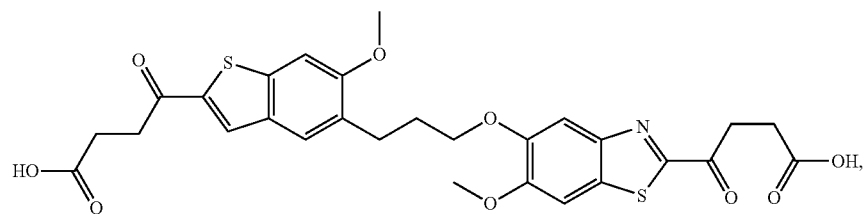
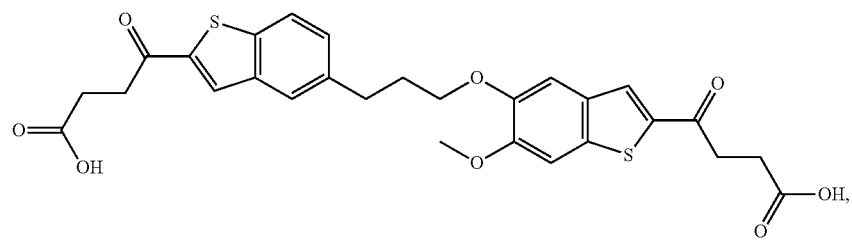
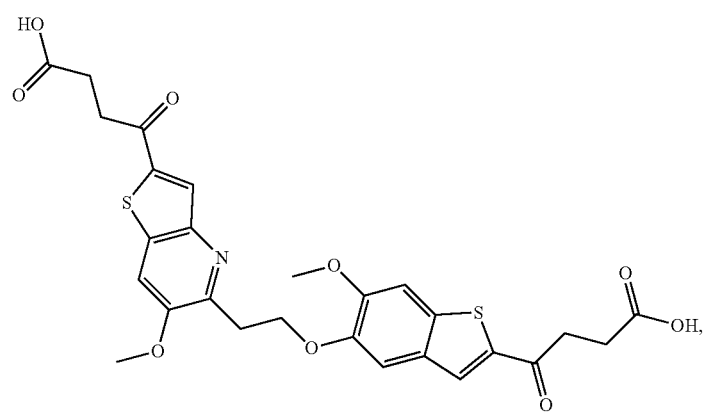

-continued
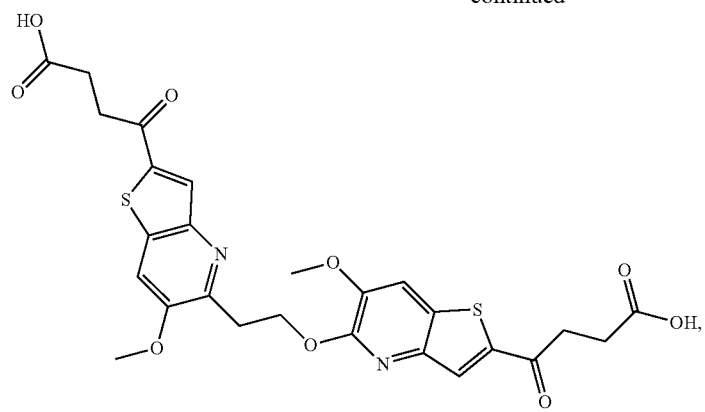
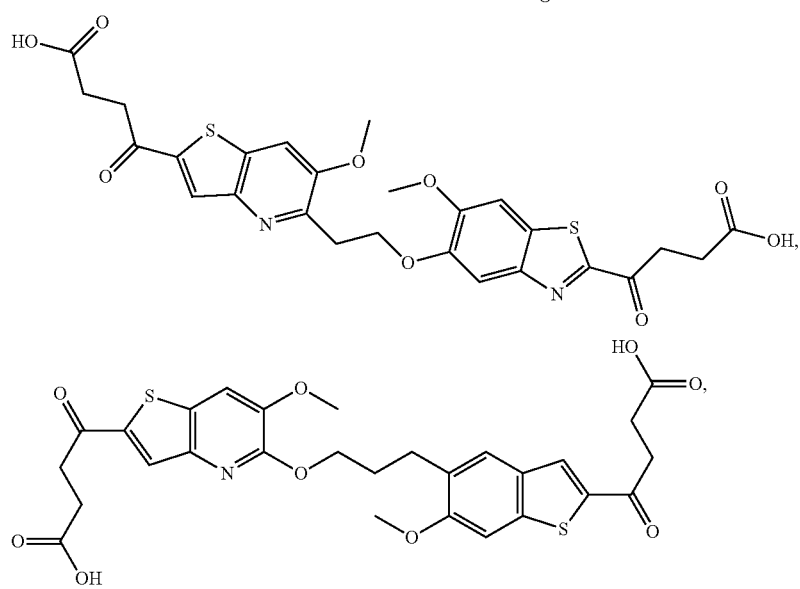
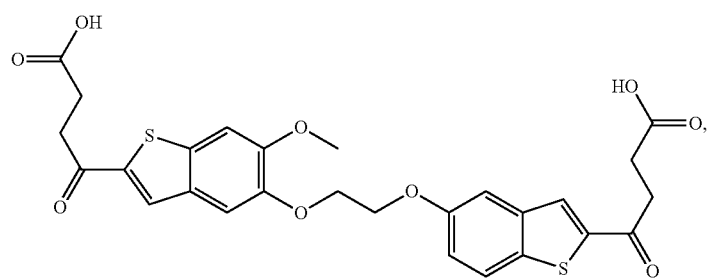
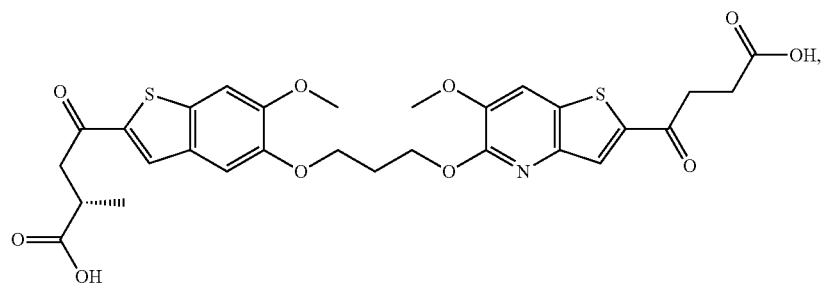

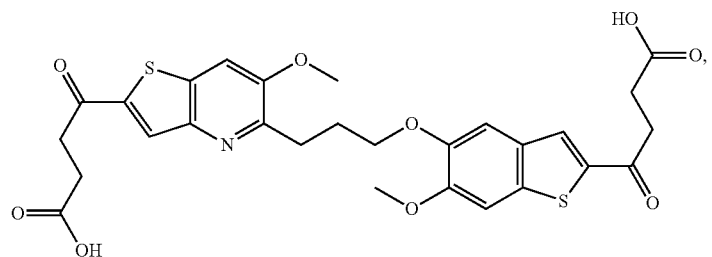
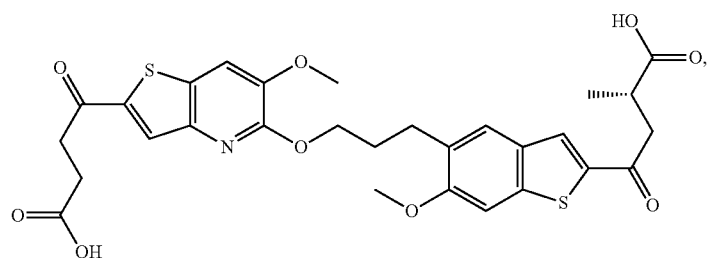
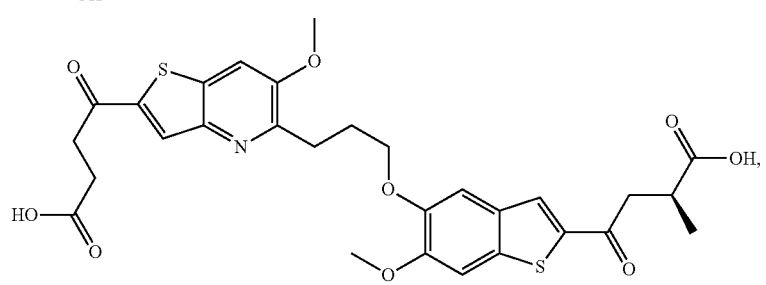
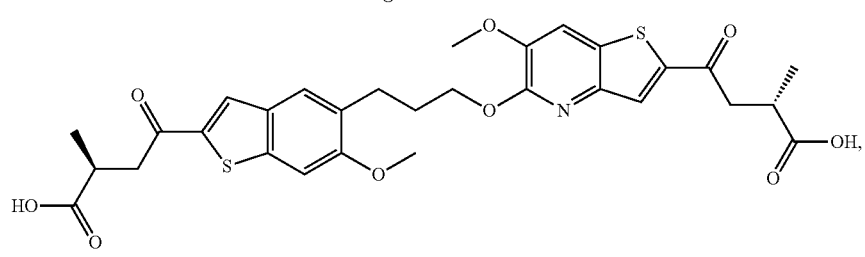
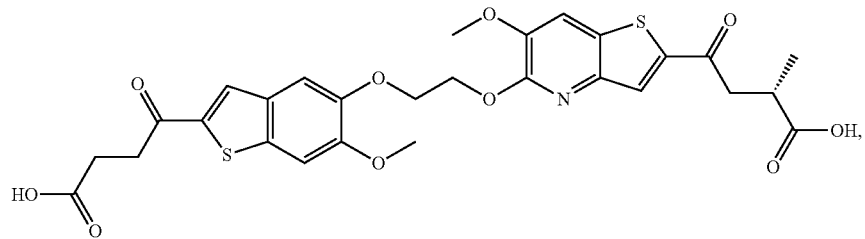
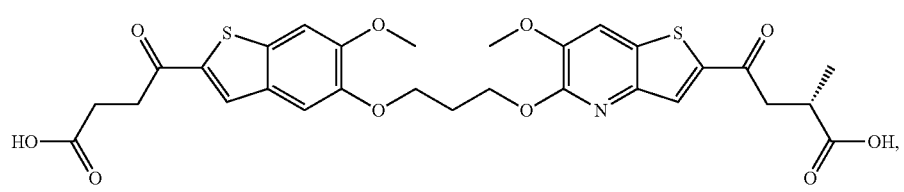
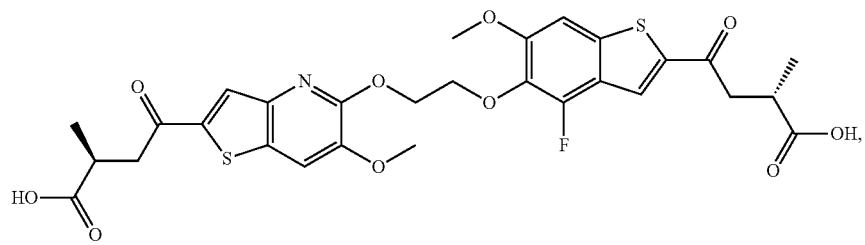

-continued
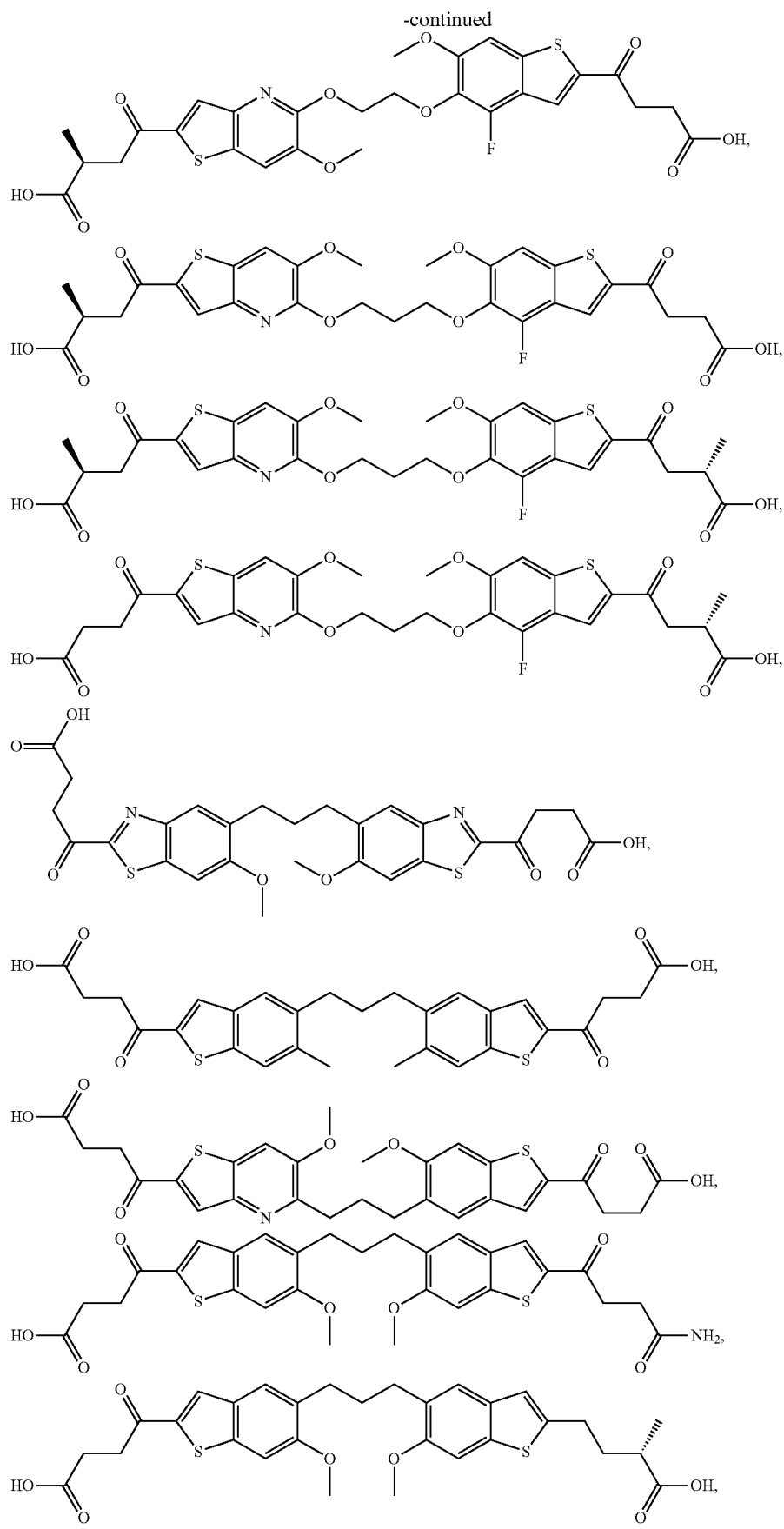

-continued
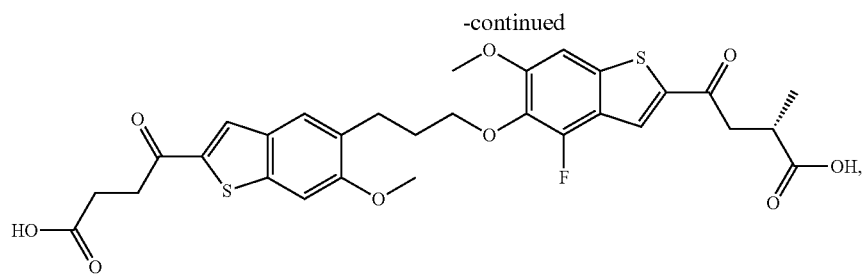
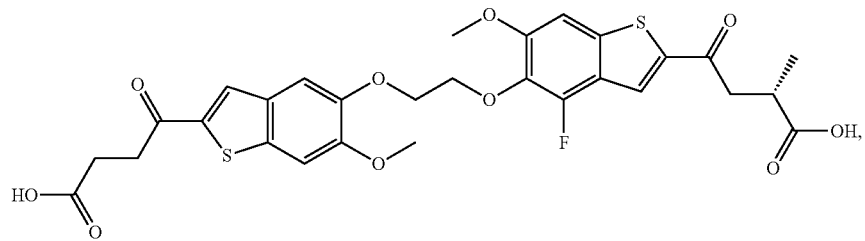
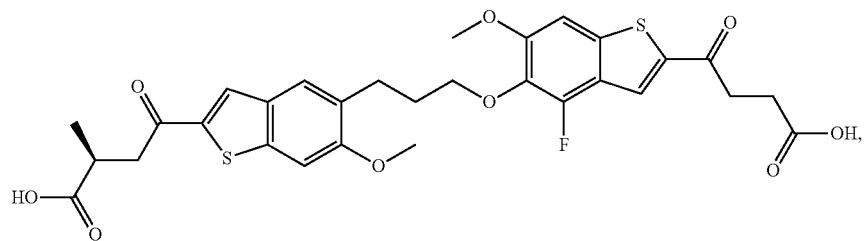
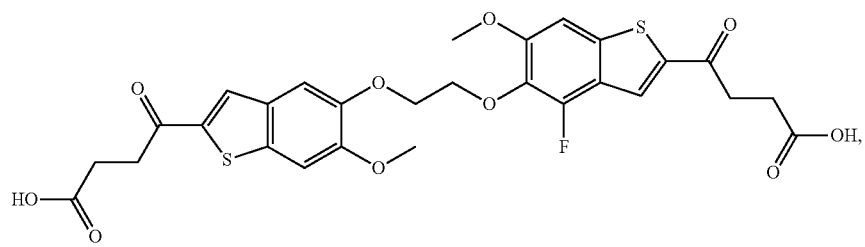
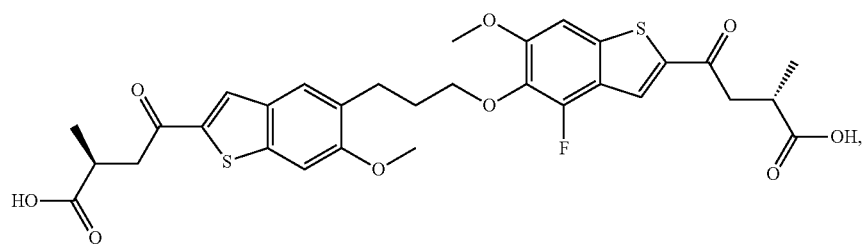
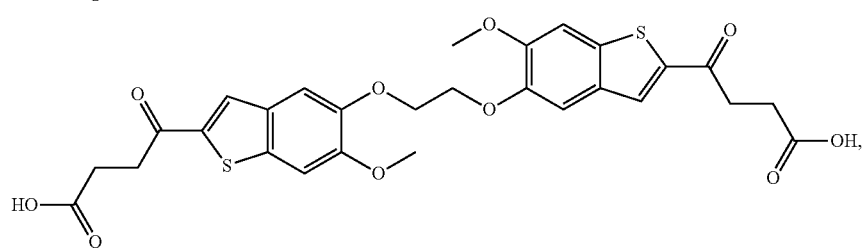
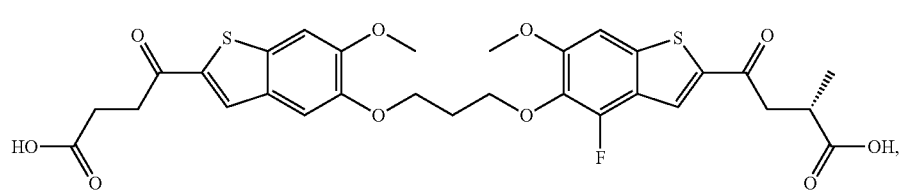

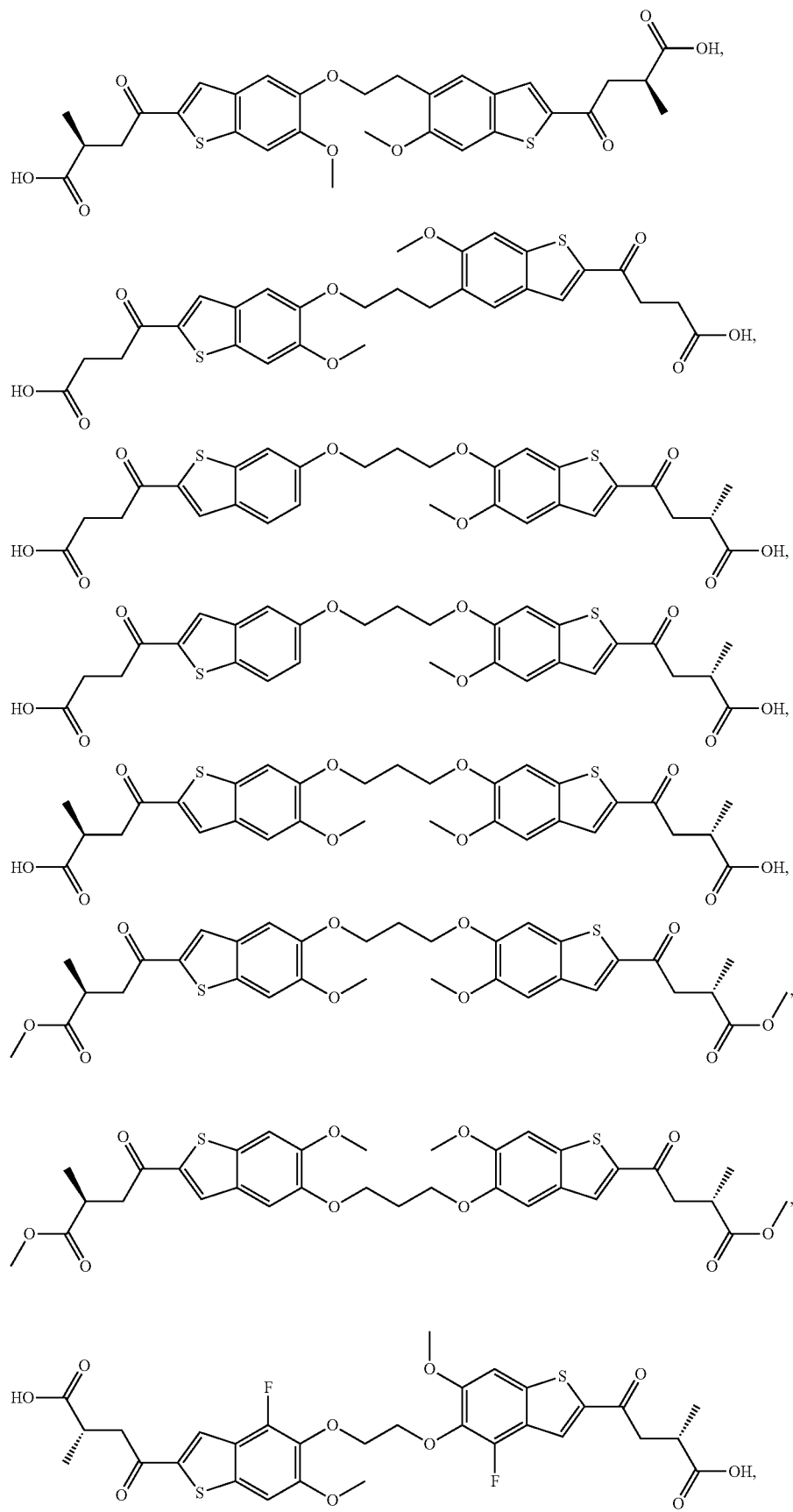

-continued
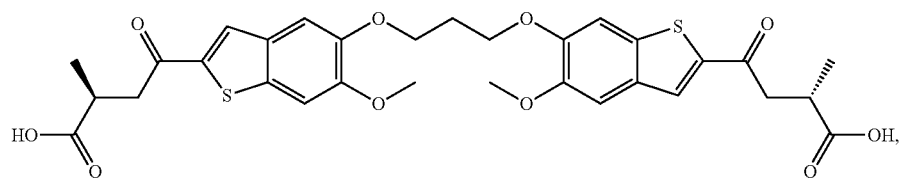
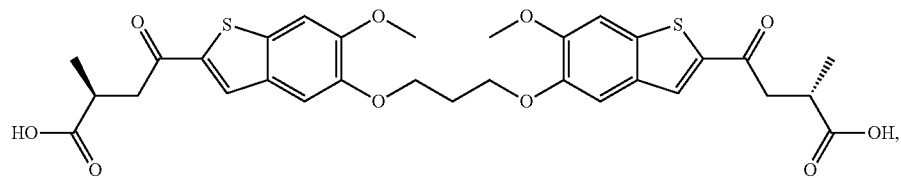
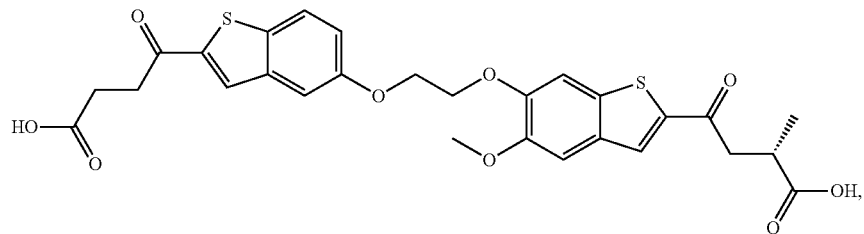
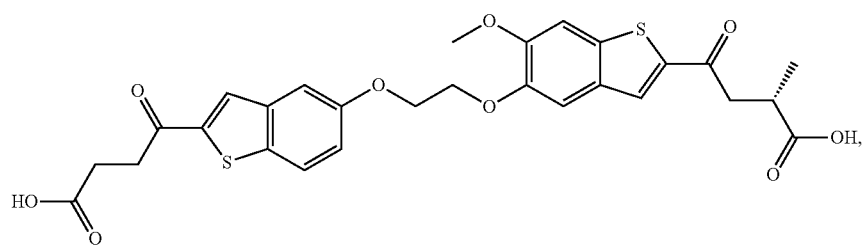
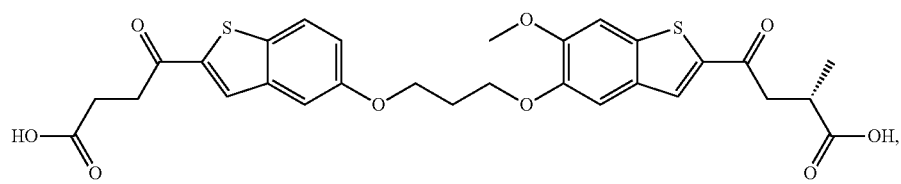
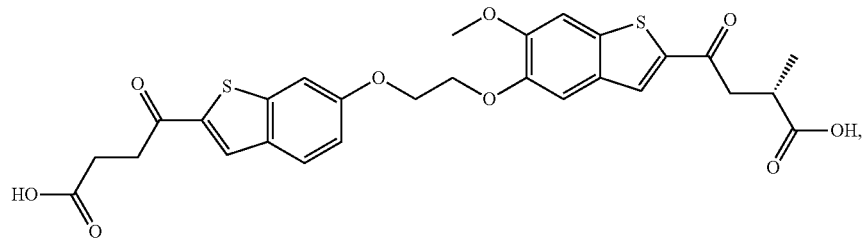
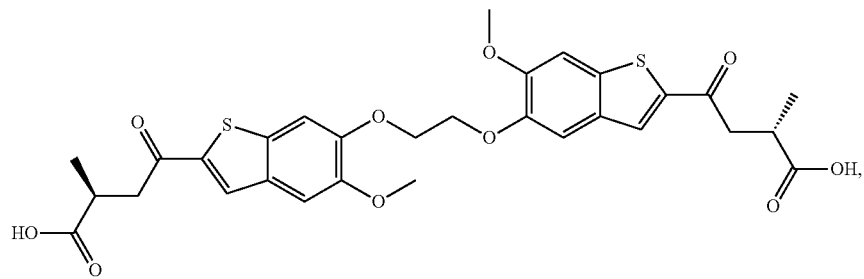

-continued
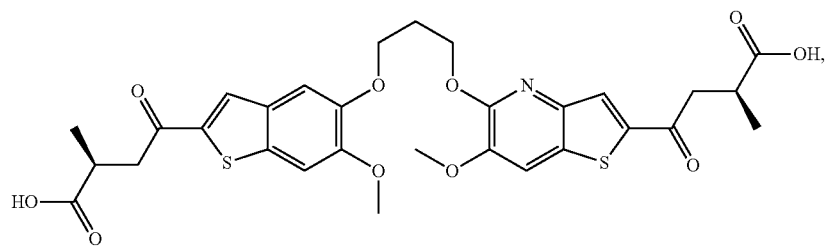
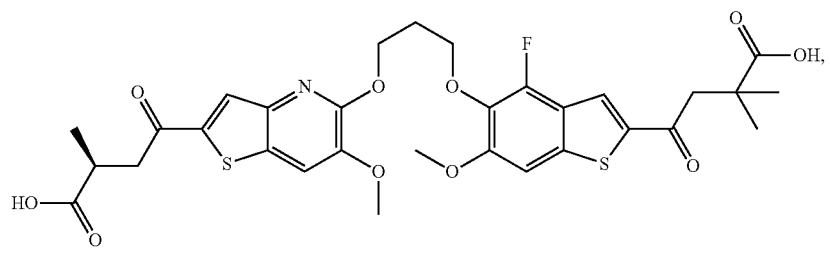
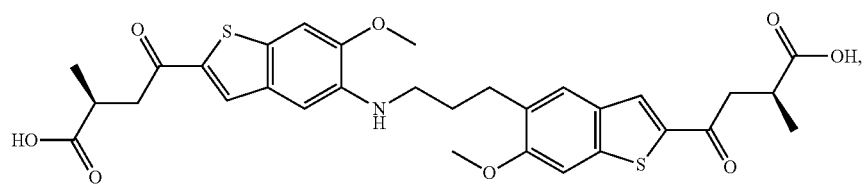
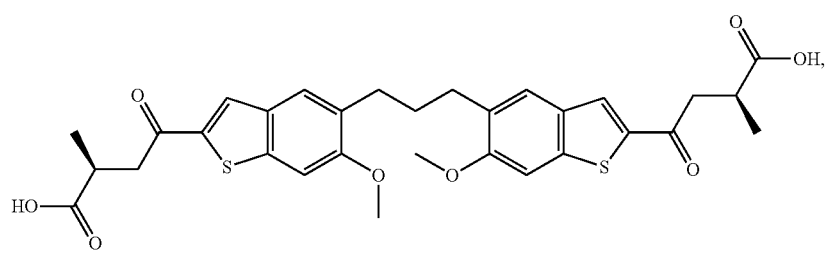
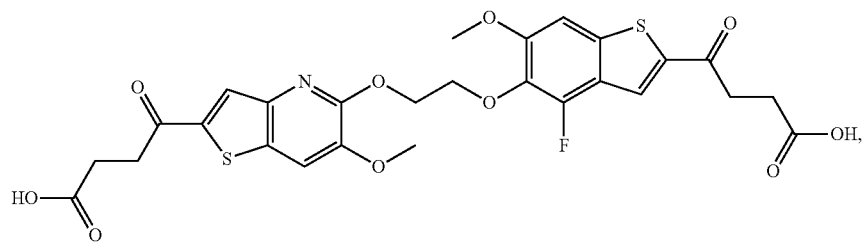
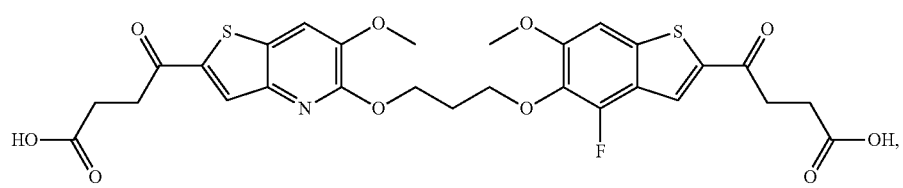
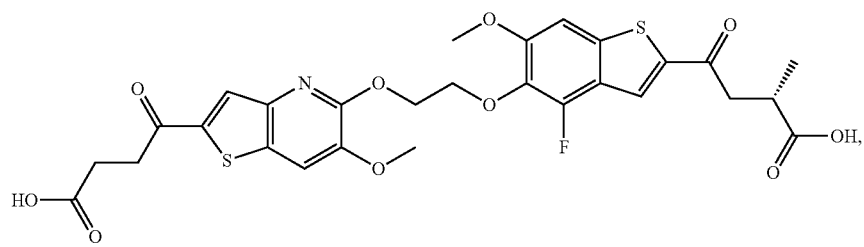

-continued
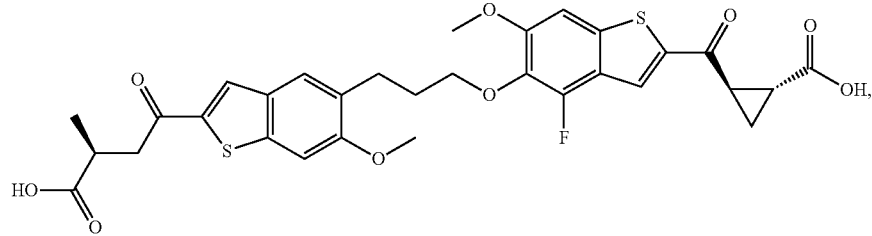
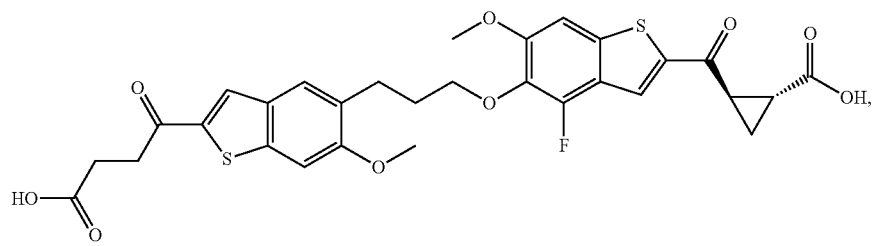
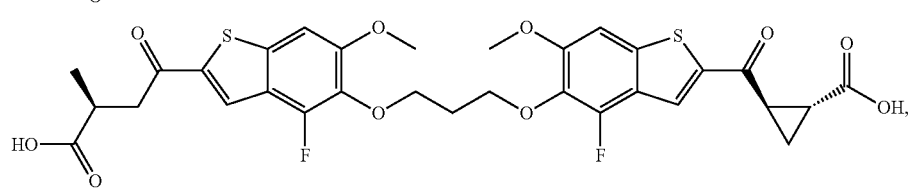
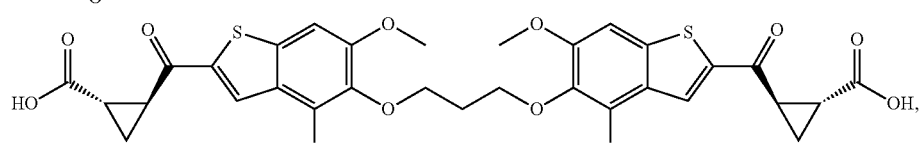
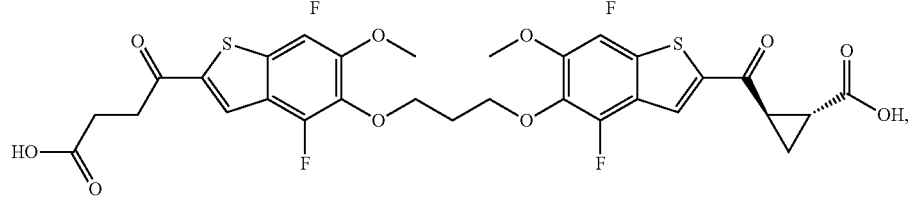
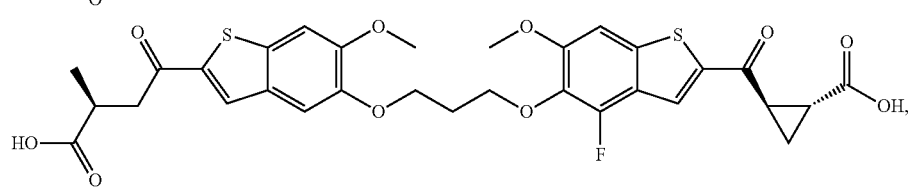
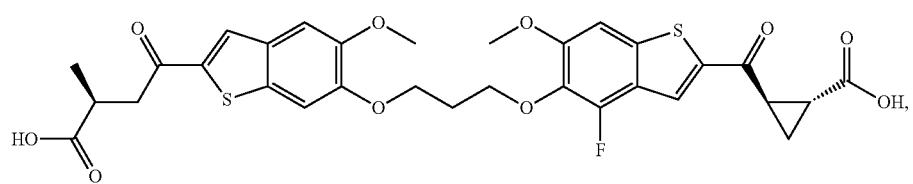
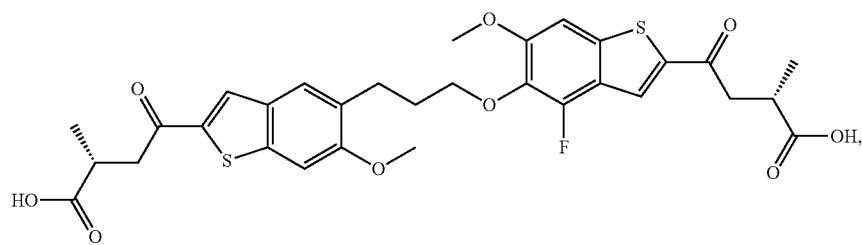

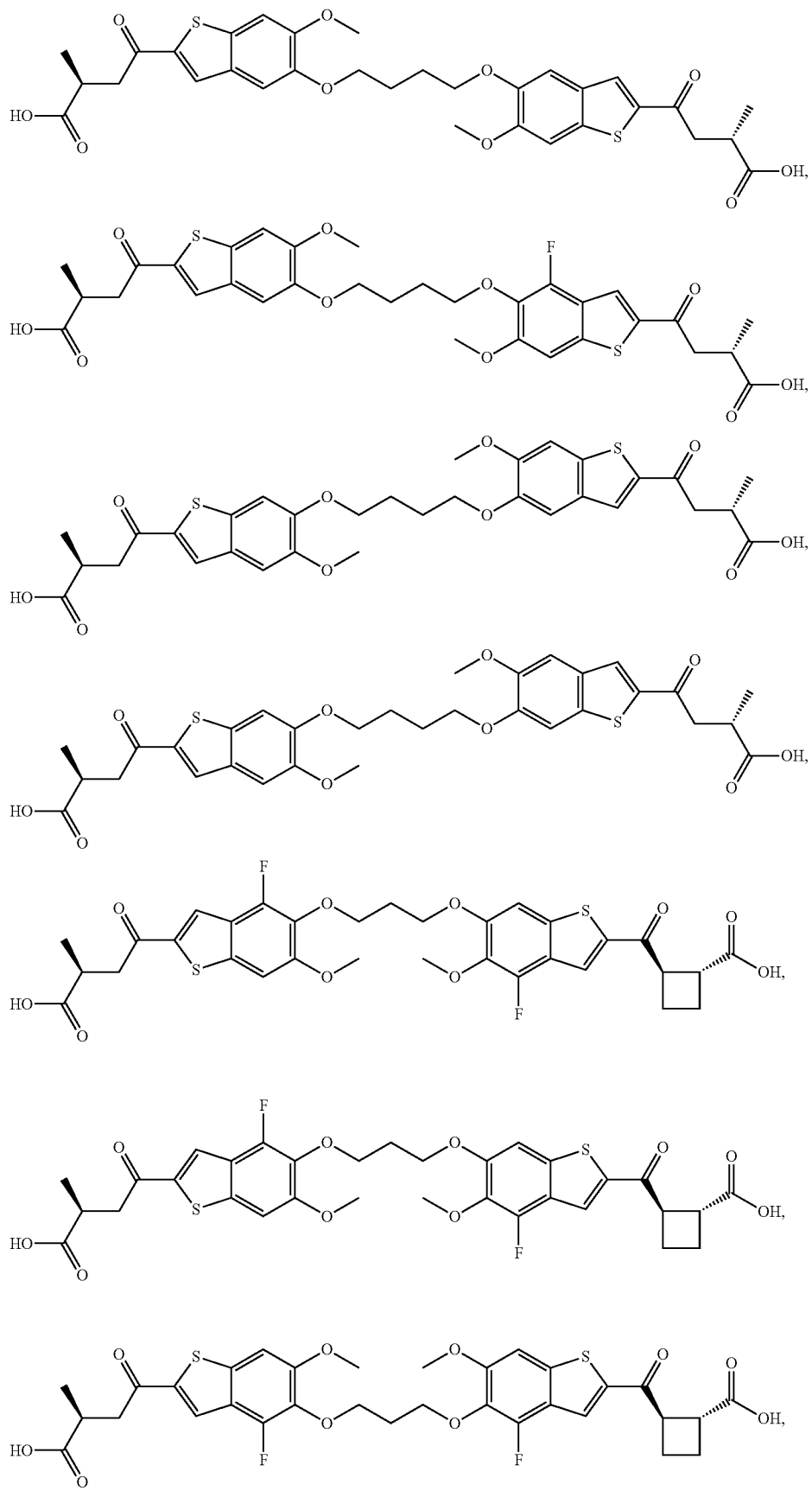

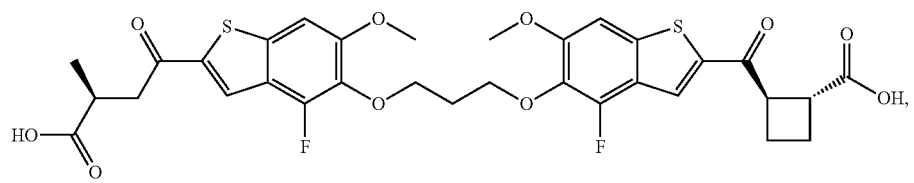
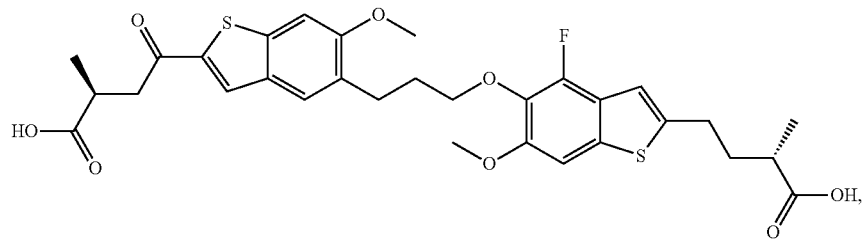
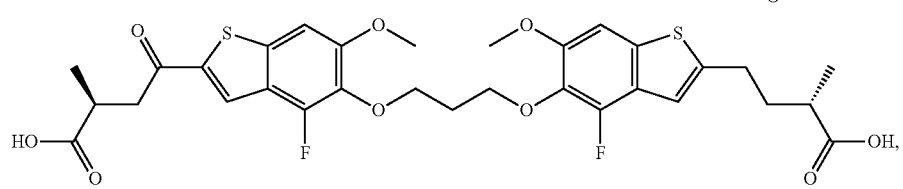
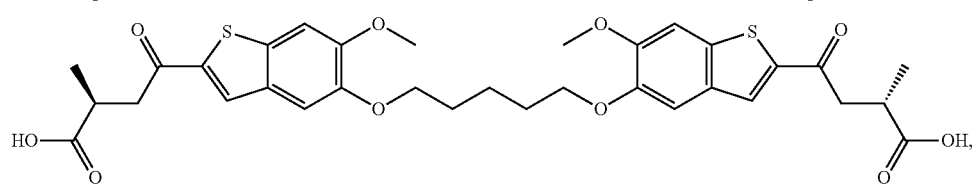
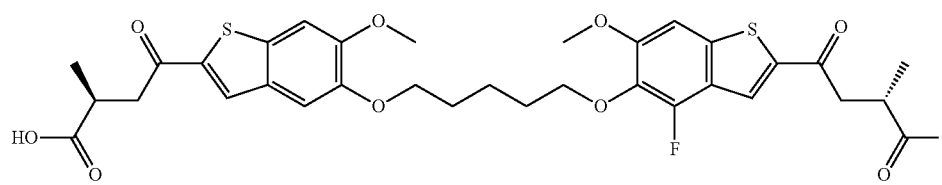
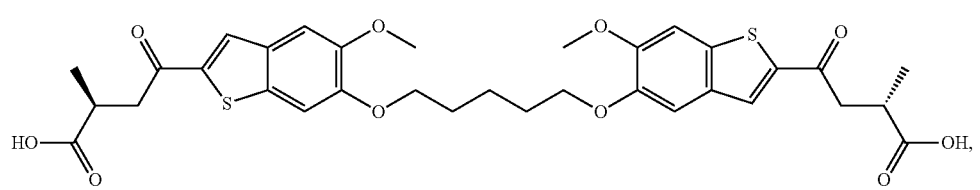
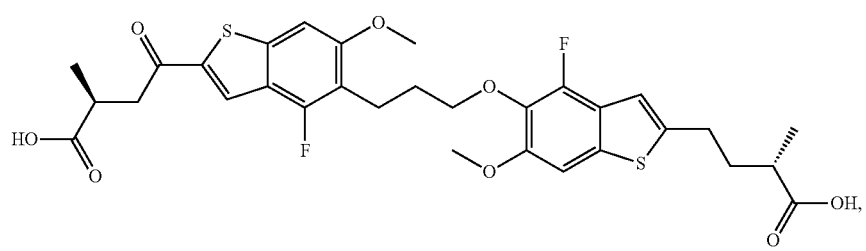
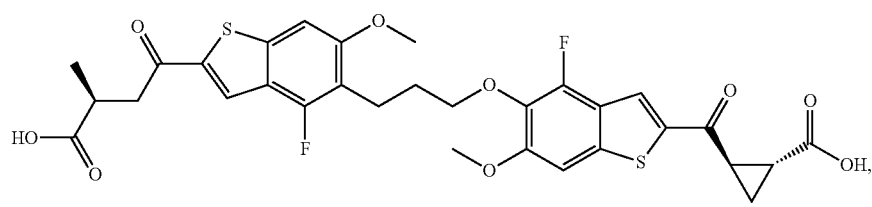

-continued
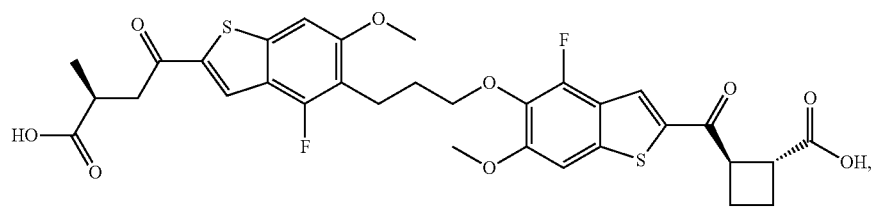
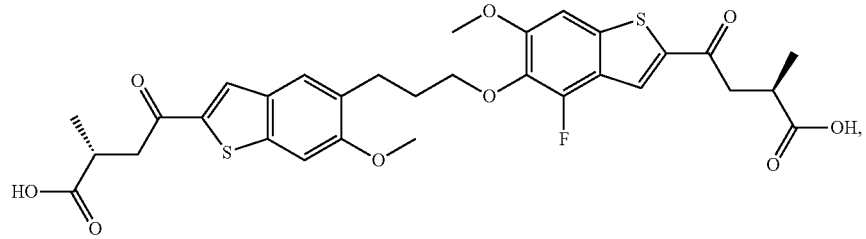
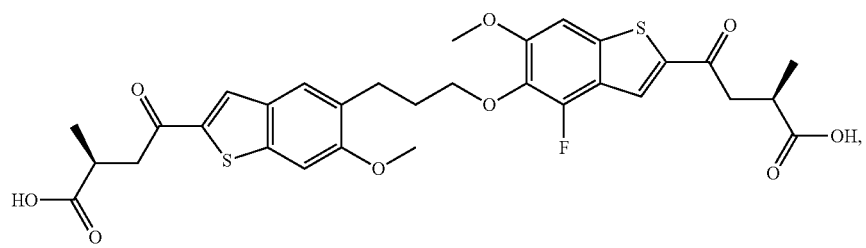
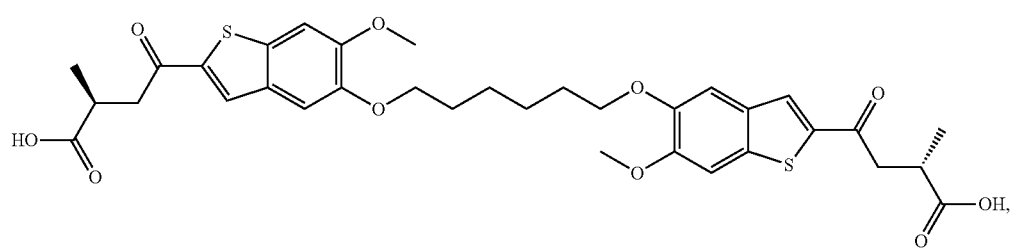
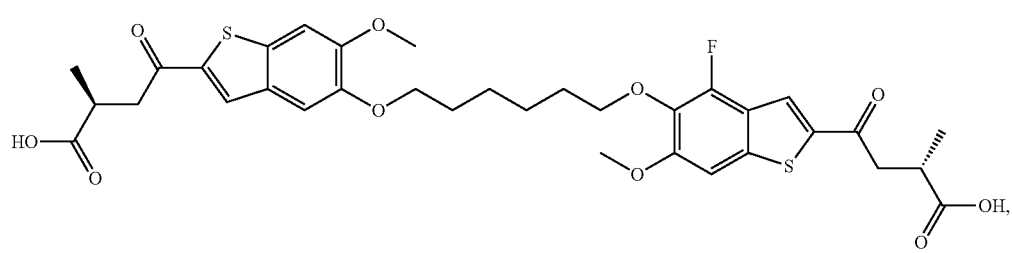
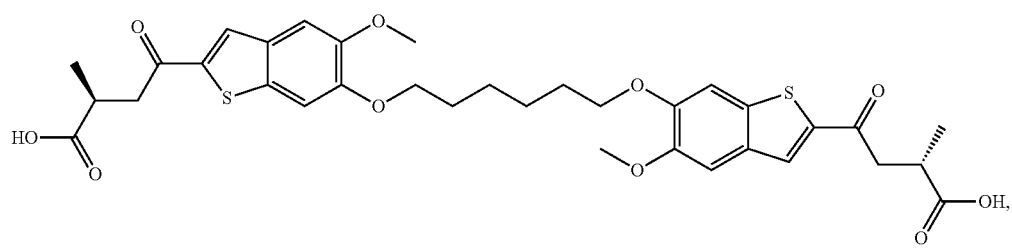
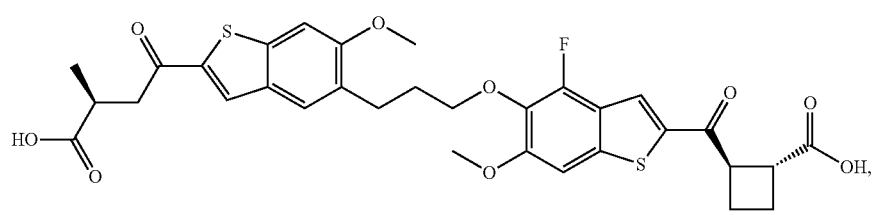

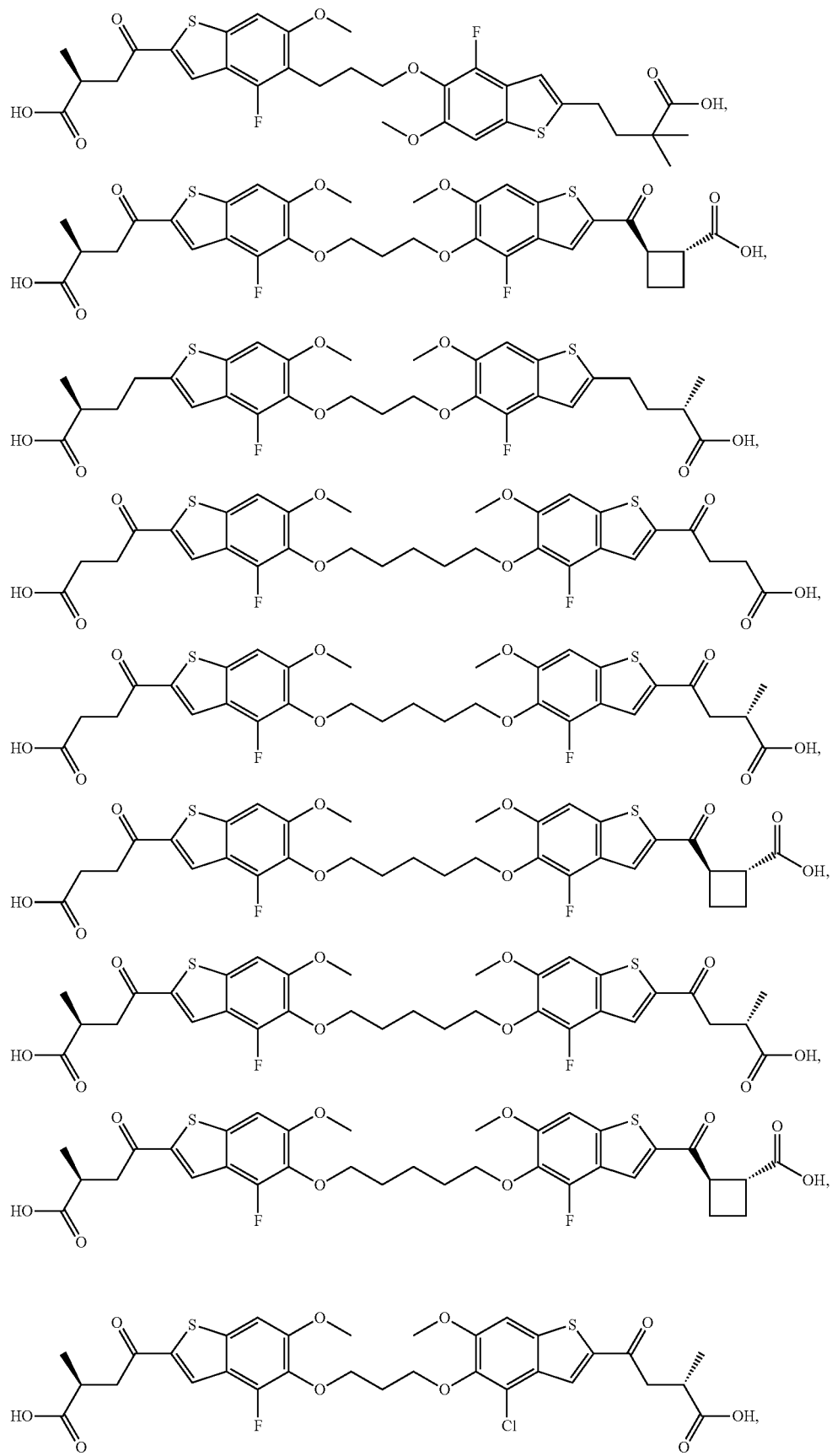

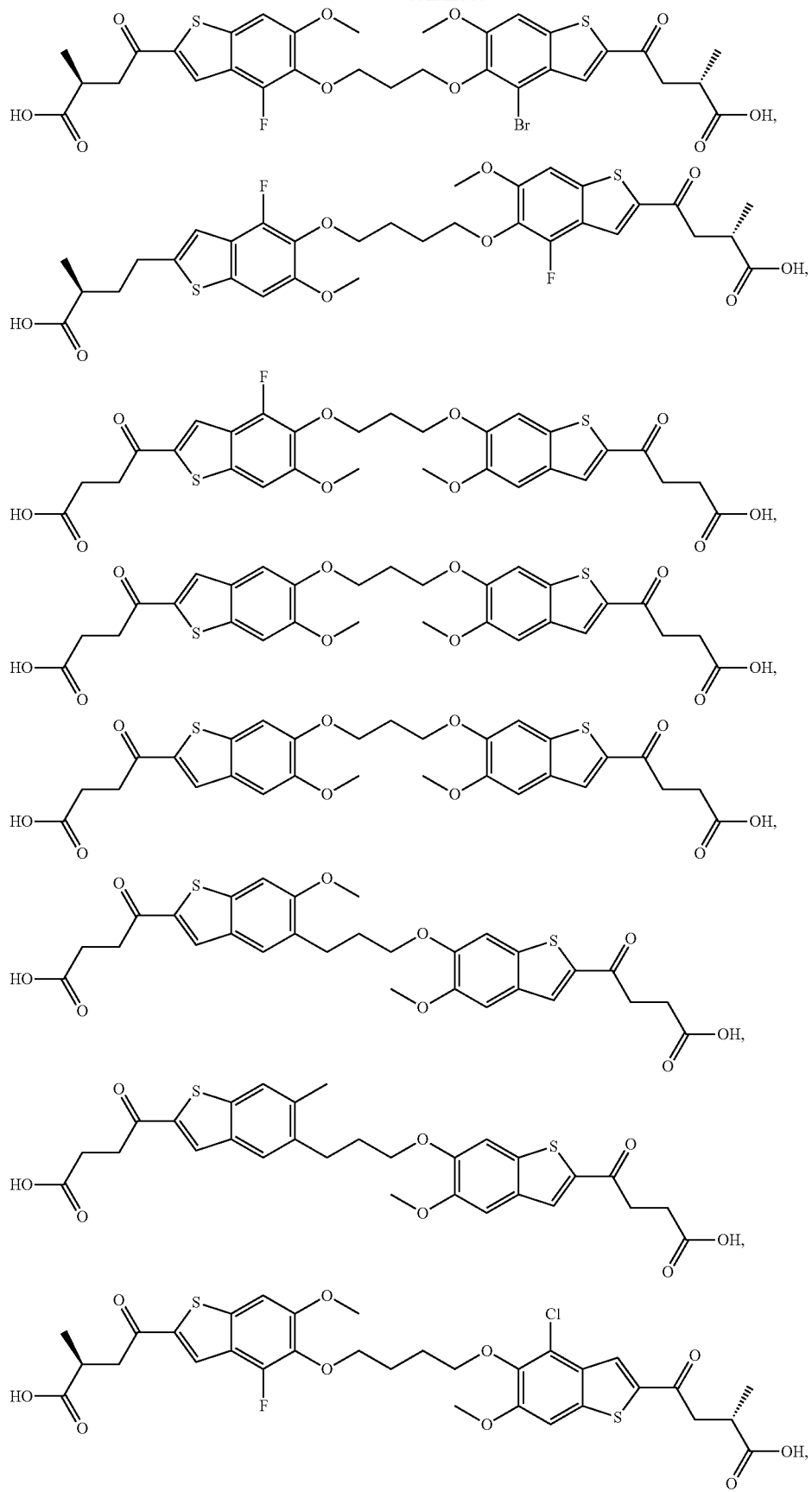

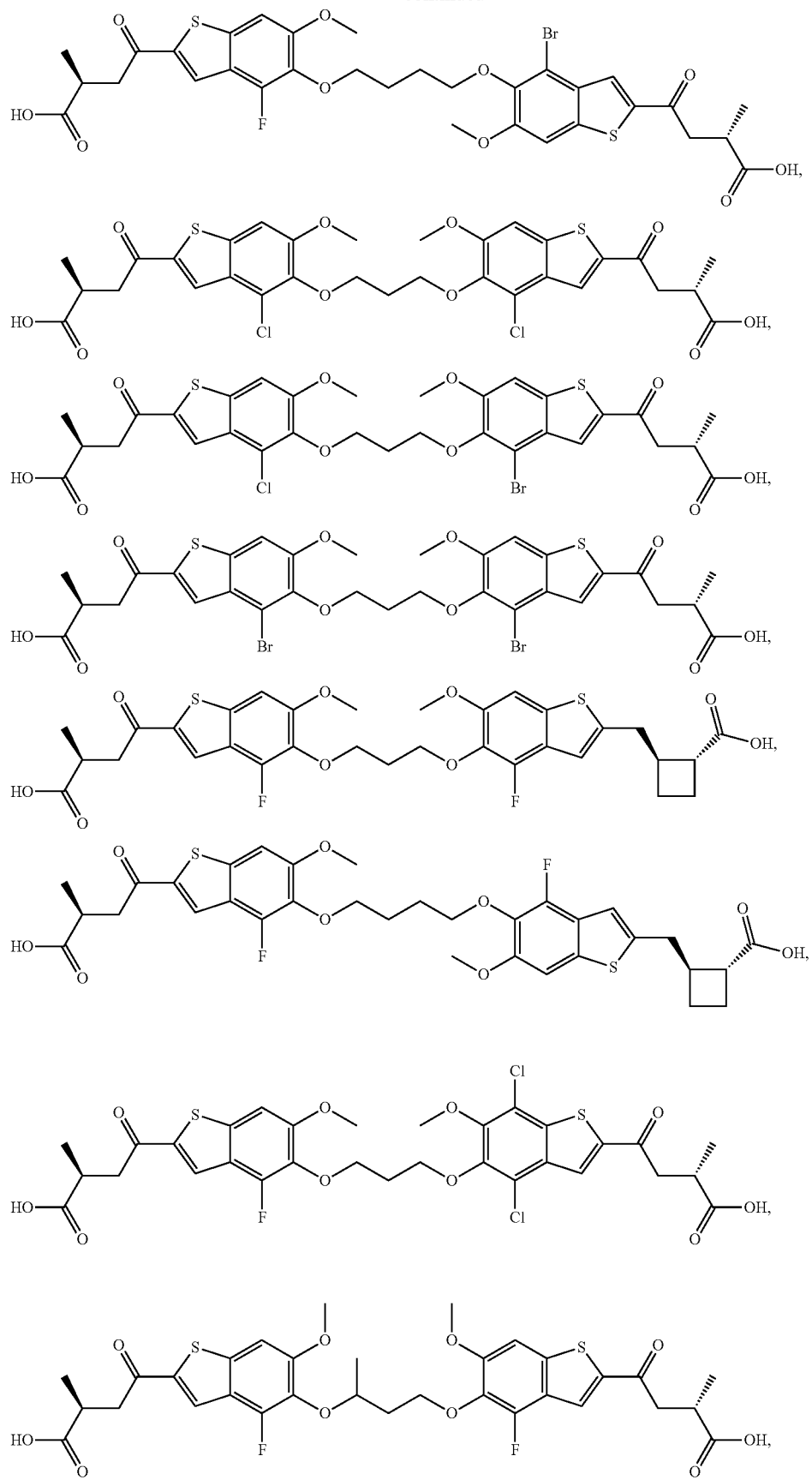

-continued
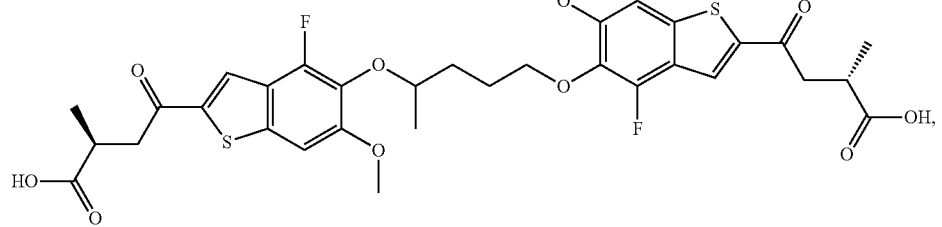
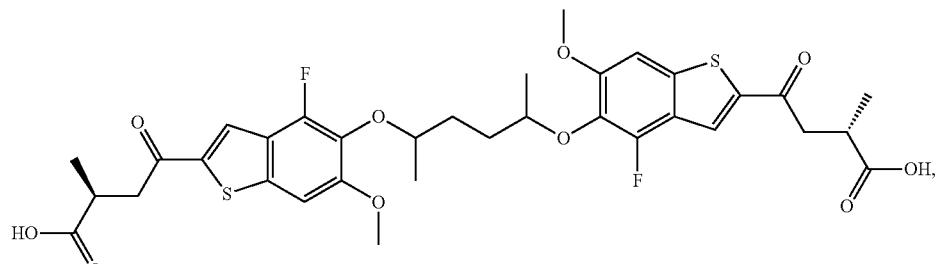
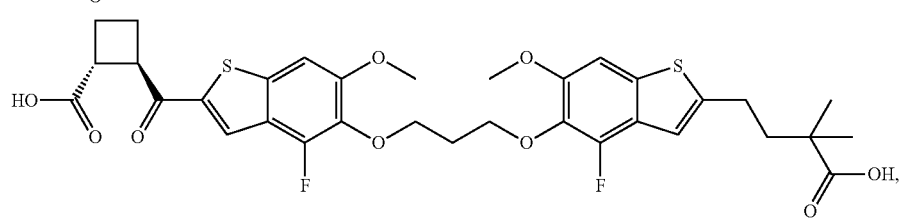
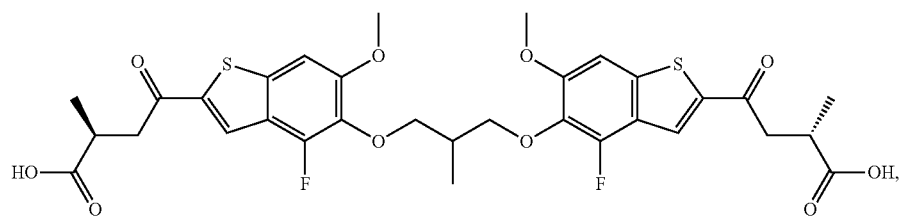
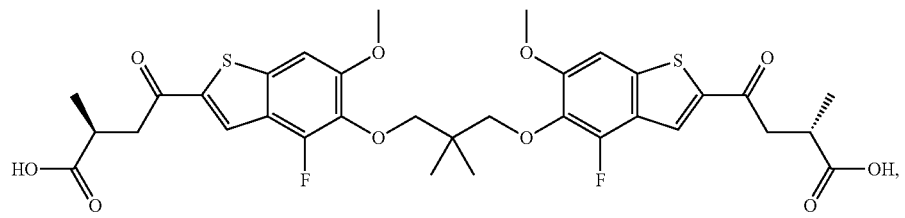
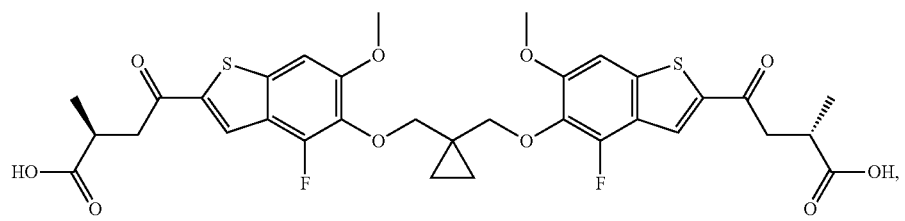
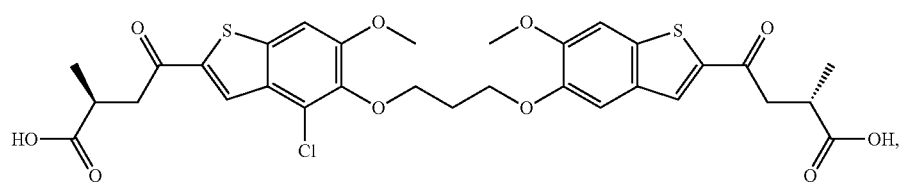

-continued
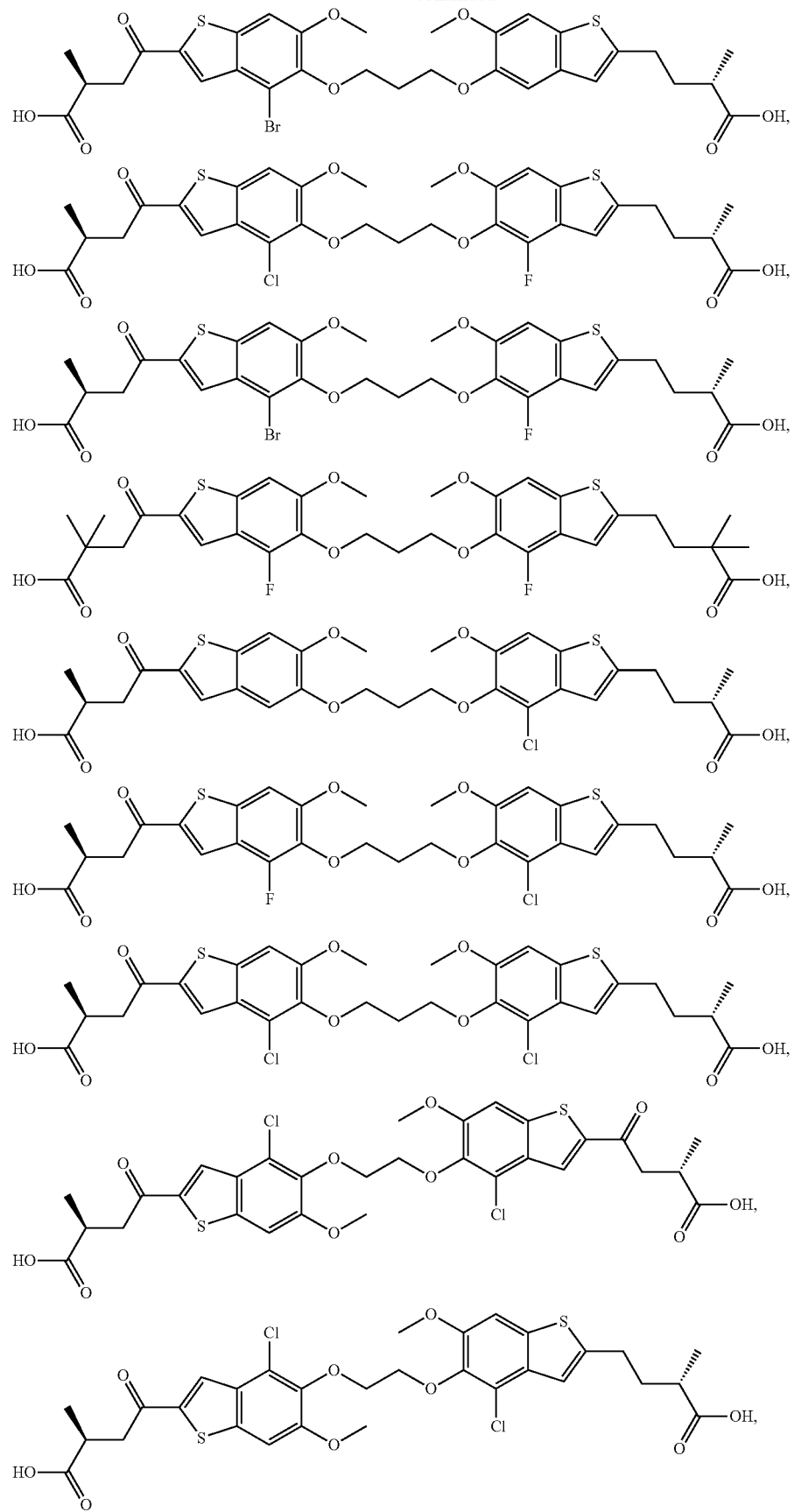

-continued
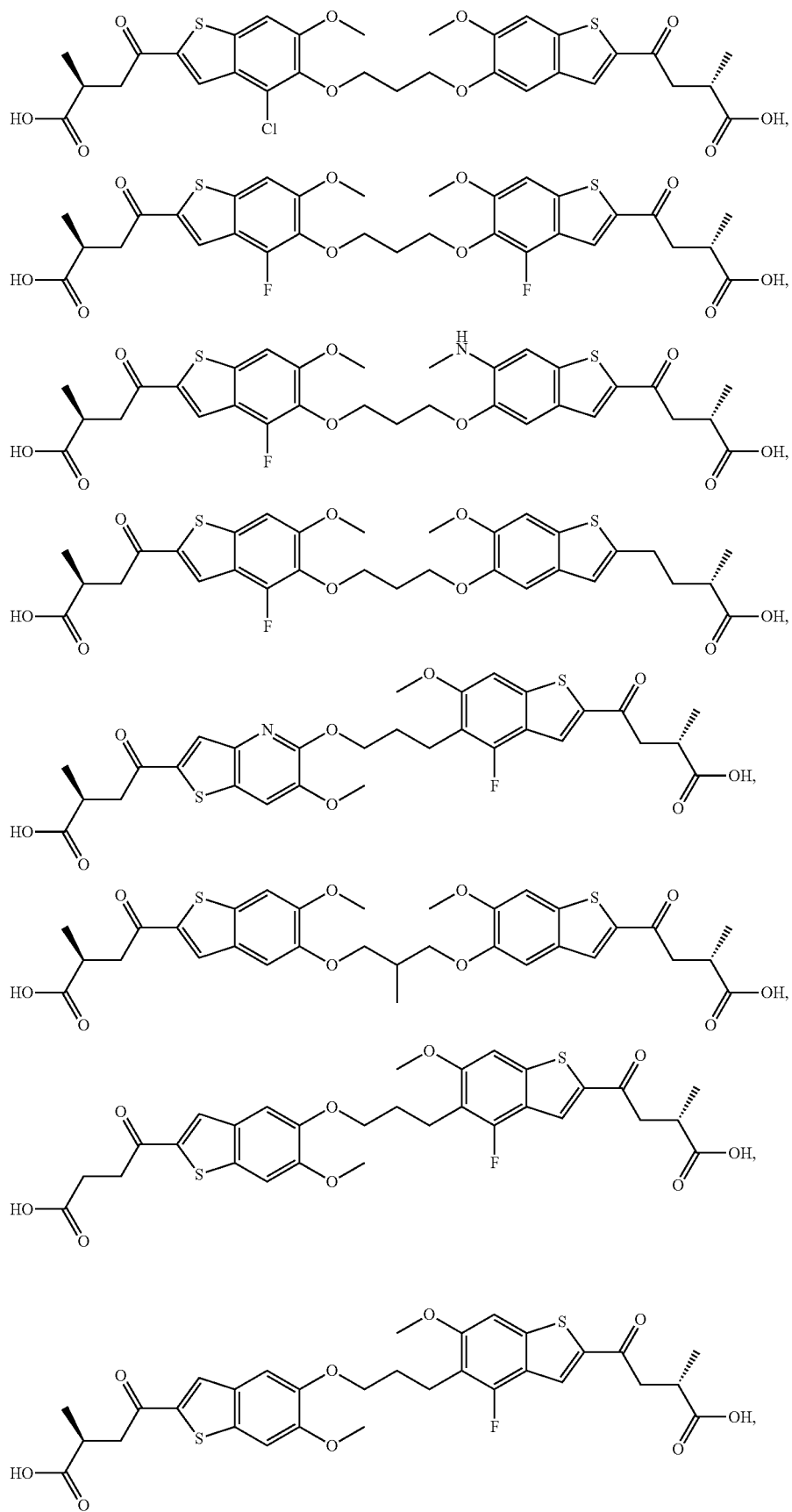

-continued
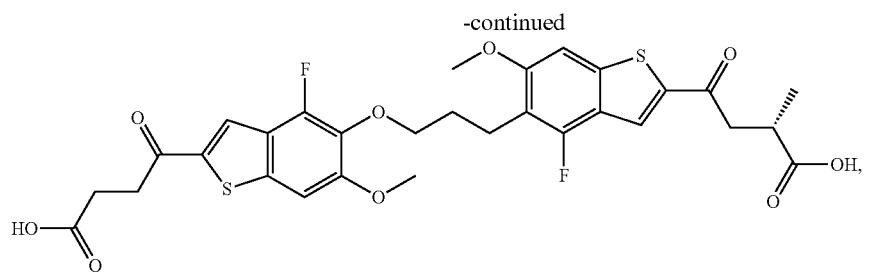
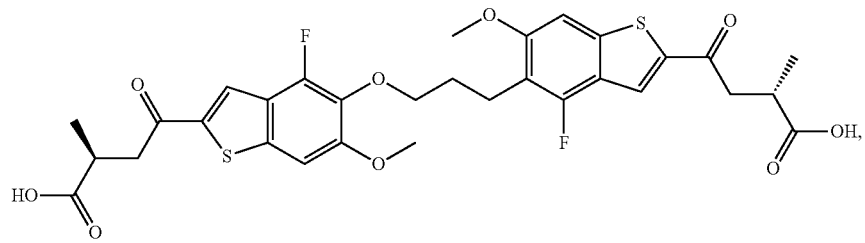
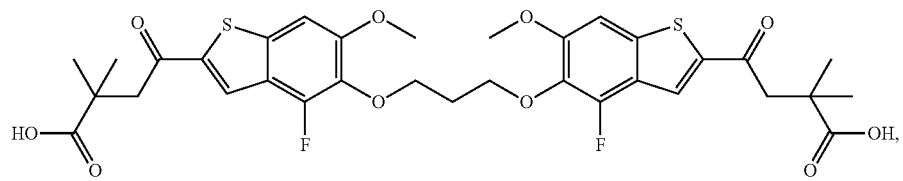
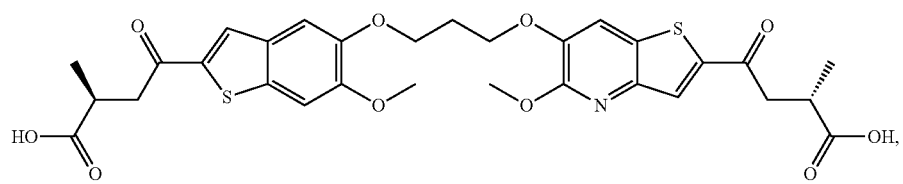
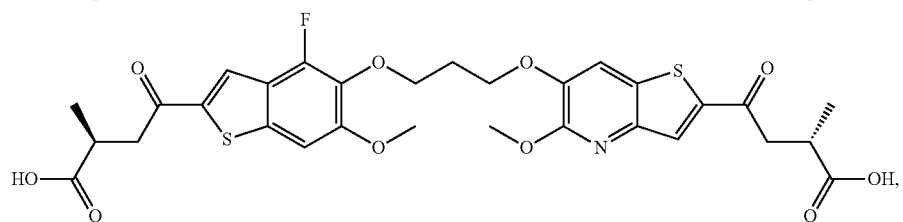
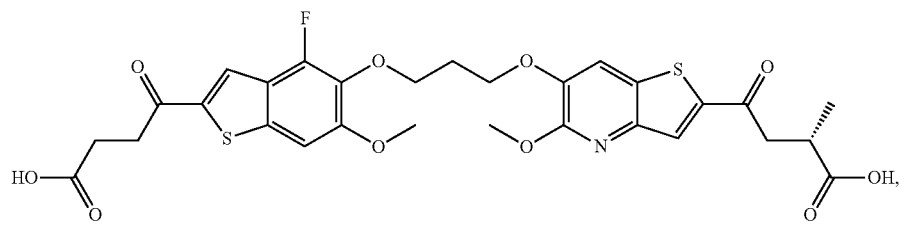
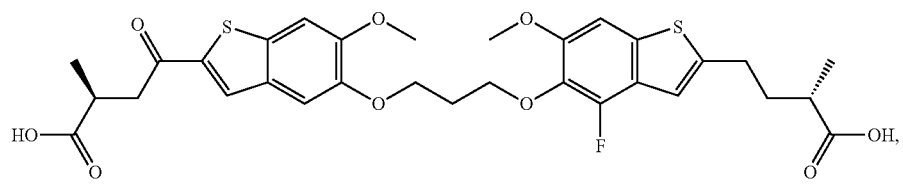
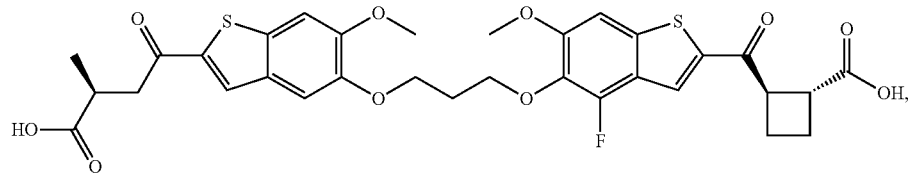

-continued
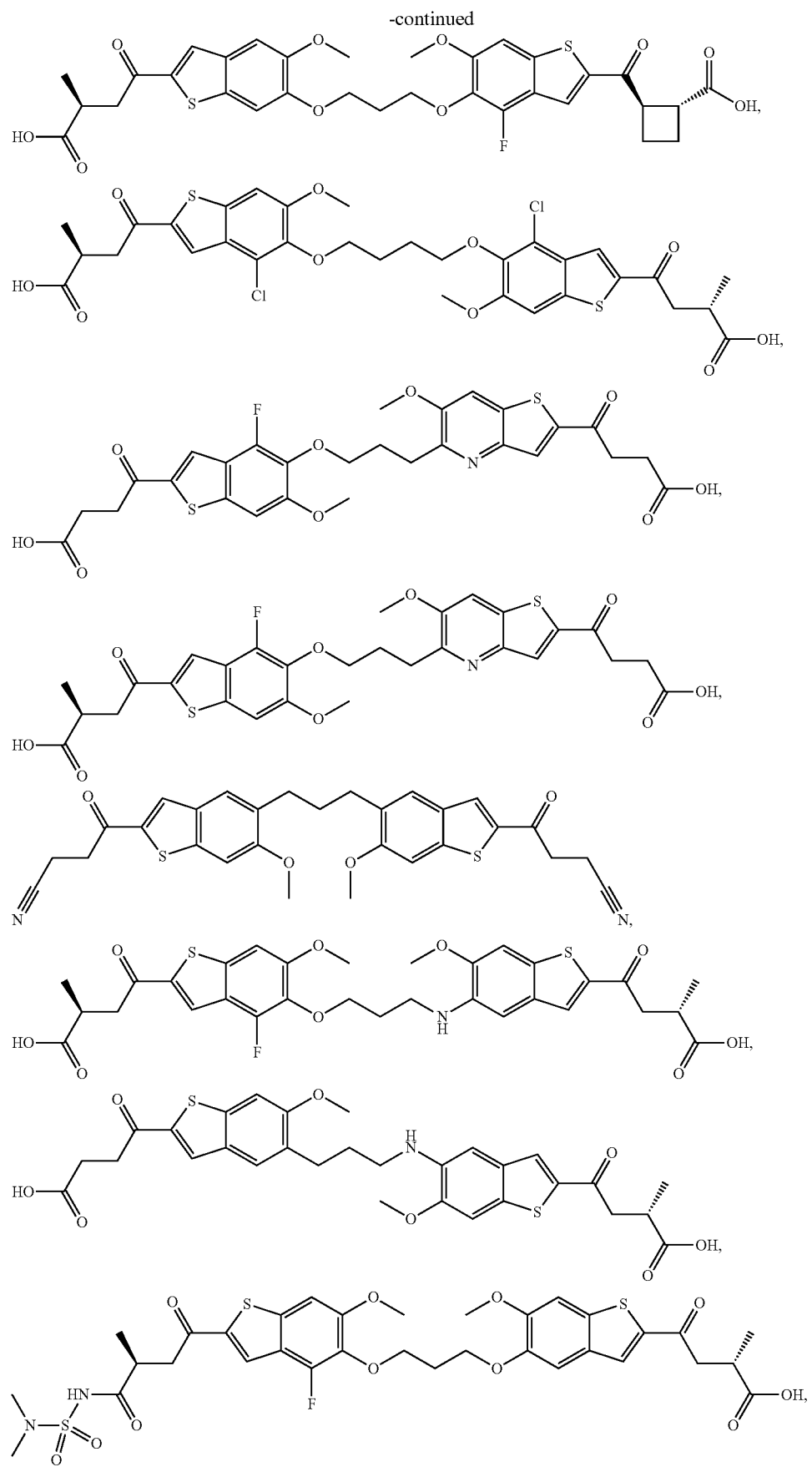

-continued
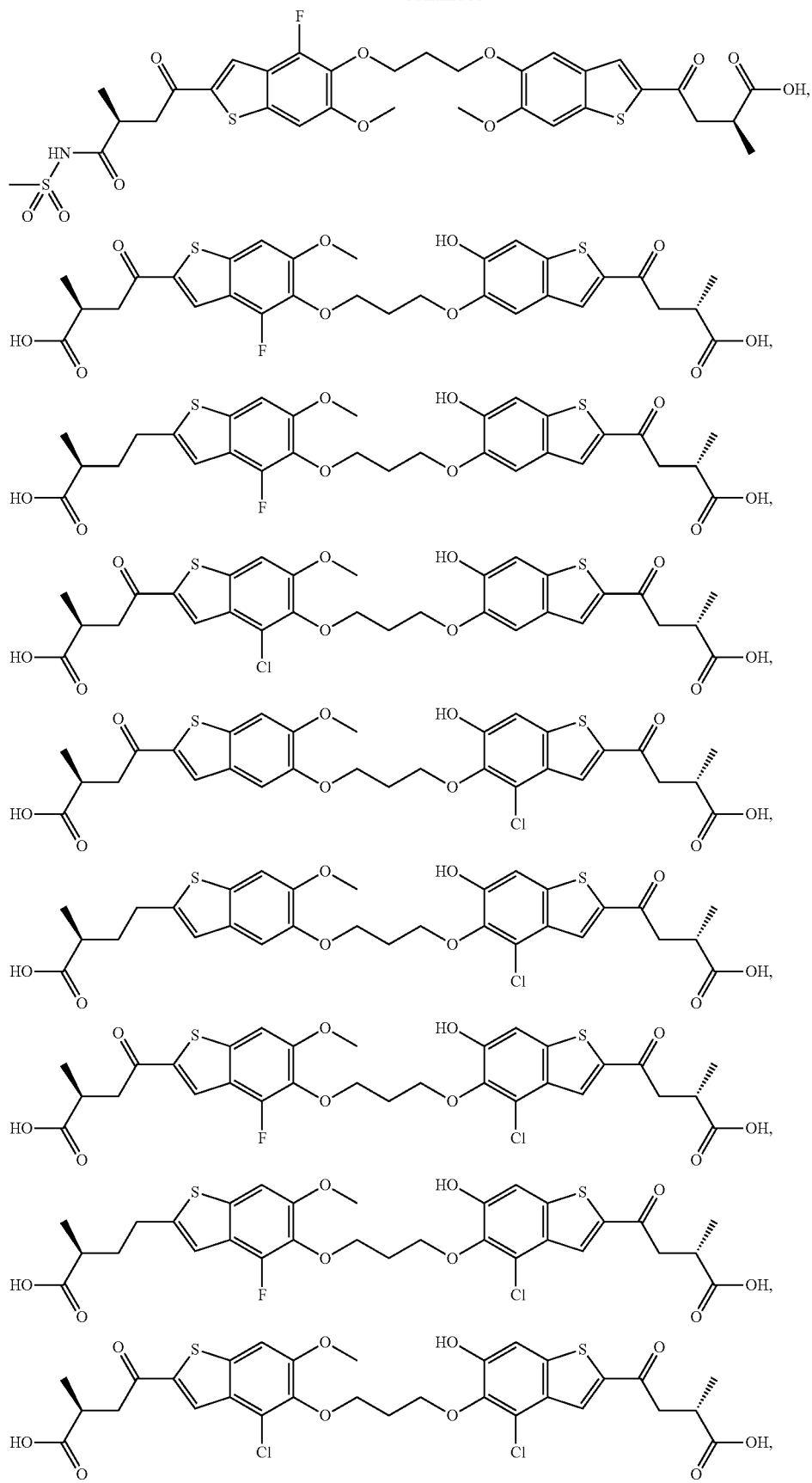

-continued
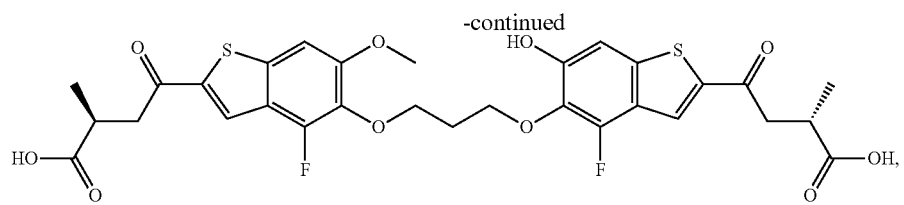
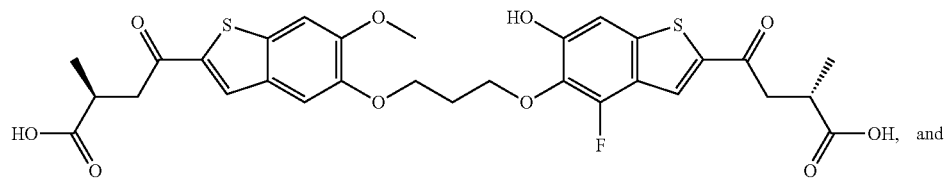
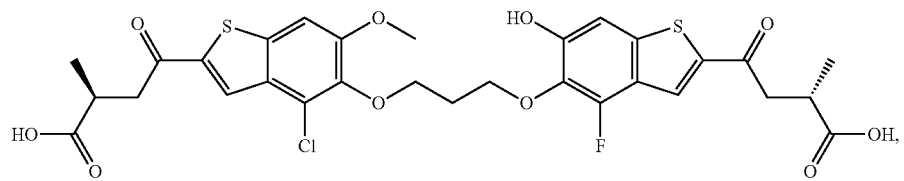
and pharmaceutically acceptable salts thereof. Particular aspects of this seventh embodiment relate to a compound selected from the group consisting of
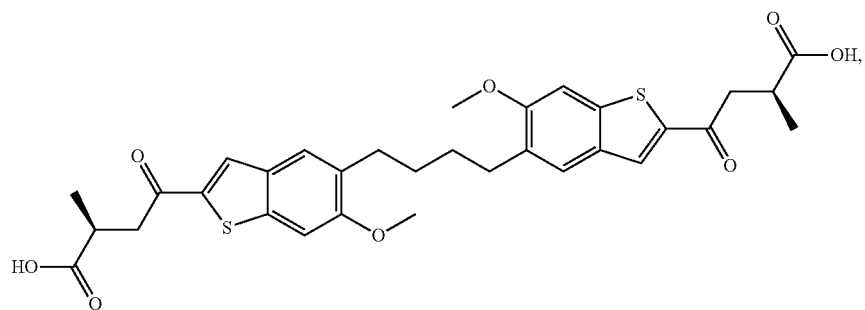
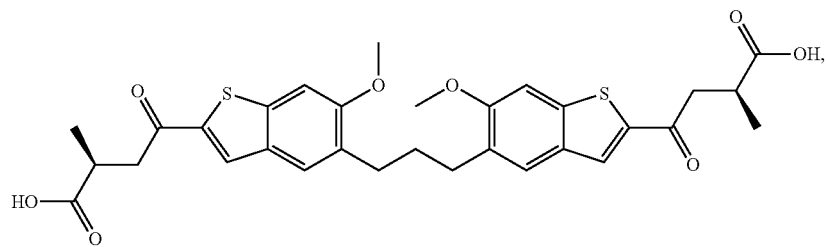
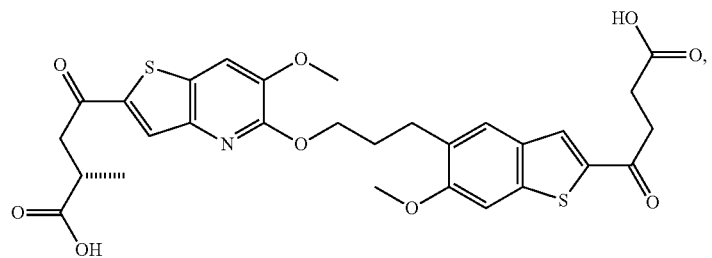

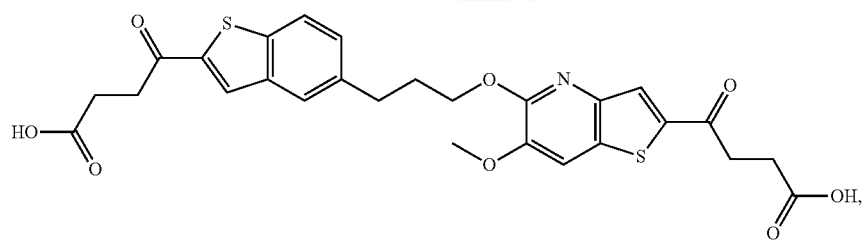
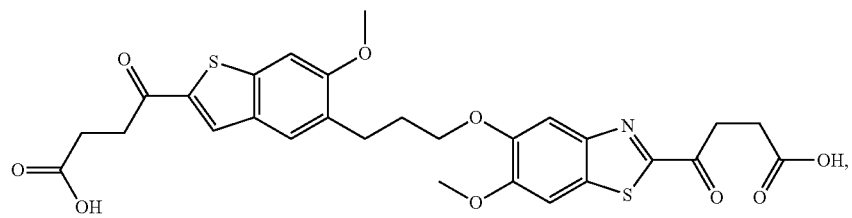
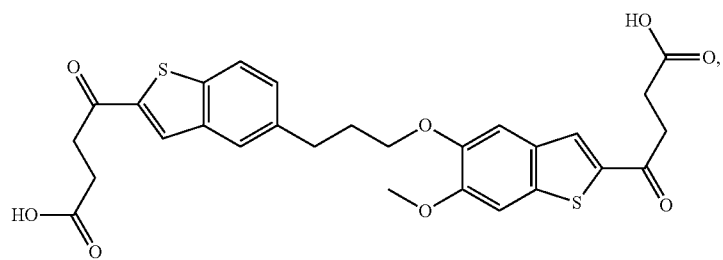
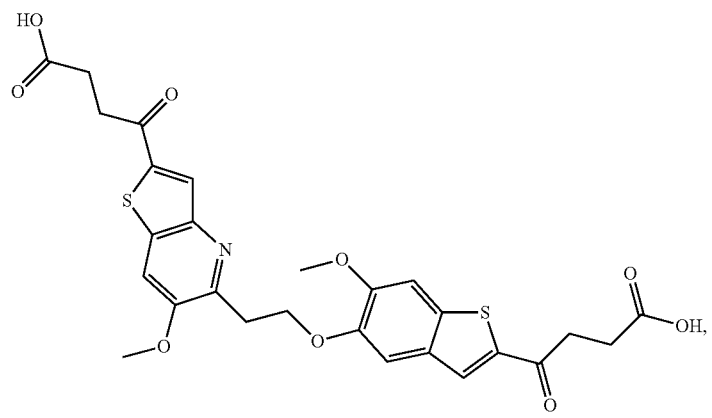
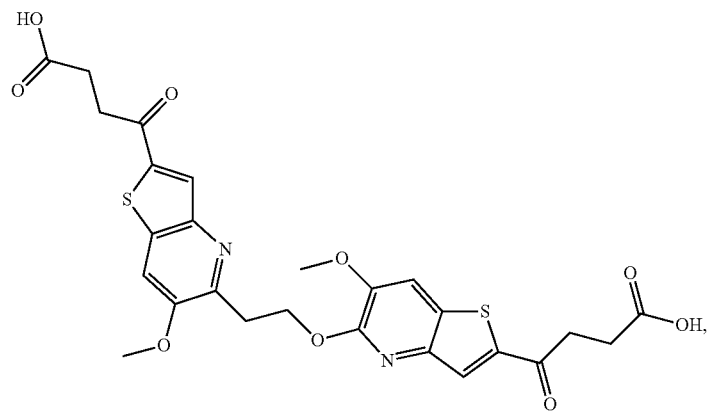

-continued
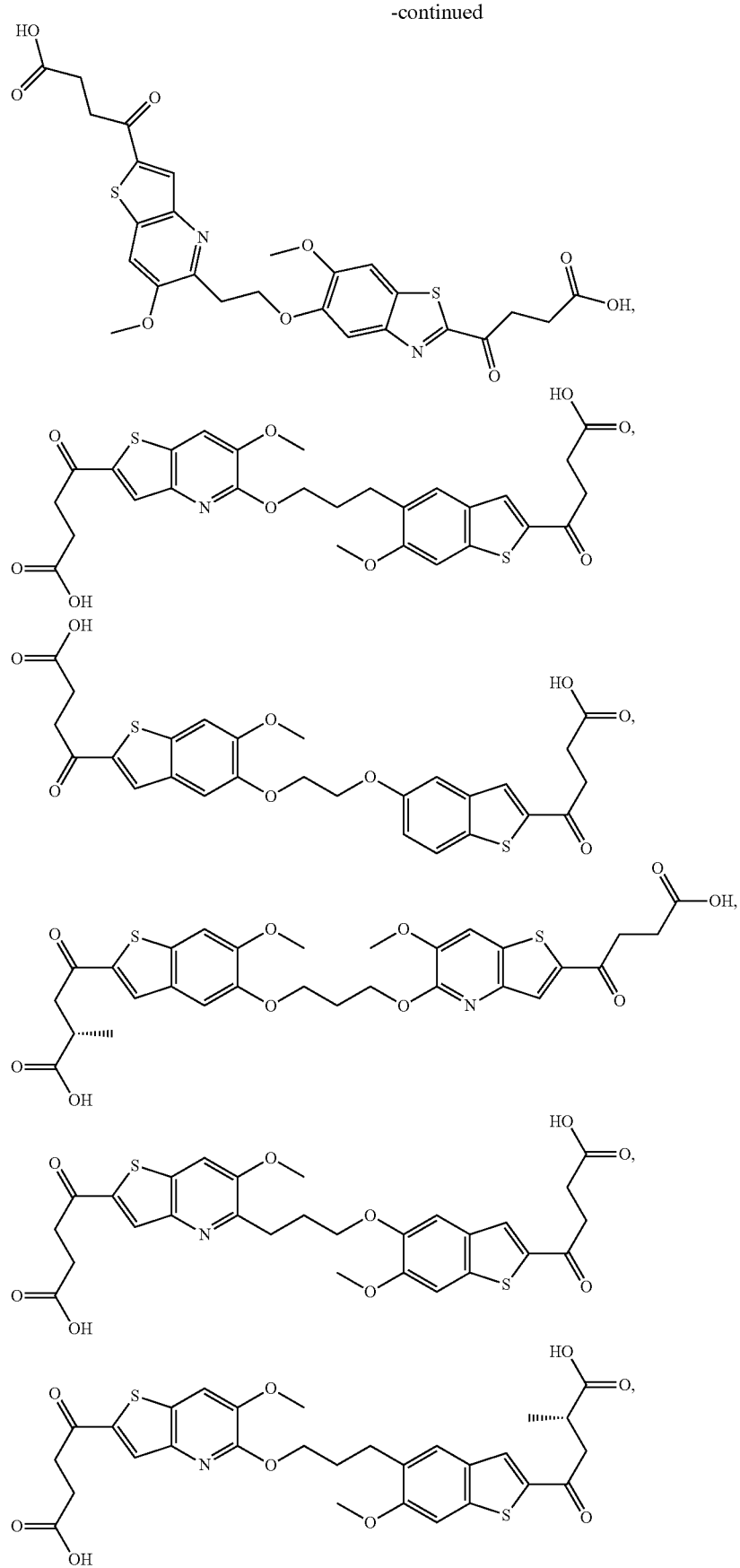

-continued
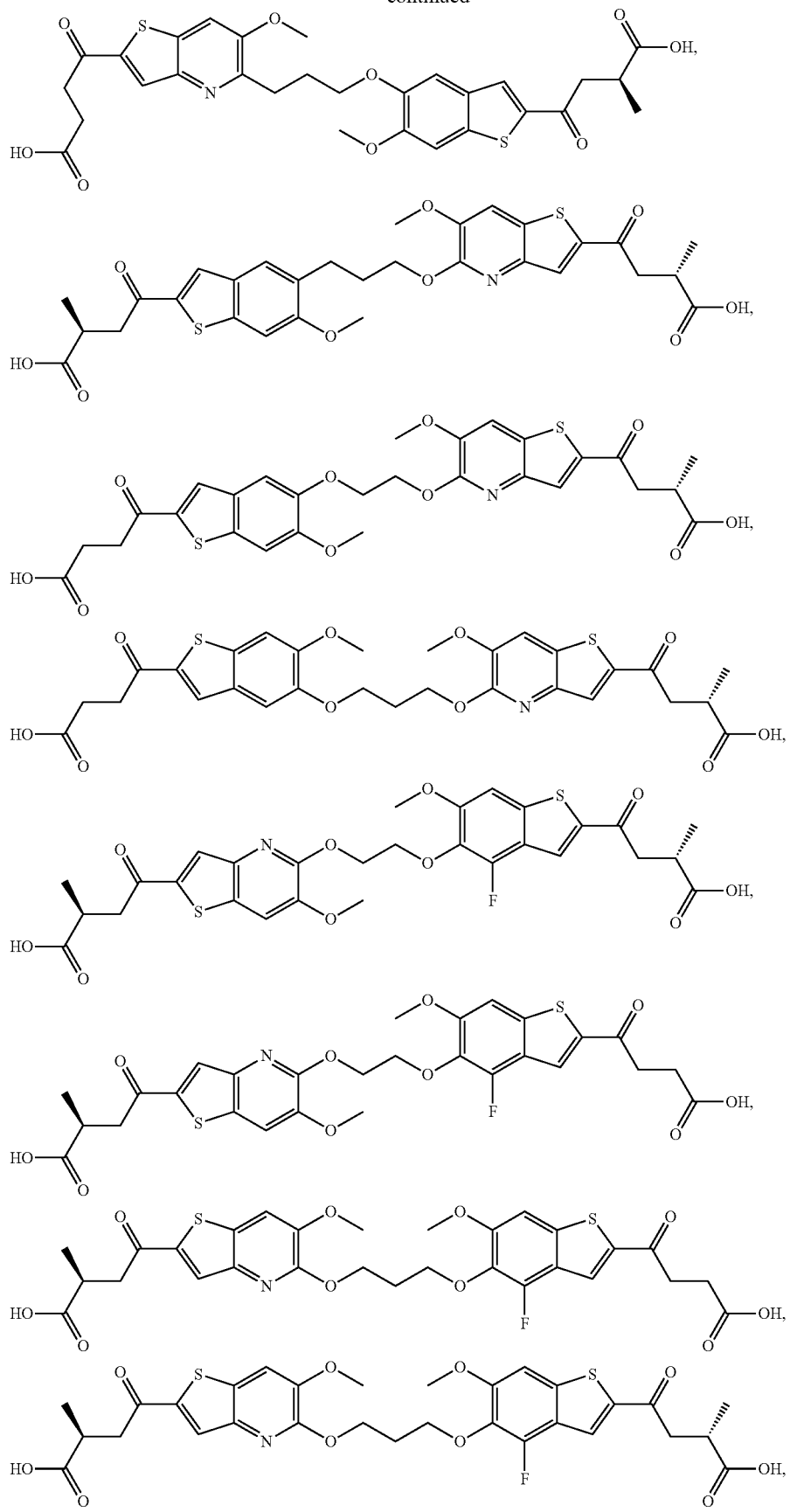

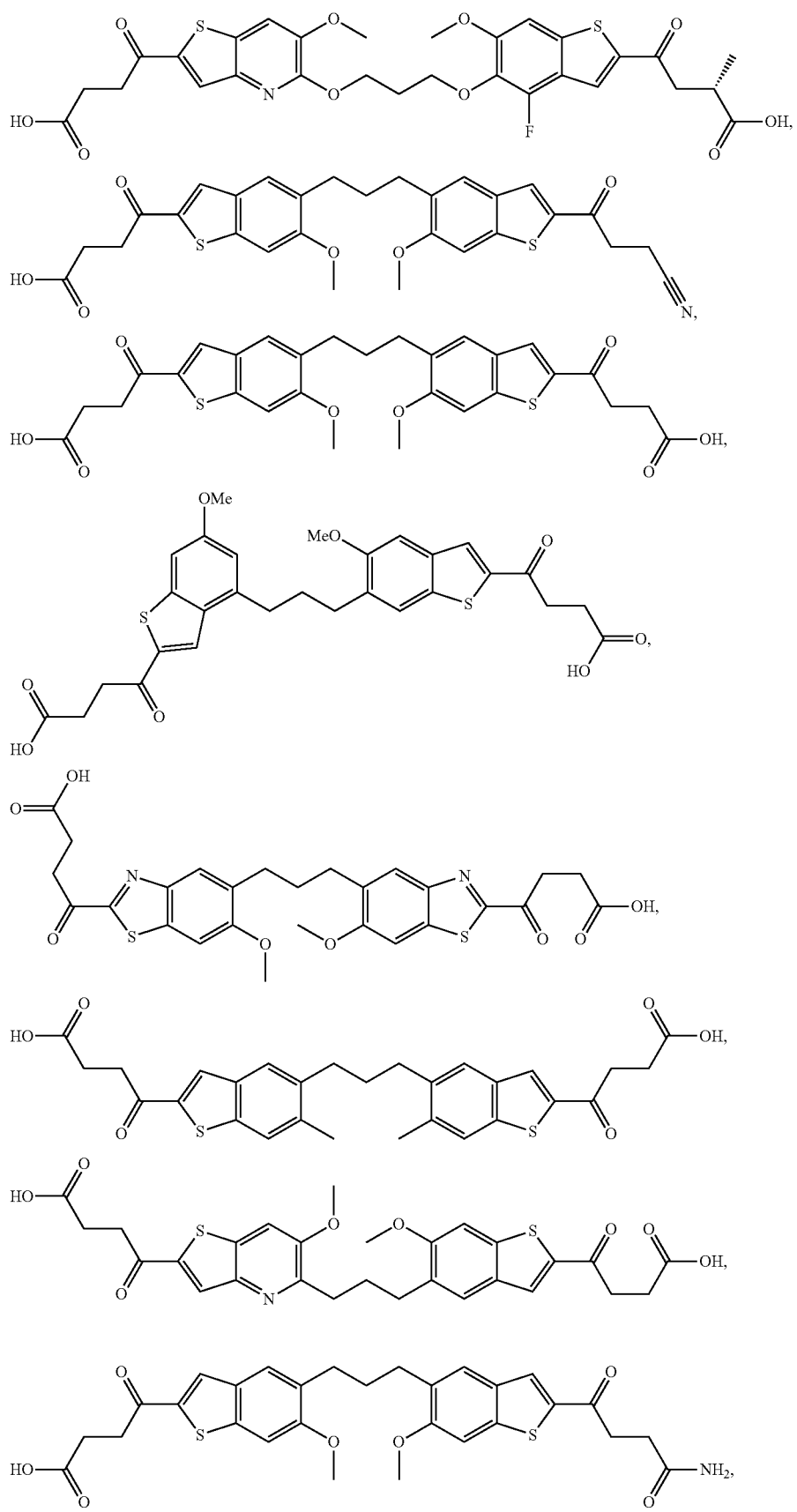

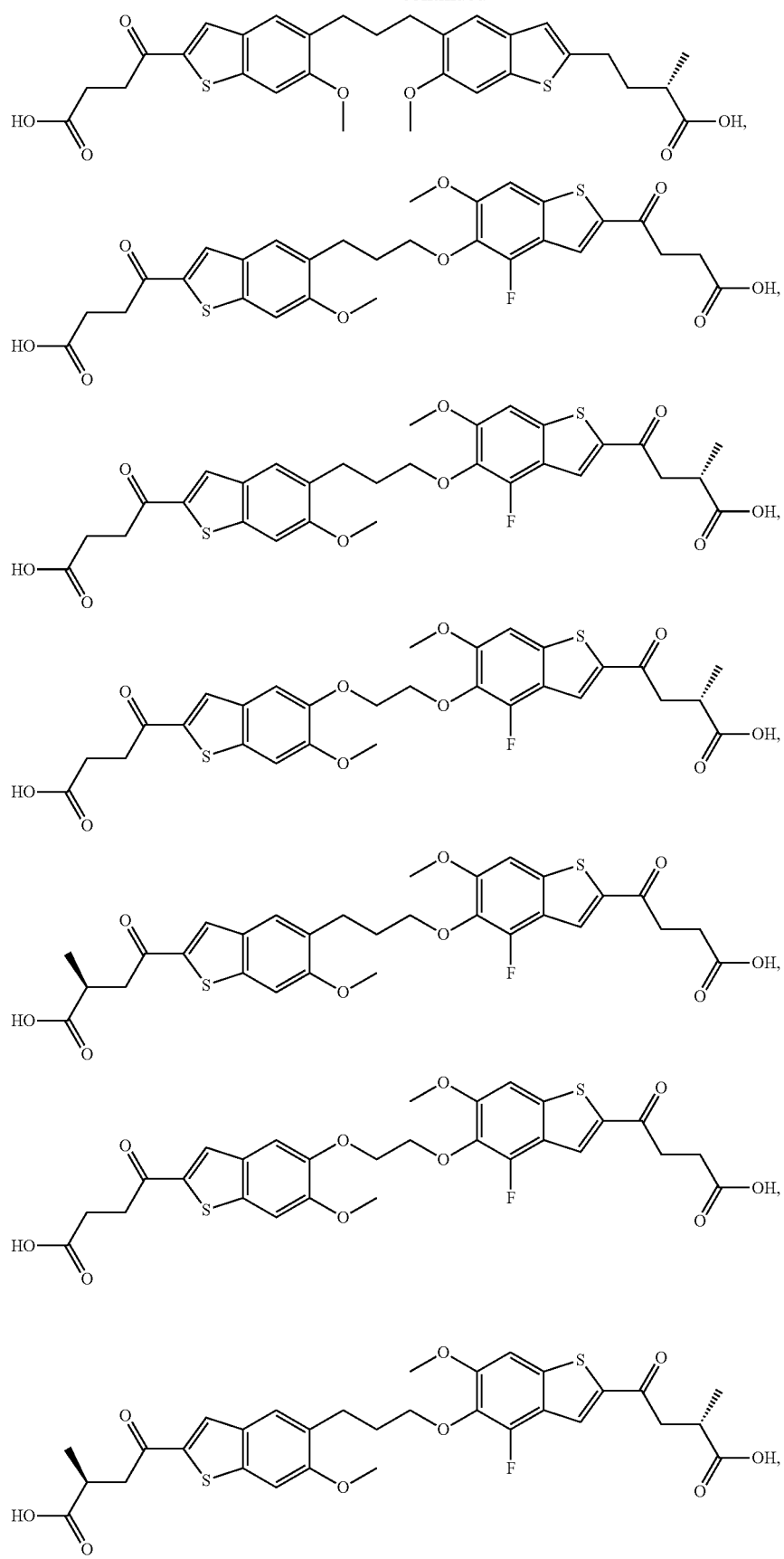

-continued
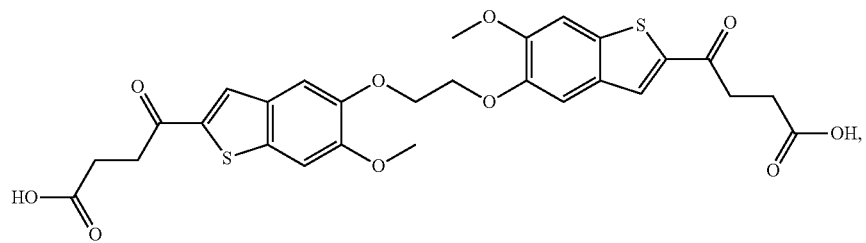
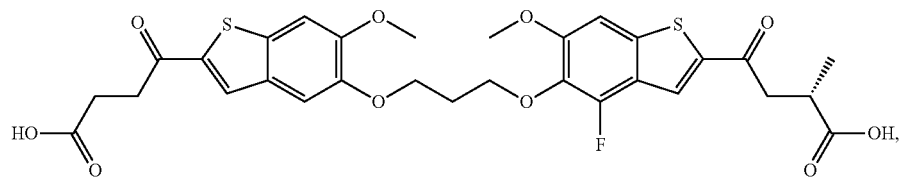
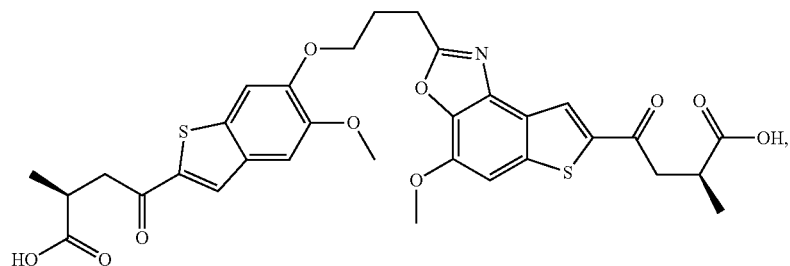
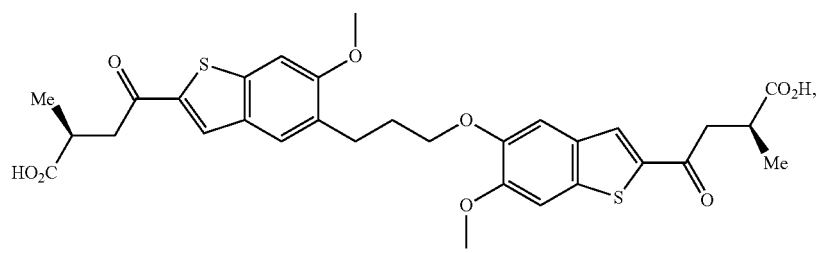
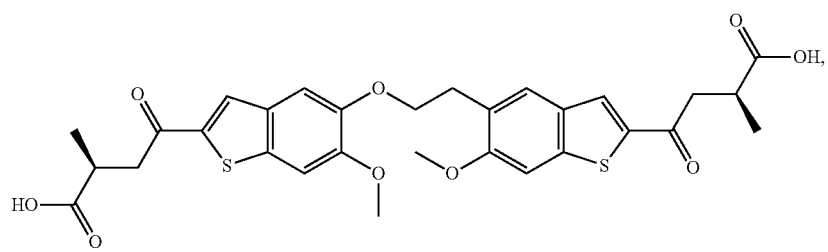
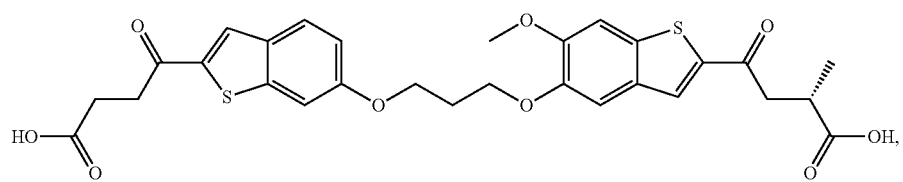
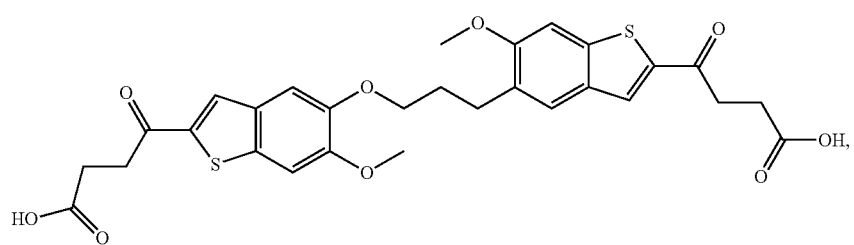

-continued
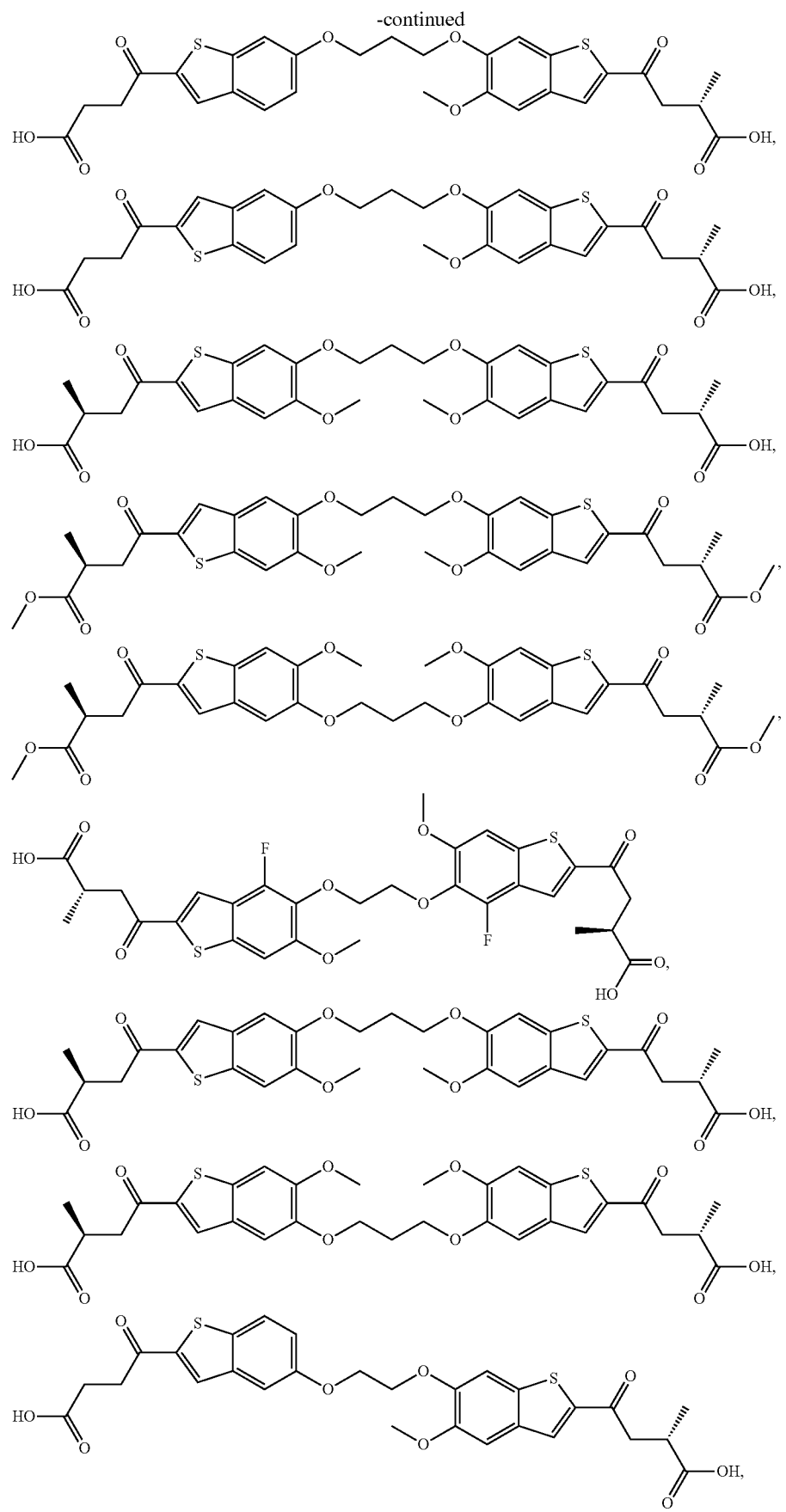

-continued
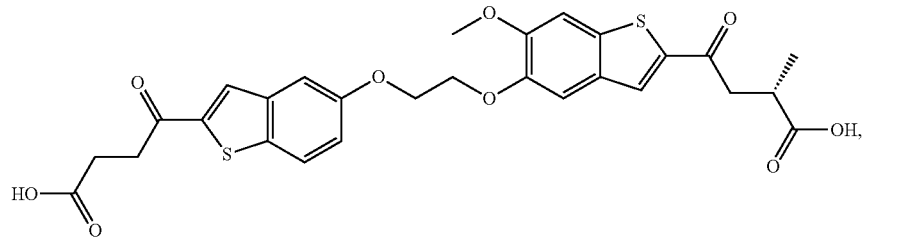
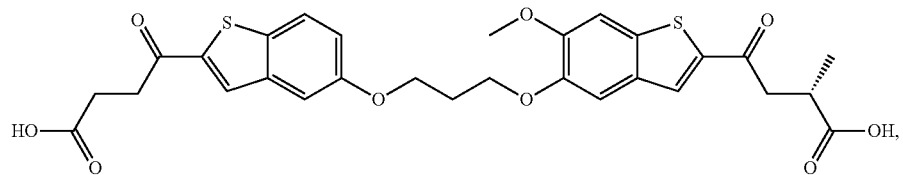
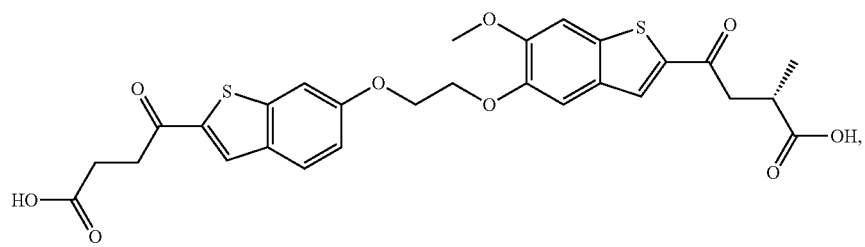
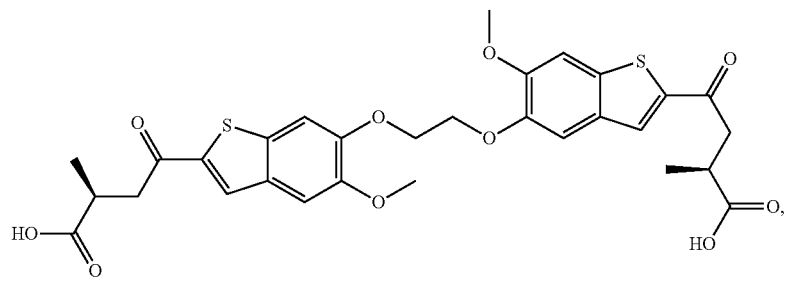
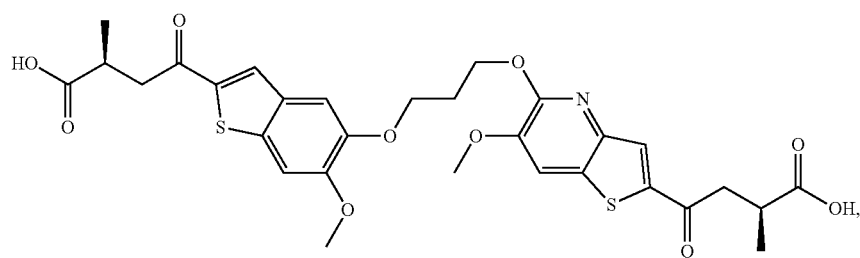
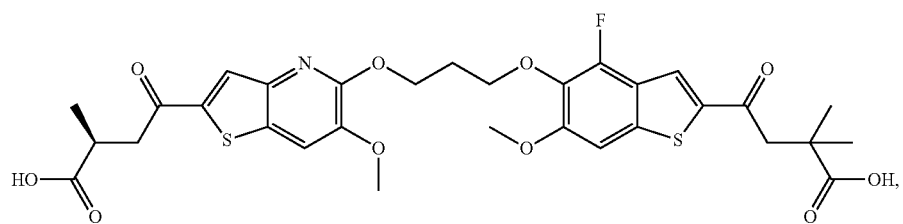
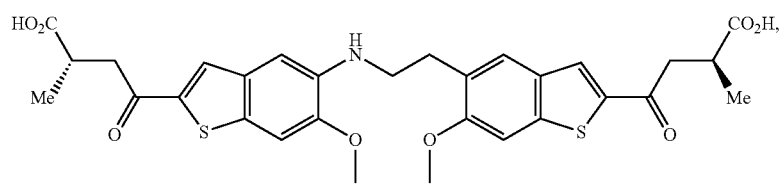

-continued
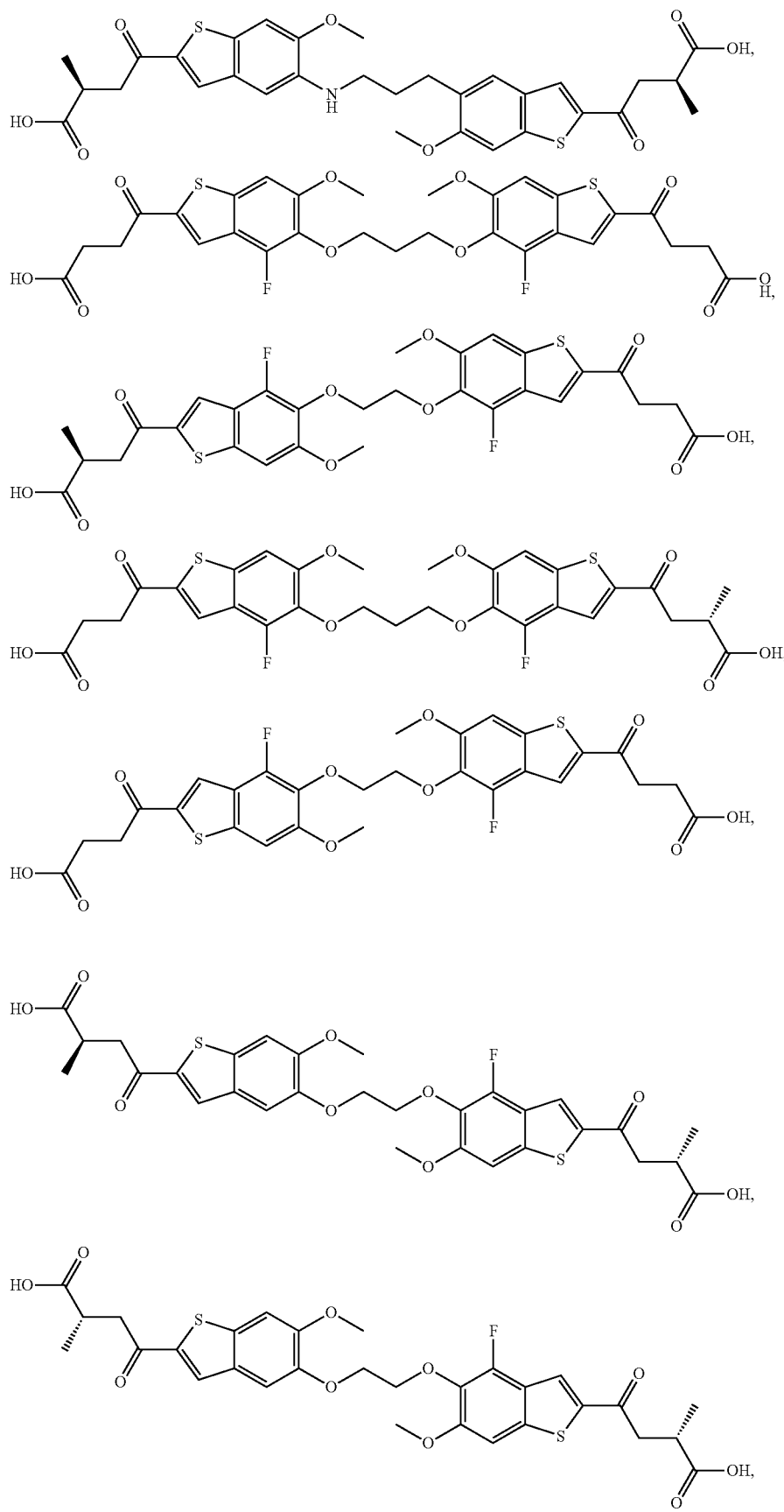

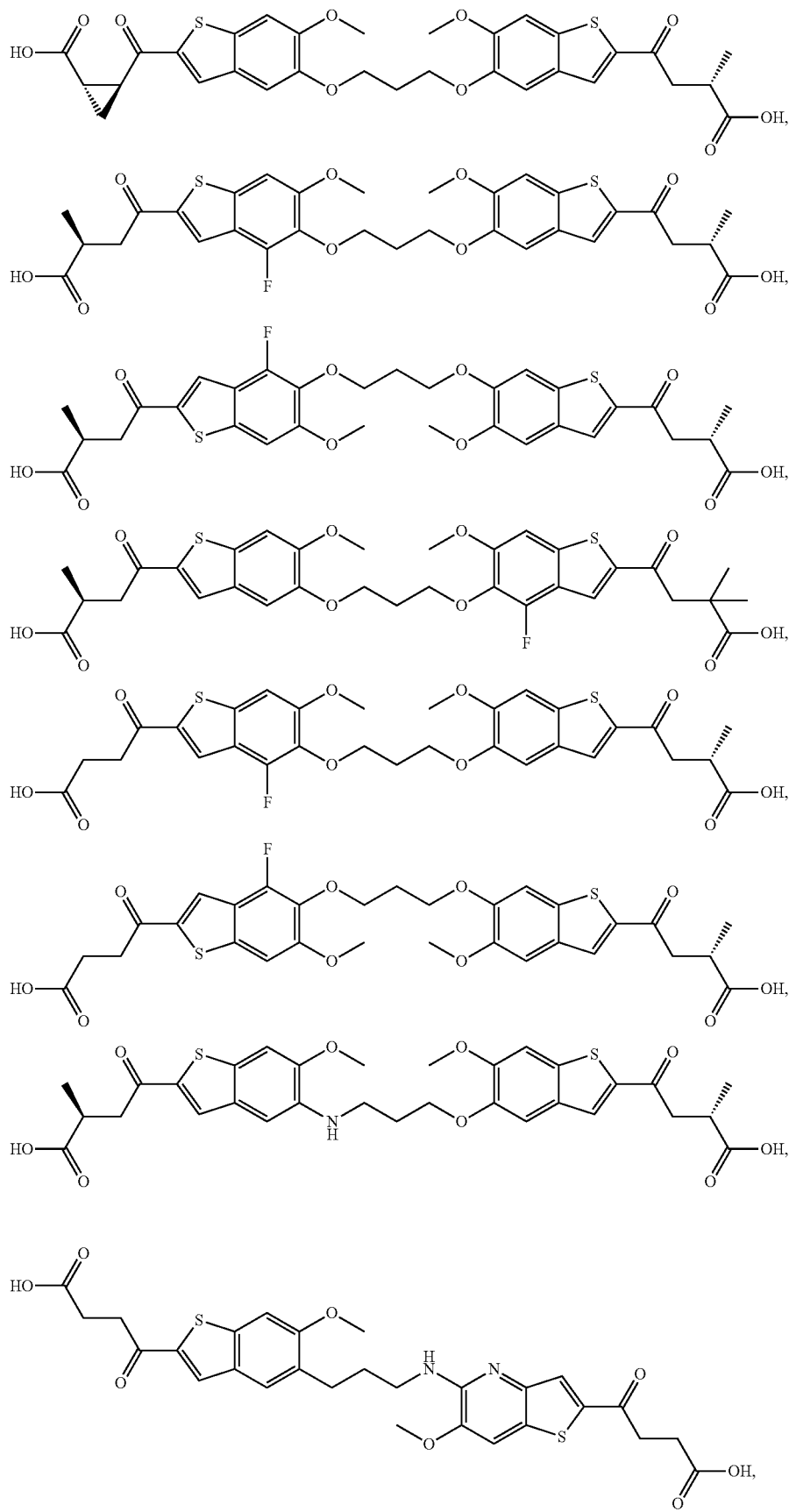

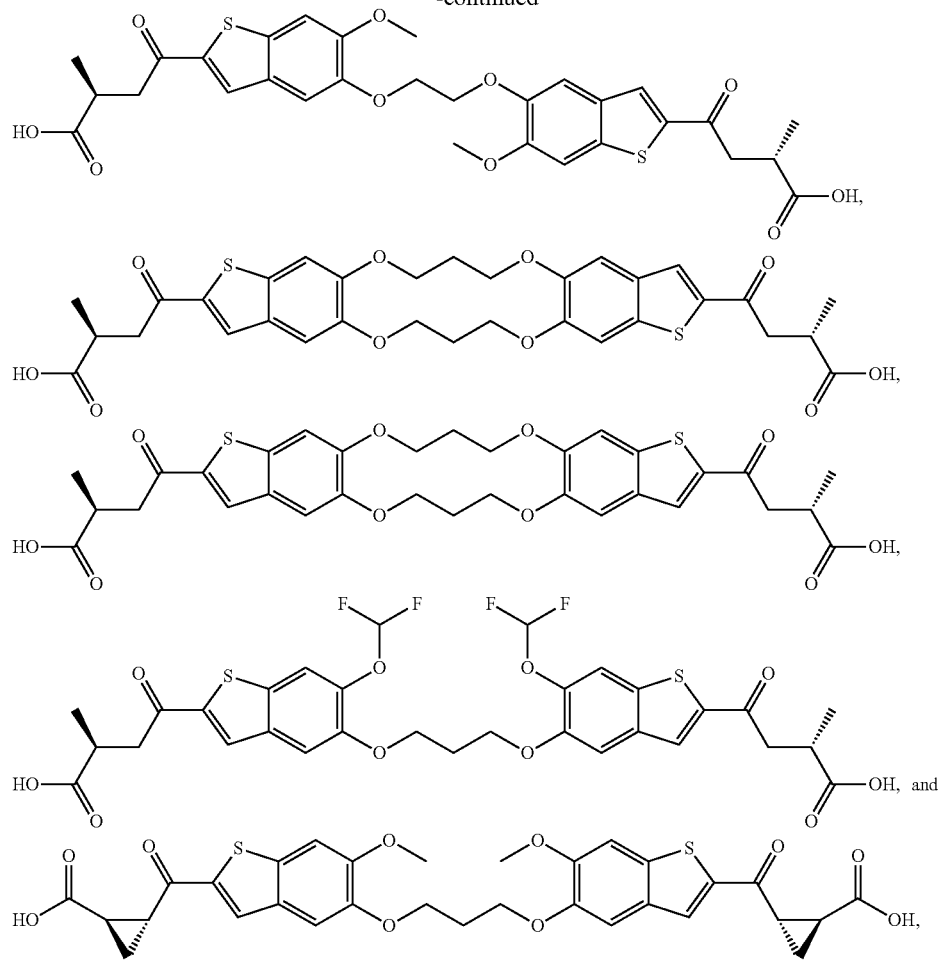

and pharmaceutically acceptable salts thereof.

A first aspect of the seventh embodiment relates to methods of inducing an immune response in a patient in need of therapy, comprising administering a therapeutically effective amount of a compound according to the seventh embodiment above or a pharmaceutically acceptable salt thereof to the patient.

A second aspect of the seventh embodiment relates to methods of inducing an immune response in a patient in need of therapy, comprising administering a therapeutically effective amount of a composition comprising a compound according to the seventh embodiment above or a pharmaceutically acceptable salt thereof to the patient.

A third aspect of the seventh embodiment relates to methods of inducing STING-dependent type I interferon production in a patient in need of therapy, comprising administering a therapeutically effective amount of a compound according to the seventh embodiment above or a pharmaceutically acceptable salt thereof to the patient.

A fourth aspect of the seventh embodiment relates to methods of inducing STING-dependent type I interferon production in a patient in need of therapy, comprising administering a therapeutically effective amount of a composition comprising a compound according to the seventh embodiment above or a pharmaceutically acceptable salt thereof to the patient.

A fifth aspect of the seventh embodiment relates to methods of inducing STING-dependent cytokine production in a patient in need of therapy, comprising administering a therapeutically effective amount of a compound according to the seventh embodiment above or a pharmaceutically acceptable salt thereof to the patient.

A sixth aspect of the seventh embodiment relates to methods of inducing a STING-dependent cytokine production in a patient in need of therapy, comprising administering a therapeutically effective amount of a composition comprising a compound according to the seventh embodiment above or a pharmaceutically acceptable salt thereof to the patient.

A seventh aspect of the seventh embodiment relates to methods of treating a cell proliferation disorder in a patient in need of therapy, comprising administering a therapeutically effective amount of a compound according to the seventh embodiment above or a pharmaceutically acceptable salt thereof to the patient. In instances of the seventh aspect of the seventh embodiment, the cell proliferation disorder is cancer.

An eighth aspect of the seventh embodiment relates to methods of treating a cell proliferation disorder in a patient in need of therapy, said method comprising administering a therapeutically effective amount of a composition comprising a compound according to the seventh embodiment above to the patient. In instances of this eighth aspect of the seventh embodiment, the cell proliferation disorder is cancer.

An eighth embodiment relates to a compound selected from the exemplary species depicted in Examples 1 through 190 shown below.

A first aspect of the eighth embodiment relates to methods of inducing an immune response in a patient in need of therapy, comprising administering a therapeutically effective amount of a compound according to the eighth embodiment above or a pharmaceutically acceptable salt thereof to the patient.

A second aspect of the eighth embodiment relates to methods of inducing an immune response in a patient in need of therapy, comprising administering a therapeutically effective amount of a composition comprising a compound according to the eighth embodiment above or a pharmaceutically acceptable salt thereof to the patient.

A third aspect of the eighth embodiment relates to methods of inducing STING-dependent type I interferon production in a patient in need of therapy, comprising administering a therapeutically effective amount of a compound according to the eighth embodiment above or a pharmaceutically acceptable salt thereof to the patient.

A fourth aspect of the eighth embodiment relates to methods of inducing STING-dependent type I interferon production in a patient in need of therapy, comprising administering a therapeutically effective amount of a composition comprising a compound according to the eighth embodiment above or a pharmaceutically acceptable salt thereof to the patient.

A fifth aspect of the eighth embodiment relates to methods of inducing STING-dependent cytokine production in a patient in need of therapy, comprising administering a therapeutically effective amount of a compound according to the eighth embodiment above or a pharmaceutically acceptable salt thereof to the patient.

A sixth aspect of the eighth embodiment relates to methods of inducing STING-dependent cytokine production in a patient in need of therapy, comprising administering a therapeutically effective amount of a composition comprising a compound according to the eighth embodiment above or a pharmaceutically acceptable salt thereof to the patient.

A seventh aspect of the eighth embodiment relates to methods of treating a cell proliferation disorder in a patient in need of therapy, comprising administering a therapeutically effective amount of a compound according to the eighth embodiment above or a pharmaceutically acceptable salt thereof to the patient. In instances of the seventh aspect of the eighth embodiment, the cell proliferation disorder is cancer.

An eighth aspect of the eighth embodiment relates to methods of treating a cell proliferation disorder in a patient in need of therapy, said method comprising administering a therapeutically effective amount of a composition comprising a compound according to the eighth embodiment above to the patient. In instances of this eighth aspect of the eighth embodiment, the cell proliferation disorder is cancer.

Other embodiments of the present disclosure include the following:

(a) A pharmaceutical composition comprising an effective amount of a compound of general formula (I), compound of general formula (II), compound of general formula (III), compound of general formula (IV), compound of general formula (V), compound of general formula (VI), or a pharmaceutically acceptable salt thereof, and a pharmaceutically acceptable carrier.

(b) The pharmaceutical composition of (a), further comprising an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents.

(c) A pharmaceutical combination that is (i) a compound of general formula (I), compound of general formula (II), compound of general formula (III), compound of general formula (IV), compound of general formula (V), compound of general formula (VI), or a pharmaceutically acceptable salt thereof, and (ii) an active agent selected from the group consisting of STING agonist compounds, anti-viral compounds, antigens, adjuvants, CTLA-4 and PD-1 pathway antagonists and other immunomodulatory agents, lipids, liposomes, peptides, anti-cancer and chemotherapeutic agents; wherein the compound of general formula (I), compound of general formula (II), compound of general formula (III), compound of general formula (IV), compound of general formula (V), compound of general formula (VI), or pharmaceutically acceptable salt thereof, and the active agent are each employed in an amount that renders the combination effective for inducing an immune response in a patient.

(d) A method of inducing an immune response in a patient, which comprises administering to the patient in need of therapy a therapeutically effective amount of a compound of general formula (I), compound of general formula (II), compound of general formula (III), compound of general formula (IV), compound of general formula (V), compound of general formula (VI), or a pharmaceutically acceptable salt thereof.

(e) A method of inducing an immune response in a patient, which comprises administering to the patient in need of therapy a therapeutically effective amount of a composition of (a), a composition of (b), or a combination of (c).

(f) A method of inducing STING-dependent type I interferon production in a patient, which comprises administering to the patient in need of therapy a therapeutically effective amount of a compound of general formula (I), compound of general formula (II), compound of general formula (III), compound of general formula (IV), compound of general formula (V), compound of general formula (VI), or a pharmaceutically acceptable salt thereof.

A method of inducing STING-dependent type I interferon production in a patient, which comprises administering to the patient in need of therapy a therapeutically effective amount of a composition of (a), a composition of (b), or a combination of (c).

(h) A method of inducing STING-dependent cytokine production in a patient, which comprises administering to the patient in need of therapy a therapeutically effective amount of a compound of general formula (I), compound of general formula (II), compound of general formula (III), compound of general formula (IV), compound of general formula (V), compound of general formula (VI), or a pharmaceutically acceptable salt thereof.

(i) A method of inducing STING-dependent cytokine production in a patient, which comprises administering to the patient in need of therapy a therapeutically effective amount of a composition of (a), a composition of (b), or a combination of (c).

(j) A method of treating a cell proliferation disorder in a patient in need of therapy, said method comprising administering a therapeutically effective amount of a compound of general formula (I), compound of general formula (II), compound of general formula (III), compound of general formula (IV), compound of general formula (V), compound of general formula (VI), or a pharmaceutically acceptable salt thereof to the patient;

(k) The method of (j), wherein the cell proliferation disorder is cancer.

(l) A method of treating a cell proliferation disorder in a patient in need of therapy, said method comprising administering a therapeutically effective amount of a composition of (a), a composition of (b), or a combination of (c) to the patient.

(m) The method of (l), wherein the cell proliferation disorder is cancer.

The present disclosure also includes a compound of the present disclosure for use (i) in, (ii) as a medicament for, or (iii) in the preparation of a medicament for: (a) inducing an immune response in a patient, or (b) inducing STING-dependent cytokine production in a patient. In these uses, the compounds of the present disclosure can optionally be employed in combination with one or more active agents selected from STING agonist compounds, anti-viral compounds, antigens, adjuvants, CTLA-4 and PD-1 pathway antagonists and other immunomodulatory agents, lipids, liposomes, peptides, anti-cancer agents, and chemotherapeutic agents.

Additional embodiments of the disclosure include the pharmaceutical compositions, combinations, and methods set forth in (a) through (m) above, and the uses set forth in the preceding paragraph, wherein the compound of the present disclosure employed therein is a compound of one of the embodiments, aspects, instances, occurrences, or features of the compounds described above. In all of these embodiments, the compound may optionally be used in the form of a pharmaceutically acceptable salt, as appropriate.

In the embodiments of the compound provided above, it is to be understood that each embodiment may be combined with one or more other embodiments, to the extent that such a combination provides a stable compound and is consistent with the description of the embodiments. It is further to be understood that the embodiments of compositions and methods provided as (a) through (m) above are understood to include all embodiments of the compounds, including such embodiments as result from combinations of embodiments.

The term "subject" (alternatively "patient") as used herein refers to a mammal that has been the object of treatment, observation, or experiment. The mammal may be male or female. The mammal may be one or more selected from the group consisting of humans, bovine (e.g., cows), porcine (e.g., pigs), ovine (e.g., sheep), capra (e.g., goats), equine (e.g., horses), canine (e.g., domestic dogs), feline (e.g., house cats), Lagomorpha (rabbits), rodents (e.g., rats or mice), *Procyon lotor* (e.g., raccoons). In particular embodiments, the subject is human.

As used herein, the term "immune response" relates to any one or more of the following: specific immune response, non-specific immune response, both specific and non-specific response, innate response, primary immune response, adaptive immunity, secondary immune response, memory immune response, immune cell activation, immune cell proliferation, immune cell differentiation, and cytokine expression. In certain embodiments, a compound of general formula (I), compound of general formula (II), compound of general formula (III), compound of general formula (IV), compound of general formula (V), compound of general formula (VI), or a pharmaceutically acceptable salt of the foregoing, is administered in conjunction with one or more additional therapeutic agents including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc. In certain embodiments, a compound of general formula (I), compound of general formula (II), compound of general formula (III), compound of general formula (IV), compound of general formula (V), compound of general formula (VI), or a pharmaceutically acceptable salt of the foregoing, is administered in conjunction with one or more additional compositions including anti-viral compounds, vaccines intended to stimulate an immune response to one or more predetermined antigens, adjuvants, CTLA-4 and PD-1 pathway antagonists and other immunomodulatory agents, lipids, liposomes, peptides, anti-cancer agents, and chemotherapeutic agents, etc.

Compounds

As used herein, the term "alkyl" refers to a monovalent straight or branched chain, saturated aliphatic hydrocarbon radical having a number of carbon atoms in the specified range. Thus, for example, "$C_{1-6}$ alkyl" (or "$C_1$-$C_6$ alkyl") refers to any of the hexyl alkyl and pentyl alkyl isomers as well as n-, iso-, sec- and tert-butyl, n- and iso-propyl, ethyl, and methyl. As another example, "$C_{14}$ alkyl" refers to n-, iso-, sec- and tert-butyl, n- and isopropyl, ethyl, and methyl.

As used herein, the term "alkylene" refers to a bivalent straight chain, saturated aliphatic hydrocarbon radical having a number of carbon atoms in the specified range.

As used herein, the term "alkenyl" refers to a monovalent straight or branched chain, unsaturated aliphatic hydrocarbon radical having a number of carbon atoms in the specified range and including one or more double bonds.

As used herein, the term "alkenylene" refers to a bivalent straight chain, unsaturated aliphatic hydrocarbon radical having a number of carbon atoms in the specified range and including one or more double bonds.

As used herein, the term "alkynyl" refers to a monovalent straight or branched chain, unsaturated aliphatic hydrocarbon radical having a number of carbon atoms in the specified range and including one or more triple bonds.

As used herein, the term "alkynylene" refers to a bivalent straight chain, unsaturated aliphatic hydrocarbon radical having a number of carbon atoms in the specified range and including one or more triple bonds.

As used herein, the term "halogen" (or "halo") refers to fluorine, chlorine, bromine, and iodine (alternatively fluoro, chloro, bromo, and iodo or F, Cl, Br, and I).

As used herein, the term "haloalkyl" refers to an alkyl group as defined above in which one or more of the hydrogen atoms have been replaced with a halogen. Thus, for example, "$C_{1-6}$ haloalkyl" (or "$C_1$-$C_6$ haloalkyl") refers to a $C_1$ to $C_6$ linear or branched alkyl group as defined above with one or more halogen substituents. The term "fluoroalkyl" has an analogous meaning except the halogen substituents are restricted to fluoro. Suitable fluoroalkyls include the series $(CH_2)_{0-4}CF_3$ (i.e., trifluoromethyl, 2,2,2-trifluoroethyl, 3,3,3-trifluoro-n-propyl, etc.).

As used herein, the term "haloalkylene" refers to an alkylene group as defined above in which one or more of the hydrogen atoms have been replaced by a halogen, as in the haloalkyl group defined above.

As used herein, the term "haloalkenyl" refers to an alkenyl group as defined above in which one or more of the hydrogen atoms have been replaced with a halogen.

As used herein, the term "haloalkenylene" refers to an alkenylene group as defined above in which one or more of the hydrogen atoms have been replaced by a halogen.

As used herein, the term "haloalkynyl" refers to an alkynyl group as defined above in which one or more of the hydrogen atoms have been replaced with a halogen.

As used herein, the term "haloalkynylene" refers to an alkynylene group as defined above in which one or more of the hydrogen atoms have been replaced by a halogen.

As used herein, the term "alkoxy" as used herein, alone or in combination, includes an alkyl group connected to the oxy connecting atom. The term "alkoxy" also includes alkyl ether groups, where the term "alkyl" is defined above, and "ether" means two alkyl groups with an oxygen atom between them. Examples of suitable alkoxy groups include methoxy, ethoxy, n-propoxy, i-propoxy, n-butoxy, s-butoxy, t-butoxy, methoxymethane (also referred to as "dimethyl ether"), and methoxyethane (also referred to as "ethyl methyl ether").

As used herein, the term "cycloalkyl" refers to a saturated hydrocarbon containing one ring having a specified number of carbon atoms. Examples of cycloalkyl include cyclopropyl, cyclobutyl, cyclopentyl, and cyclohexyl.

As used herein, the term "heterocycle", "heterocyclyl", or "heterocyclic", as used herein, represents a stable 3- to 6-membered monocyclic that is either saturated or unsaturated, and that consists of carbon atoms and from one to two heteroatoms selected from the group consisting of N, O, and S. The heterocyclic ring may be attached at any heteroatom or carbon atom which results in the creation of a stable structure. The term includes heteroaryl moieties. Examples of such heterocyclic elements include, but are not limited to, azepinyl, benzimidazolyl, benzisoxazolyl, benzofurazanyl, benzopyranyl, benzothiopyranyl, benzofuryl, benzothiazolyl, benzothienyl, benzoxazolyl, chromanyl, cinnolinyl, dihydrobenzofuryl, dihydrobenzothienyl, dihydrobenzothiopyranyl, dihydrobenzothiopyranyl sulfone, 1,3-dioxolanyl, furyl, imidazolidinyl, imidazolinyl, imidazolyl, indolinyl, indolyl, isochromanyl, isoindolinyl, isoquinolinyl, isothiazolidinyl, isothiazolyl, isothiazolidinyl, morpholinyl, naphthyridinyl, oxadiazolyl, 2-oxoazepinyl, oxazolyl, 2-oxopiperazinyl, 2-oxopiperdinyl, 2-oxopyrrolidinyl, piperidyl, piperazinyl, pyridyl, pyrazinyl, pyrazolidinyl, pyrazolyl, pyridazinyl, pyrimidinyl, pyrrolidinyl, pyrrolyl, quinazolinyl, quinolinyl, quinoxalinyl, tetrahydrofuryl, tetrahydroisoquinolinyl, tetrahydroquinolinyl, thiamorpholinyl, thiamorpholinyl sulfoxide, thiazolyl, thiazolinyl, thienofuryl, thienothienyl, triazolyl and thienyl.

As used herein, the term "fused ring" refers to a cyclic group formed by substituents on separate atoms in a straight or branched alkane, or to a cyclic group formed by substituents on separate atoms in another ring.

As used herein, the term "spirocycle" or "spirocyclic ring" refers to a pendant cyclic group formed by substituents on a single atom.

Unless expressly stated to the contrary, all ranges cited herein are inclusive; i.e., the range includes the values for the upper and lower limits of the range as well as all values in between. As an example, temperature ranges, percentages, ranges of equivalents, and the like described herein include the upper and lower limits of the range and any value in the continuum there between. Numerical values provided herein, and the use of the term "about", may include variations of 1%, +2%, +3%, +4%, +5%, +10%, +15%, and +20% and their numerical equivalents.

As used herein, the term "one or more" item includes a single item selected from the list as well as mixtures of two or more items selected from the list.

In the compounds of general formula (I), compounds of general formula (II), compounds of general formula (III), compounds of general formula (IV), compounds of general formula (V), compounds of general formula (VI), and pharmaceutically acceptable salts of the foregoing, the atoms may exhibit their natural isotopic abundances, or one or more of the atoms may be artificially enriched in a particular isotope having the same atomic number, but an atomic mass or mass number different from the atomic mass or mass number predominantly found in nature. The present disclosure is meant to include all suitable isotopic variations of the compounds of general formula (I), compounds of general formula (II), compounds of general formula (III), compounds of general formula (IV), compounds of general formula (V), compounds of general formula (VI), and pharmaceutically acceptable salts of the foregoing. For example, different isotopic forms of hydrogen (H) include protium ($^1H$), deuterium ($^2H$), and tritium ($^3H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched the compounds of general formula (I), compounds of general formula (II), compounds of general formula (III), compounds of general formula (IV), compounds of general formula (V), compounds of general formula (VI), and pharmaceutically acceptable salts of the foregoing, can be prepared without undue experimentation by conventional techniques well known to those skilled in the art or by processes analogous to those described in the Schemes and Examples herein using appropriate isotopically-enriched reagents and/or intermediates.

In particular embodiments of the compounds of general formula (I), compounds of general formula (II), compounds of general formula (III), compounds of general formula (IV), compounds of general formula (V), compounds of general formula (VI), and pharmaceutically acceptable salts of the foregoing, the compounds are isotopically enriched with deuterium. In aspects of these embodiments, one or more of $R^1$, $R^2$, $R^3$, $R^6$, $R^8$, and $R^9$ may include deuterium.

As shown in the general structural formulas and the structures of specific compounds as provided herein, a straight line at a chiral center includes both (R) and (S) stereoisomers and mixtures thereof. Also, unless otherwise specified (e.g., 100% purified compound), reference to a particular stereochemistry at a position provides a compound having the indicated stereochemistry but does not exclude the presence of stereoisomers having different stereochemistry at the indicated position.

Recitation or depiction of a specific compound in the claims (i.e., a species) without a specific stereoconfiguration designation, or with such a designation for less than all chiral centers, is intended to encompass, for such undesignated chiral centers, the racemate, racemic mixtures, each individual enantiomer, a diastereoisomeric mixture and each individual diastereomer of the compound where such forms are possible due to the presence of one or more asymmetric centers. The separation of a mixture of stereoisomers can be carried out at an intermediate step during the synthesis of a compound of general formula (I), compound of general formula (II), compound of general formula (III), compound of general formula (IV), compound of general formula (V), compound of general formula (VI), or a pharmaceutically acceptable salt of the foregoing, or it can be done on a final racemic product. Absolute stereochemistry may be determined by X-ray crystallography of crystalline products or crystalline intermediates, which are derivatized, if necessary, with a reagent containing a stereogenic center of known configuration. Alternatively, absolute stereochemistry may be determined by Vibrational Circular Dichroism (VCD) spectroscopy analysis. The present invention includes all such isomers, as well as salts, solvates (including hydrates), and solvated salts of such racemates, enantiomers, diastereomers, tautomers, and mixtures thereof.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cis/trans isomerism, the invention includes both the cis form and the trans form, as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of a compound of general formula (I), compound of general formula (II), compound of general formula (III), compound of general formula (IV), compound of general formula (V), compound of general formula (VI), or a pharmaceutically acceptable salt of the foregoing, or it can be done on a final racemic product. Absolute stereochemistry may be determined by X-ray crystallography of crystalline products or crystalline intermediates that are derivatized, if necessary, with a reagent containing a stereogenic center of known configuration. Unless a particular isomer, salt, solvate (including hydrates) or solvated salt of such racemate, enantiomer, or diastereomer is indicated, the present invention includes all such isomers, as well as salts, solvates (including hydrates), and solvated salts of such racemates, enantiomers, diastereomers, and mixtures thereof.

The term "compound" refers to the compound and, in certain embodiments, to the extent they are stable, any hydrate or solvate thereof. A hydrate is the compound complexed with water, and a solvate is the compound complexed with a solvent, which may be an organic solvent or an inorganic solvent.

A "stable" compound is a compound that can be prepared and isolated and whose structure and properties remain or can be caused to remain essentially unchanged for a period of time sufficient to allow use of the compound for the purposes described herein (e.g., therapeutic administration to a patient). The compounds of the present invention are limited to stable compounds embraced by general formula (I), general formula (II), general formula (III), general formula (IV), general formula (V), general formula (VI), or pharmaceutically acceptable salts thereof.

Salts

As indicated above, the compounds of the present invention can be employed in the form of pharmaceutically acceptable salts. Those skilled in the art will recognize those instances in which the compounds of the invention may form salts. Examples of such compounds are described herein by reference to possible salts. Such reference is for illustration only.

Pharmaceutically acceptable salts can be used with compounds for treating patients. Non-pharmaceutical salts may, however, be useful in the preparation of intermediate compounds.

The term "pharmaceutically acceptable salt" refers to a salt (including an inner salt such as a zwitterion) that possesses effectiveness similar to the parent compound and that is not biologically or otherwise undesirable (e.g., is neither toxic nor otherwise deleterious to the recipient thereof). Thus, an embodiment of the invention provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. Salts of compounds of the invention may be formed by methods known to those of ordinary skill in the art, for example, by reacting a compound of the invention with an amount of acid or base, such as an equivalent amount, in a medium such as one in which the salt precipitates or in aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates ("mesylates"), naphthalenesulfonates, nitrates, oxalates, phosphates, propionates, salicylates, succinates, sulfates, tartarates, thiocyanates, toluenesulfonates ("tosylates") and the like. Suitable salts include acid addition salts that may, for example, be formed by mixing a solution of a compound with a solution of a pharmaceutically acceptable acid such as hydrochloric acid, sulfuric acid, acetic acid, trifluoroacetic acid, or benzoic acid. Additionally, acids that are generally considered suitable for the formation of pharmaceutically useful salts from basic pharmaceutical compounds are discussed, for example, by P. Stahl et al, Camille G. (eds.), *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamine, t-butyl amine, choline, and salts with amino acids such as arginine, lysine and the like. Basic nitrogen-containing groups may be quaternized with agents such as lower alkyl halides (e.g., methyl, ethyl, and butyl chlorides, bromides and iodides), dialkyl sulfates (e.g., dimethyl, diethyl, and dibutyl sulfates), long chain halides (e.g., decyl, lauryl, and stearyl chlorides, bromides and iodides), aralkyl halides (e.g., benzyl and phenethyl bromides), and others. Compounds carrying an acidic moiety can be mixed with suitable pharmaceutically acceptable salts to provide, for example, alkali metal salts (e.g., sodium or potassium salts), alkaline earth metal salts (e.g., calcium or magnesium salts), and salts formed with suitable organic ligands such as quaternary ammonium salts. Also, in the case of an acid (—COOH) or alcohol group being present, pharmaceutically acceptable esters can be employed to modify the solubility or hydrolysis characteristics of the compound.

All such acid salts and base salts are intended to be pharmaceutically acceptable salts within the scope of the invention and all acid and base salts are considered equivalent to the free forms of the corresponding compounds for purposes of the invention.

In addition, when a compound of the invention contains both a basic moiety, such as, but not limited to an aliphatic primary, secondary, tertiary or cyclic amine, an aromatic or heteroaryl amine, pyridine or imidazole, and an acidic moiety, such as, but not limited to tetrazole or carboxylic acid, zwitterions ("inner salts") may be formed and are included within the terms "salt(s)" as used herein. It is understood that certain compounds of the invention may exist in zwitterionic form, having both anionic and cationic centers within the same compound and a net neutral charge. Such zwitterions are included within the invention.

Methods of Preparing Compounds

Several methods for preparing the compounds of general formula (I), compounds of general formula (II), compounds of general formula (III), compounds of general formula (IV), compounds of general formula (V), compounds of general formula (VI), and pharmaceutically acceptable salts of the foregoing, are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products.

In the following Methods and Schemes, LG represents a leaving group, which may be a halide or triflate group. The variables included in the Methods and Schemes have the meanings provided; exemplary catalysts are defined in the Abbreviations (below).

Method 1

Benzothiophene dimers 1D and 1E, and pharmaceutically acceptable salts thereof, can be prepared in multiple ways. One way is shown in Scheme 1. The sequence begins with allyl-benzothiophene 1A. Cross-metathesis with Grubbs catalyst 2G affords the olefinic dimers 1B and 1C. Hydrogenation and then hydrolysis affords the dimers 1D and 1E with different tether lengths.

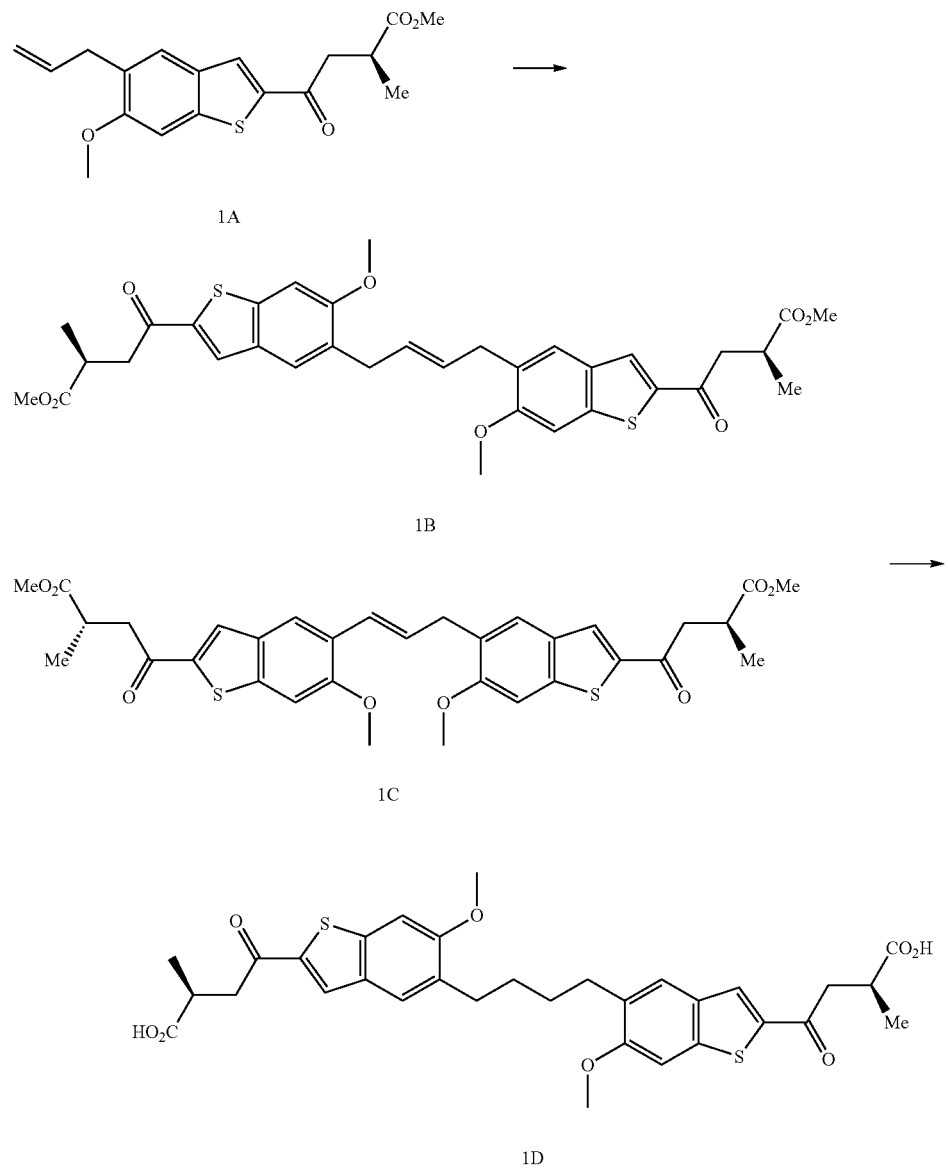

Scheme 1

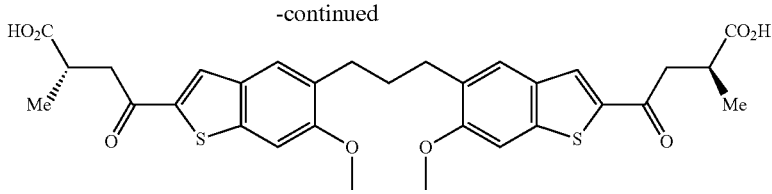

1E

Method 2

Another method for the preparation of benzothiophene dimers, and pharmaceutically salts thereof, is detailed in Scheme 2. The sequence starts with an appropriately substituted aryl halide, 2A. Cross-coupling with a primary alcohol containing benzothiophene (2B) using RockPhos Pd G3 followed by hydrolysis affords the dimer 2C.

Scheme 2

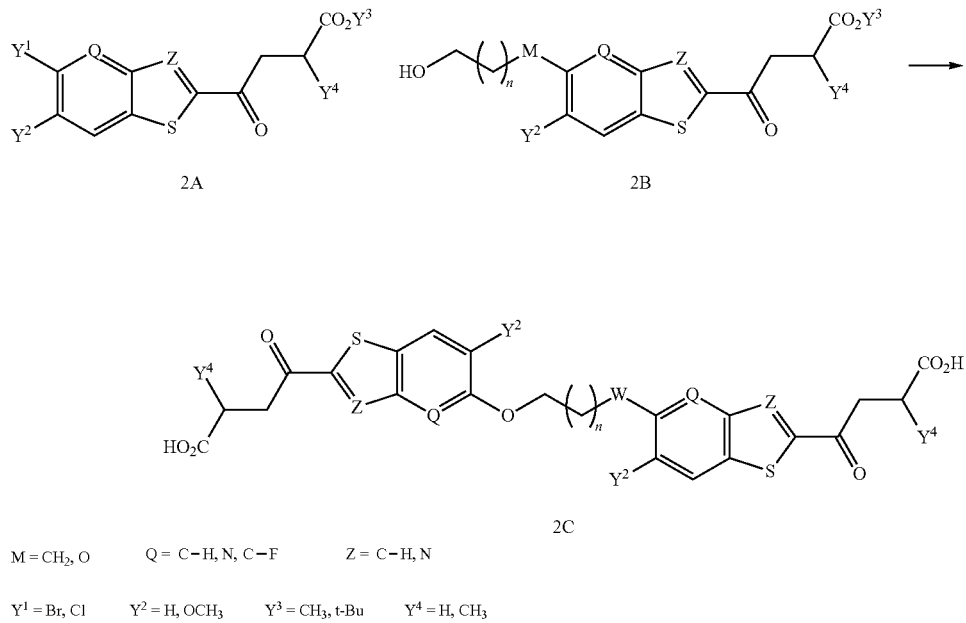

M = CH$_2$, O    Q = C—H, N, C—F    Z = C—H, N

Y$^1$ = Br, Cl    Y$^2$ = H, OCH$_3$    Y$^3$ = CH$_3$, t-Bu    Y$^4$ = H, CH$_3$

Method 3

Another method for the preparation of benzothiophene dimers, and pharmaceutically acceptable salts thereof, is detailed in Scheme 3. The cross-coupling of alkyl bromide benzothiophene 3A and an aryl bromide 3B affords the ester nitrile dimer 3C. Hydrolysis with aqueous sodium hydroxide affords the dimer 3D.

Scheme 3

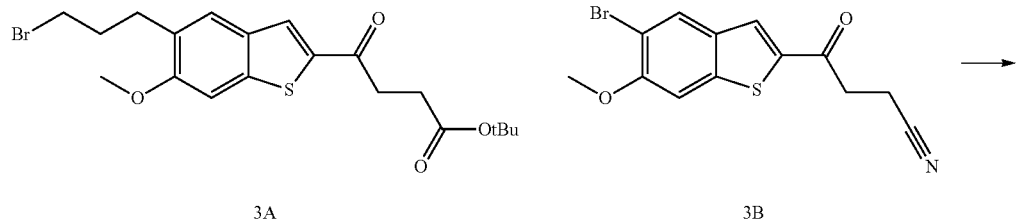

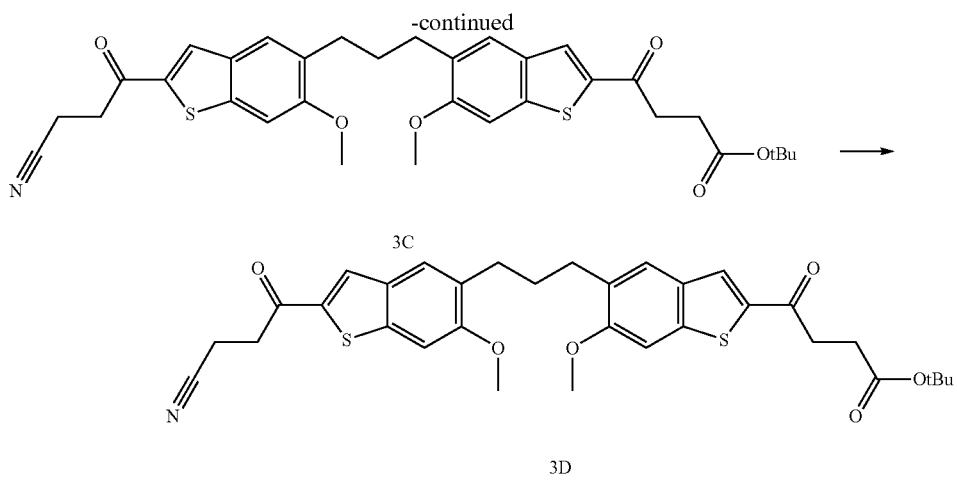

3C

3D

Method 4

Another method for the preparation of benzothiphene dimers, and pharmaceutically acceptable salts thereof, is detailed in Scheme 4. Alkyl Suzuki reaction between aryl bromide 4a and alkyl boronate ester 4B in the presence of a palladium catalyst followed by hydrolysis of the ester affords the dimer 4C.

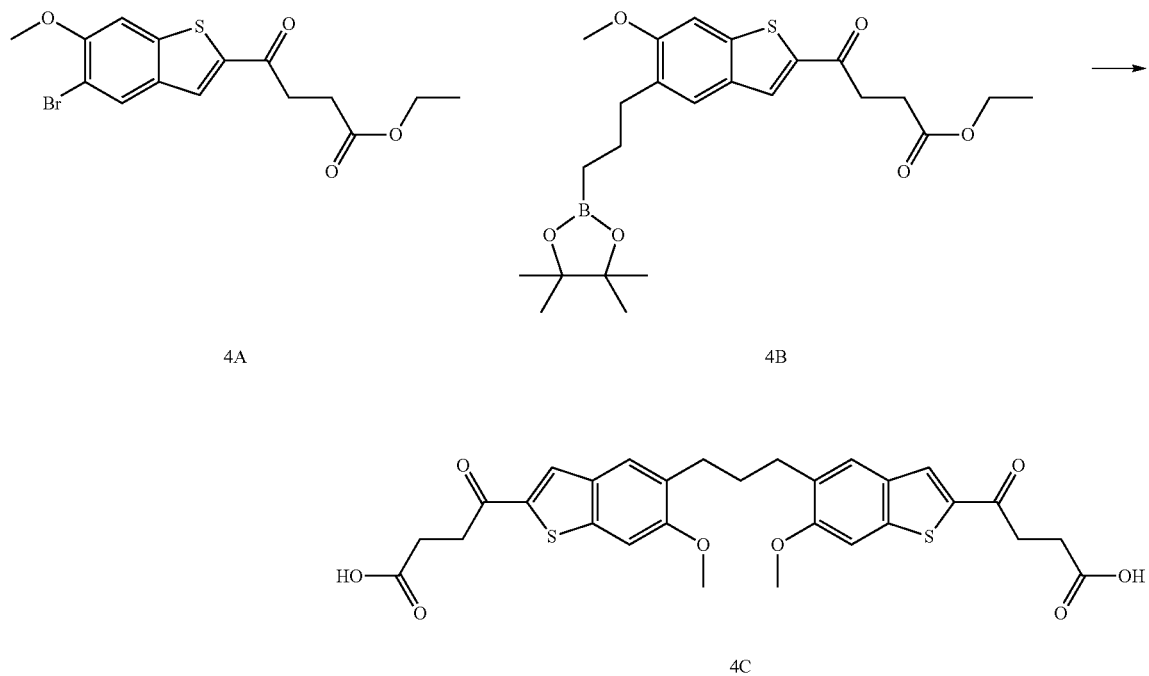

Scheme 4

4A

4B

4C

Method 5

Another method for the preparation of benzothiophene dimers, and pharmaceutically acceptable salts thereof, is detailed in Scheme 5. The cross-coupling of alkyl bromide benzothiophene 5A and an aryl bromide 5B affords the dimer 5C. Hydrolysis affords the dimer 5D. Similarly, aryl halide 5E can be coupled with alkyl bromide 5F to create intermediate 5G. Hydrolysis affords the acid affords 5H.

Scheme 5
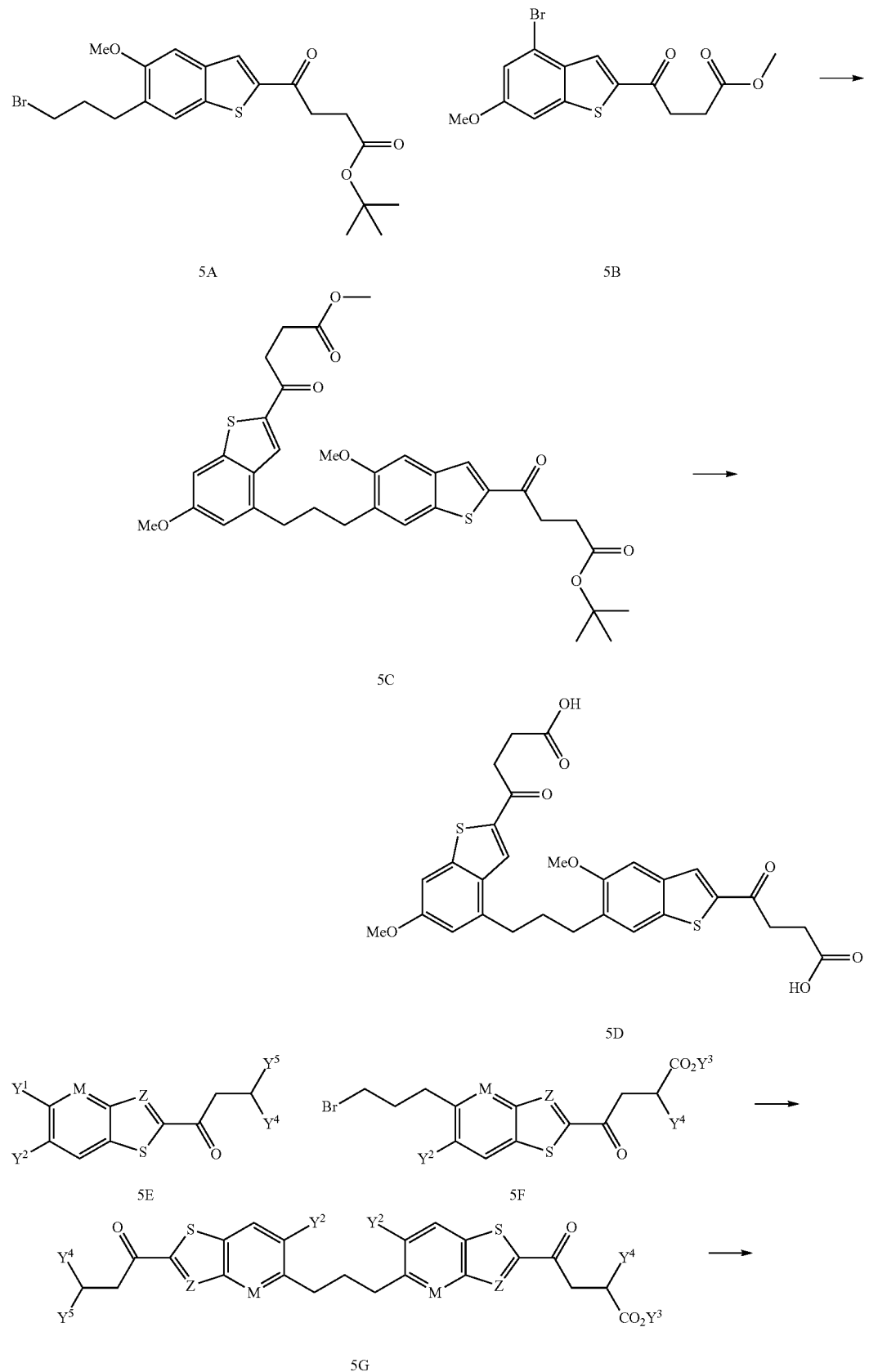

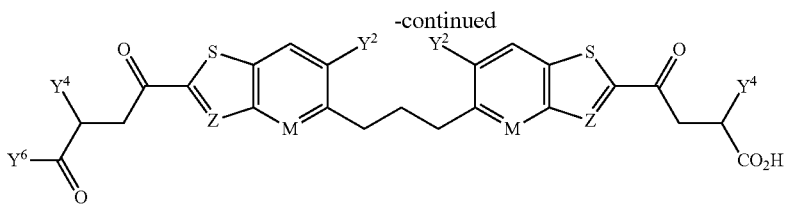

5H

M = C—H, N    Z = C—H, N    Y¹ = Br, Cl    Y² = CH₃, OCH₃

Y³ = CH₃, t-Bu    Y⁴ = H, CH₃    Y⁵ = CO₂CH₃, CO₂t-Bu, CN    Y⁶ = NH₂, OH

Method 6

Another method for the preparation of benzothiophene dimers, and pharmaceutically acceptable salts thereof, is detailed in Scheme 6. The sequence begins with alkyl halide 6A. Displacement of the halide with an appropriately substituted phenol, 6B, under basic conditions followed by hydrolysis affords dimer 6C. Similarly, alkyl chloride 6D can be displaced by phenol 6E under basic conditions to afford 6F after conversion to the diacid. Phenol 6G can also be used to displace alkyl chloride 6D to afford the desired 6H after conversion to the diacid. Finally, alkyl bromide 6I can be displaced by the phenol 6J to afford 6K after conversion to the diacid.

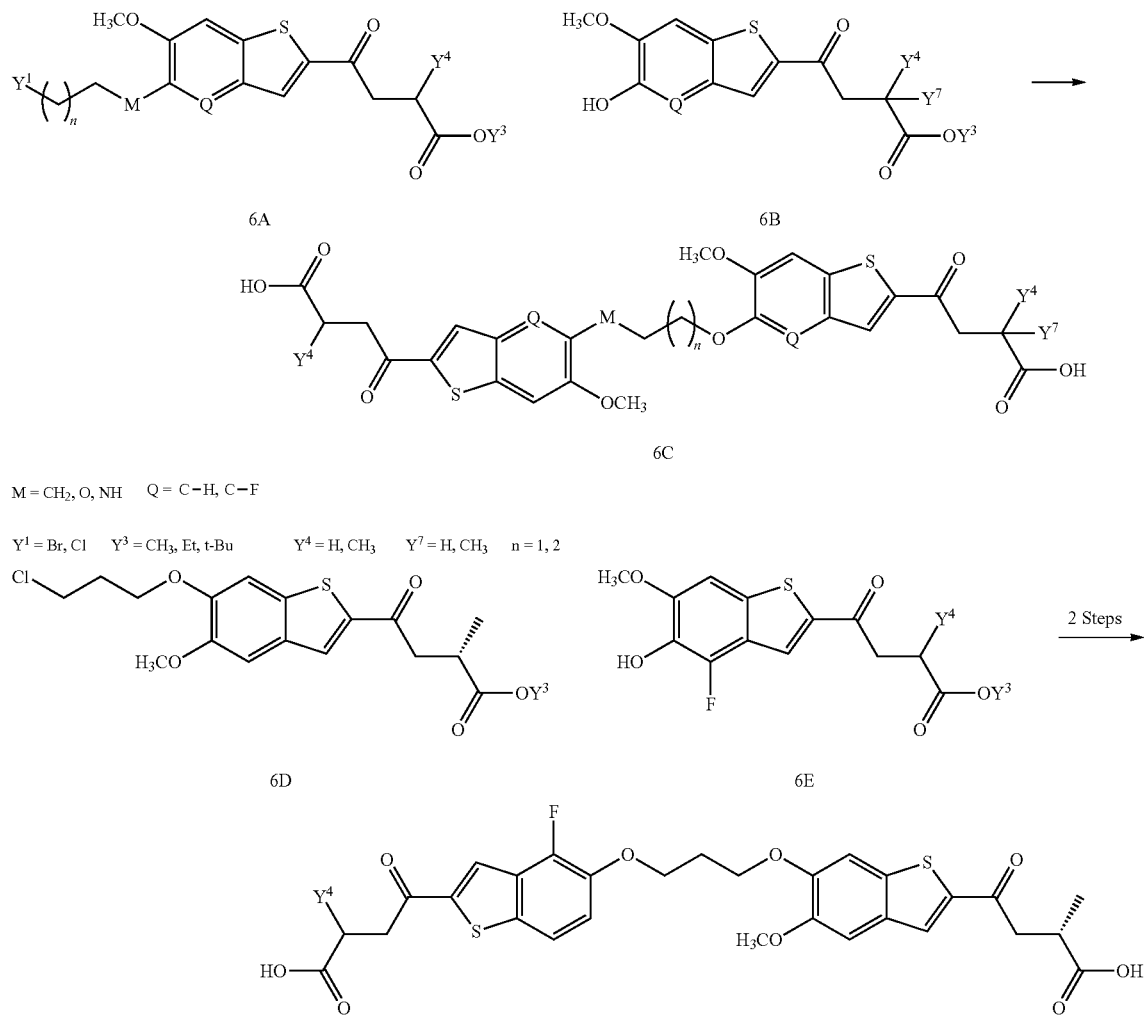

Scheme 6

M = CH₂, O, NH    Q = C—H, C—F

Y¹ = Br, Cl    Y³ = CH₃, Et, t-Bu    Y⁴ = H, CH₃    Y⁷ = H, CH₃    n = 1, 2

Y³ = CH₃, Et    Y⁴ = H, CH₃

-continued

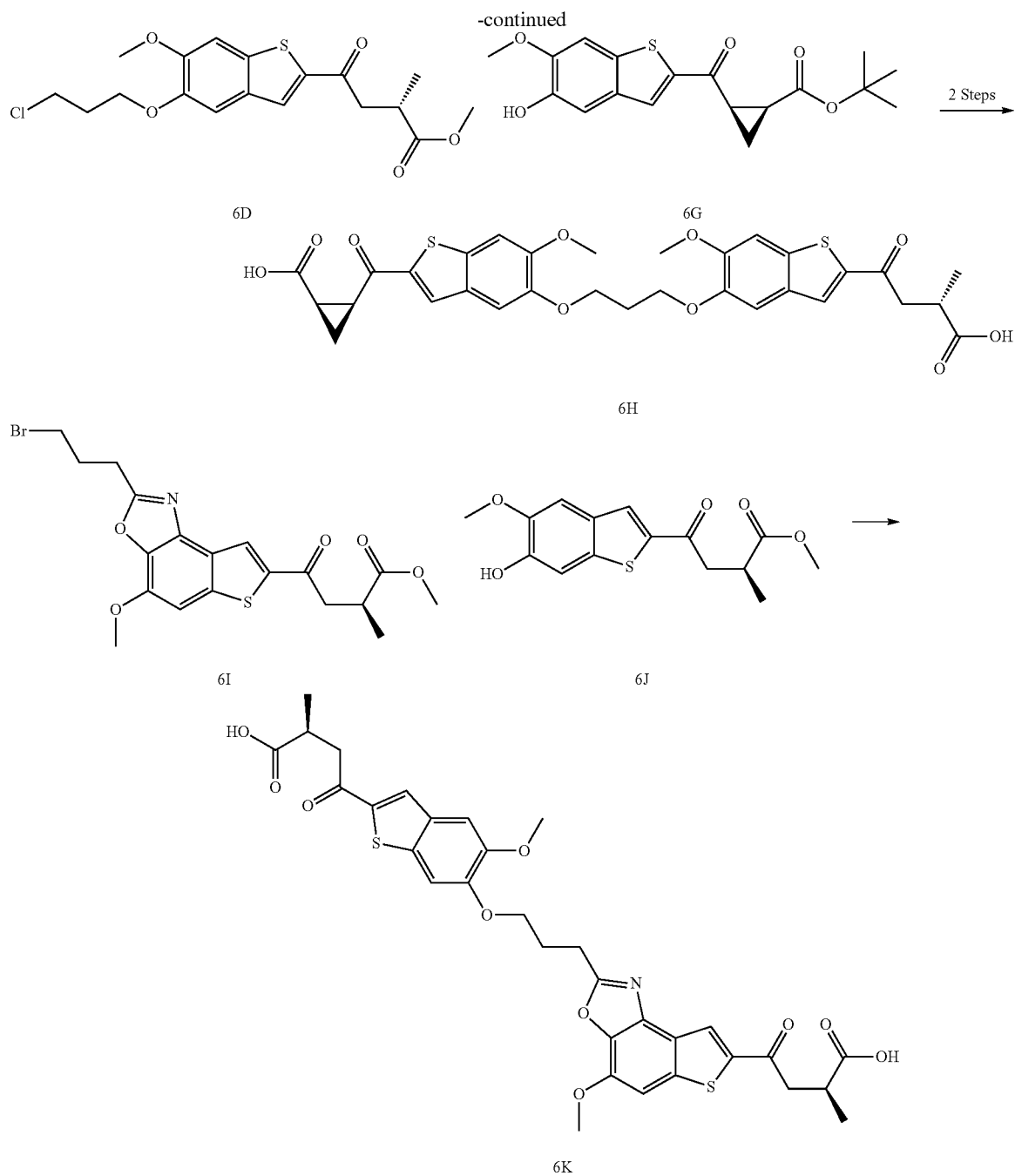

Method 7

Another method for the preparation of benzothiophene dimers, and pharmaceutically acceptable salts thereof, is detailed in Scheme 7. The sequence begins with a Mitsunobu reaction between a primary alcohol 7A and a phenol 7B to afford 7C after hydrolysis of the diester. Alternatively, phenol 7D can be reacted with alcohol 7E under Mitsunobu conditions. Subsequent saponification affords the diacid 7F. Phenol 7G can also be used in a Mitsunobu reaction with 7H to afford 7I after conversion of the diester to the diacid.

Similarly, a bis-phenol benzothiophene 7J and an appropriately substituted diol (7K) can be subjected to Mitsnobu conditions to afford a mixture of 7L and 7M. Hydrolysis affords a mixture of the diacids 7N and 7O.

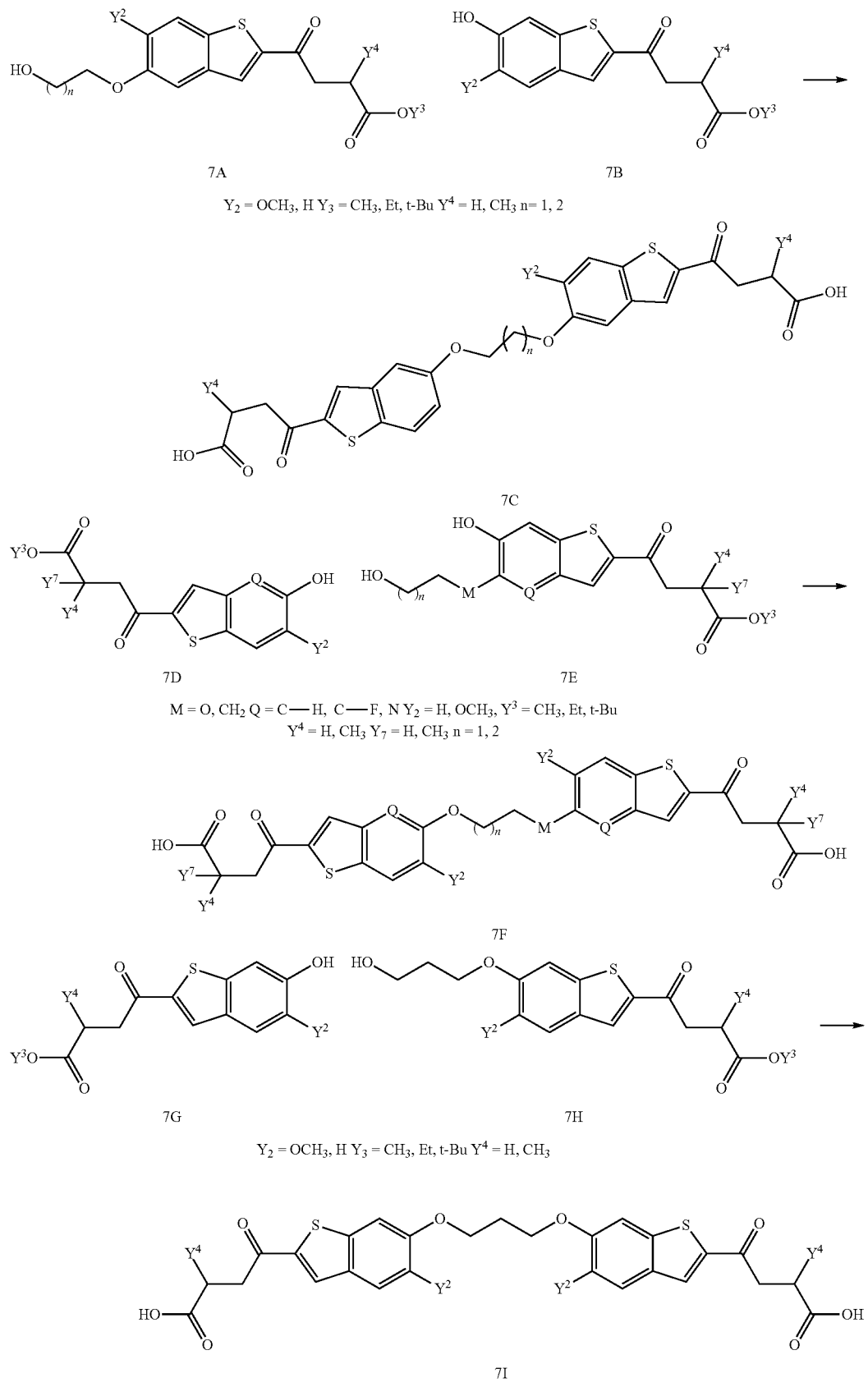

-continued

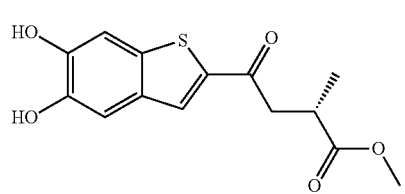

7J

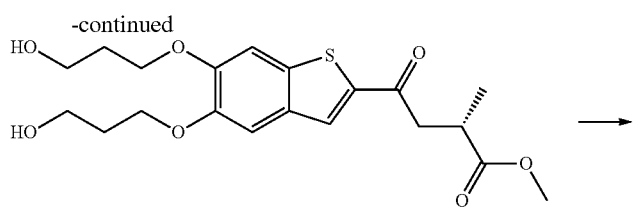

7K

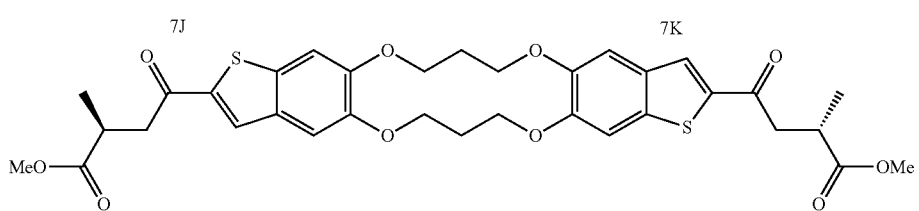

7L

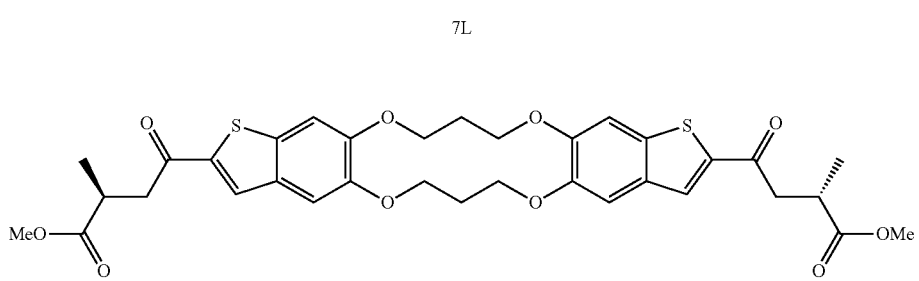

7M

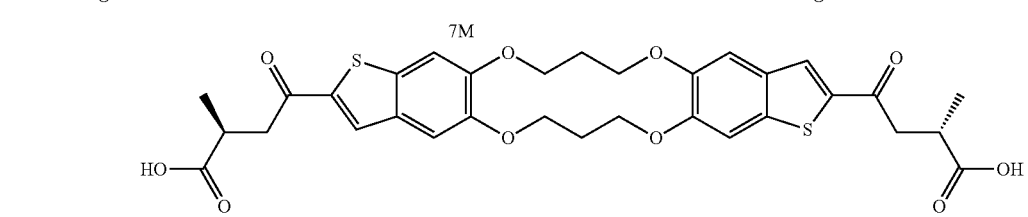

7N

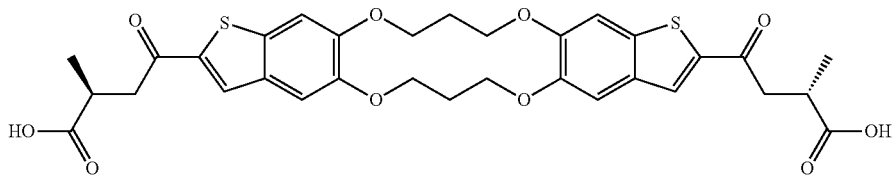

7O

Method 8

Another method for the preparation of benzothiophene dimers, and pharmaceutically acceptable salts thereof, is detailed in Scheme 8. The sequence begins with an appropriately substituted aryl bromide, 8A. Reaction with an alkyl amine 8B in the presence of a palladium catalyst affords the alkyl amino dimer diester 8C. Hydrolysis affords the desired diacid 8D.

Scheme 8

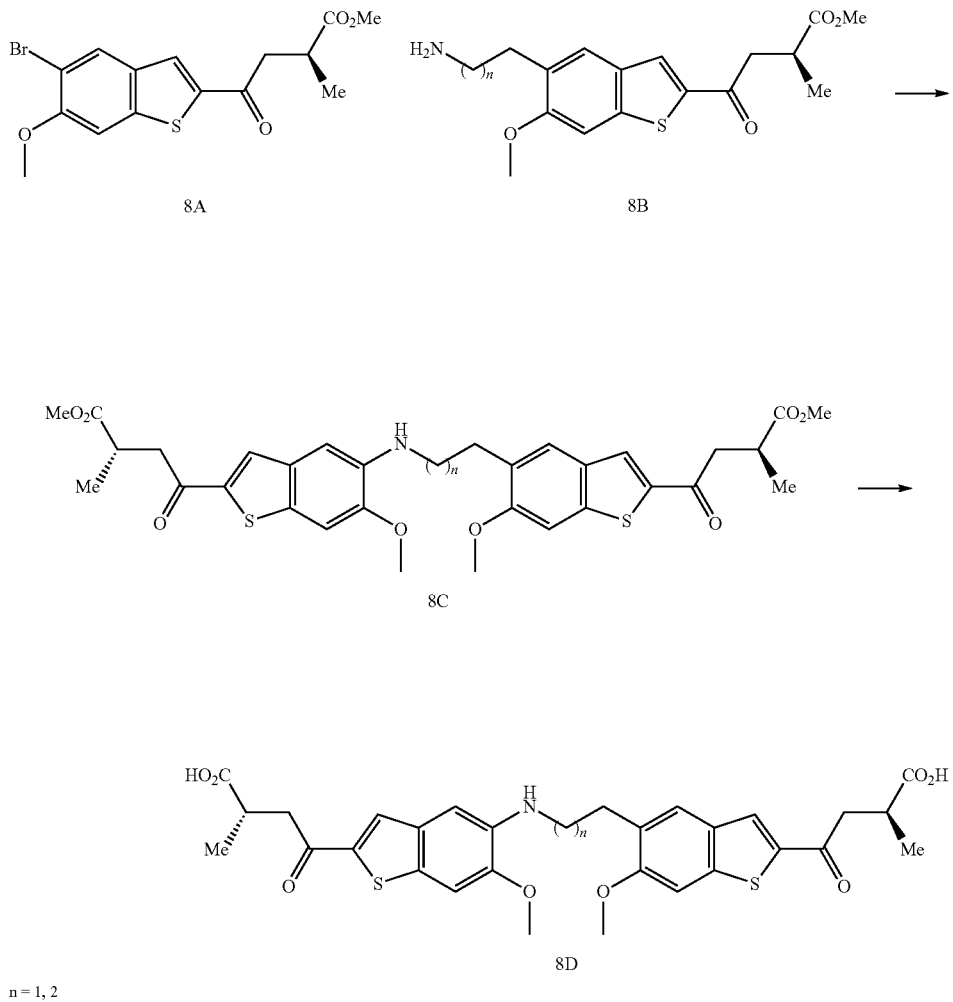

n = 1, 2

Method 9

Another method for the preparation of benzothiophene dimers, and pharmaceutically acceptable salts thereof, is detailed in Scheme 9. The sequence begins with a reductive amination between aldehyde 9A and amino azabenzothiphene 9B in the presence of sodium triacetoxyborohydride. Addition of TFA to the crude mixture affords the desired diacid 9C.

Scheme 9

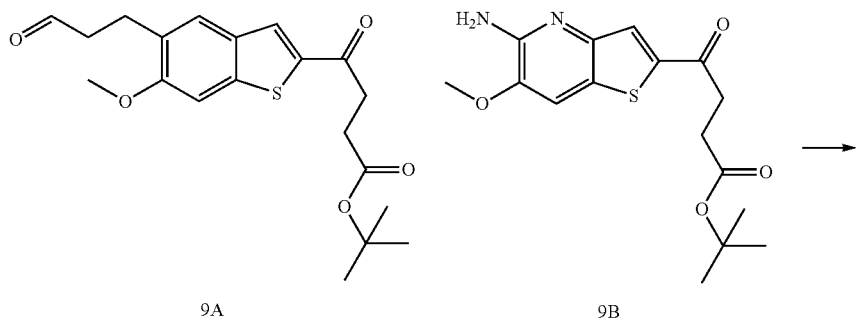

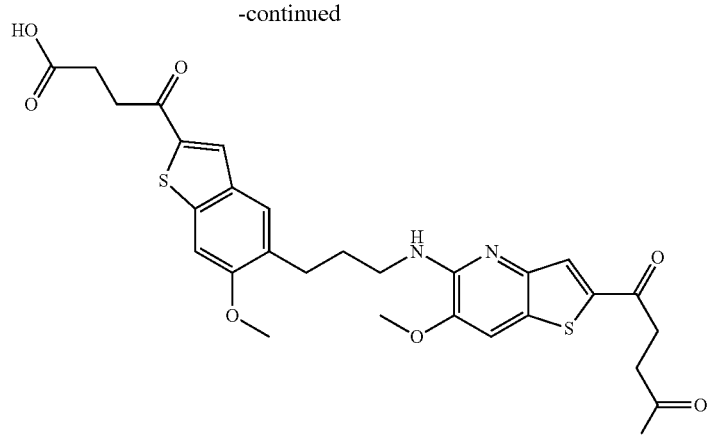

9C

Method 10

Another method for the preparation of benzothiophene dimers, and pharmaceutically acceptable salts thereof, is detailed in Scheme 10. The sequence begins with the bis-alkylation of an alkyl dihalide with an appropriately substituted phenolic benzothiophene 10A to afford the dimer diester 10B. Hydrolysis affords the desired diacid, 10C. Similarly, a dihalide can be bis-alkylated with 10D to afford the diacid 10E after conversion of the diester to the diacid.

Scheme 10

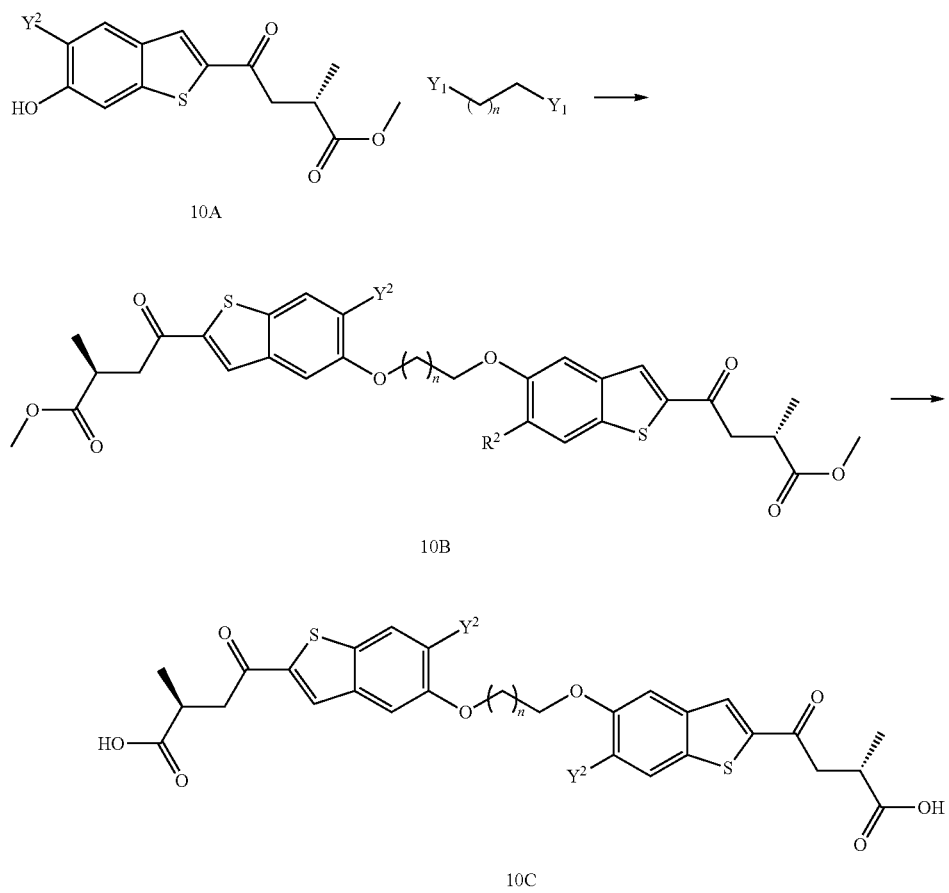

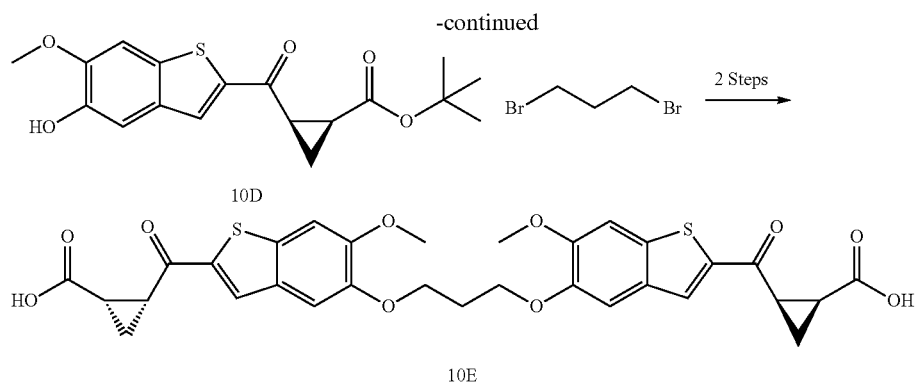
10D
10E
$Y^1$ = Br, Cl $Y_2$ = $OCH_3$, $OCHF_2$ n = 1, 2
Method 11
Another method for the preparation of benzothiophene dimers, and pharmaceutically acceptable salts thereof, is detailed in Scheme 11. The sequence begins with the alkylation of aniline 11B with the alkyl bromide 11A to afford 11C. Hydrolysis of the diester affords 11D.
Scheme 11
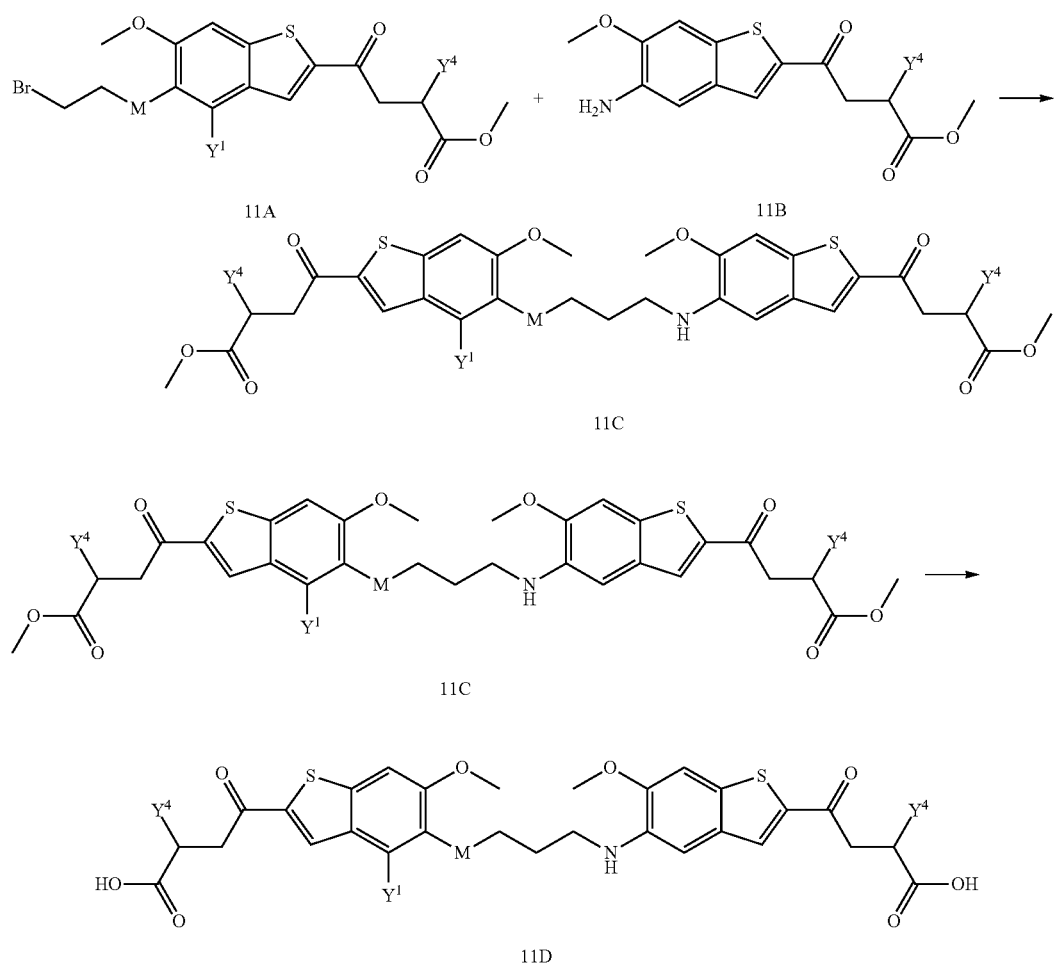
$Y^1$ = H, F $Y^4$ = H, $CH_3$ M = $CH_2$, O Method 12

Another method for the preparation of benzothiophene dimers, and pharmaceutically acceptable salts thereof, is detailed in Scheme 12. The sequence begins with the alkylation of phenol 12B with the alkyl bromide 12A to afford 12C. Selective base-mediated hydrolysis affords the monoacid 12D. Coupling of 12D with either a sulfonamide or a sulfamide affords 12E. Acid-mediated hydrolysis affords 12F.

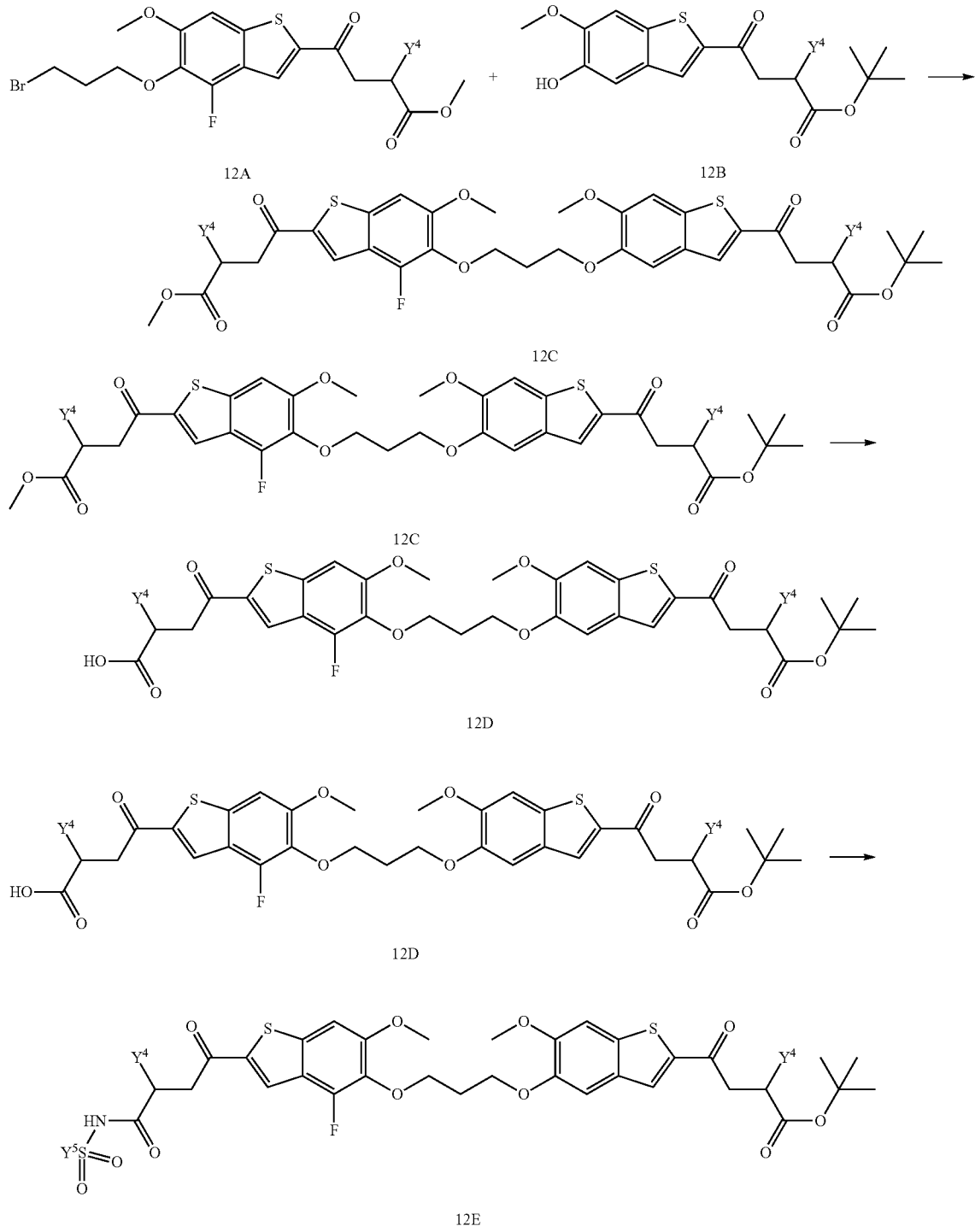

Scheme 12

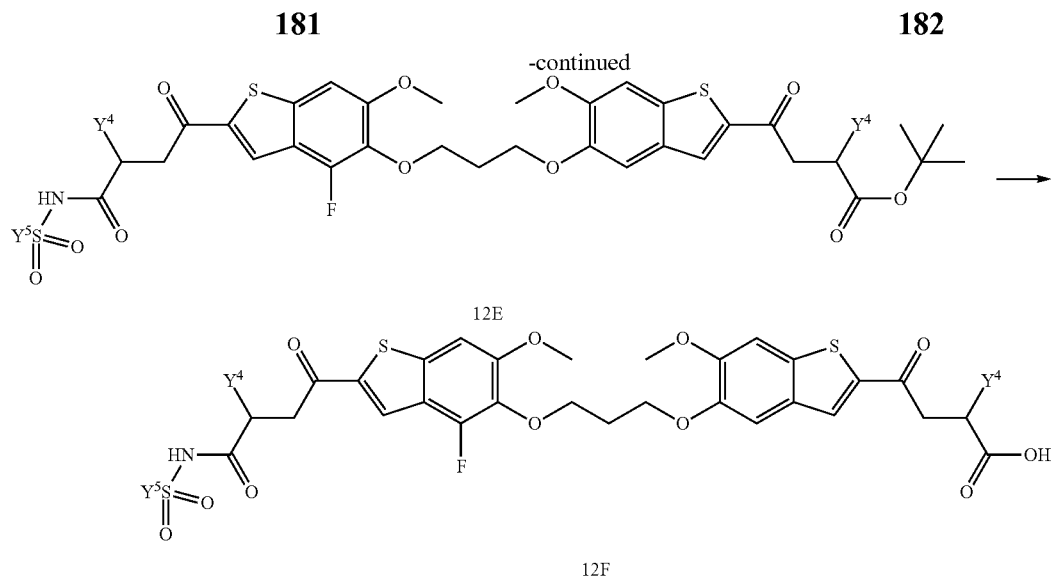

12E

12F $Y^4$ = H, CH$_3$ $Y^5$ = Me, N(Me)$_2$

Method 13

Another method for the preparation of benzothiophene dimers, and pharmaceutically acceptable salts thereof, is detailed in Scheme 13. The sequence begins with the alkylation of phenol 13B with the alkyl bromide 13A to afford 13C. Hydrolysis of the diester followed by acid-mediated deprotection of the methoxymethyl acetal (MOM)-protected phenol affords 13D.

Scheme 13

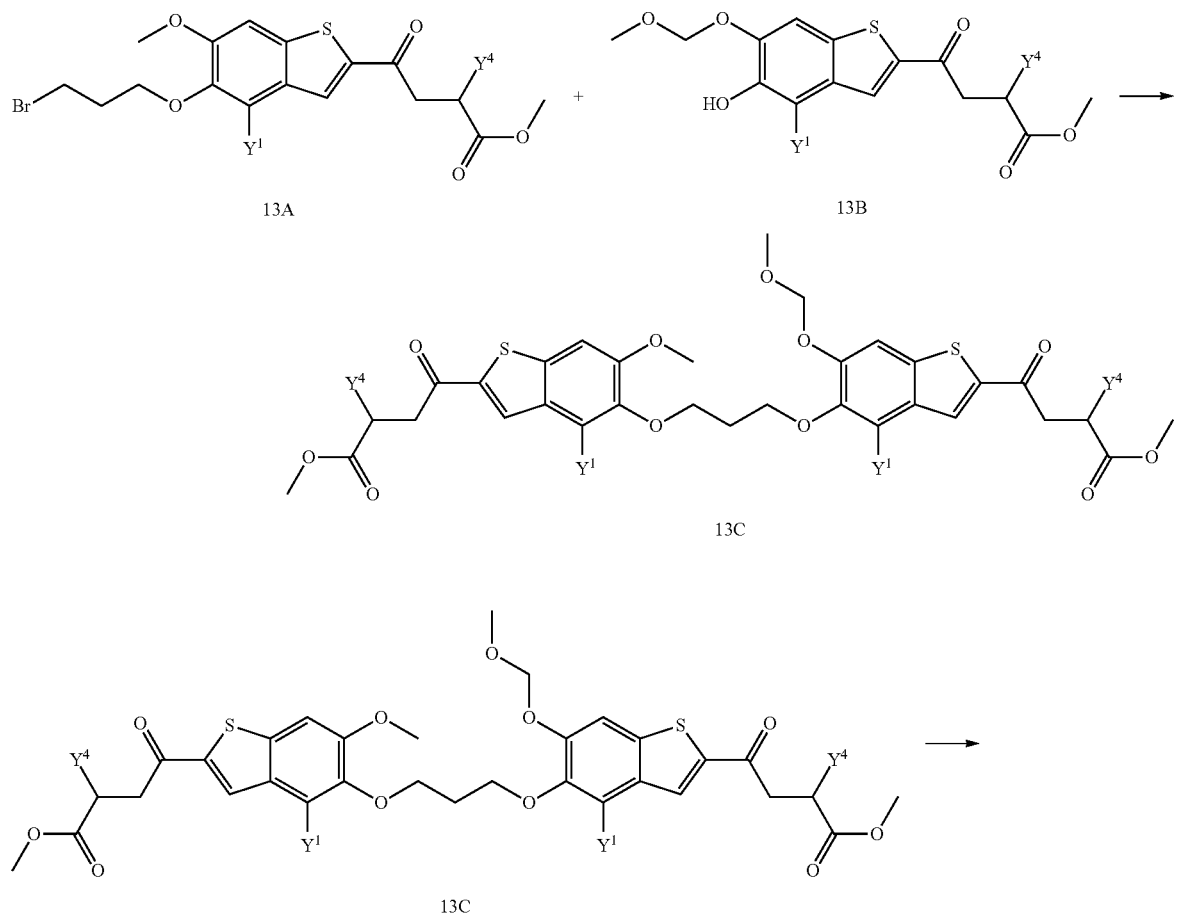

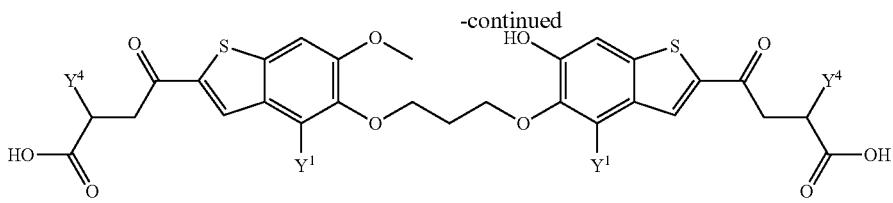

13D

Y¹ = H, F, Cl  Y⁴ = H, CH₃

Methods of Use

Compounds described herein having therapeutic applications, such as the compounds of general formula (I), compounds of general formula (II), compounds of general formula (III), compounds of general formula (IV), compounds of general formula (V), compounds of general formula (VI), the compounds of the Examples 1 through 190, and pharmaceutically acceptable salts of the foregoing, may be administered to a patient for the purpose of inducing an immune response, inducing STING-dependent cytokine production and/or inducing anti-tumor activity. The term "administration" and variants thereof (e.g., "administering" a compound) means providing the compound to the individual in need of treatment. When a compound is provided in combination with one or more additional active agents (e.g., antiviral agents useful for treating HCV infection or anti-tumor agents for treating cancers), "administration" and its variants are each understood to include concurrent and sequential provision of the compound or salt and other agents.

The compounds disclosed herein may be STING agonists. These compounds are potentially useful in treating diseases or disorders including, but not limited to, cell proliferation disorders. Cell-proliferation disorders include, but are not limited to, cancers, benign papillomatosis, gestational trophoblastic diseases, and benign neoplastic diseases, such as skin papilloma (warts) and genital papilloma.

In specific embodiments, the disease or disorder to be treated is a cell proliferation disorder. In certain embodiments, the cell proliferation disorder is cancer. In particular embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (i.e., cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In specific embodiments, the cancer is selected from brain and spinal cancers. In particular embodiments, the cancer is selected from the group consisting of anaplastic astrocytomas, glioblastomas, astrocytomas, and estheosioneuroblastomas (also known as olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sP-NET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers. In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastro-intestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (also known as hepatocellular carcinoma). In particular embodiments, the cancer is bile duct cancer (also known as cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, chordoma (cancer of the bone along the spine).

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, primary central nervous system lymphomas.

In specific embodiments, the cancer is selected from glandular cancers. In particular embodiments, the cancer is selected from the group consisting of adrenocortical cancer (also known as adrenocortical carcinoma or adrenal cortical carcinoma), pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

As used herein, the terms "treatment" and "treating" refer to all processes in which there may be a slowing, interrupting, arresting, controlling, or stopping of the progression of a disease or disorder described herein. The terms do not necessarily indicate a total elimination of all disease or disorder symptoms.

The terms "administration of" and or "administering" a compound should be understood to include providing a compound described herein, or a pharmaceutically acceptable salt thereof, and compositions of the foregoing to a patient.

The amount of a compound administered to a patient is an amount sufficient to induce an immune response and/or to induce STING-dependent type I interferon production in the patient. In an embodiment, the amount of a compound can be an "effective amount" or "therapeutically effective amount," such that the subject compound is administered in an amount that will elicit, respectively, a biological or medical (i.e., intended to treat) response of a tissue, system, animal, or human that is being sought by a researcher, veterinarian, medical doctor, or other clinician. An effective amount does not necessarily include considerations of toxicity and safety related to the administration of a compound.

An effective amount of a compound will vary with the particular compound chosen (e.g., considering the potency, efficacy, and/or half-life of the compound); the route of administration chosen; the condition being treated; the severity of the condition being treated; the age, size, weight, and physical condition of the patient being treated; the medical history of the patient being treated; the duration of the treatment; the nature of a concurrent therapy; the desired therapeutic effect; and like factors and can be routinely determined by the skilled artisan.

The compounds disclosed herein may be administered by any suitable route including oral and parenteral administration. Parenteral administration is typically by injection or infusion and includes intravenous, intramuscular, and subcutaneous injection or infusion.

The compounds disclosed herein may be administered once or according to a dosing regimen where a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound disclosed herein depend on the pharmacokinetic properties of that compound, such as absorption, distribution and half-life, which can be determined by a skilled artisan. In addition, suitable dosing regimens, including the duration such regimens are administered, for a compound disclosed herein depend on the disease or condition being treated, the severity of the disease or condition, the age and physical condition of the patient being treated, the medical history of the patient being treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as the individual patient needs change. Typical daily dosages may vary depending upon the particular route of administration chosen.

One embodiment of the present disclosure provides for a method of treating a cell proliferation disorder comprising administration of a therapeutically effective amount of a compound of general formula (I), compound of general formula (II), compound of general formula (III), compound of general formula (IV), compound of general formula (V), compound of general formula (VI), and pharmaceutically acceptable salts of the foregoing, to a patient in need of treatment thereof. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

In one embodiment, disclosed herein is the use of a compound of general formula (I), compound of general formula (II), compound of general formula (III), compound of general formula (IV), compound of general formula (V), compound of general formula (VI), or a pharmaceutically acceptable salt of the foregoing, in a therapy. The compound may be useful in a method of inducing an immune response and/or inducing STING-dependent type I interferon production in a patient, such as a mammal in need of such inhibition, comprising administering an effective amount of the compound to the patient.

In one embodiment, disclosed herein is a pharmaceutical composition comprising at least one compound of general formula (I), at least one compound of general formula (II), at least one compound of general formula (III), at least one compound of general formula (IV), at least one compound of general formula (V), at least one compound of general formula (VI), or at least one pharmaceutically acceptable salt of the foregoing, for use in potential treatment to induce an immune response and/or to induce STING-dependent type I interferon production.

One embodiment disclosed herein is the use of a compound of general formula (I), a compound of general formula (II), a compound of general formula (III), a compound of general formula (IV), a compound of general formula (V), a compound of general formula (VI), or a pharmaceutically acceptable salt of the foregoing, in the manufacture of a medicament to induce an immune response and/or to induce STING-dependent type I interferon production. In embodiments, the disease or disorder to be treated is a cell proliferation disorder. In aspects of these embodiments, the cell proliferation disorder is cancer. In further aspects of these embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary.

Compositions

The term "composition" as used herein is intended to encompass a dosage form comprising a specified compound in a specified amount, as well as any dosage form that results, directly or indirectly, from combination of a specified compound in a specified amount. Such term is intended to encompass a dosage form comprising a compound of general formula (I), a compound of general formula (II), a compound of general formula (III), a compound of general formula (IV), a compound of general formula (V), a compound of general formula (VI), or a pharmaceutically acceptable salt of the foregoing, and one or more pharmaceutically acceptable carriers or excipients. Accordingly, the compositions of the present disclosure encompass any composition made by admixing a compound of the present disclosure and one or more pharmaceutically acceptable carrier or excipients. By "pharmaceutically acceptable", it is meant the carriers or excipients are compatible with the compound disclosed herein and with other ingredients of the composition.

For the purpose of inducing an immune response and/or inducing STING-dependent type I interferon production, the compounds of general formula (I), compounds of general formula (II), compounds of general formula (III), compounds of general formula (IV), compounds of general formula (V), compounds of general formula (VI), or pharmaceutically acceptable salts of the foregoing, can be administered by means that produces contact of the active agent with the agent's site of action. The compounds can be administered by conventional means available for use in conjunction with pharmaceuticals, either as individual therapeutic agents or in a combination of therapeutic agents. The compounds can be administered alone, but typically are administered with a pharmaceutical carrier selected on the basis of the chosen route of administration and standard pharmaceutical practice.

In one embodiment, disclosed herein is a composition comprising a compound of general formula (I), a compound of general formula (II), a compound of general formula (III), a compound of general formula (IV), a compound of general formula (V), a compound of general formula (VI), or a pharmaceutically acceptable salt of the foregoing, and one or more pharmaceutically acceptable carriers or excipients. The composition may be prepared and packaged in bulk form in which a therapeutically effective amount of a compound of the disclosure can be extracted and then given to a patient, such as with powders or syrups. Alternatively, the composition may be prepared and packaged in unit dosage form in which each physically discrete unit contains a therapeutically effective amount of a compound of general formula (I), a compound of general formula (II), a compound of general formula (III), a compound of general formula (IV), a compound of general formula (V), a compound of general formula (VI), or a pharmaceutically acceptable salt of the foregoing.

The compounds disclosed herein and a pharmaceutically acceptable carrier or excipient(s) will typically be formulated into a dosage form adapted for administration to a patient by a desired route of administration. For example, dosage forms include those adapted for (1) oral administration, such as tablets, capsules, caplets, pills, troches, powders, syrups, elixirs, suspensions, solutions, emulsions, sachets, and cachets; and (2) parenteral administration, such as sterile solutions, suspensions, and powders for reconstitution. Suitable pharmaceutically acceptable carriers or excipients will vary depending upon the particular dosage form chosen. In addition, suitable pharmaceutically acceptable carriers or excipients may be chosen for a particular function that they may serve in the composition. For example, certain pharmaceutically acceptable carriers or excipients may be chosen for their ability to facilitate the production of uniform dosage forms. Certain pharmaceutically acceptable carriers or excipients may be chosen for their ability to facilitate the production of stable dosage forms. Certain pharmaceutically acceptable carriers or excipients may be chosen for their ability to facilitate the carrying or transporting of a compound disclosed herein, once administered to the patient, from one organ or portion of the body to another organ or another portion of the body. Certain pharmaceutically acceptable carriers or excipients may be chosen for their ability to enhance patient compliance.

Suitable pharmaceutically acceptable excipients include the following types of excipients: diluents, lubricants, binders, disintegrants, fillers, glidants, granulating agents, coating agents, wetting agents, solvents, co-solvents, suspending agents, emulsifiers, sweeteners, flavoring agents, flavor masking agents, coloring agents, anti-caking agents, hemectants, chelating agents, plasticizers, viscosity increasing agents, antioxidants, preservatives, stabilizers, surfactants, and buffering agents.

A skilled artisan possesses the knowledge and skill in the art to select suitable pharmaceutically acceptable carriers and excipients in appropriate amounts for the use in the compositions of the disclosure. In addition, there are a number of resources available to the skilled artisan, which describe pharmaceutically acceptable carriers and excipients and may be useful in selecting suitable pharmaceutically acceptable carriers and excipients. Examples include REMINGTON'S PHARMACEUTICAL SCIENCES (Mack Publishing Company), THE HANDBOOK OF PHARMACEUTICAL ADDITIVES (Gower Publishing Limited), and THE HANDBOOK OF PHARMACEUTICAL EXCIPIENTS (the American Pharmaceutical Association and the Pharmaceutical Press).

The compositions of the disclosure are prepared using techniques and methods known to those skilled in the art. Some methods commonly used in the art are described in REMINGTON'S PHARMACEUTICAL SCIENCES (Mack Publishing Company).

In one embodiment, the disclosure is directed to a solid oral dosage form such as a tablet or capsule comprising a therapeutically effective amount of a compound of general formula (I), a compound of general formula (II), a compound of general formula (III), a compound of general formula (IV), a compound of general formula (V), a compound of general formula (VI), or a pharmaceutically acceptable salt of the foregoing, and a diluent or filler. Suitable diluents and fillers include lactose, sucrose, dextrose, mannitol, sorbitol, starch (e.g., corn starch, potato starch, and pre-gelatinized starch), cellulose and its derivatives, (e.g., microcrystalline cellulose), calcium sulfate, and dibasic calcium phosphate. The solid oral dosage form may further comprise a binder. Suitable binders include starch (e.g., corn starch, potato starch, and pre-gelatinized starch) gelatin, acacia, sodium alginate, alginic acid, tragacanth, guar gum, povidone, and cellulose and its derivatives (e.g., microcrystalline cellulose). The solid oral dosage form may further comprise a disintegrant. Suitable disintegrants include crospovidone, sodium starch glycolate, croscarmelose, alginic acid, and sodium carboxymethyl cellulose. The solid oral dosage form may further comprise a lubricant. Suitable lubricants include stearic acid, magnesium stearate, calcium stearate, and talc.

Where appropriate, dosage unit formulations for oral administration can be microencapsulated. The composition can also be prepared to prolong or sustain the release as, for example, by coating or embedding particulate material in polymers, wax, or the like.

The compounds disclosed herein may also be coupled with soluble polymers as targetable drug carriers. Such polymers can include polyvinylpyrrolidone, pyrancopolymer, polyhydroxypropylmethacrylamidephenol, polyhydroxyethylaspartamidephenol, or polyethyleneoxidepolylysine substituted with palmitoyl residues. Furthermore, the compounds of the disclosure may be coupled to a class of biodegradable polymers useful in achieving controlled release of a drug, for example polylactic acid, polyepsilon caprolactone, polyhydroxy butyric acid, polyorthoesters, polyacetals, polydihydropyrans, polycyanacrylates, and cross-linked or amphipathic block copolymers of hydrogels.

In one embodiment, the disclosure is directed to a liquid oral dosage form. Oral liquids such as solutions, syrups, and elixirs can be prepared in dosage unit form so that a given quantity contains a predetermined amount of a compound or a pharmaceutically acceptable salt thereof disclosed herein. Syrups can be prepared by dissolving the compound of the disclosure in a suitably flavored aqueous solution; elixirs are prepared through the use of a non-toxic alcoholic vehicle. Suspensions can be formulated by dispersing a compound disclosed herein in a non-toxic vehicle. Solubilizers and emulsifiers such as ethoxylated isostearyl alcohols and polyoxy ethylene sorbitol ethers, preservatives, flavor additives such as peppermint oil, or other natural sweeteners or saccharin or other artificial sweeteners and the like can also be added.

In one embodiment, the disclosure is directed to compositions for parenteral administration. Compositions adapted for parenteral administration include aqueous and non-aqueous sterile injection solutions that may contain antioxidants, buffers, bacteriostats, and solutes that render the formulation isotonic with the blood of the intended recipient; and aqueous and non-aqueous sterile suspensions that may include suspending agents and thickening agents. The compositions may be presented in unit-dose or multi-dose containers, for example sealed ampoules and vials, and may be stored in a freeze-dried (lyophilized) condition, requiring only the addition of the sterile liquid carrier, for example water for injections, immediately prior to use. Extemporaneous injection solutions and suspensions may be prepared from sterile powders, granules, and tablets.

Combinations

The compounds of general formula (I), compounds of general formula (II), compounds of general formula (III), compounds of general formula (IV), compounds of general formula (V), compounds of general formula (VI), and/or pharmaceutically acceptable salts of the foregoing, may be administered in combination with one or more additional active agents. In embodiments, one or more compounds of general formula (I), compounds of general formula (II), compounds of general formula (III), compounds of general formula (IV), compounds of general formula (V), compounds of general formula (VI), or one or more pharmaceutically acceptable salts of the foregoing, and the one or more additional active agents may be co-administered. The additional active agent(s) may be administered in a single dosage form with the compound of general formula (I), compound of general formula (II), compound of general formula (III), compound of general formula (IV), compound of general formula (V), compound of general formula (VI), or pharmaceutically acceptable salt of the foregoing, or the additional active agent(s) may be administered in separate dosage form(s) from the dosage form containing the compound of general formula (I), compound of general formula (II), compound of general formula (III), compound of general formula (IV), compound of general formula (V), compound of general formula (VI), or pharmaceutically acceptable salt of the foregoing.

The additional active agent(s) may be provided as a pharmaceutically acceptable salt, where appropriate.

The additional active agent(s) may be one or more agents selected from the group consisting of STING agonist compounds, anti-viral compounds, antigens, adjuvants, anti-cancer agents, CTLA-4, LAG-3 and PD-1 pathway antagonists, lipids, liposomes, peptides, cytotoxic agents, chemotherapeutic agents, immunomodulatory cell lines, checkpoint inhibitors, vascular endothelial growth factor (VEGF) receptor inhibitors, topoisomerase II inhibitors, smoothen inhibitors, alkylating agents, anti-tumor antibiotics, anti-metabolites, retinoids, and immunomodulatory agents including but not limited to anti-cancer vaccines. It will be understood that such additional active agent(s) may be provided as a pharmaceutically acceptable salt. It will be understood the descriptions of the above additional active agents may be overlapping. It will also be understood that the treatment combinations are subject to optimization, and it is understood that the best combination to use of the compounds of general formula (I), compounds of general formula (II), compounds of general formula (III), compounds of general formula (IV), compounds of general formula (V), compounds of general formula (VI), or pharmaceutically acceptable salts of the foregoing, and one or more additional active agents will be determined based on the individual patient needs.

A compound disclosed herein may be used in combination with one or more other active agents, including but not limited to, other anti-cancer agents that are used in the prevention, treatment, control, amelioration, or reduction of risk of a particular disease or condition (e.g., cell proliferation disorders). In one embodiment, a compound disclosed herein is combined with one or more other anti-cancer agents for use in the prevention, treatment, control amelioration, or reduction of risk of a particular disease or condition for which the compounds disclosed herein are useful. Such other active agents may be administered, by a route and in an amount commonly used therefor, contemporaneously or sequentially with a compound of the present disclosure.

When a compound disclosed herein is used contemporaneously with one or more other active agents, a composition containing such other active agents in addition to the compound disclosed herein is contemplated. Accordingly, the compositions of the present disclosure include those that also contain one or more other active ingredients, in addition to a compound disclosed herein. A compound disclosed herein may be administered either simultaneously with, or before or after, one or more other active agent(s). A compound disclosed herein may be administered separately, by the same or different route of administration, or together in the same pharmaceutical composition as the other agent(s).

Products provided as combinations may include a composition comprising a compound of general formula (I), compound of general formula (II), compound of general formula (III), compound of general formula (IV), compound of general formula (V), compound of general formula (VI), or a pharmaceutically acceptable salt of the foregoing, and one or more other active agent(s) together in the same pharmaceutical composition, or may include a composition comprising a compound of general formula (I), compound of general formula (II), compound of general formula (III), compound of general formula (IV), compound of general formula (V), compound of general formula (VI), or a pharmaceutically acceptable salt of the foregoing, and a composition comprising one or more other active agent(s) in separate form, e.g. in the form of a kit or in any form designed to enable separate administration either concurrently or on separate dosing schedules.

The weight ratio of a compound of general formula (I), compound of general formula (II), compound of general formula (III), compound of general formula (IV), compound of general formula (V), compound of general formula (VI), or a pharmaceutically acceptable salt of the foregoing, to a second active agent may be varied and will depend upon the therapeutically effective dose of each agent. Generally, a therapeutically effective dose of each will be used. Combinations of a compound disclosed herein and other active agents will generally also be within the aforementioned range, but in each case, a therapeutically effective dose of each active agent should be used. In such combinations, the compound disclosed herein and other active agents may be administered separately or in conjunction. In addition, the administration of one element may be prior to, concurrent to, or subsequent to the administration of other agent(s).

In one embodiment, this disclosure provides a composition comprising a compound of general formula (I), compound of general formula (II), compound of general formula (III), compound of general formula (IV), compound of general formula (V), compound of general formula (VI), or a pharmaceutically acceptable salt of the foregoing, and at least one other active agent as a combined preparation for simultaneous, separate, or sequential use in therapy. In one embodiment, the therapy is the treatment of a cell proliferation disorder, such as cancer.

In one embodiment, the disclosure provides a kit comprising two or more separate pharmaceutical compositions, at least one of which contains a compound of general formula (I), compound of general formula (II), compound of general formula (III), compound of general formula (IV), compound of general formula (V), compound of general formula (VI), or a pharmaceutically acceptable salt of the foregoing. In one embodiment, the kit comprises means for separately retaining said compositions, such as a container, divided bottle, or divided foil packet. An example of such a kit is a blister pack, as typically used for the packaging of tablets, capsules, and the like.

A kit of this disclosure may be used for administration of different dosage forms, for example, oral and parenteral, for administration of the separate compositions at different dosage intervals, or for titration of the separate compositions against one another. To assist with compliance, a kit of the disclosure typically comprises directions for administration.

Disclosed herein is a use of a compound of general formula (I), compound of general formula (II), compound of general formula (III), compound of general formula (IV), compound of general formula (V), compound of general formula (VI), or a pharmaceutically acceptable salt of the foregoing, for treating a cell proliferation disorder, where the medicament is prepared for administration with another active agent. The disclosure also provides the use of another active agent for treating a cell proliferation disorder, where the medicament is administered with a compound of general formula (I), compound of general formula (II), compound of general formula (III), compound of general formula (IV), compound of general formula (V), compound of general formula (VI), or a pharmaceutically acceptable salt of the foregoing.

The disclosure also provides the use of a compound of general formula (I), compound of general formula (II), compound of general formula (III), compound of general formula (IV), compound of general formula (V), compound of general formula (VI), or a pharmaceutically acceptable salt of the foregoing, for treating a cell proliferation disorder, where the patient has previously (e.g., within 24 h) been treated with another active agent. The disclosure also provides the use of another active agent for treating a cell proliferation disorder, where the patient has previously (e.g., within 24 h) been treated with a compound of general formula (I), compound of general formula (II), compound of general formula (III), compound of general formula (IV), compound of general formula (V), compound of general formula (VI), or a pharmaceutically acceptable salt of the foregoing. The second agent may be administered a week, several weeks, a month, or several months after the administration of a compound disclosed herein.

STING agonist compounds that may be used in combination with the compounds of general formula (I), compounds of general formula (II), compounds of general formula (III), compounds of general formula (IV), compounds of general formula (V), compounds of general formula (VI), or pharmaceutically acceptable salts of the foregoing, disclosed herein include but are not limited to cyclic di-nucleotide compounds, such as those disclosed, for example, in International Patent Application Publication Nos. WO2014093936, WO2014189805, WO2014189806, WO2015185565, WO2016120305, WO2016096174, WO2016096577, WO2017027645, WO2017027646, WO2017075477, WO2017093933, and WO2018009466.

Anti-viral compounds that may be used in combination with the compounds of general formula (I), compounds of general formula (II), compounds of general formula (III), compounds of general formula (IV), compounds of general formula (V), compounds of general formula (VI), or pharmaceutically acceptable salts of the foregoing, disclosed herein include hepatitis B virus (HBV) inhibitors, hepatitis C virus (HCV) protease inhibitors, HCV polymerase inhibitors, HCV NS4A inhibitors, HCV NS5A inhibitors, HCV NS5b inhibitors, and human immunodeficiency virus (HIV) inhibitors. Such anti-viral compounds may be provided as a pharmaceutically acceptable salt, where appropriate.

Antigens and adjuvants that may be used in combination with the compounds of general formula (I), compounds of general formula (II), compounds of general formula (III), compounds of general formula (IV), compounds of general formula (V), compounds of general formula (VI), or the pharmaceutically acceptable salts of the foregoing, include B7 costimulatory molecule, interleukin-2, interferon-y, GM-CSF, CTLA-4 antagonists, OX-40/OX-40 ligand, CD40/CD40 ligand, sargramostim, levamisol, vaccinia virus, Bacille Calmette-Guerin (BCG), liposomes, alum, Freund's complete or incomplete adjuvant, detoxified endotoxins, mineral oils, surface active substances such as lipolecithin, pluronic polyols, polyanions, peptides, and oil or hydrocarbon emulsions. Adjuvants, such as aluminum hydroxide or aluminum phosphate, can be added to increase the ability of the vaccine to trigger, enhance, or prolong an immune response. Additional materials, such as cytokines, chemokines, and bacterial nucleic acid sequences, like CpG, a toll-like receptor (TLR) 9 agonist as well as additional agonists for TLR 2, TLR 4, TLR 5, TLR 7, TLR 8, TLR9, including lipoprotein, LPS, monophosphoryllipid A, lipoteichoic acid, imiquimod, resiquimod, and in addition retinoic acid-inducible gene I (RIG-I) agonists such as poly I:C, used separately or in combination with the described compositions are also potential adjuvants. Such antigens and anjuvants may be provided as a pharmaceutically acceptable salt, where appropriate.

CLTA-4 and PD-1 pathways are important negative regulators of immune response. Activated T-cells up-regulate CTLA-4, which binds on antigen-presenting cells and inhibits T-cell stimulation, IL-2 gene expression, and T-cell proliferation; these anti-tumor effects have been observed in mouse models of colon carcinoma, metastatic prostate cancer, and metastatic melanoma. PD-1 binds to active T-cells and suppresses T-cell activation; PD-1 antagonists have demonstrated anti-tumor effects as well. CTLA-4 and PD-1 pathway antagonists that may be used in combination with the compounds of general formula (I), compounds of general formula (II), compounds of general formula (III), compounds of general formula (IV), compounds of general formula (V), compounds of general formula (VI), or the pharmaceutically acceptable salts of the foregoing, disclosed herein, include ipilimumab, tremelimumab, nivolumab, pembrolizumab, CT-011, AMP-224, and MDX-1106.

"PD-1 antagonist" or "PD-1 pathway antagonist" means any chemical compound or biological molecule that blocks binding of PD-L1 expressed on a cancer cell to PD-1 expressed on an immune cell (T-cell, B-cell, or NKT-cell) and preferably also blocks binding of PD-L2 expressed on a cancer cell to the immune-cell expressed PD-1. Alternative names or synonyms for PD-1 and its ligands include: PDCD1, PD1, CD279, and SLEB2 for PD-1; PDCD1L1, PDL1, B7H1, B7-4, CD274, and B7-H for PD-L1; and PDCD1L2, PDL2, B7-DC, Btdc, and CD273 for PD-L2. In any of the treatment method, medicaments and uses of the present disclosure in which a human individual is being treated, the PD-1 antagonist blocks binding of human PD-L1 to human PD-1, and preferably blocks binding of both human PD-L1 and PD-L2 to human PD-1. Human PD-1 amino acid sequences can be found in NCBI Locus No.: NP_005009. Human PD-L1 and PD-L2 amino acid sequences can be found in NCBI Locus No.: NP_054862 and NP_079515, respectively.

PD-1 antagonists useful in any of the treatment method, medicaments and uses of the present disclosure include a monoclonal antibody (mAb), or antigen binding fragment thereof, which specifically binds to PD-1 or PD-L1, and preferably specifically binds to human PD-1 or human PD-L1. The mAb may be a human antibody, a humanized antibody, or a chimeric antibody and may include a human constant region. In some embodiments, the human constant region is selected from the group consisting of IgG1, IgG2, IgG3, and IgG4 constant regions, and in preferred embodiments, the human constant region is an IgG1 or IgG4 constant region. In some embodiments, the antigen binding fragment is selected from the group consisting of Fab, Fab'-SH, F(ab')$_2$, scFv, and Fv fragments.

Examples of mAbs that bind to human PD-1, and useful in the treatment method, medicaments and uses of the present disclosure, are described in U.S. Pat. Nos. 7,488,802, 7,521,051, 8,008,449, 8,354,509, and 8,168,757, PCT International Patent Application Publication Nos. WO2004/004771, WO2004/072286, and WO2004/056875, and U.S. Patent Application Publication No. US2011/0271358.

Examples of mAbs that bind to human PD-L1, and useful in the treatment method, medicaments and uses of the present disclosure, are described in PCT International Patent Application Nos. WO2013/019906 and WO2010/077634 A1 and in U.S. Pat. No. 8,383,796. Specific anti-human PD-L1 mAbs useful as the PD-1 antagonist in the treatment method, medicaments and uses of the present disclosure include MPDL3280A, BMS-936559, MEDI4736, MSB0010718C, and an antibody that comprises the heavy chain and light chain variable regions of SEQ ID NO:24 and SEQ ID NO:21, respectively, of WO2013/019906.

Other PD-1 antagonists useful in any of the treatment method, medicaments, and uses of the present disclosure include an immune-adhesion that specifically binds to PD-1 or PD-L1, and preferably specifically binds to human PD-1 or human PD-L1, e.g., a fusion protein containing the extracellular or PD-1 binding portion of PD-L1 or PD-L2 fused to a constant region such as an Fc region of an immunoglobulin molecule. Examples of immune-adhesion molecules that specifically bind to PD-1 are described in PCT International Patent Application Publication Nos. WO2010/027827 and WO2011/066342. Specific fusion proteins useful as the PD-1 antagonist in the treatment method, medicaments, and uses of the present disclosure include AMP-224 (also known as B7-DCIg), which is a PD-L2-FC fusion protein and binds to human PD-1.

The disclosure further relates to a method of treating cancer in a human patient comprising administration of a compound disclosed herein (i.e., a compound of general formula (I), a compound of general formula (II), a compound of general formula (III), a compound of general formula (IV), a compound of general formula (V), a compound of general formula (VI), or a pharmaceutically acceptable salt of the foregoing) and a PD-1 antagonist to the patient. The compound of the disclosure and the PD-1 antagonist may be administered concurrently or sequentially.

In particular embodiments, the PD-1 antagonist is an anti-PD-1 antibody, or antigen binding fragment thereof. In alternative embodiments, the PD-1 antagonist is an anti-PD-L1 antibody, or antigen binding fragment thereof. In some embodiments, the PD-1 antagonist is pembrolizumab (KEYTRUDA™, Merck & Co., Inc., Kenilworth, N.J., USA), nivolumab (OPDIVO™, Bristol-Myers Squibb Company, Princeton, N.J., USA), cemiplimab (LIBTAYO™, Regeneron Pharmaceuticals, Inc., Tarrytown, N.Y., USA), atezolizumab (TECENTRIQ™, Genentech, San Francisco, Calif., USA), durvalumab (IMFINZI™, AstraZeneca Pharmaceuticals LP, Wilmington, Del.), or avelumab (BAVENCIO™, Merck KGaA, Darmstadt, Germany).

In some embodiments, the PD-1 antagonist is pembrolizumab. In particular sub-embodiments, the method comprises administering 200 mg of pembrolizumab to the patient about every three weeks. In other sub-embodiments, the method comprises administering 400 mg of pembrolizumab to the patient about every six weeks.

In further sub-embodiments, the method comprises administering 2 mg/kg of pembrolizumab to the patient about every three weeks. In particular sub-embodiments, the patient is a pediatric patient.

In some embodiments, the PD-1 antagonist is nivolumab. In particular sub-embodiments, the method comprises administering 240 mg of nivolumab to the patient about every two weeks. In other sub-embodiments, the method comprises administering 480 mg of nivolumab to the patient about every four weeks.

In some embodiments, the PD-1 antagonist is cemiplimab. In particular embodiments, the method comprises administering 350 mg of cemiplimab to the patient about every 3 weeks.

In some embodiments, the PD-1 antagonist is atezolizumab. In particular sub-embodiments, the method comprises administering 1200 mg of atezolizumab to the patient about every three weeks.

In some embodiments, the PD-1 antagonist is durvalumab. In particular sub-embodiments, the method comprises administering 10 mg/kg of durvalumab to the patient about every two weeks.

In some embodiments, the PD-1 antagonist is avelumab. In particular sub-embodiments, the method comprises administering 800 mg of avelumab to the patient about every two weeks.

Examples of cytotoxic agents that may be used in combination with the compounds of general formula (I), compounds of general formula (II), compounds of general formula (III), compounds of general formula (IV), compounds of general formula (V), compounds of general formula (VI), or pharmaceutically acceptable salts of the foregoing, include, but are not limited to, arsenic trioxide (sold under the tradename TRISENOX®), asparaginase (also known as L-asparaginase, and *Erwinia* L-asparaginase, sold under the tradenames ELSPAR® and KIDROLASE®).

Chemotherapeutic agents that may be used in combination with the compounds of general formula (I), compounds of general formula (II), compounds of general formula (III), compounds of general formula (IV), compounds of general formula (V), compounds of general formula (VI), or pharmaceutically acceptable salts of the foregoing, disclosed herein include abiraterone acetate, altretamine, anhydrovinblastine, auristatin, bexarotene, bicalutamide, BMS 184476, 2,3,4,5,6-pentafluoro-N-(3-fluoro-4-methoxyphenyl) benzene sulfonamide, bleomycin, N,N-dimethyl-L-valyl-L-valyl-N-methyl-L-valyl-L-prolyl-1-Lproline-t-butylamide, cachectin, cemadotin, chlorambucil, cyclophosphamide, 3',4'-didehydro-4'deoxy-8'-norvin-caleukoblastine, docetaxol, doxetaxel, cyclophosphamide, carboplatin, carmustine, cisplatin, cryptophycin, cyclophosphamide, cytarabine, dacarbazine (DTIC), dactinomycin, daunorubicin, decitabine dolastatin, doxorubicin (adriamycin), etoposide, 5-fluorouracil, finasteride, flutamide, hydroxyurea and hydroxyurea andtaxanes, ifosfamide, liarozole, lonidamine, lomustine (CCNU), MDV3100, mechlorethamine (nitrogen mustard), melphalan, mivobulin isethionate, rhizoxin, sertenef, streptozocin, mitomycin, methotrexate, taxanes, nilutamide, nivolumab, onapristone, paclitaxel, pembrolizumab, prednimustine, procarbazine, RPR109881, stramustine phosphate, tamoxifen, tasonermin, taxol, tretinoin, vinblastine, vincristine, vindesine sulfate, and vinflunine. Such chemotherapeutic agents may be provided as a pharmaceutically acceptable salt, where appropriate.

Examples of vascular endothelial growth factor (VEGF) receptor inhibitors include, but are not limited to, bevacizumab (sold under the trademark AVASTIN), axitinib (described in PCT International Patent Publication No. WO01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy) propan-2-yl)$_2$-aminopropanoate, also known as BMS-582664), motesanib (N-(2,3-dihydro-3,3-dimethyl-1H-indol-6-yl)-2-[(4-pyridinylmethyl)amino]-3-pyridinecarboxamide. and described in PCT International Patent Application Publication No. WO02/068470), pasireotide (also known as SO 230, and described in PCT International Patent Publication No. WO02/010192), and sorafenib (sold under the tradename NEXAVAR). Such inhibitors may be provided as a pharmaceutically acceptable salt, where appropriate.

Examples of topoisomerase II inhibitors, include but are not limited to, etoposide (also known as VP-16 and Etoposide phosphate, sold under the tradenames TOPOSAR, VEPESID, and ETOPOPHOS), and teniposide (also known as VM-26, sold under the tradename VUMON). Such inhibitors may be provided as a pharmaceutically acceptable salt, where appropriate.

Examples of alkylating agents, include but are not limited to, 5-azacytidine (sold under the trade name VIDAZA), decitabine (sold under the trade name of DECOGEN), temozolomide (sold under the trade names TEMCAD, TEMODAR, and TEMODAL), dactinomycin (also known as actinomycin-D and sold under the tradename COSMEGEN), melphalan (also known as L-PAM, L-sarcolysin, and phenylalanine mustard, sold under the tradename ALKERAN), altretamine (also known as hexamethylmelamine (HMM), sold under the tradename HEXALEN), carmustine (sold under the tradename BCNU), bendamustine (sold under the tradename TREANDA), busulfan (sold under the tradenames BUSULFEX® and MYLERAN®), carboplatin (sold under the tradename PARAPLATIN®), lomustine (also known as CCNU, sold under the tradename CEENU®), cisplatin (also known as CDDP, sold under the tradenames PLATINOL® and PLATINOL®-AQ), chlorambucil (sold under the tradename LEUKERAN®), cyclophosphamide (sold under the tradenames CYTOXAN® and NEOSAR®), dacarbazine (also known as DTIC, DIC and imidazole carboxamide, sold under the tradename DTIC-DOME®), altretamine (also known as hexamethylmelamine (HMM) sold under the tradename HEXALEN®), ifosfamide (sold under the tradename IFEX®), procarbazine (sold under the tradename MATULANE®), mechlorethamine (also known as nitrogen mustard, mustine and mechloroethamine hydrochloride, sold under the tradename MUSTARGEN®), streptozocin (sold under the tradename ZANOSAR®), thiotepa (also known as thiophosphoamide, TESPA and TSPA, and sold under the tradename THIOPLEX®. Such alkylating agents may be provided as a pharmaceutically acceptable salt, where appropriate.

Examples of anti-tumor antibiotics include, but are not limited to, doxorubicin (sold under the tradenames ADRIAMYCIN® and RUBEX®), bleomycin (sold under the tradename LENOXANE®), daunorubicin (also known as dauorubicin hydrochloride, daunomycin, and rubidomycin hydrochloride, sold under the tradename CERUBIDINE®), daunorubicin liposomal (daunorubicin citrate liposome, sold under the tradename DAUNOXOME®), mitoxantrone (also known as DHAD, sold under the tradename NOVANTRONE®), epirubicin (sold under the tradename ELLENCE™), idarubicin (sold under the tradenames IDAMYCIN®, IDAMYCIN PFS®), and mitomycin C (sold under the tradename MUTAMYCIN®). Such anti-tumor antibiotics may be provided as a pharmaceutically acceptable salt, where appropriate.

Examples of anti-metabolites include, but are not limited to, claribine (2-chlorodeoxyadenosine, sold under the tradename LEUSTATIN®), 5-fluorouracil (sold under the tradename ADRUCIL®), 6-thioguanine (sold under the tradename PURINETHOL®), pemetrexed (sold under the tradename ALIMTA®), cytarabine (also known as arabinosylcytosine (Ara-C), sold under the tradename CYTOSAR-U®), cytarabine liposomal (also known as Liposomal Ara-C, sold under the tradename DEPOCYT™), decitabine (sold under the tradename DACOGEN®), hydroxyurea and (sold under the tradenames HYDREA®, DROXIA™ and MYLOCEL™), fludarabine (sold under the tradename FLUDARA®), floxuridine (sold under the tradename FUDR®), cladribine (also known as 2-chlorodeoxyadenosine (2-CdA) sold under the tradename LEUSTATIN™), methotrexate (also known as amethopterin, methotrexate sodium (MTX), sold under the tradenames RHEUMATREX® and TREXALL™), and pentostatin (sold under the tradename NIPENT®). Such anti-metabolites may be provided as a pharmaceutically acceptable salt, where appropriate.

Examples of retinoids include, but are not limited to, alitretinoin (sold under the tradename PANRETIN®), tretinoin (all-trans retinoic acid, also known as ATRA, sold under the tradename VESANOID®), Isotretinoin (13-c/s-retinoic acid, sold under the tradenames ACCUTANE®, AMNESTEEM®, CLARAVIS®, CLARUS®, DECUTAN®, ISOTANE®, IZOTECH®, ORATANE®, ISOTRET®, and SOTRET®), and bexarotene (sold under the tradename TARGRETIN®). Such compounds may be provided as a pharmaceutically acceptable salt, where appropriate.

Activity: STING Biochemical [3H]cGAMP Competition Assay

The individual compounds described in the Examples herein are defined as STING agonists by (i) binding to the STING protein as evidenced by a reduction in binding of tritiated cGAMP ligand to the STING protein by at least 20% at 20 uM (concentration of compound being tested) in a STING Biochemical [3H]cGAMP Competition Assay and/or (ii) demonstrating interferon production with a 6% or greater induction of IFN-3 secretion at 30 uM in the THP1 cell assay (where induction caused by cGAMP at 30 uM was set at 100%).

The ability of compounds to bind STING is quantified by the ability to compete with tritiated cGAMP ligand for human STING receptor membrane using a radioactive filter-binding assay. The binding assay employs STING receptor obtained from Hi-Five cell membranes overexpressing full-length HAQ STING prepared in-house and tritiated cGAMP ligand also purified in-house.

The following experimental procedures detail the preparation of specific examples of the instant disclosure. The compounds of the examples are drawn in their neutral forms in the procedures and tables below. In some cases, the compounds were isolated as salts depending on the method used for their final purification and/or intrinsic molecular properties. The examples are for illustrative purposes only and are not intended to limit the scope of the instant disclosure in any way.

EXAMPLES

Abbreviations

2',3'cGAMP, cGAMP 2',3'-cyclic guanosine monophosphate-adenosine monophosphate
18-Crown-6 1,4,7,10,13,16-hexaoxacyclooctadecane
Ac Acetyl
ACN, MeCN Acetonitrile
AcOH, HOAc Acetic acid
AMP Adenosine monophosphate
aq Aqueous
ATP Adenosine 5'-triphosphate
BIIC Baculovirus Infected Insect Cell
br Broad
Bu Butyl, $C_4H_9$
cat Catalog number
CBZ Benzyl chlorocarbonate
$CD_3OD$ Deuterium-enriched methyl alcohol, deuterium-enriched methanol
$CDCl_3$ Deuterated trichloromethane, deuterated chloroform
CDI Carbonyl diimidazole
cGAMP Cyclic GMP-AMP synthase
Ci Curie, a non-standard unit of radioactivity; 1 Ci=3.7× $10^{10}$Bq, where Bq is Becquerel, the SI unit of radioactivity, equivalent to 1 disintegration per second (dps)
C-Phos Pd G3 [(2-Dicyclohexylphosphino-2',6'-bis(N,N-dimethylamino)-1,1'-biphenyl)-2-(2'-amino-1,1'-biphenyl)] palladium(II) methanesulfonate
C-Phos Pd G4 2-Aminobiphenylpalladium methanesulfonate palladium CPhos precatalyst (4$^{th}$ generation precatalyst); [(2-Dicyclohexylphosphino-2',6'-bis(N,N-dimethylamino)-1,1'-biphenyl)-2-(2'-methylamino-1,1'-biphenyl)] palladium(II) methanesulfonate
Cy Cyclohexyl
d Doublet
DBU 1,8-Diazabicyclo[5.4.0]undec-7-ene
DCE 1,2-Dichloroethane
DCM, $CH_2Cl_2$ Dichloromethane
ddd Doublet of doublet of doublet
ddt Doublet of doublet of triplet
DIAD Diisopropyl azodicarboxylate
DIPEA N,N-Diisopropylethylamine
DMA Dimethylacetamide
DMAP 4-dimethylaminopyridine
DME Dimethylether
DMEA N,N-dimethyl ethyl amine
DMF N,N-dimethylformamide
DMPU 1,3-Dimethyl-3,4,5,6-tetrahydro-2-pyrimidinone
DMSO Dimethylsulfoxide
DMTr 4,4'-dimethoxytrityl
DMTrCl 4,4'-dimethoxytrityl chloride
dq Doublet of quartet
$EC_{50}$ half maximal effective concentration; concentration of a drug, antibody, or toxicant that induces a response halfway between the baseline and maximum after a specified exposure time
EDC Ethylene dichloride
eq Equivalents
ES Electron spray
Et Ethyl, $C_2H_5$
GMP Guanosine 5'-monophosphate
Grubbs catalyst 2G (1,3-Bis(2,4,6-trimethylphenyl)-2-imidazolidinylidene)dichloro (phenylmethyl ene)(tricyclohexylphosphine)ruthenium; Benzylidene[1,3-bis(2,4,6-trimethylphenyl)-2-imidazolidinylidene] dichloro(tricyclohexylphosphine)ruthenium; Dichloro[1,3-bis(2,4,6-trimethylphenyl)-2-imidazolidinylidene] (benzylidene) (tricyclohexylphosphine)ruthenium(II)
GTP Guanosine 5'-triphosphate
h Hour
HAQ STING Common STING variant containing the three mutations R71H-G230A-R293Q (DNA construct used herein: STING(1-379)R71H, G230A,H232R, R293Q-GG-AviTag-GS-HRV3C-HIS8/pBAC1)
HEPES 2-[4-(2-hydroxyethyl)piperazin-1-yl]ethanesulfonic acid, a zwitterionic organic chemical buffering agent
hept Heptet
Hex Hexanes
HPLC High performance liquid chromatography
$IC_{50}$ half maximal inhibitory concentration; concentration of a drug, antibody, or toxicant required for 50% inhibition of response or binding
Inh Inhibition
IPA Isopropyl alcohol, $CH_3CHOHCH_3$
LAH Lithium aluminum hydride
Lawesson's reagent 2,4-Bis(4-methoxyphenyl)-1,3,2,4-dithiadiphosphetane-2,4-dithione
LCMS Liquid chromatography-mass spectroscopy
LDA Lithium di-isopropyl amide
m Multiplet
M Molar, moles per liter
m/z Mass-to-charge ratio
M+H Protonated mass, mass measurement produced by mass spectrometry
Me Methyl, $CH_3$
min Minute(s)
MOI Multiplicity of infection
MOM-Cl Cloromethyl methyl ether
MP-TsOH para-Tolune sulfonated macroporous polystyrene resin
n-BuLi n-Butyl lithium
NBS N-Bromosuccinamide
NCS N-Chlorosuccinamide
NMP N-methyl-2-pyrrolidone
OXONE® Potassium peroxymonosulfate, specifically $2KHSO_5KHSO_4K_2SO_4$
Pd/C Palladium on carbon
$PdCl_2$(dppf)-$CH_2C_2$[1,1'-Bis(diphenylphosphino)ferrocene]dichloropalladiumn(II), complex with dichloromethane
Pd($Ph_3P)_4$ Tetrakis(triphenyl phosphine) palladium(0)
$Pd_2$(dba)$_3$ Tris(dibenzylidene acetone) dipalladium(0)
PE Petroleum ether
pfu Plaque-forming unit
$Ph_3P$ Triphenyl phosphine
prep-HPLC Preparative high performance liquid chromatography
prep-TLC Preparative thin layer liquid chromatography
PS-TPP Polymer-supported triphenylphospine
PSI Pounds per square inch
pTsOH para-Tolunesulfonic acid
Py, py Pyridine
q Quartet
Rac, rac Racemic
Rac BINAP Pd G3 2-(2-aminophenyl)benzen-1-ide methanesulfonic acid {1-[2-(diphenyl-phosphanyl)naphthalen-1-yl]naphthalen-2-yl}diphenylphosphane palladium RockPhos Pd G3 [(2-Di-tert-butylphosphino-3-methoxy-6-methyl-2',4',6'-triisopropyl-1,1'-biphenyl)-2-(2-aminobiphenyl)]palladium(II) methanesulfonate RP-HPLC Reverse-phase high performance liquid chromatography RPM, rpm Revolutions per minute RT, rt Room temperature, approximately 25° C.

s Singlet sat Saturated

SFC Supercritical fluid chromatography t Triplet

TBAF, nBu₄NF Tetra-n-Butylammonium fluoride

TBS, TBDMS tert-Butyldimethylsilyl

TBTU 2-(1H-Benzotriazole-1-yl)-1,1,3,3-tetramethyluronium tetrafluoroborate

TEA Triethylamine

TFA Trifluoroacetic acid

THF Tetrahydrofuran

TLC Thin layer chromatography

TMS Trimethylsilyl $T_R$ Retention time

TrisCl Tris(hydroxymethyl)aminomethane hydrochloride v/v Volume/volume

WT STING Wild type (most abundant) variant of STING in humans (DNA construct used herein: STING(1-379) H232R-gg-AviTag-gs-HRV3C-HIS8/pBAC1)

X-Phos 2-Dicyclohexylphosphino-2',4',6'-triisopropylbiphenyl

Xantphos 4,5-Bis(diphenylphosphino)-9,9-dimethylxanthene $\lambda_{em}$ Emission wavelength $\lambda_{ex}$ Excitation wavelength Preparation 1: Magnesium 3-(tert-butoxy)-3-oxopropanoate

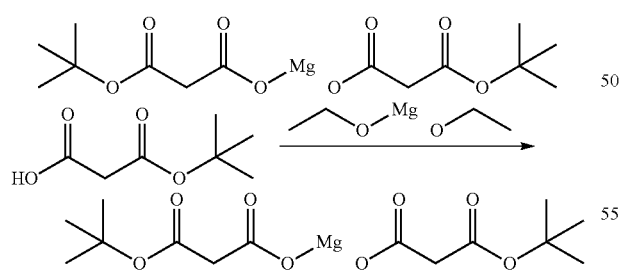

Magnesium ethanolate (3.57 g, 31.2 mmol) was added to a mixture of 3-(tert-butoxy)-3-oxopropanoic acid (10.0 g, 62.4 mmol) in THF (100 mL) at 20° C. The reaction mixture was stirred at 20° C. for 18 h under Ar. The reaction mixture was then concentrated under reduced pressure. The residue was dried under reduced pressure to afford magnesium 3-(tert-butoxy)-3-oxopropanoate. ¹H NMR (499 MHz, DMSO-$d_6$) δ 2.96 (s, 4H), 1.39 (s, 18H).

Preparation 2: tert-Butyl 3-(2,3-dimethoxythieno[2,3-b]pyrazin-6-yl)-3-oxopropanoate

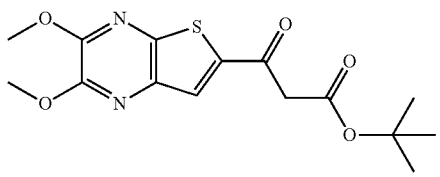

Step 1: 3-Bromo-5,6-dimethoxypyrazine-2-carbaldehyde

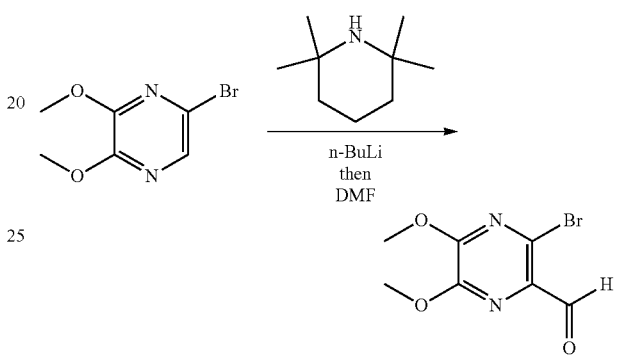

To a solution of 2,2,6,6-tetramethylpiperidine (5.12 mL, 30.1 mmol) in THF (40 mL) at −78° C. was added dropwise a solution of n-BuLi (2.5M in Hex, 11.5 mL, 28.8 mmol). The reaction mixture was stirred for 10 min at −78° C. and then warmed to 0° C. and stirred for 20 min. The reaction mixture was then cooled back to −78° C., and a solution of 5-bromo-2,3-dimethoxypyrazine (3.00 g, 13.7 mmol) in THF (10 mL) was added over 5 min. The reaction mixture was stirred at −78° C. for 1 h and then quenched with DMF (1.06 mL, 13.7 mmol). The reaction mixture was warmed to 0° C. and stirred for an additional 20 min. AcOH (3.0 mL) was added at 0° C., and the reaction mixture was warmed to RT and stirred overnight. The mixture was diluted with EtOAc (300 mL) and then washed with H₂O (2×150 mL) and sat aq NaCl. The organic layer was separated, dried over Na₂SO₄, filtered, and concentrated under reduced pressure. The residue was purified by silica gel chromatography (eluting EtOAc in Hex) to afford 3-bromo-5,6-dimethoxypyrazine-2-carbaldehyde. LCMS ($C_7H_8BrN_2O_3$) (ES, m/z): 247, 249 [M+H]⁺. ¹H NMR (500 MHz, CDCl₃) δ 10.19 (s, 1H), 4.17 (s, 3H), 4.14 (s, 3H).

Step 2: tert-Butyl 2,3-dimethoxythieno[2,3-b]pyrazine-6-carboxylate

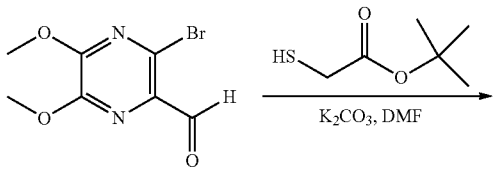

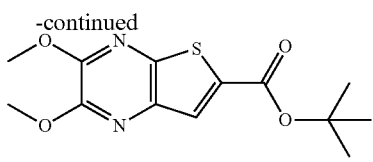

tert-Butyl 2-sulfanylacetate (424 µL, 2.92 mmol) and DMF (2.9 mL) were added to 3-bromo-5,6-dimethoxypyrazine-2-carbaldehyde (650 mg, 2.63 mmol) at RT. $K_2CO_3$ (1090 mg, 7.89 mmol) was then added portion-wise to the reaction mixture at RT. The reaction mixture was heated to 80° C. and stirred overnight. The reaction mixture was then cooled to RT, diluted with $Et_2O$, and quenched with $H_2O$. The reaction mixture was extracted with $Et_2O$, and the combined organics were washed with sat aq NaCl, dried over $Na_2SO_4$, filtered, and concentrated under reduced pressure. The residue was purified by silica gel chromatography (eluting EtOAc in Hex) to yield tert-butyl 2,3-dimethoxythieno[2,3-b]pyrazine-6-carboxylate. LCMS ($C_{13}H_{17}N_2O_4S$) (ES, m/z): 297 [M+H]$^+$. $^1$H NMR (500 MHz, DMSO-$d_6$) δ 7.89 (s, 1H), 4.02 (s, 3H), 3.99 (s, 3H), 1.55 (s, 9H).

Step 3: 2,3-Dimethoxthieno[2,3-b]pyrazine-6-carboxylic acid

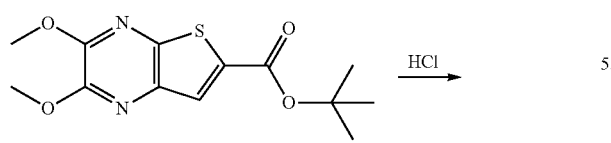 HCl →

To a stirred solution of tert-butyl 2,3-dimethoxythieno[2,3-b]pyrazine-6-carboxylate (400 mg, 1.35 mmol) in DCM (6.0 mL) was added HCl (4.0M in dioxane, 1.7 mL, 6.8 mmol) at RT. The reaction mixture was stirred overnight at RT, and then diluted by the dropwise addition of Hex (50 mL) and stirred for 1 h at RT. The reaction mixture was filtered, and the collected materials were washed with Hex (2×10 mL) and dried under reduced pressure to afford 2,3-dimethoxythieno[2,3-b]pyrazine-6-carboxylic acid. LCMS ($C_9H_9N_2O_4S$) (ES, m/z): 241 [M+H]$^+$. $^1$H NMR (500 MHz, DMSO-$d_6$) δ 12.71 (br s, 1H), 7.90 (s, 1H), 4.03 (s, 3H), 3.99 (s, 3H).

Step 4: tert-Butyl 3-(2,3-dimethoxythieno[2,3-b]pyrazin-6-yl)-3-oxopropanoate

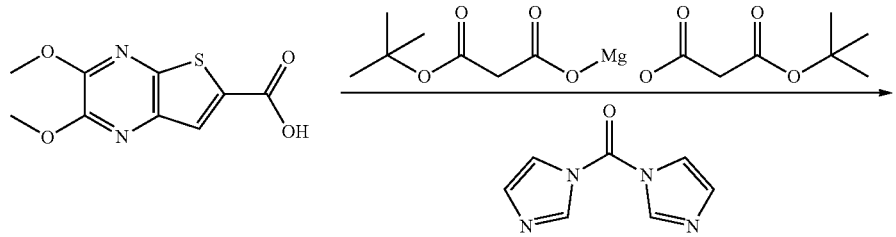

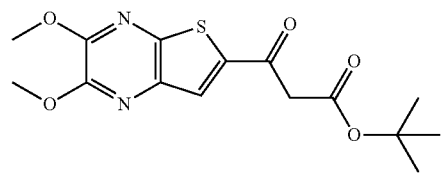 [SMILES: COc1nc2cc(C(=O)CC(=O)OC(C)(C)C)sc2nc1OC]

A mixture of 2,3-dimethoxythieno[2,3-b]pyrazine-6-carboxylic acid (80 mg, 0.33 mmol) and CDI (324 mg, 2.00 mmol) in THF (5.5 mL) was stirred at RT for 3 h. Magnesium bis(3-tert-butoxy-3-oxopropanoate) (628 mg, 1.83 mmol) was added to the mixture, and the resulting mixture was stirred overnight at RT. The reaction mixture was concentrated under reduced pressure. The residue was purified by silica gel chromatography (eluting (25% EtOH in EtOAc) in Hex) to afford tert-butyl 3-(2,3-dimethoxythieno[2,3-b]pyrazin-6-yl)-3-oxopropanoate. LCMS ($C_{15}H_{19}N_2O_5S$) (ES, m/z): 339 [M+H]$^+$. $^1$H NMR (500 MHz, DMSO-$d_6$) δ 8.32 (s, 1H), 4.13 (s, 2H), 4.04 (s, 3H), 4.00 (s, 3H), 1.41 (s, 9H).

Preparation 3: 5,6-Dimethoxythieno[3,2-b]pyridine-2-carboxylic acid

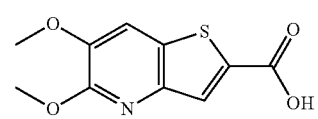 [SMILES: COc1cc2sc(C(=O)O)cc2nc1OC]

Step 1: tert-Butyl 5,6-dimethoxythieno[3,2-b]pyridine-2-carboxylate

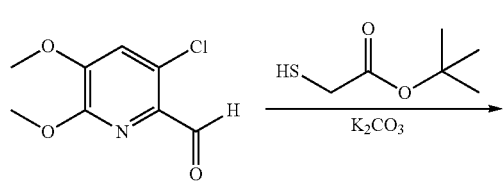

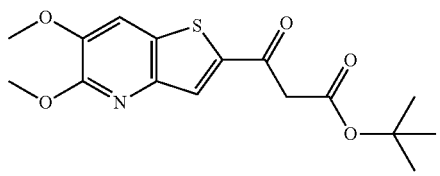

K$_2$CO$_3$ (1180 mg, 8.56 mmol) was added to a mixture of 3-chloro-5,6-dimethoxypicolinaldehyde (575 mg, 2.86 mmol) and tert-butyl 2-sulfanylacetate (0.456 mL, 3.14 mmol) in DMF (8.3 mL) at RT. The reaction mixture was stirred and heated to 60° C. for 3 days. The reaction mixture was cooled to RT, and then diluted with Et$_2$O and H$_2$O. The organic layer was separated, washed with sat aq NaCl, dried over Na$_2$SO$_4$, filtered, and concentrated under reduced pressure. The residue was purified by silica gel chromatography (eluting EtOAc in Hex) to afford tert-butyl 5,6-dimethoxythieno[3,2-b]pyridine-2-carboxylate. $^1$H NMR (499 MHz, DMSO-d$_6$) δ 7.95 (s, 1H), 7.84 (s, 1H), 3.93 (s, 3H), 3.87 (s, 3H), 1.54 (s, 9H).

Step 2: 5,6-dimethoxythieno[3,2-b]pyridine-2-carboxylic acid

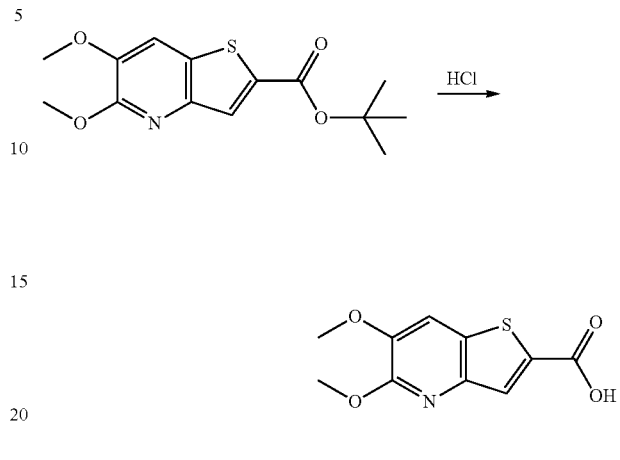

HCl (4.0M in H$_2$O, 2.1 mL, 8.4 mmol) was added to a solution of tert-butyl 5,6-dimethoxythieno[3,2-b]pyridine-2-carboxylate (493 mg, 1.67 mmol) in DCM (7.4 mL) at RT. The reaction mixture was stirred overnight at RT, and then diluted by the dropwise addition of Hex (50 mL). The mixture was stirred for 1 h and then filtered. The collected materials were washed with Hex (2×10 mL) and then dried under reduced pressure to afford 5,6-dimethoxythieno[3,2-b]pyridine-2-carboxylic acid. LCMS (C$_{10}$H$_{10}$NO$_4$S) (ES, m/z): 240 [M+H]$^+$. $^1$H NMR (499 MHz, DMSO-d$_6$) δ 7.97 (s, 1H), 7.85 (s, 1H), 3.95 (s, 3H), 3.88 (s, 3H).

Preparation 4: tert-Butyl 3-(5,6-dimethoxythieno[3,2-b]pyridin-2-yl)-3-oxopropanoate

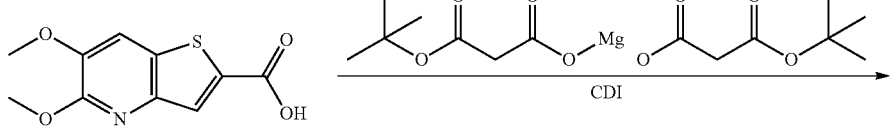

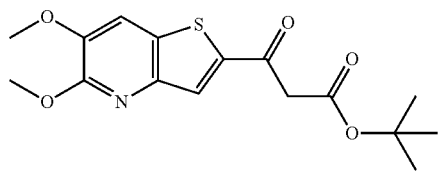

CDI (508 mg, 3.13 mmol) was added to a mixture of 5,6-dimethoxythieno[3,2-b]pyridine-2-carboxylic acid (500 mg, 2.09 mmol) in THF (5 mL). The reaction mixture was stirred at RT for 3 h. The reaction mixture was added to a separate flask containing magnesium 3-(tert-butoxy)-3-oxopropanoate (1220 mg, 3.55 mmol). The reaction mixture was diluted with additional THF (4 mL) and was stirred overnight at RT. The reaction mixture was then heated to 50° C. for 1 h. The reaction mixture was cooled to RT and diluted with H$_2$O (20 mL). Sodium citrate tribasic dihydrate (2 g) and EtOAc (50 mL) were added. The organic layer was separated, and the aqueous layer was extracted with EtOAc. The organic layers were combined, washed with sat aq NaCl, dried over anhydrous Na$_2$SO$_4$, filtered, and concentrated under reduced pressure. The residue was purified via silica gel chromatography (eluting EtOAc in Hex) to afford tert-butyl 3-(5,6-dimethoxythieno[3,2-b]pyridin-2-yl)-3-oxopropanoate. LCMS (C$_{16}$H$_{20}$NO$_5$S) (ES, m/z): 338 [M+H]$^+$. $^1$H NMR (500 MHz, CDCl$_3$) δ 7.97 (s, 1H), 7.44 (s, 1H), 4.13 (s, 3H), 3.99 (s, 3H), 3.92 (s, 2H), 1.48 (s, 9H).

Preparation 5: C-Phos Pd G4

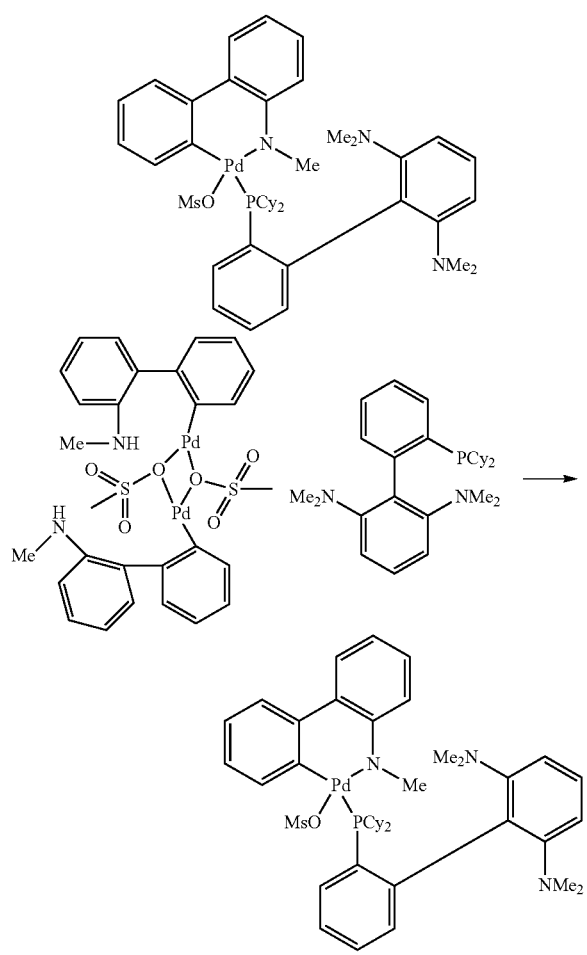

A mixture of (2'-methylamino-1,1'-biphenyl-2-yl)methanesulfonatopalladium (II) dimer (439 mg, 0.573 mmol) and 2'-(dicyclohexylphosphino)-N2,N2,N6,N6-tetramethyl-[1,1'-biphenyl]-2,6-diamine (500 mg, 1.15 mmol) in DCM (6 mL) was stirred at RT for 2 h. The solution was then diluted with Et$_2$O (30 mL). The solution was filtered and concentrated under reduced pressure. The residue was then slurried in pentanes and again concentrated under reduced pressure to afford C-Phos Pd G4. See Bruno, N. C.; Niljianskul, N.; Buchwald, S. L. *J. Org. Chem.* 2014, 79, 4161.

Intermediate 1: methyl (S)-4-(5-chloro-6-methoxythieno[3,2-b]pyridin-2-yl)-2-methyl-4-oxobutanoate

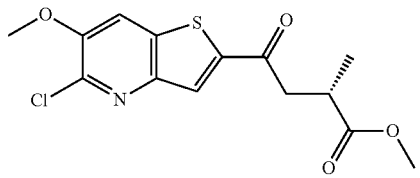

Step 1: 5-Chloro-6-methoxythieno[3,2-b]pyridine-2-carbonyl chloride

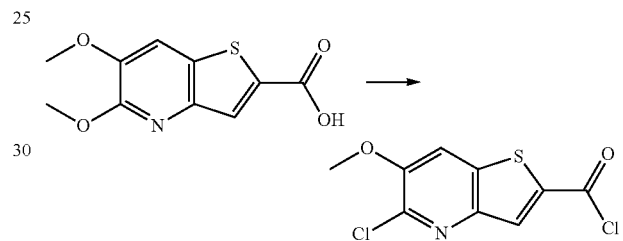

POCl$_3$ (1.17 mL, 12.5 mmol) was added dropwise to a stirred mixture of 5,6-dimethoxythieno[3,2-b]pyridine-2-carboxylic acid (1.00 g, 4.1 mmol) in DMF (10.45 ml) at 0° C. under N$_2$. After 10 min, the reaction mixture was allowed to warm to RT. The reaction mixture was then heated to 100° C. and stirred for 45 min. The reaction mixture was added ice water (100 mL) and stirred. The mixture was filtered, and the collected materials were washed with water (2×30 mL) and Hex (50 mL). The collected materials were diluted with Et$_2$O (50 mL) and filtered. The collected materials were dissolved in CH$_2$Cl$_2$ (60 mL), and the mixture was dried over anhydrous Na$_2$SO$_4$, filtered, and concentrated under reduced pressure to afford 5-chloro-6-methoxythieno[3,2-b]pyridine-2-carbonyl chloride. $^1$H NMR (500 MHz, CDCl$_3$) δ 8.32 (s, 1H), 7.60 (s, 1H), 4.06 (s, 3H).

Step 2: Methyl (S)-4-(5-chloro-6-methoxythieno[3,2-b]pyridin-2-yl)-2-methyl-4-oxobutanoate

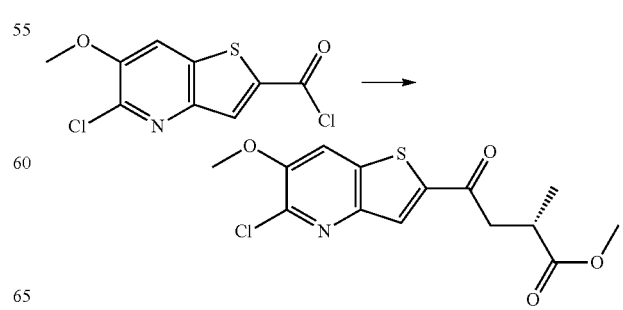

CuI (0.073 g, 0.38 mmol) was placed under vacuum and heated for 1 min with a heat gun. The flask was allowed to cool to RT and was then opened to $N_2$. Twice more the flask was evacuated then backfilled with $N_2$. The flask was kept under positive $N_2$ pressure with a rubber septum and $N_2$ inlet attached. THF (2 mL) was added to the flask, and the reaction mixture was cooled in an ice water bath. A solution of (R)-(3-methoxy-2-methyl-3-oxopropyl) zinc(II) bromide in THF (0.50M, 1.68 mL, 0.84 mmol) was added dropwise to the reaction mixture over a period of 5 min. The reaction mixture was stirred for 105 min at 0° C. A mixture of 5-chloro-6-methoxythieno[3,2-b]pyridine-2-carbonyl chloride (0.200 g, 0.763 mmol) in NMP (3 mL) was then added dropwise over 5 min. The reaction mixture was then stirred for 3 h at 0° C. The reaction mixture was then added to a stirred mixture of isopropyl acetate (50 mL) and sodium citrate (20% w/v in water, 50 mL). After stirring for 20 min, the layers were separated, and the aqueous layer was extracted with isopropyl acetate (30 mL). The organic layers were combined, washed with sat aq NaCl (2×50 mL), dried over anhydrous $Na_2SO_4$, filtered, and concentrated under reduced pressure. The residue was purified by silica gel chromatography (eluting EtOAc in Hex) to afford (S)-methyl 4-(5-chloro-6-methoxythieno[3,2-b]pyridin-2-yl)-2-methyl-4-oxobutanoate. LCMS ($C_{14}H_{15}ClNO_4S$) (ES, m/z): 328 [M+H]$^+$. $^1$H NMR (500 MHz, CDCl$_3$) δ 7.99 (s, 1H), 7.60 (s, 1H), 4.03 (s, 3H), 3.72 (s, 3H), 3.51 (dd, J=17.2, 7.9 Hz, 1H), 3.21-3.12 (m, 1H), 3.06 (dd, J=17.2, 5.2 Hz, 1H), 1.32 (d, J=7.1 Hz, 3H).

Intermediate 2: tert-Butyl 4-(5-(3-hydroxypropyl)-6-methoxybenzo[b]thiophen-2-yl)-4-oxobutanoate

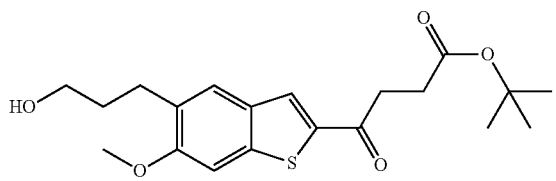 [SMILES: COc1cc2sc(C(=O)CCC(=O)OC(C)(C)C)cc2cc1CCCO]

Step 1: tert-butyl 4-(5-(3-((tert-butyldimethylsilyl)oxy)propyl)-6-methoxybenzo[b]thiophen-2-yl)-4-oxobutanoate

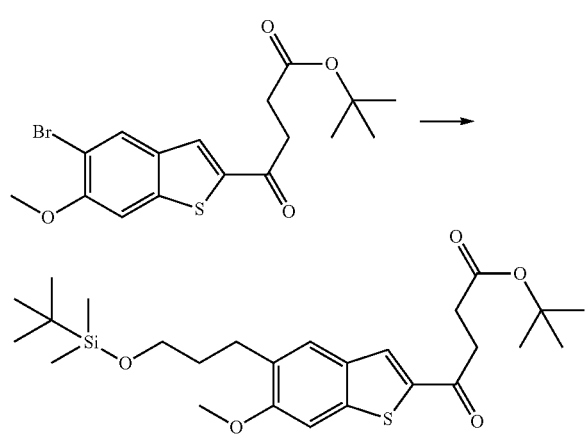

tert-Butyl 4-(5-bromo-6-methoxybenzo[b]thiophen-2-yl)-4-oxobutanoate (1.75 g, 4.38 mmol; 81% pure) and C-Phos Pd G3 (0.177 g, 0.219 mmol) were added to a 40 mL vial with a septum-containing screw cap. The vial was evacuated and backfilled with $N_2$ three times. THF (15.7 mL) was added to the vial under $N_2$ with stirring. While stirring the resulting suspension at RT, (3-((tert-butyldimethylsilyl)oxy)propyl)zinc(II) bromide (0.50M in THF, 17.5 mL, 8.75 mmol) was added dropwise with stirring. The mixture was stirred at RT for 18 h. The reaction was then partitioned between EtOAc (75 mL) and 10% aq sodium citrate (75 mL) and stirred vigorously for 5 min. The layers were separated, and the aqueous layer was extracted with EtOAc (20 mL). The organic layers were combined, washed with sat aq NaCl (50 mL), dried over anhydrous $Na_2SO_4$, filtered and concentrated under reduced pressure. The residue was purified by silica gel chromatography (0→40% EtOAc gradient in Hex) to afford tert-butyl 4-(5-(3-((tert-butyldimethylsilyl)oxy)propyl)-6-methoxybenzo[b]thiophen-2-yl)-4-oxobutanoate. LCMS ($C_{26}H_{40}NaO_5SSi$) (ES, m/z): 515 [M+Na]$^+$. $^1$H NMR (500 MHz, CDCl$_3$) δ 7.89 (s, 1H), 7.62 (s, 1H), 7.24 (s, 1H), 3.92 (s, 3H), 3.67 (t, J=6.3 Hz, 2H), 3.28 (t, J=6.8 Hz, 2H), 2.76 (t, J=7.2 Hz, 2H), 2.72 (t, J=7.2 Hz, 2H), 1.85 (p, J=6.5 Hz, 2H), 1.46 (s, 9H), 0.94 (s, 9H), 0.08 (s, 6H).

Step 2: tert-butyl 4-(5-(3-hydroxypropyl)-6-methoxybenzo[b]thiophen-2-yl)-4-oxobutanoate

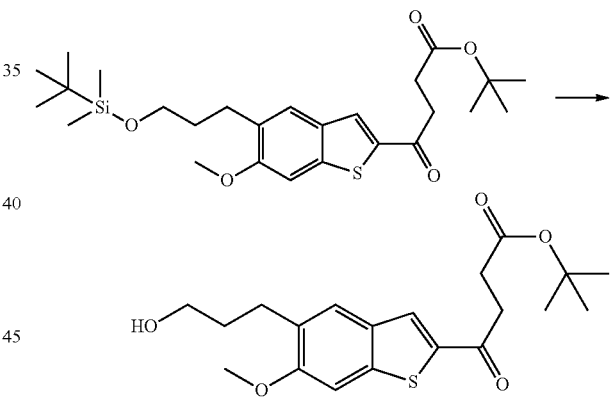

To a mixture of tert-butyl 4-(5-(3-((tert-butyldimethylsilyl)oxy)propyl)-6-methoxybenzo[b]thiophen-2-yl)-4-oxobutanoate (1.45 g, 2.94 mmol) in MeOH (5.0 mL) was added water (5.0 mL) and HOAc (5.0 mL). The resulting suspension was stirred at RT for 18 h. The reaction was partitioned between EtOAc and aq NaCl. The layers were separated, and the aqueous layer was extracted with EtOAc. The organic layers were combined, washed with sat aq NaCl twice, dried over anhydrous $Na_2SO_4$, filtered and concentrated under reduced pressure to afford a crude residue. The resulting residue was purified by silica gel chromatography (0→100% EtOAc gradient in Hex) to afford tert-butyl 4-(5-(3-hydroxypropyl)-6-methoxybenzo[b]thiophen-2-yl)-4-oxobutanoate. LCMS ($C_{20}H_{26}NaO_5S$) (ES, m/z): 401 [M+Na]$^+$. $^1$H NMR (500 MHz, CDCl$_3$) δ 7.89 (s, 1H), 7.64 (s, 1H), 7.26 (s, 1H), 3.94 (s, 3H), 3.68 (t, J=5.5 Hz, 2H), 3.28 (t, J=6.6 Hz, 2H), 2.82 (t, J=7.3 Hz, 2H), 2.72 (t, J=6.6 Hz, 2H), 1.96-1.83 (m, 2H), 1.46 (s, 9H).

Intermediate 3: tert-butyl 4-(5-(3-bromopropyl)-6-methoxybenzo[b]thiophen-2-yl)-4-oxobutanoate

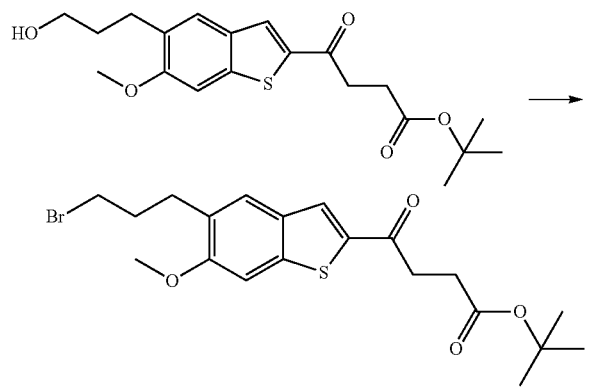

Triphenylphosphine (0.24 g, 0.91 mmol) was added to a mixture of tert-butyl 4-(5-(3-hydroxypropyl)-6-methoxybenzo[b]thiophen-2-yl)-4-oxobutanoate (0.22 g, 0.57 mmol) in THF (2.8 mL). The resulting mixture was cooled to 0° C., and NBS (0.15 g, 0.85 mmol) was added in a single portion. After stirring for 30 min at 0° C., the reaction was diluted with sat aq $AlCl_3$ and EtOAc. The organic layer was separated, dried over $Na_2SO_4$, filtered and concentrated under reduced pressure. The resulting product was then purified by silica gel chromatography to afford tert-butyl 4-(5-(3-bromopropyl)-6-methoxybenzo[b]thiophen-2-yl)-4-oxobutanoate. LCMS ($C_{16}H_{18}BrO_4S$) (ES, m/z): 385, 387 [M-$C_4Hs$]$^+$. $^1$H NMR (500 MHz, DMSO-$d_6$) δ 8.27 (s, 1H), 7.78 (s, 1H), 7.62 (s, 1H), 3.90 (s, 3H), 3.60-3.49 (m, 2H), 3.30-3.21 (m, 2H), 2.88-2.75 (m, 2H), 2.67-2.56 (m, 2H), 2.18-2.06 (m, 2H), 1.38 (s, 9H).

Intermediate 4: 4-(5-bromo-6-methoxybenzo[b]thiophen-2-yl)-4-oxobutanenitrile

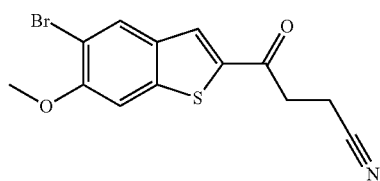 [SMILES: COc1cc2sc(C(=O)CCC#N)cc2cc1Br]

Step 1: methyl 5-bromo-6-methoxybenzo[b]thiophene-2-carboxylate

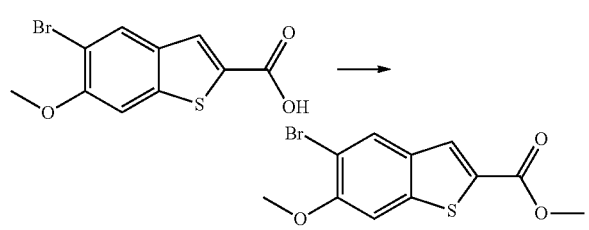

Concentrated $H_2SO_4$ (3.0 mL, 56 mmol) was added to a suspension of 5-bromo-6-methoxybenzo[b]thiophene-2-carboxylic acid (5.0 g, 17 mmol) in MeOH (60 mL). The reaction mixture was heated to 70° C. for 4.5 days. The mixture was then cooled to RT and diluted with water. To the mixture was added 30% IPA in $CHCl_3$. The organic layer was separated, dried over $Na_2SO_4$, filtered and concentrated under reduced pressure to afford methyl 5-bromo-6-methoxybenzo[b]thiophene-2-carboxylate. $^1$H NMR (500 MHz, DMSO-$d_6$) δ 8.30 (s, 1H), 8.09 (s, 1H), 7.83 (s, 1H), 3.95 (s, 3H), 3.88 (s, 3H).

Step 2: (5-bromo-6-methoxybenzo[b]thiophen-2-yl)methanol

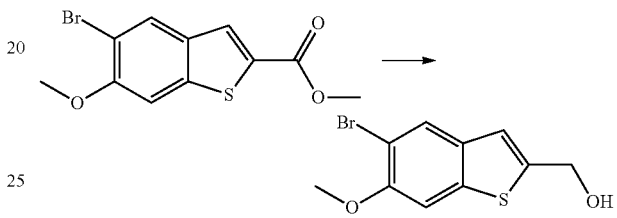

LAH (1.0M in THF, 2.8 mL, 2.8 mmol) was slowly added to a mixture of methyl 5-bromo-6-methoxybenzo[b]thiophene-2-carboxylate (0.78 g, 2.3 mmol) in THF (9.0 mL) at 0° C. After 40 min, the reaction mixture was diluted with sat aq $AlCl_3$. EtOAc was added, and the organic layer was separated, dried over $Na_2SO_4$, filtered and concentrated under reduced pressure. The resulting material was purified by silica gel chromatography to afford (5-bromo-6-methoxybenzo[b]thiophen-2-yl)methanol. LCMS ($C_{10}H_8BrOS$) (ES, m/z): 255, 257 [M-OH]$^+$. $^1$H NMR (500 MHz, DMSO-$d_6$) δ 8.01 (s, 1H), 7.69 (s, 1H), 7.14 (s, 1H), 5.69-5.59 (m, 1H), 4.73-4.64 (m, 2H), 3.89 (s, 3H).

Step 3: 5-bromo-6-methoxybenzo[b]thiophene-2-carbaldehyde

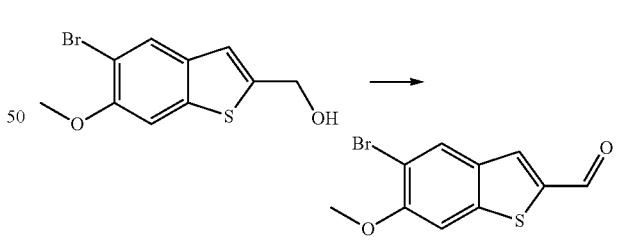

Manganese dioxide (6.3 g, 73 mmol) was added to a mixture of (5-bromo-6-methoxybenzo[b]thiophen-2-yl)methanol (4.0 g, 15 mmol) in DCM (97 mL). The reaction mixture was stirred at RT for 20 h then filtered through a plug of CELITE. The filtrate was concentrated under reduced pressure. The resulting product was triturated in MeOH and the mixture was passed through a glass frit to collect 5-bromo-6-methoxybenzo[b]thiophene-2-carbaldehyde. LCMS ($C_{10}H_8BrO_2S$) (ES, m/z): 271, 273 [M+H]$^+$. $^1$H NMR (500 MHz, DMSO-$d_6$) δ 10.07 (s, 1H), 8.40 (s, 1H), 8.29 (s, 1H), 7.87 (s, 1H), 3.97 (s, 3H).

Step 4: 4-(5-bromo-6-methoxybenzo[b]thiophen-2-yl)-4-oxobutanenitrile

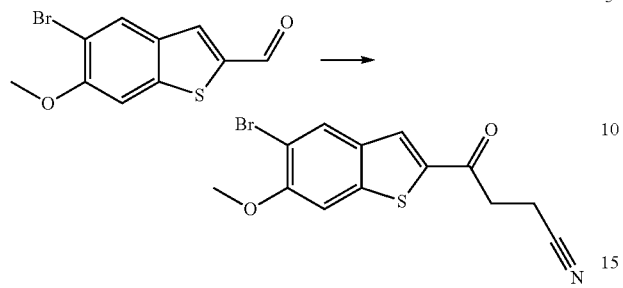

ACN (0.15 mL, 2.2 mmol) was added to a suspension of 5-bromo-6-methoxybenzo[b]thiophene-2-carbaldehyde (0.30 g, 1.1 mmol), 2-mesityl-2,5,6,7-tetrahydro-pyrrolo[2,1-c][1,2,4]triazol-4-ium chloride (0.029 g, 0.1 mmol) and $K_3PO_4$ (0.24 g, 1.1 mmol) in toluene (2.2 mL). The reaction mixture was placed under Ar and stirred at RT for 18 h. The reaction mixture was then concentrated under reduced pressure, and the resulting residue was purified by silica gel chromatography to afford 4-(5-bromo-6-methoxybenzo[b]thiophen-2-yl)-4-oxobutanenitrile. LCMS ($C_{13}H_{11}BrNO_2S$) (ES, m/z): 324, 326 [M+H]$^+$. $^1$H NMR (500 MHz, DMSO-$d_6$) δ 8.33-8.22 (m, 2H), 7.84 (s, 1H), 3.96 (s, 3H), 3.59-3.44 (m, 2H), 2.88-2.73 (m, 2H).

Intermediate 5: ethyl 4-(5-bromo-6-methoxybenzo[b]thiophen-2-yl)-4-oxobutanoate

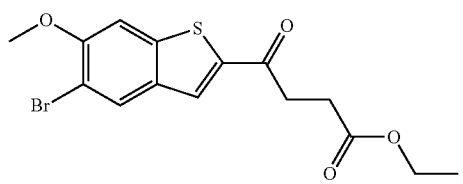 [SMILES: CCOC(=O)CCC(=O)c1cc2cc(Br)c(OC)cc2s1]

Step 1: 5-Bromo-2-fluoro-4-methoxybenzaldehyde

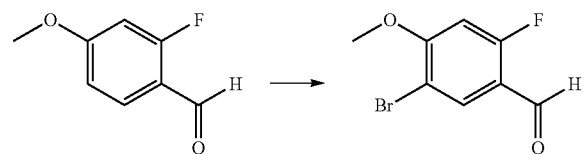

2-Fluoro-4-methoxybenzaldehyde (9.0 g, 58 mmol) was added slowly (portion-wise) to a solution of $Br_2$ (6.0 mL, 120 mmol) in MeOH (40 mL) at 0° C. The reaction mixture was stirred at 0° C. for 2 h. A solution of $NaHSO_3$ (24.3 g, 234 mmol) in $H_2O$ (300 mL) was added slowly to the reaction mixture at 0° C. The resulting suspension was then stirred for 30 min at 0° C. The reaction mixture was filtered, and the filtrate was washed with additional $H_2O$ (3×25 mL). The filtrate was then dried under reduced pressure to afford 5-bromo-2-fluoro-4-methoxybenzaldehyde. The product was used without purification. $^1$H NMR (500 MHz, DMSO-$d_6$): δ 10.02 (s, 1H), 7.98 (d, J=7.5 Hz, 1H), 7.26 (d, J=13.0 Hz, 1H), 3.97 (s, 3H).

Step 2: tert-Butyl 5-bromo-6-methoxybenzo[b]thiophene-2-carboxylate

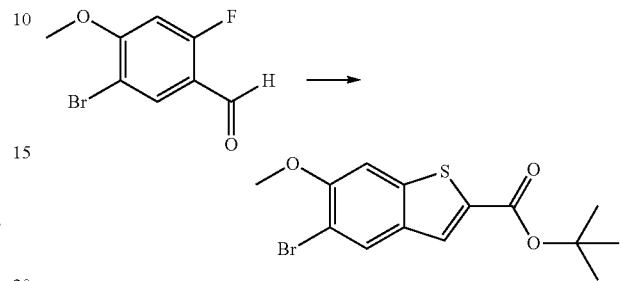

$K_2CO_3$ (19.0 g, 137 mmol) was added slowly (portion-wise) to a solution of 5-bromo-2-fluoro-4-methoxybenzaldehyde (10.7 g, 45.8 mmol) and tert-butyl 2-mercaptoacetate (6.65 mL, 45.8 mmol) in DMF (50 mL) at 20° C. under Ar. The reaction mixture was stirred and heated to 100° C. for 16 h. The reaction mixture was then cooled to RT and diluted with $Et_2O$ (1000 mL). The mixture was then washed with $H_2O$ (500 mL, then 2×250 mL), and the combined aq layers were extracted with $Et_2O$ (2×200 mL). The organic layers were then combined and washed with sat aq NaCl (50 mL). The organic layer was separated, dried over $MgSO_4$, filtered, and concentrated under reduced pressure to afford tert-butyl 5-bromo-6-methoxybenzo[b]thiophene-2-carboxylate. The product was used without purification. $^1$H NMR (500 MHz, DMSO-$d_6$): δ 8.26 (s, 1H), 7.96 (s, 1H), 7.78 (s, 1H), 3.92 (s, 3H), 1.55 (s, 9H).

Step 3: 5-Bromo-6-methoxybenzo[b]thiophene-2-carboxylic acid

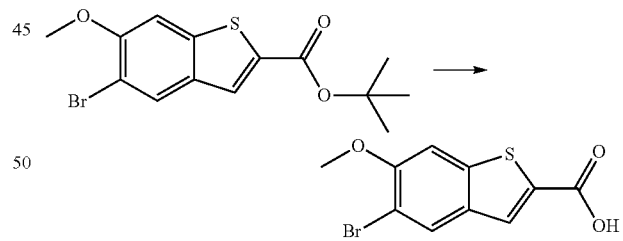

HCl (56 mL, 4.0M in 1,4-dioxane, 230 mmol) was added to a solution of tert-butyl 5-bromo-6-methoxybenzo[b]thiophene-2-carboxylate (15.5 g, 45.0 mmol) in DCM (200 mL) at 20° C. The reaction mixture was stirred at 20° C. for 3 days. The reaction mixture was then diluted by the dropwise addition of Hex (500 mL). The resulting suspension was stirred for an additional 2 h post-addition at RT. The reaction mixture was filtered, and the collected material was washed with Hex (2×50 mL) and dried under reduced pressure to afford 5-bromo-6-methoxybenzo[b]thiophene-2-carboxylic acid, which was used without purification. $^1$H NMR (500 MHz, DMSO-$d_6$): δ 13.42 (s, 1H), 8.26 (s, 1H), 7.98 (s, 1H), 7.80 (s, 1H), 3.93 (s, 3H).

Step 4: 5-Bromo-6-methoxybenzo[b]thiophene-2-carbonyl chloride

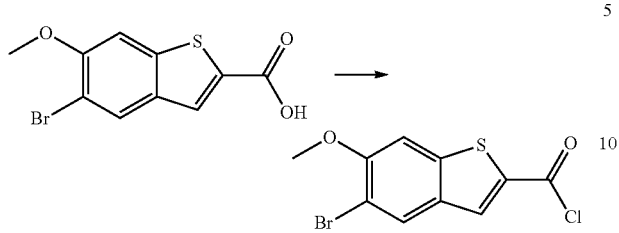

DMF (0.049 mL, 0.63 mmol) was added slowly (dropwise) to a solution of 5-bromo-6-methoxybenzo[b]thiophene-2-carboxylic acid (6.0 g, 21 mmol) and $(COCl)_2$ (5.5 mL, 63 mmol) in THF (100 mL) at 0° C. under Ar. The reaction mixture was stirred at 0° C. for 2 h and then allowed to warm to RT. The reaction mixture was stirred for 18 h at RT. The reaction mixture was then concentrated under reduced pressure to afford 5-bromo-6-methoxybenzo[b]thiophene-2-carbonyl chloride. The product was used without purification.

Step 5: Ethyl 4-(5-bromo-6-methoxybenzo[b]thiophen-2-yl)-4-oxobutanoate

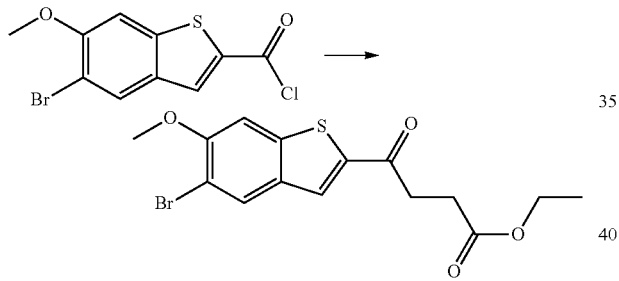

A solution of (3-ethoxy-3-oxopropyl)zinc(II) bromide (13.8 mL, 0.50M in THF, 6.9 mmol) was added to an oven-dried flask containing ((thiophene-2-carbonyl)oxy)copper (1.31 g, 6.87 mmol) under Ar at 0° C. The reaction mixture was stirred for 20 min at 0° C. under Ar. An Ar-degassed solution of 5-bromo-6-methoxybenzo[b]thiophene-2-carbonyl chloride (1.52 g, 4.98 mmol) in THF (25.0 mL) was then added via cannula to the reaction mixture at 0° C.; the resulting suspension was allowed to warm to RT and was stirred for 3 h. The reaction mixture was cooled to 0° C. and quenched with sat aq $NH_4Cl$ (50 mL). The mixture was allowed to warm to RT and stirred for 10 min. The mixture was filtered, and the filtrate was diluted with EtOAc (500 mL) and sat aq NaCl (50 mL). The organic layer was separated, washed with sat aq NaCl (25 mL), dried over $MgSO_4$, filtered, and concentrated under reduced pressure. The residue was purified by silica gel column chromatography (EtOAc in DCM) to afford ethyl 4-(5-bromo-6-methoxybenzo[b]thiophen-2-yl)-4-oxobutanoate. LCMS ($C_{15}H_{16}BrO_4S$) (ES, m/z): 371, 373 [M+H]$^+$. $^1$H NMR (500 MHz, DMSO-$d_6$): δ 8.27 (s, 1H), 8.26 (s, 1H), 7.81 (s, 1H), 4.07-4.02 (m, 2H), 3.94 (s, 3H), 3.35-3.25 (m, 2H), 2.68-2.64 (m, 2H), 1.20-1.14 (m, 3H).

Intermediate 6: tert-butyl 4-(5-bromo-6-methoxybenzo[b]thiophen-2-yl)-4-oxobutanoate

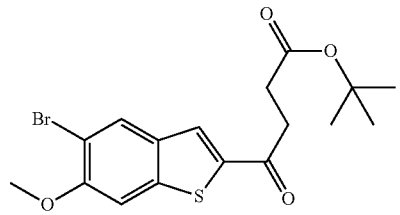 [SMILES: COc1cc2sc(C(=O)CCC(=O)OC(C)(C)C)cc2cc1Br]

Intermediate 6 may be prepared according to procedures analogous to those outlined for Intermediate 5 above using the appropriate starting materials, described as Preparations or as obtained from commercially available sources.

Intermediate 7: Ethyl 4-(6-methoxy-5-(3-(4,4,5,5-tethyl-1,3,2-dioxaborolan-2-yl)propyl)benzo[b]thiophen-2-yl)-4-oxobutanoate

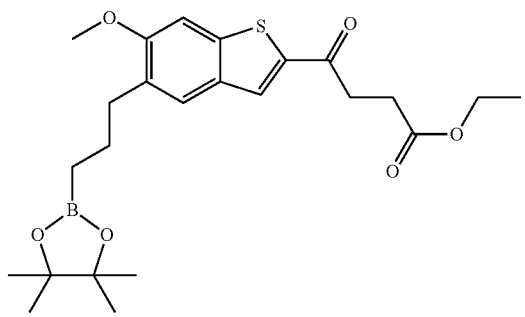 [SMILES: CCOC(=O)CCC(=O)c1cc2cc(CCCB3OC(C)(C)C(C)(C)O3)c(OC)cc2s1]

Step 1: Ethyl 4-(5-allyl-6-methoxybenzo[b]thiophen-2-yl)-4-oxobutanoate

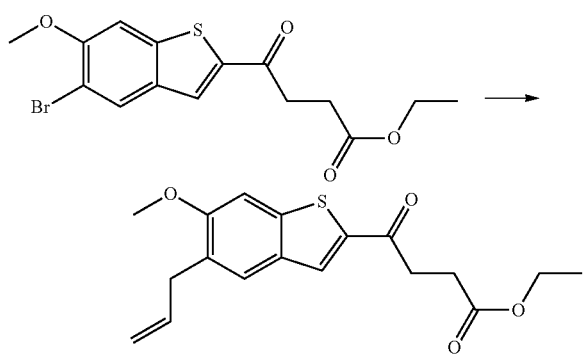

To a vial containing ethyl 4-(5-bromo-6-methoxybenzo[b]thiophen-2-yl)-4-oxobutanoate (5.0 g, 13 mmol), Pd(Ph$_3$P)$_4$ (1.6 g, 1.3 mmol), and dioxane (15 mL), was added allyltri-n-butyltin (5.4 mL, 18 mmol). The reaction was heated to 90° C. for 18 h. Upon cooling to RT, the mixture was diluted with DCM, filtered through CELITE and added to flask containing aq KF (0.5M, 200 mL). The mixture stirred, and the organic layer was then separated, dried over Na$_2$SO$_4$, filtered and concentrated under reduced pressure. The resulting residue was purified by silica gel column chromatography (0→30% EtOAc gradient in Hex) to afford ethyl 4-(5-allyl-6-methoxybenzo[b]thiophen-2-yl)-4-oxobutanoate. LCMS (C$_{18}$H$_{21}$O$_4$S) (ES, m/z): 333 [M+H]$^+$. $^1$H NMR (600 MHz, DMSO-d$_6$) δ 8.23 (s, 1H), 7.69 (s, 1H), 7.58 (s, 1H), 5.96 (dq, J=15.9, 6.6 Hz, 1H), 5.04 (d, J=4.5 Hz, 1H), 5.02 (s, 1H), 4.01 (q, J=7.0 Hz, 2H), 3.85 (s, 3H), 3.37 (d, J=6.3 Hz, 2H), 3.27 (dd, J=11.0, 4.3 Hz, 2H), 2.62 (t, J=6.1 Hz, 2H), 1.13 (t, J=7.1 Hz, 3H).

Step 2: Ethyl 4-(6-methoxy-5-(3-(4,4,5,5-tetramethyl-1,3,2-dioxaborolan-2-yl)propyl)benzo[b]thiophen-2-yl)-4-oxobutanoate

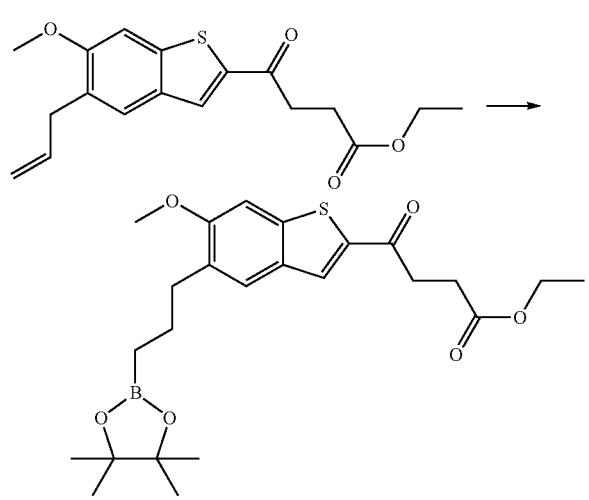

To a mixture of 1,4-bis(diphenylphosphino)butane (0.45 g, 1.1 mmol), chloro(1,5-cyclooctadiene)iridium(i) dimer (0.35 g, 0.53 mmol), ethyl 4-(5-allyl-6-methoxybenzo[b]thiophen-2-yl)-4-oxobutanoate (3.5 g, 11 mmol), and THF (20 mL) was added pinacolborane (1.0M in THF, 15.8 mL, 15.8 mmol). The reaction was stirred at RT for 4 h. The solvent was then removed under reduced pressure, and the residue was purified by silica gel column chromatography (0→20% EtOAc gradient in Hex) to afford ethyl 4-(6-methoxy-5-(3-(4,4,5,5-tetramethyl-1,3,2-dioxaborolan-2-yl)propyl)benzo[b]thiophen-2-yl)-4-oxobutanoate. $^1$H NMR (600 MHz, DMSO-d$_6$) δ 8.21 (s, 1H), 7.66 (s, 1H), 7.53 (s, 1H), 4.02 (q, J=7.0 Hz, 2H), 3.84 (s, 3H), 3.27 (t, J=6.2 Hz, 2H), 2.62 (t, J=6.1 Hz, 2H), 2.58 (t, J=7.4 Hz, 2H), 1.58 (p, J=7.4 Hz, 2H), 1.16-1.11 (m, 15H), 0.67 (t, J=7.6 Hz, 2H).

Intermediate 8: tert-Butyl 4-(6-(3-bromopropyl)-5-methoxybenzo[b]thiophen-2-yl)-4-oxobutanoate

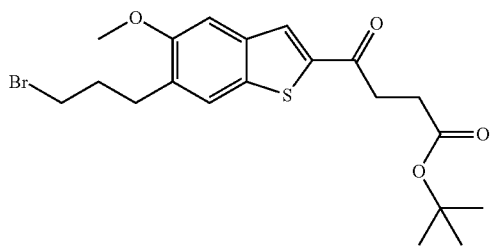 [SMILES: COc1cc2cc(C(=O)CCC(=O)OC(C)(C)C)sc2cc1CCCBr]

Step 1: Methyl 6-bromo-5-methoxybenzo[b]thiophene-2-carboxylate

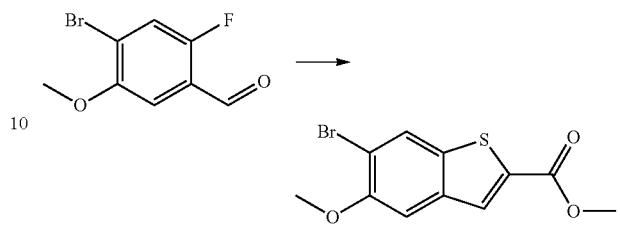

To a stirred solution of 4-bromo-2-fluoro-5-methoxybenzaldehyde (5.00 g, 21.5 mmol) in DMF (100 mL) was added methyl 2-mercaptoacetate (2.51 g, 23.6 mmol) and K$_2$CO$_3$ (8.90 g, 64.4 mmol). The reaction mixture was degassed with N$_2$ 3 times. The resulting mixture was then stirred at RT for 15 h. EtOAc (500 mL) and H$_2$O (1200 mL) were added to the reaction mixture. The organic layer was separated and washed with sat aq NaCl (2×200 mL), dried over anhydrous Na$_2$SO$_4$, filtered, and concentrated under reduced pressure. The residue was purified by silica gel column chromatography (EtOAc in PE) to give methyl 6-bromo-5-methoxybenzo [b]thiophene-2-carboxylate. LCMS (C$_{11}$H$_{10}$BrO$_3$S) (ES, m/z): 301, 303 [M+H]$^+$. $^1$H NMR (400 MHz, CDCl$_3$): δ=8.01 (s, 1H), 7.93 (s, 1H), 7.26 (s, 1H), 3.96 (s, 3H), 3.94 (s, 3H).

Step 2: 6-Bromo-5-methoxybenzo[b]thiophene-2-carboxylic acid

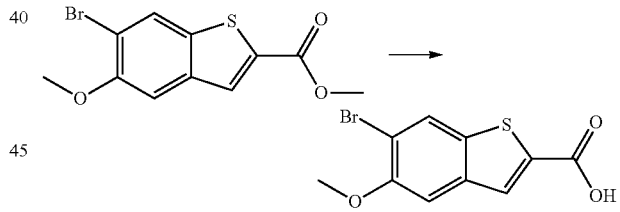

To a suspension of methyl 6-bromo-5-methoxybenzo[b]thiophene-2-carboxylate (1.45 g, 4.81 mmol) in MeOH (20 mL), THF (20 mL), and H$_2$O (20 mL) was added NaOH (1.93 g, 48.1 mmol). The resulting suspension was heated to 50° C. for 0.5 h. The reaction mixture was concentrated under reduced pressure to remove the solvent. H$_2$O (200 mL) was added to the residue, and citric acid was added to adjust the solution to pH=6. The remaining aq suspension was extracted with EtOAc (3×50 mL). The combined organic layers were washed with sat aq NaCl (100 mL), dried over Na$_2$SO$_4$, filtered, and concentrated under reduced pressure to give 6-bromo-5-methoxybenzo[b]thiophene-2-carboxylic acid, which was used without further purification. $^1$H NMR (400 MHz, DMSO-d$_6$): δ=13.52 (br s, 1H), 8.35 (s, 1H), 8.01 (s, 1H), 7.65 (s, 1H), 3.90 (s, 3H).

Step 3: 6-Bromo-5-methoxybenzo[b]thiophene-2-carbonyl chloride

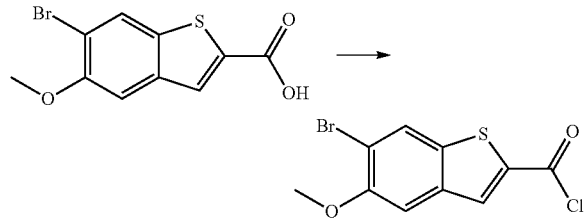

To a stirred solution of 6-bromo-5-methoxybenzo[b]thiophene-2-carboxylic acid (800 mg, 2.79 mmol) in anhydrous THF (6 mL) was added (COCl)$_2$ (1.06 g, 8.36 mmol) dropwise at 0° C. The mixture was then heated at 75° C. for 15 h and then cooled to RT. The solvent was removed under reduced pressure to give the crude 6-bromo-5-methoxybenzo[b]thiophene-2-carbonyl chloride, which was used without further purification.

Step 4: tert-Butyl 4-(6-bromo-5-methoxybenzo[b]thiophen-2-yl)-4-oxobutanoate

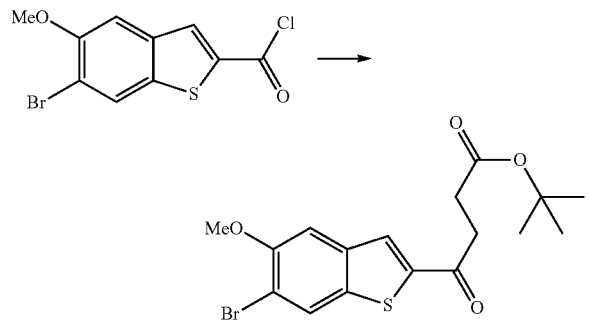

To a round bottom flask was added CuI (0.24 g, 2.4 mmol). The flask was evacuated and then opened to N$_2$. This was repeated three times. THF (4.0 mL) was added and the mixture was cooled to 0° C. A mixture of (3-(tert-butoxy)-3-oxopropyl)zinc(II) bromide (0.50M in THF, 9.6 mL, 4.8 mmol) was added dropwise at 0° C. over 10 min. The resulting mixture was allowed to stir for 30 min. 6-bromo-5-methoxybenzo[b]thiophene-2-carbonyl chloride (0.73 g, 2.4 mmol) was added. The mixture was removed from the ice bath and allowed to warm to RT. The mixture was stirred for 2 h. The mixture was then cooled to 0° C., and concentrated NH$_4$OH (4.5 mL) was added. To the resulting suspension was added water (240 mL) and MeOH (60 mL). The mixture was stirred for 5 min and sonicated in a bath sonicator. The mixture was then diluted with EtOAc, and the organic layer was separated, dried over MgSO$_4$, filtered, and concentrated under reduced pressure. The crude product residue was purified by silica gel chromatography to afford tert-butyl 4-(6-bromo-5-methoxybenzo[b]thiophen-2-yl)-4-oxobutanoate. LCMS (C$_{17}$H$_{19}$BrO$_4$S) (ES, m/z): 421, 423 [M+Na]$^+$.

Step 5: tert-Butyl 4-(6-(3-((tert-butyldimethylsilyl)oxy)propyl)-5-methoxybenzo[b]thiophen-2-yl)-4-oxobutanoate

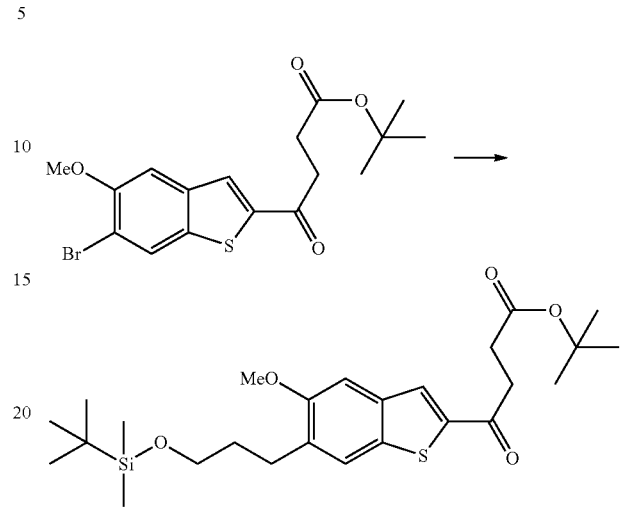

To a flask containing tert-butyl 4-(6-bromo-5-methoxybenzo[b]thiophen-2-yl)-4-oxobutanoate (0.16 g, 0.40 mmol) and THF (2.0 mL) was added [(2-dicyclohexylphosphino-2',6'-bis(N,N-dimethylamino)-1,1'-biphenyl)-2-(2'-amino-1,1'-biphenyl)] palladium(II) methane sulfonate (C-Phos Pd G3, 16 mg, 0.020 mmol). The flask was evacuated and backfilled 3 times with N$_2$. (3-((tert-butyldimethylsilyl)oxy)propyl)zinc(II) bromide (0.50M in THF, 2.4 mL, 1.2 mmol) was added, and the mixture was allowed to stir at RT for 2.5 h. The mixture was then quenched with a mixture of EtOAc and 10% aqueous sodium citrate. The organic layer was separated, washed with sat aq NaCl, dried over MgSO$_4$, filtered and concentrated under reduced pressure. The crude residue was purified by silica gel chromatography to afford tert-butyl 4-(6-(3-((tert-butyldimethylsilyl)oxy)propyl)-5-methoxybenzo[b]thiophen-2-yl)-4-oxobutanoate. LCMS (C$_{26}$H$_{41}$O$_5$SSi-C$_4$H$_8$) (ES, m/z): 437 [M-C$_4$H$_8$]$^+$.

Step 6: tert-Butyl 4-(6-(3-hydroxypropyl)-5-methoxybenzo[b]thiophen-2-yl)-4-oxobutanoate

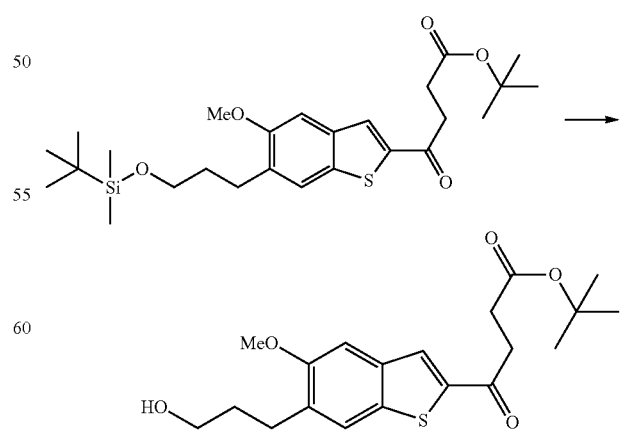

To a flask containing tert-butyl 4-(6-(3-((tert-butyldimethylsilyl)oxy)propyl)-5-methoxybenzo[b]thiophen-2-yl)-4- oxobutanoate (0.11 g, 0.23 mmol) was added MeOH (1.5 mL), water (1.5 mL) and HOAc (1.5 mL). The mixture was allowed to stir for 4 h. The mixture was diluted with EtOAc and then washed with water (3×50 mL). The organic layer was dried over MgSO$_4$, filtered, and concentrated under reduced pressure. The crude residue was purified by silica gel column chromatography to afford tert-butyl 4-(6-(3-hydroxypropyl)-5-methoxy-benzo[b]thiophen-2-yl)-4-oxobutanoate. LCMS (C$_{20}$H$_{27}$O$_5$S—C$_4$H$_8$) (ES, m/z): 323 [M-C$_4$Hs]$^+$.

Step 7: tert-Butyl 4-(6-(3-bromopropyl)-5-methoxy-benzo[b]thiophen-2-yl)-4-oxobutanoate

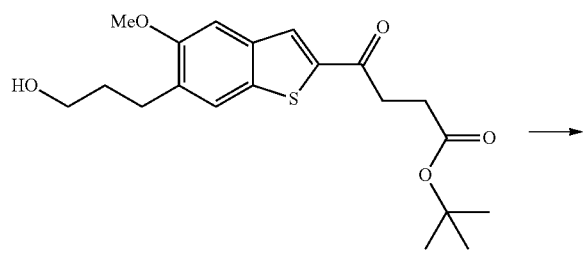

To a mixture of tert-butyl 4-(6-(3-hydroxypropyl)-5-methoxybenzo[b]thiophen-2-yl)-4-oxobutanoate (74 mg, 0.20 mmol) and triphenylphosphine (82 mg, 0.31 mmol) in THF (1.0 mL) at 0° C. was added NBS (52 mg, 0.29 mmol). After 15 min at 0° C., the mixture was quenched with sat aq NH$_4$Cl and diluted with EtOAc. The organic layer was separated, dried over MgSO$_4$, filtered, and concentrated under reduced pressure. The crude residue was purified by silica gel column chromatography to afford tert-butyl 4-(6-(3-bromopropyl)-5-methoxybenzo[b]thiophen-2-yl)-4-oxobutanoate. LCMS (C$_{20}$H$_{26}$BrO$_4$S—C$_4$H$_8$) (ES, m/z): 385, 387 [M-C$_4$H$_8$].

Intermediate 9: Methyl 4-(4-bromo-6-methoxy-benzo[b]thiophen-2-yl)-4-oxobutanoate

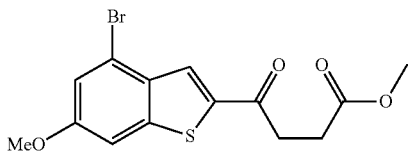 [SMILES: COC(=O)CCC(=O)c1cc2c(Br)cc(OC)cc2s1]

Step 1: 2-Bromo-6-fluoro-4-methoxybenzaldehyde

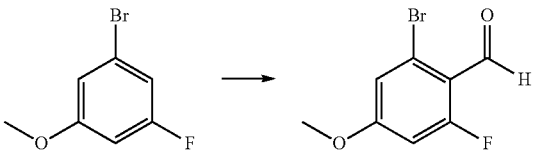

To a mixture of 1-bromo-3-fluoro-5-methoxybenzene (7.5 g, 37 mmol) in THF (120 mL) at −78° C. was added LDA (2.0M in THF, 22 mL, 44 mmol), and the mixture was allowed to stir for 30 min at −78° C. After 30 min, DMF (3.4 mL, 44 mmol) was added dropwise, and the mixture was then allowed to stir for 30 min. The mixture was then quenched with water, warmed to RT, and then EtOAc was added. The layers were separated, and the water layer was extracted with EtOAc two more times. The combined organic layers were dried over MgSO$_4$, filtered, and concentrated under reduced pressure. The crude product residue was purified by silica gel chromatography to afford 2-bromo-6-fluoro-4-methoxybenzaldehyde. LCMS (C$_8$H$_7$BrFO$_2$) (ES, m/z): 233, 235 [M+H]$^+$.

Step 2: Methyl 4-bromo-6-methoxybenzo[b]thiophene-2-carboxylate

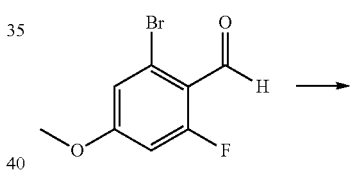

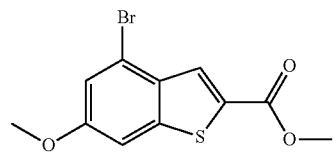

To a mixture of 2-bromo-6-fluoro-4-methoxybenzaldehyde (2.5 g, 11 mmol) in DMSO (54 mL) was added TEA (3.0 mL, 21 mmol). After 10 min, methyl thioglycolate (3.1 mL, 32 mmol) was added, and the mixture was allowed to stir for 30 min at RT. After 30 min, the mixture was heated to 60° C. for 1 h. Upon cooling to RT, the mixture was diluted with sat aq NaHCO$_3$ and EtOAc. The organic layer was separated, dried over MgSO$_4$, filtered, and concentrated under reduced pressure. The crude product residue was purified by silica gel chromatography (0→15% EtOAc gradient in Hex) to afford methyl 4-bromo-6-methoxybenzo[b]thiophene-2-carboxylate. LCMS (C$_{11}$H$_{10}$BrO$_3$S) (ES, m/z): 301, 303 [M+H]$^+$. $^1$H NMR (500 MHz, DMSO-d$_6$) δ 7.93 (s, 1H), 7.73 (s, 1H), 7.44-7.37 (m, 1H), 3.89 (s, 3H), 3.87 (s, 3H).

Step 3: 4-Bromo-6-methoxybenzo[b]thiophene-2-carboxylic acid

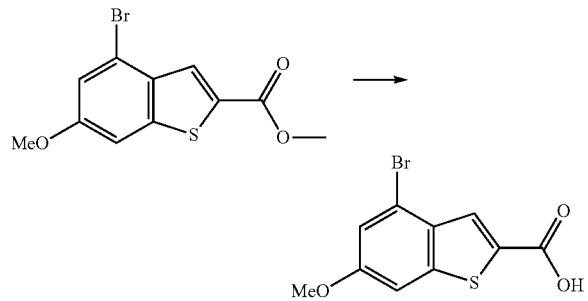

To a mixture of methyl 4-bromo-6-methoxybenzo[b]thiophene-2-carboxylate (1.7 g, 5.5 mmol) in THF (14 mL), MeOH (7.0 mL), and water (7.0 mL) was added LiOH (0.66 g, 28 mmol), and the mixture was heated to 40° C. for 2 h. After 2 h, the mixture was allowed to cool to RT. The mixture was quenched with aq HCl (2.0M in water, 14 mL, 28 mmol). The mixture was filtered, and the residue was washed with EtOAc. The residue was then dried under vacuum and used without further purification. LCMS ($C_{10}H_8BrO_3S$) (ES, m/z): 287, 289 [M+H]$^+$. $^1$H NMR (500 MHz, DMSO-d$_6$) δ 13.57 (s, 1H), 7.86 (s, 1H), 7.71 (s, 1H), 7.38 (d, J=1.7 Hz, 1H), 3.86 (s, 3H).

Intermediate 10: Ethyl 4-(5-(3-bromopropyl)-6-methoxybenzo[b]thiophen-2-yl)-4-oxobutanoate

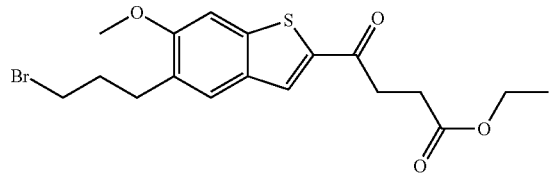 [SMILES: CCOC(=O)CCC(=O)c1cc2cc(CCCBr)c(OC)cc2s1]

Step 1: Ethyl 4-(6-methoxy-5-(3-((tetrahydro-2H-pyran-2-yl)oxy)propyl)benzo[b]thiophen-2-yl)-4-oxobutanoate

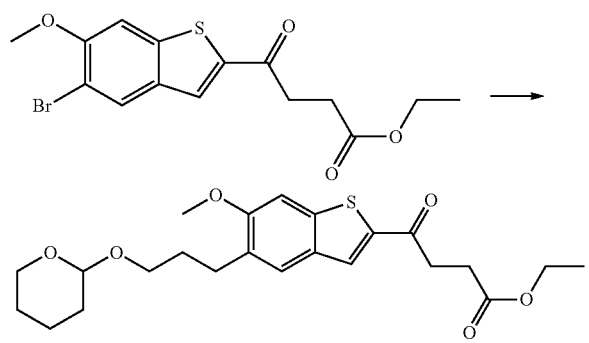

To a mixture of ethyl 4-(5-bromo-6-methoxybenzo[b]thiophen-2-yl)-4-oxobutanoate (13 g, 35 mmol), and C-Phos Pd G4 (1.4 g, 1.7 mmol) was added (3-((tetrahydro-2H-pyran-2-yl)oxy)propyl)zinc(II) bromide (0.50M in THF, 100 mL, 50 mmol) at once. The reaction was heated to 40° C. for 2 h. The mixture was then allowed to cool to RT and filtered through CELITE.

The filtrate was concentrated under reduced pressure. The resulting residue was purified by silica gel column chromatography (0→30% EtOAc gradient in Hex) to afford ethyl 4-(6-methoxy-5-(3-((tetrahydro-2H-pyran-2-yl)oxy)propyl)benzo[b]thiophen-2-yl)-4-oxobutanoate. LCMS ($C_{23}H_{31}O_6S$) (ES, m/z): 435 [M+H]$^+$. $^1$H NMR (600 MHz, DMSO-d$_6$) δ 8.21 (s, 1H), 7.71 (s, 1H), 7.55 (s, 1H), 4.50 (s, 1H), 4.02 (q, J=7.0 Hz, 2H), 3.85 (s, 3H), 3.70 (t, J=8.1 Hz, 1H), 3.65-3.58 (m, 1H), 3.40-3.34 (m, 1H), 3.33-3.29 (m, 3H), 2.73-2.59 (m, 4H), 1.79 (p, J=6.7 Hz, 2H), 1.69 (d, J=8.7 Hz, 1H), 1.58 (t, J=7.9 Hz, 1H), 1.48-1.34 (m, 4H), 1.14 (t, J=7.1 Hz, 3H).

Step 2: Ethyl 4-(5-(3-bromopropyl)-6-methoxy-benzo[b]thiophen-2-yl)-4-oxobutanoate

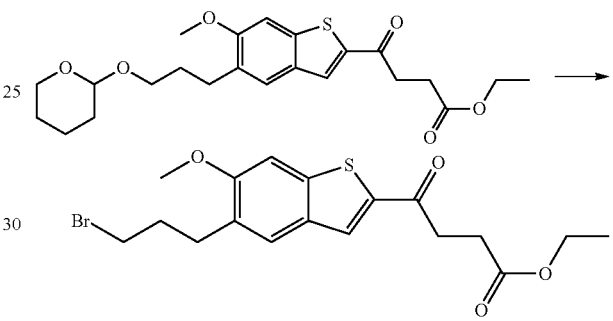

To a mixture of 4-(6-methoxy-5-(3-((tetrahydro-2H-pyran-2-yl)oxy)propyl)benzo [b]thiophen-2-yl)-4-oxobutanoate (6.2 g, 14 mmol) and DCM (100 mL) at 0° C. was added triphenylphosphine dibromide (9.03 g, 21.4 mmol) portion-wise. The mixture was allowed to warm to RT and then stirred for 1 h. The mixture was then quenched with water and diluted with DCM. The organic layer was separated, dried over Na$_2$SO$_4$, filtered and concentrated under reduced pressure. The resulting residue was purified by silica gel column chromatography (0→30% EtOAc gradient in Hex) to afford ethyl 4-(5-(3-bromopropyl)-6-methoxy-benzo[b]thiophen-2-yl)-4-oxobutanoate. LCMS ($C_{18}H_{22}BrO_4S$) (ES, m/z): 413, 415 [M+H]+. $^1$H NMR (600 MHz, DMSO-d$_6$) δ 8.23 (s, 1H), 7.73 (s, 1H), 7.58 (s, 1H), 4.02 (q, J=7.0 Hz, 2H), 3.86 (s, 3H), 3.50 (t, J=6.5 Hz, 2H), 3.27 (d, J=6.4 Hz, 2H), 2.75 (t, J=7.3 Hz, 2H), 2.63 (t, J=6.2 Hz, 2H), 2.07 (p, J=6.7 Hz, 2H), 1.14 (t, J=7.1 Hz, 3H).

Intermediate 11: Ethyl 4-(4-fluoro-5-hydroxy-6-methoxybenzo[b]thiophen-2-yl)-4-oxobutanoate

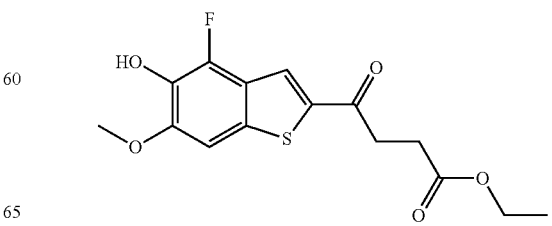

Step 1: Methyl 4-fluoro-5,6-dimethoxybenzo[b]thiophene-2-carboxylate

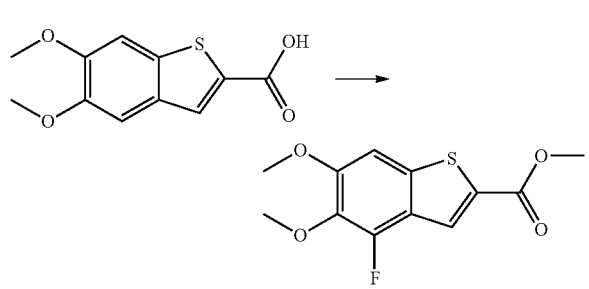

1-Chloromethyl-4-fluoro-1,4-diazoniabicyclo[2.2.2]octane bis(tetrafluoroborate) (S$_{ELECTFLUOR}$™, 77 mg, 0.22 mmol) was added to a mixture of methyl 5,6-dimethoxybenzo[b]thiophene-2-carboxylate (50 mg, 0.20 mmol) in ACN (1 ml) at RT. The resulting mixture was stirred at 45° C. for 15 h. The mixture was cooled to RT, diluted with sat aq NaHCO$_3$ (10 mL), and extracted with EtOAc (3×10 mL). The combined organic layers were washed with sat aq NaCl (10 mL), dried over anhydrous Na$_2$SO$_4$, filtered, and concentrated under reduced pressure. The residue was purified by prep-TLC (SiO$_2$, EtOAc in PE) to give methyl 4-fluoro-5,6-dimethoxybenzo[b]thiophene-2-carboxylate. LCMS (C$_{12}$H$_{12}$FO$_4$S) (ES, m/z): 293 [M+H]$^+$. $^1$H NMR (400 MHz, CDCl$_3$): δ 8.05 (s, 1H), 7.08 (s, 1H), 3.99 (s, 3H), 3.97 (s, 3H), 3.94 (s, 3H).

Step 2: 4-Fluoro-5,6-dimethoxybenzo[b]thiophene-2-carboxylic acid

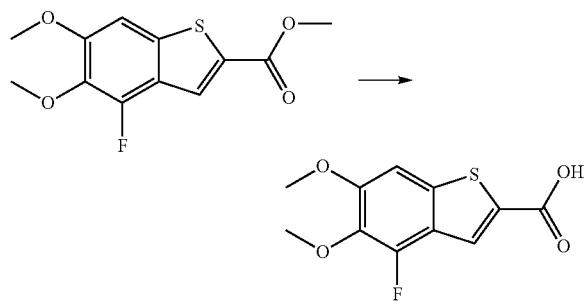

LiOH.H$_2$O (71.4 mg, 1.70 mmol) was added portion-wise to a mixture of methyl 4-fluoro-5,6-dimethoxybenzo[b]thiophene-2-carboxylate (46 mg, 0.170 mmol) in THF (3 ml), MeOH (1 ml), and H$_2$O (1 ml) at RT. Then, the mixture was stirred for 15 h. The mixture was adjusted to pH=5 with 1N HCl and extracted with EtOAc (3×10 ml). The combined organic layers were washed with sat aq NaCl (10 mL), dried over anhydrous Na$_2$SO$_4$, filtered, and concentrated under reduced pressure. The residue was purified by prep-HPLC (ACN/H$_2$O with 0.1% TFA) to give 4-fluoro-5,6-dimethoxybenzo[b]thiophene-2-carboxylic acid. LCMS (C$_{11}$H$_9$FO$_4$S) (ES, m/z): 257 [M+H]$^+$. $^1$H NMR (400 MHz, CDCl$_3$): δ 8.12 (s, 1H), 7.09 (s, 1H), 3.99 (s, 3H), 3.97 (s, 3H).

Step 3: 4-Fluoro-5,6-dimethoxybenzo[b]thiophene-2-carbonyl chloride

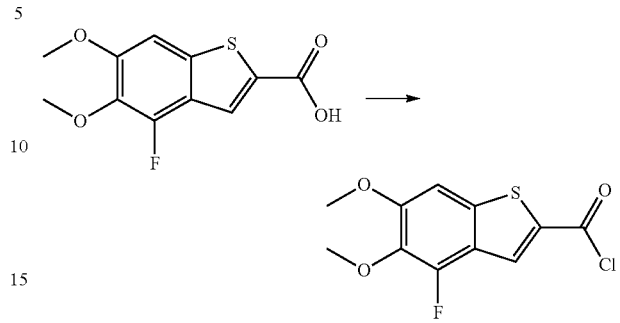

To a stirred solution of 4-fluoro-5,6-dimethoxybenzo[b]thiophene-2-carboxylic acid (153 mg, 0.60 mmol) in anhydrous THF (5 mL) was added (COCl)$_2$ (0.21 mL, 2.40 mmol) dropwise at 0° C. The mixture was stirred at 0° C. for 1 h and then at RT for 1 h. The solvent was removed under reduced pressure to give 4-fluoro-5,6-dimethoxybenzo[b]thiophene-2-carbonyl chloride, which was used without further purification.

Step 4: Ethyl 4-(4-fluoro-5,6-dimethoxybenzo[b]thiophen-2-yl)-4-oxobutanoate

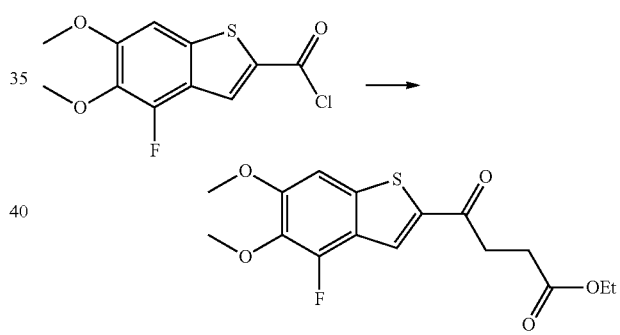

A suspension of copper(I) thiophene-2-carboxylate (125 mg, 0.65 mmol) was sparged with N$_2$ for 5 min and then cooled to 0° C. A solution of (3-ethoxy-3-oxopropyl)zinc(II) bromide (17.7 mL, 0.5M in THF, 8.83 mmol) was added under N$_2$ at 0° C., and the reaction mixture was stirred for 20 min at 0° C. A N$_2$-sparged solution of 4-fluoro-5,6-dimethoxybenzo[b]thiophene-2-carbonyl chloride (130 mg, 0.47 mmol) in THF (3 mL) was then added at 0° C. The resulting suspension was allowed to warm to RT and was stirred for 8 h. The mixture was poured into sat aq NH$_4$Cl (20 mL) with stirring. The mixture was extracted with EtOAc (2×20 mL). The combined organic layers were washed with H$_2$O and sat aq NaCl, dried over MgSO$_4$, filtered, and concentrated under reduced pressure. The residue was purified by silica gel column chromatography (EtOAc in Hex) to give ethyl 4-(4-fluoro-5,6-dimethoxybenzo[b]thiophen-2-yl)-4-oxobutanoate. LCMS (C$_{16}$H$_{18}$FO$_5$S) (ES, m/z): 341 [M+H]$^+$. $^1$H NMR (500 MHz, CDCl$_3$) δ 8.02 (d, J=0.7 Hz, 1H), 7.10 (t, J=1.0 Hz, 1H), 4.19 (q, J=7.2 Hz, 2H), 4.05-3.97 (m, 6H), 3.36 (t, J=6.7 Hz, 2H), 2.81 (t, J=6.7 Hz, 2H), 1.29 (t, J=7.2 Hz, 3H).

Step 5: Ethyl 4-(4-fluoro-5-hydroxy-6-methoxy-benzo[b]thiophen-2-yl)-4-oxobutanoate

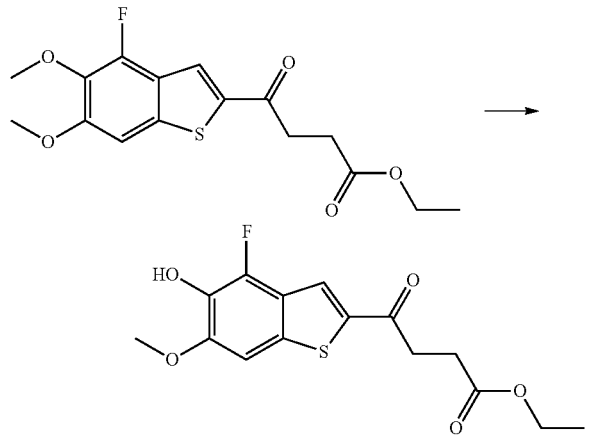

To a mixture of ethyl 4-(4-fluoro-5,6-dimethoxybenzo[b]thiophen-2-yl)-4-oxobutanoate (3.6 g, 11 mmol) and DCM (50 mL) was added AlCl$_3$ (5.64 g, 42.3 mmol). The reaction mixture was allowed to stir at RT for 18 h. An addition funnel was then connected to the reaction vessel, and water (50 mL) was added slowly to the mixture with vigorous stirring followed by aq HCl (1N, 50 mL). The mixture was then diluted with 20% IPA/DCM. The organic layer was separated, dried over Na$_2$SO$_4$, filtered and concentrated under reduced pressure. The resulting residue was purified by silica gel column chromatography (100% DCM) to afford ethyl 4-(4-fluoro-5-hydroxy-6-methoxybenzo[b]thiophen-2-yl)-4-oxobutanoate. LCMS (C$_{15}$H$_{16}$FO$_5$S) (ES, m/z): 327 [M+H]$^+$. $^1$H NMR (600 MHz, DMSO-d$_6$) δ 9.53 (s, 1H), 8.25 (s, 1H), 7.47 (s, 1H), 4.06 (q, J=7.1 Hz, 2H), 3.92 (s, 3H), 3.39-3.34 (m, 2H), 2.68-2.63 (m, 2H), 1.18 (t, J=7.1 Hz, 3H).

Intermediate 12: (S)-methyl 4-(5-(3-hydroxypropyl)-6-methoxybenzo[b]thiophen-2-yl)-2-methyl-4-oxobutanoate

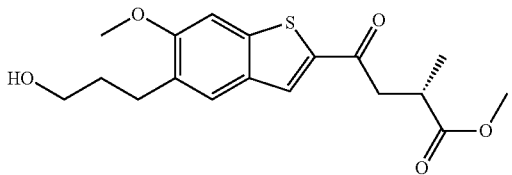 [SMILES: COC(=O)[C@@H](C)CC(=O)c1cc2cc(CCCO)c(OC)cc2s1]

Step 1: (2S)-methyl-4-(6-methoxy-5-(3-((tetrahydro-2H-pyran-2-yl)oxy)propyl) benzo[b]thiophen-2-yl)-2-methyl-4-oxobutanoate

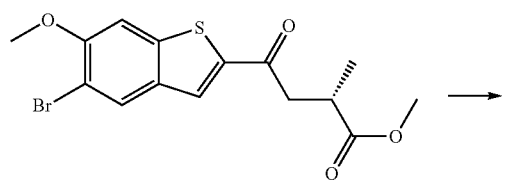

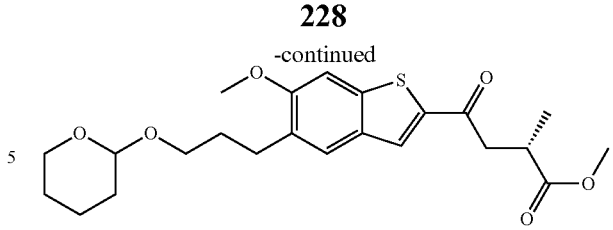

To a mixture of (S)-methyl-4-(5-bromo-6-methoxybenzo[b]thiophen-2-yl)-2-methyl-4-oxobutanoate (7.0 g, 19 mmol), and C-Phos Pd G4 (0.76 g, 0.94 mmol) was added (3-((tetrahydro-2H-pyran-2-yl)oxy)propyl)zinc(II) bromide (0.50M in THF, 100 mL, 50 mmol). The mixture was heated to 40° C. for 2 h. The mixture was then allowed to cool to RT and filtered through CELITE. The filtrate was concentrated under reduced pressure. The residue was purified by silica gel column chromatography (0→30% EtOAc gradient in Hex) to afford ethyl (2S)-methyl-4-(6-methoxy-5-(3-((tetrahydro-2H-pyran-2-yl)oxy)propyl)benzo[b]thiophen-2-yl)-2-methyl-4-oxobutanoate. LCMS (C$_{23}$H$_{31}$O$_6$S) (ES, m/z): 435 [M+H]$^+$. $^1$H NMR (600 MHz, DMSO-d$_6$) δ 8.21 (s, 1H), 7.70 (s, 1H), 7.55 (s, 1H), 4.50 (s, 1H), 3.85 (s, 3H), 3.70 (dd, J=13.2, 5.3 Hz, 1H), 3.64-3.58 (m, 1H), 3.56 (s, 3H), 3.42-3.35 (m, 2H), 3.35-3.29 (m, 1H), 3.15 (dd, J=17.4, 4.9 Hz, 1H), 2.94 (dt, J=12.9, 7.1 Hz, 1H), 2.67 (hept, J=7.6, 7.1 Hz, 2H), 1.79 (p, J=6.7 Hz, 2H), 1.69 (d, J=8.7 Hz, 1H), 1.58 (t, J=7.9 Hz, 1H), 1.48-1.35 (m, 4H), 1.18-1.11 (m, 3H).

Step 2: (S)-methyl 4-(5-(3-hydroxypropyl)-6-methoxybenzo[b]thiophen-2-yl)-2-methyl-4-oxobutanoate

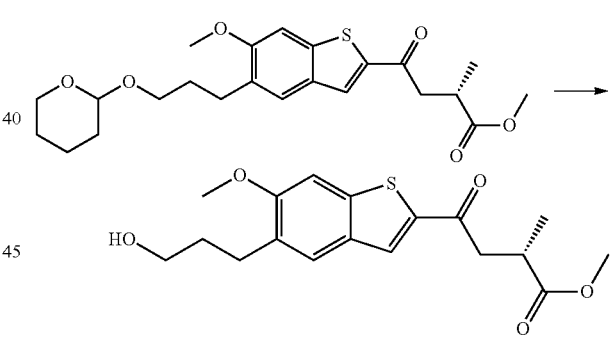

To a mixture of (2S)-methyl-4-(6-methoxy-5-(3-((tetrahydro-2H-pyran-2-yl)oxy) propyl)benzo[b]thiophen-2-yl)-2-methyl-4-oxobutanoate (2.62 g, 6.03 mmol) and MeOH (50 mL) was added pTsOH (1.72 g, 9.04 mmol). The mixture was allowed to stir at RT for 1 h. The mixture was then quenched with water and diluted with DCM. The organic layer was separated and then washed with aq sat NaHCO$_3$. The organic layer was then dried over Na$_2$SO$_4$, filtered and concentrated under reduced pressure afford (S)-methyl 4-(5-(3-hydroxypropyl)-6-methoxybenzo[b]thiophen-2-yl)-2methyl-4-oxobutanoate. LCMS (C$_{18}$H$_{23}$O$_5$S) (ES, m/z): 351 [M+H]$^+$. $^1$H NMR (600 MHz, DMSO-d$_6$) δ 8.21 (s, 1H), 7.69 (s, 1H), 7.54 (s, 1H), 4.44 (t, J=5.0 Hz, 1H), 3.85 (s, 3H), 3.56 (s, 3H), 3.42-3.35 (m, 3H), 3.15 (dd, J=17.4, 4.9 Hz, 1H), 2.93 (h, J=7.0 Hz, 1H), 2.64 (t, J=7.6 Hz, 2H), 1.68 (p, J=6.6 Hz, 2H), 1.15 (d, J=7.1 Hz, 3H).

Intermediate 13: Methyl 4-(5-(3-bromopropyl)-6-methylbenzo[b]thiophen-2-yl)-4-oxobutanoate

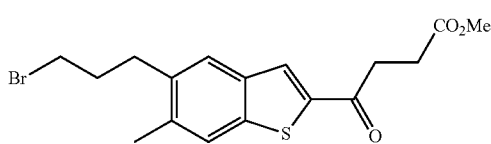 [SMILES: COC(=O)CCC(=O)c1cc2cc(CCCBr)c(C)cc2s1]

Step 1: Methyl 5-bromo-6-methylbenzo[b]thiophene-2-carboxylate

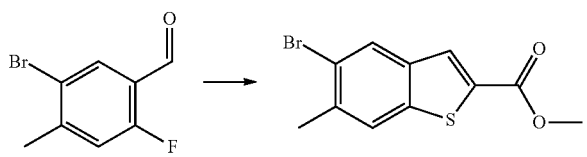

To a mixture of 5-bromo-2-fluoro-4-methylbenzaldehyde (5.0 g, 23 mmol) in DMSO (120 mL) was added TEA (6.4 mL, 46 mmol). After 10 min, methyl thioglycolate (6.7 mL, 69 mmol) was added, and the mixture was then heated to 60° C. for 18 h. After 18 h, the mixture was cooled to RT, and the mixture was diluted with EtOAc and water. The organic layer was separated, dried over $MgSO_4$, filtered, and concentrated under reduced pressure. The mixture was diluted with DCM. The mixture was filtered, and the residue was dried under vacuum. To the mother liquor was added silica gel (50 g), and the mixture was concentrated. The mixture was then purified by silica gel chromatography to afford methyl 5-bromo-6-methylbenzo[b]thiophene-2-carboxylate. $^1$H NMR (500 MHz, DMSO-$d_6$) δ 8.31 (s, 1H), 8.13 (s, 1H), 8.08 (s, 1H), 3.89 (s, 3H), 2.48 (s, 3H).

Step 2: 5-Bromo-6-methylbenzo[b]thiophene-2-carboxylic acid

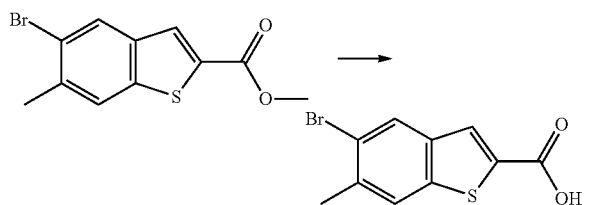

To a mixture of methyl 5-bromo-6-methylbenzo[b]thiophene-2-carboxylate (2.76 g, 9.68 mmol) in THF (24 ml), water (12 ml), and MeOH (12 ml) was added LiOH (1.16 g, 48.4 mmol), and the mixture was stirred for 30 min at RT. The mixture was then acidified to near neutral with HCl (1.0M in water, 48 ml, 48 mmol). The mixture was then diluted with EtOAc and water. The organic layer was separated, dried over $MgSO_4$, filtered, and concentrated to afford 5-bromo-6-methylbenzo[b]thiophene-2-carboxylic acid. The product was used without purification. LCMS ($C_{10}H_8BrO_2S$) (ES, m/z): 271, 273 [M+H]$^+$. $^1$H NMR (499 MHz, DMSO-$d_6$) δ 13.56 (s, 1H), 8.29 (s, 1H), 8.05 (s, 1H), 8.04 (s, 1H), 2.47 (s, 3H).

Step 3: 5-Bromo-6-methylbenzo[b]thiophene

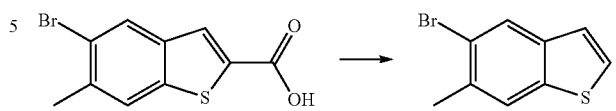

To 5-bromo-6-methylbenzo[b]thiophene-2-carboxylic acid (5.7 g, 21 mmol) was added DMA (100 mL). The mixture was then split evenly among 5 vials. DBU (1.6 mL) was added to each vial, and each vial was then irradiated in the microwave to 200° C. for 2 h. Upon completion, the five vials were combined and then diluted with EtOAc and sat aq $NaHCO_3$. The organic layer was separated, dried over $MgSO_4$, filtered, and concentrated under reduced pressure. The residue was purified by silica gel chromatography to afford 5-bromo-6-methylbenzo[b]thiophene. $^1$H NMR (500 MHz, DMSO-$d_6$) δ 8.15 (s, 1H), 8.00 (s, 1H), 7.75 (d, J=5.4 Hz, 1H), 7.39 (d, J=5.3 Hz, 1H), 2.45 (s, 3H).

Step 4: 4-(5-Bromo-6-methylbenzo[b]thiophen-2-yl)-4-oxobutanoic acid

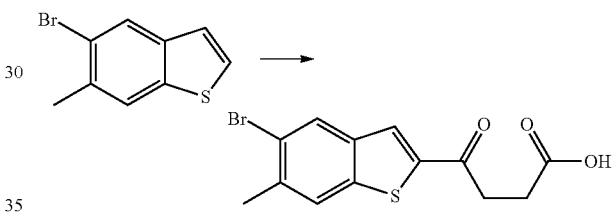

To a mixture of 5-bromo-6-methylbenzo[b]thiophene (2.0 g, 8.8 mmol) in DCM (88 mL) at 0° C. was added succinic anhydride (1.1 g, 11 mmol) and then $AlCl_3$ (2.3 g, 18 mmol). The mixture was warmed to RT and stirred for 18 h. The mixture was then diluted with EtOAc and HCl (1.0N in water). The organic layer was separated, dried over $MgSO_4$ and filtered. To the filtrate was added silica gel (10 g), and the mixture was concentrated under reduced pressure. The mixture was put under vacuum for 18 h and then was purified by silica gel chromatography (0→50% EtOAc gradient in Hex) to afford 4-(5-bromo-6-methylbenzo[b]thiophen-2-yl)-4-oxobutanoic acid. LCMS ($C_{13}H_{12}BrO_3S$) (ES, m/z): 327, 329 [M+H]$^+$.

Step 5: Methyl 4-(5-bromo-6-methylbenzo[b]thiophen-2-yl)-4-oxobutanoate

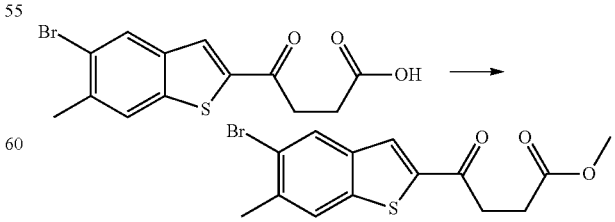

To a mixture of 4-(5-bromo-6-methylbenzo[b]thiophen-2-yl)-4-oxobutanoic acid (0.99 g, 3.0 mmol) in DMF (20 mL) was added $K_2CO_3$ (1.0 g, 7.6 mmol). After 10 min, CH₃I (0.95 mL, 15 mmol) was added, and the mixture was allowed to stir until complete by LCMS. The mixture was then diluted with EtOAc and water. The organic layer was separated, dried over MgSO₄, filtered, and concentrated under reduced pressure. The resulting residue was purified by silica gel chromatography to afford methyl 4-(5-bromo-6-methylbenzo[b]thiophen-2-yl)-4-oxobutanoate. LCMS (C₁₄H₁₄BrO₃S) (ES, m/z): 341, 343 [M+H]⁺. ¹H NMR (500 MHz, DMSO-d₆) δ 8.32 (s, 1H), 8.30 (s, 1H), 8.07 (s, 1H), 3.61 (s, 3H), 3.37 (t, J=6.3 Hz, 2H), 2.70 (t, J=6.3 Hz, 2H), 2.48 (s, 3H).

Step 6: Methyl 4-(5-(3-((tert-butyldimethylsilyl)oxy)propyl)-6-methylbenzo[b]thiophen-2-yl)-4-oxobutanoate

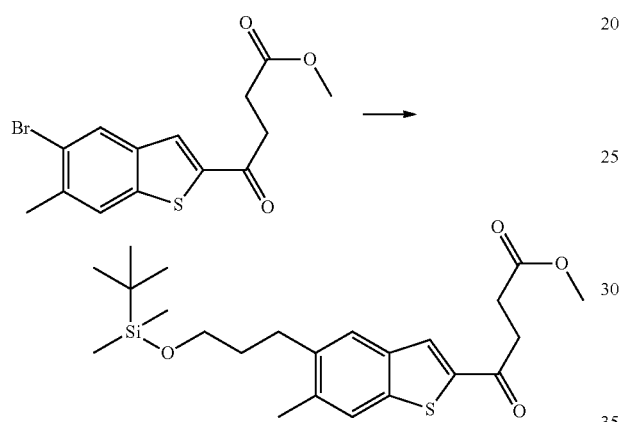

To a flask containing methyl 4-(5-bromo-6-methylbenzo[b]thiophen-2-yl)-4-oxobutanoate (0.40 g, 1.2 mmol) and THF (5.9 mL) was added C-Phos Pd G3 (47 mg, 0.059 mmol), and the mixture was evacuated and backfilled with N₂ three times. (3-((tert-butyldimethylsilyl)oxy)propyl)zinc (II) bromide (0.50M in THF, 7.0 mL, 3.5 mmol) was added, and the mixture was allowed to stir at RT for 2.5 h. The mixture was then quenched with a mixture of EtOAc and 10% aq sodium citrate. The organic layer was separated, washed with sat aq NaCl, dried over MgSO₄, filtered, and concentrated under reduced pressure. The residue was purified by silica gel chromatography to afford methyl 4-(5-(3-((tert-butyldimethylsilyl)oxy) propyl)-6-methylbenzo[b]thiophen-2-yl)-4-oxobutanoate. LCMS (C₂₃H₃₅O₄SSi) (ES, m/z): 435 [M+H]⁺.

Step 7: Methyl 4-(5-(3-hydroxypropyl)-6-methylbenzo[b]thiophen-2-yl)-4-oxobutanoate

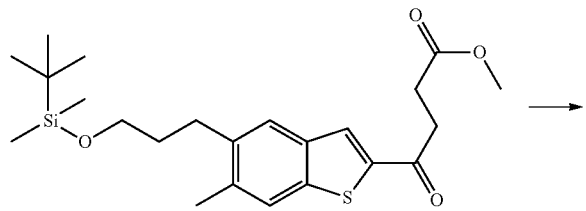

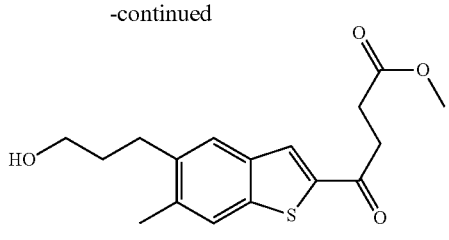

To a mixture of methyl 4-(5-(3-((tert-butyldimethylsilyl)oxy)propyl)-6-methylbenzo[b]thiophen-2-yl)-4-oxobutanoate (0.23 g, 0.54 mmol) in THF (2.7 mL) was added TBAF (1.0M in THF, 1.0 mL, 1.0 mmol). After 1.5 h, the mixture was diluted with EtOAc and sat aq NH₄Cl. The organic layer was separated, dried over MgSO₄, filtered, and concentrated under reduced pressure. The residue was purified by silica gel chromatography (0→70% EtOAc gradient in Hex) to afford methyl 4-(5-(3-hydroxypropyl)-6-methylbenzo[b]thiophen-2-yl)-4-oxobutanoate. LCMS (C₁₇H₂₁O₄S) (ES, m/z): 321 [M+H]⁺. ¹H NMR (499 MHz, DMSO-d₆) δ 8.30 (s, 1H), 7.81 (s, 1H), 7.78 (s, 1H), 4.55 (t, J=5.1 Hz, 1H), 3.61 (s, 3H), 3.51-3.46 (m, 2H), 3.38-3.34 (m, 2H), 2.77-2.66 (m, 4H), 2.41 (s, 3H), 1.79-1.67 (m, 2H).

Step 8: Methyl 4-(5-(3-bromopropyl)-6-methylbenzo[b]thiophen-2-yl)-4-oxobutanoate

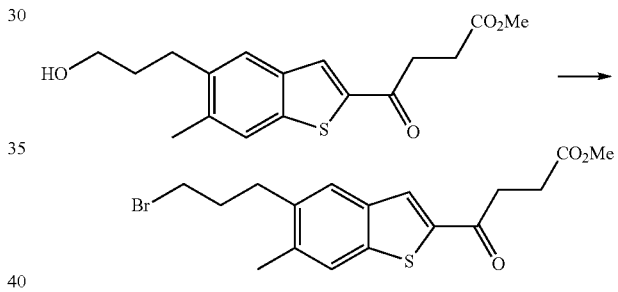

To a stirred mixture of methyl 4-(5-(3-hydroxypropyl)-6-methylbenzo[b]thiophen-2-yl)-4-oxobutanoate (97 mg, 0.30 mmol) and Ph₃P (130 mg, 0.48 mmol) in THF (1.5 mL) at 0° C. was added NBS (81 mg, 0.45 mmol) in one portion. After 30 min, the reaction was quenched with sat aq NH₄Cl and EtOAc. The organic layer was separated, dried over MgSO₄, filtered and concentrated under reduced pressure. The residue was purified by silica gel chromatography (0→25% EtOAc gradient in Hex) to afford methyl 4-(5-(3-bromopropyl)-6-methylbenzo[b]thiophen-2-yl)-4-oxobutanoate. LCMS (C₁₇H₂₀BrO₃S) (ES, m/z): 383, 385 [M+H]⁺.

Intermediate 14: tert-butyl 4-(5-(3-hydroxypropyl)-6-methoxythieno[3,2-b]pyridin-2-yl)-4-oxobutanoate

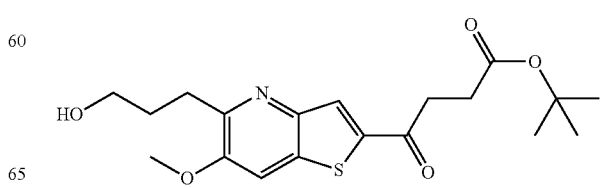

Step 1: tert-butyl 4-(5-chloro-6-methoxythieno[3,2-b]pyridin-2-yl)-4-oxobutanoate

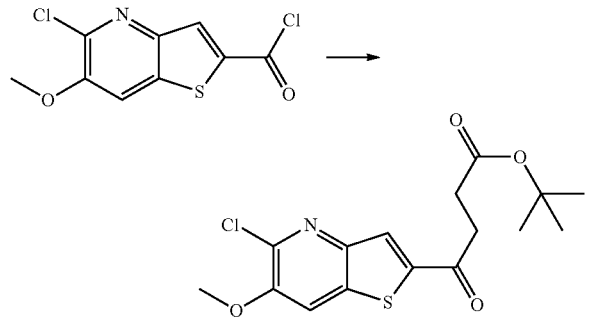

CuCl (0.721 g, 7.29 mmol) was added to a 250 mL round bottom flask with a stir bar. The flask was evacuated and then purged with N₂ three times. THF (14.6 mL) was added to the flask, which was then stirred and cooled to 0° C. with an ice water bath. (3-(tert-butoxy)-3-oxopropyl)zinc(II) (0.50M THF, 30 mL, 15 mmol) was then added dropwise over 10 min while stirring at 0° C. The resulting mixture was stirred at 0° C. for 35 min. 5-chloro-6-methoxy thieno [3,2-b]pyridine-2-carbonyl chloride (1.91 g, 7.29 mmol) was added, followed by NMP (14.6 mL). The resulting mixture was stirred for 7 h at 0° C. Concentrated NH₄OH (4 mL) was added to the reaction with rapid stirring at 0° C. To this suspension was added water:MeOH (4:1 140 mL) along with ~20 g sodium citrate tribasic dihydrate. The mixture was stirred for 20 min. The resulting suspension was filtered, and the filter cake was washed with water. The cake was then slurried in Hex and filtered twice. Vacuum was pulled through the cake with N₂ sweep over 72 h to afford tert-butyl 4-(5-chloro-6-methoxythieno[3,2-b]pyridin-2-yl)-4-oxobutanoate. LCMS ($C_{16}H_{19}ClNO_4S$) (ES, m/z): 356 [M+H]⁺. ¹H NMR (500 MHz, CDCl₃) δ 8.03 (s, 1H), 7.61 (s, 1H), 4.03 (s, 3H), 3.30 (t, J=6.5 Hz, 2H), 2.87-2.59 (m, 2H), 1.46 (s, 9H).

Step 2: tert-butyl 4-(5-(3-((tert-butyldimethylsilyl)oxy)propyl)-6-methoxythieno[3,2-b]pyridin-2-yl)-4-oxobutanoate

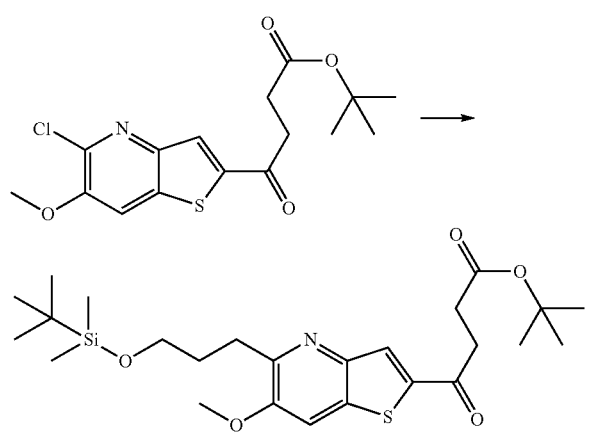

tert-Butyl 4-(5-chloro-6-methoxythieno[3,2-b]pyridin-2-yl)-4-oxobutanoate (1.00 g, 2.81 mmol) and CPhos Pd G3 (0.113 g, 0.141 mmol) were added to a 40 mL vial with a septum-containing screw cap. The vial was evacuated and backfilled with N₂ three times. THF (10.0 mL) was added to the vial under N₂ with stirring. While stirring the resulting suspension at RT, (3-((tert-butyldimethylsilyl)oxy)propyl)zinc(II) bromide (0.50M in THF, 11.2 mL, 5.60 mmol) was added dropwise. The resulting mixture was stirred for 3 h at RT. The mixture was partitioned between EtOAc (75 mL) and 10% aqueous sodium citrate (75 mL) and stirred vigorously for 5 min. The layers were separated, and the aqueous layer was extracted with EtOAc (20 mL). The organic layers were combined, washed with sat aq NaCl (50 mL), dried over anhydrous Na₂SO₄, concentrated under reduced pressure to afford a crude residue. The resulting residue was purified by silica gel chromatography (0→40% EtOAc gradient in Hex) to afford tert-butyl 4-(5-(3-((tert-butyldimethylsilyl)oxy)propyl)-6-methoxythieno[3,2-b]pyridin-2-yl)-4-oxobutanoate. LCMS ($C_{25}H_{40}NO_5SSi$) (ES, m/z): 494 [M+H]⁺. ¹H NMR (500 MHz, CDCl₃) δ 8.08 (s, 1H), 7.48 (s, 1H), 3.94 (s, 3H), 3.75 (t, J=6.5 Hz, 2H), 3.30 (t, J=6.6 Hz, 2H), 3.02-2.95 (m, 2H), 2.73 (t, J=6.6 Hz, 2H), 2.03-1.96 (m, 2H), 1.46 (s, 9H), 0.92 (s, 9H), 0.07 (s, 6H).

Step 3: tert-butyl 4-(5-(3-hydroxypropyl)-6-methoxythieno[3,2-b]pyridin-2-yl)-4-oxobutanoate

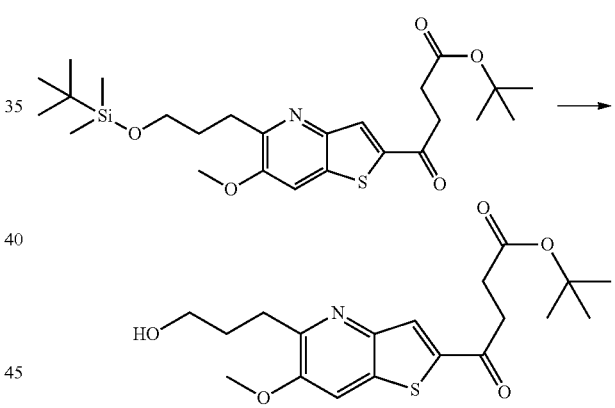

To a mixture of tert-butyl 4-(5-(3-((tert-butyldimethylsilyl)oxy)propyl)-6-methoxythieno[3,2-b]pyridin-2-yl)-4-oxobutanoate (0.735 g, 1.49 mmol) in MeOH (3.0 mL) was added water (3.0 mL) and then HOAc (3.0 mL). The resulting mixture was stirred at RT for 18 h. The mixture was then partitioned between EtOAc (50 mL), water (25 mL) and sat aq NaCl (25 mL). The layers were separated, and the aqueous layer was extracted with EtOAc (50 mL). The organic layers were combined, washed with sat aq NaCl (50 mL), dried over anhydrous Na₂SO₄, filtered and concentrated under reduced pressure. The resulting residue was purified by silica gel chromatography (0→100% EtOAc gradient in Hex then isocratic at 100% EtOAc) to afford tert-butyl 4-(5-(3-hydroxypropyl)-6-methoxythieno[3,2-b]pyridin-2-yl)-4-oxobutanoate. LCMS ($C_{19}H_{26}NO_5S$) (ES, m/z): 380 [M+H]⁺. ¹H NMR (500 MHz, CDCl₃) δ 8.06 (s, 1H), 7.51 (s, 1H), 3.95 (s, 3H), 3.73 (t, J=5.8 Hz, 2H), 3.28 (t, J=6.6 Hz, 2H), 3.10 (t, J=6.9 Hz, 2H), 2.72 (t, J=6.6 Hz, 2H), 2.06 (p, J=6.5 Hz, 2H), 1.45 (s, 9H).

Intermediate 15: tert-Butyl 4-(5-bromo-6-methoxy-benzo[d]thiazol-2-yl)-4-oxobutanoate

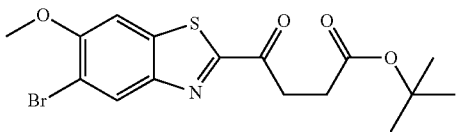 [SMILES: COc1cc2sc(C(=O)CCC(=O)OC(C)(C)C)nc2cc1Br]

Step 1: Methyl 2-((3-bromo-4-methoxyphenyl)amino)-2-oxoacetate

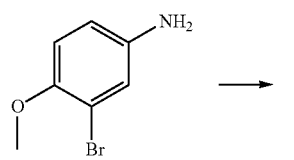

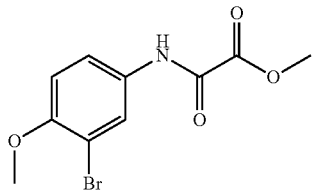

Into a 5-L 4-necked round-bottom flask that was purged and maintained with an inert atmosphere of N₂ was placed a mixture of 3-bromo-4-methoxyaniline (232 g, 1.15 mol) in DCM (3.0 L), DIPEA (171 g, 1.32 mol), and methyl 2-chloro-2-oxoacetate (148 g, 1.21 mol). The resulting mixture was stirred for 1 h at RT. The mixture was then quenched by the addition of water/ice (2 L). The resulting mixture was extracted with DCM (3×1 L). The organic layers were combined and concentrated under reduced pressure to afford methyl 2-((3-bromo-4-methoxyphenyl)amino)-2-oxoacetate, which was used without purification or characterization.

Step 2: O-Methyl 2-((3-bromo-4-methoxyphenyl)amino)-2-oxoethanethiolate

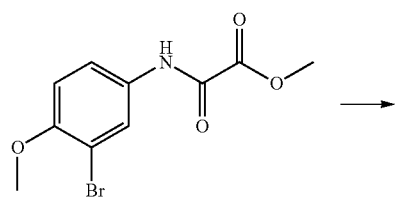

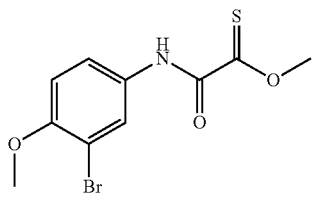

Into a 3-L 4-necked round-bottom flask that was purged and maintained with an inert atmosphere of N₂ was placed a mixture of methyl 2-((3-bromo-4-methoxyphenyl)amino)-2-oxoacetate (111 g, 386 mmol) in toluene (1.5 L) and Lawesson's reagent (86.4 g, 214 mmol). The resulting mixture was heated to 85° C. for 16 h. The reaction mixture was then cooled to RT. The resulting materials were removed by filtration and washed with DCM (3×500 mL). The filtrate was concentrated under reduced pressure, and the residue was purified by silica gel chromatography (EtOAc/PE (1:20)) to afford O-methyl 2-((3-bromo-4-methoxyphenyl)amino)-2-oxoethanethioate, which was used without characterization.

Step 3: 5-Bromo-6-methoxybenzo[d]thiazole-2-carboxylic acid, potassium salt and 7-bromo-6-methoxybenzo[d]thiazole-2-carboxylic acid, potassium salt (2:1 mixture of isomers)

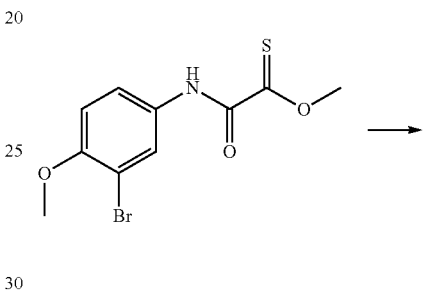

Ratio: ~2:1

Into a 2-L 4-necked round-bottom flask that was purged and maintained with an inert atmosphere of N₂, was placed methyl O-methyl 2-((3-bromo-4-methoxyphenyl)amino)-2-oxoethanethiolate (84.5 g, 278 mmol). A mixture of KOH (50 g, 90 mmol) in H₂O (500 mL) was added to the reaction mixture over a period of 10 min. A mixture of potassium ferricyanide (III) hydrate (242 g, 735 mmol) in H₂O (2 L) was then added to the reaction mixture over a period of 10 min. The pH of the resulting mixture was adjusted to 2 with aq HCl (2.0M). Water (500 mL) was then added. The resulting mixture was allowed to stir for 1 h at RT. The resulting product was then collected by filtration and washed with DCM (1 L). The cake was slurried in aq KOH (2.0M, 500 mL, 1 mol) for 0.5 h. The resulting product was then collected by filtration and washed with H₂O (2×500 mL) to afford a 2:1 a mixture of 5-bromo-6-methoxybenzo[d]thiazole-2-carboxylic acid, potassium salt and 7-bromo-6-methoxybenzo[d] thiazole-2-carboxylic acid, potassium salt. Characterization data for 5-bromo-6-methoxybenzo[d]thiazole-2-carboxylic acid, potassium salt (major isomer): ¹H NMR (400 MHz, DMSO-d₆, ppm) δ 8.13 (s, 1H), 7.70 (s, 1H), 3.80 (s, 3H). Characterization data 7-bromo-6-methoxybenzo [d]thiazole-2-carboxylic acid, potassium salt (minor isomer): ¹H NMR (400 MHz, DMSO-d₆, ppm) 7.90 (d, J=8.9 Hz, 1H), 7.26 (d, J=8.9 Hz, 1H), 3.91 (s, 3H).

Step 4: 5-Bromo-6-methoxybenzo[d]thiazole-2-carboxylic acid and 7-bromo-6-methoxybenzo[d]thiazole-2-carboxylic acid (2:1 mixture of isomers)

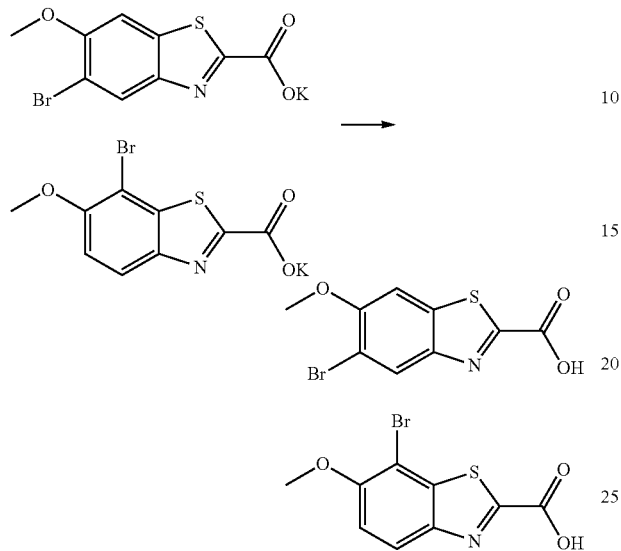

To a 1 L flask were added 5-bromo-6-methoxybenzo[d]thiazole-2-carboxylic acid, potassium salt and 7-bromo-6-methoxybenzo[d]thiazole-2-carboxylic acid, potassium salt (2:1 mixture of isomers) (22.4 g, 49.4 mmol), water (300 mL), ACN (180 mL), MeOH (120 mL), and TFA (11.4 mL, 148 mmol). The mixture was stirred vigorously for 15 min at RT. The resulting product were collected by filtration and washed with water (2×20 mL), MeOH (2×5 mL), and Et$_2$O (2×10 mL) to afford a 2:1 mixture of 5-bromo-6-methoxybenzo[d] thiazole-2-carboxylic acid and 7-bromo-6-methoxybenzo[d]thiazole-2-carboxylic acid. Characterization data for 5-bromo-6-methoxybenzo[d]thiazole-2-carboxylic acid (major isomer): $^1$H NMR (500 MHz, DMSO-d$_6$) δ 8.45 (s, 1H), 7.97 (s, 1H), 3.96 (s, 3H). Characterization data for 7-bromo-6-methoxybenzo[d]thiazole-2-carboxylic acid (minor isomer): $^1$H NMR (500 MHz, DMSO-d$_6$) δ 8.21 (d, J=9.0 Hz, 1H), 7.51 (d, J=9.0 Hz, 1H), 4.00 (s, 3H).

Step 5: Methyl 5-bromo-6-methoxybenzo[d]thiazole-2-carboxylate

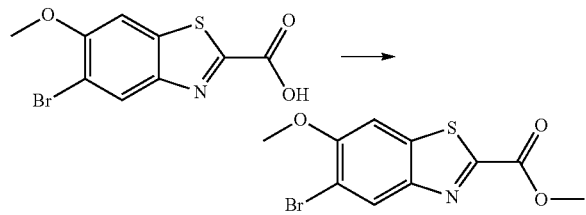

To a 250 mL flask was added 5-bromo-6-methoxybenzo[d]thiazole-2-carboxylic acid and 7-bromo-6-methoxybenzo[d]thiazole-2-carboxylic acid (2:1 mixture of isomers) (17.2 g, 41.8 mmol) and MeOH (150 mL). The mixture was stirred vigorously and cooled to 0° C. To the stirring mixture was added SOCl$_2$ (6.1 mL, 84 mmol) dropwise over a period of 10 min. The mixture was then heated to reflux for 18 h. Upon cooling to RT, the resulting product was collected by filtration and washed with MeOH (2×20 mL). The product was purified by silica gel chromatography (0→30% EtOAc gradient in DCM) to afford methyl 5-bromo-6-methoxybenzo [d]thiazole-2-carboxylate as a single isomer. LCMS (C$_{10}$H$_9$BrNO$_3$S) (ES, m/z): 302, 304 (M+H)$^+$. $^1$H NMR (500 MHz, CDCl$_3$) δ 8.42 (s, 1H), 7.40 (s, 1H), 4.09 (s, 3H), 4.02 (s, 3H).

Step 6: 5-Bromo-6-methoxybenzo[d]thiazole-2-carboxylic acid

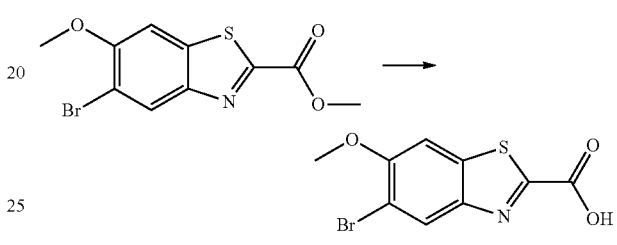

To a 500 mL round bottom flask was added methyl 5-bromo-6-methoxybenzo[d]thiazole-2-carboxylate (7.3 g, 24 mmol) and MeOH (150 mL). To the vigorously stirring mixture was added aq NaOH (2.0M, 37 mL, 74 mmol). The mixture was heated to reflux for 30 min. Upon cooling to RT, aq HCl (2.0M, 37 mL, 74 mmol) was added dropwise. The mixture was stirred vigorously at RT for 18 h. The resulting product was collected by filtration and washed with water (2×50 mL) and MeOH (2×20 mL) to afford 5-bromo-6-methoxybenzo[d] thiazole-2-carboxylic acid. LCMS (C$_9$H$_7$BrNO$_3$S) (ES, m/z): 288, 290 (M+H). $^1$H NMR (500 MHz, DMSO-d$_6$) δ 8.45 (s, 1H), 7.97 (s, 1H), 3.96 (s, 3H).

Step 7: 5-Bromo-6-methoxybenzo[d]thiazole-2-carbonyl chloride

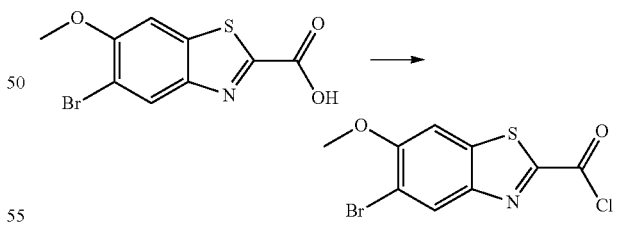

To a 100 mL round bottom flask was added 5-bromo-6-methoxybenzo[d]thiazole-2-carboxylic acid (1.46 g, 5.07 mmol), DCM (25 mL), and DMF (0.080 mL, 1.0 mmol). To the mixture was added (COCl)$_2$ (5.32 mL, 10.6 mmol) dropwise over 1 min, and the mixture was vigorously stirred at RT for 15 min. The mixture was then filtered through CELITE. The filtrate was concentrated under reduced pressure to afford 5-bromo-6-methoxybenzo[d]thiazole-2-carbonyl chloride used without further purification or characterization.

Step 8: tert-Butyl 4-(5-bromo-6-methoxybenzo[d]thiazol-2-yl)-4-oxobutanoate

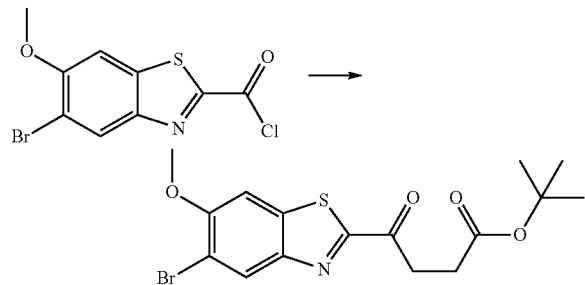

To a 250 mL round bottom flask was added CuCl (0.45 g, 4.6 mmol). The flask was evacuated and refilled with $N_2$ three times. THF (10 mL) was added, and the mixture was stirred and cooled to 0° C. To the mixture was added (3-(tert-butoxy)-3-oxopropyl)zinc(II) bromide (0.50M in THF, 18 mL, 9.0 mmol). After 10 min, a mixture of 5-bromo-6-methoxy-benzo[d]thiazole-2-carbonyl chloride (1.4 g, 4.6 mmol) in NMP (30 mL) was added dropwise over a period of 5 min. After 5 min, the mixture was allowed to warm to RT and was then stirred for 1 h. To the mixture was added water (30 mL) and concentrated aq $NH_4OH$ (15 mL). The mixture was extracted with EtOAc (125 mL), and the organic layer was washed with water (2×75 mL). The organic layer was dried over $Na_2SO_4$, filtered, and concentrated under reduced pressure. The residue was purified by silica gel chromatography (0→75% EtOAc gradient in Hex) to afford tert-butyl 4-(5-bromo-6-methoxybenzo[d]thiazol-2-yl)-4-oxobutanoate. LCMS ($C_{16}H_{18}BrNO_4S$+Na) (ES, m/z): 422, 424 [M+Na]$^+$. $^1$H NMR (500 MHz, CDCl$_3$) δ 8.38 (s, 1H), 7.40 (s, 1H), 4.02 (s, 3H), 3.51 (t, J=6.6 Hz, 2H), 2.75 (t, J=6.6 Hz, 2H), 1.46 (s, 9H).

Intermediate 16: tert-butyl 4-(5-(3-bromopropyl)-6-methoxybenzo[d]thiazol-2-yl)-4-oxobutanoate

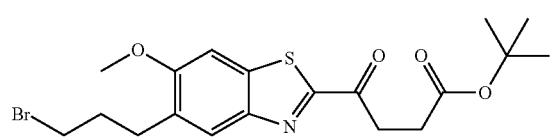 [SMILES: COc1cc2sc(C(=O)CCC(=O)OC(C)(C)C)nc2cc1CCCBr]

Step 1: tert-butyl 4-(5-(3-((tert-butyldimethylsilyl)oxy)propyl)-6-methoxybenzo[d]thiazol-2-yl)-4-oxobutanoate

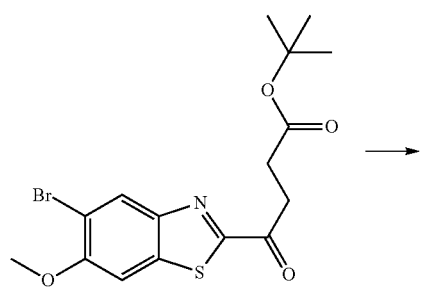

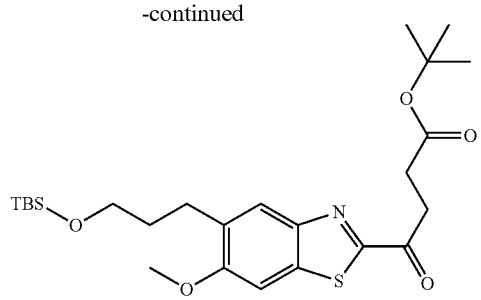

To a 4 mL vial was added tert-butyl 4-(5-bromo-6-methoxybenzo[d]thiazol-2-yl)-4-oxobutanoate (233 mg, 0.581 mmol) and C-Phos Pd G3 (14 mg, 0.018 mmol). The vial was evacuated and refilled with $N_2$ three times. To the vial was added THF (0.60 mL) followed by (3-((tert-butyldimethylsilyl)oxy)propyl)zinc(II) bromide (0.50M in THF, 2.90 mL, 1.45 mmol). The mixture was stirred at RT for 20 min. To the mixture was added additional (3-((tert-butyldimethylsilyl)oxy)-propyl)zinc(II) bromide (0.50M in THF, 1.4 mL, 0.73 mmol). After 30 min, the mixture was diluted in EtOAc (30 mL) and washed with 10% aq tribasic sodium citrate (30 mL). The organic layer was separated, dried over $Na_2SO_4$, filtered and concentrated under reduced pressure. The resulting residue was purified by silica gel chromatography (0→40% EtOAc gradient in Hex) to afford tert-butyl 4-(5-(3-((tert-butyldimethylsilyl)oxy) propyl)-6-methoxybenzo[d]thiazol-2-yl)-4-oxobutanoate. LCMS ($C_{25}H_{40}NO_5SSi$) (ES, m/z): 494 [M+H]$^+$. $^1$H NMR (500 MHz, CDCl$_3$) δ 7.93 (s, 1H), 7.31 (s, 1H), 3.94 (s, 3H), 3.70 (t, J=6.3 Hz, 2H), 3.53 (t, J=6.6 Hz, 2H), 2.86-2.78 (m, 2H), 2.74 (t, J=6.6 Hz, 2H), 1.94-1.84 (m, 2H), 1.45 (s, 9H), 0.93 (s, 9H).

Step 2: tert-butyl 4-(5-(3-hydroxypropyl)-6-methoxybenzo[d]thiazol-2-yl)-4-oxobutanoate

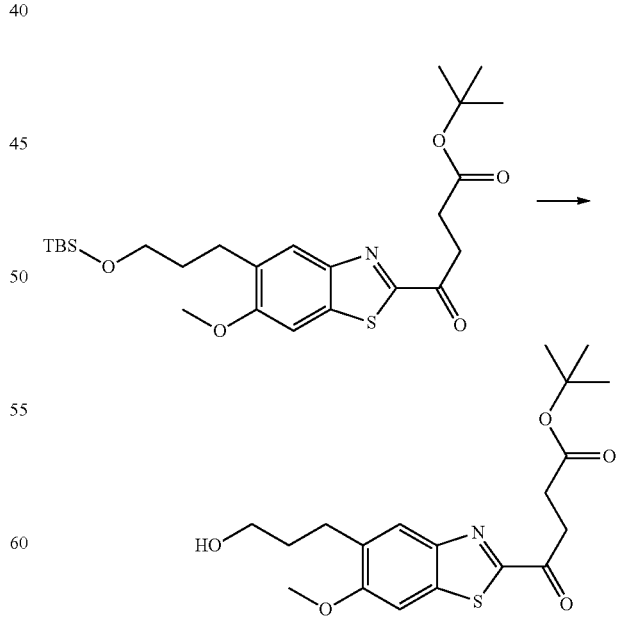

To a 100 mL flask was added tert-butyl 4-(5-(3-((tert-butyldimethylsilyl)oxy) propyl)-6-methoxybenzo[d]thiazol-2-yl)-4-oxobutanoate (229 mg, 0.464 mmol), MeOH (5.0 mL), water (5.0 mL), and AcOH (5.0 mL). The mixture was allowed to stir at RT for 4 h. The mixture was then diluted with EtOAc (50 mL) and washed with water (3×50 mL). The organic layer was separated, dried over $Na_2SO_4$, filtered and concentrated under reduced pressure to afford tert-butyl 4-(5-(3-hydroxypropyl)-6-methoxybenzo[d]thiazol-2-yl)-4-oxobutanoate. LCMS ($C_{19}H_{26}NO_5S$) (ES, m/z): 380 [M+H]$^+$. $^1$H NMR (500 MHz, $CDCl_3$) δ 7.95 (s, 1H), 7.34 (s, 1H), 3.96 (s, 3H), 3.70 (t, J=6.3 Hz, 2H), 3.52 (t, J=6.7 Hz, 2H), 2.87 (t, J=7.5 Hz, 2H), 2.75 (t, J=6.6 Hz, 2H), 2.00-1.90 (m, 2H), 1.46 (s, 9H).

Step 3: tert-butyl 4-(5-(3-bromopropyl)-6-methoxy-benzo[d]thiazol-2-yl)-4-oxobutanoate

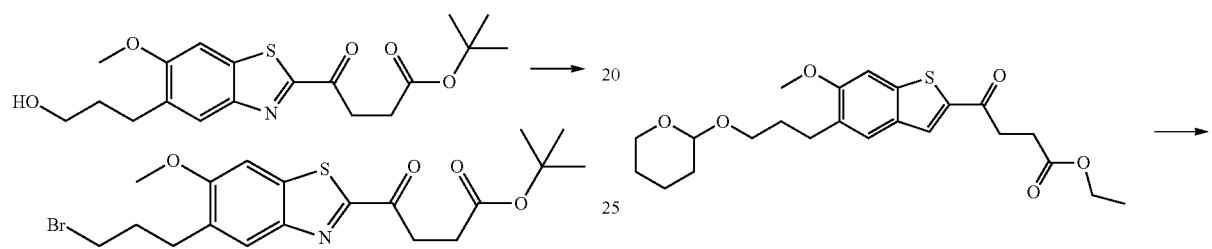

To a 4 mL vial was added $CBr_4$ (72 mg, 0.22 mmol), triphenylphosphine (62 mg, 0.24 mmol), and tert-butyl 4-(5-(3-hydroxypropyl)-6-methoxybenzo[d]thiazol-2-yl)-4-oxobutanoate (69 mg, 0.18 mmol). The vial was cooled to 0° C., and the DCM (1.0 mL) was added. The mixture was allowed to warm to RT for 90 min. The mixture was then directly purified by silica gel chromatography (0→30% EtOAc gradient in Hex) to afford tert-butyl 4-(5-(3-bromopropyl)-6-methoxybenzo[d]thiazol-2-yl)-4-oxobutanoate. LCMS ($C_{19}H_{25}BrNO_4S$) (ES, m/z): 442, 444 [M+H]$^+$. $^1$H NMR (499 MHz, $CDCl_3$) δ 7.96 (s, 1H), 7.33 (s, 1H), 3.52 (t, J=6.6 Hz, 2H), 3.95 (s, 3H), 3.45 (t, J=6.6 Hz, 2H), 2.93 (t, J=7.2 Hz, 2H), 2.75 (t, J=6.6 Hz, 2H), 2.30-2.19 (m, 2H), 1.46 (s, 9H).

Intermediate 17: tert-butyl 4-(5-hydroxy-6-methoxybenzo[b]thiophen-2-yl)-4-oxobutanoate

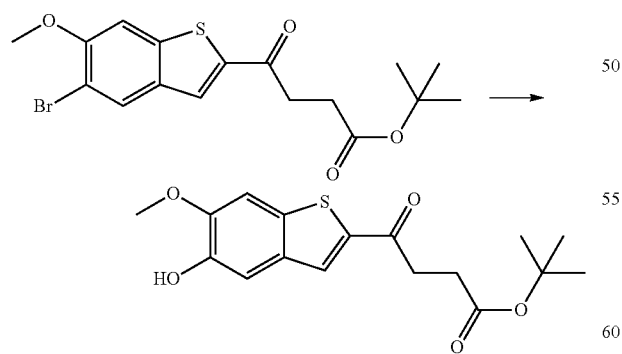

To a mixture of RockPhos Pd G3 (0.105 g, 0.125 mmol), benzaldoxime (3.03 g, 25.0 mmol), tert-butyl 4-(5-bromo-6-methoxybenzo[b]thiophen-2-yl)-4-oxobutanoate (5.0 g, 13 mmol), and $Cs_2CO_3$ (12.2 g, 37.6 mmol) was added DMF (40 mL). The reaction was heated to 80° C. for 18 h. The reaction mixture was then allowed to cool to RT and poured into a flask containing aq HCl (0.5M, 100 mL). The resulting mixture was extracted with DCM. The organic layer was then dried over $Na_2SO_4$, filtered, and concentrated under reduced pressure. The resulting residue was purified by silica gel column chromatography (0→50% EtOAc gradient in Hex) to afford tert-butyl 4-(5-hydroxy-6-methoxybenzo[b]thiophen-2-yl)-4-oxobutanoate. LCMS ($C_{17}H_{20}O_5SNa$) (ES, m/z): 359 [M+Na]$^+$. $^1$H NMR (600 MHz, DMSO-$d_6$) δ 9.35 (s, 1H), 8.12 (s, 1H), 7.49 (s, 1H), 7.27 (s, 1H), 3.83 (s, 3H), 3.18 (t, J=6.2 Hz, 2H), 2.52 (t, J=6.2 Hz, 2H), 1.33 (s, 9H).

Intermediate 18: Ethyl 4-(5-(3-hydroxypropyl)-6-methoxybenzo[b]thiophen-2-yl)-4-oxobutanoate

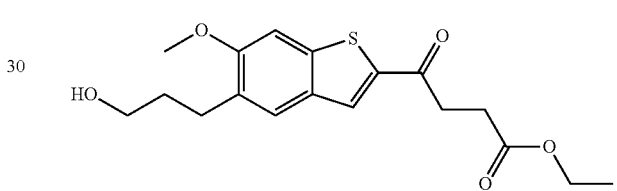

To a mixture ethyl 4-(6-methoxy-5-(3-((tetrahydro-2H-pyran-2-yl)oxy)propyl) benzo[b]thiophen-2-yl)-4-oxobutanoate (5.0 g, 12 mmol) and EtOH (100 mL) was added pTsOH (4.4 g, 23 mmol). The reaction was allowed to stir at RT for 1 h. The reaction was then quenched with water and diluted with DCM. The organic layer was separated and then washed with aq sat $NaHCO_3$. The organic layer was then dried over $Na_2SO_4$, filtered and concentrated under reduced pressure to afford ethyl 4-(5-(3-hydroxypropyl)-6-methoxy-benzo[b]thiophen-2-yl)-4-oxobutanoate. LCMS ($C_{18}H_{23}O_5S$) (ES, m/z): 351 [M+H]$^+$. $^1$H NMR (600 MHz, DMSO-$d_6$) δ 8.21 (s, 1H), 7.70 (s, 1H), 7.55 (s, 1H), 4.44 (t, J=5.0 Hz, 1H), 4.02 (q, J=7.0 Hz, 2H), 3.85 (s, 3H), 3.40 (q, J=6.0 Hz, 2H), 3.27 (d, J=6.4 Hz, 2H), 2.63 (q, J=7.0, 5.9 Hz, 4H), 1.68 (p, J=6.6 Hz, 2H), 1.14 (t, J=7.1 Hz, 3H).

Intermediate 19: methyl (2S)-4-[5-(2-aminoethyl)-6-methoxy-1-benzothiophen-2-yl]-2-methyl-4-oxobutanoate

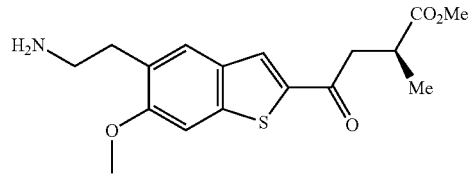 [SMILES: COC(=O)[C@@H](C)CC(=O)c1cc2cc(CCN)c(OC)cc2s1]

Step 1: methyl (2S)-4-(5-{2-[(tert-butoxycarbonyl)amino]ethyl}-6-methoxy-1-benzothiophen-2-yl)-2-methyl-4-oxobutanoate

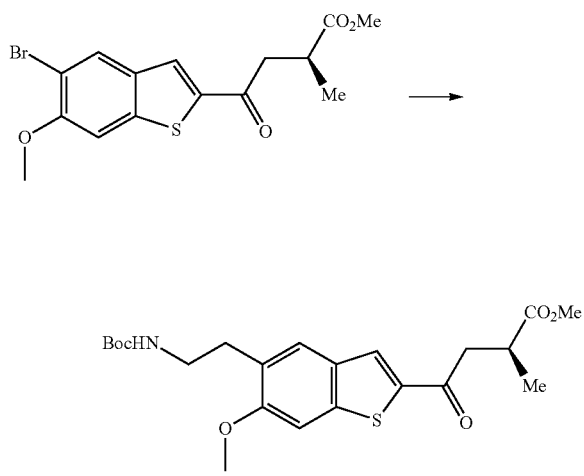

To the stirred mixture of methyl (2S)-4-(5-bromo-6-methoxy-1-benzothiophen-2-yl)-2-methyl-4-oxobutanoate (124 mg, 0.334 mmol), tris(trimethylsilyl)silane (103 μL, 0.334 mmol), and anhydrous $Na_2CO_3$ (71 mg, 0.67 mmol) in degassed DME (1.7 mL) under $N_2$, was added a mixture of Ir(2-(2,4-difluorophenyl)-5-(trifluoromethyl) pyridine)$_2$ (4,4'-di-tert-butyl-2,2'-bipyridine)PF$_6$ (3.8 mg, 3.3 μmol) in degassed DME (1.2 mL). A suspension of Nickel(II) chloride ethylene glycol dimethyl ether complex (0.37 mg, 1.7 mol) and 4,4'-di-tert-butyl-2,2'-bipyridine (0.45 mg, 1.7 mol) in degassed DME (445 μL) was added, and the resulting mixture was stirred under $N_2$ for 15 min at RT. tert-butyl N-(2-bromoethyl)carbamate (150 mg, 0.67 mmol) was added in one portion under $N_2$, and the reaction mixture was stirred and irradiated with two 34 W blue LED lamps (7 cm away on each side) for 18 h at RT. The mixture was then directly purified by silica gel flash column chromatography (EtOAc in Hex) to afford methyl (2S)-4-(5-{2-[(tert-butoxycarbonyl)amino] ethyl}-6-methoxy-1-benzothiophen-2-yl)-2-methyl-4-oxobutanoate. LCMS ($C_{22}H_{30}NO_6S$) (ES, m/z): 436 [M+H]$^+$. $^1$H NMR (500 MHz, DMSO-d$_6$): δ 8.25 (s, 1H), 7.70 (s, 1H), 7.60 (s, 1H), 6.86 (br, 1H), 3.88 (s, 3H), 3.59 (s, 3H), 3.43 (dd, J=17.5, 8.6 Hz, 1H), 3.19 (dd, J=17.5, 5.0 Hz, 1H), 3.15 (t, J=7.0 Hz, 2H), 3.01-2.93 (m, 1H), 2.77 (t, J=7.0 Hz, 2H), 1.34 (s, 9H), 1.19 (d, J=7.1 Hz, 3H).

Step 2: methyl (2S)-4-[5-(2-amino]ethyl)-6-methoxy-1-benzothiophen-2-yl-2-methyl-4-oxobutanoate

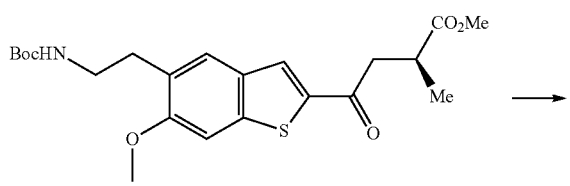

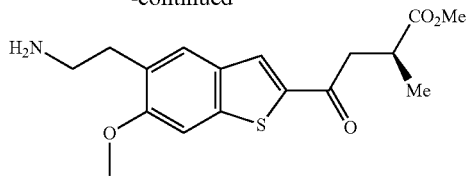

To the stirred solution of methyl (2S)-4-(5-{2-[(tert-butoxycarbonyl)amino] ethyl}-6-methoxy-1-benzothiophen-2-yl)-2-methyl-4-oxobutanoate (54 mg, 0.12 mmol) in $CH_2Cl_2$ (2.8 mL) was added TFA (476 μL, 6.18 mmol) in one portion at RT, and the reaction mixture was stirred at RT for 2 h. The mixture was concentrated, and the residue was dissolved in $CH_3CN$ and water and lyophilized overnight to afford methyl (2S)-4-[5-(2-aminoethyl)-6-methoxy-1-benzothiophen-2-yl]-2-methyl-4-oxobutanoate. LCMS ($C_{17}H_{22}NO_4S$) (ES, m/z): 336 [M+H]$^+$. $^1$H NMR (500 MHz, DMSO-d$_6$): δ 8.29 (s, 1H), 7.80 (br, 2H), 7.79 (s, 1H), 7.68 (s, 1H), 3.91 (s, 3H), 3.60 (s, 3H), 3.45-3.39 (m, 1H), 3.20 (dd, J=17.5, 5.0 Hz, 1H), 3.10-3.01 (m, 2H), 3.01-2.93 (m, 1H), 2.95 (t, J=7.0 Hz, 2H), 1.20 (d, J=7.1 Hz, 3H).

Intermediate 20: Ethyl 4-(5-(3-bromopropyl)-6-methoxybenzo[b]thiophen-2-yl)-4-oxobutanoate

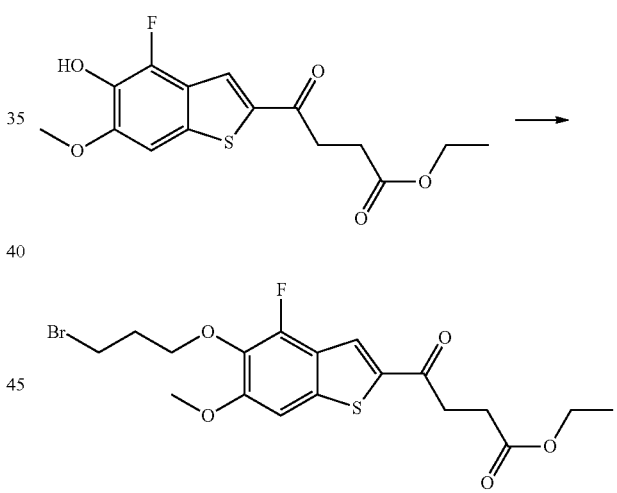

To a mixture of ethyl 4-(4-fluoro-5-hydroxy-6-methoxybenzo[b]thiophen-2-yl)-4-oxobutanoate(0.065 g, 0.2 mmol), $Cs_2CO_3$ (0.326 g, 1.00 mmol), and ACN (2 mL) was added 1,3-dibromopropane (1.0 mL, 9.9 mmol). The mixture was heated to 65° C. for 2 h. Upon cooling to RT, the mixture was filtered, and the filtered material was washed with THF. The filtrate was diluted with Hex, and the mixture was then concentrated under reduced pressure to afford ethyl 4-(6-methoxy-5-(3-((tetrahydro-2H-pyran-2-yl)oxy)propyl)benzo[b]thiophen-2-yl)-4-oxobutanoate. LCMS ($C_{18}H_{21}BrFO_5S$) (ES, m/z): 447, 449 [M+H]$^+$.

Intermediates 21 through 23 and 62 through 86, as shown in Table 1 below, were or may be prepared according to procedures analogous to those outlined in Intermediate 20 above using the appropriate starting materials, described as Preparations or as obtained from commercial sources.

TABLE 1

| Intermediate | Structure | Name | Mass [M + H]+ |
|---|---|---|---|
| 21 | 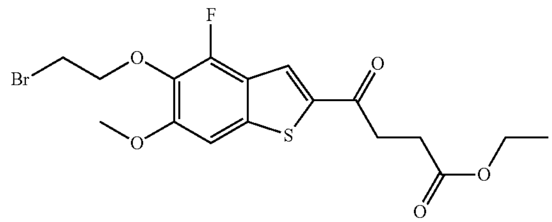 [SMILES: CCOC(=O)CCC(=O)c1cc2c(F)c(OCCBr)c(OC)cc2s1] | ethyl 4-(5-(2-bromoethoxy)-4-fluoro-6-methoxybenzo[b]thiophen-2-yl)-4-oxobutanoate | 433, 435 |
| 22 | 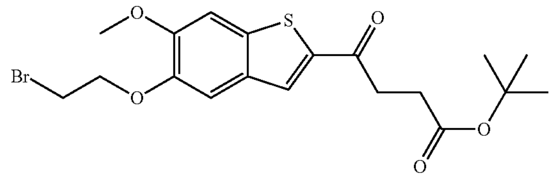 [SMILES: COc1cc2sc(C(=O)CCC(=O)OC(C)(C)C)cc2cc1OCCBr] | tert-butyl 4-(5-(2-bromoethoxy)-6-methoxybenzo[b]thiophen-2-yl)-4-oxobutanoate | 387, 389 [M − C₄H₈]+ |
| 23 | 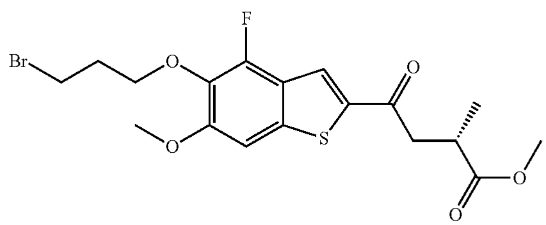 [SMILES: COC(=O)[C@@H](C)CC(=O)c1cc2c(F)c(OCCCBr)c(OC)cc2s1] | methyl (S)-4-(5-(3-bromopropoxy)-4-fluoro-6-methoxybenzo[b] thiophen-2-yl)-2-methyl-4-oxobutanoate | 447, 449 |
| 62 | 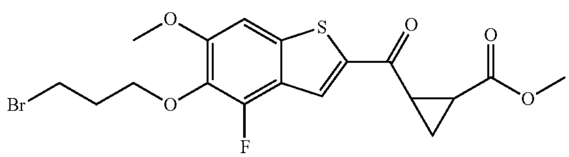 [SMILES: COC(=O)C1CC1C(=O)c1cc2c(F)c(OCCCBr)c(OC)cc2s1] | methyl 2-(5-(3-bromopropoxy)-4-fluoro-6-methoxybenzo[b]thiophene-2-carbonyl)cyclopropane-1-carboxylate | 445, 447 |
| 63 | 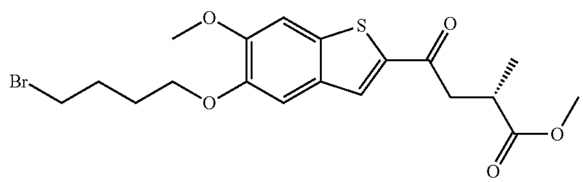 [SMILES: COC(=O)[C@@H](C)CC(=O)c1cc2cc(OCCCCBr)c(OC)cc2s1] | methyl (S)-4-(5-(4-bromobutoxy)-6-methoxybenzo[b]thiophen-2-yl)-2-methyl-4-oxobutanoate | 443, 445 |
| 64 | 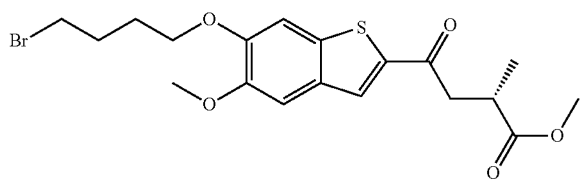 [SMILES: COC(=O)[C@@H](C)CC(=O)c1cc2cc(OC)c(OCCCCBr)cc2s1] | methyl (S)-4-(6-(4-bromobutoxy)-5-methoxybenzo[b]thiophen-2-yl)-2-methyl-4-oxobutanoate | 443, 445 |
| 65 | 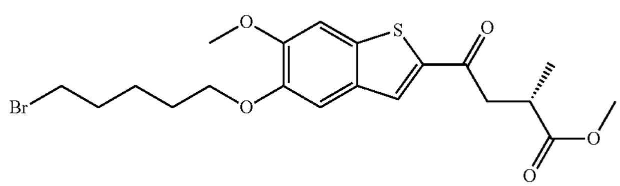 [SMILES: COC(=O)[C@@H](C)CC(=O)c1cc2cc(OCCCCCBr)c(OC)cc2s1] | (S)-methyl 4-(5-((5-bromopentyl)oxy)-6-methoxybenzo[b]thiophen-2-yl)-2-methyl-4-oxobutanoate | 457, 459 |
| 66 | 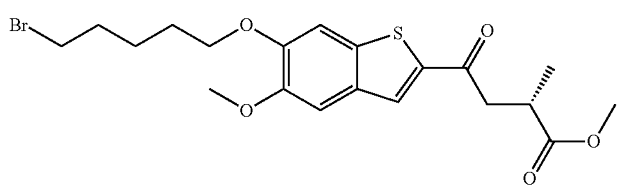 [SMILES: COC(=O)[C@@H](C)CC(=O)c1cc2cc(OC)c(OCCCCCBr)cc2s1] | (S)-methyl 4-(6-((5-bromopentyl)oxy)-5-methoxybenzo[b]thiophen-2-yl)-2-methyl-4-oxobutanoate | 457, 459 |

TABLE 1-continued

| Intermediate | Structure | Name | Mass [M + H]+ |
|---|---|---|---|
| 67 | 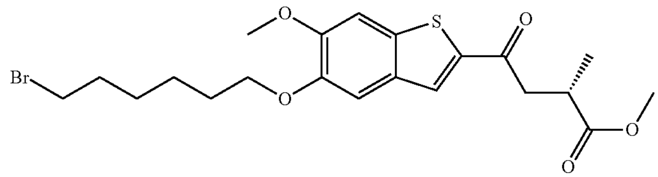 [SMILES: COC(=O)[C@@H](C)CC(=O)c1cc2cc(OCCCCCCBr)c(OC)cc2s1] | methyl (S)-4-(5-((6-bromohexyl)oxy)-6-methoxybenzo[b]thiophen-2-yl)-2-methyl-4-oxobutanoate | 471, 473 |
| 68 | 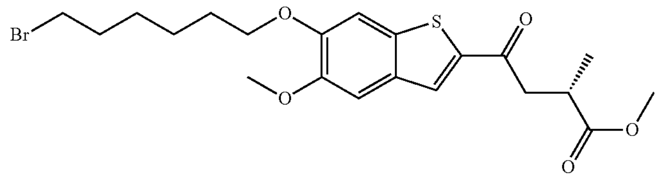 [SMILES: COC(=O)[C@@H](C)CC(=O)c1cc2cc(OC)c(OCCCCCCBr)cc2s1] | methyl (S)-4-(6-((6-bromohexyl)oxy)-5-methoxybenzo[b]thiophen-2-yl)-2-methyl-4-oxobutanoate | 471, 473 |
| 69 | 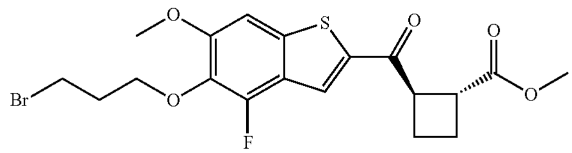 [SMILES: COC(=O)[C@@H]1CC[C@H]1C(=O)c1cc2c(F)c(OCCCBr)c(OC)cc2s1] | trans-methyl 2-(5-(3-bromopropoxy)-4-fluoro-6-methoxybenzo[b]thiophene-2-carbonyl)cyclobutane-carboxylate | 459, 461 |
| 70 | 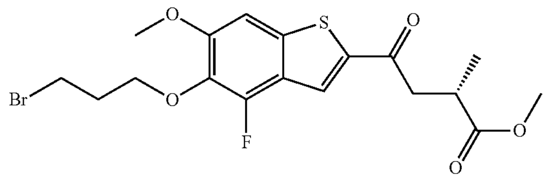 | (S)-methyl 4-(5-(3-bromopropoxy)-4-fluoro-6-methoxybenzo[b]thiophen-2-yl)-2-methylbutanoate | 450, 452 (M + H$_2$O) |
| 71 | 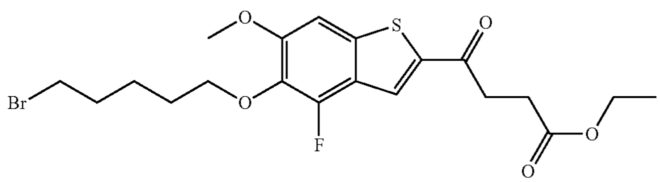 [SMILES: CCOC(=O)CCC(=O)c1cc2c(F)c(OCCCCCBr)c(OC)cc2s1] | ethyl 4-(5-((5-bromopentyl)oxy)-4-fluoro-6-methoxybenzo[b]thiophen-2-yl)-4-oxobutanoate | 475, 477 |
| 72 | 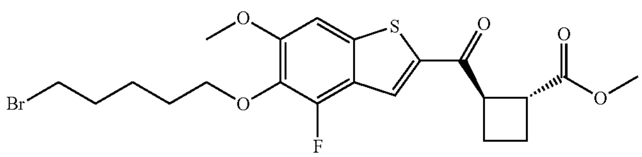 [SMILES: COC(=O)[C@@H]1CC[C@H]1C(=O)c1cc2c(F)c(OCCCCCBr)c(OC)cc2s1] | trans-methyl 2-(5-((5-bromopentyl)oxy)-4-fluoro-6-methoxybenzo[b]thiophene-2-carbonyl)cyclobutane-carboxylate | 487, 489 |
| 73 | 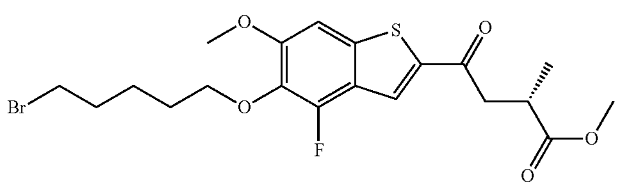 [SMILES: COC(=O)[C@@H](C)CC(=O)c1cc2c(F)c(OCCCCCBr)c(OC)cc2s1] | (S)-methyl 4-(5-((5-bromopentyl)oxy)-4-fluoro-6-methoxybenzo[b]thiophen-2-yl)-2-methyl-4-oxobutanoate | 475, 477 |
| 74 | 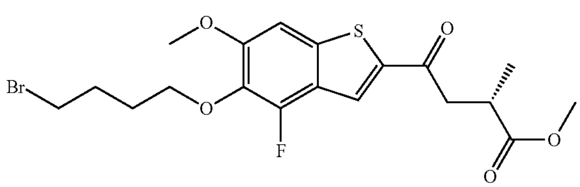 [SMILES: COC(=O)[C@@H](C)CC(=O)c1cc2c(F)c(OCCCCBr)c(OC)cc2s1] | (S)-methyl 4-(5-(4-bromobutoxy)-4-fluoro-6-methoxybenzo[b]thiophen-2-yl)-2-methyl-4-oxobutanoate | 461, 463 |

TABLE 1-continued

| Intermediate | Name | Mass [M + H]+ |
|---|---|---|
| 75 | methyl 4-(6-(3-bromopropoxy)-5-methoxybenzo[b]thiophen-2-yl)-4-oxobutanoate | 415, 417 |
| 76 | methyl (S)-4-(5-(3-bromopropoxy)-4-chloro-6-methoxybenzo[b]thiophen-2-yl)-2-methyl-4-oxobutanoate | 463, 465 |
| 77 | methyl (S)-4-(4-bromo-5-(3-bromopropoxy)-6-methoxybenzo[b]thiophen-2-yl)-2-methyl-4-oxobutanoate | 507, 509, 511 |
| 78 | methyl (2S)-4-(5-(3-bromobutoxy)-4-fluoro-6-methoxybenzo[b]thiophen-2-yl)-2-methyl-4-oxobutanoate | 461, 463 |
| 79 | methyl (2S)-4-(5-((4-bromopentyl)oxy)-4-fluoro-6-methoxybenzo[b]thiophen-2-yl)-2-methyl-4-oxobutanoate | 475, 477 |
| 80 | methyl (2S)-4-(5-((5-bromohexan-2-yl)oxy)-4-fluoro-6-methoxybenzo[b]thiophen-2-yl)-2-methyl-4-oxobutanoate | 489, 491 |
| 81 | methyl (2S)-4-(5-(3-bromo-2-methylpropoxy)-4-fluoro-6-methoxybenzo[b]thiophen-2-yl)-2-methyl-4-oxobutanoate | 461, 463 |
| 82 | methyl 4-(5-(3-bromopropoxy)-4-fluoro-6-methoxybenzo[b]thiophen-2-yl)-2,2-dimethylbutanoate | 464, 466 (M + H$_2$O) |

TABLE 1-continued

| Intermediate | Structure | Name | Mass [M + H]+ |
|---|---|---|---|
| 83 | 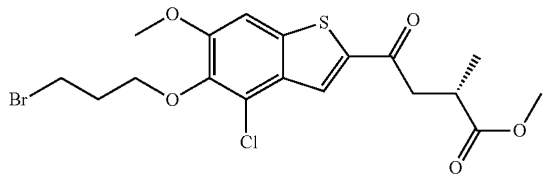 | methyl (S)-4-(5-(3-bromopropoxy)-4-chloro-6-methoxybenzo[b]thiophen-2-yl)-2-methylbutanoate | 466, 468 (M + H₂O) |
| 84 | 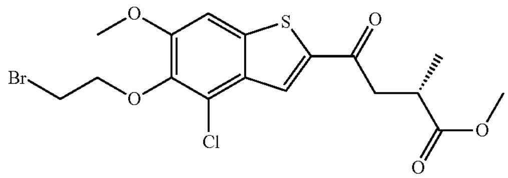 | methyl (S)-4-(5-(2-bromoethoxy)-4-chloro-6-methoxybenzo[b]thiophen-2-yl)-2-methyl-4-oxobutanoate | 449, 451 |
| 85 | 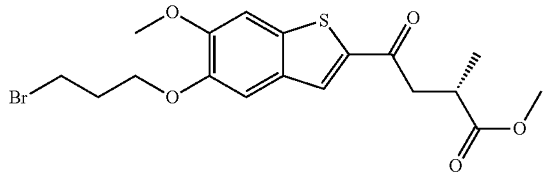 | methyl (S)-4-(5-(3-bromopropoxy)-6-methoxybenzo[b]thiophen-2-yl)-2-methyl-4-oxobutanoate | 429, 431 |
| 86 | 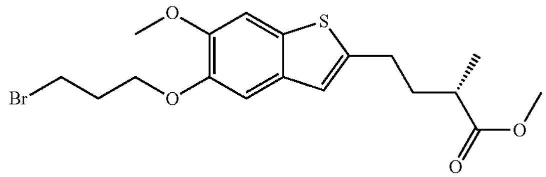 [SMILES: COC(=O)[C@@H](C)CCc1cc2cc(OCCCBr)c(OC)cc2s1] | methyl (S)-4-(5-(3-bromopropoxy)-6-methoxybenzo[b]thiophen-2-yl)-2-methylbutanoate | 415, 417 |

Intermediate 24: (S)-methyl 4-(4-fluoro-5-hydroxy-6-methoxybenzo[b]thiophen-2-yl)-2-methyl-4-oxobutanoate

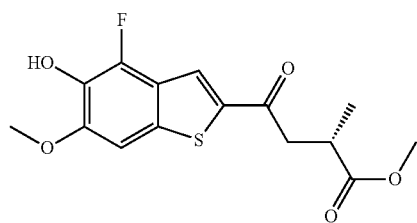

Step 1: (S)-methyl 4-(4-fluoro-5,6-dimethoxybenzo[b]thiophen-2-yl)-2-methyl-4-oxobutanoate

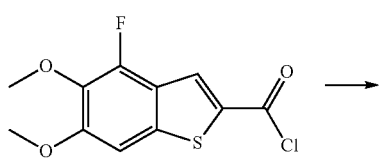

→

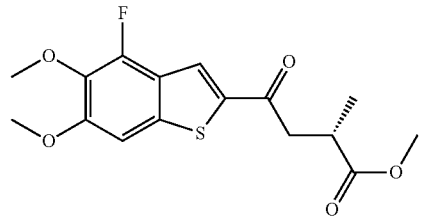

To a mixture of 4-fluoro-5,6-dimethoxybenzo[b]thiophene-2-carbonyl chloride (4.3 g, 16 mmol), C-Phos Pd G4 (0.26 g, 0.31 mmol), and THF (25 mL) was added (R)-(3-methoxy-2-methyl-3-oxopropyl)zinc(II) bromide (0.50M in THF, 25.0 mL, 12.5 mmol). The reaction was allowed to stir for 2 h at RT. The reaction was then quenched with aq sat NH₄Cl and diluted with DCM. The organic layer was separated, dried over Na₂SO₄, filtered, and concentrated under reduced pressure. The resulting residue was purified by silica gel column chromatography (0→50% EtOAc gradient in Hex) to afford (S)-methyl 4-(4-fluoro-5,6-dimethoxybenzo[b]thio phen-2-yl)-2-methyl-4-oxobutanoate. LCMS ($C_{16}H_{18}FO_5S$) (ES, m/z): 341 [M+H]+. $^1$H NMR (600 MHz, DMSO-$d_6$) δ 8.33 (s, 1H), 7.58 (s, 1H), 3.92 (s, 3H), 3.86 (s, 3H), 3.60 (s, 3H), 3.50 (dd, J=17.7, 8.7 Hz, 1H), 3.25 (dd, J=17.7, 5.0 Hz, 1H), 3.00-2.92 (m, 1H), 1.20 (d, J=7.3 Hz, 3H).

Step 2: (S)-methyl 4-(4-fluoro-5-hydroxy-6-methoxybenzo[b]thiophen-2-yl)-2-methyl-4-oxobutanoate

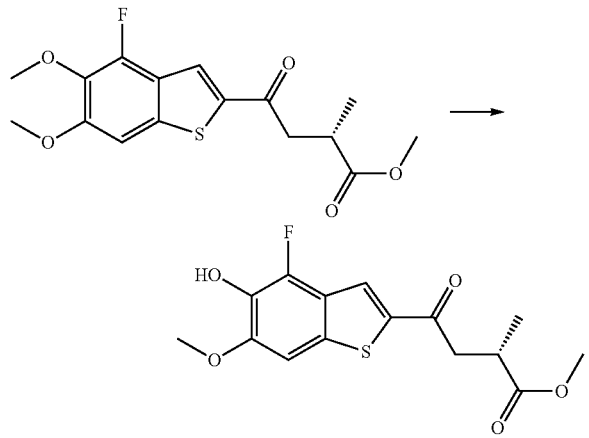

To a mixture of (S)-methyl 4-(4-fluoro-5,6-dimethoxybenzo[b]thiophen-2-yl)-2-methyl-4-oxobutanoate (4.0 g, 12 mmol), and DCM (50 mL), was added AlCl$_3$ (6.27 g, 47.0 mmol). The reaction mixture was allowed to stir at RT for 18 h. An addition funnel was then added to the reaction, and water (50 mL) was added slowly to the mixture with vigorous stirring followed by aq HCl (1N, 50 mL). The mixture was then poured into a separatory funnel, and 20% IPA/DCM was added. The organic layer was separated, dried over Na$_2$SO$_4$, filtered, and the filtrate was concentrated under reduced pressure. The resulting residue was purified by silica gel column chromatography (100% DCM) to afford (S)-methyl 4-(4-fluoro-5-hydroxy-6-methoxy benzo[b]thiophen-2-yl)-2-methyl-4-oxobutanoate. LCMS (C$_{15}$H$_{16}$FO$_5$S) (ES, m/z): 327 [M+H]+. $^1$H NMR (600 MHz, DMSO-d$_6$) δ 9.53 (s, 1H), 8.25 (s, 1H), 7.47 (s, 1H), 3.92 (s, 3H), 3.60 (s, 3H), 3.48 (dd, J=17.7, 8.7 Hz, 1H), 3.24 (dd, J=17.7, 5.0 Hz, 1H), 3.01-2.89 (m, 1H), 1.19 (d, J=7.2 Hz, 3H).

Intermediate 25: methyl (R)-4-(5-hydroxy-6-methoxybenzo[b]thiophen-2-yl)-2-methyl-4-oxobutanoate

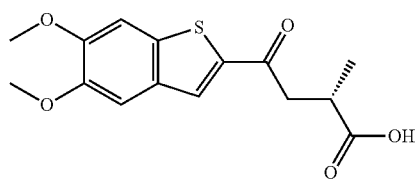 [SMILES: COc1cc2cc(C(=O)C[C@H](C)C(=O)O)sc2cc1OC]

Step 1: 5,6-Dimethoxybenzo[b]thiophene-2-carbonyl chloride

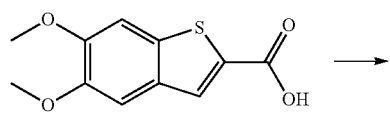

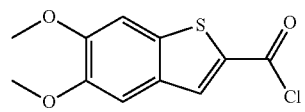

To a stirring solution of 5,6-dimethoxybenzo[b]thiophene-2-carboxylic acid (5.0 g, 21 mmol) in THF (200 mL) at 0° C. under Ar was added (COCl)$_2$ (5.5 ml, 63 mmol) followed by DMF (0.1 ml, 1.3 mmol). The reaction mixture was stirred at 0° C. for 1 h and then allowed to warm to RT and stirred overnight. The reaction mixture was concentrated under reduced pressure, and the resulting 5,6-dimethoxybenzo[b]thiophene-2-carbonyl chloride was used without purification. $^1$H NMR (600 MHz, CH$_3$CN-d$_3$): δ 8.25 (s, 1H), 7.46 (s, 1H), 7.45 (s, 1H), 3.92 (s, 3H), 3.88 (s, 3H).

Step 2: Methyl (S)-4-(5,6-dimethoxybenzo[b]thiophen-2-yl)-2-methyl-4-oxobutanoate

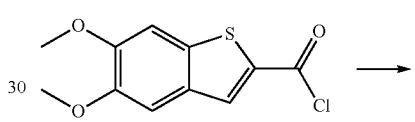

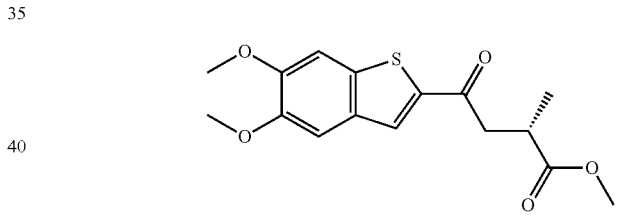

To an oven-dried, Ar-purged, round-bottomed flask containing copper (I) thiophene-2-carboxylate (797 mg, 4.2 mmol) at 0° C. was added (R)-(3-methoxy-2-methyl-3-oxopropyl)zinc(II) bromide (7.8 mL, 0.5M in THF, 3.9 mmol) dropwise. The reaction mixture was stirred at 0° C. for 20 min. A suspension of 5,6-dimethoxybenzo[b]thiophene-2-carbonyl chloride (777 mg, 3.0 mmol) in THF (15 mL) was added dropwise to the reaction mixture. The reaction mixture was allowed to warm to RT and stirred for 6 h. The reaction mixture was diluted with sat aq NH$_4$Cl solution (15 mL), followed by DCM (30 mL). Precipitates were removed by filtration prior to extraction. The layers were separated, and the aq layer was extracted with DCM (3×30 mL). The combined organic layers were concentrated under reduced pressure. The residue was purified by silica gel column chromatography ((25% EtOH in EtOAc) in Hex) to afford methyl (S)-4-(5,6-dimethoxybenzo[b]thiophen-2-yl)-2-methyl-4-oxobutanoate. LCMS (C$_{16}$H$_{19}$O$_5$S) (ES, m/z): 323 [M+H]$^+$. $^1$H NMR (500 MHz, CDCl$_3$): δ 7.89 (s, 1H), 7.26 (s, 2H), 4.00 (s, 3H), 3.97 (s, 3H), 3.72 (s, 3H), 3.48 (dd, J=16.9, 7.6 Hz, 1H), 3.22-3.16 (m, 1H), 3.05 (dd, J=16.9, 6.0 Hz, 1H), 1.31 (d, J=7.2 Hz, 3H).

Step 3: methyl (R)-4-(5-hydroxy-6-methoxybenzo[b]thiophen-2-yl)-2-methyl-4-oxobutanoate

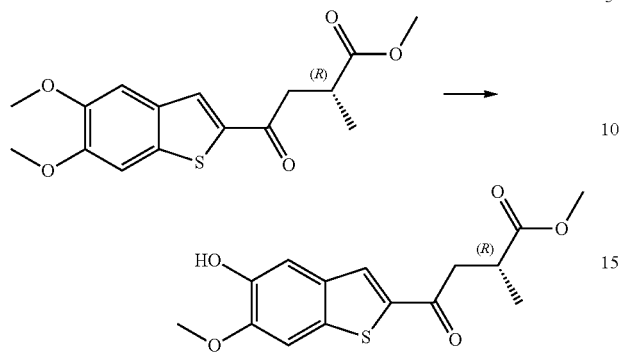

AlCl₃ (1.0 g, 7.5 mmol) was added to (R)-methyl 4-(5,6-dimethoxybenzo[b]thiophen-2-yl)-2-methyl-4-oxobutanoate (1.0 g, 3.0 mmol) in CH₂Cl₂ (40 mL) at 0° C. The reaction mixture was allowed to warm to RT for 18 h. The reaction mixture was then cooled to 0° C., and MeOH (85 mL) was added. The mixture was allowed to stir at 0° C. for 30 min. The mixture was then allowed to warm to RT and concentrated under reduced pressure. The resulting residue was purified by silica gel column chromatography (EtOAc gradient in Hex) to afford impure methyl (R)-4-(5-hydroxy-6-methoxybenzo[b]thiophen-2-yl)-2-methyl-4-oxobutanoate. The mixture was then purified by chiral-SFC (Column AD-H (21×250 mm), 30% MeOH with 0.25% DMEA in CO₂) to afford methyl (R)-4-(5-hydroxy-6-methoxybenzo[b]thiophen-2-yl)-2-methyl-4-oxobutanoate with a retention time of 4.7 min. LCMS ($C_{15}H_{17}O_5S$) (ES, m/z): 309 [M+H]⁺. ¹H NMR (DMSO-d₆) δ: 9.41 (s, 1H), 8.17 (s, 1H), 7.54 (s, 1H), 7.31 (s, 1H), 3.87 (s, 3H), 3.60 (s, 3H), 3.40 (dd, J=17.4, 8.6 Hz, 1H), 3.17 (dd, J=17.5, 5.1 Hz, 1H), 3.02-2.91 (m, 1H), 1.19 (d, J=7.1 Hz, 3H).

Intermediates 26 through 27, as shown in Table 2 below, were or may be prepared according to procedures analogous to those outlined in Intermediate 25 above using the appropriate starting materials, described as Preparations or as obtained from commercial sources.

Intermediate 28: methyl (S)-4-(5-(2-chloroethoxy)-4-fluoro-6-methoxybenzo[b]thiophen-2-yl)-2-methyl-4-oxobutanoate

Step 1: methyl (S)-4-(4-fluoro-5,6-dimethoxybenzo[b]thiophen-2-yl)-2-methyl-4-oxobutanoate

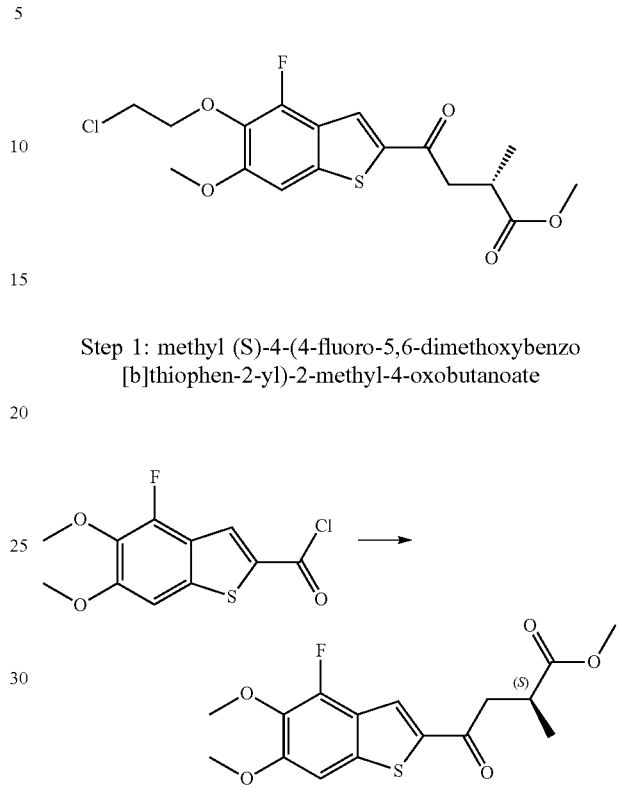

A flask containing CuCl (2.5 g, 25 mmol) was sparged with Ar and then cooled to 0° C. 3-Methoxy-(2R)-(+)-methyl-3-oxopropylzinc bromide (0.50M in THF, 50 mL, 25 mmol) was added dropwise. A mixture of 4-fluoro-5,6-dimethoxybenzo[b]thiophene-2-carbonyl chloride (5.0 g, 20 mmol) in THF (25 mL) and NMP (25 mL) was added dropwise to the stirring reaction mixture. The reaction mixture was then allowed to warm to RT for 18 h. The reaction mixture was then quenched with sat aq NH₄Cl (100

TABLE 2

| Intermediate | Structure | Name | Mass [M + H]⁺ |
|---|---|---|---|
| 26 | 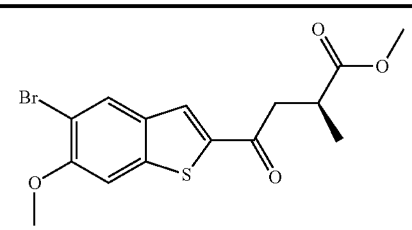 | methyl (S)-4-(5-bromo-6-methoxybenzo[b]thiophen-2-yl)-2-methyl-4-oxobutanoate | 371, 373 |
| 27 |  | methyl (S)-4-(5-hydroxy-6-methoxybenzo[b]thiophen-2-yl)-2-methyl-4-oxobutanoate | 309 | mL) and extracted with EtOAc (3×100 mL). The combined organics were dried over MgSO₄, filtered, and concentrated under reduced pressure. The resulting residue was purified by normal phase silica column chromatography (EtOAc in Hex) to afford (S)-methyl 4-(4-fluoro-5,6-dimethoxybenzo[b]thiophen-2-yl)-2-methyl-4-oxobutanoate. LCMS ($C_{16}H_{18}FO_5S$) (ES, m/z): 341 [M+H]⁺. ¹H NMR (CDCl₃) δ: 7.99 (s, 1H), 7.09 (s, 1H), 4.00 (s, 3H), 3.98 (s, 3H), 3.73 (s, 3H), 3.51 (dd, J=17.0, 7.9 Hz, 1H), 3.24-3.12 (m, 1H), 3.06 (dd, J=17.0, 5.6 Hz, 1H), 1.32 (d, J=7.1 Hz, 3H).

Step 2: (S)-methyl 4-(4-fluoro-5-hydroxy-6-methoxybenzo[b]thiophen-2-yl)-2-methyl-4-oxobutanoate

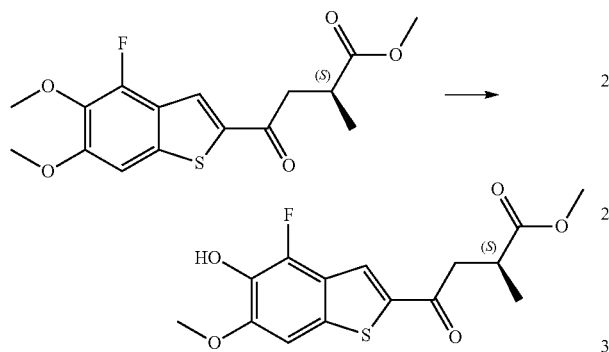

To a mixture of methyl (S)-4-(4-fluoro-5,6-dimethoxybenzo[b]thiophen-2-yl)-2-methyl-4-oxobutanoate (1.0 g, 2.9 mmol) and CH=CCl₂ (40 mL) was added AlCl₃ (1.0 g, 7.5 mmol). The reaction mixture was allowed to stir at RT for 18 h. The reaction mixture was then cooled to 0° C. and diluted with MeOH (40 mL). The mixture was then allowed to warm to RT and then concentrated under reduced pressure. The resulting residue was purified by silica gel column chromatography (EtOAc in Hex) to afford (S)-methyl 4-(4-fluoro-5-hydroxy-6-methoxybenzo[b]thiophen-2-yl)-2-methyl-4-oxobutanoate. LCMS ($C_{15}H_{16}FO_5S$) (ES, m/z): 327 [M+H]⁺. ¹H NMR (methanol-d₄) δ: 8.11 (s, 1H), 7.29 (s, 1H), 3.98 (s, 3H), 3.69 (s, 3H), 3.50 (dd, J=17.5, 8.6 Hz, 1H), 3.23-3.16 (m, 1H), 3.11-3.02 (m, 1H), 1.28 (d, J=7.2 Hz, 3H).

Step 3: methyl (S)-4-(5-(2-chloroethoxy)-4-fluoro-6-methoxybenzo[b]thiophen-2-yl)-2-methyl-4-oxobutanoate

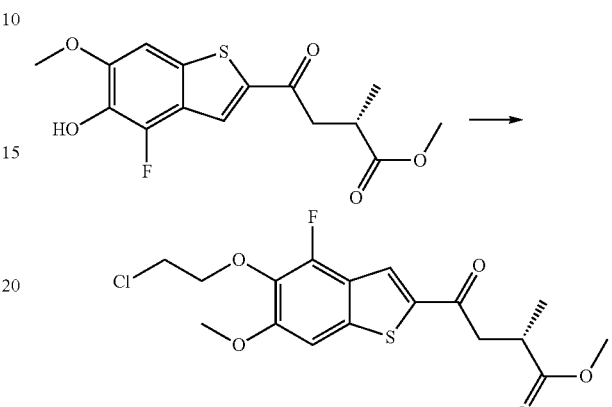

K₂CO₃ (170 mg, 1.2 mmol) was added to a stirring mixture of(S)-methyl 4-(4-fluoro-5-hydroxy-6-methoxybenzo[b]thiophen-2-yl)-2-methyl-4-oxobutanoate (200 mg, 0.61 mmol) and DMF (2.7 mL). 1-Bromo-2-chloroethane (50 µL, 0.6 mmol) was added to the stirring reaction mixture, and the reaction mixture was then heated to 80° C. for 18 h. Upon cooling to RT, the reaction mixture was concentrated under reduced pressure. The resulting residue was purified by silica gel column chromatography (EtOAc in Hex) to afford methyl (S)-4-(5-(2-chloroethoxy)-4-fluoro-6-methoxybenzo[b]thiophen-2-yl)-2-methyl-4-oxobutanoate. LCMS ($C_{17}H_{19}ClFO_5S$) (ES, m/z): 389 [M+H]⁺.

Intermediates 29 through 31 and 87, as shown in Table 3 below, were or may be prepared according to procedures analogous to those outlined in Intermediate 28 above using the appropriate starting materials, described as Preparations or as obtained from commercial sources.

TABLE 3

| Intermediate | Structure | Name | Mass [M + H]⁺ |
|---|---|---|---|
| 29 | 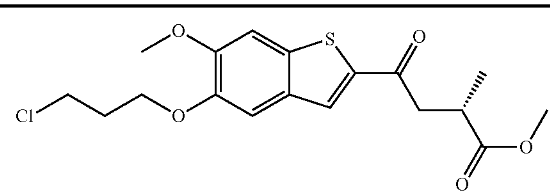 | methyl (S)-4-(5-(3-chloropropoxy)-6-methoxybenzo[b]thiophen-2-yl)-2-methyl-4-oxobutanoate | 385 |
| 30 | 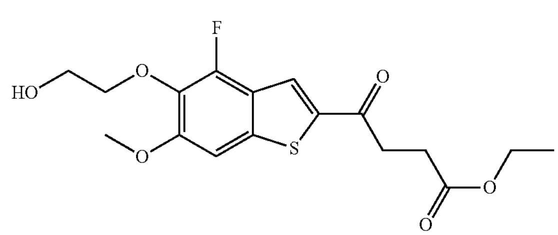 [SMILES: CCOC(=O)CCC(=O)c1cc2c(F)c(OCCO)c(OC)cc2s1] | ethyl 4-(4-fluoro-5-(2-hydroxyethoxy)-6-methoxybenzo[b]thiophen-2-yl)-4-oxobutanoate | 371 |

TABLE 3-continued

| Intermediate | Structure | Name | Mass [M + H]+ |
|---|---|---|---|
| 31 | 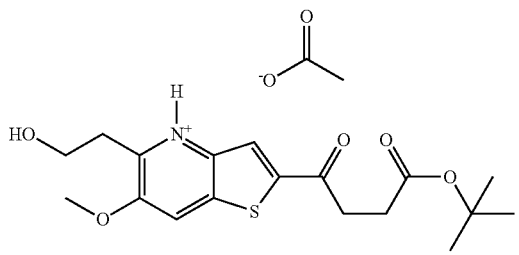 | methyl (S)-4-(6-(2-hydroxyethoxy)-5-methoxybenzo[b]thiophen-2-yl)-2-methyl-4-oxobutanoate | 353 |
| 87 | 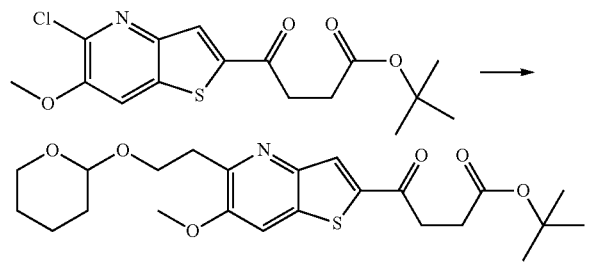 | methyl 4-(5-(3-chloro-propoxy)-4-fluoro-6-methoxybenzo[b]thiophen-2-yl)-2,2-dimethyl-4-oxobutanoate | 417 |

Intermediate 32: tert-butyl 4-(5-(2-hydroxyethyl)-6-methoxythieno[3,2-b]pyridin-2-yl)-4-oxobutanoate, acetate salt

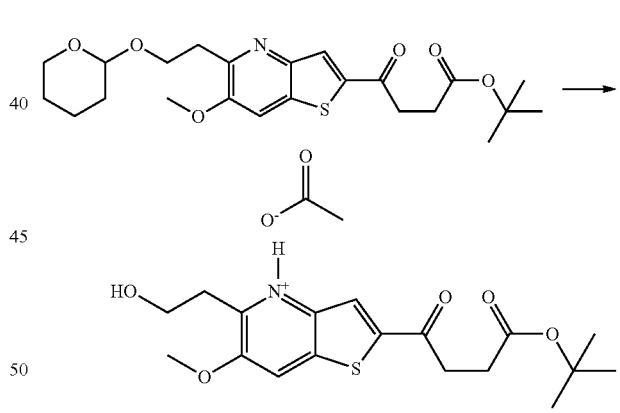

Step 1: tert-butyl 4-(6-methoxy-5-(2-((tetrahydro-2H-pyran-2-yl)oxy)ethyl)thieno[3,2-b]pyridin-2-yl)-4-oxobutanoate To a 4 mL vial was added bis(di-tert-butyl(4-dimethylaminophenyl)phosphine) dichloro-palladium(II) (5.0 mg, 7.0 µmol), $Cs_2CO_3$ (137 mg, 0.422 mmol), tert-butyl 4-(5-chloro-6-methoxythieno[3,2-b]pyridin-2-yl)-4-oxobutanoate (50.0 mg, 0.141 mmol), and potassium trifluoro(2-((tetrahydro-2H-pyran-2-yl)oxy)ethyl)borate (39.8 mg, 0.169 mmol). To the vial was added toluene (0.50 mL) and water (0.10 mL). The vial was degassed with $N_2$ for 5 min. The mixture was heated to 100° C. for 18 h. Upon cooling to RT, the mixture was filtered through CELITE, and the CELITE was washed with EtOAc. The filtrate was concentrated under reduced pressure, and the resulting residue was purified by silica gel chromatography (0→75% EtOAc gradient in Hex) to afford tert-butyl 4-(6-methoxy-5-(2-((tetrahydro-2H-pyran-2-yl)oxy) ethyl)thieno[3,2-b]pyridin-2-yl)-4-oxobutanoate. LCMS ($C_{23}H_{32}NO_6S$) (ES, m/z): 450 [M+H]+. $^1$H NMR (500 MHz, $CDCl_3$) δ 8.45 (s, 1H), 7.80 (s, 1H), 4.71 (s, 1H), 4.26-4.15 (m, 1H), 4.04 (s, 3H), 3.78 (t, J=8.3 Hz, 1H), 3.65-3.42 (m, 4H), 3.33 (t, J=6.3 Hz, 2H), 2.73 (t, J=6.3 Hz, 2H), 1.64-1.48 (m, 6H), 1.46 (s, 9H).

Step 2: tert-butyl 4-(5-(2-hydroxyethyl)-6-methoxythieno[3,2-b]pyridin-2-yl)-4-oxobutanoate, acetate salt To a 4 mL vial was added tert-butyl 4-(6-methoxy-5-(2-((tetrahydro-2H-pyran-2-yl)oxy)ethyl)-thieno[3,2-b]pyridin-2-yl)-4-oxobutanoate (28 mg, 0.062 mmol), HOAc (0.50 mL), MeOH (0.50 mL), and water (0.5 mL). The mixture was heated to 50° C. for 75 min. Upon cooling to RT, the mixture was diluted with EtOAc (30 mL) and washed with water (2×30 mL). The organic layer was dried over $Na_2SO_4$, filtered, and concentrated under reduced pressure to afford tert-butyl 4-(5-(2-hydroxyethyl)-6-methoxythieno[3,2-b]pyridin-2-yl)-4-oxobutanoate, acetate salt. LCMS ($C_{18}H_{24}NO_5S$) (ES, m/z): 366 [M+H]+. $^1$H NMR (500 MHz, $CDCl_3$) δ 8.22 (s, 1H), 7.68 (s, 1H), 4.13 (t, J=5.4 Hz, 2H), 4.01 (s, 3H), 3.39-3.22 (m, 4H), 2.74 (t, J=6.5 Hz, 2H), 1.46 (s, 9H).

Intermediate 33: tert-butyl 4-(5-(3-hydroxypropyl)benzo[b]thiophen-2-yl)-4-oxobutanoate

Step 1: tert-butyl 4-(5-(3-((tert-butyldimethylsilyl)oxy)propyl)benzo[b]thiophen-2-yl)-4-oxobutanoate

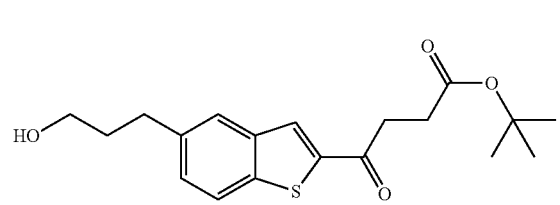 [SMILES: CC(C)(C)OC(=O)CCC(=O)c1cc2cc(CCCO)ccc2s1]

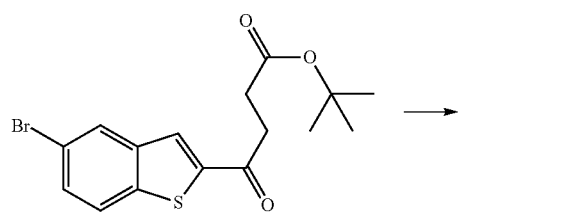

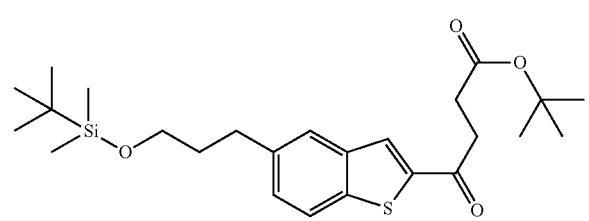

tert-Butyl 4-(5-bromobenzo[b]thiophen-2-yl)-4-oxobutanoate (0.207 g, 0.561 mmol) and chloro(2-dicyclohexylphosphino-2',4',6'-triisopropyl-1,1'-biphenyl)[2-(2'-amino-1,1'-biphenyl)]palladium(II) (0.022 g, 0.028 mmol) were placed in a 20 mL screw cap vial with a magnetic stir bar. The vial was evacuated and backfilled with $N_2$ 3 times. The vial was capped with a $N_2$ inlet and then THF (2.0 mL) was added. (3-((tert-butyldimethylsilyl)oxy)propyl) zinc(II) bromide (0.50M in THF, 3.4 mL, 1.7 mmol) was added dropwise with stirring. After the addition was complete, the reaction was stirred at RT under $N_2$ for 1.5 h. The reaction was then partitioned between EtOAc (50 mL) and 10% aqueous sodium citrate (10 mL) and stirred for 30 min. The layers were then separated, and the organic layer was washed with sat aq NaCl, dried over anhydrous $MgSO_4$, filtered and concentrated under reduced pressure. The resulting residue was purified by silica gel chromatography (0→55% EtOAc gradient in Hex) to afford tert-butyl 4-(5-(3-((tert-butyldimethylsilyl)oxy)propyl)benzo[b]thiophen-2-yl)-4-oxobutanoate. LCMS ($C_{25}H_{38}NaO_4SSi$) (ES, m/z): 485 [M+Na]$^+$. $^1$H NMR (500 MHz, CDCl$_3$) δ 7.96 (s, 1H), 7.78 (d, J=8.2 Hz, 1H), 7.70 (s, 1H), 7.33 (d, J=8.2 Hz, 1H), 3.66 (t, J=5.8 Hz, 2H), 3.31 (t, J=6.5 Hz, 2H), 2.82 (t, J=7.5 Hz, 2H), 2.73 (t, J=6.5 Hz, 2H), 1.93-1.86 (m, 2H), 1.47 (s, 9H), 0.94 (s, 9H), 0.08 (s, 6H).

Step 2: tert-butyl 4-(5-(3-hydroxypropyl)benzo[b]thiophen-2-yl)-4-oxobutanoate

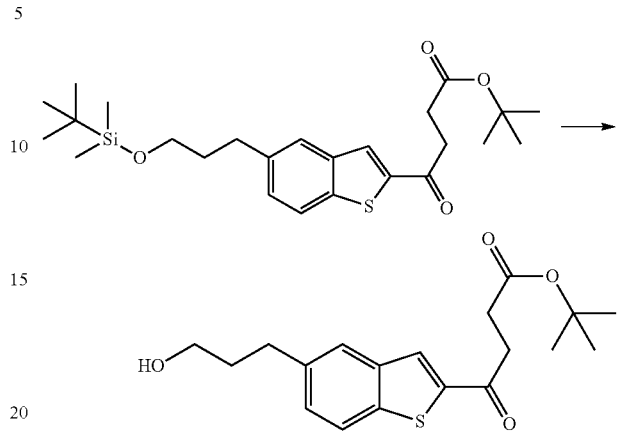

TBAF (1.0M in THF, 0.44 mL, 0.44 mmol) was added to a stirred mixture of tert-butyl 4-(5-(3-((tert-butyldimethylsilyl)oxy)propyl)benzo[b]thiophen-2-yl)-4-oxobutanoate (102 mg, 0.220 mmol) in THF (1.3 mL) at RT under $N_2$. The resulting mixture was stirred at RT for 4.5 h. The reaction was then partitioned between $Et_2O$ and sat aq $NH_4Cl$ and stirred at RT for 1 h. The layers were separated, and the organic layer was washed with sat aq NaCl, dried over anhydrous $MgSO_4$, filtered and concentrated under reduced pressure to afford a crude residue. The resulting residue was purified by silica gel chromatography (0→60% EtOAc gradient in Hex) to afford tert-butyl 4-(5-(3-hydroxypropyl)benzo[b]thiophen-2-yl)-4-oxobutanoate. LCMS ($C_{19}H_{24}NaO_4S$) (ES, m/z): 371 [M+Na]$^+$. $^1$H NMR (500 MHz, CDCl$_3$) δ 7.95 (s, 1H), 7.77 (d, J=8.3 Hz, 1H), 7.70 (s, 1H), 7.33 (d, J=8.3 Hz, 1H), 3.71 (t, J=6.3 Hz, 2H), 3.30 (t, J=6.7 Hz, 2H), 2.84 (t, J=7.7 Hz, 2H), 2.72 (t, J=6.7 Hz, 2H), 1.98-1.91 (m, 2H), 1.46 (s, 9H).

Intermediate 34: (S)-methyl 4-(4-fluoro-5-(3-hydroxypropoxy)-6-methoxybenzo[b]thiophen-2-yl)-2-methyl-4-oxobutanoate

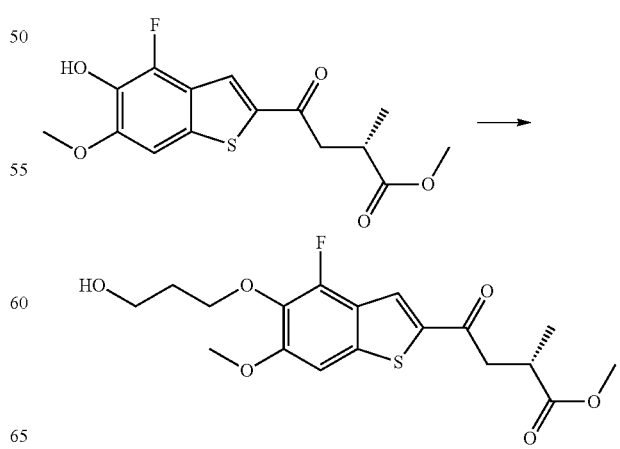

To a mixture of (S)-methyl 4-(4-fluoro-5-hydroxy-6-methoxybenzo[b]thiophen-2-yl)-2-methyl-4-oxobutanoate (0.065 g, 0.2 mmol) and Cs$_2$CO$_3$ (0.33 g, 1.0 mmol) in ACN (2.0 mL) was added (3-bromopropoxy)(tert-butyl)dimethylsilane (0.10 mL, 0.20 mmol). The reaction was then heated to 65° C. for 2 h. Upon cooling to RT, the mixture was then filtered and washed with THF (5 mL). Water (2 mL) was added to the resulting filtrate followed by MP-TsOH (4.38 mmol/g loading, 1.00 g, 4.38 mmol). The mixture was then heated to 60° C. for 30 min. Upon cooling to RT, the mixture was filtered and washed with THF. The filtrate was concentrated under reduced pressure to afford (S)-methyl 4-(4-fluoro-5-(3-hydroxypropoxy)-6-methoxybenzo[b]thiophen-2-yl)-2-methyl-4-oxobutanoate that was used without further purification. LCMS (C$_{18}$H$_{22}$FO$_6$S) (ES, m/z): 385 [M+H]+.

Intermediates 35 through 36, as shown in Table 4 below, were or may be prepared according to procedures analogous to those outlined in Intermediate 34 above using the appropriate starting materials, described as Preparations or as obtained from commercial sources.

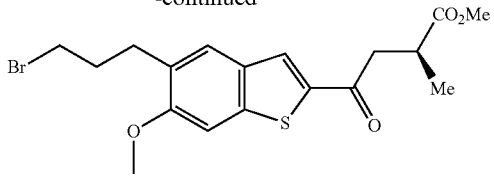

To the stirred mixture of methyl (2S)-4-[5-(3-hydroxypropyl)-6-methoxy-1-benzothiophen-2-yl]-2-methyl-4-oxobutanoate (187 mg, 0.534 mmol) and Ph$_3$P (224 mg, 0.854 mmol) in THF (2.7 mL) at 0° C. was added NBS (142 mg, 0.800 mmol) in one portion under N$_2$. The reaction mixture was stirred for 20 min at 0° C. The mixture was directly purified by silica gel flash column chromatography (EtOAc in Hex) to afford methyl (2S)-4-[5-(3-bromopropyl)-6-methoxy-1-benzothiophen-2-yl]-2-methyl-4-oxobutanoate. LCMS (C$_{18}$H$_{22}$BrO$_4$S) (ES, m/z): 413, 415 [M+H] V. $^1$H NMR (500 MHz, DMSO-d$_6$): δ 8.27 (s, 1H), 7.76 (s, 1H), 7.62 (s, 1H), 3.89 (s, 3H), 3.59 (s, 3H), 3.54 (t, J=6.8 Hz, 2H), 3.43 (dd, J=17.5, 8.6 Hz, 1H), 3.19 (dd, J=17.5, 5.0 Hz, 1H), 3.02-2.92 (m, 1H), 2.79 (t, J=7.0 Hz, 2H), 2.10 (pentet, J=6.9 Hz, 2H), 1.19 (d, J=7.1 Hz, 3H).

Intermediate 38: tert-butyl 4-(5-(3-hydroxypropoxy)-6-methoxythieno[3,2-b]pyridin-2-yl)-4-oxobutanoate

TABLE 4

| Intermediate | Structure | Name | Mass [M + H]$^+$ |
|---|---|---|---|
| 35 | ![structure] | ethyl 4-(4-fluoro-5-(3-hydroxypropoxy)-6-methoxybenzo[b]thiophen-2-yl)-4-oxobutanoate | 385 |
| 36 | ![structure] | methyl (S)-4-(4-fluoro-5-(2-hydroxyethoxy)-6-methoxybenzo[b]thiophen-2-yl)-2-methyl-4-oxobutanoate | 371 |

Intermediate 37: methyl (2S)-4-[5-(3-bromopropyl)-6-methoxy-1-benzothiophen-2-yl]-2-methyl-4-oxobutanoate

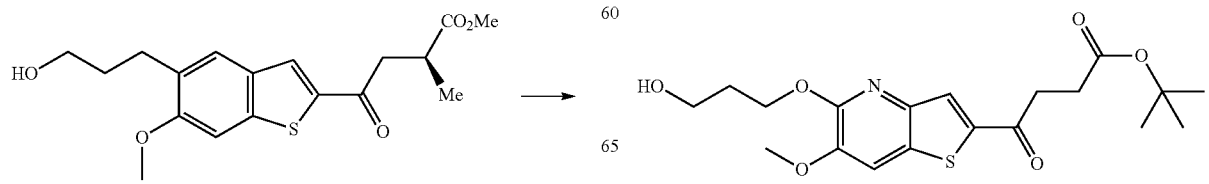

265

Step 1: tert-butyl 4-(5-(3-((tert-butyldimethylsilyl)oxy)propoxy)-6-methoxythieno[3,2-b]pyridin-2-yl)-4-oxobutanoate

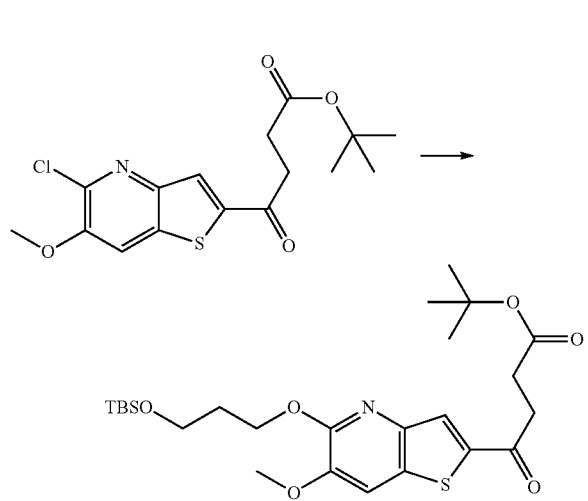

tert-Butyl 4-(5-chloro-6-methoxythieno[3,2-b]pyridin-2-yl)-4-oxobutanoate (265 mg, 0.745 mmol), 3-((tert-butyldimethylsilyl)oxy)propan-1-ol (156 mg, 0.819 mmol), RockPhos Pd G3 (31 mg, 0.037 mmol) and $Cs_2CO_3$ (364 mg, 1.12 mmol) were added to a 20 mL screw-cap vial with a magnetic stir bar. The vial was capped, and a $N_2$ inlet needle was inserted. Via this needle, the vial was evacuated and backfilled with $N_2$ three times. Under $N_2$, toluene (2.5 mL) was added, the $N_2$ inlet was removed, and the sealed vial was heated to 110° C. for 18 h. The reaction was allowed to cool to RT, and MeOH (3.0 mL), water (3.0 mL) and HOAc (3.0 mL) were added. The reaction mixture was stirred for 7 h at RT, then partitioned between EtOAc and sat aq NaCl. The layers were separated, and the aqueous layer was extracted with EtOAc. The organic layers were combined, washed with aq NaCl, dried over anhydrous $Na_2SO_4$, filtered, and concentrated under reduced pressure afford a crude residue. The residue was purified by silica gel chromatography (0→100% 3:1 EtOAc:EtOH gradient in Hex) to afford tert-butyl 4-(5-(3-((tert-butyldimethylsilyl)oxy)propoxy)-6-methoxythieno [3,2-b]pyridin-2-yl)-4-oxobutanoate. LCMS ($C_{25}H_{40}NO_6SSi$) (ES, m/z): 510 [M+H]$^+$. $^1$H NMR (500 MHz, $CDCl_3$) δ 7.95 (s, 1H), 7.39 (s, 1H), 4.56 (t, J=6.5 Hz, 2H), 3.94 (s, 3H), 3.83 (t, J=6.0 Hz, 2H), 3.26 (t, J=6.7 Hz, 2H), 2.70 (t, J=6.7 Hz, 2H), 2.12-2.05 (m, 2H), 1.44 (s, 9H), 0.89 (s, 9H), 0.07 (s, 6H).

266

Step 2: tert-butyl 4-(5-(3-hydroxypropoxy)-6-methoxythieno[3,2-b]pyridin-2-yl)-4-oxobutanoate

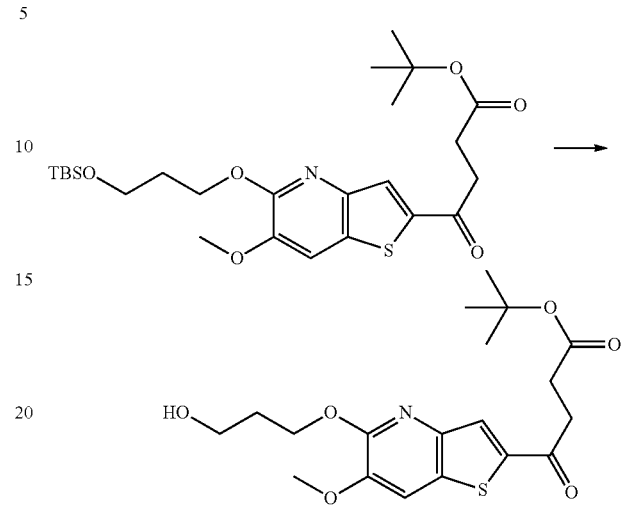

To a vial containing tert-Butyl 4-(5-(3-((tert-butyldimethylsilyl)oxy)propoxy)-6-methoxythieno[3,2-b]pyridin-2-yl)-4-oxobutanoate (83 mg, 0.16 mmol) was added MeOH (1.0 mL), water (1.0 mL) and then HOAc (1.0 mL). The resulting mixture was stirred for 30 min at RT. MeOH (1.0 mL) was added and stirring was continued. After 30 min, THF (1.0 mL) was added, and the mixture was allowed to stir for 18 h at RT. The mixture was partitioned between EtOAc (25 mL) and aq NaCl (25 mL) and stirred. The layers were separated, and the aqueous layer was extracted with EtOAc. The organic layers were combined, washed with sat aq NaCl twice, dried over anhydrous $Na_2SO_4$, filtered, and concentrated under reduced pressure to afford a crude residue. The resulting residue was purified by silica gel chromatography (0→100% EtOAc gradient in Hex, then isocratic at 100% EtOAc) to afford tert-butyl 4-(5-(3-hydroxypropoxy)-6-methoxythieno[3,2-b]pyridin-2-yl)-4-oxobutanoate. LCMS ($C_{19}H_{26}NO_6S$) (ES, m/z): 396 [M+H]$^+$. $^1$H NMR (500 MHz, $CDCl_3$) δ 7.93 (s, 1H), 7.44 (s, 1H), 4.69 (t, J=5.6 Hz, 2H), 3.97 (s, 3H), 3.80-3.76 (m, 2H), 3.31-3.20 (m, 2H), 2.71 (t, J=6.5 Hz, 2H), 2.14-2.07 (m, 2H), 1.46 (s, 9H).

Intermediate 39, as shown in Table 5 below, was or may be prepared according to procedures analogous to those outlined in Intermediate 38 above using the appropriate starting materials, described as Preparations or as obtained from commercial sources.

TABLE 5

| Intermediate | Structure | Name | Mass [M + H]$^+$ |
|---|---|---|---|
| 39 | ![structure] | methyl (S)-4-(5-(3-hydroxypropoxy)-6-methoxybenzo[b]thiophen-2-yl)-2-methyl-4-oxobutanoate | 367 |

Intermediate 40: Methyl 4-(6-hydroxybenzo[b]thiophen-2-yl)-4-oxobutanoate

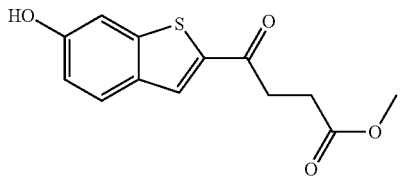 [SMILES: COC(=O)CCC(=O)c1cc2ccc(O)cc2s1]

Step 1: 6-(Benzyloxy)benzo[b]thiophene

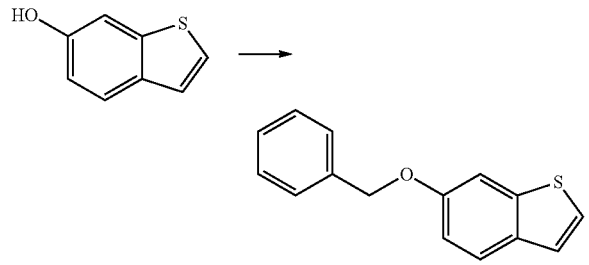

K$_2$CO$_3$ (2.62 g, 19.0 mmol) was added to a mixture of benzo[b]thiophen-6-ol (1.9 g, 13 mmol) and benzyl bromide (1.51 mL, 12.7 mmol) in DMF (10.0 mL) at 20° C. under Ar. The reaction mixture was stirred and heated to 50° C. for 18 h. Upon cooling to RT, the reaction mixture was then diluted with EtOAc (500 mL) and water (100 mL). The organic layer was separated, washed with water (50 mL) and then sat aq NaCl (50 mL), dried over MgSO$_4$, filtered, and concentrated under reduced pressure to afford the crude product residue. The crude product residue was purified by silica gel chromatography (0→100% EtOAc gradient in Hex) to afford 6-(benzyloxy)benzo[b]thiophene. LCMS (C$_{15}$H$_{13}$OS) (ES, m/z): 241 [M+H]$^+$. $^1$H NMR (500 MHz, DMSO-d$_6$) δ 7.77 (d, J=8.6 Hz, 1H), 7.67 (s, 1H), 7.54 (d, J=5.2 Hz, 1H), 7.49 (d, J=7.2 Hz, 2H), 7.44-7.38 (m, 2H), 7.37-7.32 (m, 2H), 7.08 (d, J=8.5 Hz, 1H), 5.17 (s, 2H).

Step 2: 6-(Benzyloxy)benzo[b]thiophene-2-carbaldehyde

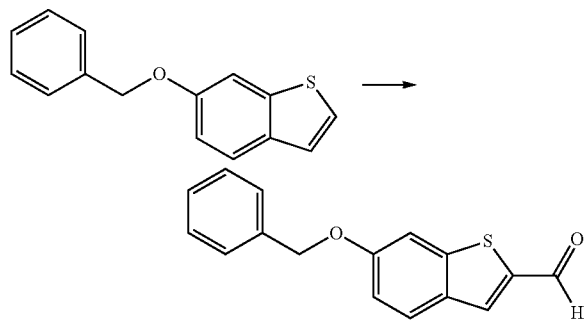

LDA (2.0M in THF, 7.3 mL, 15 mmol) was added to a mixture of 6-(benzyloxy) benzo[b]thiophene (2.92 g, 12.2 mmol) in THF (10.0 mL) at −78° C. under Ar. The reaction mixture was stirred at −78° C. for 20 min. DMF (2.4 mL, 30 mmol) was added to the reaction mixture at −78° C., and the reaction mixture was then allowed to warm slowly to RT. The reaction mixture was stirred for 15 min at RT. The reaction mixture was quenched with citric acid (1.0M in water, 24 mL, 24 mmol) at 0° C. and then diluted with EtOAc (200 mL). The suspension was stirred for 15 min. The organic layer was separated, dried over MgSO$_4$, filtered, and concentrated under reduced pressure to afford the crude residue. The crude residue was purified by silica gel chromatography (0→100% EtOAc gradient in Hex) to afford 6-(benzyloxy)benzo [b]thiophene-2-carbaldehyde. LCMS (C$_{16}$H$_{13}$O$_2$S) (ES, m/z): 269 [M+H]$^+$. $^1$H NMR (500 MHz, DMSO-d$_6$) δ 10.05 (s, 1H), 8.34 (s, 1H), 8.01 (d, J=8.8 Hz, 1H), 7.78 (s, 1H), 7.50 (d, J=7.3 Hz, 2H), 7.42 (t, J=7.3 Hz, 2H), 7.40-7.33 (m, 1H), 7.20 (d, J=8.4 Hz, 1H), 5.23 (s, 2H).

Step 3: tert-Butyl 4-(6-(benzyloxy)benzo[b]thiophen-2-yl)-4-oxobutanoate

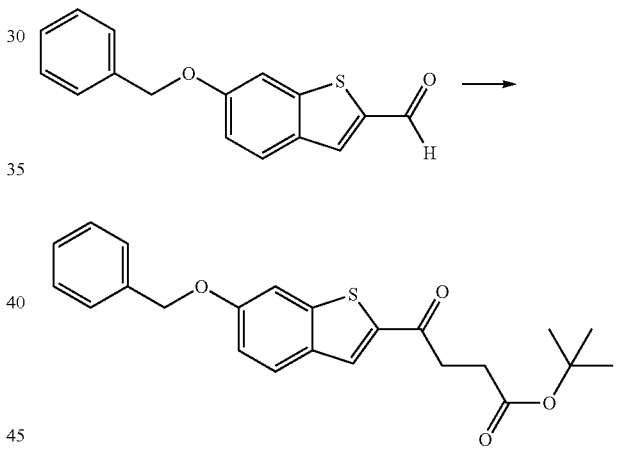

A mixture of 6-(benzyloxy)benzo[b]thiophene-2-carbaldehyde (2.02 g, 7.53 mmol), 2-mesityl-6,7-dihydro-5H-pyrrolo[2,1-c][1,2,4]triazol-2-ium chloride (0.099 g, 0.38 mmol), and potassium phosphate tribasic (1.6 g, 7.5 mmol) was flushed with Ar for 5 min at 20° C. Toluene (15 mL) and tert-butyl acrylate (2.2 mL, 15 mmol) were then added at 20° C. The reaction mixture was allowed to stir for 18 h at 20° C. The reaction mixture was then diluted with EtOAc (200 mL) and filtered to remove inorganic salts. The filtrate was concentrated under reduced pressure to afford the crude product residue. The crude product residue was purified by silica gel chromatography (0→100% EtOAc gradient in Hex) to afford tert-butyl 4-(6-(benzyl oxy)benzo[b]thiophen-2-yl)-4-oxobutanoate. LCMS (C$_{23}$H$_{25}$O$_4$S) (ES, m/z): 397 [M+H]$^+$. $^1$H NMR (500 MHz, DMSO-d$_6$) δ 8.35 (s, 1H), 7.96 (d, J=7.0 Hz, 1H), 7.75 (s, 1H), 7.56-7.39 (m, 2H), 7.47-7.33 (m, 3H), 7.25-7.15 (m, 1H), 5.24 (s, 2H), 3.34-3.23 (m, 2H), 2.65-2.55 (m, 2H), 1.40 (s, 9H).

Step 4: 4-(6-Hydroxybenzo[b]thiophen-2-yl)-4-oxobutanoic acid

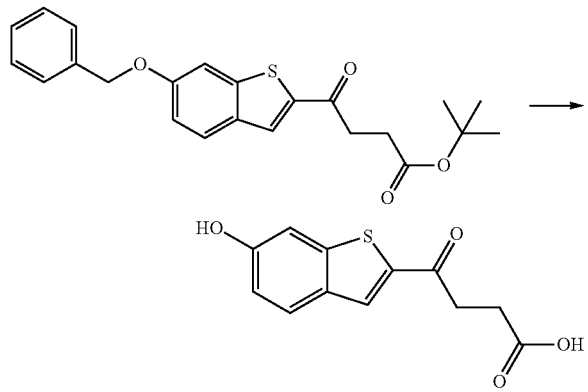

HCl (37% in water, 19.6 mL, 238 mmol) was added to a mixture of tert-butyl 4-(6-(benzyloxy)benzo[b]thiophen-2-yl)-4-oxobutanoate (2.36 g, 5.96 mmol) in dioxane (100 mL). The reaction mixture heated to 90° C. for 2 days. The reaction mixture was cooled to RT and diluted with EtOAc (500 mL). The organic layer was separated, washed with water (3×100 mL) and then sat aq NaCl (50 mL), dried over MgSO$_4$, filtered, and concentrated under reduced pressure to afford 4-(6-hydroxybenzo[b]thiophen-2-yl)-4-oxobutanoic acid, which was used without further purification. LCMS ($C_{12}H_{11}O_4S$) (ES, m/z): 251 [M+H]$^+$.

Step 5: Methyl 4-(6-hydroxybenzo[b]thiophen-2-yl)-4-oxobutanoate

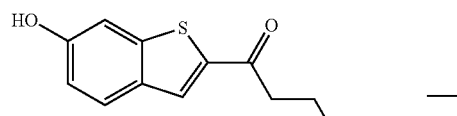

TMS-diazomethane (2.0M in Hex, 3.0 mL, 6.0 mmol) was added to a mixture of 4-(6-hydroxybenzo[b]thiophen-2-yl)-4-oxobutanoic acid (1.5 g, 6.0 mmol) in DCM (25 mL) and MeOH (25 mL) at 0° C. The reaction mixture was stirred at 0° C. for 15 min (until gas evolution ceased). HOAc (several drops) was added to quench any remaining TMS-diazomethane. The reaction mixture was then concentrated under reduced pressure to afford the crude product residue. The crude product residue was purified by silica gel chromatography (0→100% EtOAc gradient in Hex) to afford methyl 4-(6-hydroxybenzo[b]thiophen-2-yl)-4-oxobutanoate. LCMS ($C_{13}H_{13}O_4S$) (ES, m/z): 265 [M+H]$^+$. $^1$H NMR (500 MHz, DMSO-$d_6$) δ 10.17 (s, 1H), 8.26 (s, 1H), 7.84 (d, J=8.7 Hz, 1H), 7.30 (s, 1H), 6.97 (d, J=8.2 Hz, 1H), 3.76-3.65 (m, 1H), 3.60 (s, 3H), 3.54-3.44 (m, 1H), 2.72-2.67 (m, 2H).

Intermediate 41, as shown in Table 6 below, was or may be prepared according to procedures analogous to those outlined in Intermediate 40 above using the appropriate starting materials, described as Preparations or as obtained from commercial sources.

TABLE 6

| Intermediate | Structure | Name | Mass [M + H]$^+$ |
|---|---|---|---|
| 41 | 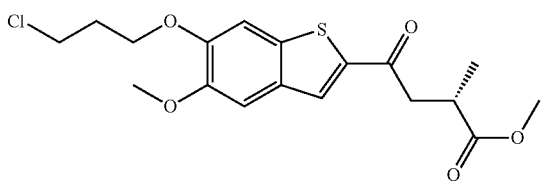 [SMILES: COC(=O)[C@@H](C)CC(=O)c1cc2cc(OC)c(OCCCCl)cc2s1] | 5-(benzyloxy)benzo[b]thiophene-2-carbaldehyde | 269 |

Intermediate 42: Methyl (S)-4-(6-(3-chloropropoxy)-5-methoxybenzo[b]thiophen-2-yl)-2-methyl-4-oxobutanoate

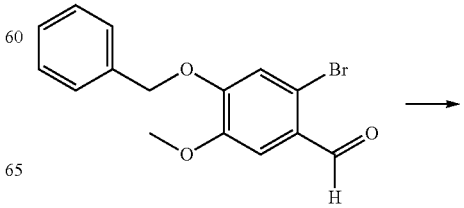

Step 1: 6-(Benzyloxy)-5-methoxybenzo[b]thiophene-2-carboxylic acid

-continued

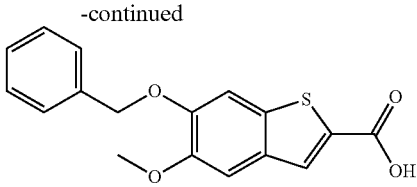

A mixture of 4-(benzyloxy)-2-bromo-5-methoxybenzaldehyde (13 g, 41 mmol), $K_2CO_3$ (11 g, 81 mmol), 18-Crown-6 (2.1 g, 8.1 mmol) and methyl 2-mercaptoacetate (6.0 mL, 67 mmol) in DMF (150 mL) was heated to 90° C. under Ar for 14 h. Upon cooling to RT, the reaction mixture was quenched with water (400 mL), acidified with 1N HCl to pH~5, and extracted with EtOAc (3×250 mL). The combined organic layers were washed with 10% aq LiCl (3×50 mL), dried over anhydrous $Na_2SO_4$, filtered, and concentrated under reduced. The residue was diluted with EtOAc/MeOH (50 mL/50 mL) and treated with aq LiOH (2.0M, 80 mL, 160 mmol) at 20° C. The reaction mixture was heated to 60° C. for 2 h. Upon cooling to RT, the mixture was concentrated under reduced pressure. The residue was diluted with aq NaOH (1.0M, 50 mL, 50 mmol), water (300 mL), and EtOAc (300 mL). The layers were separated, and the aqueous layer was washed with EtOAc (3×200 mL). The aqueous layer was then acidified with 6N HCl to pH~5, and extracted with EtOAc (3×300 mL). The organics were combined, washed with sat aq NaCl (50 mL), dried over anhydrous $Na_2SO_4$, filtered, and concentrated under reduced pressure. The residue was triturated with 1:1 EtOAc/PE (3×30 mL) and 1:1 DCM/PE (3×30 mL) to afford 6-(benzyloxy)-5-methoxybenzo[b]thiophene-2-carboxylic acid. LCMS ($C_{17}H_{15}O_4S$) (ES, m/z): 315 [M+H]$^+$. $^1$H NMR (400 MHz, DMSO-$d_6$) δ 13.16 (br s, 1H), 7.95 (s, 1H), 7.69 (s, 1H), 7.51 (s, 1H), 7.50-7.46 (m, 2H), 7.44-7.32 (m, 3H), 5.17 (s, 2H), 3.83 (s, 3H).

Step 2: 6-(Benzyloxy)-5-methoxybenzo[b]thiophene-2-carbonyl chloride

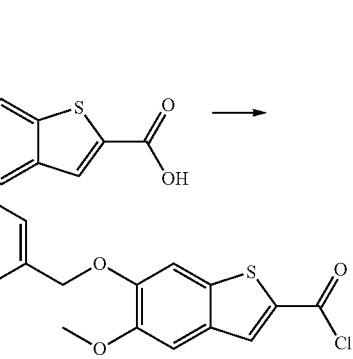

DMF (0.023 mL, 0.29 mmol) was added to a mixture of 6-(benzyloxy)-5-methoxybenzo[b]thiophene-2-carboxylic acid (3.05 g, 9.70 mmol) and (COCl)$_2$ (2.55 mL, 29.1 mmol) in THF (50 mL) at 0° C. under Ar. The mixture was stirred at 0° C. for 30 min and then warmed to RT. The reaction mixture was then stirred for 2 h at RT. The reaction mixture was concentrated under reduced pressure to afford 6-(benzyloxy)-5-methoxybenzo[b]thiophene-2-carbonyl chloride, which was used without purification.

Step 3: Methyl (S)-4-(6-(benzyloxy)-5-methoxybenzo[b]thiophen-2-yl)-2-methyl-4-oxobutanoate

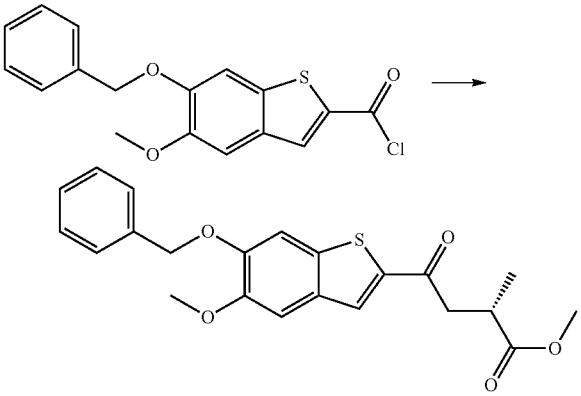

A mixture of (R)-(3-methoxy-2-methyl-3-oxopropyl)zinc (II) bromide (0.50M in THF, 25 mL, 13 mmol) was added slowly to a flask containing ((thiophene-2-carbonyl)oxy) copper (2.38 g, 12.5 mmol) under Ar at 0° C. The reaction mixture was stirred for 20 min at 0° C. under Ar. An Ar-degassed mixture of 6-(benzyloxy)-5-methoxybenzo[b]thiophene-2-carbonyl chloride (3.2 g, 9.6 mmol) in THF (50 mL) was then added slowly via cannula to the mixture at 0° C. The mixture was allowed to warm to RT, and then stirred for 16 h at RT. The reaction mixture was cooled to 0° C. and quenched by adding sat aq NH$_4$Cl (50 mL), water (100 mL), and EtOAc (500 mL). The resulting biphasic mixture was warmed to RT and stirred for 1 h at RT. The mixture was then filtered through a CELITE frit, and the filtrate was partitioned in a separatory funnel. The organic layer was separated, washed with sat aq NaCl (50 mL), dried over MgSO$_4$, filtered, and concentrated under reduced pressure. The residue was purified by silica gel chromatography (0→50% EtOAc gradient in Hex) to afford the desired product, which was repurified by silica gel chromatography (eluting 0→50% EtOAc in DCM) to afford (S)-methyl 4-(6-(benzyloxy)-5-methoxybenzo[b]thiophen-2-yl)-2-methyl-4-oxobutanoate. LCMS ($C_{22}H_{23}O_5S$) (ES, m/z): 399 [M+H]$^+$. $^1$H NMR (499 MHz, DMSO-$d_6$) δ 8.22 (s, 1H), 7.72 (s, 1H), 7.52-7.47 (m, 3H), 7.42 (t, J=7.3 Hz, 2H), 7.38-7.34 (m, 1H), 5.19 (s, 2H), 3.85 (s, 3H), 3.60 (s, 3H), 3.42 (dd, J=17.5, 8.6 Hz, 1H), 3.19 (dd, J=17.4, 4.9 Hz, 1H), 3.04-2.91 (m, 1H), 1.20 (d, J=7.1 Hz, 3H).

Step 4: Methyl (S)-4-(6-hydroxy-5-methoxybenzo[b]thiophen-2-yl)-2-methyl-4-oxobutanoate

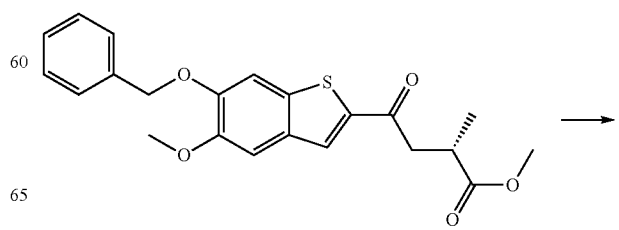

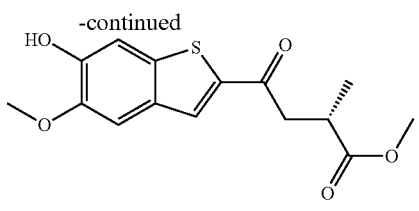

A mixture of (S)-methyl 4-(6-(benzyloxy)-5-methoxybenzo[b]thiophen-2-yl)-2-methyl-4-oxobutanoate (1.60 g, 4.02 mmol) and Pd/C (1.07 g, 1.00 mmol) was degassed with Ar. EtOAc (50 mL), MeOH (50 mL), and HCl (37% in water, 0.66 mL, 8.0 mmol) were added slowly to the mixture under Ar stream. The headspace above the reaction mixture was degassed via vacuum and backfilled with H$_2$. The reaction mixture was stirred under H$_2$ for 3 h. The reaction mixture was filtered through CELITE, washing with EtOAc. The filtrate was concentrated under reduced pressure. The residue was purified by silica gel chromatography (eluting 0→100% EtOAc in Hex) to afford (S)-methyl 4-(6-hydroxy-5-methoxybenzo[b]thiophen-2-yl)-2-methyl-4-oxobutanoate. LCMS (C$_{15}$H$_{17}$O$_5$S) (ES, m/z): 309 [M+H]$^+$. $^1$H NMR (499 MHz, DMSO-d$_6$) δ 9.93 (s, 1H), 8.17 (s, 1H), 7.44 (s, 1H), 7.30 (s, 1H), 3.85 (s, 3H), 3.60 (s, 3H), 3.44-3.38 (m, 1H), 3.16 (dd, J=17.3, 4.7 Hz, 1H), 3.01-2.92 (m, 1H), 1.19 (d, J=7.0 Hz, 3H).

Step 5: Methyl (S)-4-(6-(3-chloropropoxy)-5-methoxybenzo[b]thiophen-2-yl)-2-methyl-4-oxobutanoate

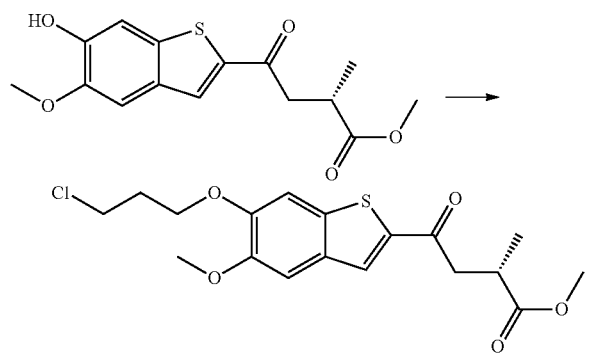

A mixture of (S)-methyl 4-(6-hydroxy-5-methoxybenzo[b]thiophen-2-yl)-2-methyl-4-oxobutanoate (141 mg, 0.457 mmol), 1-bromo-3-chloropropane (360 mg, 2.3 mmol), and K$_2$CO$_3$ (379 mg, 2.74 mmol) was degassed with Ar. ACN (4.0 mL) was added to the mixture, and the reaction mixture was heated to 50° C. for 18 h. Upon cooling to RT, the reaction mixture was then diluted with DCM (25 mL) and filtered. The filtrate was concentrated under reduced pressure and then purified by silica gel chromatography (0→100% EtOAc gradient in DCM) to afford (S)-methyl 4-(6-(3-chloropropoxy)-5-methoxybenzo [b]thiophen-2-yl)-2-methyl-4-oxobutanoate. LCMS (C$_{18}$H$_{22}$ClO$_5$S) (ES, m/z): 385 [M+H]$^+$.

Intermediate 43, as shown in Table 7 below, was or may be prepared according to procedures analogous to those outlined in Intermediate 42 above using the appropriate starting materials, described as Preparations or as obtained from commercial sources.

TABLE 7

| Intermediate | Structure | Name | Mass [M + H]$^+$ |
|---|---|---|---|
| 43 | 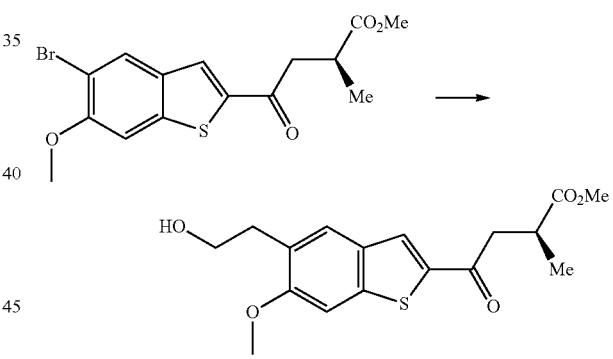 | methyl (S)-4-(5-(3-chloropropoxy)-6-methoxybenzo[b]thiophen-2-yl)-2-methyl-4-oxobutanoate | 385 |

Intermediate 44: methyl (2S)-4-[5-(2-hydroxyethyl)-6-methoxy-1-benzothiophen-2-yl]-2-methyl-4-oxobutanoate To the stirred mixture of methyl (2S)-4-(5-bromo-6-methoxy-1-benzothiophen-2-yl)-2-methyl-4-oxobutanoate (1.24 g, 3.34 mmol), tris(trimethylsilyl)silane (1.0 mL, 3.3 mmol), and anhydrous Na$_2$CO$_3$ (708 mg, 6.68 mmol) in degassed DME (16.5 mL) under N$_2$, was added a mixture of Ir(2-(2,4-difluorophenyl)-5-(trifluoromethyl)pyridine)$_2$ (4,4'-di-tert-butyl-2,2'-bipyridine)PF$_6$ (38 mg, 33 μmol) in degassed DME (12 mL). A suspension of Nickel(II) chloride ethylene glycol dimethyl ether complex (3.7 mg, 17 mol) and 4,4'-di-tert-butyl-2,2'-bipyridine (4.5 mg, 17 mol) in degassed DME (4.5 mL) was added, and the resulting mixture was stirred under N$_2$ for 15 min at RT. 2-Bromoethanol (835 mg, 6.68 mmol) was added in one portion under N$_2$, and the reaction mixture was stirred and irradiated in a photo-reactor with 20% light intensity for 24 h at RT. The mixture was then filtered, and the filtrate was concentrated under reduced pressure. The residue was purified by silica gel flash column chromatography (EtOAc in Hex) to afford methyl (2S)-4-[5-(2-hydroxyethyl)-6-methoxy-1- benzothiophen-2-yl]-2-methyl-4-oxobutanoate. LCMS (C$_{17}$H$_{21}$O$_5$S) (ES, m/z): 337 [M+H]$^+$. $^1$H NMR (500 MHz, DMSO-d$_6$): δ 8.26 (s, 1H), 7.76 (s, 1H), 7.58 (s, 1H), 4.64 (t, J=5.2 Hz, 1H), 3.88 (s, 3H), 3.64-3.55 (m, 2H), 3.59 (s, 3H), 3.42 (dd, J=17.5, 8.6 Hz, 1H), 3.19 (dd, J=17.5, 5.0 Hz, 1H), 3.01-2.92 (m, 1H), 2.81 (t, J=6.9 Hz, 2H), 1.19 (d, J=7.1 Hz, 3H).

Intermediate 45: tert-butyl 4-(6-methoxy-5-(3-oxo-propyl)benzo[b]thiophen-2-yl)-4-oxobutanoate

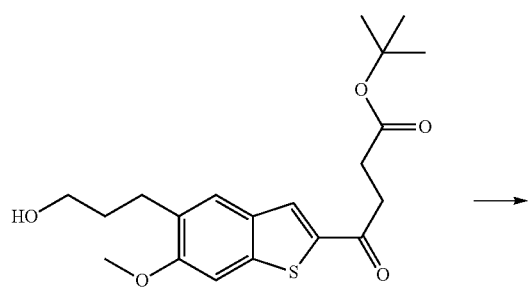

To a 4 mL vial was added tert-butyl 4-(5-(3-hydroxypropyl)-6-methoxybenzo[b]thiophen-2-yl)-4-oxobutanoate (30 mg, 0.079 mmol), Dess-Martin periodinane (1,1,1-Triacetoxy-1,1-dihydro-1,2-benziodoxol-3(1H)-one; 50 mg, 0.1 mmol), and DCM (1.0 mL). The mixture was stirred at RT for 1 h. The mixture was purified by silica gel chromatography (0→55% EtOAc gradient in Hex) to afford tert-butyl 4-(6-methoxy-5-(3-oxopropyl)benzo[b]thiophen-2-yl)-4-oxobutanoate. LCMS (C$_{20}$H$_{24}$O$_5$SNa) (ES, m/z): 399 [M+Na]$^+$. $^1$H NMR (500 MHz, CDCl$_3$) δ 9.85 (s, 1H), 7.89 (s, 1H), 7.64 (s, 1H), 3.27 (t, J=6.8 Hz, 2H), 3.05 (t, J=7.4 Hz, 2H), 2.80 (t, J=7.2 Hz, 2H), 2.72 (t, J=6.7 Hz, 2H), 1.46 (s, 9H).

Intermediate 46: tert-butyl 4-(5-amino-6-methoxythieno[3,2-b]pyridin-2-yl)-4-oxobutanoate

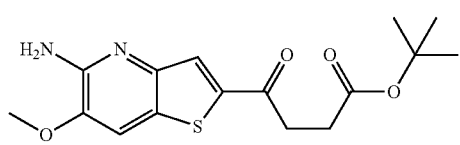 [SMILES: COc1cc2sc(C(=O)CCC(=O)OC(C)(C)C)cc2nc1N]

Step 1: tert-butyl 4-(5-((diphenylmethylene)amino)-6-methoxythieno[3,2-b]pyridin-2-yl)-4-oxobutanoate

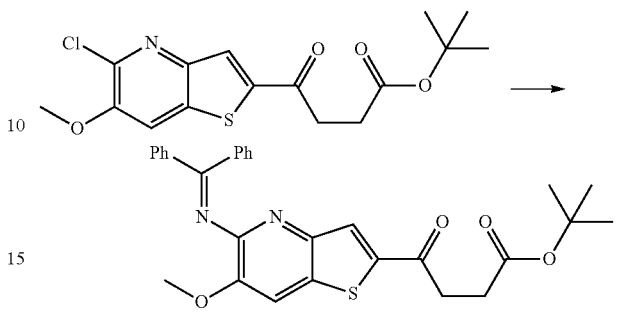

To a 4 mL vial was added Cs$_2$CO$_3$ (252 mg, 0.773 mmol), diphenylmethanimine (129 μL, 0.773 mmol), tert-butyl 4-(5-chloro-6-methoxythieno[3,2-b]pyridin-2-yl)-4-oxobutanoate (138 mg, 0.387 mmol), Rac BINAP Pd G3 (19 mg, 0.019 mmol), and toluene (2.0 mL). The mixture was heated to 120° C. for 3.5 h. Upon cooling to RT, the mixture was directly purified by silica gel chromatography (0→50% EtOAc gradient in Hex) to afford tert-butyl 4-(5-((diphenylmethylene)amino)-6-methoxythieno[3,2-b]pyridin-2-yl)-4-oxobutanoate. LCMS (C$_{29}$H$_{29}$N$_2$O$_4$S) (ES, m/z): 501 [M+H]$^+$.

Step 2: tert-butyl 4-(5-amino-6-methoxythieno[3,2-b]pyridin-2-yl)-4-oxobutanoate

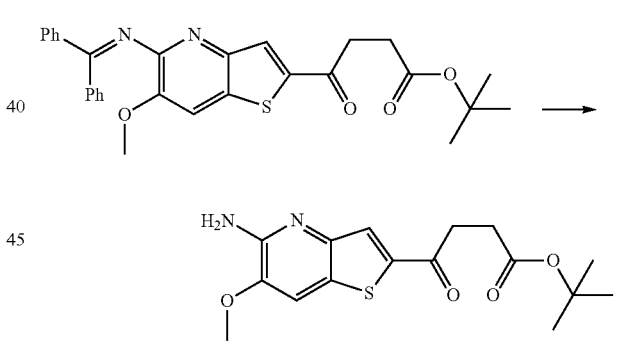

To a 20 mL vial was added tert-butyl 4-(5-((diphenylmethylene)amino)-6-methoxythieno[3,2-b]pyridin-2-yl)-4-oxobutanoate (146 mg, 0.291 mmol), AcOH (2.0 mL), MeOH (2.0 mL), water (2.0 mL), and THF (6.0 mL). The mixture was heated to 50° C. for 1 h. Upon cooling to RT, the mixture was then allowed to stir at RT for 24 h. The mixture was then diluted with EtOAc (50 mL) and washed with aq sat NaHCO$_3$ (50 mL) and water (50 mL). The organic layer was dried over Na$_2$SO$_4$, filtered and concentrated under reduced pressure. The resulting residue was purified by silica gel chromatography (0→50% EtOAc gradient in Hex) to afford tert-butyl 4-(5-amino-6-methoxythieno[3,2-b]pyridin-2-yl)-4-oxobutanoate. LCMS (C$_{16}$H$_{21}$N$_2$O$_4$S) (ES, m/z): 337 [M+H]$^+$. $^1$H NMR (500 MHz, CDCl$_3$) δ 8.02 (s, 1H), 7.53 (s, 1H), 4.11 (s, 3H), 3.24 (t, J=6.4 Hz, 2H), 2.74-2.70 (m, 2H), 1.46 (s, 9H).

277

Intermediate 47: Methyl (S)-4-(6-(3-hydroxy-propoxy)-5-methoxybenzo[b]thiophen-2-yl)-2-methyl-4-oxobutanoate

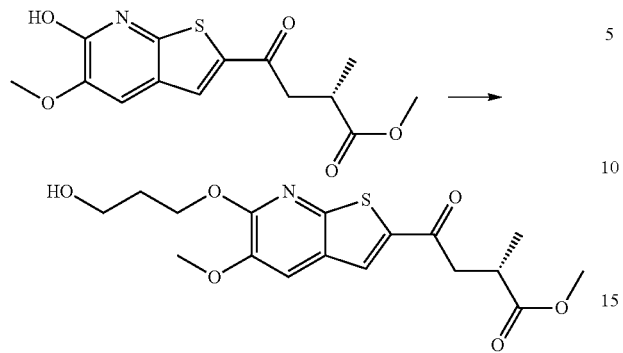

A mixture of (S)-methyl 4-(6-hydroxy-5-methoxybenzo[b]thiophen-2-yl)-2-methyl-4-oxobutanoate (25 mg, 0.081 mmol), 3-chloropropan-1-ol (10 mg, 0.1 mmol), and $K_2CO_3$ (22 mg, 0.16 mmol) was degassed with Ar. DMF (0.50 mL) was added to the mixture, and the reaction mixture was irradiated in a microwave to 100° C. for 1 h. The reaction mixture was allowed to cool to RT and then diluted with EtOAc (25 mL) and water (5 mL). The organic layer was separated, washed with additional water (5 mL) and then sat aq NaCl (5 mL), dried over $MgSO_4$, filtered, and concentrated under reduced pressure to afford the crude product residue. The crude product residue was purified by silica gel chromatography (eluting 0-100% [5% MeOH in EtOAc] in DCM) to afford (S)-methyl 4-(6-(3-hydroxypropoxy)-5-methoxybenzo [b]thiophen-2-yl)-2-methyl-4-oxobutanoate. LCMS ($C_{18}H_{23}O_6S$) (ES, m/z): 367 [M+H]$^+$.

Intermediate 48, as shown in Table 8 below, was or may be prepared according to procedures analogous to those outlined in Intermediate 47 above using the appropriate starting materials, described as Preparations or as obtained from commercial sources.

278

Step 1: tert-butyl 4-(6-methoxy-5-(3-((tetrahydro-2H-pyran-2-yl)oxy)propoxy)benzo[b]thiophen-2-yl)-4-oxobutanoate

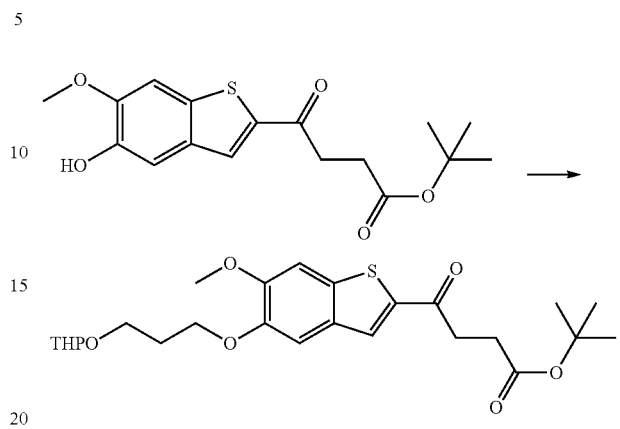

To a mixture of tert-butyl 4-(5-hydroxy-6-methoxybenzo[b]thiophen-2-yl)-4-oxobutanoate (3.0 g, 8.9 mmol), $K_2CO_3$ (7.4 g, 54 mmol) and ACN (20 mL) was added 2-(3-bromopropoxy)tetrahydro-2H-pyran (3.8 mL, 22 mmol). The reaction was heated to 65° C. for 4 h. Upon cooling to RT, the mixture was filtered, washed with ACN, and then the solvent was removed under reduced pressure. The resulting residue was dissolved in DCM (10 mL), and Hex (100 mL) was slowly added. The resulting precipitate was filtered, washed with Hex, and air dried to afford tert-butyl 4-(6-methoxy-5-(3-((tetrahydro-2H-pyran-2-yl)oxy)propoxy) benzo[b]thiophen-2-yl)-4-oxobutanoate. LCMS ($C_{25}H_{34}O_7SNa$) (ES, m/z): 501 [M+Na]$^+$. $^1$H NMR (600 MHz, DMSO-$d_6$) δ 8.16 (s, 1H), 7.56 (s, 1H), 7.46 (s, 1H), 4.54 (s, 1H), 4.06 (t, J=6.2 Hz, 2H), 3.83 (s, 3H), 3.78 (dt, J=9.6, 6.4 Hz, 1H), 3.69 (dd, J=13.5, 5.5 Hz, 1H), 3.52-3.45 (m, 1H), 3.41-3.35 (m, 1H), 3.20 (t, J=6.2 Hz, 2H), 2.54 (t, J=6.2 Hz, 2H), 2.02-1.95 (m, 2H), 1.71-1.62 (m, 1H), 1.58 (t, J=7.8 Hz, 1H), 1.47-1.39 (m, 3H), 1.36-1.33 (m, 10H).

TABLE 8

| Inter-mediate | Structure | Name | Mass [M + H]$^+$ |
|---|---|---|---|
| 48 | 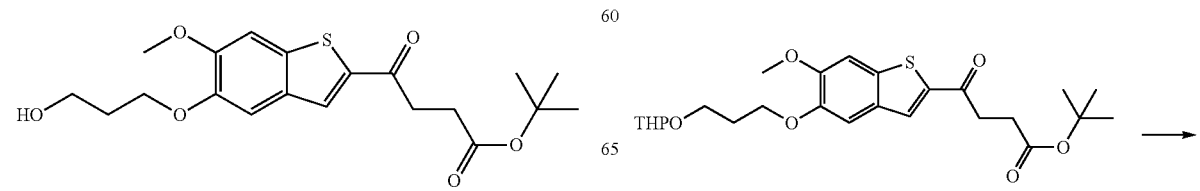 | methyl (S)-4-(5-(2-hydroxy ethoxy)-6-methoxybenzo[b] thiophen-2-yl)-2-methyl-4-oxobutanoate | 453 |

Intermediate 49: tert-butyl 4-(5-hydroxy-6-methoxybenzo[b]thiophen-2-yl)-4-oxobutanoate Step 2: tert-butyl 4-(5-hydroxy-6-methoxybenzo[b]thiophen-2-yl)-4-oxobutanoate

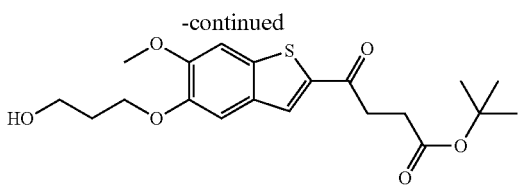

To a mixture of tert-butyl 4-(6-methoxy-5-(3-((tetrahydro-2H-pyran-2-yl)oxy) propoxy)benzo[b]thiophen-2-yl)-4-oxobutanoate (3.78 g, 7.90 mmol) and EtOH (50 mL) was added pTsOH (2.2 g, 12 mmol), and the mixture was allowed to stir at RT for 2 h. The mixture was then diluted with DCM and quenched with aq sat NaHCO$_3$. The organic layer was then separated, dried over Na$_2$SO$_4$, filtered, and concentrated under reduced pressure to afford tert-butyl 4-(5-hydroxy-6-methoxybenzo[b]thiophen-2-yl)-4-oxobutanoate. LCMS (C$_{20}$H$_{26}$O$_6$SNa) (ES, m/z): 417 [M+Na]$^+$. $^1$H NMR (600 MHz, DMSO-d$_6$) δ 8.15 (s, 1H), 7.55 (s, 1H), 7.44 (s, 1H), 4.53 (t, J=4.7 Hz, 1H), 4.05 (t, J=6.2 Hz, 2H), 3.83 (s, 3H), 3.55 (q, J=5.4 Hz, 2H), 3.20 (t, J=6.1 Hz, 2H), 2.54 (t, J=6.1 Hz, 2H), 1.88 (p, J=5.8 Hz, 2H), 1.33 (s, 9H).

Intermediate 50, as shown in Table 9 below, was or may be prepared according to procedures analogous to those outlined in Intermediate 49 above using the appropriate starting materials, described as Preparations or as obtained from commercial sources.

was then filtered through CELITE, and the CELITE was washed with EtOAc. The filtrate was concentrated under reduced pressure to afford the crude product residue. The crude product residue was purified by silica gel chromatography (0→100% EtOAc gradient in Hex) to afford methyl 4-(5-hydroxybenzo[b]thiophen-2-yl)-4-oxobutanoate.

LCMS (C$_{13}$H$_{13}$O$_4$S) (ES, m/z): 265 [M+H]$^+$. $^1$H NMR (500 MHz, DMSO-d$_6$) δ 9.74 (s, 1H), 8.28 (s, 1H), 7.85 (d, J=8.5 Hz, 1H), 7.36 (s, 1H), 7.07 (d, J=8.0 Hz, 1H), 3.63 (s, 3H), 2.75-2.67 (m, 2H); 2 aliphatic protons buried under solvent peak and not apparent.

Intermediate 52: methyl (2S)-4-(5,6-dihydroxy-1-benzothiophen-2-yl)-2-methyl-4-oxobutanoate

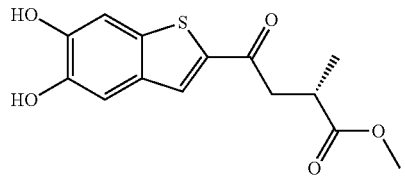 [SMILES: COC(=O)[C@@H](C)CC(=O)c1cc2cc(O)c(O)cc2s1]

TABLE 9

| Intermediate | Structure | Name | Mass [M + H]$^+$ |
|---|---|---|---|
| 50 | 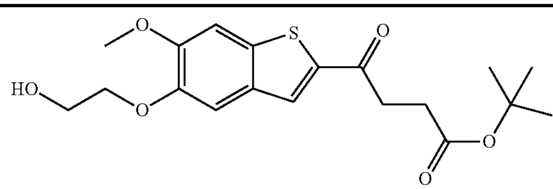 | tert-butyl 4-(5-(2-hydroxyethoxy)-6-methoxybenzo[b]thiophen-2-yl)-4-oxobutanoate | 403 [M + Na]$^+$ |

Intermediate 51: Methyl 4-(5-hydroxybenzo[b]thiophen-2-yl)-4-oxobutanoate

Step 1: (2S)-4-(5,6-dihydroxy-1-benzothiophen-2-yl)-2-methyl-4-oxobutanoic acid

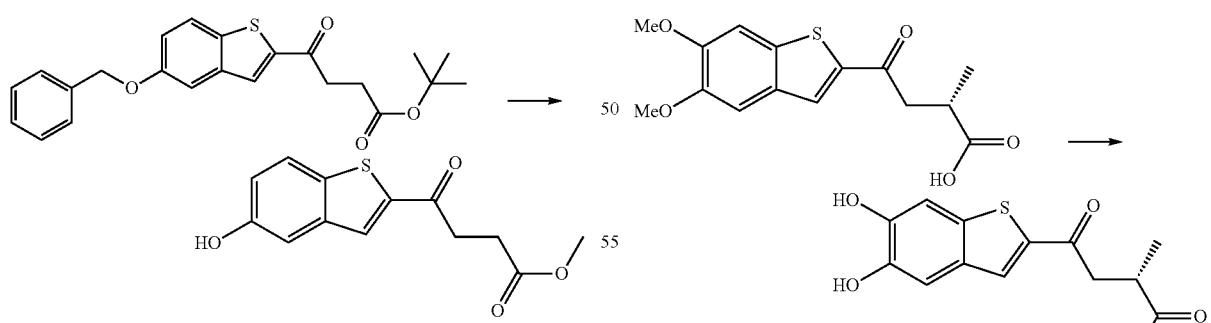

A mixture of tert-butyl 4-(5-(benzyloxy)benzo[b]thiophen-2-yl)-4-oxobutanoate (1.43 g, 3.60 mmol) and Pd/C (10% w/w, 1.5 g, 1.4 mmol) was degassed with Ar. MeOH (25 mL), EtOAc (25 mL), and HCl (37% in water, 0.59 mL, 7.2 mmol) were added slowly to the mixture under Ar stream. The headspace above the reaction mixture was degassed via vacuum and backfilled with H$_2$. The resulting mixture was stirred under H$_2$ for 24 h. The reaction mixture To a stirred solution of (2S)-4-(5,6-dimethoxy-1-benzothiophen-2-yl)-2-methyl-4-oxobutanoic acid (2.0 g, 6.5 mmol) in DCM (65 mL) was added BBr$_3$ (1M in DCM, 19.5 mL, 19.5 mmol) at 0° C. The reaction mixture was allowed to warm to RT for 2.5 h. The mixture was then cooled to 0° C., treated with water, and concentrated under reduced pressure. The residue was filtered, washed with water, and dried under high vacuum to afford (2S)-4-(5,6-dihydroxy-1-benzothiophen-2-yl)-2-methyl-4-oxobutanoic acid, which was used without further purification. LCMS (C$_{13}$H$_{13}$O$_5$S) ES, m/z): 281 [M+H]$^+$. $^1$H NMR (500 MHz, DMSO-d$_6$) δ 12.18 (s, 1H), 9.78 (brs, 1H), 9.49 (brs, 1H), 8.12 (s, 1H), 7.28 (s, 1H), 7.24 (s, 1H), 3.39-3.33 (m, 1H), 3.03 (dd, J=17.2, 5.2 Hz, 1H), 2.91-2.84 (m, 1H), 1.16 (d, J=7.1 Hz, 3H).

Step 2: methyl (2S)-4-(5,6-dihydroxy-1-benzothiophen-2-yl)-2-methyl-4-oxobutanoate

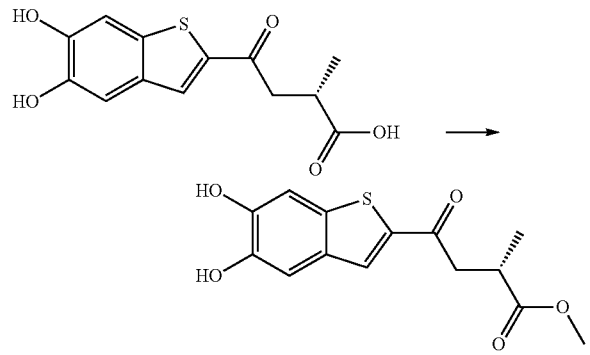

To a stirred solution of (2S)-4-(5,6-dihydroxy-1-benzothiophen-2-yl)-2-methyl-4-oxobutanoic acid (1.35 g, 4.82 mmol) in DCM (24 mL) and MeOH (24 mL) was added TMS-diazomethane (2M in Hex, 3.6 mL, 7.2 mmol). The mixture was left to stir for 30 min, treated with HOAc (0.28 mL, 4.8 mmol) and concentrated under reduced pressure. The residue was purified by silica gel chromatography (0→10% MeOH gradient in DCM) to afford methyl (2S)-4-(5,6-dihydroxy-1-benzothiophen-2-yl)-2-methyl-4-oxobutanoate. LCMS (C$_{14}$H$_{15}$O$_5$S) (ES, m/z): 295 [M+H]$^+$. $^1$H NMR (500 MHz, DMSO-d$_6$) δ 9.85 (s, 1H), 9.45 (s, 1H), 8.13 (s, 1H), 7.28 (s, 1H), 7.25 (s, 1H), 3.59 (s, 3H), 3.41-3.34 (m, 1H), 3.17-3.11 (m, 1H), 2.98-2.91 (m, 1H), 1.17 (d, J=7.1 Hz, 3H).

Intermediate 53: Methyl (2S)-4-[5,6-bis(3-hydroxypropoxy)-1-benzothiophen-2-yl]-2-methyl-4-oxobutanoate

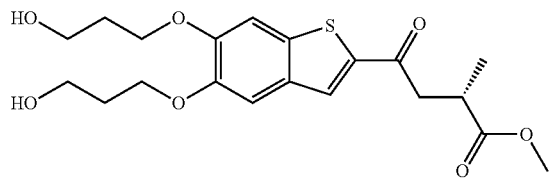 [SMILES: COC(=O)[C@@H](C)CC(=O)c1cc2cc(OCCCO)c(OCCCO)cc2s1]

A mixture of methyl (2S)-4-(5,6-dihydroxy-1-benzothiophen-2-yl)-2-methyl-4-oxobutanoate (230 mg, 0.78 mmol), 3-chloro-1-propanol (196 μL, 2.34 mmol), and K$_2$CO$_3$ (432 mg, 3.13 mmol) in DMF (7.8 mL) was irradiated in a microwave to 100° C. for 1 h. Upon cooling to RT, the mixture was diluted with EtOAc and sat aq NaCl. The organic layer was separated, dried over Na$_2$SO$_4$, filtered and then concentrated under reduced pressure. The resulting residue was purified by flash chromatography (0→10% MeOH gradient in DCM) to afford methyl (2S)-4-[5,6-bis(3-hydroxypropoxy)-1-benzothiophen-2-yl]-2-methyl-4-oxobutanoate. LCMS (C$_{20}$H$_{27}$O$_7$S) (ES, m/z): 411 [M+H]$^+$ Intermediate 54: methyl (2S)-4-[6-(difluoromethoxy)-5-hydroxy-1-benzothiophen-2-yl]-2-methyl-4-oxobutanoate

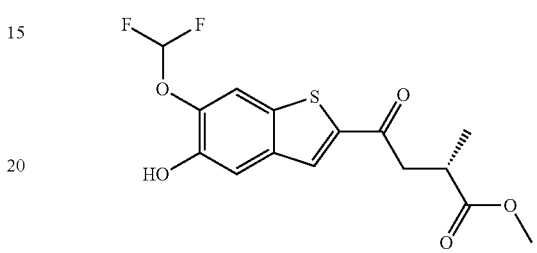

To a frozen mixture of methyl (2S)-4-(5,6-dihydroxy-1-benzothiophen-2-yl)-2-methyl-4-oxobutanoate (177 mg, 0.601 mmol) and KOH (1.0M in water, 120 μL, 1.2 mmol) in ACN (5.5 mL) and water (0.55 mL) at −78° C. was added diethyl (bromodifluoromethyl) phosphonate (170 μL, 0.96 mmol). The cooling bath was removed, and the reaction mixture was left to stir for 4 h. The mixture was diluted with EtOAc and water. The layers were separated, and the water layer was re-extracted EtOAc (×3). The combined organics were dried over Na$_2$SO$_4$, filtered, and then concentrated under reduced pressure. The resulting mixture was purified by flash chromatography (0→50% EtOAc in DCM) to afford crude methyl (2S)-4-[6-(difluoromethoxy)-5-hydroxy-1-benzothiophen-2-yl]-2-methyl-4-oxobutanoate. The desired fractions were purified by SFC (15% MeOH (+0.25% DMEA) in CO$_2$) to afford methyl (2S)-4-[6-(difluoromethoxy)-5-hydroxy-1-benzothiophen-2-yl]-2-methyl-4-oxobutanoate with a retention time of 4.4 min. LCMS (C$_{15}$H$_{15}$F$_2$O$_5$S) (ES, m/z): 345 [M+H]$^+$. $^1$H NMR (500 MHz, DMSO-d$_6$) δ 10.25 (s, 1H), 8.28 (s, 1H), 7.83 (s, 1H), 7.50 (s, 1H), 7.18 (t, J=74.4 Hz, 1H), 3.59 (s, 3H), 3.44 (dd, J=17.6, 8.7 Hz, 1H), 3.20 (dd, J=17.6, 4.9 Hz, 1H), 3.01-2.94 (m, 1H), 1.19 (d, J=7.1 Hz, 3H).

Intermediate 55: Methyl 4-(4-fluoro-5-hydroxy-6-methoxybenzo[b]thiophen-2-yl)-2,2-dimethyl-4-oxobutanoate

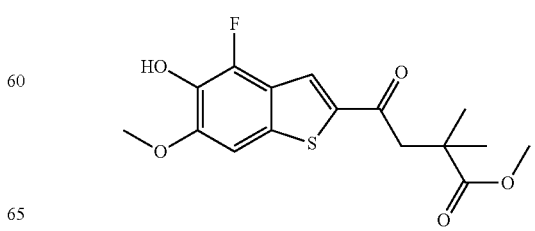

Step 1: 4-(4-Fluoro-5,6-dimethoxybenzo[b]thiophen-2-yl)-2,2-dimethyl-4-oxobutanoic acid

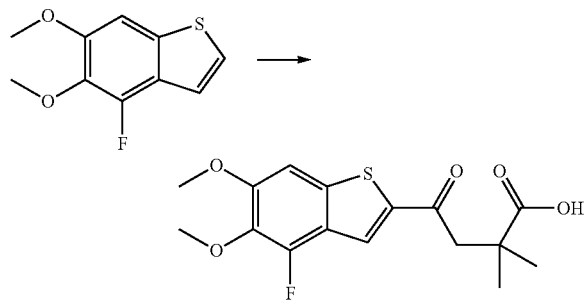

3,3-dimethyldihydrofuran-2,5-dione (4.6 g, 36 mmol) was added to a mixture of 4-fluoro-5,6-dimethoxybenzo[b]thiophene (3.8 g, 18 mmol) and AlCl$_3$ (3.1 g, 23 mmol) in DCM (100 mL) at 0° C. under Ar. The reaction mixture was stirred at 0° C. for 2 h and then warmed to RT and stirred for 16 h. The reaction mixture was then quenched by slowly adding the reaction mixture to a mixture of water (200 mL) and EtOAc (500 mL) at 0° C. The resulting mixture was stirred for 1 h at 20° C. and then diluted with HCl (2.0M in water, 36 mL, 72 mmol). The organic layer was separated, washed with sat aq NaCl (50 mL), dried over MgSO$_4$, filtered, and concentrated under reduced pressure. The mixture was then purified by silica gel chromatography to afford 4-(4-fluoro-5,6-dimethoxybenzo[b]thiophen-2-yl)-2,2-dimethyl-4-oxobutanoic acid. LCMS (C$_{16}$H$_{18}$FO$_5$S) (ES, m/z): 341 [M+H]$^+$.

Step 2: Methyl 4-(4-fluoro-5,6-dimethoxybenzo[b]thiophen-2-yl)-2,2-dimethyl-4-oxobutanoate

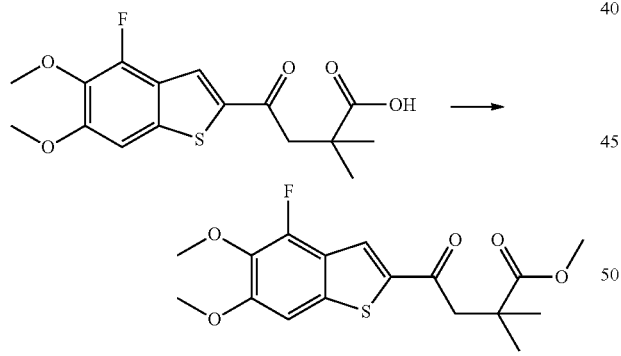

To a mixture of 4-(4-fluoro-5,6-dimethoxybenzo[b]thiophen-2-yl)-2,2-dimethyl-4-oxobutanoic acid (2.3 g, 6.8 mmol) in DMF (45 mL) was added K$_2$CO$_3$ (2.3 g, 17 mmol). After 10 min, CH$_3$I (2.1 mL, 34 mmol) was added, and the mixture was stirred for 18 h at RT. The mixture was then diluted with water and Et$_2$O. The organic layer was separated, dried over MgSO$_4$, filtered, and concentrated under reduced pressure. The mixture was then purified by silica gel chromatography to afford methyl 4-(4-fluoro-5,6-dimethoxybenzo[b]thiophen-2-yl)-2,2-dimethyl-4-oxobutanoate. LCMS (C$_{17}$H$_{20}$FO$_5$S) (ES, m/z): 355 [M+H]+. $^1$H NMR (500 MHz, DMSO-d$_6$) δ 8.32 (s, 1H), 7.59 (s, 1H), 3.92 (s, 3H), 3.85 (s, 3H), 3.57 (s, 3H), 3.44 (s, 2H), 1.23 (s, 6H).

Step 3: Methyl 4-(4-fluoro-5-hydroxy-6-methoxybenzo[b]thiophen-2-yl)-2,2-dimethyl-4-oxobutanoate

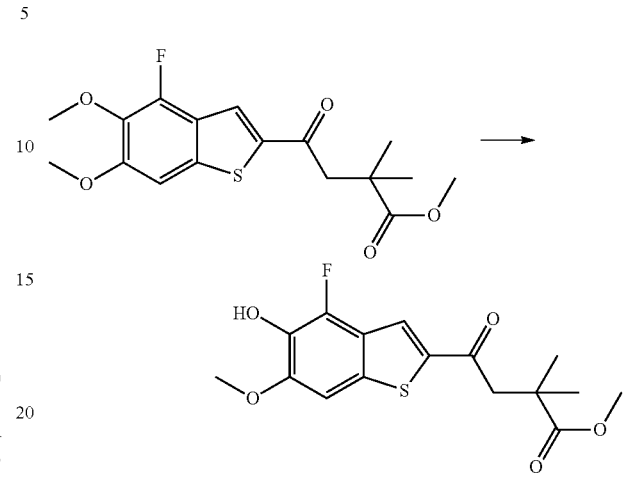

To a mixture of methyl 4-(4-fluoro-5,6-dimethoxybenzo[b]thiophen-2-yl)-2,2-dimethyl-4-oxobutanoate (1.1 g, 3.1 mmol) and DCM (20 mL) was added AlCl$_3$ (1.7 g, 12 mmol). The reaction mixture was stirred at RT for 18 h. The reaction mixture was poured into a flask containing ice and 1N HCl and stirred for 5 min. EtOAc was then added. The organic layer was separated, dried over MgSO$_4$, filtered, and concentrated under reduced pressure. The mixture was then purified by silica gel chromatography to afford methyl 4-(4-fluoro-5-hydroxy-6-methoxybenzo[b]thiophen-2-yl)-2,2-dimethyl-4-oxobutanoate. LCMS (C$_{16}$H$_{18}$F$_5$OS) (ES, m/z): 341 [M+H]$^+$. 1H NMR (500 MHz, DMSO-d$_6$) δ 9.55 (s, 1H), 8.24 (s, 1H), 7.47 (s, 1H), 3.91 (s, 3H), 3.57 (s, 3H), 3.43 (s, 2H), 1.23 (s, 6H).

Intermediate 56: tert-Butyl (1S,2R and 1R,2S)-2-(5-hydroxy-6-methoxybenzo[b]thiophene-2-carbonyl)cyclopropane-1-carboxylate

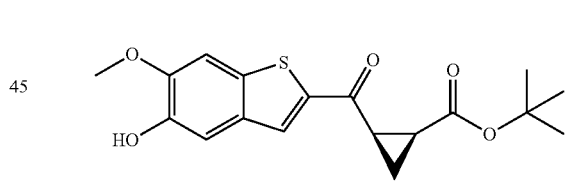

Step 1: (1S,2R and 1R,2S)-2-(5-Bromo-6-methoxybenzo[b]thiophene-2-carbonyl)cyclopropane-1-carboxylic acid

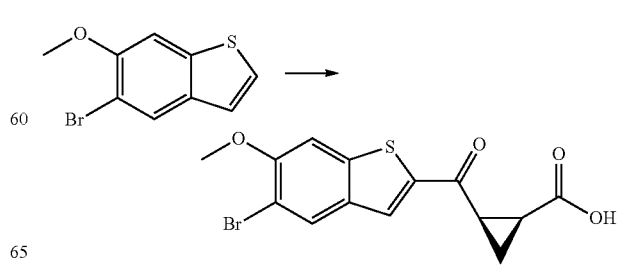

3-Oxabicyclo[3.1.0]hexane-2,4-dione (3.78 g, 33.7 mmol) was added to a mixture of 5-bromo-6-methoxybenzo[b]thiophene (4.1 g, 17 mmol) and AlCl₃ (2.92 g, 21.9 mmol) in DCM (100 mL) at 0° C. under Ar. The reaction mixture was stirred at 0° C. for 2 h and then allowed to warm to RT. The reaction mixture was stirred at RT for 16 h. The reaction mixture was then quenched by slowly adding the reaction mixture to a mixture of water (200 mL) and EtOAc (500 mL) at 0° C. The resulting mixture was allowed to warm to RT and stirred for 1 h. The mixture was then diluted with HCl (2.0M in water, 34 mL, 68 mmol). The organic layer was separated, washed with sat aq NaCl (50 mL), dried over MgSO₄, filtered, and concentrated under reduced pressure to afford the crude product residue. The crude product residue was purified by silica gel chromatography (eluting 0-100% [5% MeOH in EtOAc] in DCM) to afford (1S,2R and 1R,2S)-2-(5-bromo-6-methoxybenzo[b]thiophene-2-carbonyl)cyclopropane carboxylic acid. LCMS (C₁₄H₁₂BrO₄S) (ES, m/z): 355, 357 [M+H]⁺.

Step 2: tert-Butyl (1S,2R and 1R, 2S)-2-(5-bromo-6-methoxybenzo[b]thiophene-2-carbonyl) cyclopropane-1-carboxylate

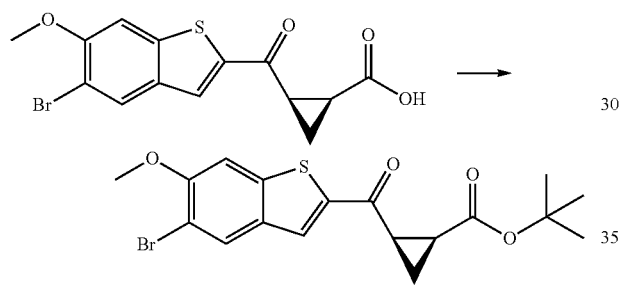

tert-Butanol (25.8 mL, 270 mmol) was added to a mixture of BOC-anhydride (6.3 mL, 27 mmol), DMAP (0.33 g, 2.7 mmol), and (1S,2R and 1R,2S)-2-(5-bromo-6-methoxybenzo[b]thiophene-2-carbonyl)cyclopropanecarboxylic acid (4.8 g, 14 mmol) in DCE (30 mL) at RT under Ar. The reaction mixture was stirred and heated to 50° C. for 2 h. The reaction mixture was then cooled to RT and concentrated under reduced pressure to afford the crude product residue. The crude product residue was purified by silica gel chromatography (0→100% EtOAc gradient in Hex) to afford (1S,2R and 1R,2S)-tert-butyl 2-(5-bromo-6-methoxybenzo[b]thiophene-2-carbonyl)cyclopropanecarboxylate. LCMS (C₁₈H₂₀BrO₄S—C₄H₈) (ES, m/z): 355, 357 [M+H-tBu]⁺. ¹H NMR (500 MHz, DMSO-d₆) δ 8.33 (s, 1H), 8.26 (s, 1H), 7.81 (s, 1H), 3.95 (s, 3H), 3.10-3.03 (m, 1H), 2.32-2.25 (m, 1H), 1.57-1.52 (m, 1H), 1.32-1.28 (m, 1H), 1.14 (s, 9H).

Step 3: tert-Butyl (1S,2R and 1R,2S)-2-(5-hydroxy-6-methoxybenzo[b]thiophene-2-carbonyl) cyclopropane-1-carboxylate

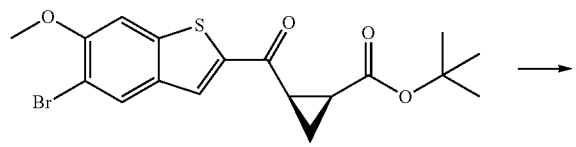

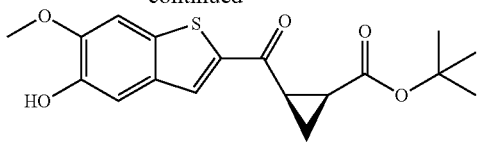

A mixture of (1 S,2R and 1R,2S)-tert-butyl 2-(5-bromo-6-methoxybenzo[b]thiophene-2-carbonyl)cyclopropanecarboxylate (1.64 g, 3.99 mmol), RockPhos Pd G3 (0.100 g, 0.120 mmol), Cs₂CO₃ (3.90 g, 12.0 mmol), and (E)-benzaldehyde oxime (0.725 g, 5.98 mmol) was degassed with Ar for 5 min. DMF (10.0 mL) was added under Ar, and the mixture was then degassed with Ar for 5 min. The reaction mixture was stirred and heated to 80° C. for 18 h. The reaction mixture was cooled to RT and diluted with water (100 mL) and EtOAc (250 mL). The organic layer was separated, washed with water (50 mL) and then sat aq NaCl (50 mL). The organic layer was separated, dried over MgSO₄, filtered, and concentrated under reduced pressure to afford the crude product residue. The crude product residue was purified by silica gel chromatography (0→75% EtOAc gradient in Hex) to afford (1 S,2R and 1R,2S)-tert-butyl 2-(5-hydroxy-6-methoxybenzo[b]thiophene-2-carbonyl) cyclopropanecarboxylate. LCMS (C₁₈H₂₀O₅SNa) (ES, m/z): 371 [M+Na]+.

Intermediate 57: (S)-Methyl-4-(5-amino-6-methoxybenzo[b]thiophen-2-yl)-2-methyl-4-oxobutanoatexylate

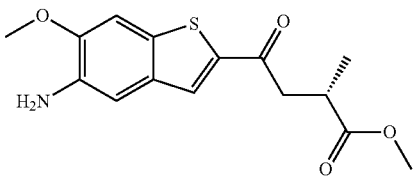

Step 1: Methyl (S)-4-(5-((diphenylmethylene)amino)-6-methoxybenzo[b]thiophen-2-yl)-2-methyl-4-oxobutanoate

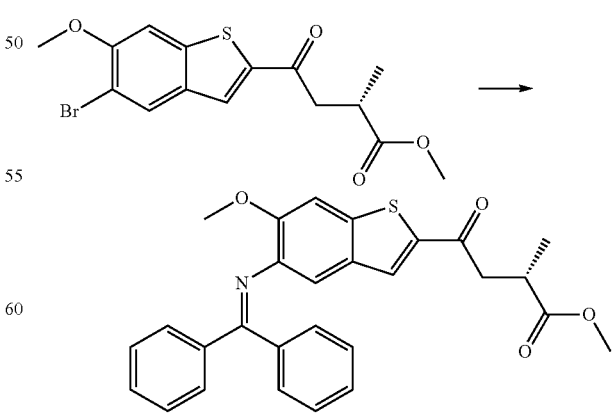

A mixture of (S)-methyl 4-(5-bromo-6-methoxybenzo[b]thiophen-2-yl)-2-methyl-4-oxobutanoate (0.50 g, 1.4 mmol), benzophenone imine (0.45 mL, 2.7 mmol), Rac BINAP Pd G3 (0.067 g, 0.067 mmol), and Cs$_2$CO$_3$ (0.878 g, 2.69 mmol) was degassed with Ar for 5 min. Toluene (10.0 mL) was added at 20° C. under Ar, and the mixture was then degassed with Ar for 5 min. The reaction mixture was stirred and heated to 110° C. for 18 h under Ar. The reaction mixture was then cooled to RT and diluted with DCM (25 mL). The mixture was filtered, and the filtrate was concentrated under reduced pressure to afford methyl (S)-4-(5-((diphenylmethylene) amino)-6-methoxybenzo[b]thiophen-2-yl)-2-methyl-4-oxobutanoate, which was used without purification. LCMS (C$_{28}$H$_{26}$NO$_4$S) (ES, m/z): 472 [M+H]$^+$.

Step 2: (S)-Methyl 4-(5-amino-6-methoxybenzo[b]thiophen-2-yl)-2-methyl-4-oxobutanoate

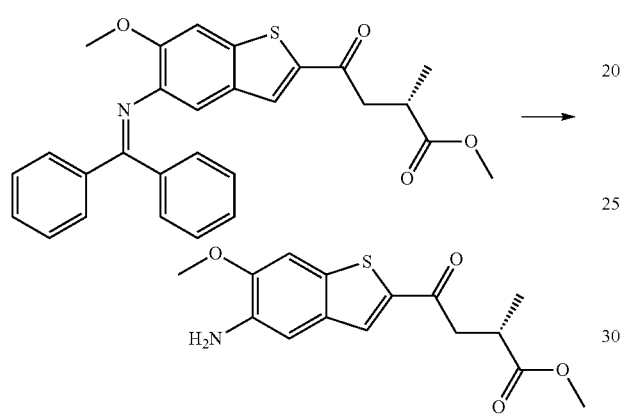

TFA (2.1 mL, 27 mmol) was added to a mixture of (S)-methyl 4-(5-((diphenyl methylene)amino)-6-methoxybenzo[b]thiophen-2-yl)-2-methyl-4-oxobutanoate (635 mg, 1.35 mmol) in DCM (5.0 mL) at 20° C. The resulting mixture was stirred at 20° C. for 30 min. The reaction mixture was then concentrated under reduced pressure to afford the crude product residue. The crude product residue was purified by silica gel chromatography (0→100% EtOAc gradient in DCM) to afford (S)-methyl 4-(5-amino-6-methoxybenzo[b]thiophen-2-yl)-2-methyl-4-oxobutanoate. LCMS (C$_{15}$H$_8$NO$_4$S) (ES, m/z): 308 [M+H]$^+$.

Intermediate 58: tert-Butyl 4-(6-hydroxybenzo[b]thiophen-2-yl)-4-oxobutanoate

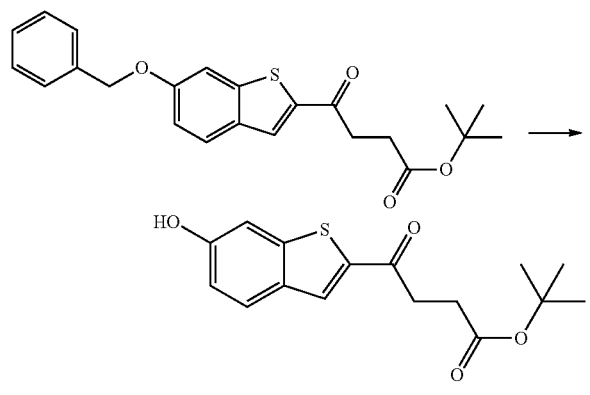

A mixture of tert-butyl 4-(6-(benzyloxy)benzo[b]thiophen-2-yl)-4-oxobutanoate (256 mg, 0.646 mmol) and Pd/C (172 mg, 0.161 mmol) was degassed with Ar. EtOAc (5.0 mL), MeOH (5.0 mL), and HCl (37% in water, 0.053 mL, 0.65 mmol) were added slowly to the mixture under Ar. The headspace above the reaction mixture was degassed via vacuum and backfilled with H$_2$. The resulting mixture was stirred under H$_2$ for 24 h. The reaction mixture was then filtered through CELITE, washing with EtOAc. The filtrate was concentrated under reduced pressure to afford the crude product residue. The crude product residue was purified by silica gel chromatography (eluting 0→100% EtOAc in Hex) to afford tert-butyl 4-(6-hydroxybenzo[b]thiophen-2-yl)-4-oxobutanoate. LCMS (C$_{16}$H$_{19}$O$_4$S—C$_4$H$_8$) (ES, m/z): 251 [M+H-tBu]$^+$.

Intermediate 59: tert-butyl 4-(5-bromobenzo[b]thiophen-2-yl)-4-oxobutanoate

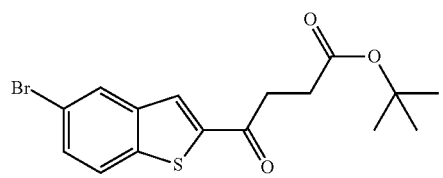 [SMILES: CC(C)(C)OC(=O)CCC(=O)c1cc2cc(Br)ccc2s1]

Step 1: 5-bromobenzo[b]thiophene-2-carbonyl chloride

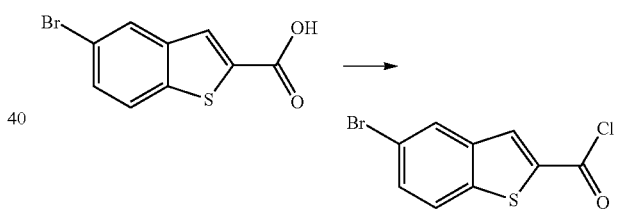

(COCl)$_2$ (0.30 mL, 3.4 mmol) was added dropwise with stirring to a 0° C. mixture of 5-bromobenzo[b]thiophene-2-carboxylic acid (0.750 g, 2.92 mmol) in CH$_2$Cl$_2$ (15 mL) over 3 min. To the reaction was added DMF (0.023 mL, 0.29 mmol) followed by additional (COCl)$_2$ (0.20 mL, 2.3 mmol). The reaction mixture was then stirred at 0° C. for 1 h. The reaction flask was removed from the ice water bath, and stirring was continued at RT for 1.5 h. The reaction was concentrated to afford 5-bromobenzo[b]thiophene-2-carbonyl chloride, which was used without further purification or characterization.

Step 2: tert-butyl 4-(5-bromobenzo[b]thiophen-2-yl)-4-oxobutanoate

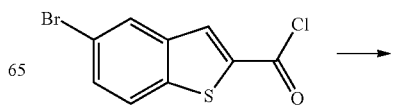

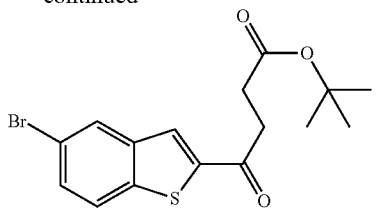

CuCl (0.269 g, 2.72 mmol) was added to a 100 mL round bottom flask with a stir bar. The flask was evacuated and then backfilled with $N_2$ three times. THF (6.0 mL) was added to the flask, which was then stirred and cooled to 0° C. with an ice water bath. (3-(tert-butoxy)-3-oxopropyl)zinc (II) bromide (0.50M in THF, 11 mL, 5.5 mmol) was added dropwise with stirring at 0° C. over a period of 3 min to the CuCl mixture. The resulting mixture was stirred at 0° C. for 30 min. A mixture of 5-bromobenzo[b]thiophene-2-carbonyl chloride (0.75 g, 2.7 mmol) in NMP (24 mL) was added dropwise to the mixture over a period of 7 min at 0° C. with stirring. The resulting mixture was stirred at 0° C. for 2 h. The reaction mixture was then partitioned between isopropyl acetate (300 mL) and 10% aq. sodium citrate (300 mL). The resulting mixture was stirred for 20 min. The layers were separated, and the aqueous layer was extracted with isopropyl acetate (150 mL). The organic layers were combined, washed with aq NaCl, then sat aq NaCl, dried over anhydrous $MgSO_4$, and filtered, and the filtrate was allowed to stand overnight. The filtrate was then filtered, and the filtrate concentrated to afford a crude residue. The crude residue was loaded onto a silica gel column with acetone. The column was dried by blowing pressurized $N_2$ through it. The dried column was then subjected to a 0→30% EtOAc gradient with Hex. All product-containing fractions were collected, concentrated, and purified by silica gel chromatography (0→25% EtOAc gradient in Hex). The product-containing fractions were concentrated and purified by achiral SFC (Phenomenex biphenyl, 21 mm×250 mm column, 90:10 $CO_2$:MeOH w/0.25% DMEA, 70 mL/min, 100 bar outlet pressure, 18.5 mg/mL in MeOH/MeCN loading concentration, 1.6 mL injection volume, 215 nm detection) to afford tert-butyl 4-(5-bromobenzo[b]thiophen-2-yl)-4-oxobutanoate. LCMS ($C_{16}H_{17}BrNaO_3S$) (ES, m/z): 391, 393 [M+Na]⁺. ¹H NMR (500 MHz, $CDCl_3$) δ 8.05 (s, 1H), 7.94 (s, 1H), 7.75 (d, J=8.6 Hz, 1H), 7.57 (d, J=8.6 Hz, 1H), 3.31 (t, J=6.6 Hz, 2H), 2.74 (t, J=6.6 Hz, 2H), 1.46 (s, 9H).

Intermediate 60: tert-Butyl 4-(5-chloro-6-methoxythieno[3,2-b]pyridin-2-yl)-4-oxobutanoate

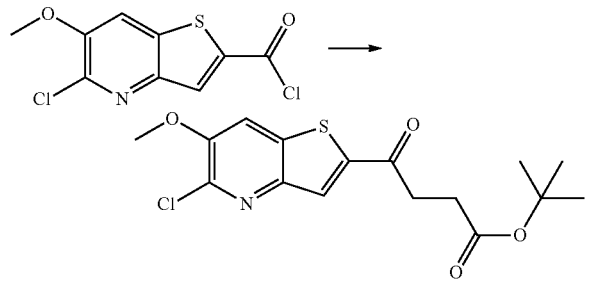

A flask containing CuCl (0.76 g, 7.6 mmol) was evacuated and then purged three times with $N_2$. THF (15 mL) was added, and the mixture was cooled to 0° C. (3-(tert-butoxy)-3-oxopropyl)zinc(II) bromide (0.50M in THF, 31 mL, 16 mmol) was added dropwise over 10 min. After 30 min, 5-chloro-6-methoxythieno[3,2-b]pyridine-2-carbonyl chloride (2.0 g, 7.6 mmol) was added followed by NMP (15 mL). The mixture was then allowed to warm to RT. After 1 h, the mixture was cooled to 0° C., and concentrated aq $NH_4OH$ (4.5 mL) was added. To this mixture was added water (240 mL) and MeOH (60 mL). The mixture was stirred for 5 min and sonicated in a water bath sonicator. The resulting mixture was filtered, and the precipitates were washed with water and then Hex. The precipitates were isolated and dried under vacuum. The precipitates were then partitioned between EtOAc and 10% aqueous sodium citrate. The layers were separated, and the aqueous layer was washed with EtOAc. The combined organic layers were dried over $Na_2SO_4$, filtered, and concentrated under reduced pressure. During the concentration, precipitation occurred, and the precipitates were collected via filtration, washed with EtOAc, and dried under vacuum to afford tert-butyl 4-(5-chloro-6-methoxythieno[3,2-b]pyridin-2-yl)-4-oxobutanoate. LCMS ($C_{16}H_{19}ClNO_4S$) (ES, m/z): 356 [M+H]⁺. ¹H NMR (500 MHz, $CDCl_3$) δ 8.03 (s, 1H), 7.62 (s, 1H), 4.04 (s, 3H), 3.30 (t, J=6.4 Hz, 2H), 2.74 (t, J=6.4 Hz, 2H), 1.46 (s, 9H).

Intermediate 61: methyl (S)-4-(2-(3-bromopropyl)-4-methoxythieno[2',3':5,6]benzo[1,2-d]oxazol-7-yl)-2-methyl-4-oxobutanoate

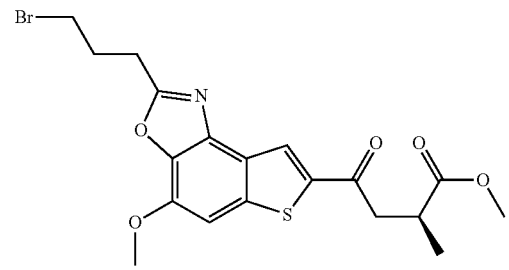 [SMILES: COC(=O)[C@@H](C)CC(=O)c1cc2c(cc(OC)c3oc(CCCBr)nc32)s1]

Step 1: methyl (S)-4-(5-hydroxy-6-methoxy-4-nitrobenzo[b]thiophen-2-yl)-2-methyl-4-oxobutanoate

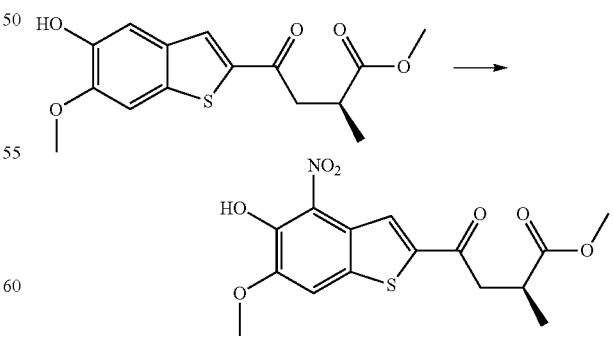

To a 20 mL vial was added (S)-methyl 4-(5-hydroxy-6-methoxybenzo[b]thiophen-2-yl)-2-methyl-4-oxobutanoate (100 mg, 0.21 mmol) and EtOAc (3.0 mL). $HNO_3$ (0.017 mL, 0.27 mmol) was added, and the mixture was allowed to stir for 1 h. After 1 h, the mixture was concentrated under reduced pressure and then triturated with Et₂O (3.0 mL). The resulting materials were collected by filtration to afford (S)-methyl 4-(5-hydroxy-6-methoxy-4-nitrobenzo [b]thiophen-2-yl)-2-methyl-4-oxobutanoate. ¹H NMR (500 MHz, CDCl₃) δ 12.08 (s, 1H), 8.75 (s, 1H), 7.53 (s, 1H), 4.07 (s, 3H), 3.74 (s, 3H), 3.59 (dd, J=17.1, 7.9 Hz, 1H), 3.23-3.16 (m, 1H), 3.16-3.09 (m, 1H), 1.35 (d, J=7.1 Hz, 3H).

Step 2: methyl (S)-4-(2-(3-bromopropyl)-4-methoxythieno[2',3':5,6]benzo[1,2-d]oxazol-7-yl)-2-methyl-4-oxobutanoate

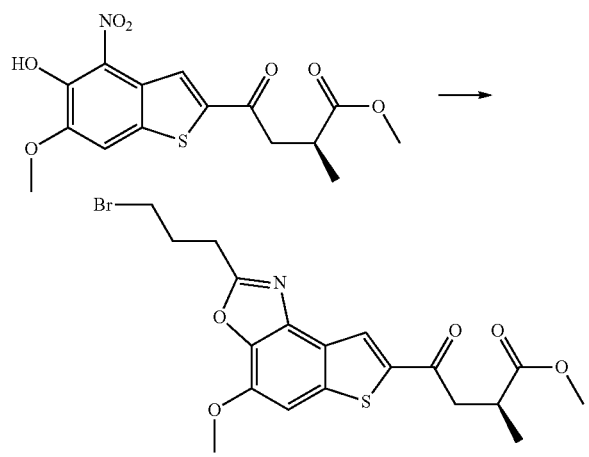

To a 4 mL vial was added (S)-methyl 4-(5-hydroxy-6-methoxy-4-nitrobenzo[b]thiophen-2-yl)-2-methyl-4-oxobutanoate (45 mg, 0.13 mmol), Pd (0.040 g, 0.038 mmol), and MeOH (0.60 mL). To the mixture was added 4-bromo-1,1,1-trimethoxybutane (0.61 mL, 3.8 mmol). The mixture was stirred under H₂ for 1 h. The mixture was then filtered, and the filtrate was concentrated under reduced pressure. The resulting residue was purified by silica gel chromatography (0→70% EtOAc gradient in Hex) to afford (S)-methyl 4-(2-(3-bromopropyl)-4-methoxythieno[2',3':5,6]benzo [1,2-d]oxazol-7-yl)-2-methyl-4-oxobutanoate. LCMS (C₁₉H₂₁BrNO₅S) (ES, m/z): 454, 456 [M+H]⁺. 1H NMR (500 MHz, CDCl₃) δ 8.36 (s, 1H), 7.25 (s, 1H), 4.11 (s, 3H), 3.73 (s, 3H), 3.62 (t, J=6.4 Hz, 2H), 3.55 (dd, J=16.7, 7.5 Hz, 1H), 3.24 (t, J=7.3 Hz, 2H), 3.18 (dd, J=13.5, 6.8 Hz, 1H), 3.12 (dd, J=16.7, 5.8 Hz, 1H), 2.53 (p, J=6.8 Hz, 2H), 1.32 (d, J=7.0 Hz, 3H).

Intermediate 88: Methyl (S)-4-(5-bromo-6-methoxybenzo[b]thiophen-2-yl)-2-methylbutanoate

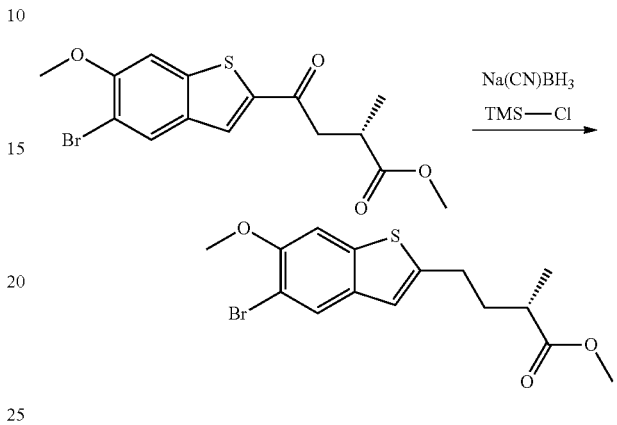

To a cooled solution of methyl (S)-4-(5-bromo-6-methoxybenzo[b]thiophen-2-yl)-2-methyl-4-oxobutanoate (0.637 g, 1.72 mmol) in ACN (15 mL) was added TMS-Cl (1.32 mL, 10.3 mmol). Sodium cyanoborohydride (0.65 g, 10 mmol) was added, and the reaction mixture was stirred at 0° C. for 2 h. The reaction mixture was quenched with sat. aq. NH₄Cl and extracted with DCM. The organic layer was separated, dried over Na₂SO₄, filtered, and concentrated under reduced pressure. The residue was purified by silica gel chromatography (EtOAc/hexanes) to afford methyl (S)-4-(5-bromo-6-methoxybenzo[b]thiophen-2-yl)-2-methylbutanoate. ¹H NMR (600 MHz, DMSO-d₆) δ 7.96 (s, 1H), 7.66 (s, 1H), 7.04 (s, 1H), 3.88 (s, 3H), 3.61 (s, 3H), 2.87-2.83 (m, 2H), 2.57-2.52 (m, 1H), 2.00-1.94 (m, 1H), 1.82-1.73 (m, 1H), 1.14 (d, J=7.0 Hz, 3H).

Intermediates 89 through 93, as shown in Table 10 below, was or may be prepared according to procedures analogous to those outlined in Intermediate 88 above using the appropriate starting materials, described as Preparations or as obtained from commercial sources.

TABLE 10

| Intermediate | Structure | Name | Mass [M + H]⁺ |
|---|---|---|---|
| 89 | ![structure] | (S)-methyl 4-(4-fluoro-5-hydroxy-6-methoxybenzo[b]thiophen-2-yl)-2-methylbutanoate | 330 (M + H₂O) |
| 90 | ![structure] | methyl 4-(4-fluoro-5-hydroxy-6-methoxybenzo[b]thiophen-2-yl)-2,2-dimethylbutanoate | 344 (M + H₂O) |

TABLE 10-continued

| Intermediate | Structure | Name | Mass [M + H]+ |
|---|---|---|---|
| 91 | 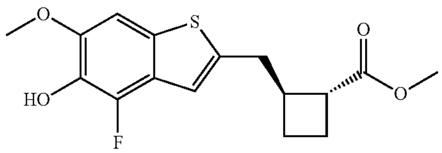 | methyl (1R,2S)-2-((4-fluoro-5-hydroxy-6-methoxybenzo[b]thiophen-2-yl)methyl)cyclobutane-1-carboxylate | 342 (M + H₂O) |
| 92 | 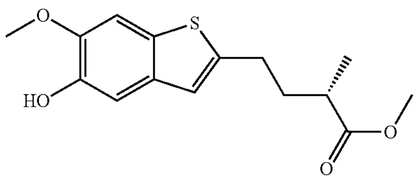 | methyl (S)-4-(5-hydroxy-6-methoxybenzo[b]thiophen-2-yl)-2-methylbutanoate | 295 |
| 93 | 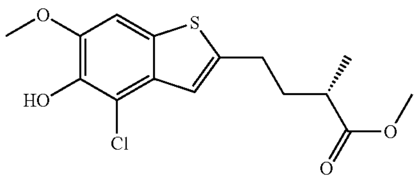 | methyl (S)-4-(4-chloro-5-hydroxy-6-methoxybenzo[b]thiophen-2-yl)-2-methylbutanoate | 346 (M + H₂O) |

Intermediate 94: Methyl (2S)-4-(5-(3-hydroxy-2-methylpropoxy)-6-methoxybenzo[b]thiophen-2-yl)-2-methyl-4-oxobutanoate

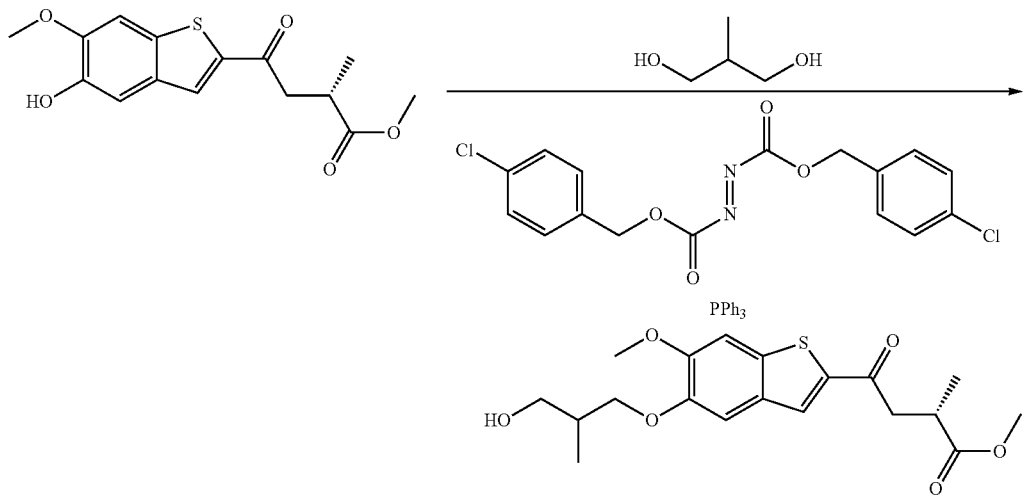

A mixture of 2-methylpropane-1,3-diol (146 mg, 1.62 mmol), (S)-methyl 4-(5-hydroxy-6-methoxybenzo[b]thiophen-2-yl)-2-methyl-4-oxobutanoate (50 mg, 0.16 mmol), (E)-bis(4-chlorobenzyl) diazene-1,2-dicarboxylate (60 mg, 0.16 mmol), and triphenylphosphine (43 mg, 0.16 mmol) in NMP (0.30 mL) was degassed with Ar and then stirred and heated to 100° C. for 3 h. The reaction mixture was cooled to RT and purified directly by reverse phase HPLC (ACN/water with 0.1% TFA) to afford (2S)-methyl 4-(5-(3-hydroxy-2-methylpropoxy)-6-methoxybenzo[b]thiophen-2-yl)-2-methyl-4-oxobutanoate. LCMS ($C_{19}H_{25}O_6S$) (ES, m/z): 381 [M+H]+.

Intermediate 95: 4-(5-(3-Bromopropyl)-6-methoxy-benzo[b]thiophen-2-yl)-4-oxobutanenitrile

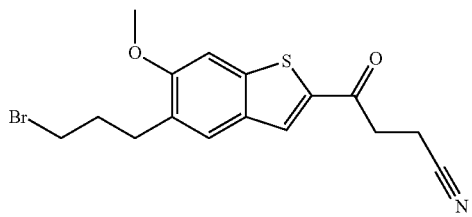 [SMILES: COc1cc2sc(C(=O)CCC#N)cc2cc1CCCBr]

Step 1: 4-(5-(3-((tert-Butyldimethylsilyl)oxy)propyl)-6-methoxybenzo[b]thiophen-2-yl)-4-oxobutanenitrile

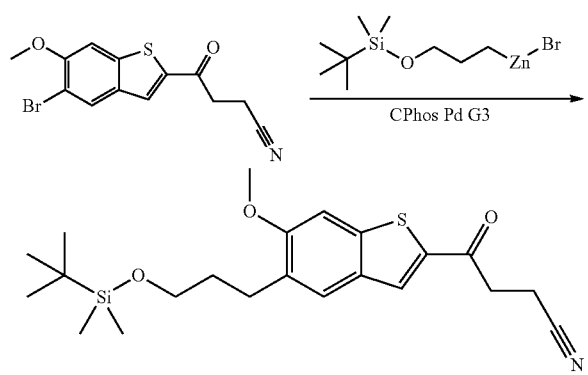

4-(5-Bromo-6-methoxybenzo[b]thiophen-2-yl)-4-oxobutanenitrile (161 mg, 0.496 mmol) and CPhos Pd G3 (20 mg, 0.025 mmol) were added to THF (2.5 mL). The reaction mixture was sealed, and the headspace above the reaction mixture was evacuated and backfilled with nitrogen (3×). 3-(tert-Butyldimethylsiloxy)propylzinc bromide (0.50M in THF, 3.0 mL, 1.5 mmol) was added to the reaction mixture, and the reaction mixture was stirred at RT for 96 h. The reaction mixture was diluted with EtOAc and then extracted with aq NaHCO₃. The aqueous layer was separated and extracted with EtOAc (3×). The organic layers were combined, washed with brine, dried over Na₂SO₄, filtered, and concentrated under reduced pressure to afford 4-(5-(3-((tert-butyldimethylsilyl)oxy)propyl)-6-methoxy-benzo[b]thiophen-2-yl)-4-oxobutanenitrile. LCMS (C$_{22}$H$_{32}$NO$_3$SSi) (ES, m/z): 418 [M+H]$^+$.

Step 2: 4-(5-(3-Hydroxypropyl)-6-methoxybenzo[b]thiophen-2-yl)-4-oxobutanenitrile

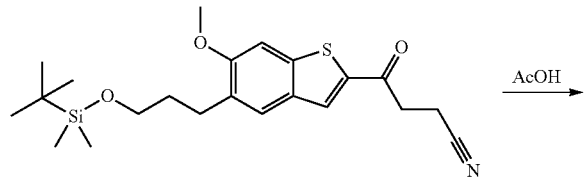

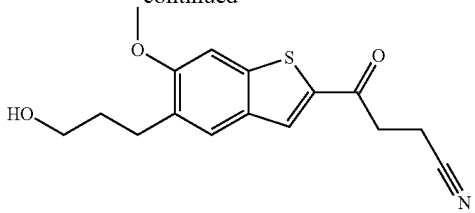

4-(5-(3-((tert-Butyldimethyl silyl)oxy)propyl)-6-methoxybenzo[b]thiophen-2-yl)-4-oxobutanenitrile (165 mg, 0.395 mmol) was suspended in a mixture of MeOH (2.0 mL), water (2.0 mL), and HOAc (2.0 mL). The resulting suspension was stirred at RT for 19 h. The reaction mixture was diluted with aq NaHCO₃ and then extracted with EtOAc (3×). The organic layers were combined, washed with brine, dried over Na₂SO₄, filtered, and concentrated under reduced pressure to afford 4-(5-(3-hydroxypropyl)-6-methoxybenzo[b]thiophen-2-yl)-4-oxobutanenitrile. LCMS (C$_{16}$H$_{18}$NO$_3$S) (ES, m/z): 304 [M+H]$^+$. $^1$H NMR (499 MHz, DMSO-d$_6$) δ 8.27 (s, 1H), 7.75 (s, 1H), 7.61 (s, 1H), 4.50-4.47 (m, 1H), 3.90 (s, 3H), 3.53-3.40 (m, 4H), 2.79 (t, J=6.5 Hz, 2H), 2.68 (t, J=7.4 Hz, 2H), 1.79-1.66 (m, 2H).

Step 3: 4-(5-(3-Bromopropyl)-6-methoxybenzo[b]thiophen-2-yl)-4-oxobutanenitrile

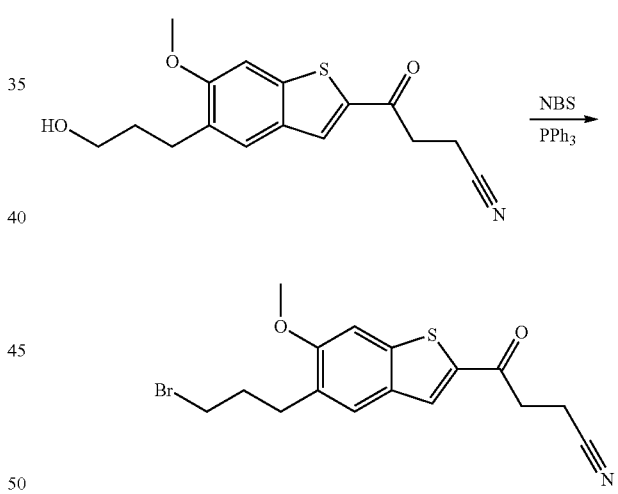

Triphenylphosphine (39 mg, 0.15 mmol) was added to a solution of 4-(5-(3-hydroxypropyl)-6-methoxybenzo[b]thiophen-2-yl)-4-oxobutanenitrile (45 mg, 0.15 mmol) in THF (1.0 mL). The mixture was cooled to 0° C., and then NBS (26 mg, 0.15 mmol) was added. After 1 h additional triphenylphosphine (23 mg, 0.089 mmol) and NBS (13 mg, 0.074 mmol) were added to the reaction mixture. The mixture was stirred for an additional 10 min at 0° C. The reaction mixture was quenched with aq sat NH₄Cl and then diluted with EtOAc. The organic layer was separated, washed with brine, dried over Na₂SO₄, filtered, and concentrated under reduced pressure. The residue was purified by silica gel chromatography (EtOAc/Hex) to afford 4-(5-(3-bromopropyl)-6-methoxy-benzo[b]thiophen-2-yl)-4-oxobutanenitrile. LCMS (C$_{16}$H$_{17}$BrNO$_2$SNa) (ES, m/z): 388, 390 [M+Na]$^+$.

Intermediate 96: Methyl (S)-4-(6-(3-chloro-propoxy)-5-methoxythieno[3,2-b]pyridin-2-yl)-2-methyl-4-oxobutanoate

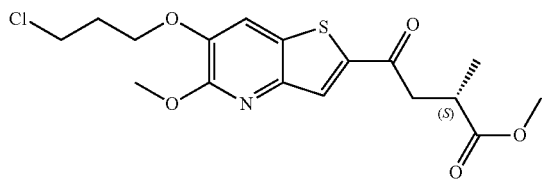

Step 1: 6-Bromothieno[3,2-b]pyridine

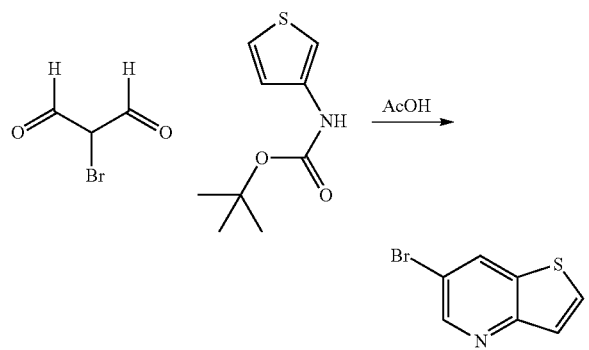

AcOH (50 mL) was added to a mixture of 2-bromomalonaldehyde (3.56 g, 23.6 mmol) and tert-butyl thiophen-3-ylcarbamate (4.70 g, 23.6 mmol) at RT under air atmosphere. The reaction mixture was stirred and heated to 100° C. for 24 h. The reaction mixture was then cooled to RT and diluted with EtOAc (300 mL). Sat aq NaHCO₃ was added until gas evolution ceased. The organic layer was separated, washed with brine (50 mL), dried over MgSO₄, filtered, and concentrated under reduced pressure. The residue was purified by silica gel chromatography (eluting EtOAc in Hex) to afford 6-bromothieno[3,2-b]pyridine. LCMS (C$_7$H$_5$BrNS) (ES, m/z): 214, 216 [M+H]⁺. ¹H NMR (499 MHz, DMSO-d₆) δ 8.86 (s, 1H), 8.74 (s, 1H), 8.18 (d, J=5.4 Hz, 1H), 7.58 (d, J=5.4 Hz, 1H).

Step 2: 6-Bromothieno[3,2-b]pyridine 4-oxide

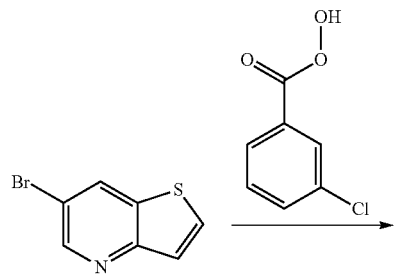

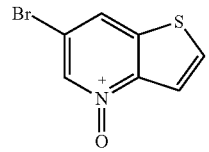

mCPBA (1.49 g, 6.63 mmol) was added to a mixture of 6-bromothieno[3,2-b]pyridine (1.42 g, 6.63 mmol) in DCM (50 mL) at 0° C. under Ar. The reaction mixture was then allowed to warm to RT and stirred for an additional 24 h. The reaction mixture was then concentrated under reduced pressure. The residue was purified by silica gel chromatography (eluting [5% MeOH in EtOAc] in DCM) to afford 6-bromothieno[3,2-b]pyridine 4-oxide. LCMS (C$_7$H$_5$BrNOS) (ES, m/z): 230, 232 [M+H]⁺.

Step 3: 6-Bromothieno[3,2-b]pyridin-5-yl acetate

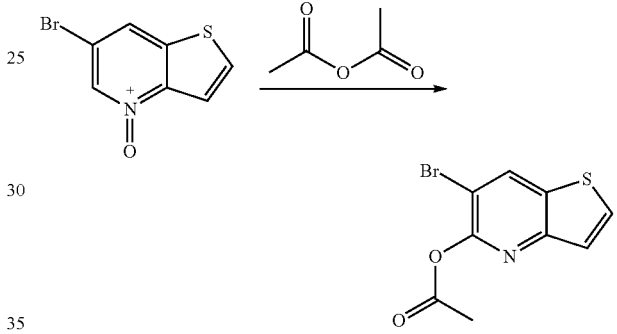

Acetic anhydride (20 mL, 210 mmol) was added to 6-bromothieno[3,2-b]pyridine 4-oxide (1.38 g, 6.00 mmol) at RT under N$_{2(g)}$. The reaction mixture was then heated to 140° C. and stirred for 4 h. The reaction mixture was then cooled to RT and diluted with EtOAc (200 mL) and H₂O (200 mL). NaHCO₃ was slowly added portionwise to the reaction mixture until all gas evolution ceased. The organic layer was separated, washed with brine (25 mL), dried over MgSO₄, filtered, and concentrated under reduced pressure. The residue was purified by silica gel chromatography (eluting [5% MeOH in EtOAc] in DCM) to afford 6-bromothieno[3,2-b] pyridin-5-yl acetate. LCMS (C$_9$H$_7$BrNO$_2$S—C$_2$H$_2$O) (ES, m/z): 230, 232 [M+H-acetate]⁺. ¹H NMR (499 MHz, DMSO-d₆) δ 9.04 (s, 1H), 8.29 (d, J=5.2 Hz, 1H), 7.54 (d, J=5.4 Hz, 1H), 2.41 (s, 3H).

Step 4: 6-Bromothieno[3,2-b]pyridin-5-ol

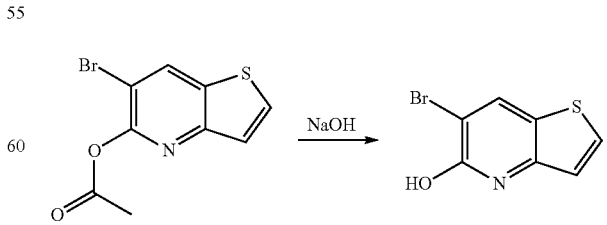

NaOH (2.0M in H₂O, 4.0 mL, 8.0 mmol) was added to a solution of 6-bromothieno [3,2-b]pyridin-5-yl acetate (431 mg, 1.58 mmol) in MeOH (5.0 mL) at 20° C. under N$_{2(g)}$.

The reaction mixture was then stirred for 1 h at 20° C. The reaction mixture was quenched with HCl (1.0M in H₂O, 8.0 mL, 8.0 mmol) and then diluted by the addition of H₂O (10 mL). The reaction mixture was stirred for 30 min and then filtered. The collected material was washed with additional H₂O (10 mL) and then dried under reduced pressure to afford 6-bromothieno[3,2-b]pyridin-5-ol. LCMS (C₇H₅BrNOS) (ES, m/z): 230, 232 [M+H]⁺. ¹H NMR (499 MHz, DMSO-d₆) δ 12.65 (s, 1H), 8.59 (s, 1H), 7.91 (d, J=5.3 Hz, 1H), 6.99 (d, J=5.1 Hz, 1H).

Step 5: 6-Bromo-5-chlorothieno[3,2-b]pyridine

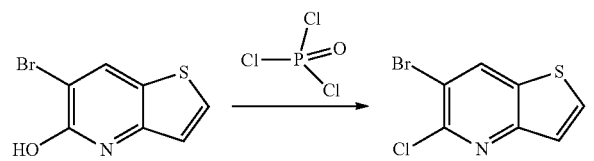 [SMILES: Oc1nc2ccsc2cc1Br ; O=P(Cl)(Cl)Cl ; Clc1nc2ccsc2cc1Br]

Phosphorus oxychloride (15.2 mL, 163 mmol) was added to 6-bromothieno[3,2-b]pyridin-5-ol (375 mg, 1.63 mmol) at 20° C. under N₂(g). The reaction mixture was then stirred and heated to 100° C. for 2 days. The reaction mixture was cooled to RT and quenched by the dropwise addition of the reaction mixture to a solution of aq sat NaHCO₃ solution. The reaction mixture was further diluted with EtOAc (250 mL) and stirred. The organic layer was separated, washed with brine (25 mL), dried over MgSO₄, filtered, and concentrated under reduced pressure to afford 6-bromo-5-chlorothieno[3,2-b]pyridine which was used without purification. LCMS (C₇H₄BrClNS) (ES, m/z): 248, 250 [M+H]⁺.

Step 6: 6-Bromo-5-methoxythieno[3,2-b]pyridine

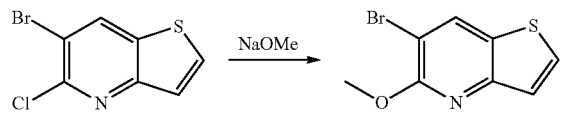

NaOMe (25% in MeOH, 3.24 mL, 14 mmol) was added to a mixture of 6-bromo-5-chlorothieno[3,2-b]pyridine (352 mg, 1.42 mmol) in MeOH (10 mL) at 20° C. under N₂(g). The reaction mixture was stirred and heated to 100° C. for 1 h in a microwave reactor. The reaction mixture was quenched with citric acid (1.0M in H₂O, 28 mL, 28 mmol) and diluted with EtOAc (250 mL). The organic layer was separated, washed with brine (25 mL), dried over MgSO₄, filtered, and concentrated under reduced pressure. The residue was purified by silica gel chromatography (eluting [5% MeOH in EtOAc] in DCM) to afford 6-bromo-5-methoxythieno [3,2-b]pyridine. LCMS (C₈H₇BrNOS) (ES, m/z): 244, 246 [M+H]⁺. ¹H NMR (499 MHz, DMSO-d₆) δ 8.78 (s, 1H), 8.09 (d, J=5.3 Hz, 1H), 7.44 (d, J=5.2 Hz, 1H), 3.99 (s, 3H).

Step 7: 6-Bromo-5-methoxythieno[3,2-b]pyridine-2-carboxylic acid

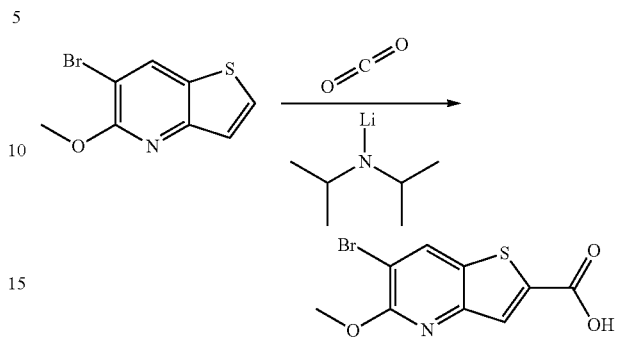

LDA (2.0M in THF, 12.3 mL, 24.6 mmol) was added to a solution of 6-bromo-5-methoxythieno[3,2-b]pyridine (5.0 g, 20 mmol) in THF (100 mL) at −78° C. The mixture was aged for 15 min, and was then quenched by the addition of CO₂(g) at −78° C. The reaction mixture was then warmed to 0° C. over 10 min. The reaction mixture was quenched with HCl (2.0M in water, 12.3 mL, 24.6 mmol) at 0° C. and then diluted with EtOAc (500 mL). The organic layer was separated, washed with brine (50 mL), dried over MgSO₄, filtered, and concentrated under reduced pressure. The residue was suspended in DCM (90 mL) and stirred for 1 h. Hex (250 mL) were then added dropwise via an addition funnel over a period of ~4 h at RT. The resulting suspension was then stirred for an additional 16 h at RT. The suspension was then filtered, and the residue was washed with a 4:1 mixture of Hex/DCM (50 mL). The residue was dried under vacuum to afford 6-bromo-5-methoxythieno[3,2-b]pyridine-2-carboxylic acid. LCMS (C₉H₇BrNO₃S) (ES, m/z): 288, 290 [M+H]⁺. ¹H NMR (499 MHz, DMSO-d₆) δ 13.79 (s, 1H), 8.87 (s, 1H), 7.93 (s, 1H), 4.01 (s, 3H).

Step 8: 6-Bromo-5-methoxythieno[3,2-b]pyridine-2-carbonyl chloride

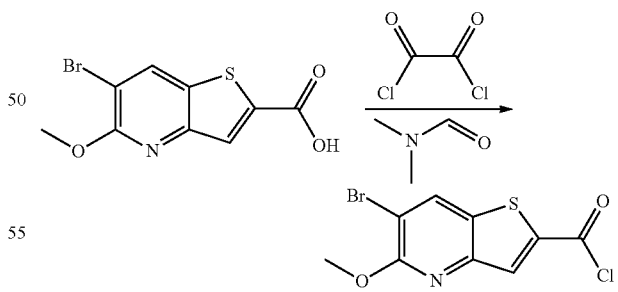

DMF (8 µl, 0.1 mmol) was added to a solution of 6-bromo-5-methoxythieno[3,2-b]pyridine-2-carboxylic acid (1.05 g, 3.64 mmol) and oxalyl chloride (0.64 mL, 7.3 mmol) in THF (40 mL) at 0° C. under Ar. The reaction mixture was stirred at 0° C. for 1 h. The reaction mixture was concentrated under reduced pressure to afford 6-bromo-5-methoxythieno[3,2-b]pyridine-2-carbonyl chloride, which was used directly in the subsequent step.

Step 9: Methyl (S)-4-(6-bromo-5-methoxythieno[3,2-b]pyridin-2-yl)-2-methyl-4-oxobutanoate

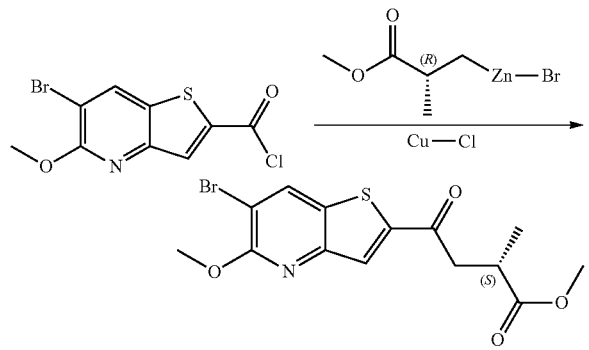

A solution of (R)-(3-methoxy-2-methyl-3-oxopropyl)zinc (II) bromide (0.5M in THF, 14.6 mL, 7.29 mmol) was added slowly to an oven-dried flask containing copper(I) chloride (0.361 g, 3.64 mmol) under Ar at 0° C. The reaction mixture was stirred for 20 min at 0° C. under Ar. An Ar-degassed solution of 6-bromo-5-methoxythieno[3,2-b]pyridine-2-carbonyl chloride (1.12 g, 3.64 mmol) in THF (10 mL) and NMP (5.0 mL) was then added slowly via cannula to the reaction mixture at 0° C.; the resulting solution was warmed to RT and was stirred for an additional 18 h at RT. The reaction mixture was cooled to 0° C. and quenched by the addition of a solution of sat aq NH$_4$Cl (50 mL) and EtOAc (100 mL). The resulting biphasic mixture was warmed to RT and stirred for an additional 1 h. The mixture was then filtered, and the filtrate was diluted with additional EtOAc (250 mL) and brine (50 mL). The organic layer was separated, washed with additional brine (50 mL), dried over MgSO$_4$, filtered, and concentrated under reduced pressure. The residue was purified by silica gel chromatography (EtOAc/Hex) to afford (S)-methyl 4-(6-bromo-5-methoxythieno[3,2-b]pyridin-2-yl)-2-methyl-4-oxobutanoate. LCMS (C$_{14}$H$_{15}$BrNO$_4$S) (ES, m/z): 372, 374 [M+H]$^+$. $^1$H NMR (499 MHz, DMSO-d$_6$) δ 8.87 (s, 1H), 8.37 (s, 1H), 4.02 (s, 3H), 3.59 (s, 3H), 3.52 (dd, J=17.9, 8.7 Hz, 1H), 3.27 (dd, J=18.0, 4.5 Hz, 1H), 3.03-2.91 (m, 1H), 1.20 (d, J=7.1 Hz, 3H).

Step 10: (S)-(5-Methoxy-2-(4-methoxy-3-methyl-4-oxobutanoyl)thieno[3,2-b]pyridin-6-yl)boronic acid

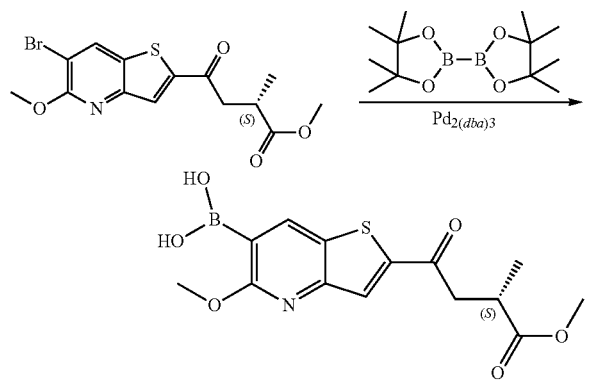

A mixture of (S)-methyl 4-(6-bromo-5-methoxythieno[3,2-b]pyridin-2-yl)-2-methyl-4-oxobutanoate (700 mg, 1.88 mmol), 4,4,4',4',5,5,5',5'-octamethyl-2,2'-bi(1,3,2-dioxaborolane) (597 mg, 2.351 mmol), Pd$_2$(dba)$_3$ (43 mg, 0.047 mmol), tricyclohexylphosphine (53 mg, 0.19 mmol), and potassium acetate (oven dried) (295 mg, 3.01 mmol) was degassed with Ar for 5 min. Dioxane (15 mL) was added at RT, and the resulting mixture was degassed with Ar for 5 min. The reaction mixture was then heated to 80° C. and stirred for 18 h under Ar. The reaction mixture was cooled to RT and then diluted with EtOAc (20 mL). The suspension was stirred at RT for 10 min, and then filtered through CELITE, washing with EtOAc (20 mL). The filtrate was concentrated under reduced pressure to afford (S)-(5-methoxy-2-(4-methoxy-3-methyl-4-oxobutanoyl)thieno[3,2-b]pyridin-6-yl)boronic acid, which was used without purification in the subsequent step. LCMS (C$_{14}$H$_{17}$BNO$_6$S) (ES, m/z): 338 [M+H]$^+$.

Step 11: Methyl (S)-4-(6-hydroxy-5-methoxythieno f3,2-b/pyridin-2-yl)-2-methyl-4-oxobutanoate

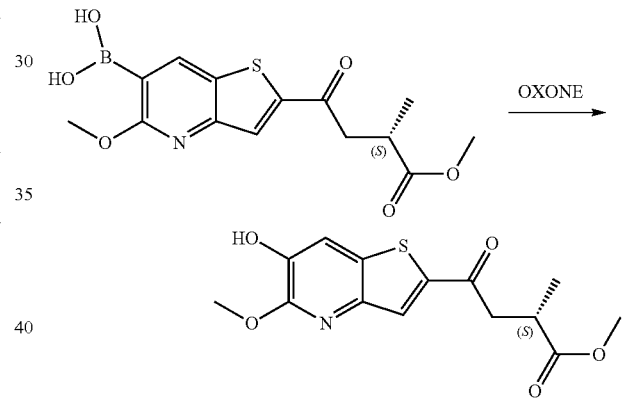

A solution of OXONE® (KHSO$_5$.½KHSO$_4$.½K$_2$SO$_4$; 0.2M in water, 14.10 mL, 2.82 mmol) was added to a mixture of (S)-(5-methoxy-2-(4-methoxy-3-methyl-4-oxobutanoyl) thieno[3,2-b]pyridin-6-yl)boronic acid (634 mg, 1.88 mmol) in acetone (20 mL) at RT. The reaction mixture was stirred at RT for 30m. The reaction mixture was quenched by the addition of a solution of sodium bisulfite (587 mg, 5.64 mmol) in water (5 mL) and then stirred for 5 min. The reaction mixture was diluted with DCM (200 mL). The organic layer was separated, and the aqueous layer was washed with additional DCM (2×50 mL). The organic layers were combined, dried over MgSO$_4$, filtered, and concentrated under reduced pressure. The residue was purified by silica gel chromatography (EtOAc/DCM) to afford (S)-methyl 4-(6-hydroxy-5-methoxythieno [3,2-b]pyridin-2-yl)-2-methyl-4-oxobutanoate. LCMS (C$_{14}$H$_{16}$NO$_5$S) (ES, m/z): 310 [M+H]$^+$. $^1$H NMR (600 MHz, DMSO-d$_6$) δ 10.46 (s, 1H), 8.23 (s, 1H), 7.66 (s, 1H), 3.97 (s, 3H), 3.60 (s, 3H), 3.44 (dd, J=17.5, 8.6 Hz, 1H), 3.20 (dd, J=17.5, 5.0 Hz, 1H), 3.00-2.92 (m, 1H), 1.19 (d, J=7.2 Hz, 3H).

303

Step 12: Methyl (S)-4-(6-(3-chloropropoxy)-5-methoxythieno[3,2-b]pyridin-2-yl)-2-methyl-4-oxobutanoate

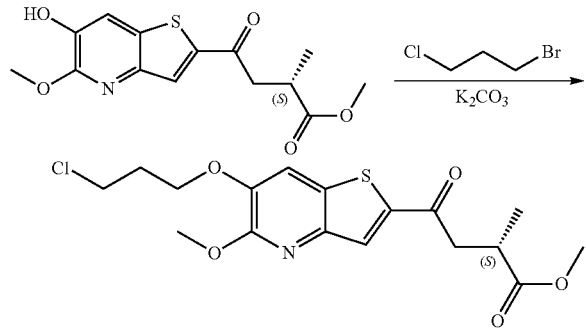

1-Bromo-3-chloropropane (244 mg, 1.55 mmol) was added to a mixture of (S)-methyl 4-(6-hydroxy-5-methoxythieno[3,2-b]pyridin-2-yl)-2-methyl-4-oxobutanoate (96 mg, 0.31 mmol) and potassium carbonate (257 mg, 1.86 mmol) in DMF (1.0 mL) at RT. The reaction mixture was stirred and heated to 50° C. for 4 h. The reaction mixture was cooled to RT and filtered, and then the solvate was purified directly by silica gel chromatography (EtOAc/DCM) to afford (S)-methyl 4-(6-(3-chloropropoxy)-5-methoxythieno[3,2-b]pyridin-2-yl)-2-methyl-4-oxobutanoate. LCMS ($C_{17}H_{21}ClNO_5S$) (ES, m/z): 386 [M+H]+.

Intermediate 97: Methyl (S)-4-(5-(3-bromopropyl)-4-fluoro-6-methoxybenzo[b]thiophen-2-yl)-2-methyl-4-oxobutanoate

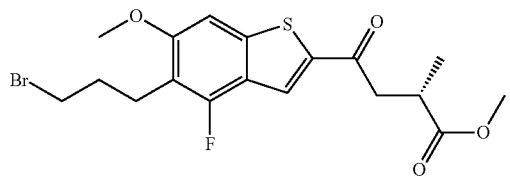 [SMILES: COC(=O)[C@@H](C)CC(=O)c1cc2c(F)c(CCCBr)c(OC)cc2s1]

Step 1: Methyl (S)-4-(4-fluoro-6-methoxy-5-(((trifluoromethyl)sulfonyl)oxy)benzo[b]thiophen-2-yl)-2-methyl-4-oxobutanoate

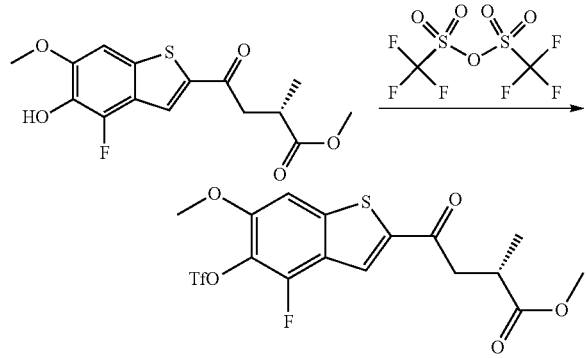

304

Methyl (S)-4-(4-fluoro-5-hydroxy-6-methoxybenzo[b]thiophen-2-yl)-2-methyl-4-oxobutanoate (750 mg, 2.30 mmol), DCM (10 mL), Hunig's base (2.0 mL, 11 mmol), and trifluoromethanesulfonic anhydride (1.0M in DCM, 3.5 mL, 3.5 mmol) were combined. The reaction mixture was stirred at RT for 20 min. The reaction mixture was then quenched with water and diluted with DCM. The organic layer was separated, washed with sat NaHCO$_3$, dried over Na$_2$SO$_4$, filtered, and concentrated under reduced pressure. The residue was purified by silica gel chromatography (EtOAc/Hex) to afford (S)-methyl 4-(4-fluoro-6-methoxy-5-(((trifluoromethyl)sulfonyl)oxy)benzo[b]thiophen-2-yl)-2-methyl-4-oxobutanoate. LCMS ($C_{16}H_{15}F_4O_7S_2$) (ES, m/z): 459 [M+H]+. $^1$H NMR (600 MHz, DMSO-d$_6$) δ 8.52 (s, 1H), 7.93 (s, 1H), 4.03 (s, 3H), 3.61 (s, 3H), 3.53 (dd, J=17.8, 8.7 Hz, 1H), 3.27 (dd, J=17.8, 5.0 Hz, 1H), 3.05-2.92 (m, 1H), 1.21 (d, J=7.2 Hz, 3H).

Step 2: Methyl (2S)-4-(4-fluoro-6-methoxy-5-(3-((tetrahydro-2H-pyran-2-yl)oxy)propyl)benzo[b]thiophen-2-yl)-2-methyl-4-oxobutanoate

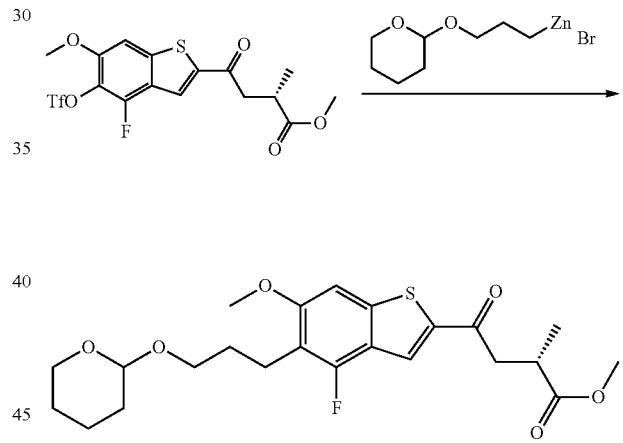

(S)-Methyl 4-(4-fluoro-6-methoxy-5-(((trifluoromethyl)sulfonyl)oxy)benzo-[b]thiophen-2-yl)-2-methyl-4-oxobutanoate (1.00 g, 2.18 mmol), CPhos Pd G4 (0.088 g, 0.11 mmol), and (3-((tetrahydro-2H-pyran-2-yl)oxy)propyl)zinc (II) bromide (0.50M in THF, 8.7 mL, 4.4 mmol) were combined in a vial. The reaction mixture was heated at 40° C. for 2 h. The reaction mixture was filtered through CELITE and then concentrated under reduced pressure. The residue was purified by silica gel chromatography (EtOAc/Hex) to afford methyl (2S)-4-(4-fluoro-6-methoxy-5-(3-((tetrahydro-2H-pyran-2-yl)oxy)propyl)benzo[b]thiophen-2-yl)-2-methyl-4-oxobutanoate. LCMS ($C_{23}H_{30}FO_6S$) (ES, m/z): 453 [M+H]+. $^1$H NMR (600 MHz, DMSO-d$_6$) δ 8.31 (s, 1H), 7.52 (s, 1H), 4.54 (t, J=3.4 Hz, 1H), 3.92 (s, 3H),

305

3.75-3.70 (m, 1H), 3.69-3.62 (m, 1H), 3.60 (s, 3H), 3.49 (dd, J=17.7, 8.7 Hz, 1H), 3.44-3.39 (m, 1H), 3.38-3.28 (m, 1H), 3.25 (dd, J=17.6, 5.0 Hz, 1H), 3.02-2.92 (m, 1H), 2.80-2.70 (m, 2H), 1.84-1.76 (m, 2H), 1.76-1.67 (m, 1H), 1.63-1.57 (m, 1H), 1.50-1.40 (m, 4H), 1.20-1.17 (m, 3H).

Step 3: Methyl (S)-4-(5-(3-bromopropyl)-4-fluoro-6-methoxybenzo[b]thiophen-2-yl)-2-methyl-4-oxobutanoate -continued

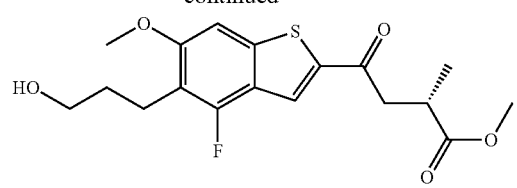

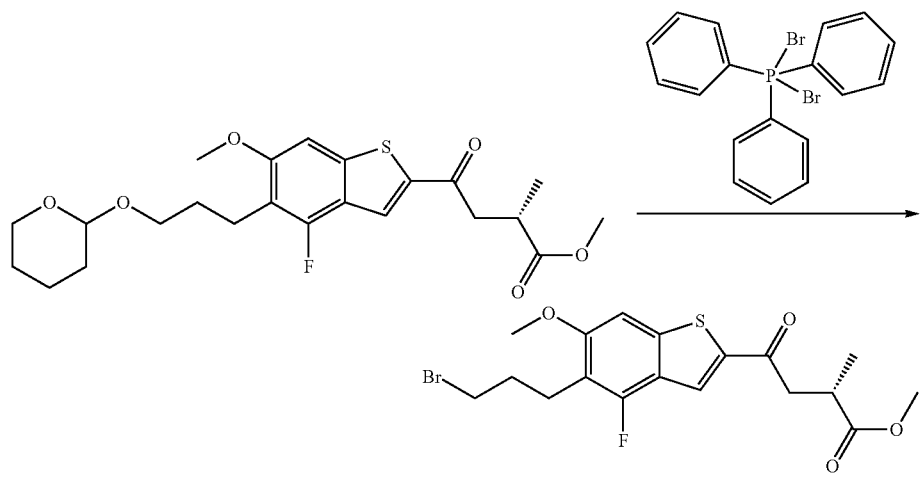

Methyl (2S)-4-(4-fluoro-6-methoxy-5-(3-((tetrahydro-2H-pyran-2-yl)oxy) propyl)benzo[b]thiophen-2-yl)-2-methyl-4-oxobutanoate (350 mg, 0.773 mmol) and DCM (5 mL) were combined in a vial. Triphenylphosphine dibromide (653 mg, 1.55 mmol) was to the reaction mixture and stirred for 30 min. The reaction mixture was quenched with water. The organic layer was separated, dried over Na$_2$SO$_4$, filtered, and concentrated under reduced pressure. The residue was purified by silica gel chromatography (EtOAc/Hex) to afford methyl (S)-4-(5-(3-bromopropyl)-4-fluoro-6-methoxybenzo[b]thiophen-2-yl)-2-methyl-4-oxobutanoate. LCMS (C$_{18}$H$_{21}$BrFO$_4$S) (ES, m/z): 431, 433 [M+H]$^+$.

Methyl (2S)-4-(4-fluoro-6-methoxy-5-(3-((tetrahydro-2H-pyran-2-yl)oxy)propyl) benzo[b]thiophen-2-yl)-2-methyl-4-oxobutanoate (350 mg, 0.773 mmol), MeOH (5 mL) and Mp-TsOH (1.00 g, 4.33 mmol) were combined in a vial. The reaction mixture was shaken for 2 h. The reaction mixture was then filtered, washed with MeOH, and concentrated under reduced pressure to afford methyl (S)-4-(4-fluoro-5-(3-hydroxypropyl)-6-methoxybenzo[b]thiophen-2-yl)-2-methyl-4-oxobutanoate. LCMS (C$_{18}$H$_{22}$FO$_5$S) (ES, m/z): 369 [M+H]$^+$. $^1$H NMR (600 MHz, DMSO-d$_6$) δ 8.31 (s, 1H), 7.51 (s, 1H), 3.92 (s, 3H), 3.60 (s, 3H), 3.50 (dd, J=17.7, 8.7 Hz, 1H), 3.44 (t, J=6.5 Hz, 2H), 3.25 (dd, J=17.4, 4.7 Hz, 1H), 3.02-2.93 (m, 1H), 2.71 (t, J=7.4 Hz, 2H), 1.69-1.63 (m, 2H), 1.20 (d, J=7.0 Hz, 3H).

Intermediate 98: Methyl (S)-4-(4-fluoro-5-(3-hydroxypropyl)-6-methoxybenzo[b]thiophen-2-yl)-2-methyl-4-oxobutanoate Intermediate 99: Methyl 2-(4-fluoro-5-hydroxy-6-methoxybenzo[b]thiophene-2-carbonyl) cyclopropane-1-carboxylate

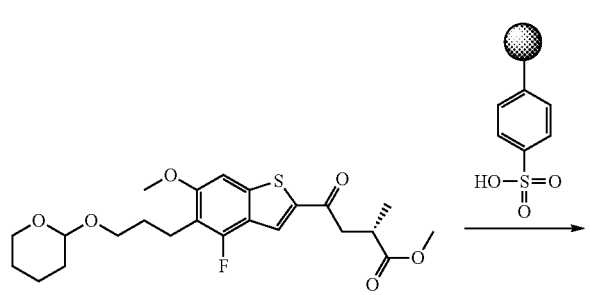

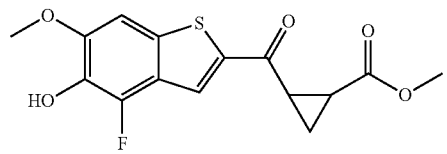

307

Step 1: 2-(4-Fluoro-5,6-dimethoxybenzo[b]thio-phene-2-carbonyl)cyclopropane-1-carboxylic acid

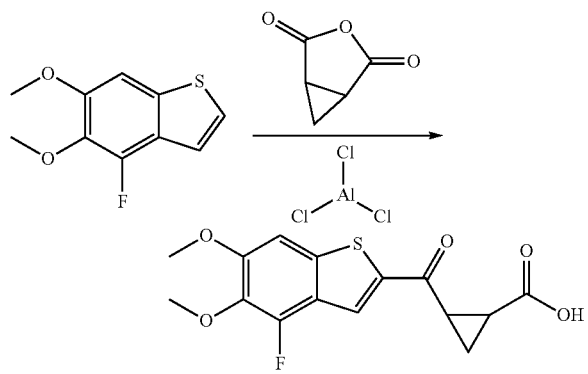

Aluminum chloride (0.923 g, 6.92 mmol) was added to a mixture of 4-fluoro-5,6-dimethoxybenzo[b]thiophene (1.13 g, 5.32 mmol) and 3-oxabicyclo[3.1.0]hexane-2,4-dione (1.19 g, 10.7 mmol) in DCM (20.0 mL) at 0° C. The reaction mixture was warmed to RT and then stirred for 18 h. The reaction mixture was cooled to 0° C. and quenched with water (50 mL). The mixture was then diluted with EtOAc (500 mL). The organic layer was separated, washed with brine, dried over MgSO$_4$, filtered, and concentrated under reduced pressure to afford 2-(4-fluoro-5,6-dimethoxybenzo[b]thiophene-2-carbonyl)cyclopropane-1-carboxylic acid, which was used without purification in the subsequent step. LCMS (C$_{15}$H$_{14}$FO$_5$S) (ES, m/z): 325 [M+H]$^+$.

Step 2: Methyl 2-(4-fluoro-5,6-dimethoxybenzo[b]thiophene-2-carbonyl)cyclopropane-1-carboxylate

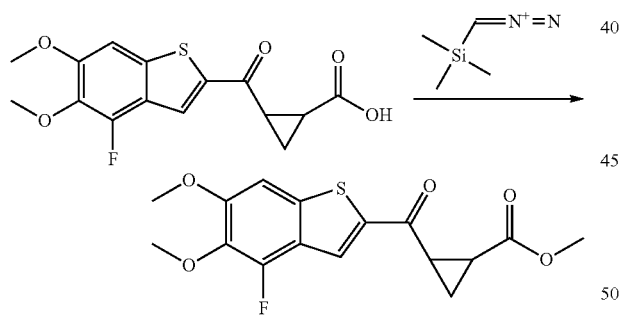

TMS-diazomethane (2.0M in diethyl ether, 4.3 mL, 8.6 mmol) was added dropwise to a mixture of 2-(4-fluoro-5,6-dimethoxybenzo[b]thiophene-2-carbonyl)cyclopropanecarboxylic acid (1.40 g, 4.32 mmol) in DCM (20 mL) and MeOH (20 mL) at 0° C. The reaction mixture was stirred at 0° C. for 15 min. The reaction mixture was quenched with HOAc. The reaction mixture was then concentrated under reduced pressure. The residue was purified by silica gel chromatography (EtOAc/DCM) to afford methyl 2-(4-fluoro-5,6-dimethoxybenzo[b]thiophene-2-carbonyl)cyclo-propanecarboxylate. LCMS (C$_{16}$H$_{16}$FO$_5$S) (ES, m/z): 339 [M+H]$^+$. $^1$H NMR (499 MHz, DMSO-d$_6$) δ 8.48 (s, 1H), 7.59 (s, 1H), 3.93 (s, 3H), 3.87 (s, 3H), 3.48 (s, 3H), 3.31-3.25 (m, 1H), 2.47-2.41 (m, 1H), 1.62-1.58 (m, 1H), 1.44-1.40 (m, 1H).

308

Step 3: Methyl 2-(4-fluoro-5-hydroxy-6-methoxy-benzo[b]thiophene-2-carbonyl)cyclopropane-1-carboxylate

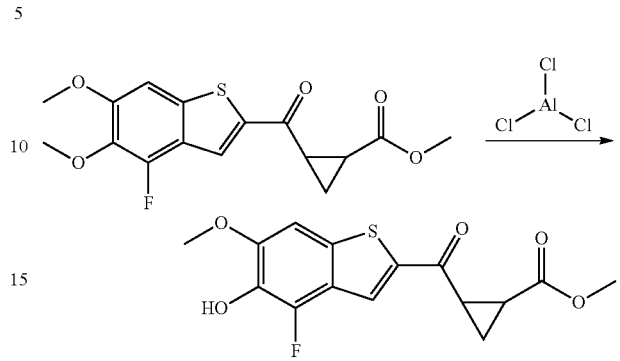

Aluminum chloride (2.66 g, 20.0 mmol) was added portionwise to a mixture of methyl 2-(4-fluoro-5,6-dimethoxybenzo[b]thiophene-2-carbonyl)cyclopropanecarboxylate (1.50 g, 4.43 mmol) in DCM (40 mL) at RT. The reaction mixture was stirred at RT for 6 h under Ar. The reaction mixture was cooled to 0° C. and then quenched slowly with water (50 mL). The reaction mixture was diluted with additional DCM (250 mL). The organic layer was separated, washed with brine (25 mL), dried over MgSO$_4$, filtered, and concentrated under reduced pressure. The residue was purified by silica gel chromatography (EtOAc/DCM) to afford methyl 2-(4-fluoro-5-hydroxy-6-methoxybenzo[b]thiophene-2-carbonyl)cyclopropanecarboxylate. LCMS (C$_{15}$H$_{14}$FO$_5$S) (ES, m/z): 325 [M+H]$^+$. $^1$H NMR (499 MHz, DMSO-d$_6$) δ 9.55 (s, 1H), 8.29 (s, 1H), 7.48 (s, 1H), 3.92 (s, 3H), 3.48 (s, 3H), 3.30-3.23 (m, 1H), 2.45-2.39 (m, 1H), 1.61-1.57 (m, 1H), 1.43-1.38 (m, 1H).

Intermediate 100: Methyl (R)-4-(5-(3-bromopropyl)-6-methoxybenzo[b]thiophen-2-yl)-2-methyl-4-oxobutanoate

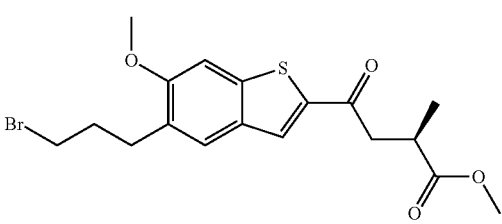 [SMILES: COC(=O)[C@H](C)CC(=O)c1cc2cc(CCCBr)c(OC)cc2s1]

Step 1: Methyl (R)-4-(5-bromo-6-methoxybenzo[b]thiophen-2-yl)-2-methyl-4-oxobutanoate

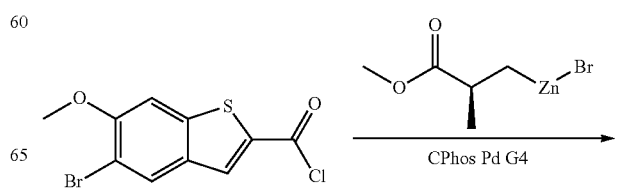

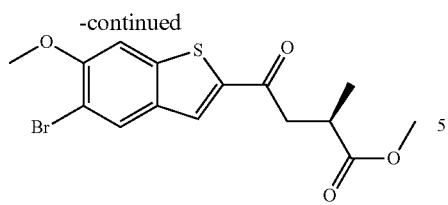

5-Bromo-6-methoxybenzo[b]thiophene-2-carbonyl chloride (3.00 g, 9.82 mmol) and THF (98 ml) were combined. The reaction mixture was then degassed with Ar for 10 min. CPhos Pd G4 (0.081 g, 0.098 mmol) was added to the reaction mixture, and the mixture was cooled to 0° C. (S)-(3-methoxy-2-methyl-3-oxopropyl)zinc(II) bromide (0.50M in THF, 21 mL, 11 mmol) was then added to the reaction mixture via addition funnel. The mixture was stirred at 0° C. for 1 h. The reaction mixture was quenched with sat aq NH$_4$Cl and diluted with EtOAc. The organic layer was separated, dried over MgSO$_4$, filtered, and concentrated under reduced pressure. The residue was purified by silica gel chromatography (EtOAc/hex) to afford methyl (R)-4-(5-bromo-6-methoxybenzo[b]thiophen-2-yl)-2-methyl-4-oxobutanoate. LCMS (C$_{15}$H$_{16}$BrO$_4$S) (ES, m/z): 371, 373 [M+H]$^+$. $^1$H NMR (499 MHz, DMSO-d$_6$) δ 8.28-8.26 (m, 2H), 7.82 (s, 1H), 3.95 (s, 3H), 3.60 (s, 3H), 3.44 (dd, J=17.6, 8.6 Hz, 1H), 3.21 (dd, J=17.6, 5.1 Hz, 1H), 3.03-2.93 (m, 1H), 1.20 (d, J=7.2 Hz, 3H).

Step 2: Methyl (R)-4-(5-(3-((tert-butyldimethylsilyl)oxy)propyl)-6-methoxybenzo[b]thiophen-2-yl)-2-methyl-4-oxobutanoate

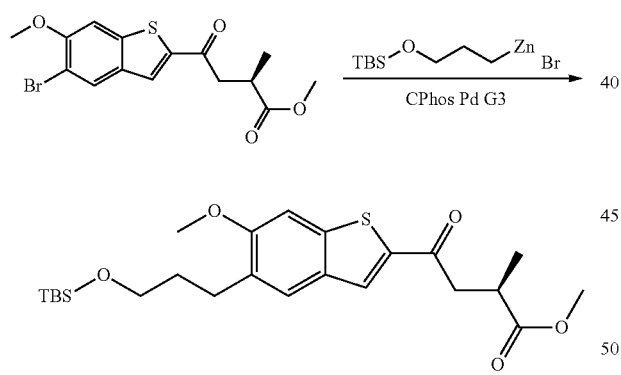

CPhos Pd G3 (174 mg, 0.215 mmol) and then (3-((tert-butyldimethylsilyl)oxy) propyl)zinc(II) bromide (0.50M in THF, 9.7 mL, 4.9 mmol) were added to a mixture of (R)-methyl 4-(5-bromo-6-methoxybenzo[b]thiophen-2-yl)-2-methyl-4-oxobutanoate (1.00 g, 2.69 mmol) in THF (13.5 mL). The reaction mixture was heated at 40° C. for 3 h. The reaction mixture was cooled to RT, quenched with water, and diluted with EtOAc. The organic layer was separated, dried over MgSO$_4$, filtered, and concentrated under reduced pressure. The residue was purified by silica gel chromatography (EtOAc/Hex) to afford methyl (R)-4-(5-(3-((tert-butyldimethylsilyl)oxy)propyl)-6-methoxybenzo[b]thiophen-2-yl)-2-methyl-4-oxobutanoate. LCMS (C$_{24}$H$_{37}$O$_5$SSi) (ES, m/z): 465 [M+H]$^+$.

Step 3: Methyl (R)-4-(5-(3-hydroxypropyl)-6-methoxybenzo[b]thiophen-2-yl)-2-methyl-4-oxobutanoate

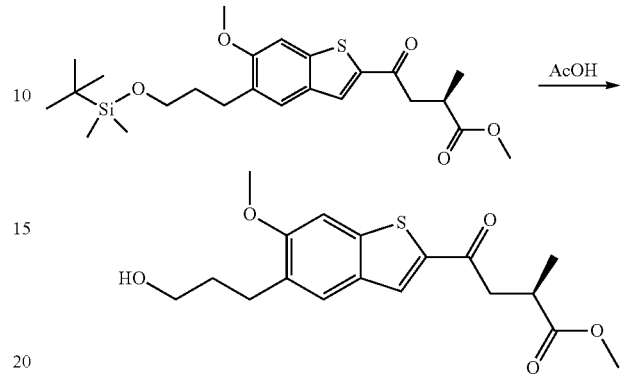

(R)-Methyl 4-(5-(3-((tert-butyldimethylsilyl)oxy)propyl)-6-methoxybenzo[b]thiophen-2-yl)-2-methyl-4-oxobutanoate (1.04 g, 2.24 mmol) was suspended in a mixture of MeOH (4 mL), water (4 mL) and HOAc (4 mL). The reaction mixture was stirred at RT for 3.5 h. The reaction mixture was diluted with EtOAc and water. The aqueous layer was separated and extracted with additional EtOAc (3×). The organic layers were combined, washed with brine, dried over Na$_2$SO$_4$, filtered, and concentrated under reduced pressure. The residue was purified by silica gel chromatography (EtOAc/Hex) to afford methyl (R)-4-(5-(3-hydroxypropyl)-6-methoxybenzo[b]thiophen-2-yl)-2-methyl-4-oxobutanoate. LCMS (C$_{18}$H$_{23}$O$_5$S) (ES, m/z): 351 [M+H]$^+$.

Step 4: Methyl (R)-4-(5-(3-bromopropyl)-6-methoxybenzo[b]thiophen-2-yl)-2-methyl-4-oxobutanoate

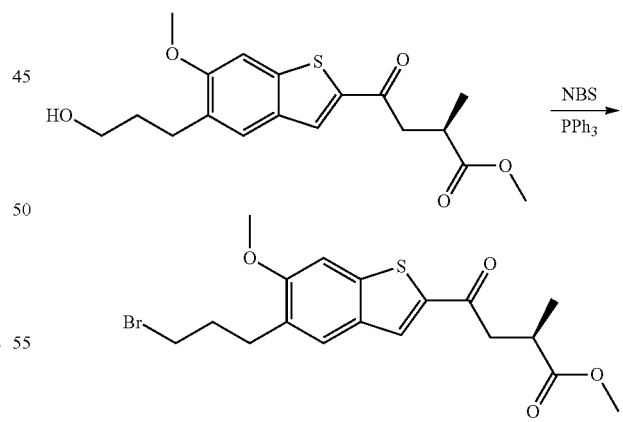

NBS (518 mg, 2.91 mmol) was added to a mixture of (R)-methyl 4-(5-(3-hydroxypropyl)-6-methoxybenzo[b]thiophen-2-yl)-2-methyl-4-oxobutanoate (680 mg, 1.94 mmol) and triphenylphosphine (814 mg, 3.10 mmol) in THF (9.7 mL) at 0° C. After 1.5 h, the reaction mixture was quenched with sat aq NH$_4$Cl and then diluted with EtOAc. The organic layer was separated, washed with brine, dried over MgSO$_4$, filtered, and concentrated under reduced pressure. The residue was purified by silica gel chromatography (EtOAc/Hex) to afford methyl (R)-4-(5-(3-bromopropyl)-6-methoxybenzo[b]thiophen-2-yl)-2-methyl-4-oxobutanoate. LCMS ($C_{18}H_{22}BrO_4S$) (ES, m/z): 413, 415 [M+H]$^+$. $^1$H NMR (499 MHz, DMSO-d$_6$) δ 8.27 (s, 1H), 7.77 (s, 1H), 7.62 (s, 1H), 3.90 (s, 3H), 3.60 (s, 3H), 3.55 (t, J=6.6 Hz, 2H), 3.43 (dd, J=17.5, 8.6 Hz, 1H), 3.20 (dd, J=17.5, 5.1 Hz, 1H), 3.04-2.94 (m, 1H), 2.83-2.77 (m, 2H), 2.14-2.08 (m, 2H), 1.20 (d, J=7.2 Hz, 3H).

Intermediates 101, 102, 103, and 104: Methyl (1R, 2R or 1S,2S)-2-(4-fluoro-6-hydroxy-5-methoxy-benzo[b]thiophene-2-carbonyl)cyclobutane-1-carboxylate, methyl (1R,2R or 1S,2S)-2-(4-fluoro-6-hydroxy-5-methoxybenzo[b]thiophene-2-carbonyl)cyclobutane-1-carboxylate, methyl (1R,2R or 1S,2S)-2-(4-fluoro-5-hydroxy-6-methoxybenzo[b]thiophene-2-carbonyl)cyclobutane-1-carboxylate, methyl (1R,2R or 1S,2S)-2-(4-fluoro-5-hydroxy-6-methoxybenzo[b]thiophene-2-carbonyl)cyclobutane-1-carboxylate

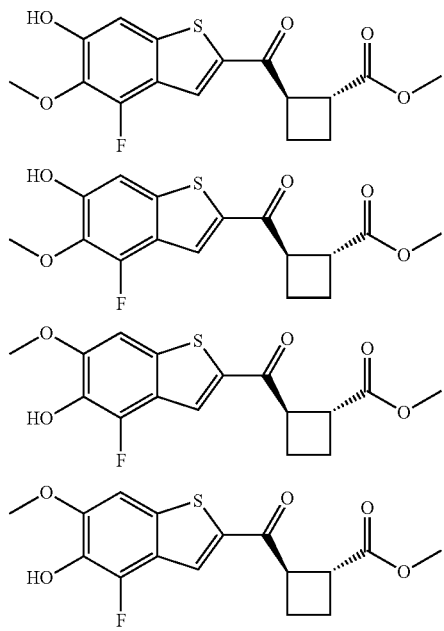

Step 1: (cis)-2-(4-Fluoro-5,6-dimethoxybenzo[b]thiophene-2-carbonyl)cyclobutane-1-carboxylic acid

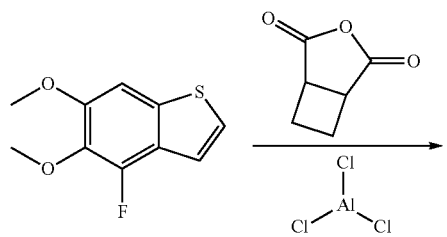

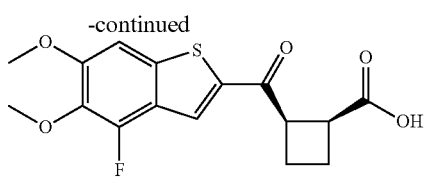

Aluminum chloride (776 mg, 5.82 mmol) was added to a mixture of 4-fluoro-5,6-dimethoxybenzo[b]thiophene (950 mg, 4.48 mmol) and 3-oxabicyclo[3.2.0]heptane-2,4-dione (1130 mg, 8.95 mmol) in DCM (20.0 mL) at 0° C. The reaction mixture was warmed to RT and then stirred for 18 h. The reaction mixture was cooled to 0° C. and then quenched by the dropwise addition of water (50 mL). The mixture was then diluted with additional DCM (200 mL). The organic layer was separated, washed with brine, dried over MgSO$_4$, filtered, and concentrated under reduced pressure to afford (cis)-2-(4-fluoro-5,6-dimethoxybenzo[b]thiophene-2-carbonyl)cyclobutane-1-carboxylic acid, which was used without purification in the next step. LCMS ($C_{16}H_{16}FO_5S$) (ES, m/z): 339 [M+H]$^+$.

Step 2: Methyl (cis)-2-(4-fluoro-5,6-dimethoxy-benzo[b]thiophene-2-carbonyl)cyclobutane-1-carboxylate

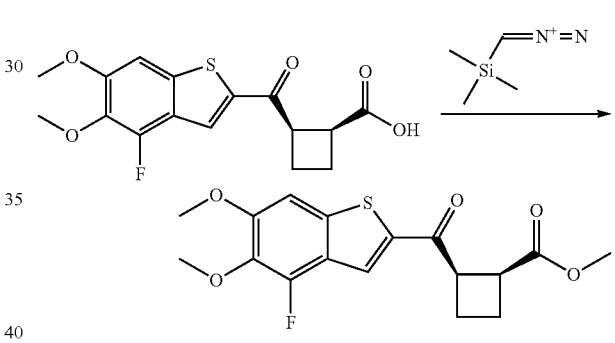

TMS-diazomethane (2.0M in diethyl ether, 4.0 mL, 8.0 mmol) was added dropwise to a mixture of (cis)-2-(4-fluoro-5,6-dimethoxybenzo[b]thiophene-2-carbonyl)cyclobutane carboxylic acid (1.35 g, 3.99 mmol) in DCM (20 mL) and MeOH (20 mL) at 0° C. The reaction mixture was stirred at 0° C. for 15 min. The reaction mixture was quenched with HOAc. The reaction mixture was then concentrated under reduced pressure. The residue was purified by silica gel chromatography (EtOAc/DCM) to afford (cis)-methyl 2-(4-fluoro-5,6-dimethoxybenzo [b]thiophene-2-carbonyl)cyclobutanecarboxylate. LCMS ($C_{17}H_{18}FO_5S$) (ES, m/z): 353 [M+H]$^+$. $^1$H NMR (499 MHz, DMSO-d$_6$) δ 8.15 (s, 1H), 7.58 (s, 1H), 4.59-4.50 (m, 1H), 3.93 (s, 3H), 3.86 (s, 3H), 3.68 (q, J=8.9, 8.5 Hz, 1H), 3.41 (s, 3H), 2.34-2.10 (m, 4H).

Step 3: (trans)-2-(4-Fluoro-5,6-dimethoxybenzo[b]thiophene-2-carbonyl)cyclobutane-1-carboxylic acid

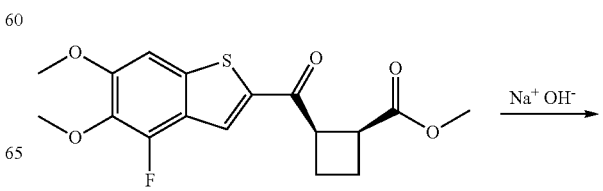

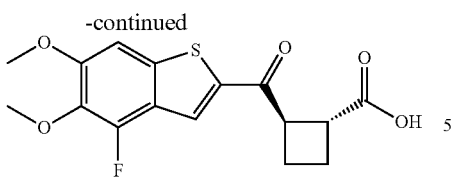

NaOH (5.0M, 1.8 mL, 9.0 mmol) was added to a mixture of (cis)-methyl 2-(4-fluoro-5,6-dimethoxybenzo[b]thiophene-2-carbonyl)cyclobutanecarboxylate (650 mg, 1.85 mmol) in MeOH (25 mL) at RT. The reaction mixture was stirred at RT for 4 h. The reaction mixture was quenched with TFA (0.85 mL, 11 mmol) and then diluted with DCM (250 mL). The organic layer was separated, washed with brine (50 mL), dried over MgSO$_4$, filtered, and concentrated under reduced pressure. The residue was purified by silica gel chromatography (MeOH/DCM) to afford (trans)-2-(4-fluoro-5,6-dimethoxybenzo[b]thiophene-2-carbonyl)cyclobutanecarboxylic acid. LCMS ($C_{16}H_{16}FO_5S$) (ES, m/z): 339 [M+H]$^+$.

clobutane carboxylic acid (570 mg, 1.69 mmol) in DCM (20 mL) and MeOH (20 mL) at 0° C. The reaction mixture was stirred at 0° C. for 15 min. The reaction mixture was quenched with HOAc. The reaction mixture was then concentrated under reduced pressure. The residue was purified by silica gel chromatography (EtOAc/DCM) to afford (trans)-methyl 2-(4-fluoro-5,6-dimethoxy benzo[b]thiophene-2-carbonyl)cyclobutanecarboxylate. LCMS ($C_{17}H_{18}FO_5S$) (ES, m/z): 353 [M+H]$^+$. $^1$H NMR (499 MHz, DMSO-d$_6$) δ 8.22 (s, 1H), 7.60 (s, 1H), 4.42 (q, J=9.0 Hz, 1H), 3.93 (s, 3H), 3.86 (s, 3H), 3.63 (s, 3H), 3.58-3.48 (m, 1H), 2.38-2.30 (m, 1H), 2.26-2.18 (m, 1H), 2.17-2.10 (m, 2H).

Step 5: Methyl (1R,2R or 1S,2S)-2-(4-fluoro-6-hydroxy-5-methoxybenzo[b]thiophene-2-carbonyl) cyclobutane-1-carboxylate, methyl (1R,2R or 1S,2S)-2-(4-fluoro-6-hydroxy-5-methoxybenzo[b] thiophene-2-carbonyl)cyclobutane-1-carboxylate, methyl (1R,2R or 1S,2S)-2-(4-fluoro-5-hydroxy-6-methoxybenzo[b]thiophene-2-carbonyl)cyclobutane-1-carboxylate, methyl (1R,2R or 1S,2S)-2-(4-fluoro-5-hydroxy-6-methoxybenzo[b]thiophene-2-carbonyl)cyclobutane-1-carboxylate

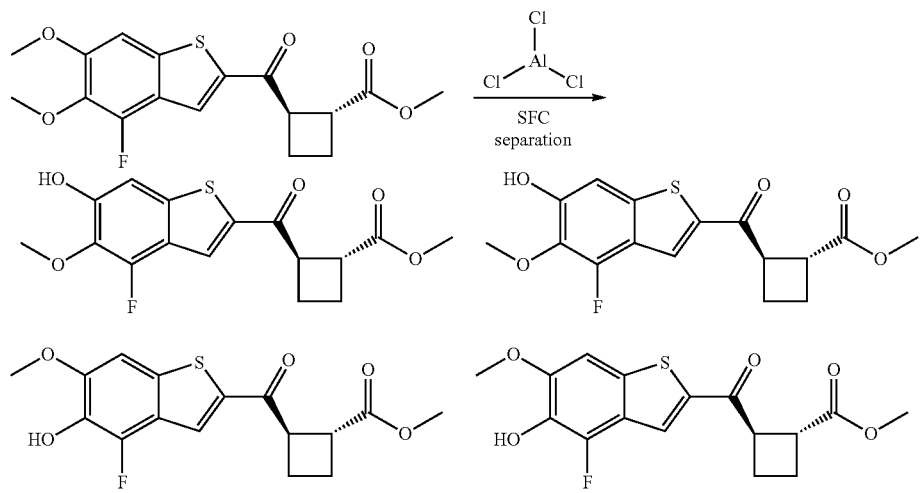

Step 4: Methyl (trans)-2-(4-fluoro-5,6-dimethoxybenzo[b]thiophene-2-carbonyl)cyclobutane-1-carboxylate

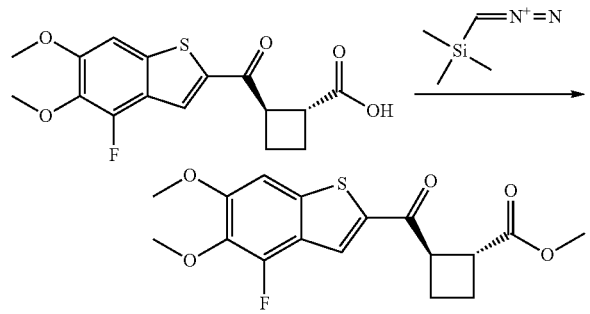

TMS-diazomethane (2.0M in diethyl ether, 1.7 mL, 3.4 mmol) was added dropwise to a mixture of (trans)-2-(4-fluoro-5,6-dimethoxybenzo[b]thiophene-2-carbonyl)cy- AlCl$_3$ (1.10 g, 8.27 mmol) was added to a mixture of (trans)-methyl 2-(4-fluoro-5,6-dimethoxybenzo[b]thiophene-2-carbonyl)cyclobutanecarboxylate (530 mg, 1.50 mmol) in DCM (40 mL) at RT. The reaction mixture was stirred at RT for 6 h under Ar. The reaction mixture was cooled to 0° C. and then quenched slowly with water (50 mL). The reaction mixture was then diluted with additional DCM (250 mL). The organic layer was separated, washed with brine (25 mL), dried over MgSO$_4$, filtered, and concentrated under reduced pressure. The residue was purified by silica gel chromatography (EtOAc/DCM) to afford a mixture of (+/−trans)-methyl-2-(4-fluoro-5-hydroxy-6-methoxybenzo[b]thiophene-2-carbonyl)cyclobutane-1-carboxylate and (+/−trans)-methyl-2-(4-fluoro-6-hydroxy-5-methoxybenzo[b]thiophene-2-carbonyl)cyclobutane-1-carboxylate. The mixture of racemic regioisomers was purified by chiral SFC (CCA column, 20% [MeOH with 0.25% DMEA] in CO$_2$) to afford:

Peak 1 (3.0 min): methyl (1R,2R or 1S,2S)-2-(4-fluoro-6-hydroxy-5-methoxybenzo[b]thiophene-2-carbonyl)cyclobutane-1-carboxylate. LCMS ($C_{16}H_{16}FO_5S$) (ES, m/z): 339 [M+H]$^+$. $^1$H NMR (499 MHz, DMSO-d$_6$) δ 10.58 (br s, 1H), 8.15 (s, 1H), 7.24 (s, 1H), 4.45-4.34 (m, 1H), 3.86 (s, 3H), 3.62 (s, 3H), 3.56-3.47 (m, 1H), 2.36-2.24 (m, 1H), 2.25-2.16 (m, 1H), 2.16-2.07 (m, 2H).

Peak 2 (3.5 min): methyl (1R,2R or 1S,2S)-2-(4-fluoro-6-hydroxy-5-methoxybenzo[b]thiophene-2-carbonyl)cyclobutane-1-carboxylate. LCMS ($C_{16}H_{16}FO_5S$) (ES, m/z): 339 [M+H]$^+$.

Peak 3 (3.9 min): methyl (1R,2R or 1S,2S)-2-(4-fluoro-5-hydroxy-6-methoxybenzo[b]thiophene-2-carbonyl)cyclobutane-1-carboxylate. LCMS ($C_{16}H_{16}FO_5S$) (ES, m/z): 339 [M+H]$^+$. $^1$H NMR (499 MHz, DMSO-$d_6$) δ 9.55 (s, 1H), 8.14 (s, 1H), 7.48 (s, 1H), 4.45-4.38 (m, 1H), 3.92 (s, 3H), 3.62 (s, 3H), 3.58-3.49 (m, 1H), 2.38-2.27 (m, 1H), 2.25-2.19 (m, 1H), 2.17-2.09 (m, 2H).

Peak 4 (5.0 min): methyl (1R,2R or 1S,2S)-2-(4-fluoro-5-hydroxy-6-methoxybenzo[b]thiophene-2-carbonyl)cyclobutane-1-carboxylate. LCMS ($C_{16}H_{16}FO_5S$) (ES, m/z): 339 [M+H]$^+$. $^1$H NMR (499 MHz, DMSO-$d_6$) δ 9.54 (s, 1H), 8.14 (s, 1H), 7.48 (s, 1H), 4.44-4.38 (m, 1H), 3.92 (s, 3H), 3.62 (s, 3H), 3.55-3.49 (m, 1H), 2.38-2.26 (m, 1H), 2.26-2.17 (m, 1H), 2.17-2.10 (m, 2H).

Intermediate 105: Methyl (R)-4-(4-fluoro-5-hydroxy-6-methoxybenzo[b]thiophen-2-yl)-2-methyl-4-oxobutanoate

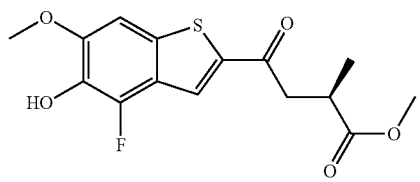

Step 1: Methyl (R)-4-(4-fluoro-5,6-dimethoxybenzo[b]thiophen-2-yl)-2-methyl-4-oxobutanoate

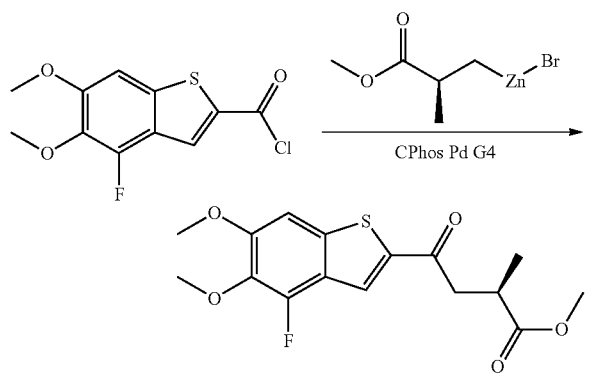

A mixture of 4-fluoro-5,6-dimethoxybenzo[b]thiophene-2-carbonyl chloride (1.00 g, 3.64 mmol) and THF (36.4 mL) was degassed with Ar for 10 min. CPhos Pd G4 (0.030 g, 0.036 mmol) was added to the mixture, and the reaction mixture was cooled to 0° C. (S)-(3-methoxy-2-methyl-3-oxopropyl)zinc(II) bromide (0.50M in THF, 8.0 mL, 4.0 mmol) was then added to the reaction mixture via an addition funnel. The mixture was stirred at 0° C. for 1 h. The reaction mixture was quenched with sat aq NH$_4$Cl and then diluted with EtOAc. The organic layer was separated, dried over MgSO$_4$, filtered, and concentrated under reduced pressure. The residue was purified by silica gel chromatography (EtOAc/Hex) to afford methyl (R)-4-(4-fluoro-5,6-dimethoxybenzo[b]thiophen-2-yl)-2-methyl-4-oxobutanoate. LCMS ($C_{16}H_{18}FO_5S$) (ES, m/z): 341 [M+H]$^+$.

Step 2: Methyl (R)-4-(4-fluoro-5-hydroxy-6-methoxybenzo[b]thiophen-2-yl)-2-methyl-4-oxobutanoate

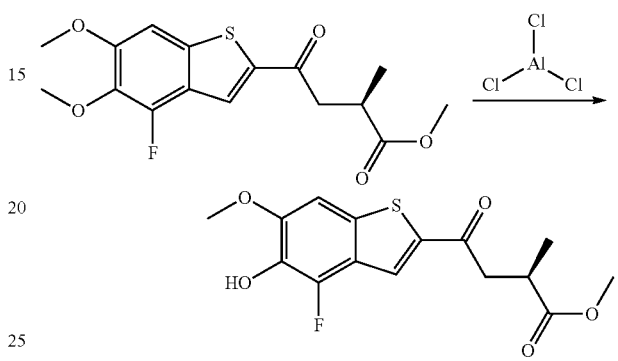

AlCl$_3$ (1.16 g, 8.72 mmol) was added to a mixture of (R)-methyl 4-(4-fluoro-5,6-dimethoxybenzo[b]thiophen-2-yl)-2-methyl-4-oxobutanoate (0.742 g, 2.18 mmol) in DCM (22 mL) at RT. The reaction mixture was stirred for 18 h. The reaction mixture was then cooled to 0° C. and quenched by the addition of water (50 mL) and HCl (1.0M in water, 50 mL, 50 mmol). The reaction mixture was then diluted with EtOAc. The organic layer was separated, dried over MgSO$_4$, filtered, and concentrated under reduced pressure to afford methyl (R)-4-(4-fluoro-5-hydroxy-6-methoxybenzo[b]thiophen-2-yl)-2-methyl-4-oxobutanoate which was used without purification. LCMS ($C_{15}H_{16}FO_5S$) (ES, m/z): 327 [M+H]$^+$.

Intermediate 106: Methyl (S)-4-(4-chloro-5-hydroxy-6-methoxybenzo[b]thiophen-2-yl)-2-methyl-4-oxobutanoate

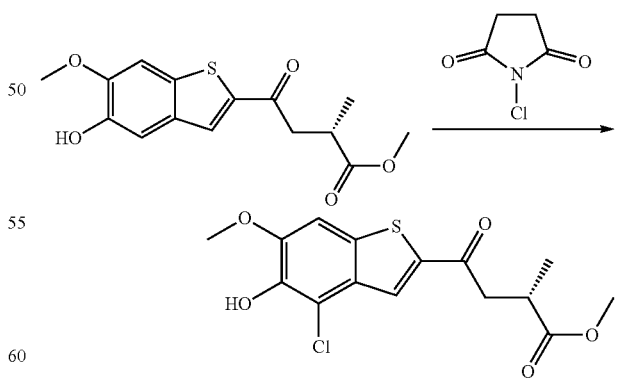

NCS (11 mg, 0.081 mmol) was added to a mixture of (S)-methyl 4-(5-hydroxy-6-methoxybenzo[b]thiophen-2-yl)-2-methyl-4-oxobutanoate (25 mg, 0.081 mmol) in DMF (0.25 mL) at RT. The reaction mixture was then heated to 40° C. and stirred for 2 h. The reaction mixture was cooled to RT and purified directly by silica gel chromatography (EtOAC/Hex) to afford (S)-methyl 4-(4-chloro-5-hydroxy-6-methoxybenzo[b]thiophen-2-yl)-2-methyl-4-oxobutanoate. LCMS ($C_{15}H_{16}ClO_5S$) (ES, m/z): 343 [M+H]$^+$. $^1$H NMR (499 MHz, DMSO-d$_6$) δ 9.78 (s, 1H), 8.16 (s, 1H), 7.63 (s, 1H), 3.94 (s, 3H), 3.60 (s, 3H), 3.50 (dd, J=17.8, 8.7 Hz, 1H), 3.31-3.23 (m, 1H), 3.02-2.92 (m, 1H), 1.20 (d, J=7.2 Hz, 3H).

Intermediate 107: Methyl (S)-4-(4-bromo-5-hydroxy-6-methoxybenzo[b]thiophen-2-yl)-2-methyl-4-oxobutanoate Intermediate 108: Methyl 4-(6-hydroxy-5-methoxybenzo[b]thiophen-2-yl)-4-oxobutanoate

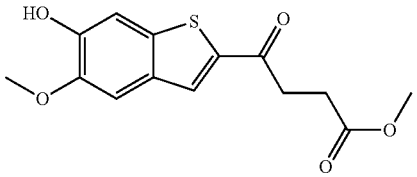

Step 1: Methyl 4-(5,6-dimethoxybenzo[b]thiophen-2-yl)-4-oxobutanoate

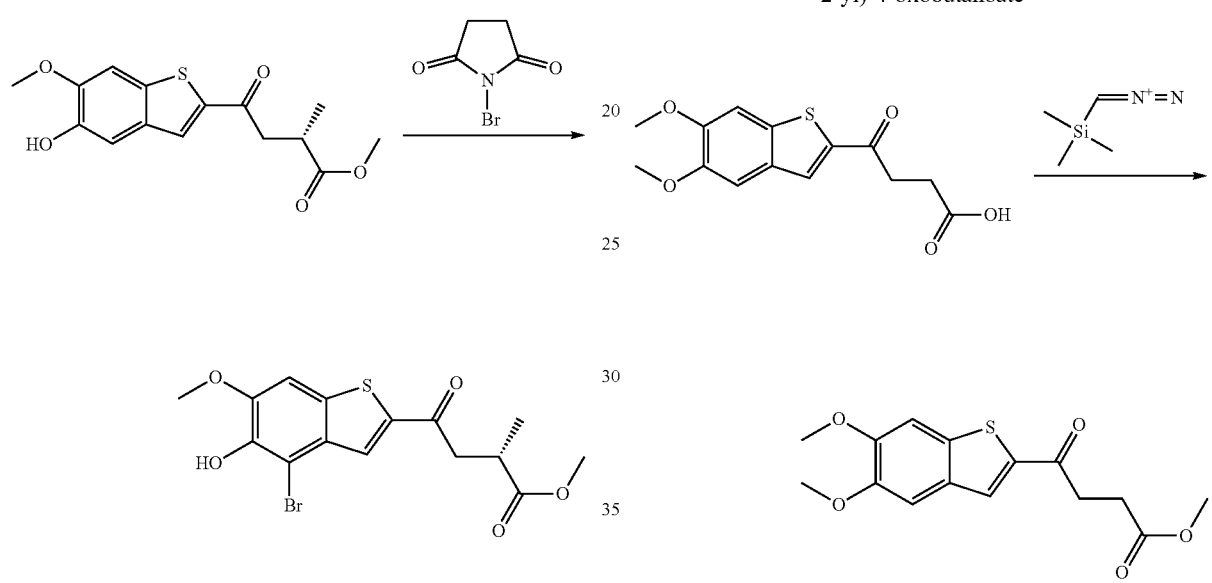

NBS (14 mg, 0.081 mmol) was added to a mixture of (S)-methyl 4-(5-hydroxy-6-methoxybenzo[b]thiophen-2-yl)-2-methyl-4-oxobutanoate (25 mg, 0.081 mmol) in DMF (0.25 mL) at RT. The reaction mixture was then heated to 40° C. and stirred for 2 h. The reaction mixture was cooled to RT and purified directly by silica gel chromatography (EtOAc/DCM) to afford (S)-methyl 4-(4-bromo-5-hydroxy-6-methoxybenzo[b]thiophen-2-yl)-2-methyl-4-oxobutanoate. LCMS ($C_{15}H_{16}BrO_5S$) (ES, m/z): 387, 389 [M+H]$^+$. $^1$H NMR (499 MHz, DMSO-d$_6$) δ 9.82 (s, 1H), 8.08 (s, 1H), 7.66 (s, 1H), 3.94 (s, 3H), 3.60 (s, 3H), 3.50 (dd, J=17.8, 8.7 Hz, 1H), 3.31-3.24 (m, 1H), 3.03-2.92 (m, 1H), 1.21 (d, J=7.2 Hz, 3H).

TMS-diazomethane (2.0M in diethyl ether, 5.5 mL, 11 mmol) was added dropwise to a mixture of 4-(5,6-dimethoxybenzo[b]thiophen-2-yl)-4-oxobutanoic acid (2.15 g, 7.30 mmol) in DCM (50 mL) and MeOH (50 mL) at 0° C. The reaction mixture was stirred at 0° C. for 1 h. The reaction mixture was quenched with HOAc. The reaction mixture was concentrated under reduced pressure to afford methyl 4-(5,6-dimethoxybenzo[b]thiophen-2-yl)-4-oxobutanoate, which was used without purification in the next step. LCMS ($C_{15}H_{17}O_5S$) (ES, m/z): 309 [M+H]$^+$. $^1$H NMR (499 MHz, DMSO-d$_6$) δ 8.22 (s, 1H), 7.61 (s, 1H), 7.49 (s, 1H), 3.87 (s, 3H), 3.84 (s, 3H), 3.61 (s, 3H), 3.35-3.30 (m, 2H), 2.71-2.66 (m, 2H).

Step 2: Methyl 4-(6-hydroxy-5-methoxybenzo[b]thiophen-2-yl)-4-oxobutanoate and methyl 4-(5-hydroxy-6-methoxybenzo[b]thiophen-2-yl)-4-oxobutanoate

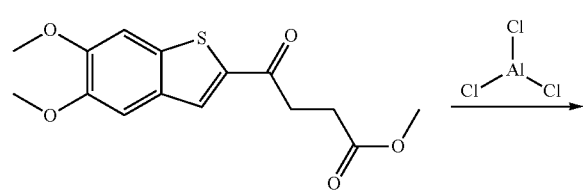

319

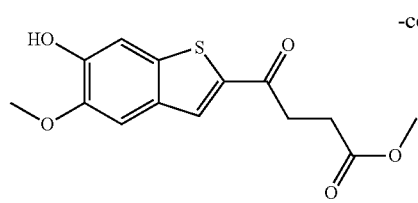

-continued

320

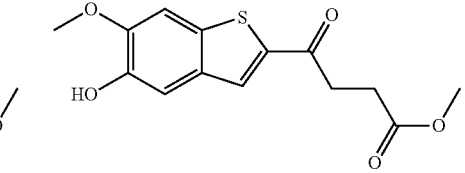

AlCl₃ (5.71 g, 42.8 mmol) was added to a mixture of methyl 4-(5,6-dimethoxy benzo[b]thiophen-2-yl)-4-oxobutanoate (2.20 g, 7.13 mmol) in DCM (250 mL) at RT. The reaction mixture was stirred at RT for 24 h. The reaction mixture was cooled to 0° C. and quenched with water (50 mL, added dropwise via addition funnel). The reaction mixture was then warmed to RT and diluted with additional DCM (250 mL). The organic layer was separated, dried over MgSO₄, filtered, and concentrated under reduced pressure. The residue was purified by silica gel chromatography (EtOAc/DCM) to afford an inseparable mixture of methyl 4-(6-hydroxy-5-methoxybenzo[b]thiophen-2-yl)-4-oxobutanoate (77%) and methyl 4-(5-hydroxy-6-methoxybenzo[b]thiophen-2-yl)-4-oxobutanoate (23%). LCMS (C$_{14}$H$_{15}$O$_5$S) (ES, m/z): 295 [M+H]⁺.

Step 3: Methyl 4-(5-((((benzyloxy)carbonyl)oxy)-6-methoxybenzo[b]thiophen-2-yl)-4-oxobutanoate and methyl 4-(6-((((benzyloxy)carbonyl)oxy)-5-methoxybenzo[b]thiophen-2-yl)-4-oxobutanoate

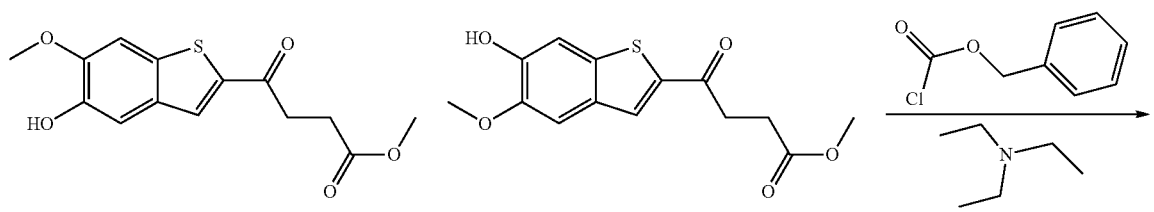

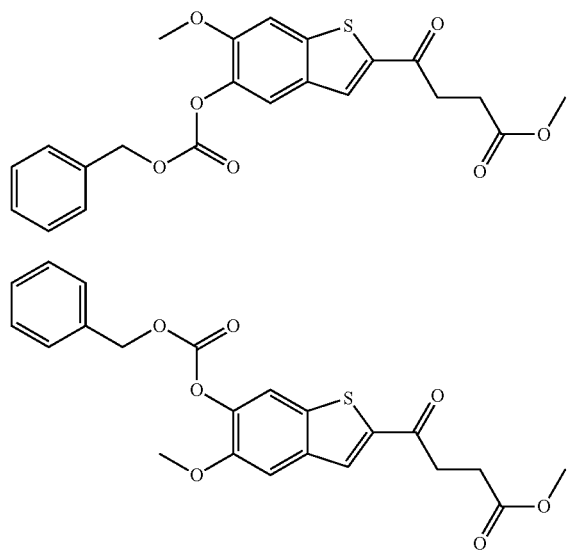

CBZ—Cl (1.06 mL, 7.42 mmol) was added to a mixture of methyl 4-(6-hydroxy-5-methoxybenzo[b]thiophen-2-yl)-4-oxobutanoate (77%) and methyl 4-(5-hydroxy-6-methoxybenzo[b]thiophen-2-yl)-4-oxobutanoate (23%) (1.82 g, 6.18 mmol) and TEA (1.29 mL, 9.28 mmol) in DCM (30 mL) at 0° C. The reaction mixture was then warmed to RT and stirred for an additional 2 h. The reaction mixture was concentrated under reduced pressure and the residue was purified by silica gel chromatography (EtOAc/Hex) to afford:

Peak 1: methyl 4-(5-(((benzyloxy)carbonyl)oxy)-6-methoxybenzo[b]thiophen-2-yl)-4-oxobutanoate. LCMS ($C_{22}H_{21}O_7S$) (ES, m/z): 429 [M+H]$^+$. $^1$H NMR (499 MHz, DMSO-$d_6$) δ 8.30 (s, 1H), 7.89 (s, 1H), 7.84 (s, 1H), 7.48-7.38 (m, 5H), 5.30 (s, 2H), 3.87 (s, 3H), 3.61 (s, 3H), 3.40-3.33 (m, 2H), 2.69 (t, J=6.4 Hz, 2H).

Peak 2: methyl 4-(6-(((benzyloxy)carbonyl)oxy)-5-methoxybenzo[b]thiophen-2-yl)-4-oxobutanoate. LCMS ($C_{22}H_{21}O_7S$) (ES, m/z): 429 [M+H]$^+$. $^1$H NMR (499 MHz, DMSO-$d_6$) δ 8.32 (s, 1H), 8.01 (s, 1H), 7.71 (s, 1H), 7.47-7.37 (m, 5H), 5.31 (s, 2H), 3.85 (s, 3H), 3.62 (s, 3H), 3.41-3.36 (m, 2H), 2.74-2.68 (m, 2H).

Step 4: Methyl 4-(6-hydroxy-5-methoxybenzo[b]thiophen-2-yl)-4-oxobutanoate

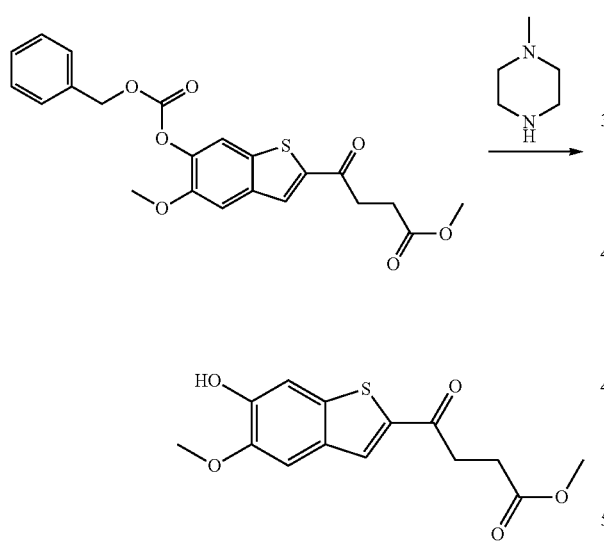

1-Methylpiperazine (1.4 mL, 13 mmol) was added to a mixture of methyl 4-(6-(((benzyloxy)carbonyl)oxy)-5-methoxybenzo[b]thiophen-2-yl)-4-oxobutanoate (1.84 g, 4.29 mmol) in DMF (5 mL) and MeOH (5 mL) at RT. The reaction mixture was then heated to 50° C. and stirred for an additional 30 min. The reaction mixture was cooled to RT and partially concentrated under reduced pressure. The crude mixture was purified by silica gel chromatography (EtOAc/DCM) to afford methyl 4-(6-hydroxy-5-methoxybenzo[b]thiophen-2-yl)-4-oxobutanoate. LCMS ($C_{14}H_{15}O_5S$) (ES, m/z): 295 [M+H]$^+$. $^1$H NMR (499 MHz, DMSO-$d_6$) δ 9.88 (s, 1H), 8.18 (s, 1H), 7.47 (s, 1H), 7.32 (s, 1H), 3.86 (s, 3H), 3.61 (s, 3H), 3.33-3.29 (m, 2H), 2.71-2.66 (m, 2H).

Intermediate 109: tert-Butyl (S)-4-(5-hydroxy-6-methoxybenzo[b]thiophen-2-yl)-2-methyl-4-oxobutanoate

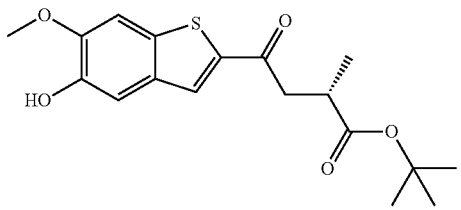 [SMILES: COc1cc2sc(C(=O)C[C@H](C)C(=O)OC(C)(C)C)cc2cc1O]

Step 1: (S)-4-(5-Hydroxy-6-methoxybenzo[b]thiophen-2-yl)-2-methyl-4-oxobutanoic acid

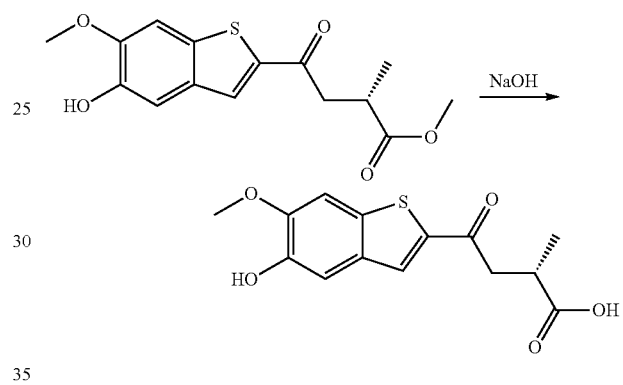

To a mixture of (S)-methyl 4-(5-hydroxy-6-methoxybenzo[b]thiophen-2-yl)-2-methyl-4-oxobutanoate (3.00 g, 9.73 mmol) in MeOH (97 mL) and THF (97 mL) was added NaOH (5.0M in water, 39 mL, 200 mmol). The mixture was heated to 50° C. for 1.5 h. The reaction mixture was cooled to RT and acidified to a pH-3 with HCl (2.0M in water, 100 ml, 200 mmol). The mixture was diluted with EtOAc and water. The organic layer was separated, dried over MgSO$_4$, filtered, and concentrated under reduced pressure to afford (S)-4-(5-hydroxy-6-methoxybenzo[b]thiophen-2-yl)-2-methyl-4-oxobutanoic acid. LCMS ($C_{14}H_{15}O_5S$) (ES, m/z): 295 [M+H]$^+$. $^1$H NMR (499 MHz, DMSO-$d_6$) δ 12.18 (s, 1H), 9.39 (s, 1H), 8.17 (s, 1H), 7.54 (s, 1H), 7.32 (s, 1H), 3.88 (s, 3H), 3.38 (dd, J=17.3, 8.5 Hz, 1H), 3.07 (dd, J=17.3, 5.3 Hz, 1H), 2.94-2.83 (m, 1H), 1.18 (d, J=7.2 Hz, 3H).

Step 2: tert-Butyl (S)-4-(5-hydroxy-6-methoxybenzo[b]thiophen-2-yl)-2-methyl-4-oxobutanoate

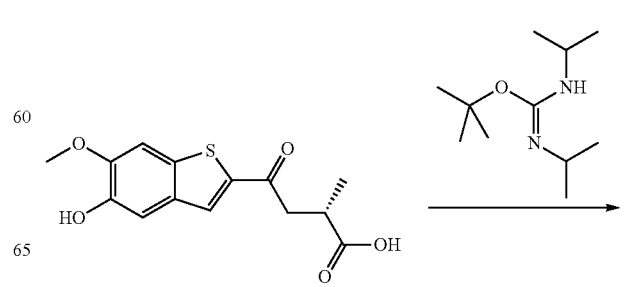

-continued

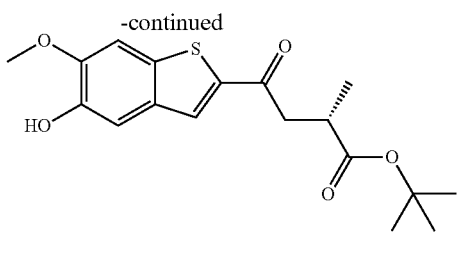

2-tert-Butyl-1,3-diisopropylisourea (2.3 mL, 10 mmol) was added to a mixture of (S)-4-(5-hydroxy-6-methoxybenzo[b]thiophen-2-yl)-2-methyl-4-oxobutanoic acid (1.00 g, 3.40 mmol) in DMF (6.8 mL) at RT. The reaction mixture was stirred at RT for 2 h. The mixture was diluted with EtOAc and water. The organic layer was separated, dried over MgSO$_4$, filtered, and concentrated under reduced pressure. The residue was purified by silica gel chromatography (EtOAc/Hex) to afford tert-butyl (S)-4-(5-hydroxy-6-methoxybenzo[b]thiophen-2-yl)-2-methyl-4-oxobutanoate. LCMS (C$_{18}$H$_{23}$O$_5$S+Na) (ES, m/z): 373 [M+Na]$^+$. $^1$H NMR (499 MHz, DMSO-d$_6$) δ 9.40 (s, 1H), 8.17 (s, 1H), 7.54 (s, 1H), 7.31 (s, 1H), 3.88 (s, 3H), 3.36-3.30 (m, 1H), 3.05 (dd, J=17.1, 5.0 Hz, 1H), 2.90-2.79 (m, 1H), 1.35 (s, 9H), 1.16 (d, J=7.2 Hz, 3H).

Intermediate 110: Methyl (S)-4-(4,7-dichloro-5-hydroxy-6-methoxybenzo[b]thiophen-2-yl)-2-methyl-4-oxobutanoate

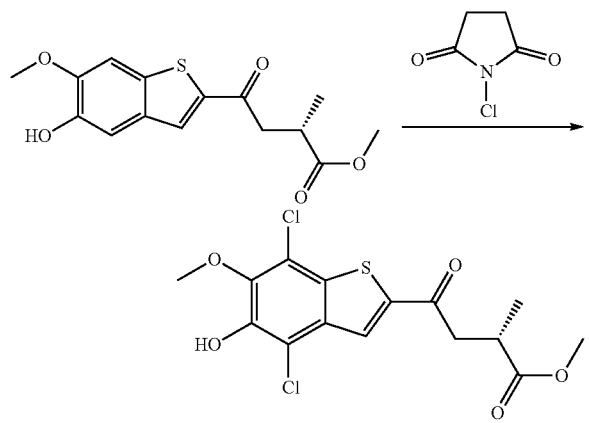

NCS (433 mg, 3.24 mmol) was added to a mixture of (S)-methyl 4-(5-hydroxy-6-methoxybenzo[b]thiophen-2-yl)-2-methyl-4-oxobutanoate (500 mg, 1.62 mmol) in DMF (4.0 mL) at 20° C. The reaction mixture was then heated to 40° C. and stirred for 2 h. The reaction mixture was cooled to RT and diluted with EtOAc (100 mL). The mixture was washed with water (3×25 mL) and brine (1×25 mL). The organic layer was separated, dried over MgSO$_4$, filtered, and concentrated under reduced pressure. The residue was purified by silica gel chromatography (EtOAc/Hex) followed by additional purification by silica gel chromatography (EtOAc/DCM) to afford methyl (S)-4-(4,7-dichloro-5-hydroxy-6-methoxybenzo[b]thiophen-2-yl)-2-methyl-4-oxobutanoate. LCMS (C$_{15}$H$_{15}$Cl$_2$O$_5$S) (ES, m/z): 377, 379 [M+H]$^+$.

Intermediate 111: Methyl (S)-4-(5-(3-bromo-2,2-dimethylpropoxy)-4-fluoro-6-methoxybenzo[b]thiophen-2-yl)-2-methyl-4-oxobutanoate

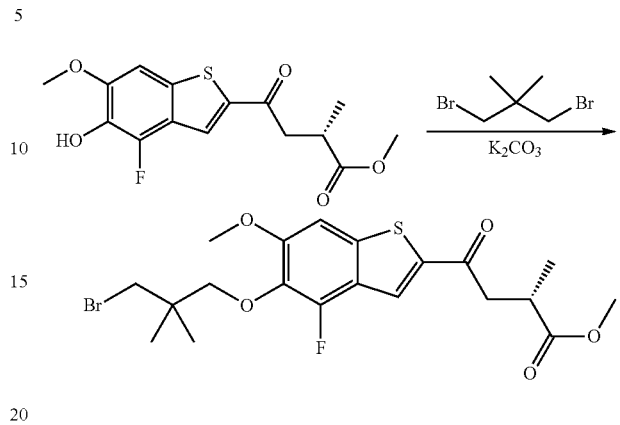

1,3-Dibromo-2,2-dimethylpropane (176 mg, 0.766 mmol) was added to a mixture of (S)-methyl 4-(4-fluoro-5-hydroxy-6-methoxybenzo[b]thiophen-2-yl)-2-methyl-4-oxobutanoate (25 mg, 0.077 mmol) and potassium carbonate (42 mg, 0.3 mmol) in DMF (0.5 mL) at RT. The reaction mixture was then stirred and heated to 100° C. for 24 h. The reaction mixture was cooled to RT, diluted with DCM (2 mL), and filtered. The filtrate was directly purified by silica gel chromatography (EtOAc/Hex) to afford methyl (S)-4-(5-(3-bromo-2,2-dimethylpropoxy)-4-fluoro-6-methoxybenzo[b]thiophen-2-yl)-2-methyl-4-oxobutanoate. LCMS (C$_{20}$H$_{25}$BrFO$_5$S) (ES, m/z): 475, 477 [M+H]+.

Intermediate 112: Methyl (S)-4-(5-((1-(bromomethyl)cyclopropyl)methoxy)-4-fluoro-6-methoxybenzo[b]thiophen-2-yl)-2-methyl-4-oxobutanoate

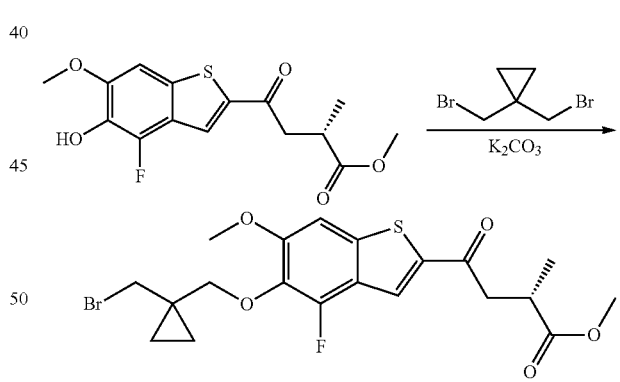

1,1-Bis(bromomethyl)cyclopropane (175 mg, 0.766 mmol) was added to a mixture of (S)-methyl 4-(4-fluoro-5-hydroxy-6-methoxybenzo[b]thiophen-2-yl)-2-methyl-4-oxobutanoate (25 mg, 0.077 mmol) and potassium carbonate (42 mg, 0.3 mmol) in DMF (0.5 mL) at RT. The reaction mixture was then stirred and heated to 40° C. for 4 h. The reaction mixture was cooled to RT, diluted with DCM (2 mL), and filtered. The filtrate was directly purified by silica gel chromatography (EtOAc/Hex) to afford methyl (S)-4-(5-((1-(bromomethyl) cyclopropyl)methoxy)-4-fluoro-6-methoxybenzo[b]thiophen-2-yl)-2-methyl-4-oxobutanoate. LCMS (C$_{20}$H$_{23}$BrFO$_5$S) (ES, m/z): 473, 475 [M+H]$^+$.

Intermediate 113: Methyl (S)-4-(5-hydroxy-6-(methoxymethyl)benzo[b]thiophen-2-yl)-2-methyl-4-oxobutanoate

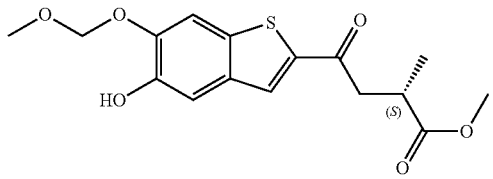

Step 1: Methyl (S)-4-(5-bromo-6-hydroxybenzo[b]thiophen-2-yl)-2-methyl-4-oxobutanoate

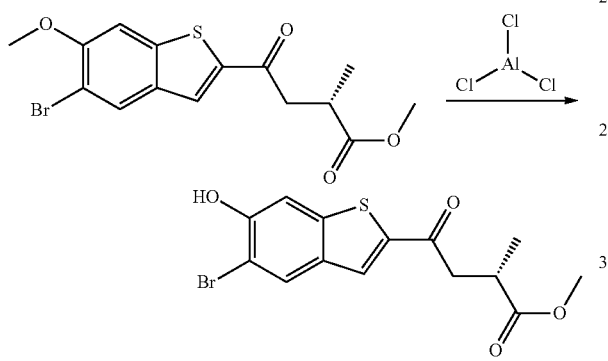

AlCl$_3$ (3.23 g, 24.2 mmol) was added to a mixture of methyl (S)-4-(5-bromo-6-methoxybenzo[b]thiophen-2-yl)-2-methyl-4-oxobutanoate (1.50 g, 4.04 mmol) in DCM (35 mL) at RT. The reaction mixture was stirred and heated to 35° C. for 24 h. The reaction mixture was cooled to 0° C. and then quenched by the slow addition of water (10 mL). The mixture was then warmed to RT and stirred for an additional 15 min. The reaction mixture was diluted with DCM (250 mL), and the organic layer was separated. The organic layer was washed with brine (50 mL). The organic layer was separated, dried over MgSO$_4$, filtered, and concentrated under reduced pressure. The residue was purified by silica gel chromatography (EtOAc/Hex) to afford methyl (S)-4-(5-bromo-6-hydroxybenzo[b]thiophen-2-yl)-2-methyl-4-oxobutanoate. LCMS (C$_{14}$H$_{14}$BrO$_4$S) (ES, m/z): 357, 359 [M+H]$^+$.

Step 2: Methyl (S)-4-(5-bromo-6-(methoxymethoxy)benzo[b]thiophen-2-yl)-2-methyl-4-oxobutanoate

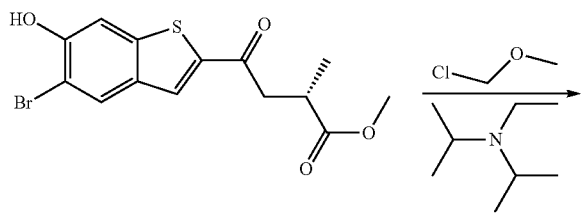

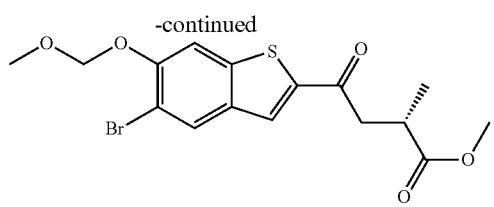

MOM-Cl (0.91 mL, 12 mmol) was added to a mixture of methyl (S)-4-(5-bromo-6-hydroxybenzo[b]thiophen-2-yl)-2-methyl-4-oxobutanoate (1.42 g, 3.98 mmol) and Hunig's base (4.2 mL, 24 mmol) in DCM (25 mL) at 0° C. The reaction mixture was stirred at 0° C. for 1 h and then warmed to RT and stirred for an additional 24 h. The reaction mixture was quenched by the addition of sat aq NaHCO$_3$ (10 mL) and then diluted with EtOAc (250 mL) and water (50 mL). The organic layer was separated, washed with brine (25 mL), dried over MgSO$_4$, filtered, and concentrated under reduced pressure. The residue was purified by silica gel chromatography (EtOAc/Hex) to afford methyl (S)-4-(5-bromo-6-(methoxymethoxy)benzo[b]thiophen-2-yl)-2-methyl-4-oxobutanoate. LCMS (C$_{16}$H$_{18}$BrO$_5$S) (ES, m/z): 401, 403 [M+H]$^+$. $^1$H NMR (499 MHz, DMSO-d$_6$) δ 8.30 (s, 1H), 8.28 (s, 1H), 7.87 (s, 1H), 5.41 (s, 2H), 3.60 (s, 3H), 3.48-3.42 (m, 1H), 3.45 (s, 3H), 3.22 (dd, J=17.6, 5.1 Hz, 1H), 3.04-2.93 (m, 1H), 1.20 (d, J=7.4 Hz, 3H).

Step 3: Methyl (S)-4-(6-(methoxymethoxy)-5-(4,4,5,5-tetramethyl-1,3,2-dioxaborolan-2-yl)benzo[b]thiophen-2-yl)-2-methyl-4-oxobutanoate

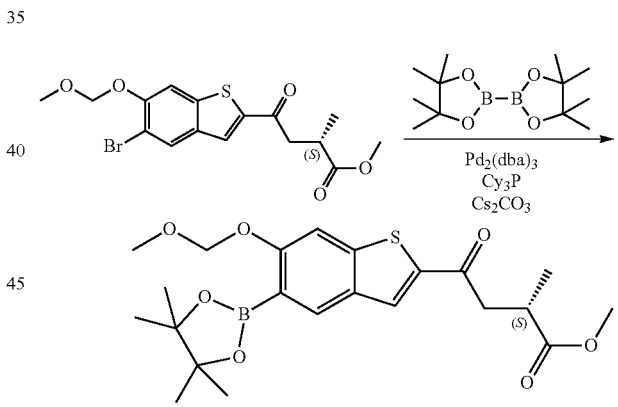

A mixture of methyl (S)-4-(5-bromo-6-(methoxymethoxy)benzo[b]thiophen-2-yl)-2-methyl-4-oxobutanoate (1.57 g, 3.91 mmol), 4,4,4',4',5,5,5',5'-octamethyl-2,2'-bi(1,3,2-dioxaborolane) (1.19 g, 4.70 mmol), Pd$_2$(dba)$_3$ (0.179 g, 0.196 mmol), tricyclohexylphosphine (0.219 g, 0.783 mmol), and potassium acetate (0.614 g, 6.26 mmol) was degassed with Ar for 5 min. Dioxane (20 mL) was added at RT, and the resulting mixture was degassed with Ar for 5 min. The reaction mixture was then heated to 90° C. and stirred for 6 h under Ar. The reaction mixture was cooled to RT and then diluted with EtOAc (50 mL). The suspension was stirred at RT for 10 min, and then filtered through CELITE, washing with EtOAc (50 mL). The filtrate was concentrated under reduced pressure to afford methyl (S)-4-(6-(methoxymethoxy)-5-(4,4,5,5-tetramethyl-1,3,2-dioxaborolan-2-yl)benzo[b]thiophen-2-yl)-2-methyl-4-

Step 4: Methyl (S)-4-(5-hydroxy-6-(methoxymethoxy) benzo[b]thiophen-2-yl)-2-methyl-4-oxobutanoate

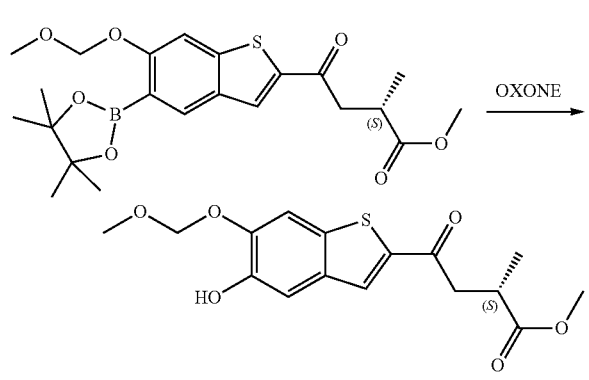

A solution of OXONE® (0.20M in water, 21 mL, 4.3 mmol) was added to a solution of methyl (S)-4-(6-(methoxymethoxy)-5-(4,4,5,5-tetramethyl-1,3,2-dioxaborolan-2-yl)benzo[b]thiophen-2-yl)-2-methyl-4-oxobutanoate (1.75 g, 3.90 mmol) in acetone (50 mL) at RT. The reaction mixture was stirred at RT for 60 min. The reaction mixture was quenched by the addition of a solution of sodium bisulfite (0.81 g, 7.8 mmol) in water (5 mL) and then stirred for 5 min. The reaction mixture was diluted with EtOAc (250 mL). The organic layer was separated, and the aqueous layer was washed with additional EtOAc e (2×100 mL). The organic layers were combined, washed with brine (25 mL), dried over $MgSO_4$, filtered, and concentrated under reduced pressure. The residue was purified by silica gel chromatography (EtOAc/Hex) to afford methyl (S)-4-(5-hydroxy-6-(methoxymethoxy)benzo[b]thiophen-2-yl)-2-methyl-4-oxobutanoate contaminated with pinacol byproduct. The isolated material was repurified by silica gel chromatography (EtOAc/DCM) to afford methyl (S)-4-(5-hydroxy-6-(methoxymethoxy)-benzo[b]thiophen-2-yl)-2-methyl-4-oxobutanoate. LCMS ($C_{16}H_{19}O_6S$) (ES, m/z): 339 $[M+H]^+$. $^1H$ NMR (499 MHz, DMSO-$d_6$) δ 9.52 (s, 1H), 8.20 (s, 1H), 7.61 (s, 1H), 7.37 (s, 1H), 5.29 (s, 2H), 3.60 (s, 3H), 3.44 (s, 3H), 3.43-3.38 (m, 1H), 3.18 (dd, J=17.5, 5.1 Hz, 1H), 3.03-2.91 (m, 1H), 1.19 (d, J=7.2 Hz, 3H).

Intermediate 114: Methyl (S)-4-(4-chloro-5-hydroxy-6-(methoxymethoxy)benzo[b]thiophen-2-yl)-2-methyl-4-oxobutanoate

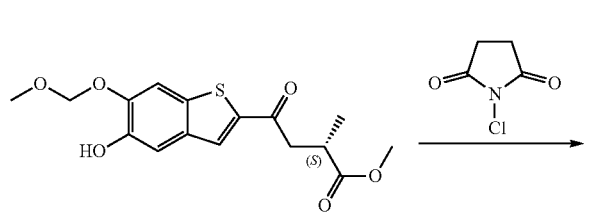

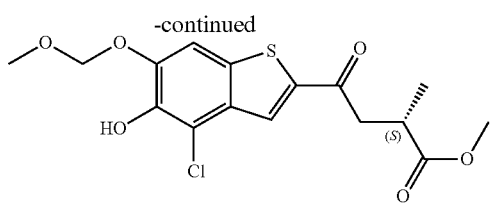

NCS (99 mg, 0.74 mmol) was added to a mixture of methyl (S)-4-(5-hydroxy-6-(methoxymethoxy)benzo[b]thiophen-2-yl)-2-methyl-4-oxobutanoate (250 mg, 0.74 mmol) in DMF (2.0 mL) at RT. The reaction mixture was stirred and heated to 40° C. for 2 h. The reaction mixture was cooled to RT and then directly purified by silica gel chromatography (EtOAc/Hex) to afford methyl (S)-4-(4-chloro-5-hydroxy-6-(methoxymethoxy)benzo[b]thiophen-2-yl)-2-methyl-4-oxobutanoate. LCMS ($C_{16}H_{18}ClO_6S$) (ES, m/z): 373 $[M+H]^+$. $^1H$ NMR (499 MHz, DMSO-$d_6$) δ 9.83 (s, 1H), 8.17 (s, 1H), 7.67 (s, 1H), 5.35 (s, 2H), 3.60 (s, 3H), 3.51 (dd, J=17.8, 8.7 Hz, 1H), 3.46 (s, 3H), 3.27 (dd, J=17.8, 5.0 Hz, 1H), 3.02-2.91 (m, 1H), 1.20 (d, J=7.2 Hz, 3H).

Intermediate 115: Methyl (S)-4-(5-(3-bromopropoxy)-4-fluoro-6-(methoxymethoxy)benzo[b]thiophen-2-yl)-2-methyl-4-oxobutanoate

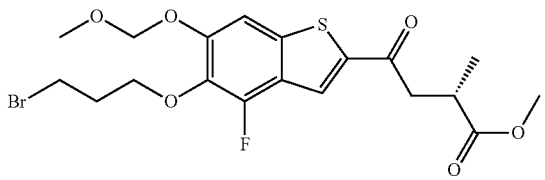 [SMILES: COCOc1cc2sc(C(=O)C[C@H](C)C(=O)OC)cc2c(F)c1OCCCBr]

Step 1: (S)-4-(4-Fluoro-5,6-dihydroxybenzo[b]thiophen-2-yl)-2-methyl-4-oxobutanoic acid

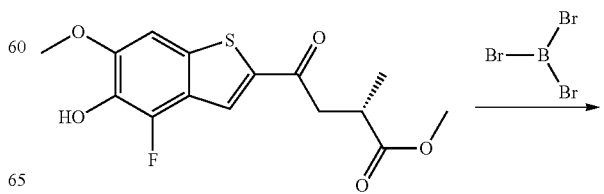

329

-continued

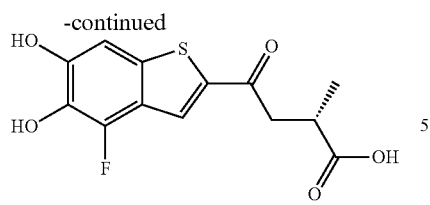

330

-continued

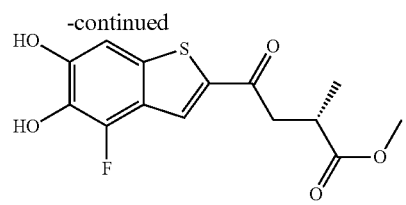

Boron tribromide (1.0M in DCM, 31 ml, 31 mmol) was added to a mixture of methyl (S)-4-(4-fluoro-5-hydroxy-6-methoxybenzo[b]thiophen-2-yl)-2-methyl-4-oxobutanoate (2.0 g, 6.1 mmol) in DCM (100 ml) at 0° C. The reaction mixture was stirred and heated to 30° C. for 2 h. The reaction mixture was cooled to 0° C. and then quenched by the dropwise addition of MeOH (10 ml). The reaction mixture was stirred for an additional 15 min. The reaction mixture was then diluted with water (100 ml) and additional DCM (500 ml). The organic layer was separated, washed with brine (50 ml), dried over MgSO$_4$, filtered, and concentrated under reduced pressure to afford (S)-4-(4-fluoro-5,6-dihydroxybenzo[b]thiophen-2-yl)-2-methyl-4-oxobutanoic acid, which was used without purification in the subsequent step. LCMS (C$_{13}$H$_{12}$FO$_5$S) (ES, m/z): 299 [M+H]+.

Step 2: Methyl (S)-4-(4-fluoro-5,6-dihydroxybenzo[b]thiophen-2-yl)-2-methyl-4-oxobutanoate TMS-diazomethane (2.0 M in diethyl ether, 3.1 ml, 6.2 mmol) was added to a mixture of (S)-4-(4-fluoro-5,6-dihydroxybenzo[b]thiophen-2-yl)-2-methyl-4-oxobutanoic acid (1.83 g, 6.14 mmol) in DCM (10 ml) and MeOH (10 ml) at 0° C. The reaction mixture was then stirred at 0° C. for 15 min. The reaction mixture was quenched with HOAc and then concentrated under reduced pressure. The residue was purified by silica gel chromatography (EtOAc/Hex) to afford the desired product. The isolated material was purified by silica gel chromatography ([25% EtOH in EtOAc]/Hex) to afford methyl (S)-4-(4-fluoro-5,6-dihydroxybenzo[b]thiophen-2-yl)-2-methyl-4-oxobutanoate. LCMS (C$_{14}$H$_{14}$FO$_5$S) (ES, m/z): 313 [M+H]$^+$.

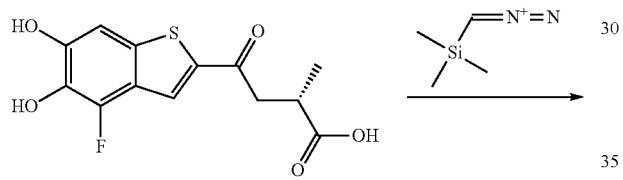

Step 3: Methyl (S)-4-(4-fluoro-5-hydroxy-6-(methoxymethoxy)benzo[b]thiophen-2-yl)-2-methyl-4-oxobutanoate and methyl (S)-4-(4-fluoro-6-hydroxy-5-(methoxy)benzo[b]thiophen-2-yl)-2-methyl-4-oxobutanoate

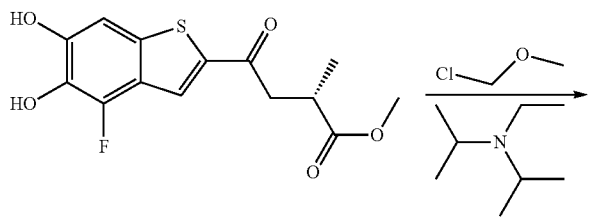

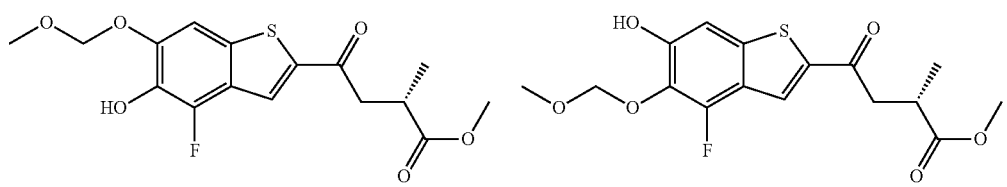

MOM-Cl (0.12 ml, 1.6 mmol) was added to a mixture of methyl (S)-4-(4-fluoro-5,6-dihydroxybenzo[b]thiophen-2-yl)-2-methyl-4-oxobutanoate (460 mg, 1.47 mmol) and Hunig's base (0.52 ml, 3.0 mmol) in DCM (25 ml) at 0° C. The reaction mixture was stirred at 0° C. for 1 h and then warmed to RT and stirred for an additional 24 h. The reaction mixture was quenched by the addition of sat aq NaHCO₃ (10 ml) and then diluted with EtOAc (250 ml) and water (50 ml). The organic layer was separated, washed with brine (25 ml), dried over MgSO₄, filtered, and concentrated under reduced pressure. The residue was purified by silica gel chromatography (EtOAc/Hex) to afford an inseparable mixture of methyl (S)-4-(4-fluoro-5-hydroxy-6-(methoxymethoxy)benzo[b]thiophen-2-yl)-2-methyl-4-oxobutanoate and methyl (S)-4-(4-fluoro-6-hydroxy-5-(methoxymethoxy)benzo[b]thiophen-2-yl)-2-methyl-4-oxobutanoate. The mixture was used in the subsequent reaction without further purification. LCMS ($C_{18}H_{18}FO_6S$) (ES, m/z): 357 [M+H]⁺.

Step 4: Methyl (S)-4-(6-(3-bromopropoxy)-4-fluoro-5-(methoxymethoxy)benzo[b]thiophen-2-yl)-2-methyl-4-oxobutanoate and methyl (S)-4-(5-(3-bromopropoxy)-4-fluoro-6-(methoxymethoxy)benzo[b]thiophen-2-yl)-2-methyl-4-oxobutanoate

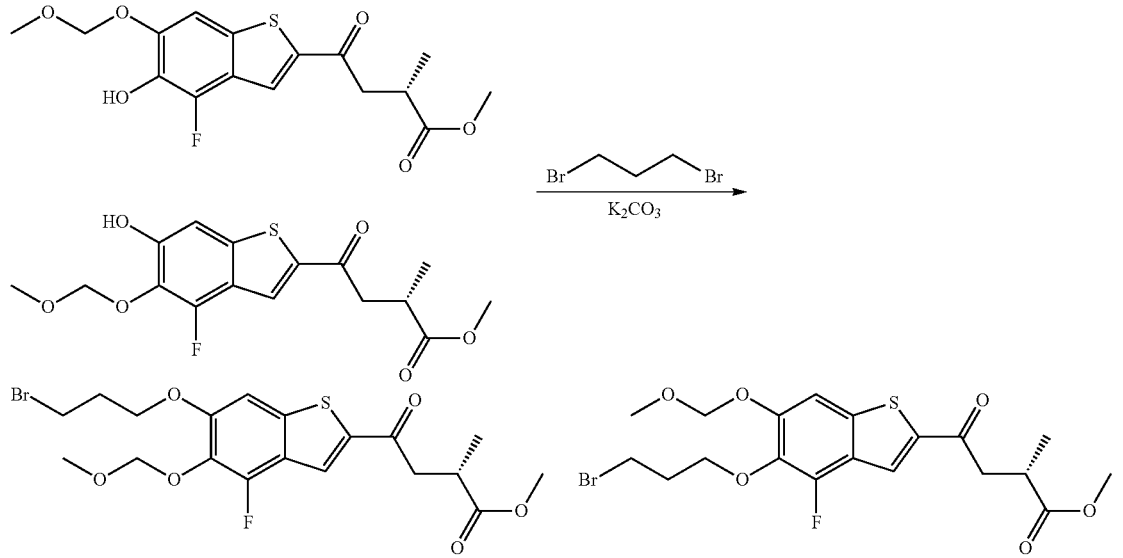

1,3-dibromopropane (0.58 ml, 5.6 mmol) was added to a mixture of methyl (S)-4-(4-fluoro-5-hydroxy-6-(methoxymethoxy)benzo[b]thiophen-2-yl)-2-methyl-4-oxobutanoate and methyl (S)-4-(4-fluoro-6-hydroxy-5-(methoxymethoxy)benzo[b]thiophen-2-yl)-2-methyl-4-oxobutanoate (270 mg, 0.75 mmol) and potassium carbonate (260 mg, 1.9 mmol) in DMF (2.0 ml) at RT. The mixture was stirred at RT for 18 h. The reaction mixture was diluted with EtOAc (250 ml) and water (50 ml). The organic layer was separated, washed with brine (50 ml), dried over MgSO₄, filtered, and concentrated under reduced pressure. The residue was purified by silica gel chromatography (EtOAc/hexanes) to afford a mixture of the regioisomers. The mixture of regioisomers was purified by reverse phase HPLC (ACN/water with 0.1% TFA) to afford:

First eluting peak on HPLC: methyl (S)-4-(6-(3-bromopropoxy)-4-fluoro-5-(methoxymethoxy)benzo[b]thiophen-2-yl)-2-methyl-4-oxobutanoate. LCMS ($C_{19}H_{23}BrFO_6S$) (ES, m/z): 477, 479 [M+H]⁺.

Second eluting peak on HPLC: methyl (S)-4-(5-(3-bromopropoxy)-4-fluoro-6-(methoxymethoxy)benzo[b]thiophen-2-yl)-2-methyl-4-oxobutanoate. LCMS ($C_{19}H_{23}BrFO_6S$) (ES, m/z): 477, 479 [M+H]⁺.

Intermediate 116: Methyl (S)-4-(5-hydroxy-6-(methylamino)benzo[b]thiophen-2-yl)-2-methyl-4-oxobutanoate

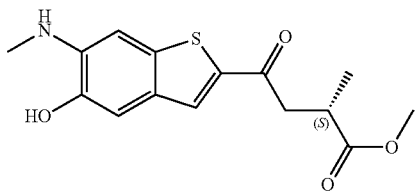

Step 1: Methyl (S)-4-(6-bromo-5-methoxybenzo[b]thiophen-2-yl)-2-methyl-4-oxobutanoateoate

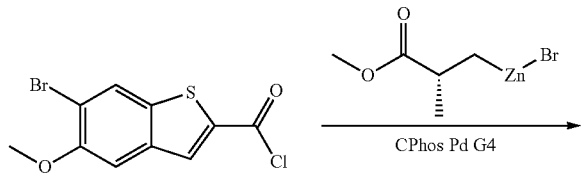

333

-continued

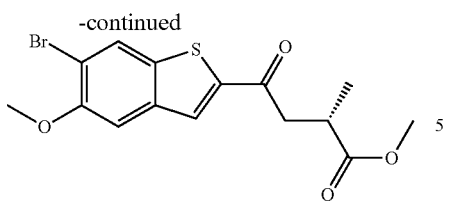

6-bromo-5-methoxybenzo[b]thiophene-2-carbonyl chloride (5.96 g, 19.5 mmol) and CPhos Pd G4 (0.160 g, 0.195 mmol) were combined in a flask and degassed with Ar for 5 min. THF (75 ml) was added under Ar stream, and the mixture was cooled to 0° C. (R)-(3-methoxy-2-methyl-3-oxopropyl)zinc(II) bromide (0.50 M in THF, 40 ml, 20 mmol) was then added dropwise, and the resulting mixture was stirred at 0° C. for 2 h and then warmed to RT. The mixture was stirred at RT for 3 days.

The reaction mixture was quenched with sat aq NH$_4$Cl (25 ml) and then diluted with EtOAc (500 ml). The organic layer was separated, washed with brine (50 ml), dried over MgSO$_4$, filtered, and concentrated under reduced pressure. The residue was purified by silica gel chromatography (EtOAc/hexanes) to afford methyl (S)-4-(6-bromo-5-methoxybenzo[b]thiophen-2-yl)-2-methyl-4-oxobutanoate. LCMS (C$_{15}$H$_{16}$BrO$_4$S) (ES, m/z): 371, 373 [M+H]$^+$. $^1$H NMR (499 MHz, DMSO-d$_6$) δ 8.39 (s, 1H), 8.30 (s, 1H), 7.65 (s, 1H), 3.94 (s, 3H), 3.61 (s, 3H), 3.52-3.43 (m, 1H), 3.28-3.18 (m, 1H), 3.05-2.95 (m, 1H), 1.23-1.18 (m, 3H).

Step 2: Methyl (S)-4-(6-bromo-5-hydroxybenzo[b]thiophen-2-yl)-2-methyl-4-oxobutanoate

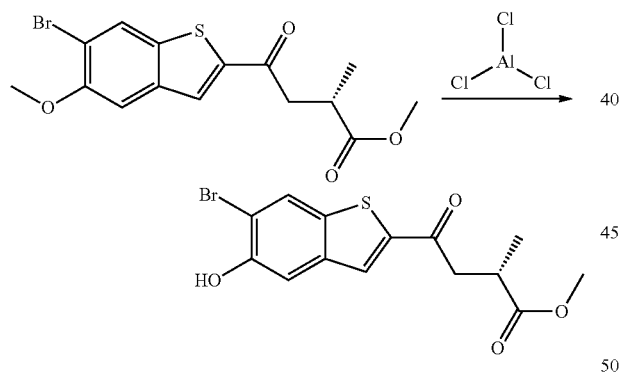

AlCl$_3$ (366 mg, 2.75 mmol) was added to a mixture of methyl (S)-4-(6-bromo-5-methoxybenzo[b]thiophen-2-yl)-2-methyl-4-oxobutanoate (170 mg, 0.458 mmol) in DCM (35 ml) at RT. The reaction mixture was stirred and heated to 45° C. for 3 days. The reaction mixture was cooled to 0° C. and then quenched by the slow addition of water (10 ml). The mixture was then warmed to RT and stirred for an additional 15 min. The reaction mixture was diluted with DCM (250 ml), and the organic layer was separated. The organic layer was washed with brine (50 ml). The organic layer was separated, dried over MgSO$_4$, filtered, and concentrated under reduced pressure. The residue was purified by silica gel chromatography (EtOAc/Hex) to afford methyl (S)-4-(6-bromo-5-hydroxybenzo[b]thiophen-2-yl)-2-methyl-4-oxobutanoate. LCMS (C$_{14}$H$_{14}$BrO$_4$S) (ES, m/z): 357, 359 [M+H]$^+$.

334

Step 3: Methyl (S)-4-(6-bromo-5-(methoxymethoxy)benzo[b]thiophen-2-yl)-2-methyl-4-oxobutanoate

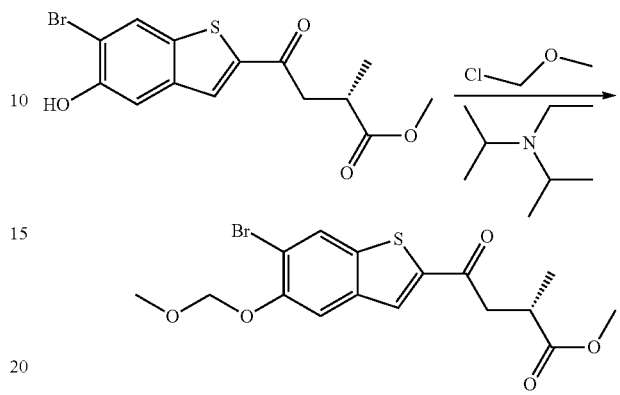

Hunig's base (0.44 ml, 2.5 mmol) was added to a mixture of methyl (S)-4-(6-bromo-5-hydroxybenzo[b]thiophen-2-yl)-2-methyl-4-oxobutanoate (150 mg, 0.42 mmol) and MOM-Cl (0.096 ml, 1.3 mmol) in DCM (5.0 ml) at 0° C. The reaction mixture was stirred at 0° C. for 1 h. The reaction mixture was directly purified by silica gel chromatography (EtOAc/Hex) to afford methyl (S)-4-(6-bromo-5-(methoxymethoxy)benzo[b]thiophen-2-yl)-2-methyl-4-oxobutanoate. LCMS (C$_{16}$H$_{18}$BrO$_5$S) (ES, m/z): 401, 403 [M+H]$^+$. $^1$H NMR (499 MHz, DMSO-d$_6$) δ 8.42 (s, 1H), 8.33 (s, 1H), 7.77 (s, 1H), 5.38 (s, 2H), 3.61 (s, 3H), 3.53-3.42 (m, 4H), 3.23 (dd, J=17.7, 3.0 Hz, 1H), 3.07-2.95 (m, 1H), 1.21 (d, J=5.0 Hz, 3H).

Step 4: Methyl (S)-4-(6-((tert-butoxycarbonyl)(methyl)amino)-5-(methoxymethoxy)benzo[b]thiophen-2-yl)-2-methyl-4-oxobutanoate

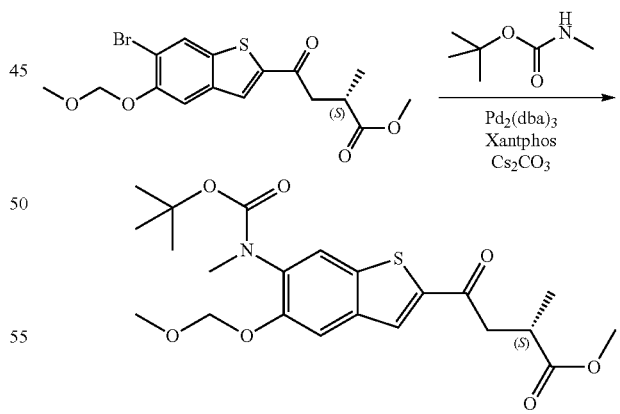

To an Ar-degassed mixture of methyl (S)-4-(6-bromo-5-(methoxymethoxy)benzo[b]thiophen-2-yl)-2-methyl-4-oxobutanoate (144 mg, 0.359 mmol), tert-butyl methylcarbamate (71 mg, 0.54 mmol), Pd$_2$(dba)$_3$ (16 mg, 0.018 mmol), XANTPHOS (31 mg, 0.054 mmol), and cesium carbonate (234 mg, 0.718 mmol) was added dioxane (4.0 ml) at RT while degassing with Ar. The mixture was stirred for 5 min while degassing with Ar, after which the mixture was heated to 90° C. and stirred under Ar for 18 h. The reaction mixture was cooled to RT and diluted with EtOAc (20 ml). The resulting suspension was filtered through CELITE. The filtrate was concentrated under reduced pressure. The residue was purified by silica gel chromatography (EtOAc/Hex) to afford the product. LCMS ($C_{22}H_{30}NO_7S$) (ES, m/z): 452 [M+H]$^+$.

Step 5: Methyl (S)-4-(5-hydroxy-6-(methylamino)benzo[b]thiophen-2-yl)-2-methyl-4-oxobutanoate

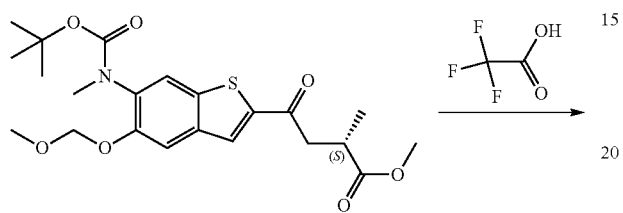

TFA (1.0 ml, 13 mmol) was added to a mixture of methyl (S)-4-(6-((tert-butoxycarbonyl)(methyl)amino)-5-(methoxymethoxy)benzo[b]thiophen-2-yl)-2-methyl-4-oxobutanoate (18 mg, 0.040 mmol) in DCM (2.0 ml) at RT. The reaction mixture was stirred at RT for 2 h. The reaction mixture was diluted with EtOAc (10 ml) and quenched slowly by the addition of sat aq NaHCO$_3$ solution (10 ml). The resulting mixture was stirred for 10 min. The organic layer was separated, washed with brine (5 ml), dried over MgSO$_4$, filtered, and concentrated under reduced pressure. The residue was purified by silica gel chromatography (EtOAc/Hex) to afford methyl (S)-4-(5-hydroxy-6-(methylamino)benzo[b]thiophen-2-yl)-2-methyl-4-oxobutanoate. LCMS ($C_{15}H_{18}NO_4S$) (ES, m/z): 308 [M+H]$^+$.

Example 1 (2S,2'S)-4,4'-[butane-1,4-diylbis(6-methoxy-1-benzothiene-5,2-diyl)]bis(2-methyl-4-oxobutanoic acid) and Example 2: (2S,2'S)-4,4'-[propane-1,3-diylbis(6-methoxy-1-benzothiene-5,2-diyl)]bis(2-methyl-4-oxobutanoic acid)

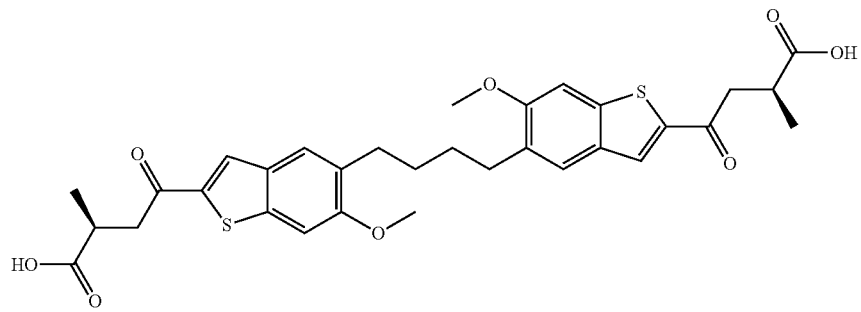

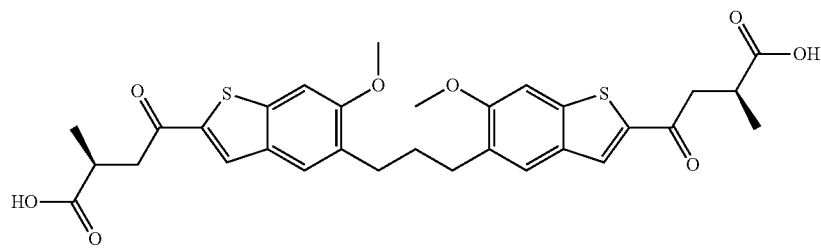

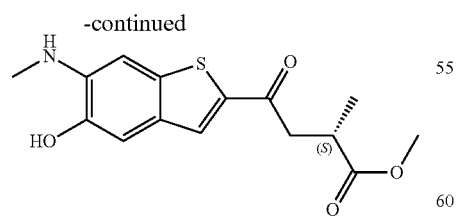

Step 1: Methyl (2S)-4-[6-methoxy-5-(prop-2-en-1-yl)-1-benzothiphen-2-yl]-2-methyl-4-oxobutanoate

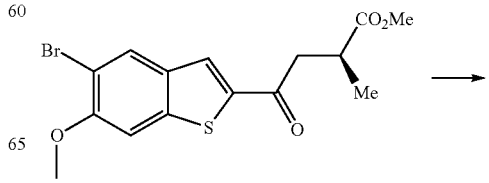

-continued

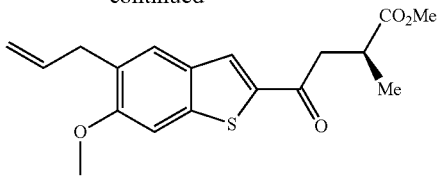

To the stirred mixture of methyl (2S)-4-(5-bromo-6-methoxy-1-benzothiophen-2-yl)-2-methyl-4-oxobutanoate (120 mg, 0.32 mmol), bis(dibenzylideneacetone)palladium (7.1 mg, 12 mol), and allyltributylstannane (120 μL, 0.39 mmol) in toluene (0.49 mL) was added tri-tert-butylphosphine (1.0M in toluene, 26 μL, 26 mol) under $N_2$. The reaction mixture was heated to 65° C. for 18 h. Upon cooling to RT, the mixture was diluted with $Et_2O$, and then CsF was added. The crude mixture was stirred for 5 min at RT. The mixture was then filtered, and the filtrate was directly purified by silica gel column chromatography (EtOAc in Hex) to afford methyl (2S)-4-[6-methoxy-5-(prop-2-en-1-yl)-1-benzothiophen-2-yl]-2-methyl-4-oxobutanoate.

LCMS ($C_{18}H_{21}O_1S$) (ES, m/z): 333 [M+H]. $^1$H NMR (500 MHz, DMSO-$d_6$): δ 8.27 (s, 1H), 7.72 (s, 1H), 7.62 (s, 1H), 6.06-5.94 (m, 1H), 5.07 (d, J=12.5 Hz, 2H), 3.89 (s, 3H), 3.59 (s, 3H), 3.46-3.38 (m, 3H), 3.19 (dd, J=17.5, 5.0 Hz, 1H), 3.02-2.92 (m, 1H), 1.19 (d, J=7.1 Hz, 3H).

Step 2: dimethyl (2S,2'S)-4,4'-[but-2-ene-1,4-diylbis(6-methoxy-1-benzothiene-5,2-diyl)]bis(2-methyl-4-oxobutanoate) and dimethyl (2S,2'S)-4,4'-[prop-1-ene-1,3-diylbis(6-methoxy-1-benzothiene-5,2-diyl)]bis(2-methyl-4-oxobutanoate)

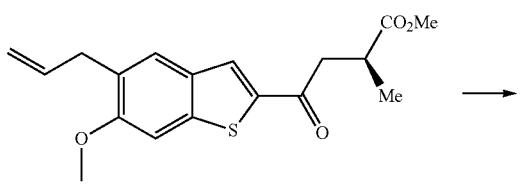

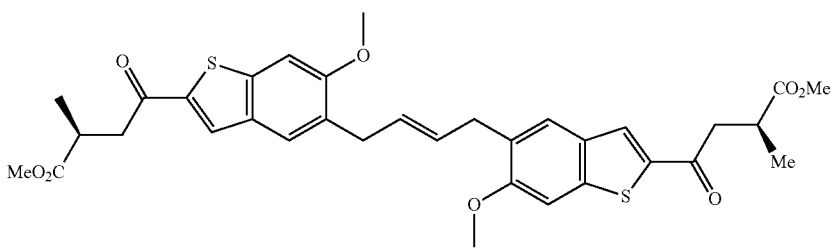

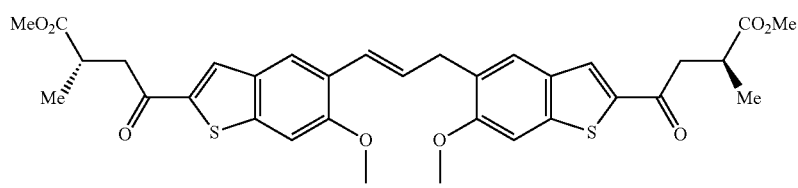

To a mixture of methyl (2S)-4-[6-methoxy-5-(prop-2-en-1-yl)-1-benzothiophen-2-yl]-2-methyl-4-oxobutanoate (44 mg, 0.13 mmol) in $CH_2Cl_2$ (1.3 mL) was added Grubbs catalyst 2G (11 mg, 0.013 mmol) in $CH_2Cl_2$ (1.3 mL) in one portion under $N_2$. The reaction mixture was heated to 65° C. for 18 h. Upon cooling to RT, the mixture was directly purified by silica gel column chromatography (EtOAc in Hex) to afford a mixture of dimethyl (2S,2'S)-4,4'-[but-2-ene-1,4-diylbis(6-methoxy-1-benzothiene-5,2-diyl)]bis(2-methyl-4-oxobutanoate) and dimethyl (2S,2'S)-4,4'-[prop-1-ene-1,3-diylbis(6-methoxy-1-benzothiene-5,2-diyl)]bis(2-methyl-4-oxobutanoate). Characterization of dimethyl (2S,2'S)-4,4'-[but-2-ene-1,4-diylbis(6-methoxy-1-benzothiene-5,2-diyl)]bis(2-methyl-4-oxobutanoate): LCMS ($C_{34}H_{37}O_8S_2$) (ES, m/z): 637 [M+H]$^+$. Characterization of dimethyl (2S,2'S)-4,4'-[prop-1-ene-1,3-diylbis(6-methoxy-1-benzothiene-5,2-diyl)]bis(2-methyl-4-oxobutanoate): LCMS ($C_{33}H_{35}O_8S_2$) (ES, m/z): 623 [M+H]$^+$.

Step 3: dimethyl (2S,2'S)-4,4'-[butane-1,4-diylbis(6-methoxy-1-benzothiene-5,2-diyl)]bis(2-methyl-4-oxobutanoate) and dimethyl (2S,2'S)-4,4'-[propane-1,3-diylbis(6-methoxy-1-benzothiene-5,2-diyl)]bis(2-methyl-4-oxobutanoate)

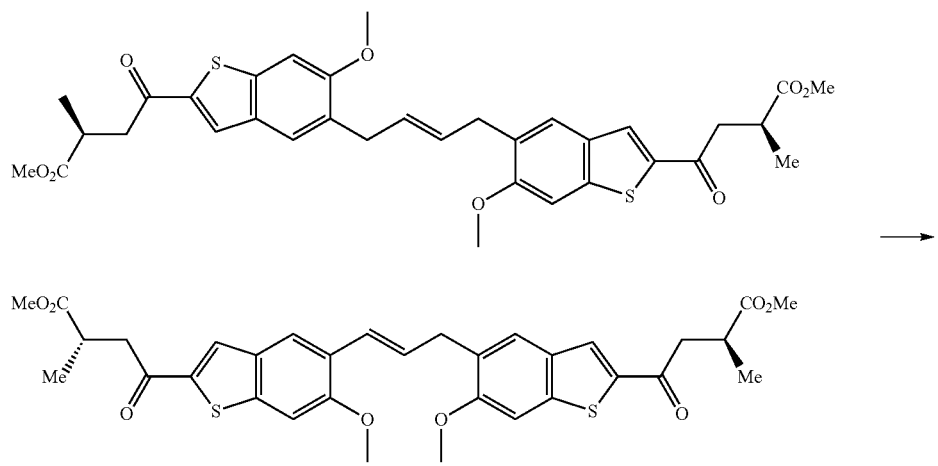

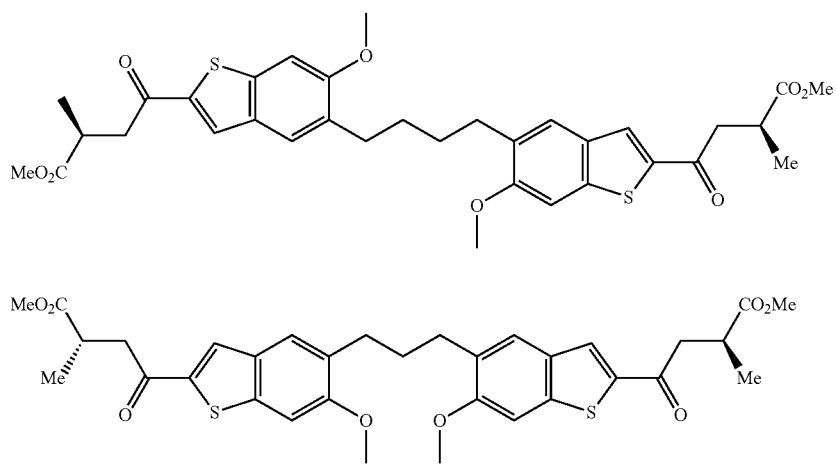

To a mixture of dimethyl (2S,2'S)-4,4'-[but-2-ene-1,4-diylbis(6-methoxy-1-benzothiene-5,2-diyl)]bis(2-methyl-4-oxobutanoate) and dimethyl (2S,2'S)-4,4'-[prop-1-ene-1,3-diylbis(6-methoxy-1-benzothiene-5,2-diyl)]bis(2-methyl-4-oxobutanoate) (57.0 mg, ~3/2 mixture by $^1$H-NMR) in EtOAc (0.5 mL) under $N_2$ was added 10% Pd/C (6.0 mg, 5.4 µmol) in one portion at RT. The reaction mixture was degassed and backfilled with $H_2$ (three times), and stirred under $H_2$ (balloon) for 18 h at RT. The mixture was then concentrated under reduced pressure to afford a crude mixture of dimethyl (2S,2'S)-4,4'-[butane-1,4-diylbis(6-methoxy-1-benzothiene-5,2-diyl)]bis (2-methyl-4-oxobutanoate) and dimethyl (2S,2'S)-4,4'-[propane-1,3-diylbis(6-methoxy-1-benzothiene-5,2-diyl)]bis(2-methyl-4-oxobutanoate). The mixture was used without further purification or characterization.

Step 4: (2S,2'S)-4,4'-[butane-1,4-diylbis(6-methoxy-1-benzothiene-5,2-diyl)]bis(2-methyl-4-oxobutanoic acid) and (2S,2'S)-4,4'-[propane-1,3-diylbis(6-methoxy-1-benzothiene-5,2-diyl)]bis(2-methyl-4-oxobutanoic acid)

one portion at RT. The reaction mixture was stirred at RT for 1 h and then quenched with aq HCl (2N, 0.52 mL). The mixture was diluted with DMSO, and the resulting mixture was filtered. The filtrate was purified by RP-HPLC [C18 column, water (0.1% TFA)-CH$_3$CN] to afford (2S,2'S)-4,4'-[butane-1,4-diylbis(6-methoxy-1-benzothiene-5,2-diyl)]bis(2-methyl-4-oxobutanoic acid) and (2S,2'S)-4,4'-[propane-1,3-diylbis(6-methoxy-1-benzothiene-5,2-diyl)]bis(2-methyl-4-oxobutanoic acid).

Characterization data for (2S,2'S)-4,4'-[butane-1,4-diylbis(6-methoxy-1-benzothiene-5,2-diyl)]bis(2-methyl-4-oxobutanoic acid): LCMS ($C_{32}H_{34}O_8S_2Na$) (ES, m/z): 633 [M+Na]$^+$. $^1$H NMR (500 MHz, DMSO-d$_6$): δ 12.20 (br, 2H), 8.21 (s, 2H), 7.72 (s, 2H), 7.57 (s, 2H), 3.87 (s, 6H), 3.39 (dd, J=17.5, 8.6 Hz, 2H), 3.07 (dd, J=17.5, 5.0 Hz, 2H), 2.94-2.84 (m, 2H), 2.69 (br, 4H), 1.62 (br, 4H), 1.18 (d, J=7.1 Hz, 6H).

Characterization data for (2S,2'S)-4,4'-[propane-1,3-diylbis(6-methoxy-1-benzothiene-5,2-diyl)]bis(2-methyl-4-

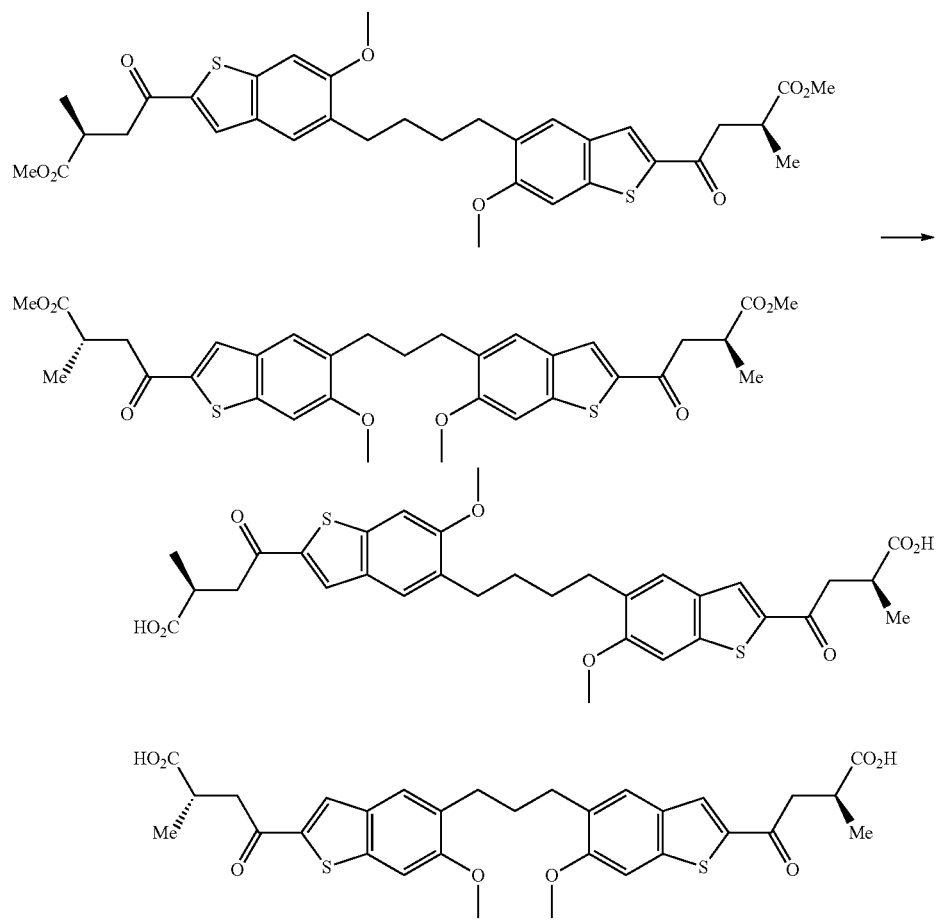

To a mixture of dimethyl (2S,2'S)-4,4'-[butane-1,4-diylbis(6-methoxy-1-benzothiene-5,2-diyl)]bis(2-methyl-4-oxobutanoate) and dimethyl (2S,2'S)-4,4'-[propane-1,3-diylbis(6-methoxy-1-benzothiene-5,2-diyl)]bis(2-methyl-4-oxobutanoate) (57 mg) in THF (1.0 mL), MeOH (1.0 mL) and water (0.20 mL) was added LiOH (26 mg, 1.1 mmol) in oxobutanoic acid): LCMS ($C_{31}H_{32}O_8S_2Na$) (ES, m/z): 619 [M+Na]$^+$. 1H NMR (500 MHz, DMSO-d$_6$): δ 12.21 (br, 2H), 8.23 (s, 2H), 7.76 (s, 2H), 7.59 (s, 2H), 3.88 (s, 6H), 3.40 (dd, J=17.5, 8.6 Hz, 2H), 3.08 (dd, J=17.5, 5.0 Hz, 2H), 2.94-2.85 (m, 2H), 2.71 (t, J=7.1 Hz, 4H), 1.91 (pentet, J=7.1 Hz, 2H), 1.18 (d, J=7.1 Hz, 6H).

Example 3: (S)-4-(5-(3-(2-(3-carboxypropanoyl)-6-methoxybenzo[b]thiophen-5-yl)propoxy)-6-methoxythieno[3,2-b]pyridin-2-yl)-2-methyl-4-oxobutanoic acid

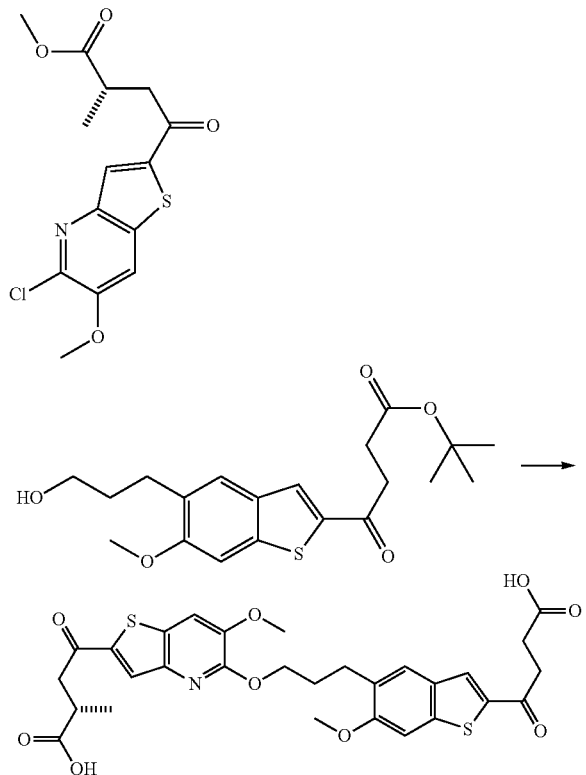

A 1 dram screw cap vial with a magnetic stir bar was charged with (S)-methyl 4-(5-chloro-6-methoxythieno[3,2-b]pyridin-2-yl)-2-methyl-4-oxobutanoate (60 mg, 0.18 mmol), tert-butyl 4-(5-(3-hydroxypropyl)-6-methoxybenzo[b]thiophen-2-yl)-4-oxobutanoate (76 mg, 0.20 mmol), RockPhos Pd G3 (7.7 mg, 9.2 mol) and $Cs_2CO_3$ (89 mg, 0.28 mmol) was sealed with a septum-containing cap. The vial was evacuated and backfilled with $N_2$ 3 times. Toluene (0.61 mL) was added, and the suspension was vortexed, sonicated, and then heated to 110° C. with stirring for 2.25 h. The reaction was then allowed to cool to RT. TFA (0.60 mL, 7.8 mmol) was added, and the mixture was stirred at RT for 1.5 h. The mixture was then concentrated under reduced pressure. To the resulting residue was added THF (1.0 mL) and MeOH (0.50 mL). Aq NaOH (2.0M, 0.50 mL, 1.0 mmol) was added, and the resulting mixture was heated to 40° C. for 5 h. Upon cooling to RT, additional aq NaOH (2.0M, 0.50 mL, 1.0 mmol) was added, and the mixture was heated to 40° C. for an additional 2.5 h. The reaction was then allowed to cool to RT and concentrated under reduced pressure. DMSO (1.0 mL) was added, and the resulting mixture was filtered through a syringe filter. The filtrate was then purified by RP-HPLC (C18, MeCN/water gradient, $NH_4OH$ modifier). The product-containing fraction was concentrated under reduced pressure and then purified further by RP-HPLC (C18, MeCN/water gradient, TFA modifier) to afford (S)-4-(5-(3-(2-(3-carboxypropanoyl)-6-methoxybenzo[b]thiophen-5-yl)propoxy)-6-methoxythieno[3,2-b]pyridin-2-yl)-2-methyl-4-oxobutanoic acid. LCMS ($C_{29}H_{30}NO_9S_2$) (ES, m/z): 600 $[M+H]^+$. $^1H$ NMR (500 MHz, DMSO-$d_6$) δ 12.18 (s, 2H), 8.22 (s, 1H), 8.20 (s, 1H), 7.97 (s, 1H), 7.78 (s, 1H), 7.60 (s, 1H), 4.39 (t, J=6.3 Hz, 2H), 3.90 (s, 3H), 3.87 (s, 3H), 3.43 (dd, J=17.5, 8.6 Hz, 1H), 3.29-3.22 (m, 2H), 3.15-3.06 (m, 1H), 2.91-2.80 (m, 3H), 2.63-2.56 (m, 2H), 2.18-2.06 (m, 2H), 1.17 (d, J=7.2 Hz, 3H).

Examples 4 through 23 and 81-83, as shown in Table 11 below, were or may be prepared according to procedures analogous to those outlined in Example 3 above using the appropriate starting materials, described in the Preparations or Intermediates above, or as obtained from commercial sources.

TABLE 11

| Example | Structure | Name | Mass $[M + H]^+$ |
|---|---|---|---|
| 4 | 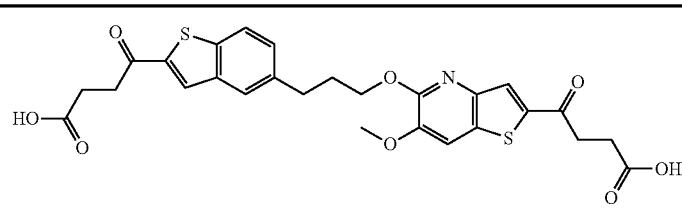 | 4-(5-(3-((2-(3-carboxy propanoyl)-6-methoxythieno [3,2-b] pyridin-5-yl)oxy) propyl)benzo[b]thiophen-2-yl)-4-oxobutanoic acid | 556 |
| 5 | 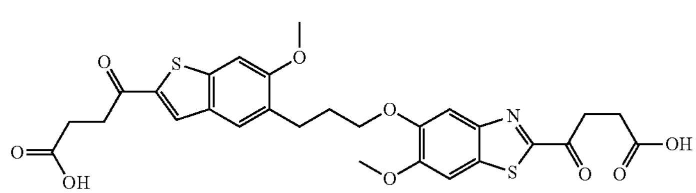 [SMILES: COc1cc2sc(C(=O)CCC(=O)O)cc2cc1CCCOc1cc2nc(C(=O)CCC(=O)O)sc2cc1OC] | 4-(5-(3-(2-(3-carboxy propanoyl)-6-methoxybenzo [b]thiophen-5-yl)propoxy)-6-methoxybenzo[d]thiazol-2-yl)-4-oxobutanoic acid | 586 |

TABLE 11-continued

| Example | Structure | Name | Mass [M + H]+ |
|---|---|---|---|
| 6 | 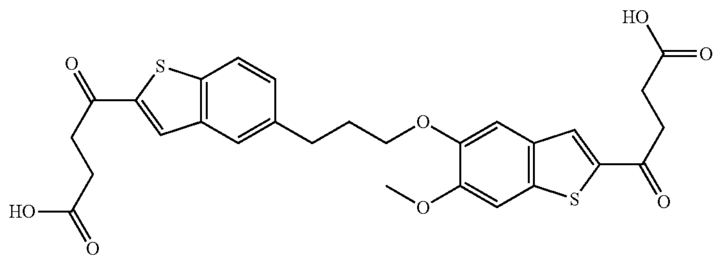 [SMILES: COc1cc2sc(C(=O)CCC(=O)O)cc2cc1OCCCc1ccc2sc(C(=O)CCC(=O)O)cc2c1] | 4-(5-(3-((2-(3-carboxy propanoyl)-6-methoxybenzo[b]thiophen-5-yl)oxy)propyl)benzo[b]thiophen-2-yl)-4-oxobutanoic acid | 555 |
| 7 | 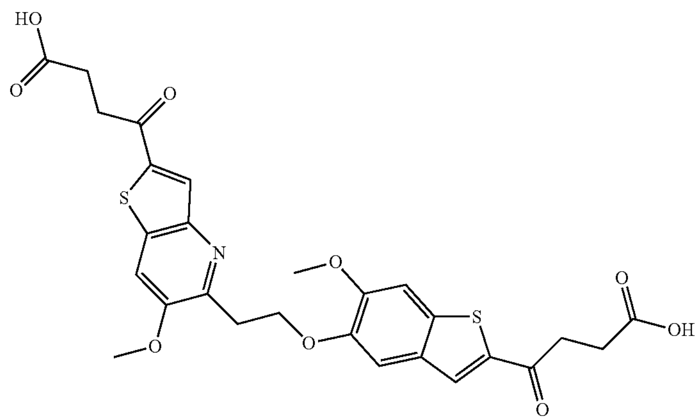 [SMILES: COc1cc2sc(C(=O)CCC(=O)O)cc2cc1OCCc1nc2cc(C(=O)CCC(=O)O)sc2cc1OC] | 4-(5-(2-((2-(3-carboxy propanoyl)-6-methoxybenzo[b]thiophen-5-yl)oxy)ethyl)-6-methoxythieno[3,2-b]pyridin-2-yl)-4-oxobutanoic acid | 572 |
| 8 | 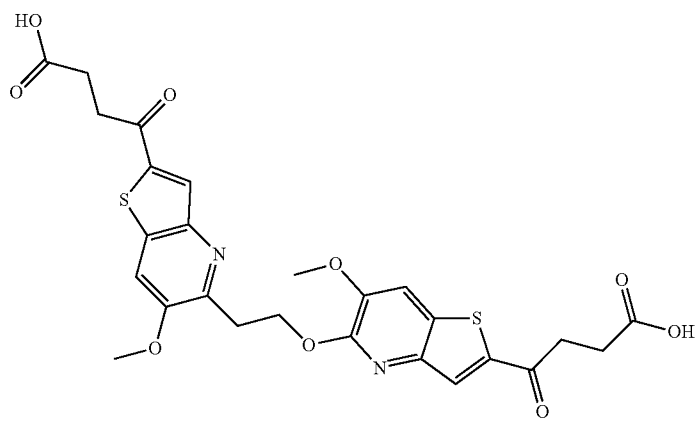 [SMILES: COc1cc2sc(C(=O)CCC(=O)O)cc2nc1CCOc1nc2cc(C(=O)CCC(=O)O)sc2cc1OC] | 4-(5-(2-(2-(3-carboxypropanoyl)-6-methoxythieno[3,2-b]pyridin-5-yl)ethoxy)-6-methoxythieno[3,2-b]pyridin-2-yl)-4-oxobutanoic acid | 573 |
| 9 | 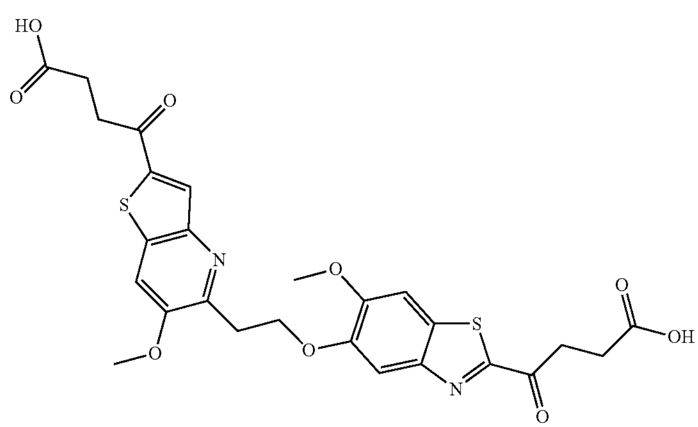 | 4-(5-(2-((2-(3-carboxypropanoyl)-6-methoxybenzo[d]thiazol-5-yl)oxy)ethyl)-6-methoxythieno[3,2-b]pyridin-2-yl)-4-oxobutanoic acid | 573 |

TABLE 11-continued

| Example | Structure | Name | Mass [M + H]+ |
|---|---|---|---|
| 10 | 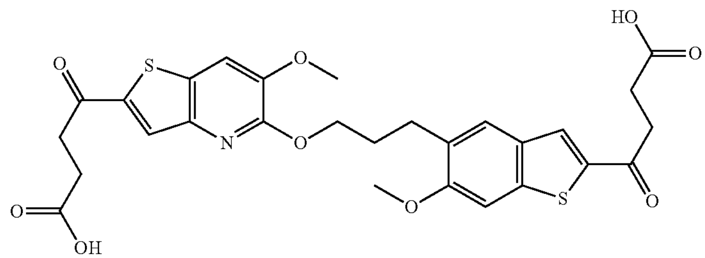 [SMILES: COc1cc2sc(C(=O)CCC(=O)O)cc2cc1CCCOc1nc2cc(C(=O)CCC(=O)O)sc2cc1OC] | 4-(5-(3-(2-(3-carboxy propanoyl)-6-methoxybenzo[b]thiophen-5-yl)propoxy)-6-methoxythieno[3,2-b]pyridin-2-yl)-4-oxobutanoic acid | 586 |
| 11 | 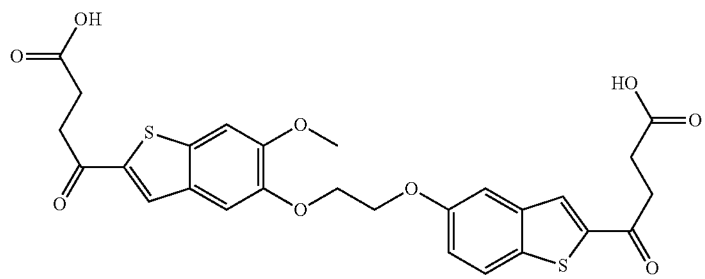 [SMILES: COc1cc2sc(C(=O)CCC(=O)O)cc2cc1OCCOc1ccc2sc(C(=O)CCC(=O)O)cc2c1] | 4-(5-(2-((2-(3-carboxy propanoyl)-6-methoxybenzo[b]thiophen-5-yl)oxy)ethoxy)benzo[b]thiophen-2-yl)-4-oxobutanoic acid | 557 |
| 12 | 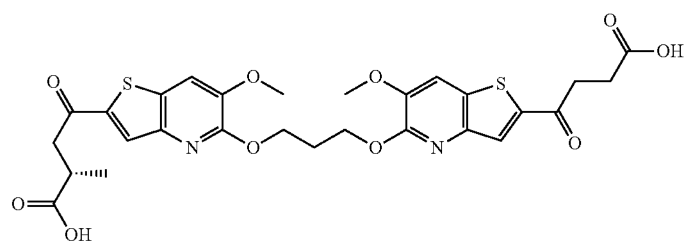 [SMILES: COc1cc2sc(C(=O)CCC(=O)O)cc2nc1OCCCOc1nc2cc(C(=O)C[C@H](C)C(=O)O)sc2cc1OC] | (S)-4-(5-(3-((2-(3-carboxy propanoyl)-6-methoxythieno[3,2-b] pyridin-5-yl)oxy)propoxy)-6-methoxybenzo[b]thiophen-2-yl)-2-methyl-4-oxobutanoic acid | 616 |
| 13 | 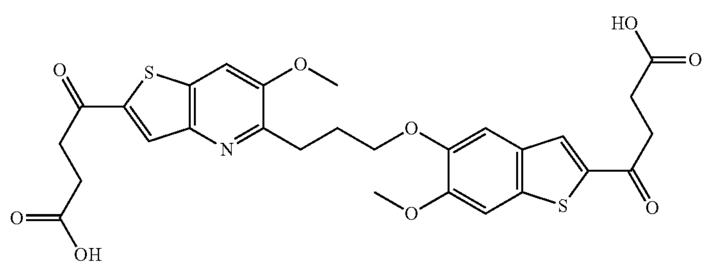 | 4-(5-(3-((2-(3-carboxypropanoyl)-6-methoxybenzo[b]thiophen-5-yl)oxy)propyl)-6-methoxythieno[3,2-b]pyridin-2-yl)-4-oxobutanoic acid | 586 |
| 14 | 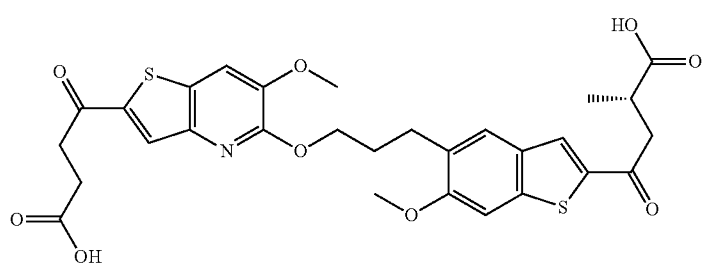 [SMILES: COc1cc2sc(C(=O)C[C@H](C)C(=O)O)cc2cc1CCCOc1nc2cc(C(=O)CCC(=O)O)sc2cc1OC] | (S)-4-(5-(3-((2-(3-carboxypropanoyl)-6-methoxythieno[3,2-b]pyridin-5-yl)oxy)propyl)-6-methoxybenzo[b]thiophen-2-yl)-2-methyl-4-oxobutanoic acid | 600 |
| 15 | 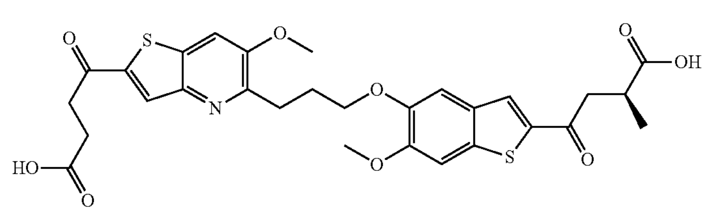 [SMILES: COc1cc2sc(C(=O)C[C@H](C)C(=O)O)cc2cc1OCCCc1nc2cc(C(=O)CCC(=O)O)sc2cc1OC] | (S)-4-(5-(3-(2-(3-carboxy propanoyl)-6-methoxythieno[3,2-b]pyridin-5-yl)propoxy)-6-methoxybenzo[b]thiophen-2-yl)-2-methyl-4-oxobutanoic acid | 600 |

TABLE 11-continued

| Example | Structure | Name | Mass [M + H]+ |
|---|---|---|---|
| 16 | 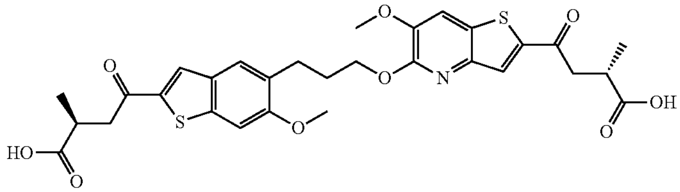 [SMILES: COc1cc2sc(C(=O)C[C@H](C)C(=O)O)cc2cc1CCCOc1nc2cc(C(=O)C[C@H](C)C(=O)O)sc2cc1OC] | (S)-4-(5-(3-(2-((S)-3-carboxy butanoyl)-6-methoxybenzo [b]thiophen-5-yl)propoxy)-6-methoxythieno[3,2-b]pyridin-2-yl)-2-methyl-4-oxobutanoic acid | 614 |
| 17 | 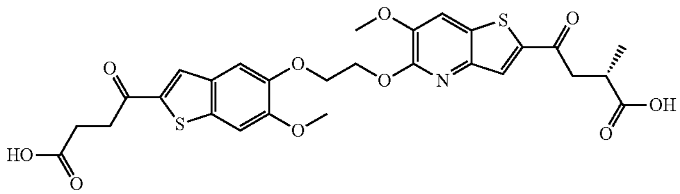 [SMILES: COc1cc2sc(C(=O)CCC(=O)O)cc2cc1OCCOc1nc2cc(C(=O)C[C@H](C)C(=O)O)sc2cc1OC] | (S)-4-(5-(2-((2-(3-carboxy propanoyl)-6-methoxybenzo [b]thiophen-5-yl)oxy)ethoxy)-6-methoxythieno[3,2-b]pyridin-2-yl)-2-methyl-4-oxobutanoic acid | 602 |
| 18 | 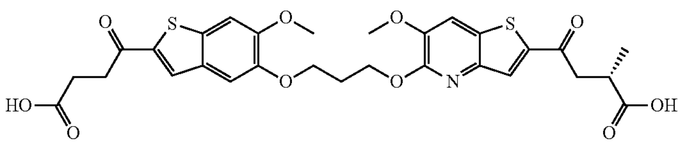 [SMILES: COc1cc2sc(C(=O)CCC(=O)O)cc2cc1OCCCOc1nc2cc(C(=O)C[C@H](C)C(=O)O)sc2cc1OC] | (S)-4-(5-(3-((2-(3-carboxy propanoyl)-6-methoxybenzo [b]thiophen-5-yl)oxy) propoxy)-6-methoxythieno [3,2-b]pyridin-2-yl)-2-methyl-4-oxobutanoic acid | 616 |
| 19 | (Rac) | rac-(R)-4-(5-(2-((2-((R)-3-carboxybutanoyl)-4-fluoro-6-methoxybenzo[b]thiophen-5-yl)oxy)ethoxy)-6-methoxy thieno[3,2-b]pyridin-2-yl)-2-methyl-4-oxobutanoic acid | 634 |
| 20 | 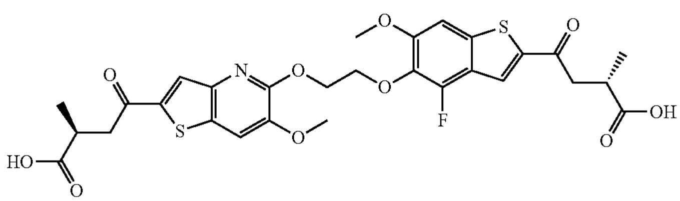 | (S)-4-(5-(2-((2-(3-carboxypropanoyl)-4-fluoro-6-methoxybenzo[b]thiophen-5-yl)oxy)ethoxy)-6-methoxy thieno[3,2-b]pyridin-2-yl)-2-methyl-4-oxobutanoic acid | 620 |
| 21 | 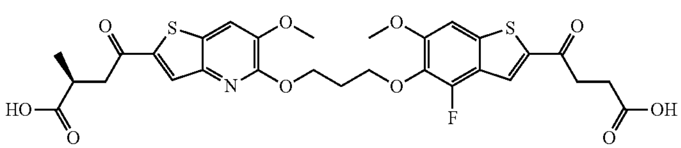 [SMILES: COc1cc2sc(C(=O)C[C@H](C)C(=O)O)cc2nc1OCCCOc1c(OC)cc2sc(C(=O)CCC(=O)O)cc2c1F] | (S)-4-(5-(3-((2-(3-carboxypropanoyl)-4-fluoro-6-methoxybenzo[b]thiophen-5-yl)oxy)propoxy)-6-methoxy thieno[3,2-b]pyridin-2-yl)-2-methyl-4-oxobutanoic acid | 634 |
| 22 | (Rac) | rac-(R)-4-(5-(3-((2-((R)-3-carboxybutanoyl)-4-fluoro-6-methoxybenzo[b] thiophen-5-yl)oxy)propoxy)-6-methoxy thieno[3,2-b]pyridin-2-yl)-2-methyl-4-oxobutanoic acid | 648 |
| 23 | 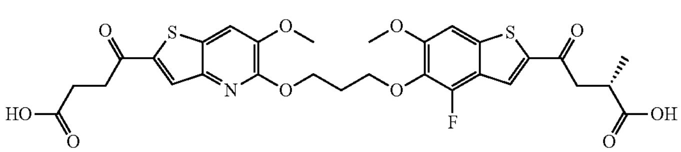 [SMILES: COc1cc2sc(C(=O)CCC(=O)O)cc2nc1OCCCOc1c(OC)cc2sc(C(=O)C[C@H](C)C(=O)O)cc2c1F] | (S)-4-(5-(3-((2-(3-carboxy propanoyl)-6-methoxythieno [3,2-b]pyridin-5-yl)oxy) propoxy)-4-fluoro-6-methoxy benzo[b]thiophen-2-yl)-2-methyl-4-oxobutanoic acid | 634 |

TABLE 11-continued

| Example | Structure | Name | Mass [M + H]+ |
|---|---|---|---|
| 81 | 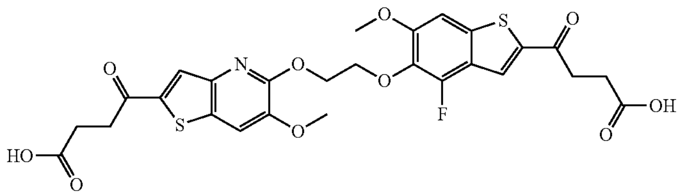 [SMILES: COc1cc2sc(C(=O)CCC(=O)O)cc2nc1OCCOc1c(OC)cc2sc(C(=O)CCC(=O)O)cc2c1F] | 4-(5-(2-((2-(3-carboxypropanoyl)-4-fluoro-6-methoxybenzo[b]thiophen-5-yl)oxy)ethoxy)-6-methoxythieno[3,2-b]pyridin-2-yl)-4-oxobutanoic acid | 606 |
| 82 | 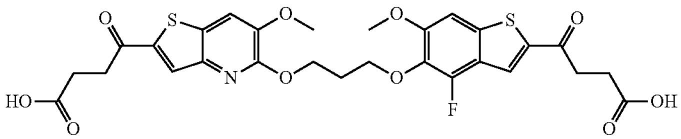 [SMILES: COc1cc2sc(C(=O)CCC(=O)O)cc2nc1OCCCOc1c(OC)cc2sc(C(=O)CCC(=O)O)cc2c1F] | 4-(5-(3-((2-(3-carboxypropanoyl)-4-fluoro-6-methoxybenzo[b]thiophen-5-yl)oxy)propoxy)-6-methoxythieno[3,2-b]pyridin-2-yl)-4-oxobutanoic acid | 620 |
| 83 | 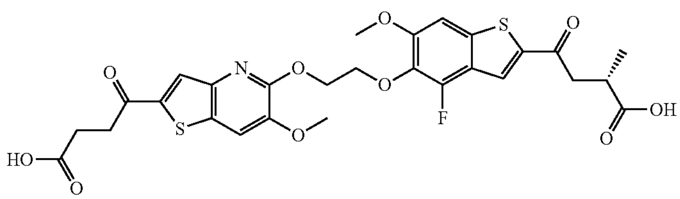 [SMILES: COc1cc2sc(C(=O)CCC(=O)O)cc2nc1OCCOc1c(OC)cc2sc(C(=O)C[C@H](C)C(=O)O)cc2c1F] | (S)-4-(5-(2-((2-(3-carboxypropanoyl)-6-methoxythieno[3,2-b]pyridin-5-yl)oxy)ethoxy)-4-fluoro-6-methoxybenzo[b]thiophen-2-yl)-2-methyl-4-oxobutanoic acid | 620 |

Example 24: 4-(5-(3-(2-(3-cyanopropanoyl)-6-methoxybenzo[b]thiophen-5-yl)propyl)-6-methoxy-benzo[b]thiophen-2-yl)-4-oxobutanoic acid Step 1: tert-butyl 4-(5-(3-(2-(3-cyanopropanoyl)-6-methoxybenzo[b]thiophen-5-yl)propyl)-6-methoxy-benzo[b]thiophen-2-yl)-4-oxobutanoate

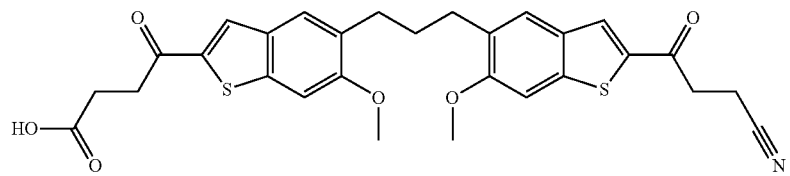 [SMILES: COc1cc2sc(C(=O)CCC#N)cc2cc1CCCc1cc2cc(C(=O)CCC(=O)O)sc2cc1OC]
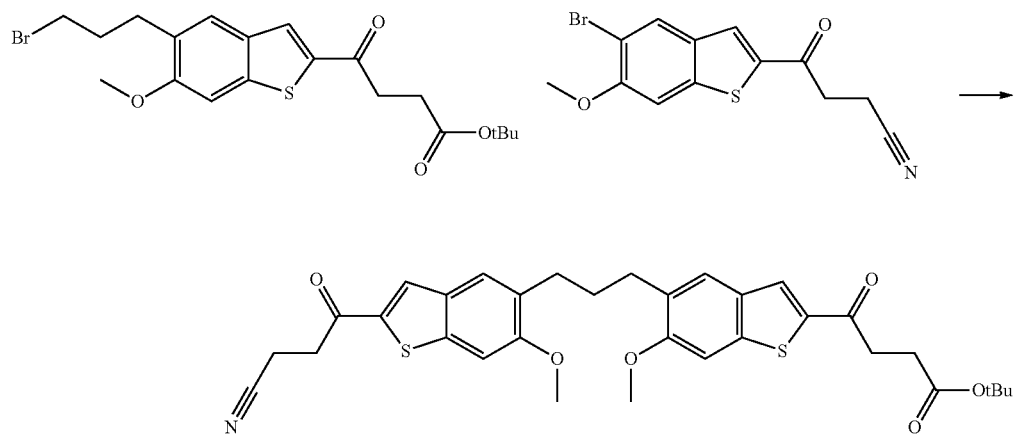

To a vial was added tert-butyl 4-(5-(3-bromopropyl)-6-methoxybenzo[b]thio phen-2-yl)-4-oxobutanoate (45 mg, 0.10 mmol), 4-(5-bromo-6-methoxybenzo[b]thiophen-2-yl)-4-oxobutanenitrile (33 mg, 0.10 mmol), NaI (7.6 mg, 0.051 mmol), nickel(II) bromide ethylene glycol dimethyl ether complex (9.4 mg, 0.031 mmol), Mn (22 mg, 0.41 mmol) and 4,4'-dimethoxy-2,2'-bipyridine (6.6 mg, 0.031 mmol). To the vial was added DMPU (1.0 mL) followed by the addition of 5% v/v solutions in DMPU of Py (82 µl, 0.051 mmol) and TMS-Cl (78 µl, 0.031 mmol). The vial was degassed with Ar for 5 min. The mixture was heated to 90° C. for 2 h. After 2 h, the mixture was allowed to cool to RT and directly purified by prep-HPLC (ACN/H$_2$O with 0.1% TFA) to afford tert-butyl 4-(5-(3-(2-(3-cyanopropanoyl)-6-methoxybenzo[b]thiophen-5-yl)propyl)-6-methoxybenzo[b]thiophen-2-yl)-4-oxobutanoate. LCMS (C$_{33}$H$_{35}$NO$_6$S$_2$Na) (ES, m/z): 628 [M+Na]$^+$.

Step 2: 4-(5-(3-(2-(3-cyanopropanoyl)-6-methoxybenzo[b]thiophen-5-yl)propyl)-6-methoxybenzo[b]thiophen-2-yl)-4-oxobutanoic acid

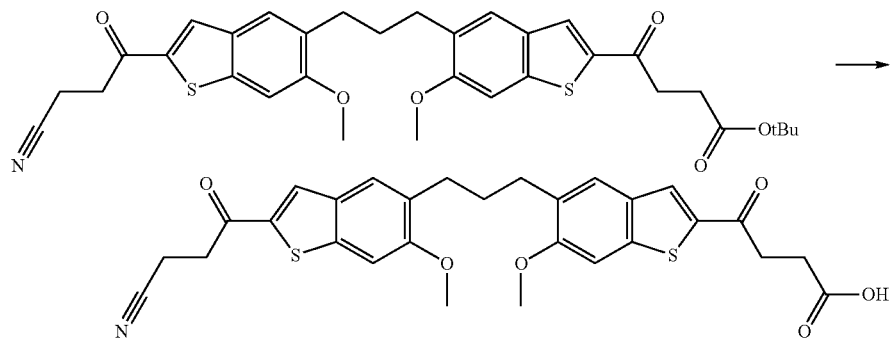

To a mixture of tert-butyl 4-(5-(3-(2-(3-cyanopropanoyl)-6-methoxybenzo[b]thiophen-5-yl)propyl)-6-methoxybenzo[b]thiophen-2-yl)-4-oxobutanoate (8.5 mg, 0.014 mmol), MeOH (500 µL) and ACN (500 µL) was added NaOH (5.0M in water, 0.56 µL, 0.28 mmol). The mixture was heated to 40° C. for 4 h. Upon cooling to RT, the mixture was purified by prep-HPLC (ACN/H$_2$O with 0.1% TFA) to afford 4-(5-(3-(2-(3-cyanopropanoyl)-6-methoxybenzo [b]thiophen-5-yl)propyl)-6-methoxybenzo[b]thiophen-2-yl)-4-oxobutanoic acid. LCMS (C$_{29}$H$_{28}$NO$_6$S$_2$) (ES, m/z): 550 [M+H]$^+$. $^1$H NMR (500 MHz, DMSO-d$_6$) δ 12.20 (s, 1H), 8.30-8.20 (m, 2H), 7.82-7.75 (m, 2H), 7.65-7.56 (m, 2H), 3.89 (s, 6H), 3.54-3.46 (m, 2H), 2.82-2.76 (m, 2H), 2.76-2.58 (m, 8H), 1.99-1.86 (m, 2H).

Example 25: 4,4'-(5,5'-(propane-1,3-diyl)bis(6-methoxybenzo[b]thiophene-5,2-diyl))bis(4-oxobutanoic acid)

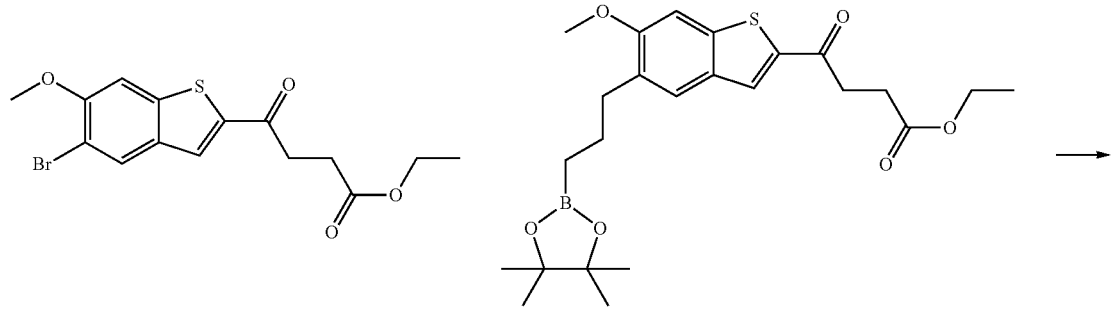

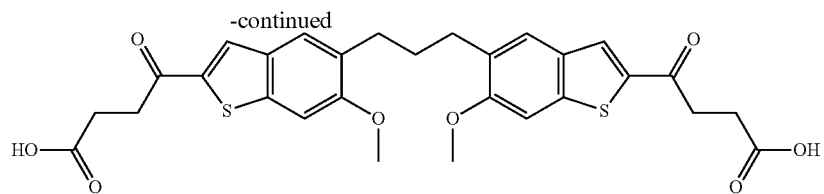

To a mixture of ethyl 4-(6-methoxy-5-(3-(4,4,5,5-tetramethyl-1,3,2-dioxaborolan-2-yl)propyl)benzo[b]thiophen-2-yl)-4-oxobutanoate (69 mg, 0.15 mmol), ethyl 4-(5-bromo-6-methoxybenzo[b]thiophen-2-yl)-4-oxobutanoate (84 mg, 0.23 mmol), $PdCl_2$(dppf)-$CH_2Cl_2$ (25 mg, 0.030 mmol) and $Cs_2CO_3$ (195 mg, 0.600 mmol) was added dioxane (0.80 mL) and water (0.2 mL). The reaction was heated to 100° C. for 18 h. Upon cooling to RT, the mixture was then filtered, and the residual materials were washed with dioxane. The filtrate was concentrated under reduced pressure. The resulting residue was then purified via prep-HPLC (ACN/$H_2O$ with 0.1% $NH_4OH$) to afford 4,4'-(5,5'-(propane-1,3-diyl)bis(6-methoxybenzo[b]thiophene-5,2-diyl))bis(4-oxobutanoic acid). LCMS ($C_{29}H_{27}O_8S_2$) (ES, m/z): 566 [M–H]⁻. ¹H NMR (600 MHz, DMSO-$d_6$) δ 8.11 (s, 2H), 7.68 (s, 2H), 7.50 (s, 2H), 3.82 (s, 6H), 3.16-3.09 (m, 4H), 2.66 (t, J=6.6 Hz, 4H), 2.40 (s, 4H), 1.93-1.83 (m, 2H).

Example 26: 4-(4-(3-(2-(3-carboxypropanoyl)-5-methoxbenzo[b]thiophen-6-yl)propyl)-6-methoxy-benzo[b]thiophen-2-yl)-4-oxobutanoic acid

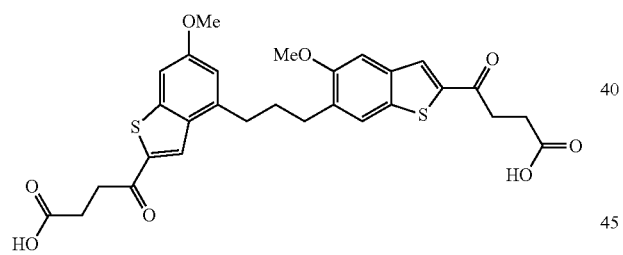

Step 1: tert-butyl 4-(5-methoxy-6-(3-(6-methoxy-2-(4-methoxy-4-oxobutanoyl)benzo[b]thiophen-4-yl)propyl) benzo[b]thiophen-2-yl)-4-oxobutanoate

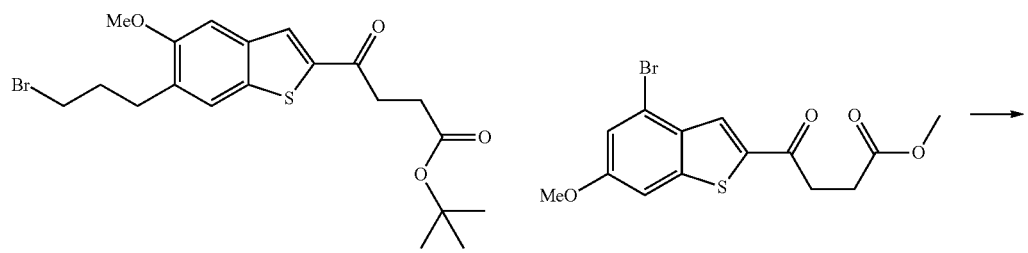

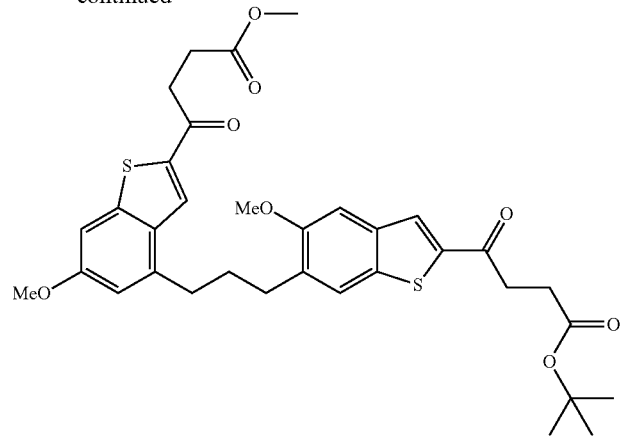

To a vial was added tert-butyl 4-(6-(3-bromopropyl)-5-methoxybenzo[b]thiophen-2-yl)-4-oxobutanoate (72 mg, 0.16 mmol), methyl 4-(4-bromo-6-methoxybenzo[b]thiophen-2-yl)-4-oxobutanoate (58 mg, 0.16 mmol), NaI (12 mg, 0.082 mmol), nickel(II) bromide ethylene glycol dimethyl ether complex (15 mg, 0.049 mmol), Mn (36 mg, 0.65 mmol) and 4,4'-dimethoxy-2,2'-bipyridine (11 mg, 0.049 mmol). To the vial was added DMPU (1.6 mL) followed by the addition of 5% v/v solutions in DMPU of Py (130 µl, 0.082 mmol) and TMS-Cl (130 µl, 0.049 mmol). The vial was degassed with Ar for 5 min. The mixture was heated to 90° C. for 1 h. After 1 h, the mixture was allowed to cool to RT and then diluted with EtOAc and water. The organic layer was separated, dried over MgSO$_4$, filtered and concentrated under reduced pressure. The resulting mixture was used without further purification or characterization.

Step 2: 4-(4-(3-(2-(3-carboxypropanoyl)-5-methoxybenzo[b]thiophen-6-yl)propyl)-6-methoxybenzo[b]thiophen-2-yl)-4-oxobutanoic acid

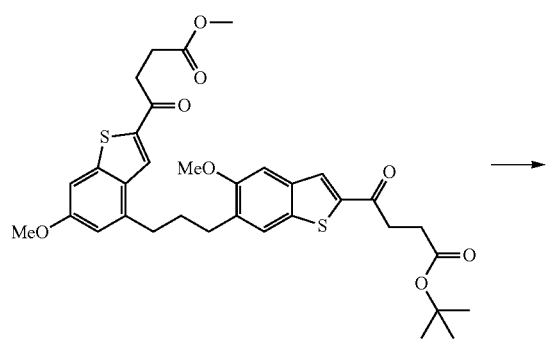

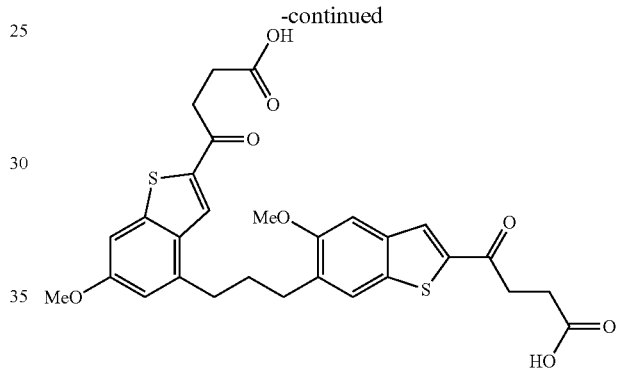

To a mixture of tert-butyl 4-(5-methoxy-6-(3-(6-methoxy-2-(4-methoxy-4-oxobutanoyl)benzo[b]thiophen-4-yl)propyl)benzo[b]thiophen-2-yl)-4-oxobutanoate (100 mg, 0.16 mmol) and MeOH (1.6 mL) was added NaOH (5M in water, 0.65 mL, 3.3 mmol), and the mixture was heated to 50° C. for 1 h. Upon cooling to RT, the mixture was purified by prep-HPLC (ACN/H$_2$O with 0.1% TFA) to afford 4-(4-(3-(2-(3-carboxypropanoyl)-5-methoxybenzo [b]thiophen-6-yl)propyl)-6-methoxybenzo[b]thiophen-2-yl)-4-oxobutanoic acid. LCMS (C$_{29}$H$_{29}$O$_8$S$_2$) (ES, m/z): 569 [M+H]$^+$. $^1$H NMR (500 MHz, DMSO-d$_6$) δ 12.23 (s, 2H), 8.27 (s, 1H), 8.25 (s, 1H), 7.82 (s, 1H), 7.50 (s, 1H), 7.44 (s, 1H), 6.93 (s, 1H), 3.89-3.79 (m, 6H), 3.34-3.19 (m, 4H), 3.03 (t, J=7.3 Hz, 2H), 2.82-2.74 (m, 2H), 2.66-2.55 (m, 4H), 2.06-1.96 (m, 2H).

Examples 27 through 31, as shown in Table 12 below, were or may be prepared according to procedures analogous to those outlined in Example 26 above using the appropriate starting materials, described in the Preparations or Intermediates above, or as obtained from commercial sources.

TABLE 12

| Example | Structure | Name | Mass [M + H]+ |
|---|---|---|---|
| 27 | 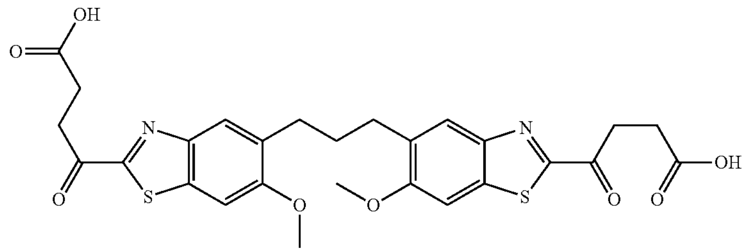 [SMILES: COc1cc2sc(C(=O)CCC(=O)O)nc2cc1CCCc1cc2nc(C(=O)CCC(=O)O)sc2cc1OC] | 4,4'-(propane-1,3-diylbis(6-methoxybenzo[d]thiazole-5,2-diyl))bis(4-oxobutanoic acid) | 571 |
| 28 | 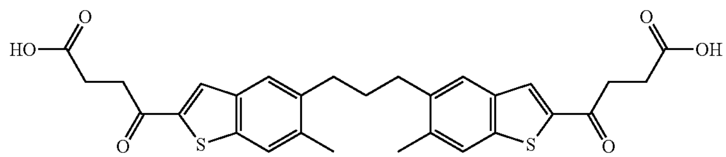 [SMILES: Cc1cc2sc(C(=O)CCC(=O)O)cc2cc1CCCc1cc2cc(C(=O)CCC(=O)O)sc2cc1C] | 4,4'-(propane-1,3-diylbis(6-methylbenzo[b]thiophene-5,2-diyl))bis(4-oxobutanoic acid) | 537 |
| 29 | 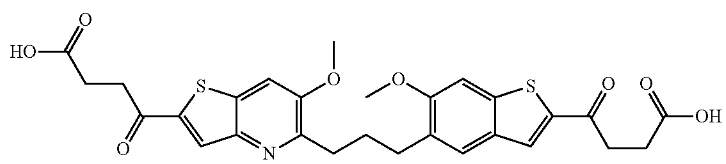 [SMILES: COc1cc2sc(C(=O)CCC(=O)O)cc2cc1CCCc1nc2cc(C(=O)CCC(=O)O)sc2cc1OC] | 4-(5-(3-(2-(3-carboxy propanoyl)-6-methoxybenzo[b]thiophen-5-yl)propyl)-6-methoxythieno[3,2-b]pyridin-2-yl)-4-oxobutanoic acid | 570 |
| 30 | 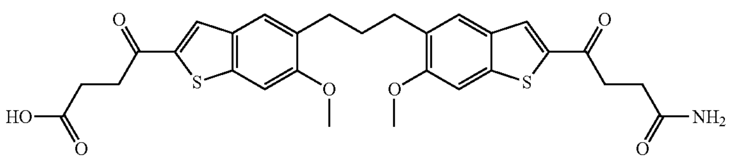 [SMILES: COc1cc2sc(C(=O)CCC(N)=O)cc2cc1CCCc1cc2cc(C(=O)CCC(=O)O)sc2cc1OC] | 4-(5-(3-(2-(4-amino-4-oxobutanoyl)-6-methoxy benzo[b]thiophen-5-yl)propyl)-6-methoxybenzo[b]thiophen-2-yl)-4-oxobutanoic acid | 568 |
| 31 | 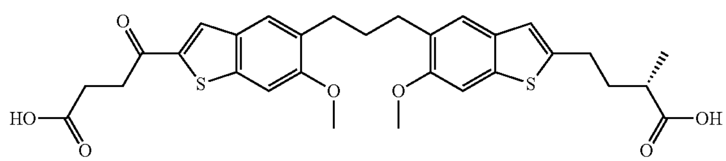 [SMILES: COc1cc2sc(CC[C@H](C)C(=O)O)cc2cc1CCCc1cc2cc(C(=O)CCC(=O)O)sc2cc1OC] | (S)-4-(5-(3-(2-(3-carboxy butyl)-6-methoxybenzo[b]thiophen-5-yl)propyl)-6-methoxybenzo[b]thiophen-2-yl)-4-oxobutanoic acid | 569 |

Example 32: 4-(5-(3-((2-(3-carboxypropanoyl)-4-fluoro-6-methoxybenzo[b]thiophen-5-yl)oxy)propyl)-6-methoxybenzo[b]thiophen-2-yl)-4-oxobutanoic acid

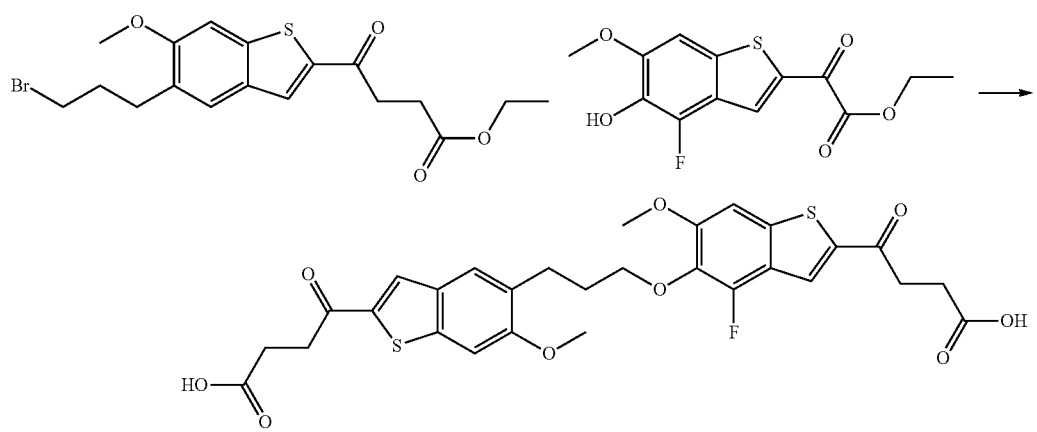

To a mixture of ethyl 4-(5-(3-bromopropyl)-6-methoxybenzo[b]thiophen-2-yl)-4-oxobutanoate (83 mg, 0.20 mmol), ethyl 4-(4-fluoro-5-hydroxy-6-methoxybenzo[b]thiophen-2-yl)-4-oxobutanoate (78 mg, 0.24 mmol), and K$_2$CO$_3$ (28 mg, 0.20 mmol) was added ACN (1 mL). The reaction was heated to 65° C. for 18 h. Upon cooling to RT, the mixture was diluted with ACN (4 mL) and filtered. The filtrate was then concentrated under reduced pressure. THF (2.0 mL), MeOH (0.50 mL), water (1.0 mL) and LiOH (48 mg, 2.0 mmol) were then added, and the mixture was allowed to stir at RT for 2 h. The mixture was then quenched with AcOH (0.40 mL), and the mixture was concentrated under reduced pressure. The resulting residue was then purified via prep-HPLC (ACN/H$_2$O with 0.1% TFA) to afford 4-(5-(3-((2-(3-carboxypropanoyl)-4-fluoro-6-methoxybenzo[b]thiophen-5-yl)oxy)propyl)-6-methoxybenzo[b]thiophen-2-yl)-4-oxobutanoic acid. LCMS (C$_{29}$H$_{28}$FO$_9$S2) (ES, m/z): 603 [M+H]$^+$. $^1$H NMR (600 MHz, DMSO-d$_6$) δ 8.28 (s, 1H), 8.20 (s, 1H), 7.73 (d, J=13.7 Hz, 1H), 7.55 (d, J=11.4 Hz, 2H), 4.06-4.00 (m, 2H), 3.90-3.81 (m, 6H), 3.28 (t, J=6.1 Hz, 2H), 3.23 (t, J=6.2 Hz, 2H), 2.82 (s, 2H), 2.58-2.56 (m, 4H), 1.95-193 (m, 2H).

Examples 33 through 40 and 84 through 157, as shown in Table 13 below, were or may be prepared according to procedures analogous to those outlined in Example 32 above using the appropriate starting materials, described in the Preparations or Intermediates above, or as obtained from commercial sources.

TABLE 13

| Example | Structure | Name | Mass [M + H]$^+$ |
|---|---|---|---|
| 33 | 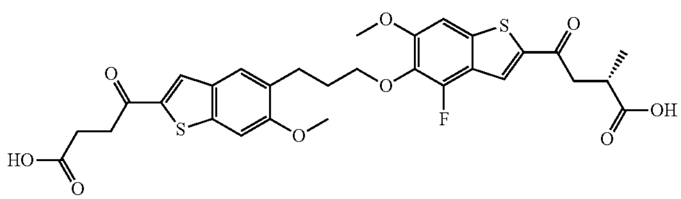 | (S)-4-(5-(3-(2-(3-carboxypropanoyl)-6-methoxybenzo[b]thiophen-5-yl)propoxy)-4-fluoro-6-methoxybenzo[b]thiophen-2-yl)-2-methyl-4-oxobutanoic acid | 617 |
| 34 | 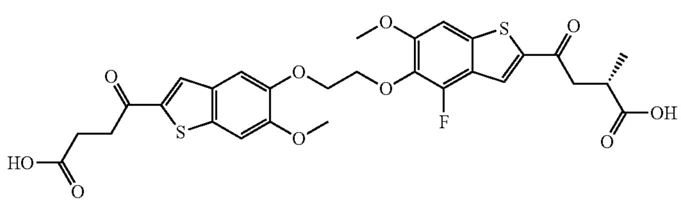 [SMILES: COc1cc2sc(C(=O)CCC(=O)O)cc2cc1CCCOc1c(OC)cc2sc(C(=O)C[C@H](C)C(=O)O)cc2c1F] | (S)-4-(5-(2-((2-(3-carboxypropanoyl)-6-methoxybenzo[b]thiophen-5-yl)oxy)ethoxy)-4-fluoro-6-methoxybenzo[b]thiophen-2-yl)-2-methyl-4-oxobutanoic acid | 619 |
| 35 | 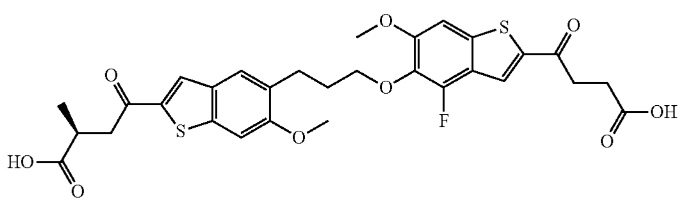 [SMILES: COc1cc2sc(C(=O)C[C@H](C)C(=O)O)cc2cc1CCCOc1c(OC)cc2sc(C(=O)CCC(=O)O)cc2c1F] | (S)-4-(5-(3-((2-(3-carboxypropanoyl)-4-fluoro-6-methoxybenzo[b]thiophen-5-yl)oxy)propyl)-6-methoxybenzo[b]thiophen-2-yl)-2-methyl-4-oxobutanoic acid | 617 |
| 36 | 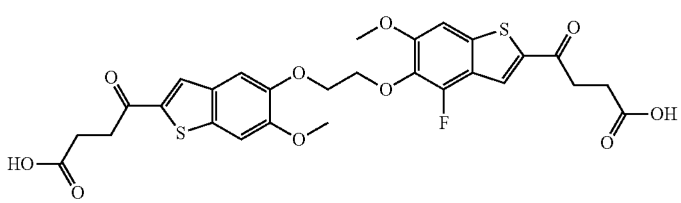 | 4-(5-(2-((2-(3-carboxypropanoyl)-4-fluoro-6-methoxybenzo[b]thiophen-5-yl)oxy)ethoxy)-6-methoxybenzo[b]thiophen-2-yl)-4-oxobutanoic acid | 605 |
| 37 | 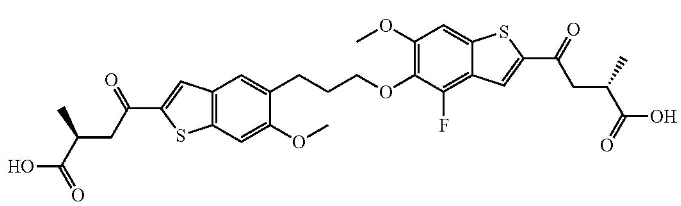 | (S)-4-(5-(3-((2-((S)-3-carboxybutanoyl)-4-fluoro-6-methoxybenzo[b]thiophen-5-yl)oxy)propyl)-6-methoxybenzo[b]thiophen-2-yl)-2-methyl-4-oxobutanoic acid | 613 |

TABLE 13-continued

| Example | Structure | Name | Mass [M + H]+ |
|---|---|---|---|
| 38 | 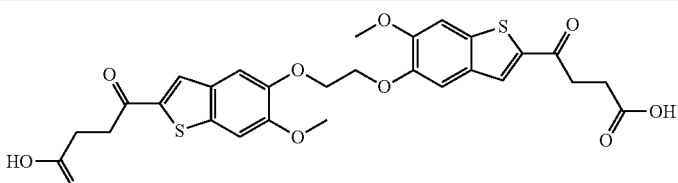 | 4,4'-((ethane-1,2-diylbis (oxy))bis(6-methoxybenzo [b]thiophene-5,2-diyl))bis(4-oxobutanoic acid) | 587 |
| 39 | 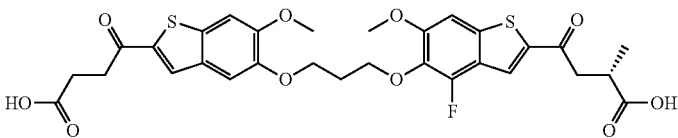 [SMILES: COc1cc2sc(C(=O)CCC(=O)O)cc2cc1OCCCOc1c(OC)cc2sc(C(=O)C[C@H](C)C(=O)O)cc2c1F] | (S)-4-(5-(3-((2-(3-carboxy propanoyl)-6-methoxybenzo [b]thiophen-5-yl)oxy) propoxy)-4-fluoro-6-methoxy benzo[b]thiophen-2-yl)-2-methyl-4-oxobutanoic acid | 633 |
| 40 | 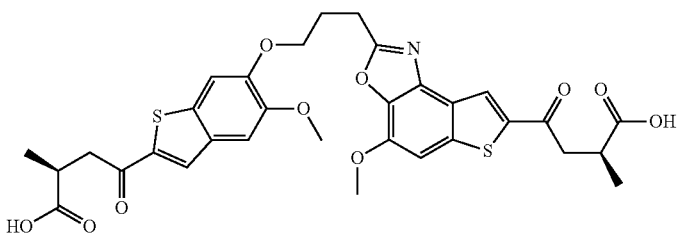 [SMILES: COc1cc2cc(C(=O)C[C@H](C)C(=O)O)sc2cc1OCCCc1nc2c(o1)c(OC)cc1sc(C(=O)C[C@H](C)C(=O)O)cc12] | (S)-4-(6-(3-(7-((S)-3-carboxybutanoyl)-4-methoxythieno[2',3':5,6] benzo[1,2-d]oxazol-2-yl) propoxy)-5-methoxybenzo [b]thiophen-2-yl)-2-methyl-4-oxobutanoic acid | 654 |
| 84 | 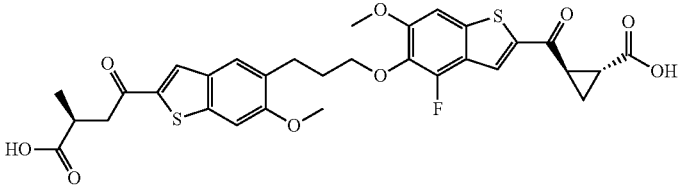 [SMILES: COc1cc2sc(C(=O)C[C@H](C)C(=O)O)cc2cc1CCCOc1c(OC)cc2sc(C(=O)[C@@H]3C[C@H]3C(=O)O)cc2c1F] | trans-2-(5-(3-(2-((S)-3-carboxybutanoyl)-6-methoxybenzo[b]thiophen-5-yl)propoxy)-4-fluoro-6-methoxybenzo[b]thiophene-2-carbonyl)-cyclopropanecarboxylic acid | 629 |
| 85 | 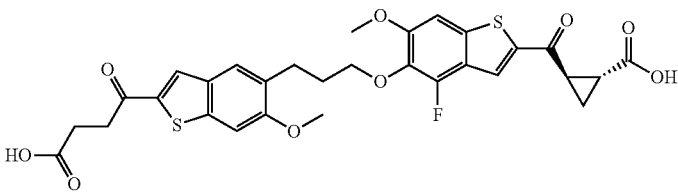 [SMILES: COc1cc2sc(C(=O)CCC(=O)O)cc2cc1CCCOc1c(OC)cc2sc(C(=O)[C@@H]3C[C@H]3C(=O)O)cc2c1F] | trans-2-(5-(3-(2-(3-carboxypropanoyl)-6-methoxybenzo[b]thiophen-5-yl)propoxy)-4-fluoro-6-methoxybenzo[b]thiophene-2-carbonyl)cyclopropane carboxylic acid | 615 |
| 86 | 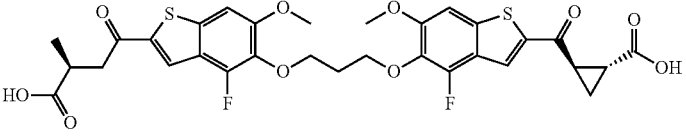 [SMILES: COc1cc2sc(C(=O)C[C@H](C)C(=O)O)cc2c(F)c1OCCCOc1c(OC)cc2sc(C(=O)[C@@H]3C[C@H]3C(=O)O)cc2c1F] | trans-2-(5-(3-((2-((S)-3-carboxybutanoyl)-4-fluoro-6-methoxybenzo[b]thiophen-5-yl)oxy)propoxy)-4-fluoro-6-methoxybenzo[b]thiophene-2-carbonyl)cyclopropane carboxylic acid | 663 |
| 87 | 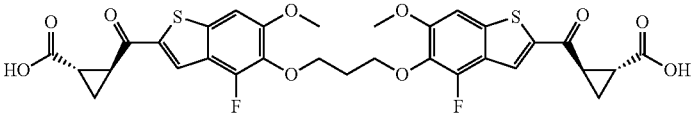 [SMILES: COc1cc2sc(C(=O)[C@H]3C[C@@H]3C(=O)O)cc2c(F)c1OCCCOc1c(OC)cc2sc(C(=O)[C@@H]3C[C@H]3C(=O)O)cc2c1F] | trans-2-(5-(3-((2-((1R,2R)-2-carboxycyclopropane carbony)-4-fluoro-6-methoxybenzo[b]thiophen-5-yl)oxy)propoxy)-4-fluoro-6-methoxybenzo[b]thiophene-2-carbonyl)cyclopropane carboxylic acid | 661 |
| 88 | 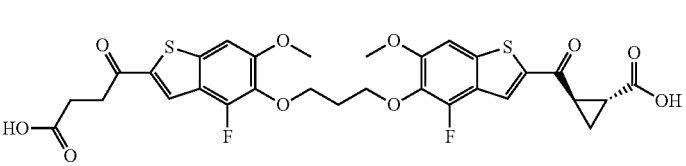 [SMILES: COc1cc2sc(C(=O)CCC(=O)O)cc2c(F)c1OCCCOc1c(OC)cc2sc(C(=O)[C@@H]3C[C@H]3C(=O)O)cc2c1F] | trans-2-(5-(3-((2-(3-carboxypropanoyl)-4-fluoro-6-methoxybenzo[b]thiophen-5-yl)oxy)propoxy)-4-fluoro-6-methoxybenzo[b]thiophene-2-carbonyl)cyclopropane carboxylic acid | 649 |

TABLE 13-continued

| Example | Structure | Name | Mass [M + H]+ |
|---|---|---|---|
| 89 | 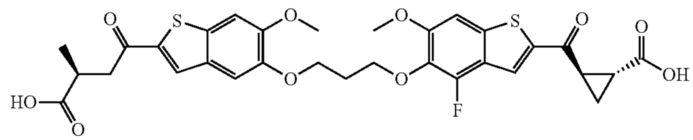 [SMILES: COc1cc2sc(C(=O)C[C@H](C)C(=O)O)cc2cc1OCCCOc1c(OC)cc2sc(C(=O)[C@@H]3C[C@H]3C(=O)O)cc2c1F] | trans-2-(5-(3-((2-((S)-3-carboxybutanoyl)-6-methoxybenzo[b]thiophen-5-yl)oxy)propoxy)-4-fluoro-6-methoxybenzo[b]thiophene-2-carbonyl)cyclopropane carboxylic acid | 645 |
| 90 | 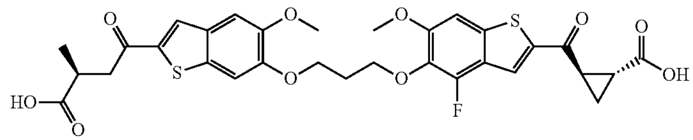 [SMILES: COc1cc2cc(C(=O)C[C@H](C)C(=O)O)sc2cc1OCCCOc1c(OC)cc2sc(C(=O)[C@@H]3C[C@H]3C(=O)O)cc2c1F] | trans-2-(5-(3-((2-((S)-3-carboxybutanoyl)-5-methoxybenzo[b]thiophen-6-yl)oxy)propoxy)-4-fluoro-6-methoxybenzo[b]thiophene-2-carbonyl)cyclopropane carboxylic acid | 645 |
| 91 | 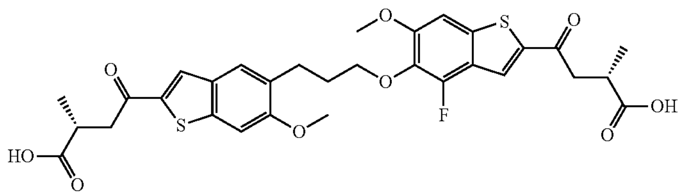 [SMILES: COc1cc2sc(C(=O)C[C@@H](C)C(=O)O)cc2cc1CCCOc1c(OC)cc2sc(C(=O)C[C@H](C)C(=O)O)cc2c1F] | (R)-4-(5-(3-((2-((S)-3-carboxybutanoyl)-4-fluoro-6-methoxybenzo[b]thiophen-5-yl)oxy)propyl)-6-methoxybenzo[b]thiophen-2-yl)-2-methyl-4-oxobutanoic acid | 631 |
| 92 | 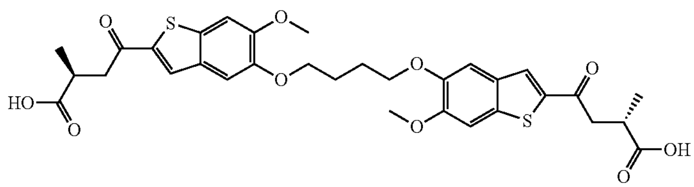 [SMILES: COc1cc2sc(C(=O)C[C@H](C)C(=O)O)cc2cc1OCCCCOc1cc2cc(C(=O)C[C@H](C)C(=O)O)sc2cc1OC] | (2S,2'S)-4,4'-(5,5'-(butane-1,4-diylbis(oxy))bis(6-methoxybenzo[b]thiophene-5,2-diyl))bis(2-methyl-4-oxobutanoic acid) | 643 |
| 93 | 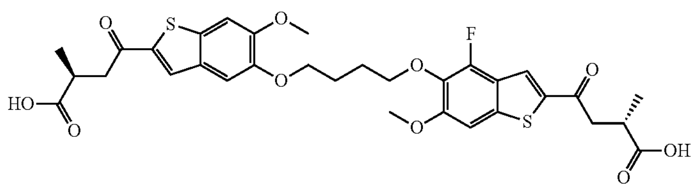 [SMILES: COc1cc2sc(C(=O)C[C@H](C)C(=O)O)cc2cc1OCCCCOc1c(OC)cc2sc(C(=O)C[C@H](C)C(=O)O)cc2c1F] | (S)-4-(5-(4-((2-((S)-3-carboxybutanoyl)-4-fluoro-6-methoxybenzo[b]thiophen-5-yl)oxy)butoxy)-6-methoxybenzo[b]thiophen-2-yl)-2-methyl-4-oxobutanoic acid | 661 |
| 94 | 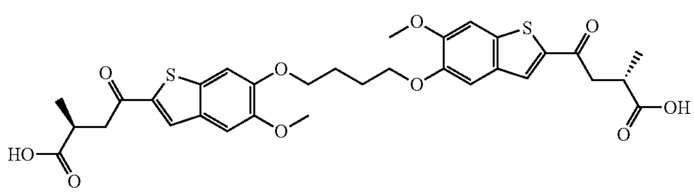 [SMILES: COc1cc2sc(C(=O)C[C@H](C)C(=O)O)cc2cc1OCCCCOc1cc2sc(C(=O)C[C@H](C)C(=O)O)cc2cc1OC] | (S)-4-(5-(4-((2-((S)-3-carboxybutanoyl)-5-methoxybenzo[b]thiophen-6-yl)oxy)butoxy)-6-methoxybenzo[b]thiophen-2-yl)-2-methyl-4-oxobutanoic acid | 643 |
| 95 | 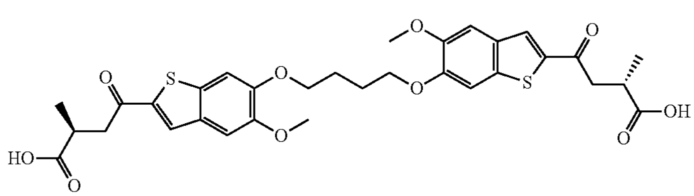 [SMILES: COc1cc2cc(C(=O)C[C@H](C)C(=O)O)sc2cc1OCCCCOc1cc2sc(C(=O)C[C@H](C)C(=O)O)cc2cc1OC] | (2S,2'S)-4,4'-(6,6'-(butane-1,4-diylbis(oxy))bis(5-methoxybenzo[b]thiophene-6,2-diyl))bis(2-methyl-4-oxobutanoic acid) | 643 |
| 96 | 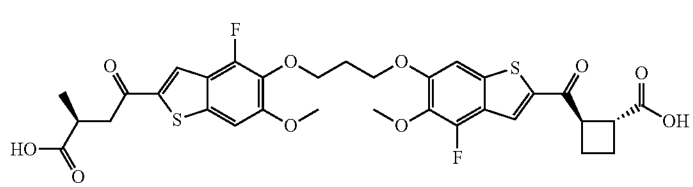 [SMILES: COc1cc2sc(C(=O)C[C@H](C)C(=O)O)cc2c(F)c1OCCCOc1cc2sc(C(=O)[C@@H]3CC[C@H]3C(=O)O)cc2c(F)c1OC] | trans-2-(6-(3-((2-((S)-3-carboxybutanoyl)-4-fluoro-6-methoxybenzo[b]thiophen-5-yl)oxy)propoxy)-4-fluoro-5-methoxybenzo[b]thiophene-2-carbonyl)cyclobutane carboxylic acid | 677 |

TABLE 13-continued

| Example | Structure | Name | Mass [M + H]+ |
|---|---|---|---|
| 97 | 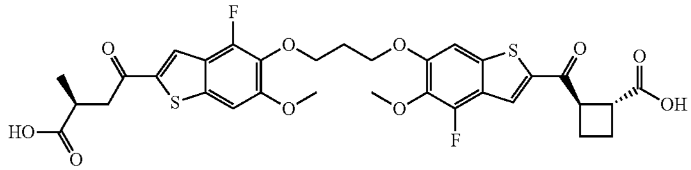 [SMILES: COc1cc2sc(C(=O)C[C@H](C)C(=O)O)cc2c(F)c1OCCCOc1cc2sc(C(=O)[C@@H]3CC[C@H]3C(=O)O)cc2c(F)c1OC] | trans-2-(6-(3-((2-((S)-3-carboxybutanoyl)-4-fluoro-6-methoxybenzo[b]thiophen-5-yl)oxy)propoxy)-4-fluoro-5-methoxybenzo[b]thiophene-2-carbonyl)cyclobutane carboxylic acid | 677 |
| 98 | 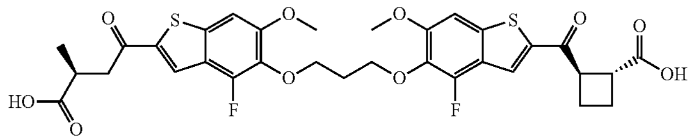 [SMILES: COc1cc2sc(C(=O)C[C@H](C)C(=O)O)cc2c(F)c1OCCCOc1c(OC)cc2sc(C(=O)[C@@H]3CC[C@H]3C(=O)O)cc2c1F] | trans-2-(5-(3-((2-((S)-3-carboxybutanoyl)-4-fluoro-6-methoxybenzo[b]thiophen-5-yl)oxy)propoxy)-4-fluoro-6-methoxybenzo[b]thiophene-2-carbonyl)cyclobutane carboxylic acid | 677 |
| 99 | 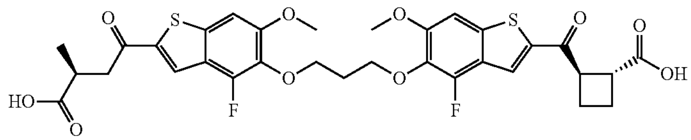 [SMILES: COc1cc2sc(C(=O)C[C@H](C)C(=O)O)cc2c(F)c1OCCCOc1c(OC)cc2sc(C(=O)[C@@H]3CC[C@H]3C(=O)O)cc2c1F] | trans-2-(5-(3-((2-((S)-3-carboxybutanoyl)-4-fluoro-6-methoxybenzo[b]thiophen-5-yl)oxy)propoxy)-4-fluoro-6-methoxybenzo[b]thiophene-2-carbonyl)cyclobutane carboxylic acid | 677 |
| 100 | 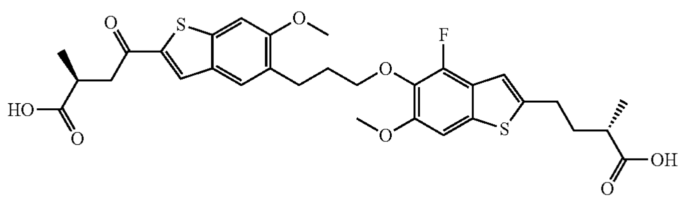 | (S)-4-(5-(3-((2-((S)-3-carboxybutyl)-4-fluoro-6-methoxybenzo[b]thiophen-5-yl)oxy)propyl)-6-methoxybenzo[b]thiophen-2-yl)-2-methyl-4-oxobutanoic acid | 617 |
| 101 | 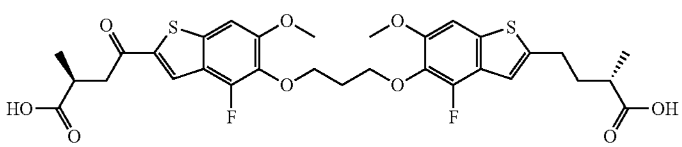 [SMILES: COc1cc2sc(CC[C@H](C)C(=O)O)cc2c(F)c1OCCCOc1c(OC)cc2sc(C(=O)C[C@H](C)C(=O)O)cc2c1F] | (S)-4-(5-(3-((2-((S)-3-carboxybutyl)-4-fluoro-6-methoxybenzo[b]thiophen-5-yl)oxy)propoxy)-4-fluoro-6-methoxybenzo[b]thiophen-2-yl)-2-methyl-4-oxobutanoic acid | 651 |
| 102 | 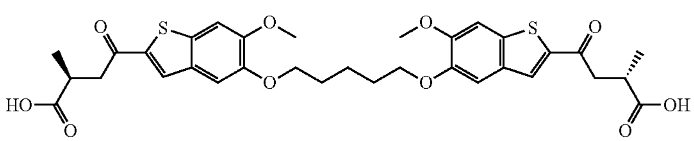 [SMILES: COc1cc2sc(C(=O)C[C@H](C)C(=O)O)cc2cc1OCCCCCOc1cc2cc(C(=O)C[C@H](C)C(=O)O)sc2cc1OC] | (2S,2'S)-4,4'-(5,5'-(pentane-1,5-diylbis(oxy))bis(6-methoxybenzo[b]thiophene-5,2-diyl))bis(2-methyl-4-oxobutanoic acid) | 657 |
| 103 | 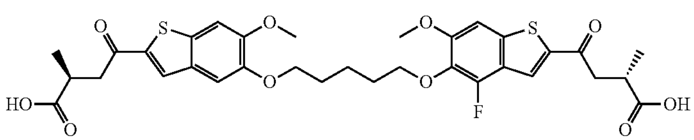 | (S)-4-(5-((5-((2-((S)-3-carboxybutanoyl)-4-fluoro-6-methoxybenzo[b]thiophen-5-yl)oxy)pentyl)oxy)-6-methoxybenzo[b]thiophen-2-yl)-2-methyl-4-oxobutanoic acid | 675 |
| 104 | 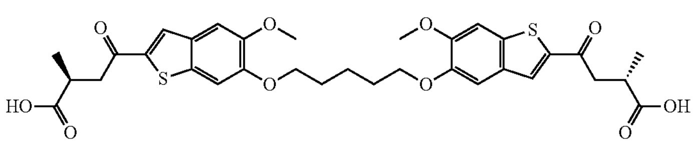 [SMILES: COc1cc2sc(C(=O)C[C@H](C)C(=O)O)cc2cc1OCCCCCOc1cc2sc(C(=O)C[C@H](C)C(=O)O)cc2cc1OC] | (S)-4-(5-((5-((2-((S)-3-carboxybutanoyl)-5-methoxybenzo[b]thiophen-6-yl)oxy)pentyl)oxy)-6-methoxybenzo[b]thiophen-2-yl)-2-methyl-4-oxobutanoic acid | 657 |
| 105 | 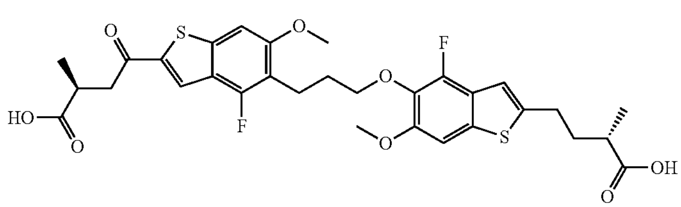 [SMILES: COc1cc2sc(C(=O)C[C@H](C)C(=O)O)cc2c(F)c1CCCOc1c(OC)cc2sc(CC[C@H](C)C(=O)O)cc2c1F] | (S)-4-(5-(3-((2-((S)-3-carboxybutyl)-4-fluoro-6-methoxybenzo[b]thiophen-5-yl)oxy)propyl)-4-fluoro-6-methoxybenzo[b]thiophen-2-yl)-2-methyl-4-oxobutanoic acid | 635 |

TABLE 13-continued

| Example | Structure | Name | Mass [M + H]+ |
|---|---|---|---|
| 106 | 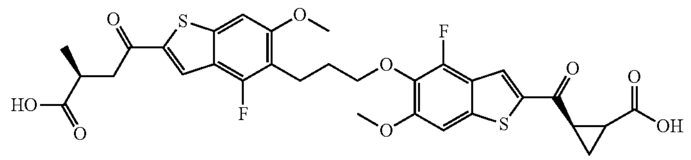 [SMILES: COc1cc2sc(C(=O)C[C@H](C)C(=O)O)cc2c(F)c1CCCOc1c(OC)cc2sc(C(=O)[C@@H]3CC3C(=O)O)cc2c1F] | trans-2-(5-(3-(2-((S)-3-carboxybutanoyl)-4-fluoro-6-methoxybenzo[b]thiophen-5-yl)propoxy)-4-fluoro-6-methoxybenzo[b]thiophene-2-carbonyl)cyclopropane carboxylic acid | 647 |
| 107 | 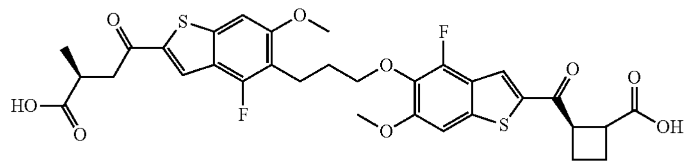 [SMILES: COc1cc2sc(C(=O)C[C@H](C)C(=O)O)cc2c(F)c1CCCOc1c(OC)cc2sc(C(=O)[C@@H]3CCC3C(=O)O)cc2c1F] | trans-2-(5-(3-(2-((S)-3-carboxybutanoyl)-4-fluoro-6-methoxybenzo[b]thiophen-5-yl)propoxy)-4-fluoro-6-methoxybenzo[b]thiophene-2-carbonyl)cyclobutane carboxylic acid | 661 |
| 108 | 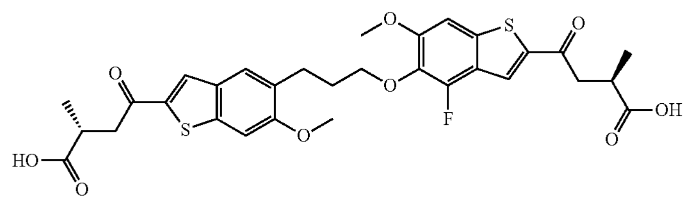 [SMILES: COc1cc2sc(C(=O)C[C@@H](C)C(=O)O)cc2cc1CCCOc1c(OC)cc2sc(C(=O)C[C@@H](C)C(=O)O)cc2c1F] | (R)-4-(5-(3-((2-((R)-3-carboxybutanoyl)-4-fluoro-6-methoxybenzo[b]thiophen-5-yl)oxy)propyl)-6-methoxybenzo[b]thiophen-2-yl)-2-methyl-4-oxobutanoic acid | 631 |
| 109 | 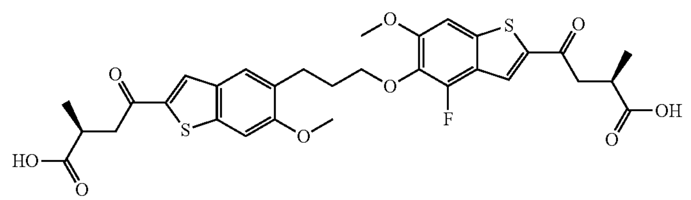 [SMILES: COc1cc2sc(C(=O)C[C@H](C)C(=O)O)cc2cc1CCCOc1c(OC)cc2sc(C(=O)C[C@@H](C)C(=O)O)cc2c1F] | (S)-4-(5-(3-((2-((R)-3-carboxybutanoyl)-4-fluoro-6-methoxybenzo[b]thiophen-5-yl)oxy)propyl)-6-methoxybenzo[b]thiophen-2-yl)-2-methyl-4-oxobutanoic acid | 631 |
| 110 | 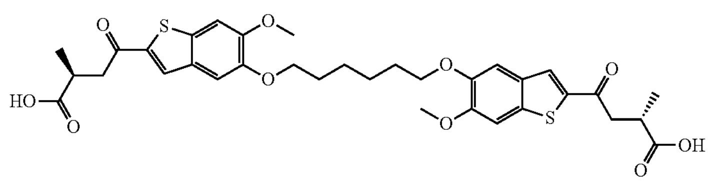 [SMILES: COc1cc2sc(C(=O)C[C@H](C)C(=O)O)cc2cc1OCCCCCCOc1cc2cc(C(=O)C[C@H](C)C(=O)O)sc2cc1OC] | (2S,2'S)-4,4'-(5,5'-(hexane-1,6-diylbis(oxy))bis(6-methoxybenzo[b]thiophene-5,2-diyl))bis(2-methyl-4-oxobutanoic acid) | 671 |
| 111 | 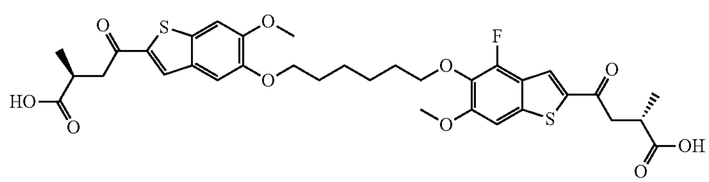 | (S)-4-(5-((6-((2-((S)-3-carboxybutanoyl)-4-fluoro-6-methoxybenzo[b]thiophen-5-yl)oxy)hexyl)oxy)-6-methoxybenzo[b]thiophen-2-yl)-2-methyl-4-oxobutanoic acid | 689 |
| 112 | 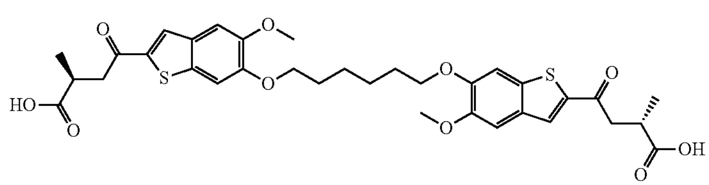 [SMILES: COc1cc2cc(C(=O)C[C@H](C)C(=O)O)sc2cc1OCCCCCCOc1cc2sc(C(=O)C[C@H](C)C(=O)O)cc2cc1OC] | (2S,2'S)-4,4'-(6,6'-(hexane-1,6-diylbis(oxy))bis(5-methoxybenzo[b]thiophene-6,2-diyl))bis(2-methyl-4-oxobutanoic acid) | 671 |
| 113 | 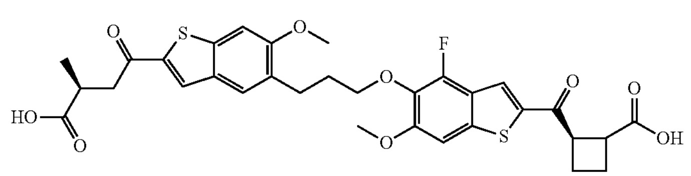 [SMILES: COc1cc2sc(C(=O)C[C@H](C)C(=O)O)cc2cc1CCCOc1c(OC)cc2sc(C(=O)[C@@H]3CCC3C(=O)O)cc2c1F] | trans-2-(5-(3-(2-((S)-3-carboxybutanoyl)-6-methoxybenzo[b]thiophen-5-yl)propoxy)-4-fluoro-6-methoxybenzo[b]thiophene-2-carbonyl)cyclobutane carboxylic acid | 643 |

TABLE 13-continued

| Example | Structure | Name | Mass [M + H]+ |
|---|---|---|---|
| 114 | 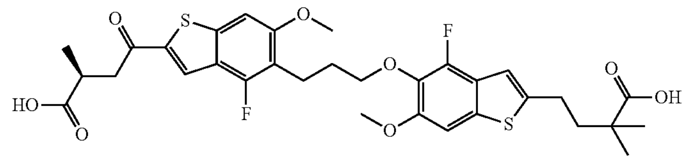 [SMILES: COc1cc2sc(C(=O)C[C@H](C)C(=O)O)cc2c(F)c1CCCOc1c(OC)cc2sc(CCC(C)(C)C(=O)O)cc2c1F] | (S)-4-(5-(3-((2-(3-carboxy-3-methylbutyl)-4-fluoro-6-methoxybenzo[b]thiophen-5-yl)oxy)propyl)-4-fluoro-6-methoxybenzo[b]thiophen-2-yl)-2-methyl-4-oxobutanoic acid | 649 |
| 115 | 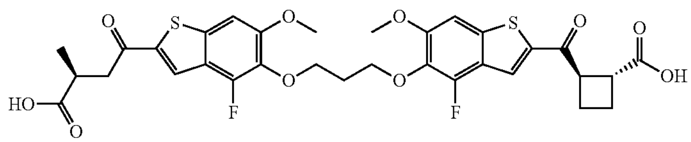 [SMILES: COc1cc2sc(C(=O)C[C@H](C)C(=O)O)cc2c(F)c1OCCCOc1c(OC)cc2sc(C(=O)[C@@H]3CC[C@H]3C(=O)O)cc2c1F] | trans-2-(5-(3-((2-((S)-3-carboxybutyl)-4-fluoro-6-methoxybenzo[b]thiophen-5-yl)oxy)propoxy)-4-fluoro-6-methoxybenzo[b]thiophene-2-carbonyl)cyclobutanecarboxylic acid | 663 |
| 116 | 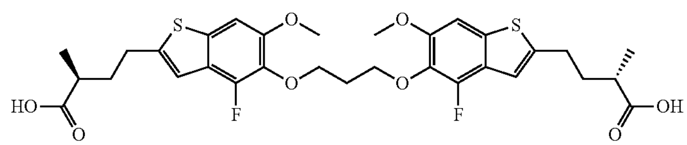 [SMILES: COc1cc2sc(CC[C@H](C)C(=O)O)cc2c(F)c1OCCCOc1c(OC)cc2sc(CC[C@H](C)C(=O)O)cc2c1F] | (2S,2'S)-4,4'-(5,5'-(propane-1,3-diylbis(oxy))bis(4-fluoro-6-methoxybenzo[b]thiophene-5,2-diyl))bis(2-methylbutanoic acid) | 654 (M + H$_2$O) |
| 117 | 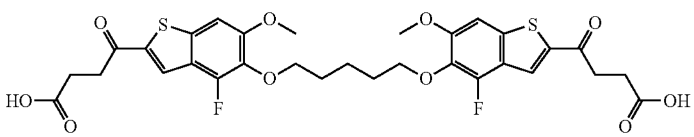 [SMILES: COc1cc2sc(C(=O)CCC(=O)O)cc2c(F)c1OCCCCCOc1c(OC)cc2sc(C(=O)CCC(=O)O)cc2c1F] | 4,4'-(5,5'-(pentane-1,5-diylbis(oxy))bis(4-fluoro-6-methoxybenzo[b]thiophene-5,2-diyl))bis(4-oxobutanoic acid) | 665 |
| 118 | 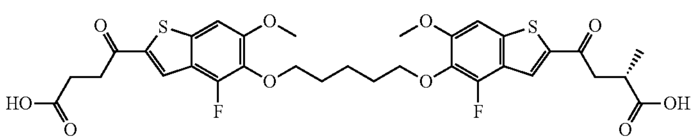 [SMILES: COc1cc2sc(C(=O)CCC(=O)O)cc2c(F)c1OCCCCCOc1c(OC)cc2sc(C(=O)C[C@H](C)C(=O)O)cc2c1F] | (S)-4-(5-((5-((2-(3-carboxypropanoyl)-4-fluoro-6-methoxybenzo[b]thiophen-5-yloxy)pentyloxy)-4-fluoro-6-methoxybenzo[b]thiophen-2-yl)-2-methyl-4-oxobutanoic acid | 679 |
| 119 | 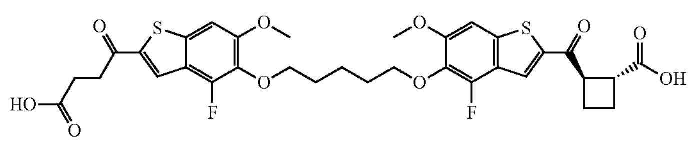 [SMILES: COc1cc2sc(C(=O)CCC(=O)O)cc2c(F)c1OCCCCCOc1c(OC)cc2sc(C(=O)[C@@H]3CC[C@H]3C(=O)O)cc2c1F] | 2-(5-((5-((2-(3-carboxypropanoyl)-4-fluoro-6-methoxybenzo[b]thiophen-5-yl)oxy)pentyl)oxy)-4-fluoro-6-methoxybenzo[b]thiophene-2-carbonyl)cyclobutanecarboxylic acid | 691 |
| 120 | 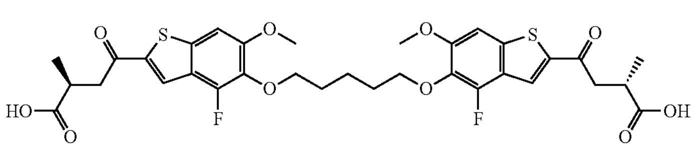 [SMILES: COc1cc2sc(C(=O)C[C@H](C)C(=O)O)cc2c(F)c1OCCCCCOc1c(OC)cc2sc(C(=O)C[C@H](C)C(=O)O)cc2c1F] | (2S,2'S)-4,4'-(5,5'-(pentane-1,5-diylbis(oxy))bis(4-fluoro-6-methoxybenzo[b]thiophene-5,2-diyl))bis(2-methyl-4-oxobutanoic acid) | 693 |
| 121 | 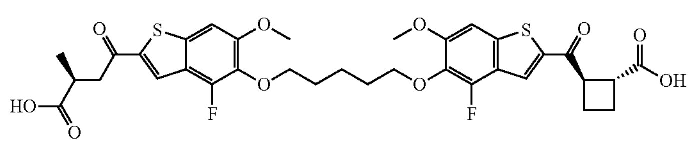 [SMILES: COc1cc2sc(C(=O)C[C@H](C)C(=O)O)cc2c(F)c1OCCCCCOc1c(OC)cc2sc(C(=O)[C@@H]3CC[C@H]3C(=O)O)cc2c1F] | trans-2-(5-((5-((2-((S)-3-carboxybutanoyl)-4-fluoro-6-methoxybenzo[b]thiophen-5-yl)oxy)pentyl)oxy)-4-fluoro-6-methoxybenzo[b]thiophene-2-carbonyl)cyclobutanecarboxylic acid | 705 |
| 122 | 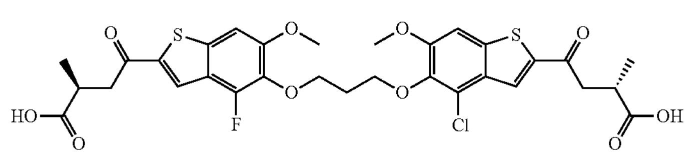 | (S)-4-(5-(3-((2-((S)-3-carboxybutanoyl)-4-chloro-6-methoxybenzo[b]thiophen-5-yl)oxy)propoxy)-4-fluoro-6-methoxybenzo[b]thiophen-2-yl)-2-methyl-4-oxobutanoic acid | 663 (M − H$_2$O + H$^+$) |

TABLE 13-continued

| Example | Structure | Name | Mass [M + H]+ |
|---|---|---|---|
| 123 | 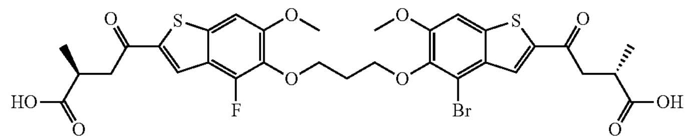 [SMILES: COc1cc2sc(C(=O)C[C@H](C)C(=O)O)cc2c(F)c1OCCCOc1c(OC)cc2sc(C(=O)C[C@H](C)C(=O)O)cc2c1Br] | (S)-4-(5-(3-((4-bromo-2-((S)-3-carboxybutanoyl)-6-methoxybenzo[b]thiophen-5-yl)oxy)propoxy)-4-fluoro-6-methoxybenzo[b]thiophen-2-yl)-2-methyl-4-oxobutanoic acid | 707, 709 (M − H$_2$O + H+) |
| 124 | 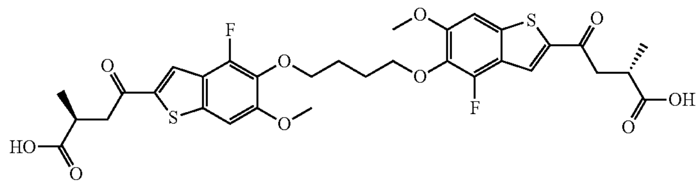 [SMILES: COc1cc2sc(C(=O)C[C@H](C)C(=O)O)cc2c(F)c1OCCCCOc1c(OC)cc2sc(C(=O)C[C@H](C)C(=O)O)cc2c1F] | (S)-4-(5-(4-((2-((S)-3-carboxybutyl)-4-fluoro-6-methoxybenzo[b]thiophen-5-yl)oxy)butoxy)-4-fluoro-6-methoxybenzo[b]thiophen-2-yl)-2-methyl-4-oxobutanoic acid | 665 |
| 125 | 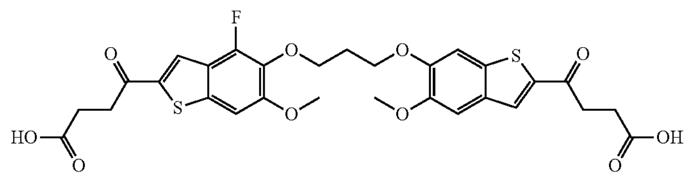 | 4-(6-(3-((2-(3-carboxypropanoyl)-4-fluoro-6-methoxybenzo[b]thiophen-5-yl)oxy)propoxy)-5-methoxybenzo[b]thiophen-2-yl)-4-oxobutanoic acid | 619 |
| 126 | 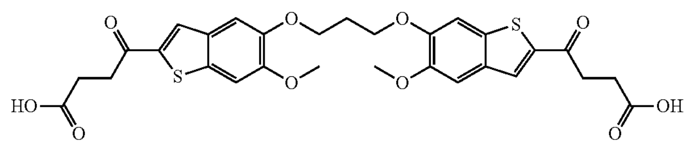 [SMILES: COc1cc2sc(C(=O)CCC(=O)O)cc2cc1OCCCOc1cc2sc(C(=O)CCC(=O)O)cc2cc1OC] | 4-(5-(3-((2-(3-carboxypropanoyl)-5-methoxybenzo[b]thiophen-6-yl)oxy)propoxy)-6-methoxybenzo[b]thiophen-2-yl)-4-oxobutanoic acid | 601 |
| 127 | 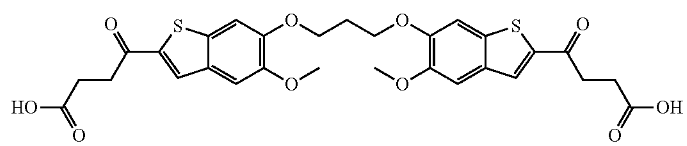 [SMILES: COc1cc2cc(C(=O)CCC(=O)O)sc2cc1OCCCOc1cc2sc(C(=O)CCC(=O)O)cc2cc1OC] | 4,4'-(6,6'-(propane-1,3-diylbis(oxy))bis(5-methoxybenzo[b]thiophene-6,2-diyl))bis(4-oxobutanoic acid) | 601 |
| 128 | 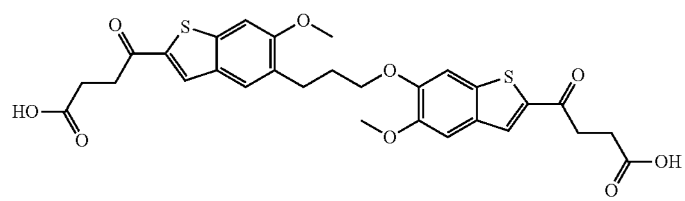 [SMILES: COc1cc2sc(C(=O)CCC(=O)O)cc2cc1CCCOc1cc2sc(C(=O)CCC(=O)O)cc2cc1OC] | 4-(5-(3-((2-(3-carboxypropanoyl)-5-methoxybenzo[b]thiophen-6-yl)oxy)propyl)-6-methoxybenzo[b]thiophen-2-yl)-4-oxobutanoic acid | 585 |
| 129 | 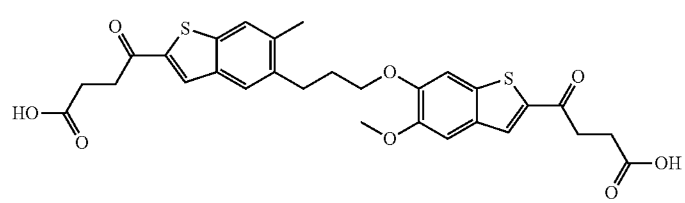 [SMILES: COc1cc2cc(C(=O)CCC(=O)O)sc2cc1OCCCc1cc2cc(C(=O)CCC(=O)O)sc2cc1C] | 4-(5-(3-((2-(3-carboxypropanoyl)-5-methoxybenzo[b]thiophen-6-yl)oxy)propyl)-6-methylbenzo[b]thiophen-2-yl)-4-oxobutanoic acid | 569 |
| 130 | 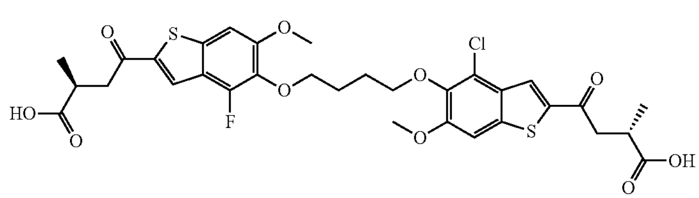 [SMILES: COc1cc2sc(C(=O)C[C@H](C)C(=O)O)cc2c(F)c1OCCCCOc1c(OC)cc2sc(C(=O)C[C@H](C)C(=O)O)cc2c1Cl] | (S)-4-(5-(4-((2-((S)-3-carboxybutanoyl)-4-chloro-6-methoxybenzo[b]thiophen-5-yl)oxy)butoxy)-4-fluoro-6-methoxybenzo[b]thiophen-2-yl)-2-methyl-4-oxobutanoic acid | 695 |

TABLE 13-continued

| Example | Structure | Name | Mass [M + H]+ |
|---|---|---|---|
| 131 | 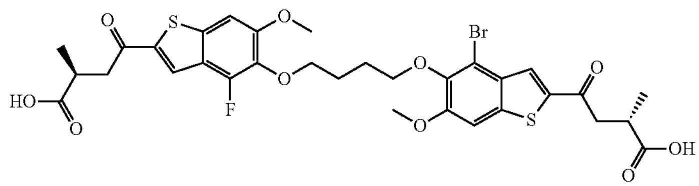 [SMILES: COc1cc2sc(C(=O)C[C@H](C)C(=O)O)cc2c(F)c1OCCCCOc1c(OC)cc2sc(C(=O)C[C@H](C)C(=O)O)cc2c1Br] | (S)-4-(5-(4-((4-bromo-2-((S)-3-carboxybutanoyl)-6-methoxybenzo[b]thiophen-5-yl)oxy)butoxy)-4-fluoro-6-methoxybenzo[b]thiophen-2-yl)-2-methyl-4-oxobutanoic acid | 739, 741 |
| 132 | 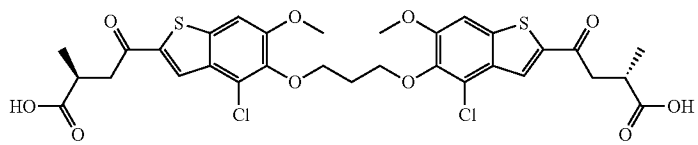 | (2S,2'S)-4,4'-(5,5'-(propane-1,3-diylbis(oxy))bis(4-chloro-6-methoxybenzo[b]thiophene-5,2-diyl))bis(2-methyl-4-oxobutanoic acid) | 697, 699 |
| 133 | 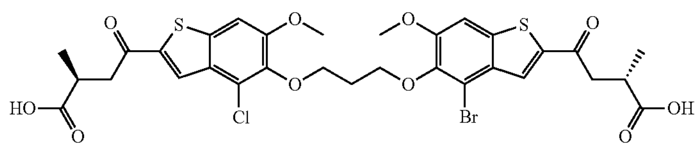 [SMILES: COc1cc2sc(C(=O)C[C@H](C)C(=O)O)cc2c(Cl)c1OCCCOc1c(OC)cc2sc(C(=O)C[C@H](C)C(=O)O)cc2c1Br] | (S)-4-(5-(3-((4-bromo-2-((S)-3-carboxybutanoyl)-6-methoxybenzo[b]thiophen-5-yl)oxy)propoxy)-4-chloro-6-methoxybenzo[b]thiophen-2-yl)-2-methyl-4-oxobutanoic acid | 723, 725 (M − H$_2$O + H+) |
| 134 | 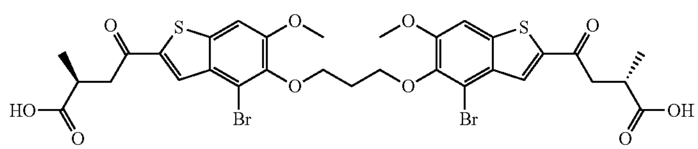 [SMILES: COc1cc2sc(C(=O)C[C@H](C)C(=O)O)cc2c(Br)c1OCCCOc1c(OC)cc2sc(C(=O)C[C@H](C)C(=O)O)cc2c1Br] | (2S,2'S)-4,4'-(5,5'-(propane-1,3-diylbis(oxy))bis(4-bromo-6-methoxybenzo[b]thiophene-5,2-diyl))bis(2-methyl-4-oxobutanoic acid) | 767, 769, 771 (M − H$_2$O + H+) |
| 135 | 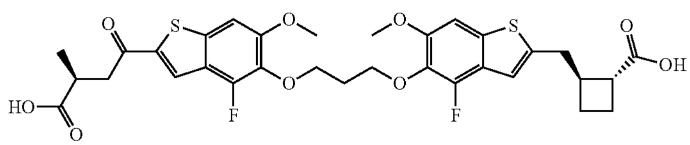 [SMILES: COc1cc2sc(C[C@@H]3CC[C@H]3C(=O)O)cc2c(F)c1OCCCOc1c(OC)cc2sc(C(=O)C[C@H](C)C(=O)O)cc2c1F] | 2-((5-(3-((2-((S)-3-carboxybutanoyl)-4-fluoro-6-methoxybenzo[b]thiophen-5-yl)oxy)propoxy)-4-fluoro-6-methoxybenzo[b]thiophen-2-yl)methyl)cyclobutanecarboxylic acid | 663 |
| 136 | 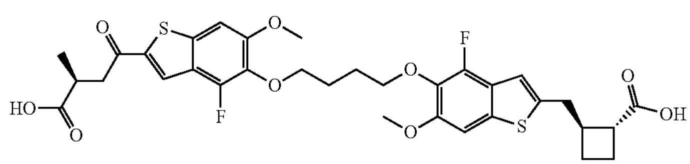 [SMILES: COc1cc2sc(C[C@@H]3CC[C@H]3C(=O)O)cc2c(F)c1OCCCCOc1c(OC)cc2sc(C(=O)C[C@H](C)C(=O)O)cc2c1F] | 2-((5-(4-((2-((S)-3-carboxybutanoyl)-4-fluoro-6-methoxybenzo[b]thiophen-5-yl)oxy)butoxy)-4-fluoro-6-methoxybenzo[b]thiophen-2-yl)methyl)cyclobutanecarboxylic acid | 677 |
| 137 | 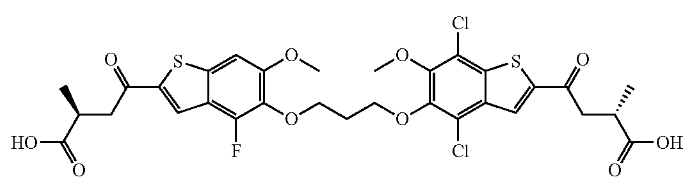 [SMILES: COc1cc2sc(C(=O)C[C@H](C)C(=O)O)cc2c(F)c1OCCCOc1c(OC)c(Cl)c2sc(C(=O)C[C@H](C)C(=O)O)cc2c1Cl] | (S)-4-(5-(3-((2-((S)-3-carboxybutanoyl)-4,7-dichloro-6-methoxybenzo[b]thiophen-5-yl)oxy)propoxy)-4-fluoro-6-methoxybenzo[b]thiophen-2-yl)-2-methyl-4-oxobutanoic acid | 715, 717 |
| 138 | 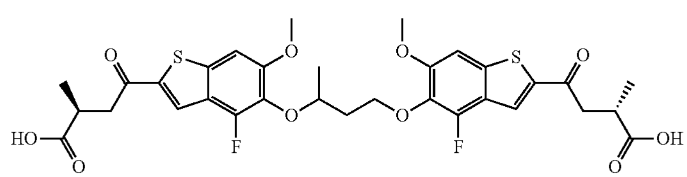 [SMILES: COc1cc2sc(C(=O)C[C@H](C)C(=O)O)cc2c(F)c1OCCC(C)Oc1c(OC)cc2sc(C(=O)C[C@H](C)C(=O)O)cc2c1F] | (2S,2'S)-4,4'-((butane-1,3-diylbis(oxy))bis(4-fluoro-6-methoxybenzo[b]thiophene-5,2-diyl))bis(2-methyl-4-oxobutanoic acid) | 679 |
| 139 | 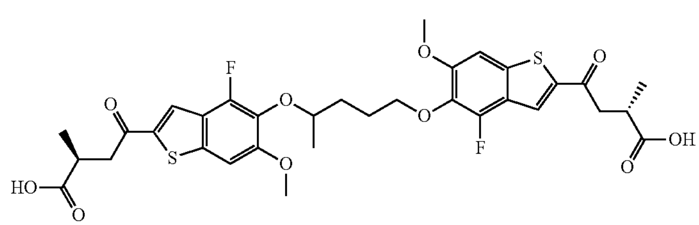 [SMILES: COc1cc2sc(C(=O)C[C@H](C)C(=O)O)cc2c(F)c1OCCCC(C)Oc1c(OC)cc2sc(C(=O)C[C@H](C)C(=O)O)cc2c1F] | (2S,2'S)-4,4'-((pentane-1,4-diylbis(oxy))bis(4-fluoro-6-methoxybenzo[b]thiophene-5,2-diyl))bis(2-methyl-4-oxobutanoic acid) | 693 |

TABLE 13-continued

| Example | Structure | Name | Mass [M + H]+ |
|---|---|---|---|
| 140 | 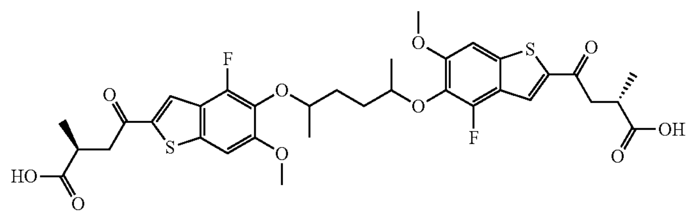 [SMILES: COc1cc2sc(C(=O)C[C@H](C)C(=O)O)cc2c(F)c1OC(C)CCC(C)Oc1c(OC)cc2sc(C(=O)C[C@H](C)C(=O)O)cc2c1F] | (2S,2'S)-4,4'-((hexane-2,5-diylbis(oxy))bis(4-fluoro-6-methoxybenzo[b]thiophene-5,2-diyl))bis(2-methyl-4-oxobutanoic acid) | 707 |
| 141 | 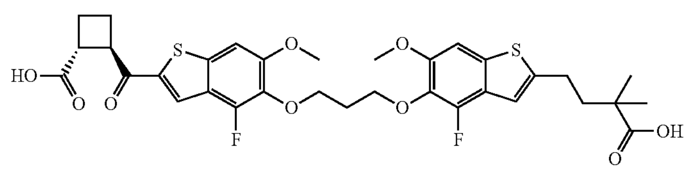 [SMILES: COc1cc2sc(CCC(C)(C)C(=O)O)cc2c(F)c1OCCCOc1c(OC)cc2sc(C(=O)[C@@H]3CC[C@H]3C(=O)O)cc2c1F] | trans-2-(5-(3-((2-(3-carboxy-3-methylbutyl)-4-fluoro-6-methoxybenzo[b]thiophen-5-yl)oxy)propoxy)-4-fluoro-6-methoxybenzo[b]thiophene-2-carbonyl)cyclobutane-1-carboxylic acid | 705 |
| 142 | 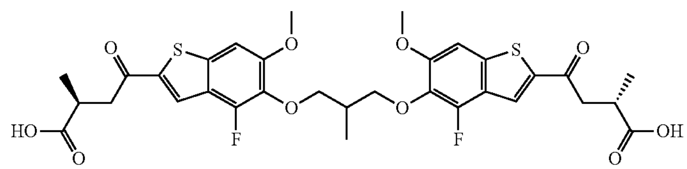 [SMILES: COc1cc2sc(C(=O)C[C@H](C)C(=O)O)cc2c(F)c1OCC(C)COc1c(OC)cc2sc(C(=O)C[C@H](C)C(=O)O)cc2c1F] | (2S,2'S)-4,4'-(((2-methylpropane-1,3-diyl)bis(oxy))bis(4-fluoro-6-methoxybenzo[b]thiophene-5,2-diyl))bis(2-methyl-4-oxobutanoic acid) | 661 (M − $H_2O$ + $H^+$) |
| 143 | 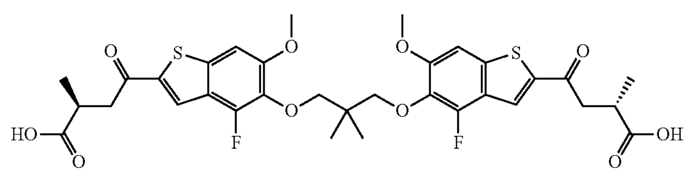 [SMILES: COc1cc2sc(C(=O)C[C@H](C)C(=O)O)cc2c(F)c1OCC(C)(C)COc1c(OC)cc2sc(C(=O)C[C@H](C)C(=O)O)cc2c1F] | (2S,2'S)-4,4'-(((2,2-dimethylpropane-1,3-diyl)bis(oxy))bis(4-fluoro-6-methoxybenzo[b]thiophene-5,2-diyl))bis(2-methyl-4-oxobutanoic acid) | 675 (M − $H_2O$ + $H^+$) |
| 144 | 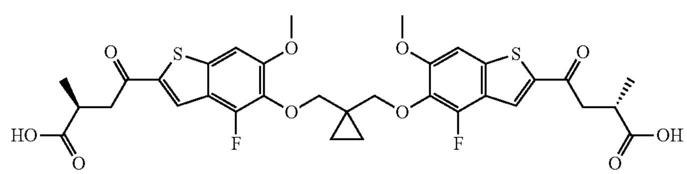 [SMILES: COc1cc2sc(C(=O)C[C@H](C)C(=O)O)cc2c(F)c1OCC1(COc2c(OC)cc3sc(C(=O)C[C@H](C)C(=O)O)cc3c2F)CC1] | (2S,2'S)-4,4'-((((cyclopropane-1,1-diylbis-(methylene))bis(oxy))bis(4-fluoro-6-methoxybenzo[b]thiophene-5,2-diyl))bis(2-methyl-4-oxobutanoic acid) | 691 |
| 145 | 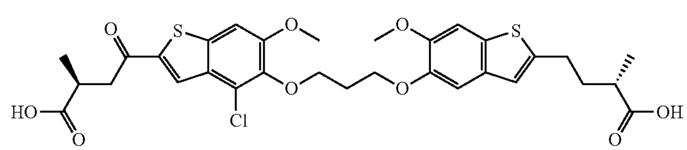 [SMILES: COc1cc2sc(CC[C@H](C)C(=O)O)cc2cc1OCCCOc1c(OC)cc2sc(C(=O)C[C@H](C)C(=O)O)cc2c1Cl] | (S)-4-(5-(3-((2-((S)-3-carboxybutyl)-6-methoxybenzo[b]thiophen-5-yl)oxy)propoxy)-4-chloro-6-methoxybenzo[b]thiophen-2-yl)-2-methyl-4-oxobutanoic acid | 649 |
| 146 | 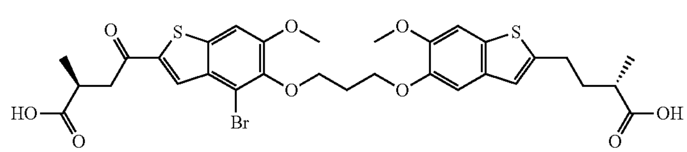 | (S)-4-(4-bromo-5-(3-((2-((S)-3-carboxybutyl)-6-methoxybenzo[b]thiophen-5-yl)oxy)propoxy)-6-methoxybenzo[b]thiophen-2-yl)-2-methyl-4-oxobutanoic acid | 693, 695 |
| 147 | 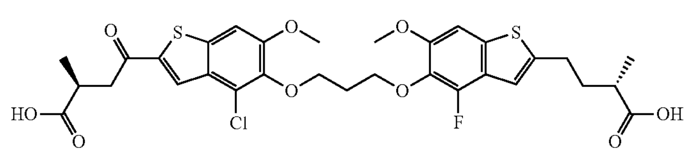 | (S)-4-(5-(3-((2-((S)-3-carboxybutyl)-4-fluoro-6-methoxybenzo[b]thiophen-5-yl)oxy)propoxy)-4-chloro-6-methoxybenzo[b]thiophen-2-yl)-2-methyl-4-oxobutanoic acid | 667 |
| 148 | 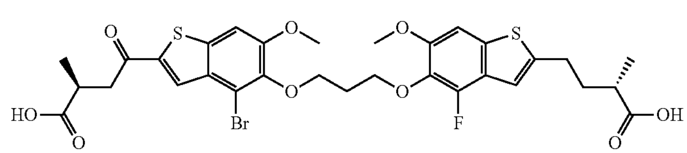 [SMILES: COc1cc2sc(CC[C@H](C)C(=O)O)cc2c(F)c1OCCCOc1c(OC)cc2sc(C(=O)C[C@H](C)C(=O)O)cc2c1Br] | (S)-4-(4-bromo-5-(3-((2-((S)-3-carboxybutyl)-4-fluoro-6-methoxybenzo[b]thiophen-5-yl)oxy)propoxy)-6-methoxybenzo[b]thiophen-2-yl)-2-methyl-4-oxobutanoic acid | 711, 713 |

TABLE 13-continued

| Example | Structure | Name | Mass [M + H]+ |
|---|---|---|---|
| 149 | 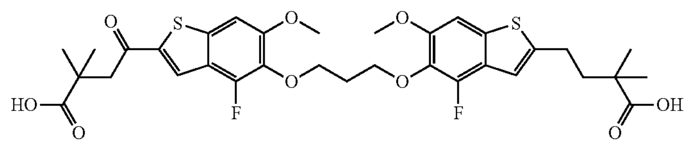 [SMILES: COc1cc2sc(CCC(C)(C)C(=O)O)cc2c(F)c1OCCCOc1c(OC)cc2sc(C(=O)CC(C)(C)C(=O)O)cc2c1F] | 4-(5-(3-((2-(3-carboxy-3-methylbutyl)-4-fluoro-6-methoxybenzo[b]thiophen-5-yl)oxy)propoxy)-4-fluoro-6-methoxybenzo[b]thiophen-2-yl)-2,2-dimethyl-4-oxobutanoic acid | 679 |
| 150 | 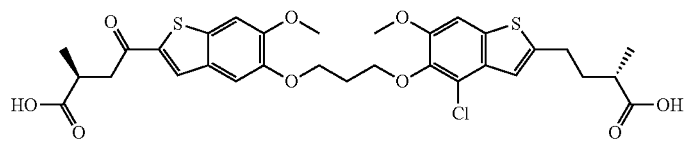 [SMILES: COc1cc2sc(C(=O)C[C@H](C)C(=O)O)cc2cc1OCCCOc1c(OC)cc2sc(CC[C@H](C)C(=O)O)cc2c1Cl] | (S)-4-(5-(3-((2-((S)-3-carboxybutyl)-4-chloro-6-methoxybenzo[b]thiophen-5-yl)oxy)propoxy)-6-methoxybenzo[b]thiophen-2-yl)-2-methyl-4-oxobutanoic acid | 649 |
| 151 | 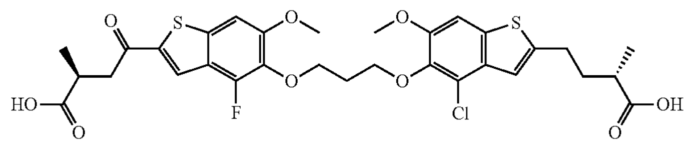 | (S)-4-(5-(3-((2-((S)-3-carboxybutyl)-4-chloro-6-methoxybenzo[b]thiophen-5-yl)oxy)propoxy)-4-fluoro-6-methoxybenzo[b]thiophen-2-yl)-2-methyl-4-oxobutanoic acid | 667 |
| 152 | 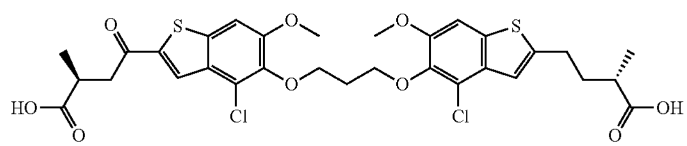 | (S)-4-(5-(3-((2-((S)-3-carboxybutyl)-4-chloro-6-methoxybenzo[b]thiophen-5-yl)oxy)propoxy)-4-chloro-6-methoxybenzo[b]thiophen-2-yl)-2-methyl-4-oxobutanoic acid | 683, 685 |
| 153 | 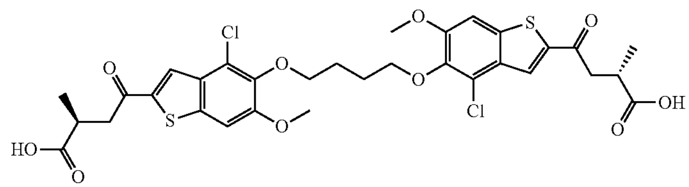 [SMILES: COc1cc2sc(C(=O)C[C@H](C)C(=O)O)cc2c(Cl)c1OCCCCOc1c(OC)cc2sc(C(=O)C[C@H](C)C(=O)O)cc2c1Cl] | (2S,2'S)-4,4'-((ethane-1,2-diylbis(oxy))bis(4-chloro-6-methoxybenzo[b]thiophene-5,2-diyl))bis(2-methyl-4-oxobutanoic acid) | 683, 685 |
| 154 | 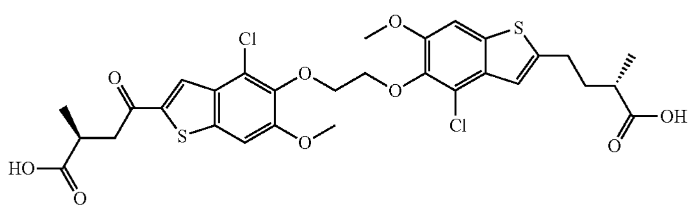 [SMILES: COc1cc2sc(CC[C@H](C)C(=O)O)cc2c(Cl)c1OCCOc1c(OC)cc2sc(C(=O)C[C@H](C)C(=O)O)cc2c1Cl] | (S)-4-(5-(2-((2-((S)-3-carboxybutyl)-4-chloro-6-methoxybenzo[b]thiophen-5-yl)oxy)ethoxy)-4-chloro-6-methoxybenzo[b]thiophen-2-yl)-2-methyl-4-oxobutanoic acid | 669, 671 |
| 155 | 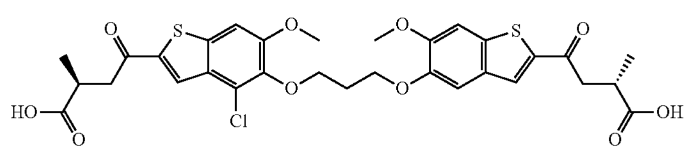 [SMILES: COc1cc2sc(C(=O)C[C@H](C)C(=O)O)cc2cc1OCCCOc1c(OC)cc2sc(C(=O)C[C@H](C)C(=O)O)cc2c1Cl] | (S)-4-(5-(3-((2-((S)-3-carboxybutanoyl)-4-chloro-6-methoxybenzo[b]thiophen-5-yl)oxy)propoxy)-6-methoxybenzo[b]thiophen-2-yl)-2-methyl-4-oxobutanoic acid | 663 |
| 156 | 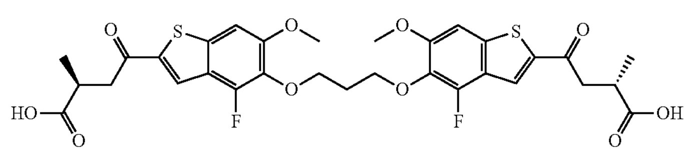 [SMILES: COc1cc2sc(C(=O)C[C@H](C)C(=O)O)cc2c(F)c1OCCCOc1c(OC)cc2sc(C(=O)C[C@H](C)C(=O)O)cc2c1F] | (2S,2'S)-4,4'-((propane-1,3-diylbis(oxy))bis(4-fluoro-6-methoxybenzo[b]thiophene-5,2-diyl))bis(2-methyl-4-oxobutanoic acid) | 647 (M − H$_2$O + H+) |
| 157 | 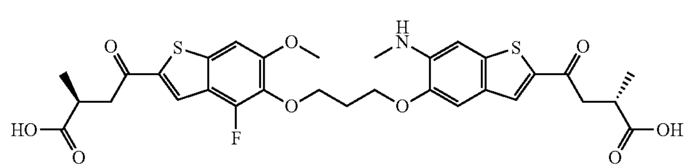 [SMILES: CNc1cc2sc(C(=O)C[C@H](C)C(=O)O)cc2cc1OCCCOc1c(OC)cc2sc(C(=O)C[C@H](C)C(=O)O)cc2c1F] | (S)-4-(5-(3-((2-((S)-3-carboxybutanoyl)-4-fluoro-6-methoxybenzo[b]thiophen-5-yl)oxy)propoxy)-6-(methylamino)benzo[b]thiophen-2-yl)-2-methyl-4-oxobutanoic acid | 646 |

Example 41: (2S)-4-{5-[3-({2-[(3S)-3-carboxybutanoyl]-6-methoxy-1-benzothiophen-5-yl}oxy)propyl]-6-methoxy-1-benzothiophen-2-yl}-2-methyl-4-oxobutanoic acid

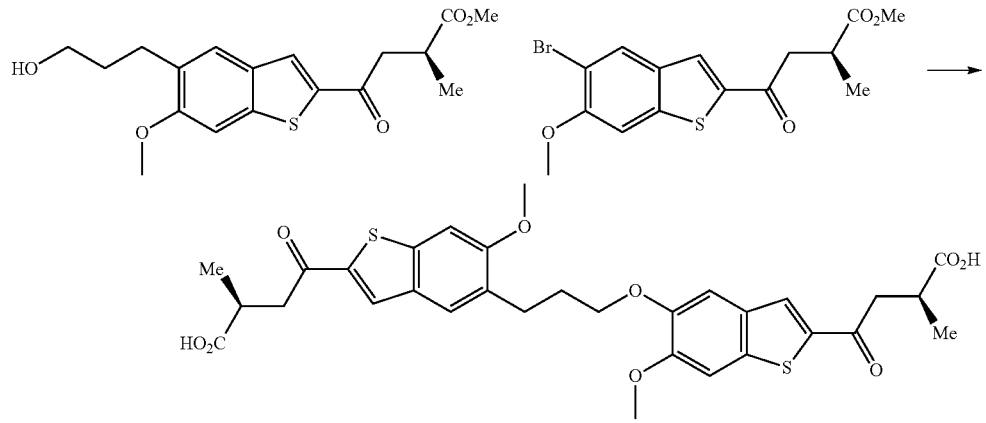

To a mixture of methyl (2S)-4-(5-bromo-6-methoxy-1-benzothiophen-2-yl)-2-methyl-4-oxobutanoate (107 mg, 0.287 mmol), RockPhos Pd G3 (11 mg, 0.013 mmol), and $Cs_2CO_3$ (128 mg, 0.392 mmol) under $N_2$ was added a mixture of methyl (2S)-4-[5-(3-hydroxy-propyl)-6-methoxy-1-benzothiophen-2-yl]-2-methyl-4-oxobutanoate (92 mg, 0.26 mmol) in toluene (870 µL). The reaction mixture was sparged with $N_2$ for 5 min and then heated to 110° C. for 2 h. Upon cooling to RT, THF (1.0 mL), MeOH (1.0 mL) and water (0.25 mL) were added followed by $LiOH.H_2O$ (157 mg, 3.75 mmol) in one portion at RT. The reaction mixture was stirred at RT for 4 h, then quenched with aq HCl (2.0N, 1.35 mL). DMSO was added, and the resulting mixture was filtered. The filtrate was purified by RP-HPLC [C18 column, water (0.1% TFA)-$CH_3CN$] to afford (2S)-4-{5-[3-({2-[(3S)-3-carboxybutanoyl]-6-methoxy-1-benzothiophen-5-yl}oxy)propyl]-6-methoxy-1-benzothiophen-2-yl}-2-methyl-4-oxobutanoic acid. LCMS ($C_{31}H_{32}O_9S_2Na$) (ES, m/z): 635 [M+Na]. $^1$H NMR (500 MHz, DMSO-$d_6$): δ 12.19 (br, 2H), 8.23 (s, 1H), 8.16 (s, 1H), 7.77 (s, 1H), 7.61 (s, 1H), 7.60 (s, 1H), 7.44 (s, 1H), 4.05 (d, J=6.2 Hz, 2H), 3.88 (s, 3H), 3.88 (s, 3H), 3.06 (dt, J=17.5, 4.3 Hz, 2H), 2.94-2.80 (m, 4H), 2.10 (pentet, J=6.9 Hz, 2H), 1.17 (d, J=7.1 Hz, 6H).

Examples 42, 158 and 159, as shown in Table 14 below, were or may be prepared according to procedures analogous to those outlined in Example 41 above using the appropriate starting materials, described in the Preparations or Intermediates above, or as obtained from commercial sources.

TABLE 14

| Example | Structure | Name | Mass [M + H]+ |
|---|---|---|---|
| 42 | (structure shown) | (S)-4-(5-(2-(2-((S)-3-carboxybutanoyl)-6-methoxybenzo[b]thiophen-5-yl)ethoxy)-6-methoxybenzo[b]thiophen-2-yl)-2-methyl-4-oxobutanoic acid | 599 |

TABLE 14-continued

| Example | Structure | Name | Mass [M + H]+ |
|---|---|---|---|
| 158 | 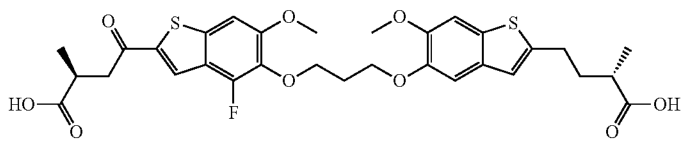 [SMILES: COc1cc2sc(CC[C@H](C)C(=O)O)cc2cc1OCCCOc1c(OC)cc2sc(C(=O)C[C@H](C)C(=O)O)cc2c1F] | (S)-4-(5-(3-((2-((S)-3-carboxybutyl)-6-methoxybenzo[b]thiophen-5-yl)oxy)propoxy)-4-fluoro-6-methoxybenzo[b]thiophen-2-yl)-2-methyl-4-oxobutanoic acid | 633 |
| 159 | 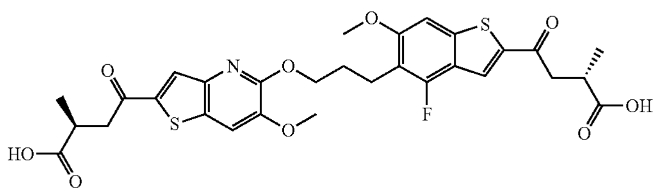 [SMILES: COc1cc2sc(C(=O)C[C@H](C)C(=O)O)cc2nc1OCCCc1c(OC)cc2sc(C(=O)C[C@H](C)C(=O)O)cc2c1F] | (S)-4-(5-(3-(2-((S)-3-carboxybutanoyl)-4-fluoro-6-methoxybenzo[b]thiophen-5-yl)propoxy)-6-methoxythieno[3,2-b]pyridin-2-yl)-2-methyl-4-oxobutanoic acid | 632 |

Example 43: (S)-4-(5-(3-((2-(3-carboxypropanoyl)benzo[b]thiophen-6-yl)oxy)propoxy)-6-methoxy-benzo[b]thiophen-2-yl)-2-methyl-4-oxobutanoic acid Step 1: Methyl (S)-4-(6-methoxy-5-(3-((2-(4-methoxy-4-oxobutanoyl)benzo[b]thiophen-6-yl)oxy)propoxy) benzo[b]thiophen-2-yl)-2-methyl-4-oxobutanoate

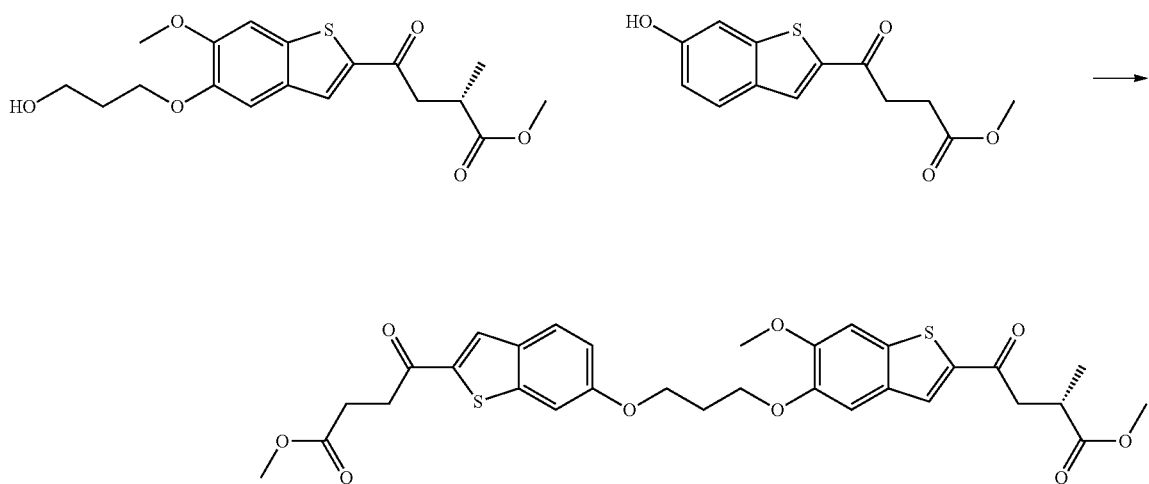

A mixture of (S)-methyl 4-(5-(3-hydroxypropoxy)-6-methoxybenzo[b]thiophen-2-yl)-2-methyl-4-oxobutanoate (16 mg, 0.044 mmol), methyl 4-(6-hydroxybenzo[b]thiophen-2-yl)-4-oxobutanoate (14 mg, 0.052 mmol), (E)-diazene-1,2-diylbis(piperidin-1-ylmethanone) (28 mg, 0.11 mmol), and Ph$_3$P (29 mg, 0.11 mmol) in THF (1.0 mL) was degassed with Ar and was then stirred at 20° C. for 18 h. The reaction mixture was then diluted with DMSO (1.0 mL) and filtered. The mixture was then directly purified by reverse phase HPLC (ACN in water, 0.1% TFA modifier, C-18 stationary phase) to afford methyl (S)-4-(6-methoxy-5-(3-((2-(4-methoxy-4-oxobutanoyl)benzo[b]thiophen-6-yl)oxy)propoxy)benzo[b]thiophen-2-yl)-2-methyl-4-oxobutanoate. LCMS (C$_{31}$H$_{33}$O$_9$S$_2$) (ES, m/z): 613 [M+H]$^+$.

Step 2: (S)-4-(5-(3-((2-(3-carboxypropanoyl)benzo[b]thiophen-6-yl)oxy)propoxy)-6-methoxybenzo[b]thiophen-2-yl)-2-methyl-4-oxobutanoic acid

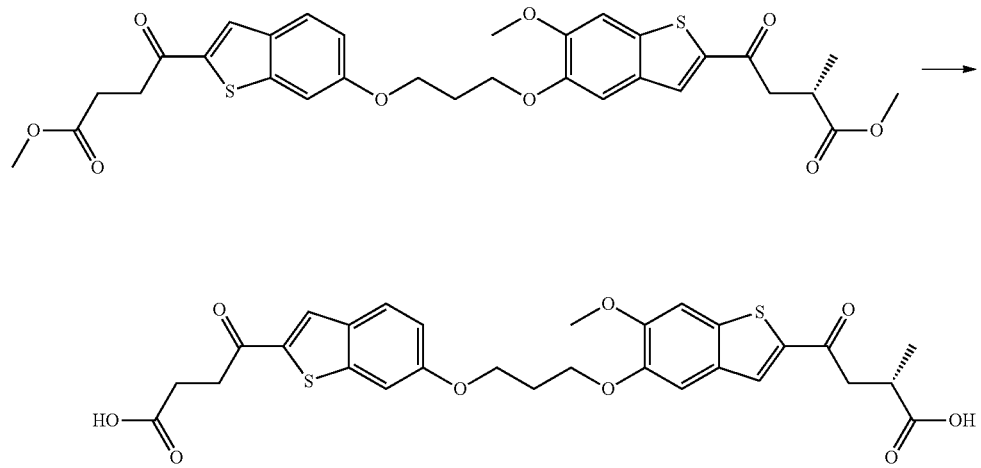

NaOH (5.0M in water, 21 µL, 0.11 mmol) was added to a mixture of methyl (S)-4-(6-methoxy-5-(3-((2-(4-methoxy-4-oxobutanoyl)benzo[b]thiophen-6-yl)oxy)propoxy)benzo[b]thiophen-2-yl)-2-methyl-4-oxobutanoate (6.3 mg, 10 µmol) in MeOH (1.0 mL) at RT. The reaction mixture was stirred and heated to 50° C. for 2 h. The crude reaction mixture was cooled to RT, quenched with TFA (16 µL, 0.21 mmol), diluted with DMSO (1.0 mL), and then filtered. The filtrate was then purified directly by reverse phase HPLC (ACN in water, 0.1% TFA modifier, C-18 stationary phase) to afford (S)-4-(5-(3-((2-(3-carboxypropanoyl)benzo[b]thiophen-6-yl)oxy) propoxy)-6-methoxybenzo[b]thiophen-2-yl)-2-methyl-4-oxobutanoic acid. LCMS (C$_{29}$H$_{29}$O$_9$S$_2$) (ES, m/z): 585 [M+H]$^+$. $^1$H NMR (500 MHz, DMSO-d$_6$) δ 12.22 (s, 2H), 8.33 (s, 1H), 8.19 (s, 1H), 7.94 (d, J=7.8 Hz, 1H), 7.69 (s, 1H), 7.63 (s, 1H), 7.55 (s, 1H), 7.15 (d, J=7.6 Hz, 1H), 4.34-4.18 (m, 4H), 3.89 (s, 3H), 3.44-3.25 (m, 3H), 3.13-3.05 (m, 1H), 2.95-2.87 (m, 1H), 2.66-2.60 (m, 2H), 2.34-2.27 (m, 2H), 1.25-1.14 (m, 3H).

Examples 44 through 59, and 160, as shown in Table 15 below, were or may be prepared according to procedures analogous to those outlined in Example 43 above using the appropriate starting materials, described in the Preparations or Intermediates above, or as obtained from commercial sources.

TABLE 15

| Example | Structure | Name | Mass [M + H]+ |
|---|---|---|---|
| 44 | 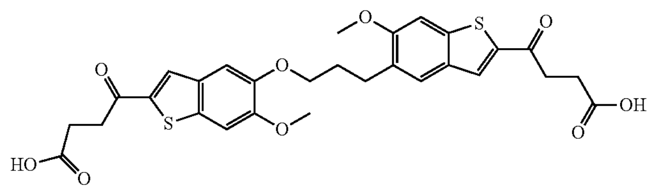 [SMILES: COc1cc2sc(C(=O)CCC(=O)O)cc2cc1CCCOc1cc2cc(C(=O)CCC(=O)O)sc2cc1OC] | 4-(5-(3-((2-(3-carboxypropanoyl)-6-methoxybenzo[b]thiophen-5-yl)oxy)propyl)-6-methoxybenzo[b]thiophen-2-yl)-4-oxobutanoic acid | 585 |
| 45 | 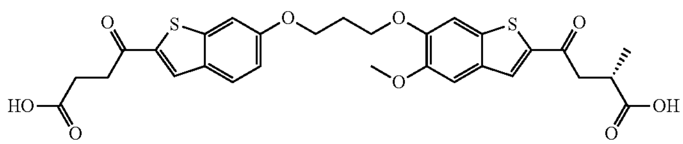 [SMILES: COc1cc2cc(C(=O)C[C@H](C)C(=O)O)sc2cc1OCCCOc1ccc2cc(C(=O)CCC(=O)O)sc2c1] | (S)-4-(6-(3-((2-(3-carboxypropanoyl)benzo[b]thiophen-6-yl)oxy)propoxy)-5-methoxybenzo[b]thiophen-2-yl)-2-methyl-4-oxobutanoic acid | 585 |
| 46 | 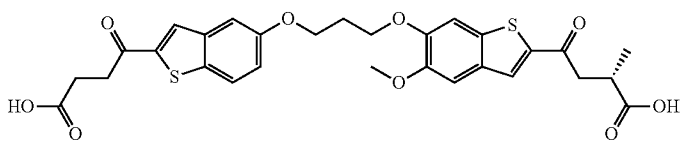 [SMILES: COc1cc2cc(C(=O)C[C@H](C)C(=O)O)sc2cc1OCCCOc1ccc2sc(C(=O)CCC(=O)O)cc2c1] | (S)-4-(6-(3-((2-(3-carboxypropanoyl)benzo[b]thiophen-5-yl)oxy)propoxy)-5-methoxybenzo[b]thiophen-2-yl)-2-methyl-4-oxobutanoic acid | 585 |
| 47 | 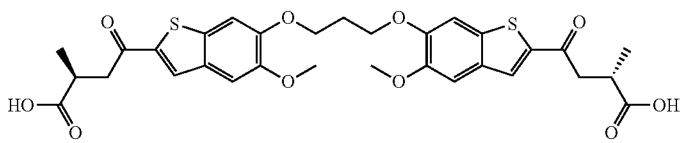 [SMILES: COc1cc2cc(C(=O)C[C@H](C)C(=O)O)sc2cc1OCCCOc1cc2sc(C(=O)C[C@H](C)C(=O)O)cc2cc1OC] | (2S,2'S)-4,4'-((propane-1,3-diylbis(oxy))bis(5-methoxybenzo[b]thiophene-6,2-diyl))bis(2-methyl-4-oxobutanoic acid) | 629 |
| 48 | 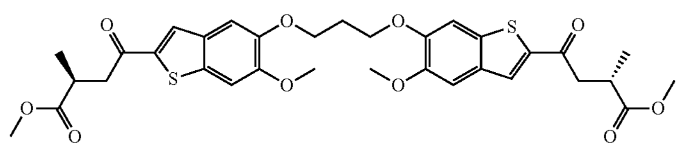 | methyl (S)-4-(6-methoxy-5-(3-((5-methoxy-2-((S)-4-methoxy-3-methyl-4-oxobutanoyl)benzo[b]thiophen-6-yl)oxy)propoxy)benzo[b]thiophen-2-yl)-2-methyl-4-oxobutanoate | 657 |
| 49 | 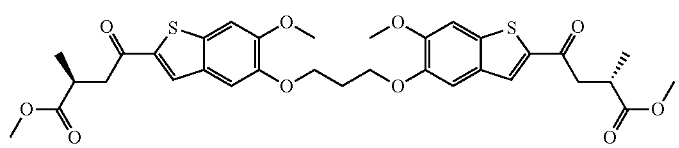 | dimethyl 4,4'-((propane-1,3-diylbis(oxy))bis(6-methoxybenzo[b]thiophene-5,2-diyl))(2S,2'S)-bis(2-methyl-4-oxobutanoate) | 657 |
| 50 | 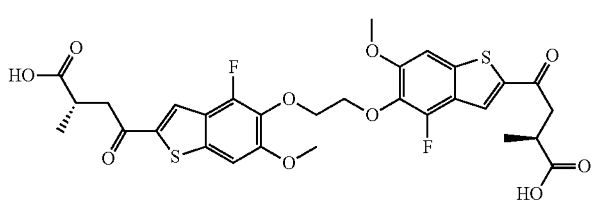 [SMILES: COc1cc2sc(C(=O)C[C@H](C)C(=O)O)cc2c(F)c1OCCOc1c(OC)cc2sc(C(=O)C[C@H](C)C(=O)O)cc2c1F] | (2S,2'S)-4,4'-((ethane-1,2-diylbis(oxy))bis(4-fluoro-6-methoxybenzo[b]thiophene-5,2-diyl))bis(2-methyl-4-oxobutanoic acid) | 673 [M + Na] |
| 51 | 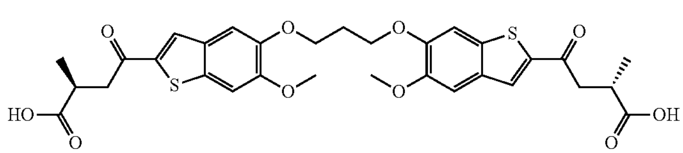 | (S)-4-(5-(3-((2-((S)-3-carboxybutanoyl)-5-methoxybenzo[b]thiophen-6-yl)oxy)propoxy)-6-methoxybenzo[b]thiophen-2-yl)-2-methyl-4-oxobutanoic acid | 629 |
| 52 | 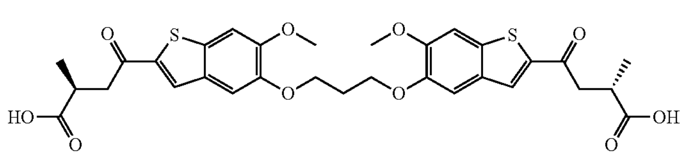 [SMILES: COc1cc2sc(C(=O)C[C@H](C)C(=O)O)cc2cc1OCCCOc1cc2cc(C(=O)C[C@H](C)C(=O)O)sc2cc1OC] | (2S,2'S)-4,4'-((propane-1,3-diylbis(oxy))bis(6-methoxybenzo[b]thiophene-5,2-diyl))bis(2-methyl-4-oxobutanoic acid) | 629 |

TABLE 15-continued

| Example | Structure | Name | Mass [M + H]+ |
|---|---|---|---|
| 53 | 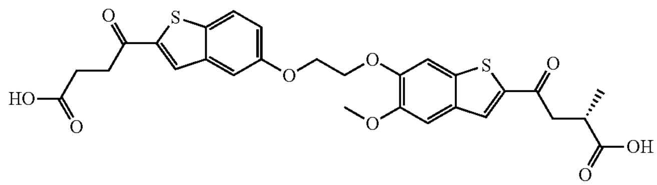 [SMILES: COc1cc2cc(C(=O)C[C@H](C)C(=O)O)sc2cc1OCCOc1ccc2sc(C(=O)CCC(=O)O)cc2c1] | (S)-4-(6-(2-((2-(3-carboxypropanoyl)benzo[b]thiophen-5-yl)oxy)ethoxy)-5-methoxybenzo[b]thiophen-2-yl)-2-methyl-4-oxobutanoic acid | 571 |
| 54 | 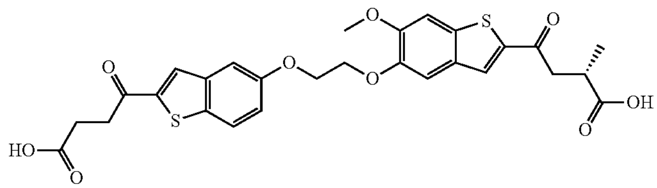 [SMILES: COc1cc2sc(C(=O)C[C@H](C)C(=O)O)cc2cc1OCCOc1ccc2sc(C(=O)CCC(=O)O)cc2c1] | (S)-4-(5-(2-((2-(3-carboxypropanoyl)benzo[b]thiophen-5-yl)oxy)ethoxy)-6-methoxybenzo[b]thiophen-2-yl)-2-methyl-4-oxobutanoic acid | 571 |
| 55 | 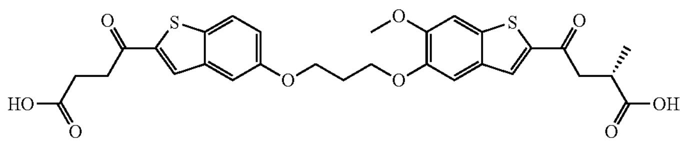 [SMILES: COc1cc2sc(C(=O)C[C@H](C)C(=O)O)cc2cc1OCCCOc1ccc2sc(C(=O)CCC(=O)O)cc2c1] | (S)-4-(5-(3-((2-(3-carboxypropanoyl)benzo[b]thiophen-5-yl)oxy)propoxy)-6-methoxybenzo[b]thiophen-2-yl)-2-methyl-4-oxobutanoic acid | 585 |
| 56 | 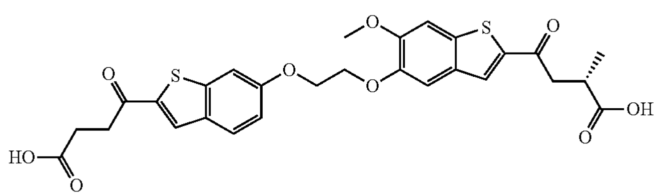 [SMILES: COc1cc2sc(C(=O)C[C@H](C)C(=O)O)cc2cc1OCCOc1ccc2cc(C(=O)CCC(=O)O)sc2c1] | (S)-4-(5-(2-((2-(3-carboxypropanoyl)benzo[b]thiophen-6-yl)oxy)ethoxy)-6-methoxybenzo[b]thiophen-2-yl)-2-methyl-4-oxobutanoic acid | 571 |
| 57 | 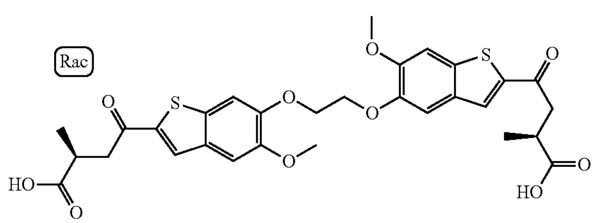 [SMILES: COc1cc2sc(C(=O)C[C@H](C)C(=O)O)cc2cc1OCCOc1cc2sc(C(=O)C[C@H](C)C(=O)O)cc2cc1OC] | rac-(R)-4-(5-(2-((2-((R)-3-carboxybutanoyl)-5-methoxybenzo[b]thiophen-6-yl)oxy)ethoxy)-6-methoxybenzo[b]thiophen-2-yl)-2-methyl-4-oxobutanoic acid | 637 [M + Na] |
| 58 | 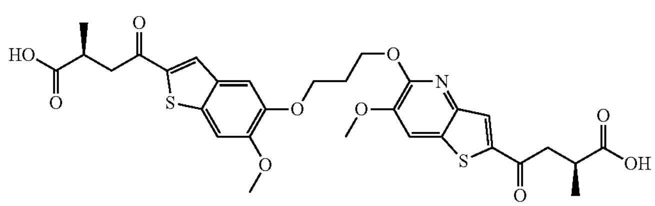 [SMILES: COc1cc2sc(C(=O)C[C@H](C)C(=O)O)cc2cc1OCCCOc1nc2cc(C(=O)C[C@H](C)C(=O)O)sc2cc1OC] | (S)-4-(5-(3-((2-((S)-3-carboxybutanoyl)-6-methoxybenzo[b]thiophen-5-yl)oxy)propoxy)-6-methoxythieno[3,2-b]pyridin-2-yl)-2-methyl-4-oxobutanoic acid | 630 |
| 59 | 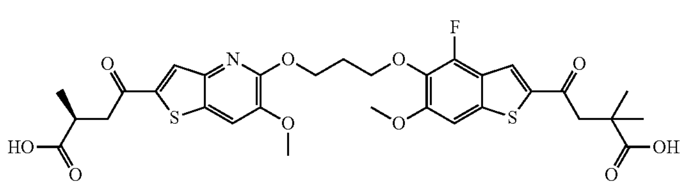 [SMILES: COc1cc2sc(C(=O)C[C@H](C)C(=O)O)cc2nc1OCCCOc1c(OC)cc2sc(C(=O)CC(C)(C)C(=O)O)cc2c1F] | (S)-4-(5-(3-((2-(3-carboxybutanoyl)-6-methoxythieno[3,2-b]pyridin-5-yl)oxy)propoxy)-4-fluoro-6-methoxybenzo[b]thiophen-2-yl)-2,2-dimethyl-4-oxobutanoic acid | 662 |
| 160 | 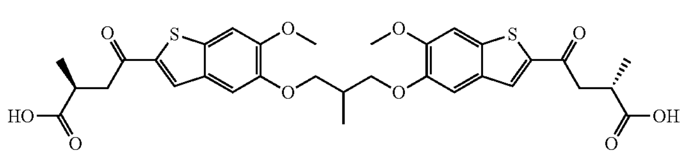 [SMILES: COc1cc2sc(C(=O)C[C@H](C)C(=O)O)cc2cc1OCC(C)COc1cc2cc(C(=O)C[C@H](C)C(=O)O)sc2cc1OC] | (2S,2'S)-4,4'-(((2-methylpropane-1,3-diyl)bis(oxy))bis(6-methoxybenzo[b]thiophene-5,2-diyl))bis(2-methyl-4-oxobutanoic acid) | 643 |

Example 60: (2S)-4-{5-[2-({2-[(3S)-3-carboxybutanoyl]-6-methoxy-1-benzothiophen-5-yl}amino)ethyl]-6-methoxy-1-benzothiophen-2-yl}-2-methyl-4-oxobutanoic acid

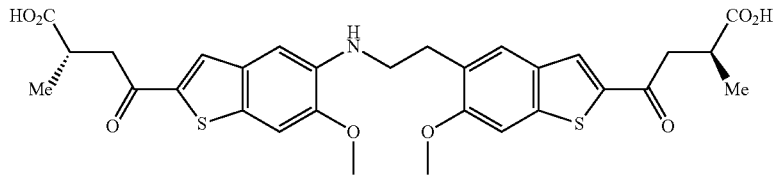 [SMILES: COc1cc2sc(C(=O)C[C@H](C)C(=O)O)cc2cc1CCNc1cc2cc(C(=O)C[C@H](C)C(=O)O)sc2cc1OC]

Step 1: methyl (2S)-4-{6-methoxy-5-[2-({6-methoxy-2-[(3S)-4-methoxy-3-methyl-4-oxobutanoyl]-1-benzothiophen-5-yl}amino)ethyl]-1-benzothiophen-2-yl}-2-methyl-4-oxobutanoate

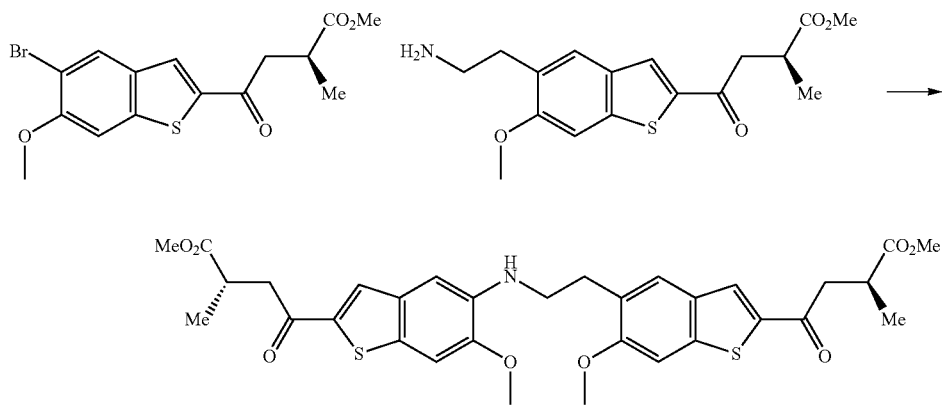

To a mixture of methyl (2S)-4-(5-bromo-6-methoxy-1-benzothiophen-2-yl)-2-methyl-4-oxobutanoate (54 mg, 0.14 mmol), Rac BINAP Pd G3 (12 mg, 0.012 mmol), and $Cs_2CO_3$ (117 mg, 0.360 mmol) under $N_2$ was added a suspension of methyl (2S)-4-[5-(2-aminoethyl)-6-methoxy-1-benzothiophen-2-yl]-2-methyl-4-oxobutanoate (54 mg, 0.120 mmol) in toluene (1.6 mL). The reaction mixture was sparged with $N_2$ for 45 min, then heated to 110° C. for 12 h. Upon cooling to RT, the mixture was purified by silica gel column chromatography (EtOAc in Hex) to afford methyl (2S)-4-{6-methoxy-5-[2-({6-methoxy-2-[(3S)-4-methoxy-3-methyl-4-oxobutanoyl]-1-benzothiophen-5-yl}amino)ethyl]-1-benzothio-phen-2-yl}-2-methyl-4-oxobutanoate. LCMS ($C_{32}H_{35}NO_8S_2Na$) (ES, m/z): 648 [M+Na]$^+$.

Step 2: (2S)-4-{5-[2-({2-[(3S)-3-carboxybutanoyl]-6-methoxy-1-benzothiophen-5-yl}amino) ethyl]-6-methoxy-1-benzothiophen-2-yl}-2-methyl-4-oxobutanoic acid

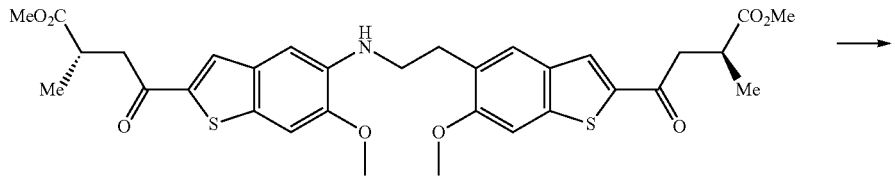

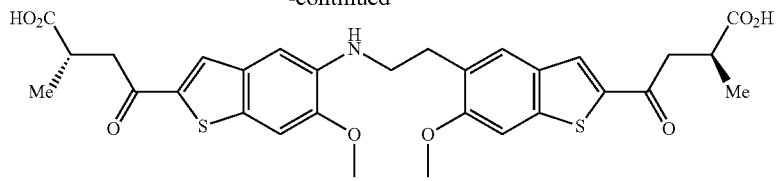

To a mixture of methyl (2S)-4-{6-methoxy-5-[2-({6-methoxy-2-[(3S)-4-methoxy-3-methyl-4-oxobutanoyl]-1-benzothiophen-5-yl}amino)ethyl]-1-benzothiophen-2-yl}-2-methyl-4-oxobutanoate (20 mg, 0.03 mmol) in THF (280 μL), MeOH (280 μL) and water (70 μL) was added LiOH.H$_2$O (13 mg, 0.32 mmol) in one portion at RT. The reaction mixture was stirred at RT for 2 h, then quenched with aq HCl (2N, 170 uL). The mixture was diluted with DMSO, and the resulting mixture was filtered. The filtrate was purified by RP-HPLC [C18 column, water (0.1% TFA)-CH$_3$CN] to afford (2S)-4-{5-[2-({2-[(3S)-3-carboxybutanoyl]-6-methoxy-1-benzothiophen-5-yl}amino)ethyl]-6-methoxy-1-benzothiophen-2-yl}-2-methyl-4-oxobutanoic acid. LCMS (C$_{30}$H$_{32}$NO$_8$S$_2$) (ES, m/z): 598 [M+H]$^+$. $^1$H NMR (500 MHz, DMSO-d$_6$): δ 12.12 (br, 2H), 8.27 (s, 1H), 8.11 (s, 1H), 7.82 (s, 1H), 7.66 (s, 1H), 7.44 (s, 1H), 7.07 (s, 1H), 3.98 (s, 3H), 3.90 (s, 3H), 3.41 (dd, J=17.5, 8.6 Hz, 2H), 3.36 (t, J=6.5 Hz, 2H), 3.14-2.96 (m, 4H), 2.94-2.84 (m, 2H), 1.18 (d, J=7.1 Hz, 6H).

Example 61, as shown in Table 16 below, was or may be prepared according to procedures analogous to those outlined in Example 60 above using the appropriate starting materials, described in the Preparations or Intermediates above, or as obtained from commercial sources.

TABLE 16

| Example | Structure | Name | Mass [M + H]$^+$ |
|---|---|---|---|
| 61 | 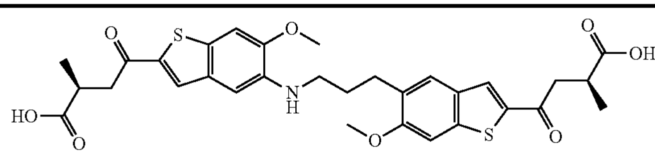 | (S)-4-(5-(3-((2-((S)-3-carboxybutanoyl)-6-methoxybenzo[b]thiophen-5-yl)amino)propyl)-6-methoxybenzo[b]thiophen-2-yl)-2-methyl-4-oxobutanoic acid | 612 |

Example 62: 4,4'-((propane-1,3-diylbis(oxy))bis(4-fluoro-6-methoxybenzo[b]thiophene-5,2-diyl))bis(4-oxobutanoic acid)

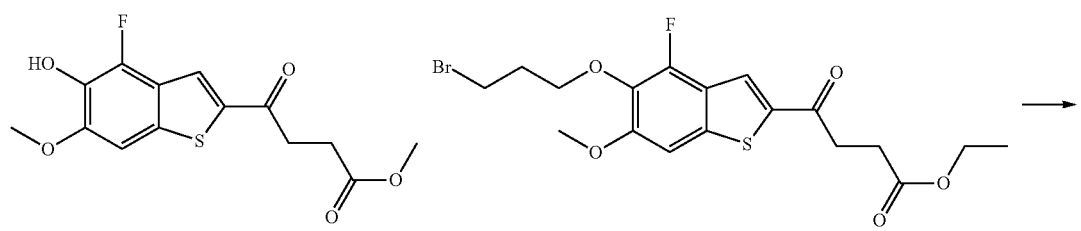

-continued

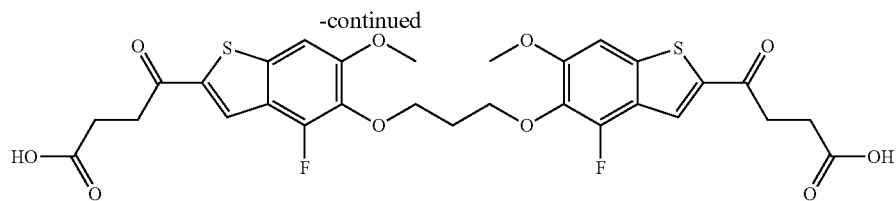

To a mixture of ethyl 4-(4-fluoro-5-hydroxy-6-methoxybenzo[b]thiophen-2-yl)-4-oxobutanoate (0.024 g, 0.073 mmol), ethyl 4-(5-(3-bromopropoxy)-4-fluoro-6-methoxybenzo[b]thiophen-2-yl)-4-oxobutanoate (0.025 g, 0.056 mmol) and Cs$_2$CO$_3$ (0.091 g, 0.28 mmol) was added ACN (1.0 mL). The reaction mixture was then heated to 65° C. for 1 h. Upon cooling to RT, the mixture was diluted with THF, filtered, and the filtrate was concentrated under reduced pressure. To the resulting residue was added THF (1.0 mL), MeOH (0.20 mL), water (0.5 mL), and LiOH (0.013 g, 0.56 mmol). The mixture was allowed to stir at RT for 2 h. The mixture was then quenched with AcOH, and the mixture was concentrated under reduced pressure. The resulting residue was purified via prep-HPLC (ACN/H$_2$O with 0.1% TFA) to afford 4,4'-((propane-1,3-diylbis(oxy))bis(4-fluoro-6-methoxybenzo[b]thiophene-5,2-diyl))bis(4-oxobutanoic acid). LCMS (C$_{29}$H$_{27}$F$_2$O$_{10}$S$_2$) (ES, m/z): 637 [M+H]$^+$. $^1$H NMR (600 MHz, DMSO-d$_6$) δ 8.26 (s, 2H), 7.55 (s, 2H), 4.31-4.24 (m, 4H), 3.99-3.80 (m, 6H), 3.34-3.32 (m, 4H), 2.60 (q, J=6.4 Hz, 4H), 2.09 (dt, J=11.5, 5.8 Hz, 2H).

Examples 63 through 65 and 161 through 164, as shown in Table 17 below, were or may be prepared according to procedures analogous to those outlined in Example 62 above using the appropriate starting materials, described in the Preparations or Intermediates above, or as obtained from commercial sources.

TABLE 17

| Example | Structure | Name | Mass [M + H]$^+$ |
|---|---|---|---|
| 63 | 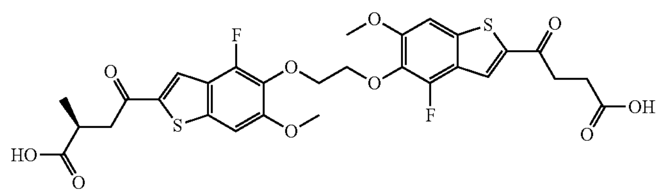 | (S)-4-(5-(2-((2-(3-carboxypropanoyl)-4-fluoro-6-methoxybenzo[b]thiophen-5-yl)oxy)ethoxy)-4-fluoro-6-methoxybenzo[b]thiophen-2-yl)-2-methyl-4-oxobutanoic acid | 637 |
| 64 | 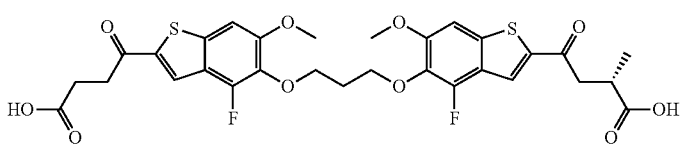 [SMILES: COc1cc2sc(C(=O)CCC(=O)O)cc2c(F)c1OCCCOc1c(OC)cc2sc(C(=O)C[C@H](C)C(=O)O)cc2c1F] | (S)-4-(5-(3-((2-(3-carboxypropanoyl)-4-fluoro-6-methoxybenzo[b]thiophen-5-yl)oxy)propoxy)-4-fluoro-6-methoxybenzo[b]thiophen-2-yl)-2-methyl-4-oxobutanoic acid | 650 |
| 65 | 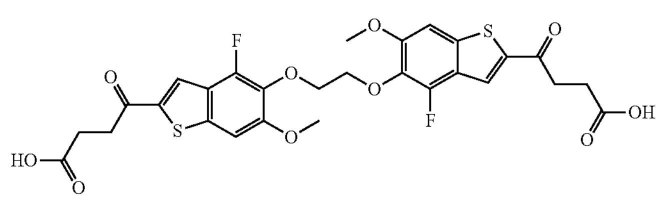 [SMILES: COc1cc2sc(C(=O)CCC(=O)O)cc2c(F)c1OCCOc1c(OC)cc2sc(C(=O)CCC(=O)O)cc2c1F] | 4,4'-((ethane-1,2-diylbis(oxy))bis(4-fluoro-6-methoxybenzo[b]thiophene-5,2-diyl))bis(4-oxobutanoic acid) | 623 |
| 161 | 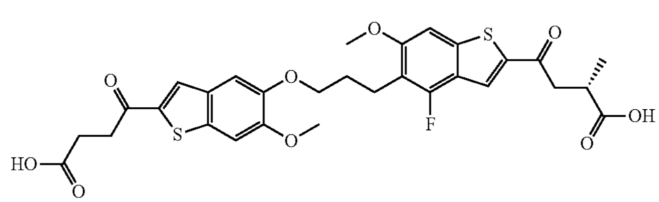 [SMILES: COc1cc2sc(C(=O)CCC(=O)O)cc2cc1OCCCc1c(OC)cc2sc(C(=O)C[C@H](C)C(=O)O)cc2c1F] | (S)-4-(5-(3-((2-(3-carboxypropanoyl)-6-methoxybenzo[b]thiophen-5-yl)oxy)propyl)-4-fluoro-6-methoxybenzo[b]thiophen-2-yl)-2-methyl-4-oxobutanoic acid | 617 |
| 162 | 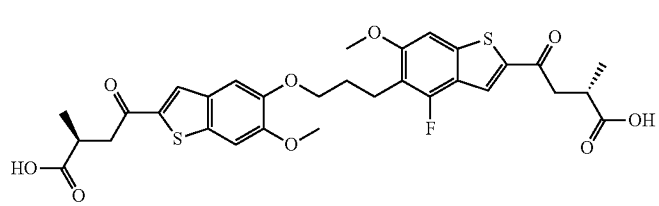 [SMILES: COc1cc2sc(C(=O)C[C@H](C)C(=O)O)cc2cc1OCCCc1c(OC)cc2sc(C(=O)C[C@H](C)C(=O)O)cc2c1F] | (S)-4-(5-(3-(2-((S)-3-carboxybutanoyl)-4-fluoro-6-methoxybenzo[b]thiophen-5-yl)propoxy)-6-methoxybenzo[b]thiophen-2-yl)-2-methyl-4-oxobutanoic acid | 631 |

TABLE 17-continued

| Example | Structure | Name | Mass [M + H]+ |
|---|---|---|---|
| 163 | 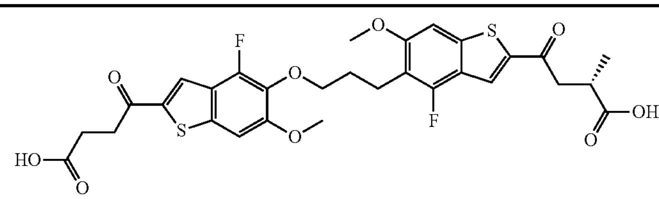 | (S)-4-(5-(3-((2-(3-carboxypropanoyl)-4-fluoro-6-methoxybenzo[b]thiophen-5-yl)oxy)propyl)-4-fluoro-6-methoxybenzo[b]thiophen-2-yl)-2-methyl-4-oxobutanoic acid | 635 |
| 164 | 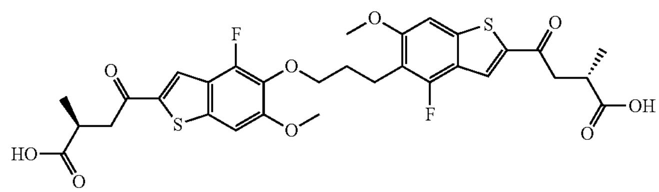 [SMILES: COc1cc2sc(C(=O)C[C@H](C)C(=O)O)cc2c(F)c1CCCOc1c(OC)cc2sc(C(=O)C[C@H](C)C(=O)O)cc2c1F] | (S)-4-(5-(3-((2-((S)-3-carboxybutanoyl)-4-fluoro-6-methoxybenzo[b]thiophen-5-yl)oxy)propyl)-4-fluoro-6-methoxybenzo[b]thiophen-2-yl)-2-methyl-4-oxobutanoic acid | 649 |

Example 66: (R)-4-(5-(2-((2-((S)-3-carboxybutanoyl)-4-fluoro-6-methoxybenzo[b]thiophen-5-yl)oxy)ethoxy)-6-methoxybenzo [b]thiophen-2-yl)-2-methyl-4-oxobutanoic acid

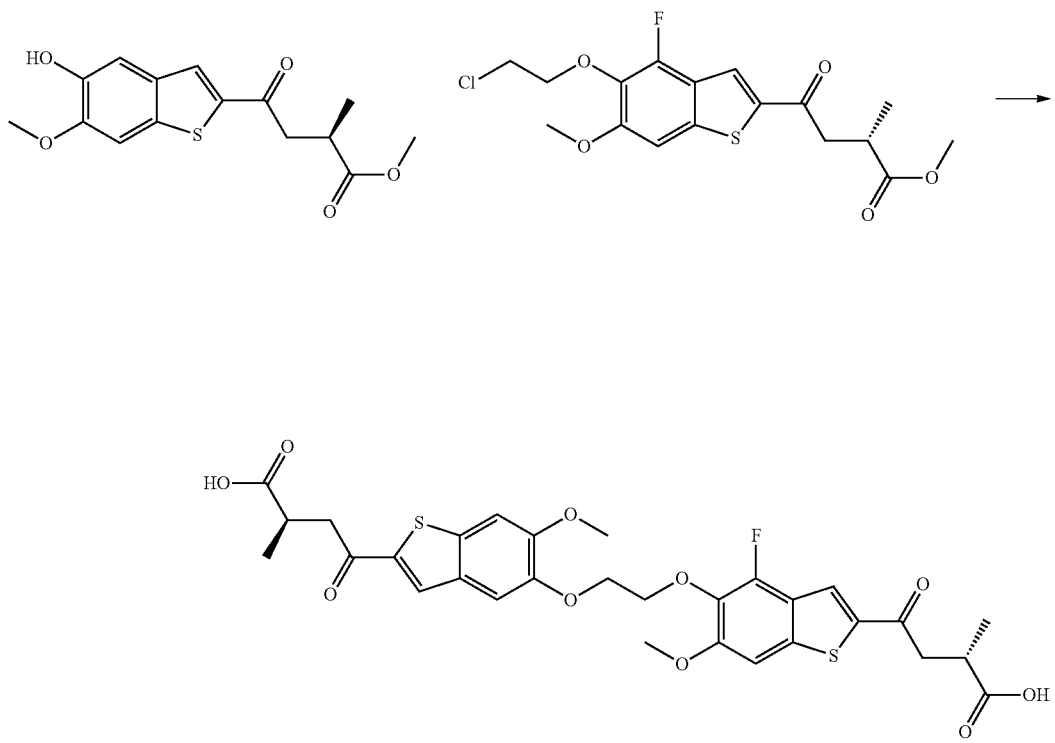

(R)-methyl 4-(5-hydroxy-6-methoxybenzo[b]thiophen-2-yl)-2-methyl-4-oxobutanoate (0.20M in DMF, 500 μL, 0.11 mmol) was added to a stirring suspension of methyl (S)-4-(5-(2-chloroethoxy)-4-fluoro-6-methoxybenzo[b]thiophen-2-yl)-2-methyl-4-oxobutanoate (0.20M in DMF, 500 μL, 0.11 mmol) and $K_2CO_3$ (30 mg, 0.2 mmol). The reaction mixture was heated to 100° C. for 18 h. Upon cooling to RT, DMSO (500 μL) was added, and the reaction mixture was filtered. Water (500 μL) was added followed by $LiOH.H_2O$ (30 mg, 0.7 mmol), and the reaction mixture was stirred at RT for 18 h. The mixture was filtered, and the product was purified mass-directed reverse phase C-18 column chromatography (ACN/water+0.1% TFA) to afford (R)-4-(5-(2-((2-((S)-3-carboxybutanoyl)-4-fluoro-6-methoxybenzo[b]thiophen-5-yl)oxy)ethoxy)-6-methoxybenzo[b]thiophen-2-yl)-2-methyl-4-oxobutanoic acid. LCMS ($C_{30}H_{29}FO_{10}S_2Na$) (ES, m/z): 655 [M+Na]$^+$. $^1$H NMR (DMSO-$d_6$) δ: 12.18 (s, 2H), 8.31 (s, 1H), 8.18 (s, 1H), 7.58 (s, 2H), 7.50 (s, 1H), 4.50-4.41 (m, 2H), 4.36-4.30 (m, 2H), 3.88 (s, 3H), 3.75 (s, 3H), 3.46 (dd, J=18, 9 Hz, 1H), 3.40 (dd, J=17, 9 Hz, 1H), 3.10 (ddd, J=22, 18, 5 Hz, 2H), 2.95-2.81 (m, 2H), 1.24-1.14 (m, 6H).

Examples 67 through 74 and 165 through 171, as shown in Table 18 below, were or may be prepared according to procedures analogous to those outlined in Example 66 above using the appropriate starting materials, described in the Preparations or Intermediates above, or as obtained from commercial sources.

TABLE 18

| Example | Structure | Name | Mass [M + H]$^+$ |
|---|---|---|---|
| 67 | 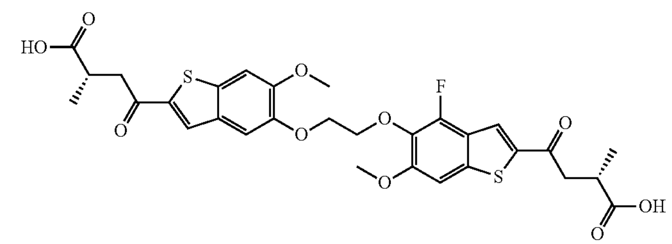 [SMILES: COc1cc2sc(C(=O)C[C@H](C)C(=O)O)cc2cc1OCCOc1c(OC)cc2sc(C(=O)C[C@H](C)C(=O)O)cc2c1F] | (S)-4-(5-(2-((2-((S)-3-carboxybutanoyl)-4-fluoro-6-methoxybenzo[b]thiophen-5-yl)oxy)ethoxy)-6-methoxybenzo[b]thiophen-2-yl)-2-methyl-4-oxobutanoic acid | 633 |
| 68 | 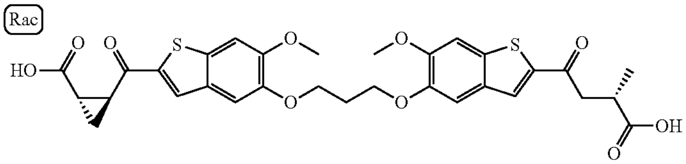 [SMILES: COc1cc2sc(C(=O)C[C@H](C)C(=O)O)cc2cc1OCCCOc1cc2cc(C(=O)[C@H]3C[C@@H]3C(=O)O)sc2cc1OC] | rac-(1R,2R)-2-(5-(3-((2-((R)-3-carboxybutanoyl)-6-methoxybenzo[b]thiophen-5-yl)oxy)propoxy)-6-methoxybenzo[b]thiophene-2-carbonyl)cyclopropane-1-carboxylic acid | 627 |
| 69 | 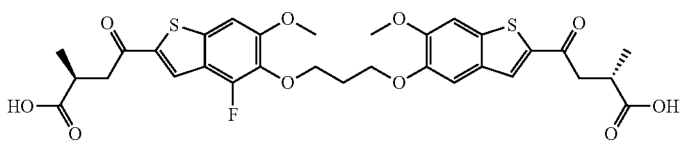 [SMILES: COc1cc2sc(C(=O)C[C@H](C)C(=O)O)cc2cc1OCCCOc1c(OC)cc2sc(C(=O)C[C@H](C)C(=O)O)cc2c1F] | (S)-4-(5-(3-((2-((S)-3-carboxybutanoyl)-4-fluoro-6-methoxybenzo[b]thiophen-5-yl)oxy)propoxy)-6-methoxybenzo[b]thiophen-2-yl)-2-methyl-4-oxobutanoic acid | 647 |
| 70 | 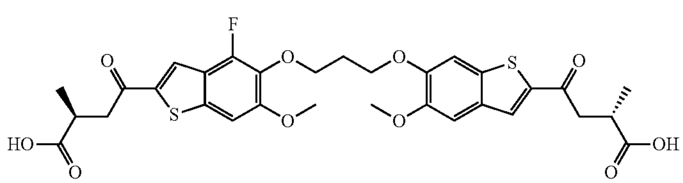 [SMILES: COc1cc2cc(C(=O)C[C@H](C)C(=O)O)sc2cc1OCCCOc1c(OC)cc2sc(C(=O)C[C@H](C)C(=O)O)cc2c1F] | (S)-4-(6-(3-((2-((S)-3-carboxybutanoyl)-4-fluoro-6-methoxybenzo[b]thiophen-5-yl)oxy)propoxy)-5-methoxybenzo[b]thiophen-2-yl)-2-methyl-4-oxobutanoic acid | 647 |
| 71 | 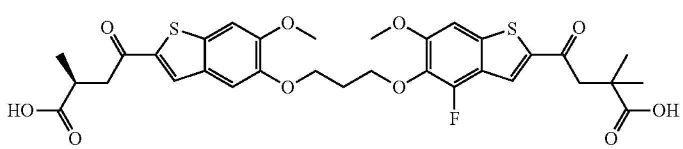 [SMILES: COc1cc2sc(C(=O)C[C@H](C)C(=O)O)cc2cc1OCCCOc1c(OC)cc2sc(C(=O)CC(C)(C)C(=O)O)cc2c1F] | (S)-4-(5-(3-((2-(3-carboxybutanoyl)-6-methoxybenzo[b]thiophen-5-yl)oxy)propoxy)-4-fluoro-6-methoxybenzo[b]thiophen-2-yl)-2,2-dimethyl-4-oxobutanoic acid | 683 [M + Na]$^+$ |
| 72 | 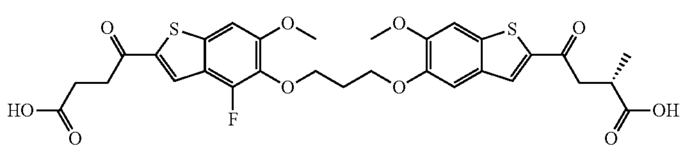 [SMILES: COc1cc2sc(C(=O)C[C@H](C)C(=O)O)cc2cc1OCCCOc1c(OC)cc2sc(C(=O)CCC(=O)O)cc2c1F] | (S)-4-(5-(3-((2-(3-carboxypropanoyl)-4-fluoro-6-methoxybenzo[b]thiophen-5-yl)oxy)propoxy)-6-methoxybenzo[b]thiophen-2-yl)-2-methyl-4-oxobutanoic acid | 633 |

TABLE 18-continued

| Example | Structure | Name | Mass [M + H]+ |
|---|---|---|---|
| 73 | 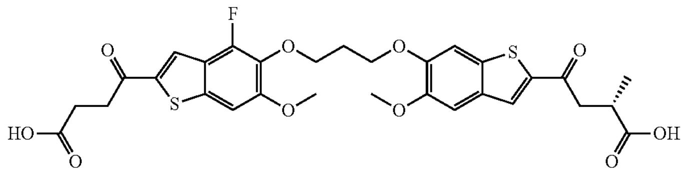 [SMILES: COc1cc2cc(C(=O)C[C@H](C)C(=O)O)sc2cc1OCCCOc1c(OC)cc2sc(C(=O)CCC(=O)O)cc2c1F] | (S)-4-(6-(3-((2-(3-carboxypropanoyl)-4-fluoro-6-methoxybenzo[b]thiophen-5-yl)oxy)propoxy)-5-methoxybenzo[b]thiophen-2-yl)-2-methyl-4-oxobutanoic acid | 633 |
| 74 | 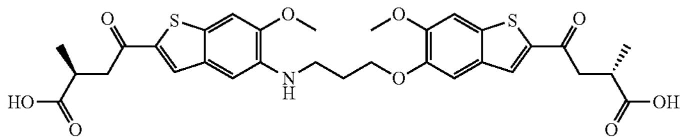 [SMILES: COc1cc2sc(C(=O)C[C@H](C)C(=O)O)cc2cc1NCCCOc1cc2cc(C(=O)C[C@H](C)C(=O)O)sc2cc1OC] | (S)-4-(5-(3-((2-((S)-3-carboxybutanoyl)-6-methoxybenzo[b]thiophen-5-yl)amino)propoxy)-6-methoxybenzo[b]thiophen-2-yl)-2-methyl-4-oxobutanoic acid | 628 |
| 165 | 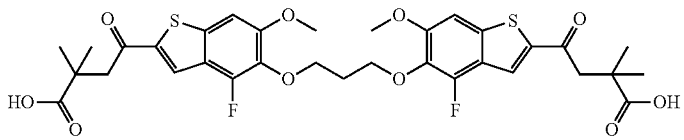 [SMILES: COc1cc2sc(C(=O)CC(C)(C)C(=O)O)cc2c(F)c1OCCCOc1c(OC)cc2sc(C(=O)CC(C)(C)C(=O)O)cc2c1F] | 4,4'-((propane-1,3-diylbis(oxy))bis(4-fluoro-6-methoxybenzo[b]thiophene-5,2-diyl))bis(2,2-dimethyl-4-oxobutanoic acid) | 693 |
| 166 | 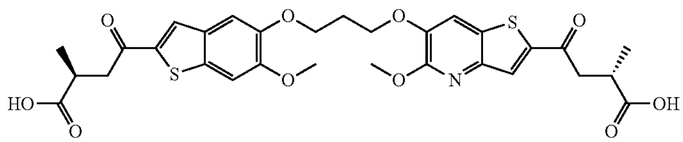 | (S)-4-(5-(3-((2-((S)-3-carboxybutanoyl)-5-methoxythieno[3,2-b]pyridin-6-yl)oxy)propoxy)-6-methoxybenzo[b]thiophen-2-yl)-2-methyl-4-oxobutanoic acid | 630 |
| 167 | 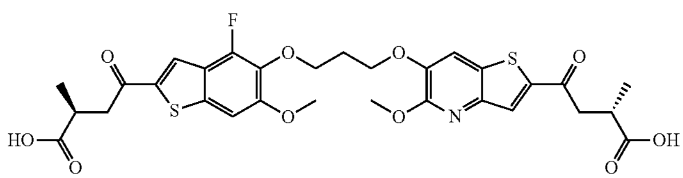 [SMILES: COc1cc2sc(C(=O)C[C@H](C)C(=O)O)cc2c(F)c1OCCCOc1cc2sc(C(=O)C[C@H](C)C(=O)O)cc2nc1OC] | (S)-4-(6-(3-((2-((S)-3-carboxybutanoyl)-4-fluoro-6-methoxybenzo[b]thiophen-5-yl)oxy)propoxy)-5-methoxythieno[3,2-b]pyridin-2-yl)-2-methyl-4-oxobutanoic acid | 648 |
| 168 | 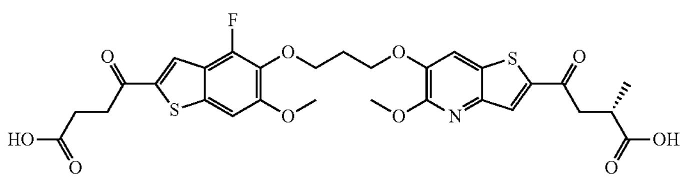 [SMILES: COc1cc2sc(C(=O)CCC(=O)O)cc2c(F)c1OCCCOc1cc2sc(C(=O)C[C@H](C)C(=O)O)cc2nc1OC] | (S)-4-(6-(3-((2-(3-carboxypropanoyl)-4-fluoro-6-methoxybenzo[b]thiophen-5-yl)oxy)propoxy)-5-methoxythieno[3,2-b]pyridin-2-yl)-2-methyl-4-oxobutanoic acid | 634 |
| 169 | 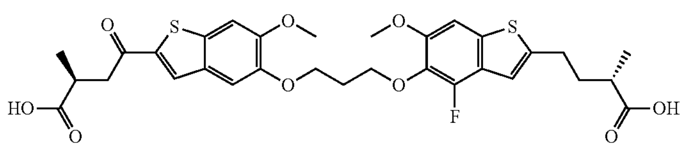 [SMILES: COc1cc2sc(C(=O)C[C@H](C)C(=O)O)cc2cc1OCCCOc1c(OC)cc2sc(CC[C@H](C)C(=O)O)cc2c1F] | (S)-4-(5-(3-((2-((S)-3-carboxybutyl)-4-fluoro-6-methoxybenzo[b]thiophen-5-yl)oxy)propoxy)-6-methoxybenzo[b]thiophen-2-yl)-2-methyl-4-oxobutanoic acid | 633 |
| 170 | 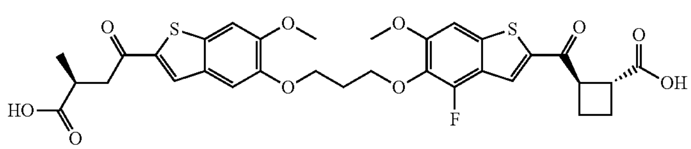 | trans-2-(5-(3-((2-((S)-3-carboxybutanoyl)-6-methoxybenzo[b]thiophen-5-yl)oxy)propoxy)-4-fluoro-6-methoxybenzo[b]thiophene-2-carbonyl)cyclobutanecarboxylic acid | 659 |
| 171 | 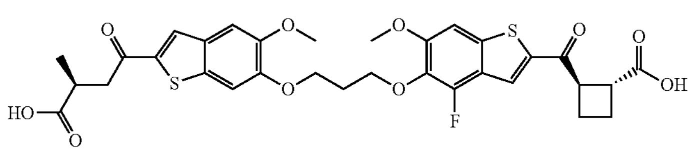 [SMILES: COc1cc2cc(C(=O)C[C@H](C)C(=O)O)sc2cc1OCCCOc1c(OC)cc2sc(C(=O)[C@@H]3CC[C@H]3C(=O)O)cc2c1F] | trans-2-(5-(3-((2-((S)-3-carboxybutanoyl)-5-methoxybenzo[b]thiophen-6-yl)oxy)propoxy)-4-fluoro-6-methoxybenzo[b]thiophene-2-carbonyl)cyclobutanecarboxylic acid | 659 |

Example 75: 4-(5-((3-(2-(3-carboxypropanoyl)-6-methoxybenzo[b]thiophen-5-yl)propyl)amino)-6-methoxythieno[3,2-b]pyridin-2-yl)-4-oxobutanoic acid

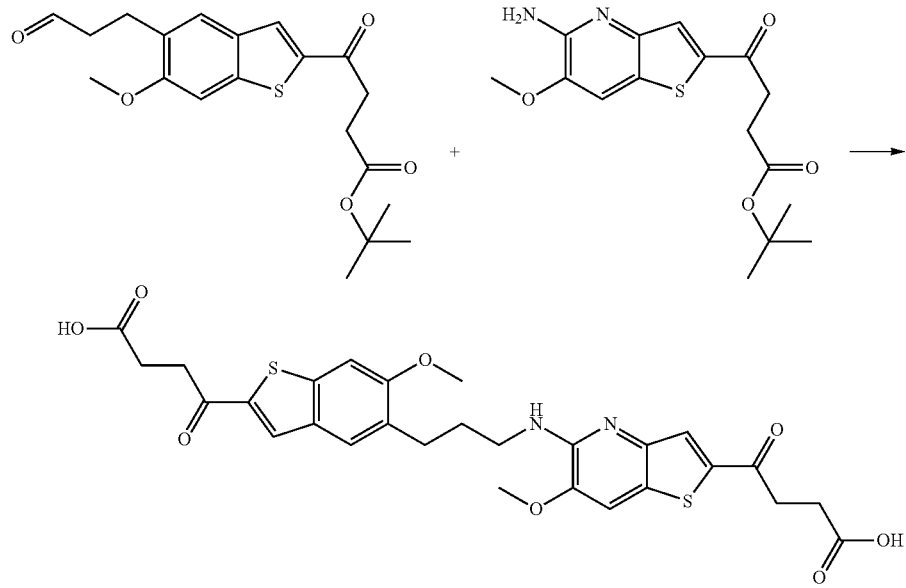

To a 4 mL vial was added tert-butyl 4-(6-methoxy-5-(3-oxopropyl)benzo[b]thiophen-2-yl)-4-oxobutanoate (10 mg, 0.03 mmol), tert-butyl 4-(5-amino-6-methoxythieno[3,2-b]pyridin-2-yl)-4-oxobutanoate (8.9 mg, 0.027 mmol), and THF (0.50 mL). To the slurry was added AcOH (0.015 mL, 0.27 mmol). The mixture was heated to 55° C. for 10 min. Upon cooling to RT, sodium triacetoxyborohydride (17 mg, 0.080 mmol) was added. The mixture was then heated to 55° C. for 3 h. Upon cooling to RT, TFA (1 mL) was added, and the mixture was allowed to stir at RT for 1 h. The mixture was then concentrated under reduced pressure and then diluted with DMSO (1 mL). The mixture was purified by prep-HPLC (ACN/H$_2$O w/0.1% TFA) to afford 4-(5-((3-(2-(3-carboxypropanoyl)-6-methoxybenzo[b]thiophen-5-yl) propyl) amino)-6-methoxythieno [3,2-b]pyridin-2-yl)-4-oxobutanoic acid. LCMS (C$_{28}$H$_{29}$N$_2$O$_8$S$_2$) (ES, m/z): 585 [M+H]$^+$. $^1$H NMR (500 MHz, DMSO-d$_6$) δ 12.18 (br, 2H), 8.22 (s, 1H), 8.03 (s, 1H), 7.79 (s, 1H), 7.63 (s, 1H), 7.59 (s, 1H), 6.55 (br s, 1H), 3.90 (s, 3H), 3.88 (s, 3H), 3.48-3.43 (m, 2H), 3.27-3.24 (m, 4H), 2.73 (t, J=7.3 Hz, 2H), 2.61-2.56 (m, 4H), 1.98-1.91 (m, 2H).

Example 76: (2S,2'S)-4,4'-((ethane-1,2-diylbis(oxy)) bis(6-methoxybenzo[b]thiophene-5,2-diyl))bis(2-methyl-4-oxobutanoic acid)

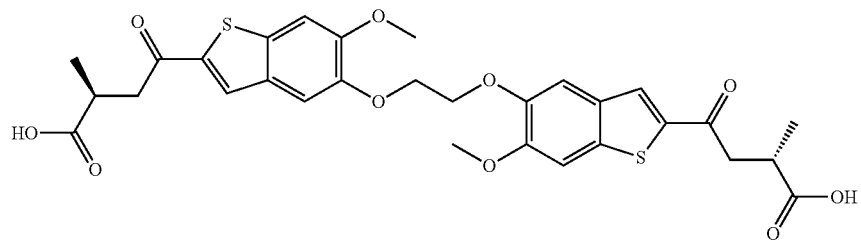 [SMILES: COc1cc2sc(C(=O)C[C@H](C)C(=O)O)cc2cc1OCCOc1cc2cc(C(=O)C[C@H](C)C(=O)O)sc2cc1OC]

Step 1: dimethyl 4,4'-((ethane-1,2-diylbis(oxy))bis(6-methoxybenzo[b]thiophene-5,2-diyl))(2S,2'S)-bis(2-methyl-4-oxobutanoate)

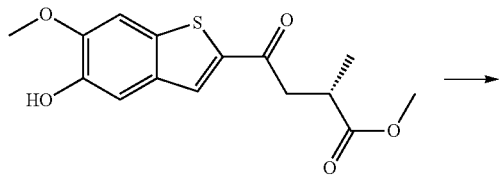

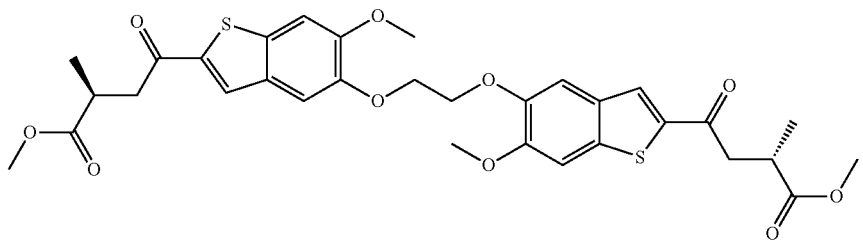

A mixture of methyl (S)-4-(5-hydroxy-6-methoxybenzo[b]thiophen-2-yl)-2-methyl-4-oxobutanoate (50 mg, 0.17 mmol) and K₂CO₃ (47 mg, 0.34 mmol) was diluted with DMF (750 µL). 1-Bromo-2-chloroethane (18 µL, 0.22 mmol) was added, and the reaction mixture was heated to 100° C. for 18 h. The reaction mixture was concentrated under reduced pressure and used without further purification or characterization.

Step 2: (2S,2'S)-4,4'-((ethane-1,2-diylbis(oxy))bis(6-methoxybenzo[b]thiophene-5,2-diyl))bis(2-methyl-4-oxobutanoic acid)

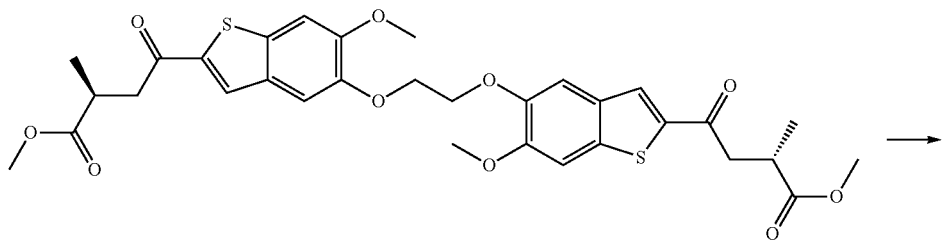

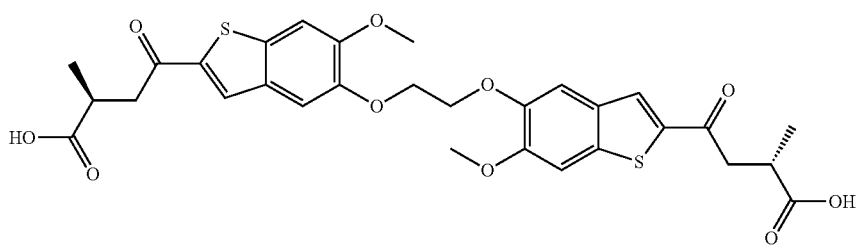

LiOH (16 mg, 0.67 mmol) was added to a stirring solution of dimethyl 4,4'-((ethane-1,2-diylbis(oxy))bis(6-methoxybenzo[b]thiophene-5,2-diyl))(2S,2'S)-bis(2-methyl-4-oxobutanoate) (50 mg, 0.08 mmol) in THF (340 µl)/Water (80 µl). The reaction mixture was allowed to stir at RT for 4 h. The reaction mixture was filtered and concentrated under reduced pressure. The residue was dissolved in DMSO (4 mL) and filtered. The product was purified by mass directed reversed-phase C18 column chromatography (ACN/water with 0.1% TFA) to afford (2S,2'S)-4,4'-(5,5'-(ethane-1,2-diylbis(oxy))bis(6-methoxybenzo[b]thiophene-5,2-diyl))bis(2-methyl-4-oxobutanoic acid). LCMS ($C_{30}H_{30}O_{10}S_2Na$) (ES, m/z): 637 [M+Na]$^+$. $^1$H NMR (500 MHz, DMSO-$d_6$) δ: 12.21 (br s, 2H), 8.20 (s, 2H), 7.64 (s, 2H), 7.59 (s, 2H), 4.44 (s, 4H), 3.87 (s, 6H), 3.41 (dd, J=17, 9 Hz, 2H), 3.09 (dd, J=17, 5 Hz, 2H), 3.05-2.58 (m, 2H), 1.19 (d, J=7 Hz, 6H).

Example 77: (2S,2'S)-4,4'-(7,8,17,18-tetrahydro-6H,16H-bis[1]benzothieno[5,6-b:6',5'-i][1,4,8,11] tetraoxacyclotetradecine-2,12-diyl)bis(2-methyl-4-oxobutanoic acid) and Example 78: (2S,2'S)-4,4'-(7,8,17,18-tetrahydro-6H,16H-bis[1]benzothieno[5,6-b:5',6'-i][1,4,8,11]tetraoxacyclotetradecine-2,12-diyl)bis(2-methyl-4-oxobutanoic acid)

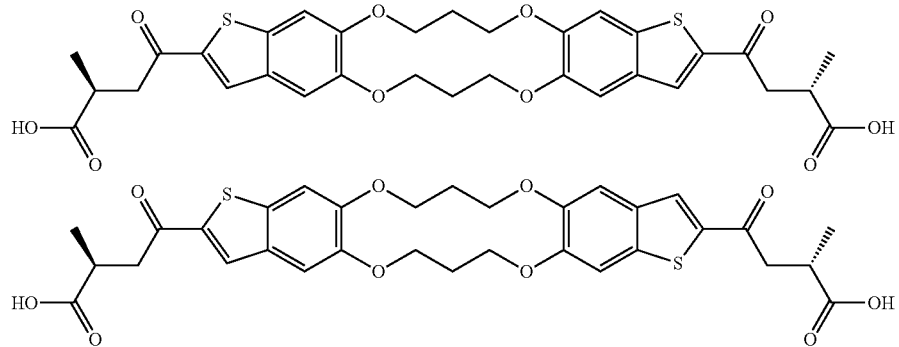

Step 1: dimethyl (2S,2'S)-4,4'-(7,8,17,18-tetrahydro-6H,16H-bis[1]benzothieno[5,6-b:5',6'-i][1,4,8,11] tetraoxacyclotetradecine-2,12-diyl)bis(2-methyl-4-oxobutanoate) and dimethyl (2S,2'S)-4,4'-(7,8,17,18-tetrahydro-6H,16H-bis[1]benzothieno[5,6-b:6',5'-i][1,4,8,11]tetraoxacyclotetradecine-2,12-diyl)bis(2-methyl-4-oxobutanoate)

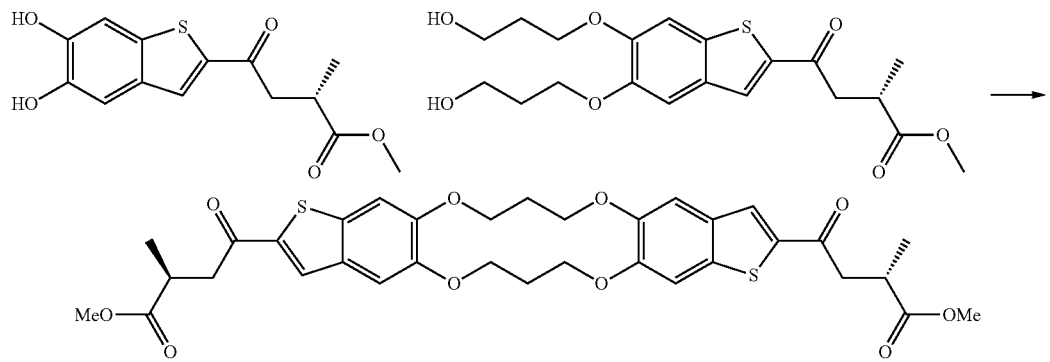

-continued

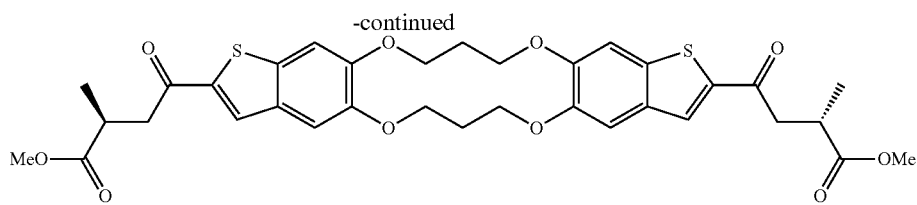

A mixture of methyl (2S)-4-(5,6-dihydroxy-1-benzothiophen-2-yl)-2-methyl-4-oxobutanoate (60 mg, 0.20 mmol), methyl (2S)-4-[5,6-bis(3-hydroxypropoxy)-1-benzothiophen-2-yl]-2-methyl-4-oxobutanoate (120 mg, 0.20 mmol), Ph$_3$P (193 mg, 0.737 mmol), and 1,1'-(azodicarbonyl)dipiperidine (186 mg, 0.737 mmol) in THF (2.0 mL) was allowed to stir at RT for 18 h. The mixture was then filtered and purified by reverse phase HPLC (gradient of MeCN/water with 0.1% TFA) to afford a 1:1 mixture of dimethyl (2S,2'S)-4,4'-(7,8,17,18-tetrahydro-6H,16H-bis[1]benzothieno[5,6-b:5',6'-i][1,4,8,11]tetraoxacyclotetradecine-2,12-diyl)bis(2-methyl-4-oxobutanoate) and dimethyl (2S,2'S)-4,4'-(7,8,17,18-tetrahydro-6H,16H-bis[1]benzothieno[5,6-b:6',5'-i][1,4,8,11]tetraoxacyclotetradecine-2,12-diyl)bis(2-methyl-4-oxobutanoate). LCMS (C$_{34}$H$_{36}$O$_{10}$S$_2$Na) (ES, m/z): 691 [M+Na]$^+$.

Step 2: (2S,2'S)-4,4'-(7,8,17,18-tetrahydro-6H,16H-bis[1]benzothieno[5,6-b:5',6'-i][1,4,8,11]tetraoxacyclotetradecine-2,12-diyl)bis(2-methyl-4-oxobutanoic acid) and (2S,2'S)-4,4'-(7,8,17,18-tetrahydro-6H,16H-bis[1]benzothieno[5,6-b:6',5'-i][1,4,8,11]tetraoxacyclotetradecine-2,12-diyl)bis(2-methyl-4-oxobutanoic acid)

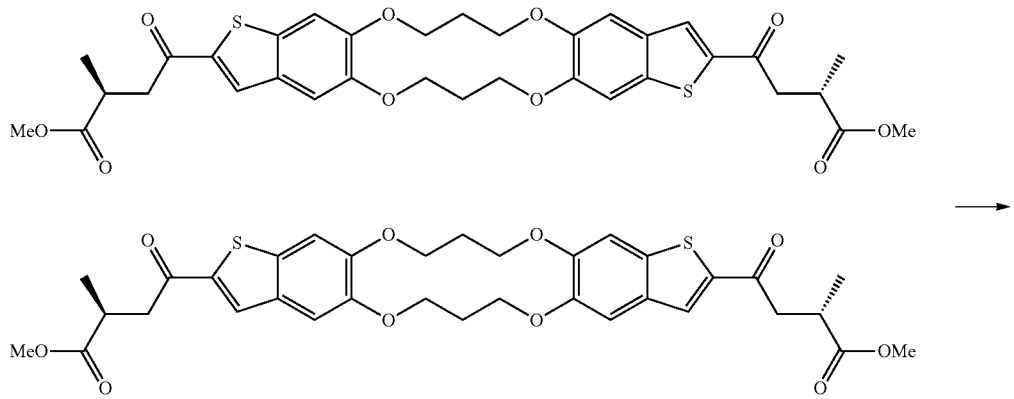

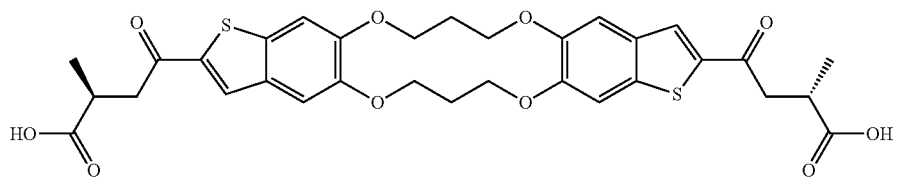

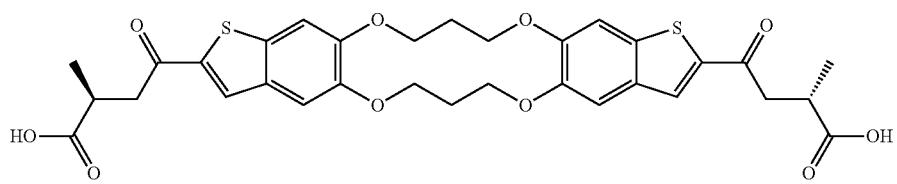

To a stirred solution of a 1:1 mixture of dimethyl (2S,2'S)-4,4'-(7,8,17,18-tetrahydro-6H,16H-bis[1]benzothieno[5,6-b:5',6'-i][1,4,8,11]tetraoxacyclotetradecine-2,12-diyl)bis(2-methyl-4-oxobutanoate) and dimethyl (2S,2'S)-4,4'-(7,8,17,18-tetrahydro-6H,16H-bis[1]benzothieno[5,6-b:6',5'-i][1,4,8,11]tetraoxacyclotetradecine-2,12-diyl)bis(2-methyl-4-oxobutanoate) (67 mg, 0.10 mmol) in MeOH (1.0 mL), THF (1.0 mL), and water (0.2 mL) was added LiOH (24 mg, 1.0 mmol). The reaction mixture was allowed to stir for 4 h and then purified by reverse phase HPLC (gradient of MeCN/water with 0.1% TFA) to afford a 1:1 mixture of (2S,2'S)-4,4'-(7,8,17,18-tetrahydro-6H,16H-bis[1]benzothieno[5,6-b:5',6'-i][1,4,8,11] tetraoxacyclo tetradecine-2,12-diyl)bis(2-methyl-4-oxobutanoic acid) and (2S,2'S)-4,4'-(7,8,17,18-tetrahydro-6H,16H-bis[1]benzothieno[5,6-b:6',5'-i][1,4,8,11]tetraoxacyclo-tetradecine-2,12-diyl)bis(2-methyl-4-oxobutanoic acid). LCMS ($C_{32}H_{33}O_{10}S_2$) (ES, m/z): 641 [M+H]$^+$. $^1$H NMR (500 MHz, DMSO-$d_6$) δ 12.20 (brs, 2H), 8.18 (s, 2H), 7.52 (s, 2H), 7.40 (s, 2H), 4.27-4.18 (m, 8H), 3.42-3.34 (m, 2H), 3.10-3.03 (m, 2H), 2.92-2.85 (m, 2H), 2.29 (brs, 4H), 1.17 (d, J=6.8 Hz, 6H).

Example 79: (2S,2'S)-4,4'-(1,3-propanediylbis{oxy[6-(difluoromethoxy)-1-benzothiene-5,2-diyl]})bis(2-methyl-4-oxobutanoic acid)

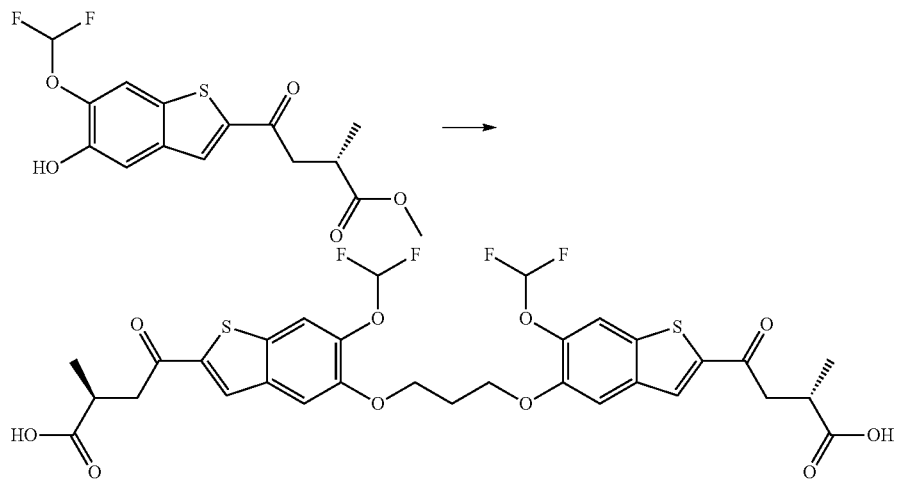

To a stirred solution of methyl (2S)-4-[6-(difluoromethoxy)-5-hydroxy-1-benzo thiophen-2-yl]-2-methyl-4-oxobutanoate (54 mg, 0.16 mmol) and $K_2CO_3$ (109 mg, 0.788 mmol) in DMF (0.8 mL) was added 1,3-dibromopropane (8 μL, 0.08 mmol). The mixture was heated to 50° C. for 4 h. Upon cooling to RT, the mixture was treated with LiOH (2M in water, 790 μL, 1.58 mmol) and allowed to stir at RT for 4 h. The mixture was then concentrated under reduced pressure and purified by RP-HPLC (gradient of MeCN/water with 0.1% TFA) to afford (2S,2'S)-4,4'-(1,3-propanediylbis {oxy[6-(difluoromethoxy)-1-benzothiene-5,2-diyl]})bis(2-methyl-4-oxobutanoic acid). LCMS ($C_{31}H_{28}F_4O_{10}S_2Na$) (ES, m/z): 723 [M+23]$^+$. $^1$H NMR (500 MHz, DMSO-$d_6$) δ 12.25 (s, 2H), 8.27 (s, 2H), 7.94 (s, 2H), 7.73 (s, 2H), 7.20 (t, J=74.0 Hz, 2H), 4.33-4.29 (m, 4H), 3.46-3.40 (m, 2H), 3.12 (dd, J=17.5, 4.9 Hz, 2H), 2.94-2.87 (m, 2H), 2.37-2.32 (m, 2H), 1.19 (d, J=7.1 Hz, 6H).

Examples 80 and 172, as shown in Table 19 below, were or may be prepared according to procedures analogous to those outlined in Example 79 above using the appropriate starting materials, described in the Preparations or Intermediates above, or as obtained from commercial sources.

TABLE 19

| Example | Structure | Name | Mass [M + H]+ |
|---|---|---|---|
| 80 | 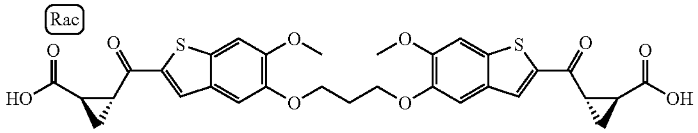 [SMILES: COc1cc2sc(C(=O)[C@H]3C[C@@H]3C(=O)O)cc2cc1OCCCOc1cc2cc(C(=O)[C@@H]3C[C@H]3C(=O)O)sc2cc1OC] | rac-(1S,2S)-2-(5-(3-((2-((1R,2R)-2-carboxy-cyclopropane-1-carbonyl)-6-methoxybenzo[b]thiophen-5-yl)oxy)propoxy)-6-methoxybenzo[b]thiophene-2-carbonyl)cyclopropane-1-carboxylic acid | 625 |
| 172 | 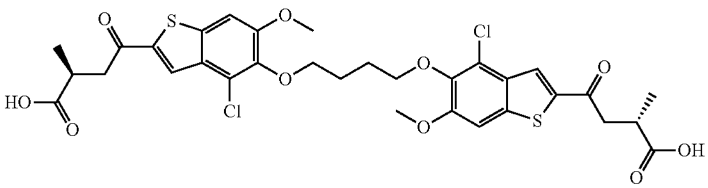 | (2S,2'S)-4,4'-(5,5'-(butane-1,4-diylbis(oxy))bis(4-chloro-6-methoxybenzo[b]thiophene-5,2-diyl))bis(2-methyl-4-oxobutanoic acid) | 711, 713 |

Example 173: (4-(5-(3-((2-(3-Carboxypropanoyl)-4-fluoro-6-methoxybenzo[b]thiophen-5-yl)oxy)propyl)-6-methoxythieno[3,2-b]pyridin-2-yl)-4-oxobutanoic acid

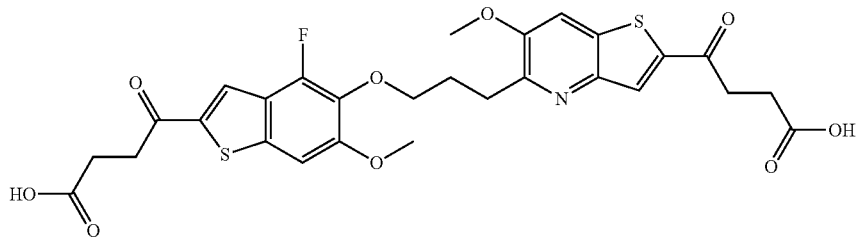 [SMILES: COc1cc2sc(C(=O)CCC(=O)O)cc2nc1CCCOc1c(OC)cc2sc(C(=O)CCC(=O)O)cc2c1F]

tert-Butyl 4-(5-(3-hydroxypropyl)-6-methoxythieno[3,2-b]pyridin-2-yl)-4-oxobutanoate (76 mg, 0.20 mmol) was added to a vial containing ethyl 4-(4-fluoro-5-hydroxy-6-methoxybenzo[b]thiophen-2-yl)-4-oxobutanoate (250 mg, 0.77 mmol), PS-TPP (319 mg, 0.600 mmol), DIAD (0.117 ml, 0.600 mmol), and THF (3 ml). The reaction mixture was stirred for 3 h at RT. The reaction mixture was filtered, washed with THF (5 ml). MeOH (2 ml), water (3 ml), and LiOH (48 mg, 2.0 mmol) were added, and the reaction mixture was stirred for an additional 2 h. The reaction mixture was then quenched with HOAc and concentrated under reduced pressure. The residue was suspended in DCM (5 ml), and TFA (1 ml) was added. The reaction mixture was stirred for 1 h. The reaction mixture was then concentrated under reduced pressure, and the residue was purified by reverse phase HPLC (acetonitrile/water gradient with 0.1% TFA) to afford (4-(5-(3-((2-(3-carboxypropanoyl)-4-fluoro-6-methoxybenzo[b]thiophen-5-yl)oxy)propyl)-6-methoxythieno[3,2-b]pyridin-2-yl)-4-oxobutanoic acid. LCMS ($C_{28}H_{27}FNO_9S_2$) (ES, m/z): 604 [M+H]+. 1H NMR (600 MHz, DMSO-$d_6$) δ 8.34 (s, 1H), 8.31 (s, 1H), 8.07 (s, 1H), 7.57 (s, 1H), 4.17 (t, J=6.3 Hz, 2H), 3.93 (s, 3H), 3.90 (s, 3H), 3.35-3.29 (m, 4H), 3.10-3.04 (m, 2H), 2.63-2.58 (m, 4H), 2.18-2.13 (m, 2H).

Example 174, as shown in Table 20 below, was or may be prepared according to procedures analogous to those outlined in Example 173 above using the appropriate starting materials, described in the Preparations or Intermediates above, or as obtained from commercial sources.

TABLE 20

| Example | Structure | Name | Mass [M + H]+ |
|---|---|---|---|
| 174 | 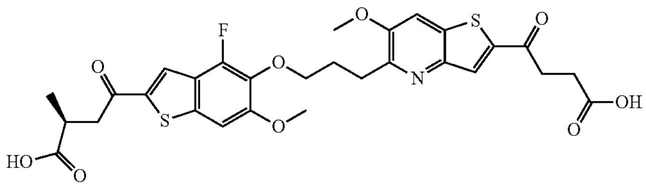 [SMILES: COc1cc2sc(C(=O)CCC(=O)O)cc2nc1CCCOc1c(OC)cc2sc(C(=O)C[C@H](C)C(=O)O)cc2c1F] | (S)-4-(5-(3-(2-(3-carboxypropanoyl)-6-methoxythieno[3,2-b]pyridin-5-yl)propoxy)-4-fluoro-6-methoxybenzo[b]thiophen-2-yl)-2-methyl-4-oxobutanoic acid | 618 |

Example 175: 4,4'-(Propane-1,3-diylbis(6-methoxybenzo[b]thiophene-5,2-diyl))bis(4-oxobutanenitrile)

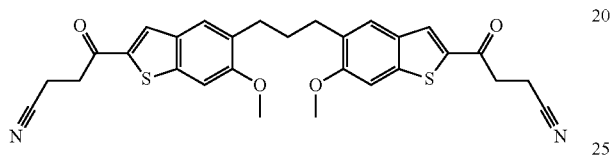

4-(5-Bromo-6-methoxybenzo[b]thiophen-2-yl)-4-oxobutanenitrile (35 mg, 0.11 mmol), nickel(II) bromide ethylene glycol dimethyl ether complex (10 mg, 0.033 mmol), manganese (24 mg, 0.44 mmol), NaI (8 mg, 0.06 mmol) and 4,4'-dimethoxy-2,2'-bipyridine (7 mg, 0.03 mmol) were combined in a vial. A solution of 4-(5-(3-bromopropyl)-6-methoxybenzo[b]thiophen-2-yl)-4-oxobutanenitrile (40 mg, 0.11 mmol) in DMPU (1.1 ml) was added to the vial. 5% v/v solutions in DMPU of Py (88 µl, 0.055 mmol) and TMS-Cl (84 µl, 0.033 mmol) were added to the reaction mixture. The reaction mixture was degassed with Ar for 5 min, and then stirred and heated at 90° C. for 2 h. The reaction mixture was cooled to RT, diluted with DMSO (2 ml), and filtered. The filtrate was purified by reverse phase HPLC (ACN/water with TFA modifier) to afford 4,4'-(propane-1,3-diylbis(6-methoxybenzo[b]thiophene-5,2-diyl))bis(4-oxobutanenitrile). LCMS ($C_{29}H_{27}N_2O_4S_2$) (ES, m/z): 531 [M+H]+. $^1$H NMR (499 MHz, DMSO-$d_6$) δ 8.26 (s, 2H), 7.78 (s, 2H), 7.61 (s, 2H), 3.89 (s, 6H), 3.55-3.45 (m, 4H), 2.81-2.76 (m, 4H), 2.74-2.69 (m, 4H), 1.95-1.90 (m, 2H).

Example 176: (S)-4-(5-((3-((2-((S)-3-Carboxybutanoyl)-4-fluoro-6-methoxybenzo[b]thiophen-5-yl)oxy)propyl)amino)-6-methoxybenzo[b]thiophen-2-yl)-2-methyl-4-oxobutanoic acid

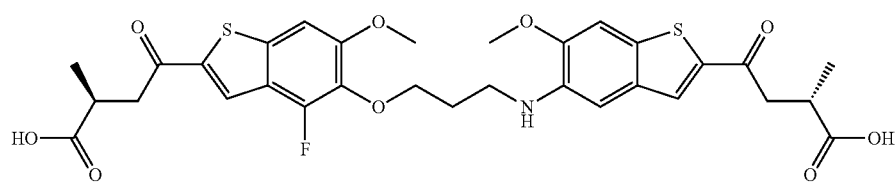 [SMILES: COc1cc2sc(C(=O)C[C@H](C)C(=O)O)cc2cc1NCCCOc1c(OC)cc2sc(C(=O)C[C@H](C)C(=O)O)cc2c1F]

A mixture of (S)-methyl 4-(5-amino-6-methoxybenzo[b]thiophen-2-yl)-2-methyl-4-oxobutanoate (37 mg, 0.12 mmol), (S)-methyl 4-(5-(3-bromopropoxy)-4-fluoro-6-methoxy benzo[b]thiophen-2-yl)-2-methyl-4-oxobutanoate (54 mg, 0.12 mmol), and potassium carbonate (67 mg, 0.48 mmol) was degassed with Ar. DMF (1.0 ml) was added to the mixture, and the reaction mixture was stirred and heated at 60° C. for 2 days. The reaction mixture was cooled to RT and then NaOH (1.0 M in water, 0.48 ml, 0.48 mmol) was added to the reaction mixture. The mixture was further diluted with DMSO (1.5 ml) and then stirred at RT for 1 h. The reaction mixture was quenched with TFA (0.056 ml, 0.72 mmol) and filtered. The filtrate was purified by reverse phase HPLC (ACN/water with 0.1% TFA) to afford (S)-4-(5-((3-((2-((S)-3-carboxy butanoyl)-4-fluoro-6-methoxybenzo[b]thiophen-5-yl)oxy)propyl)amino)-6-methoxybenzo[b]thiophen-2-yl)-2-methyl-4-oxobutanoic acid. LCMS ($C_{31}H_{33}FNO_9S_2$) (ES, m/z): 646 [M+H]$^+$. $^1$H NMR (499 MHz, DMSO-$d_6$) δ 8.32 (s, 1H), 8.11 (s, 1H), 7.60 (s, 1H), 7.45 (s, 1H), 7.04 (s, 1H), 4.17 (t, J=5.9 Hz, 2H), 3.92 (s, 3H), 3.90 (s, 3H), 3.47 (dd, J=17.6, 8.6 Hz, 1H), 3.43-3.34 (m, 3H), 3.17-3.05 (m, 2H), 2.94-2.95 (m, 2H), 2.09-2.02 (m, 2H), 1.20-1.15 (m, 6H).

Example 177, as shown in Table 21 below, was or may be prepared according to procedures analogous to those outlined in Example 176 above using the appropriate starting materials, described in the Preparations or Intermediates above, or as obtained from commercial sources.

TABLE 21

| Example | Structure | Name | Mass [M + H]$^+$ |
|---|---|---|---|
| 177 | 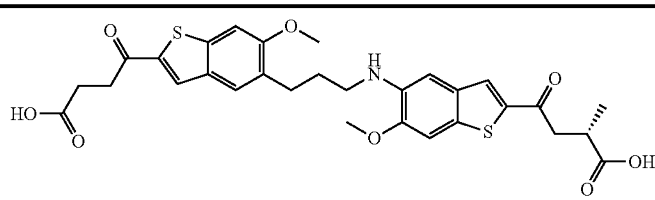 | (S)-4-(5-((3-(2-(3-carboxypropanoyl)-6-methoxybenzo[b]thiophen-5-yl)propyl)amino)-6-methoxybenzo[b]thiophen-2-yl)-2-methyl-4-oxobutanoic acid | 598 |

Example 178: (S)-4-(5-(3-((2-((S)-4-((N,N-Dimethylsulfamoyl)amino)-3-methyl-4-oxobutanoyl)-4-fluoro-6-methoxybenzo[b]thiophen-5-yl)oxy)propoxy)-6-methoxybenzo[b]thiophen-2-yl)-2-methyl-4-oxobutanoic acid

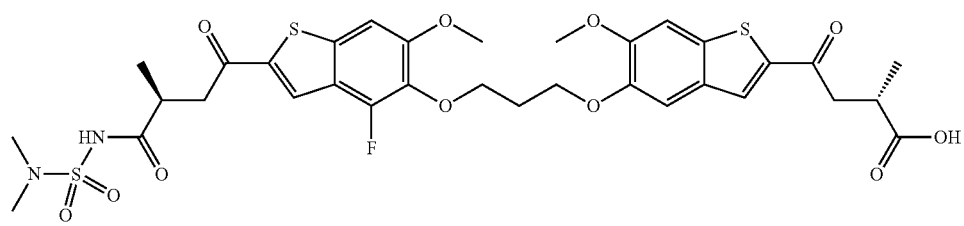 [SMILES: COc1cc2sc(C(=O)C[C@H](C)C(=O)O)cc2cc1OCCCOc1c(OC)cc2sc(C(=O)C[C@H](C)C(=O)NS(=O)(=O)N(C)C)cc2c1F]

Step 1: tert-Butyl (S)-4-(5-(3-((4-fluoro-6-methoxy-2-((S)-4-methoxy-3-methyl-4-oxobutanoyl) benzo[b]thiophen-5-yl)oxy)propoxy)-6-methoxybenzo[b]thiophen-2-yl)-2-methyl-4-oxobutanoate

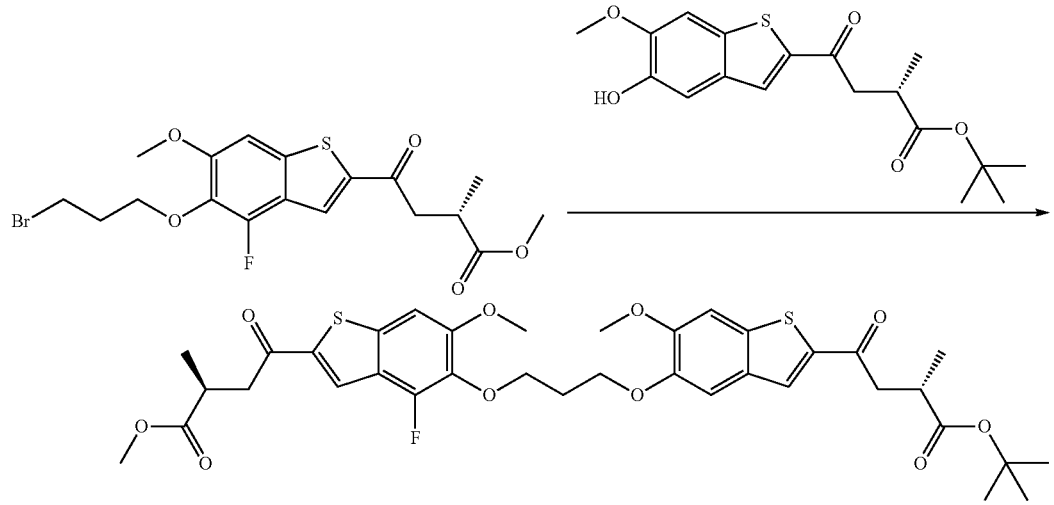

A mixture of (S)-methyl 4-(5-(3-bromopropoxy)-4-fluoro-6-methoxybenzo[b]thiophen-2-yl)-2-methyl-4-oxobutanoate (111 mg, 0.248 mmol), (S)-tert-butyl 4-(5-hydroxy-6-methoxybenzo[b]thiophen-2-yl)-2-methyl-4-oxobutanoate (87 mg, 0.25 mmol), and potassium carbonate (137 mg, 0.993 mmol) was degassed with Ar. DMF (1.Ar) was added to the mixture, and the reaction mixture was stirred and heated at 40° C. for 18 h. The reaction mixture was cooled to RT and then diluted with EtOAc and water. The organic layer was separated, dried over MgSO$_4$, filtered, and concentrated under reduced pressure. The residue was purified by silica gel chromatography (EtOAc/Hex) to afford tert-butyl (S)-4-(5-(3-((4-fluoro-6-methoxy-2-((S)-4-methoxy-3-methyl-4-oxobutanoyl)benzo[b]thiophen-5-yl)oxy)propoxy)-6-methoxybenzo [b]thiophen-2-yl)-2-methyl-4-oxobutanoate. LCMS ($C_{36}H_{42}FO_{10}S_2$) (ES, m/z): 739 [M+Na]$^+$. $^1$H NMR (499 MHz, DMSO-d$_6$) δ 8.30 (s, 1H), 8.21 (s, 1H), 7.59 (s, 1H), 7.57 (s, 1H), 7.51 (s, 1H), 4.26 (q, J=5.9 Hz, 4H), 3.86 (s, 3H), 3.85 (s, 3H), 3.60 (s, 3H), 3.48 (dd, J=17.7, 8.7 Hz, 1H), 3.39-3.33 (m, 1H), 3.23 (dd, J=17.7, 5.0 Hz, 1H), 3.07 (dd, J=17.1, 5.0 Hz, 1H), 3.02-2.93 (m, 1H), 2.91-2.81 (m, 1H), 2.23-2.18 (m, 2H), 1.35 (s, 9H), 1.20-1.15 (m, 6H).

Step 2: (S)-4-(5-(3-((2-((S)-4-(tert-Butoxy)-3-methyl-4-oxobutanoyl)-6-methoxybenzo[b]thiophen-5-yl)oxy)propoxy)-4-fluoro-6-methoxybenzo[b]thiophen-2-yl)-2-methyl-4-oxobutanoic acid

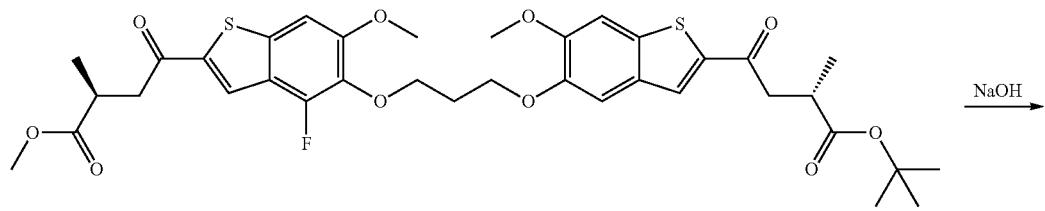

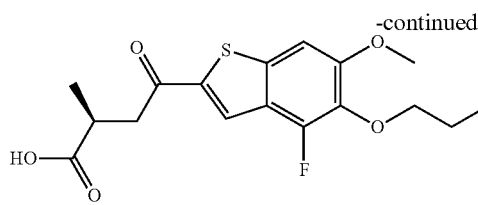

NaOH (1.0M in water, 0.94 ml, 0.94 mmol) was added to a mixture of (S)-tert-butyl 4-(5-(3-((4-fluoro-6-methoxy-2-((S)-4-methoxy-3-methyl-4-oxobutanoyl)-benzo[b]thiophen-5-yl)oxy)propoxy)-6-methoxybenzo[b]thiophen-2-yl)-2-methyl-4-oxobutanoate (135 mg, 0.188 mmol) in THF (0.94 ml) and MeOH (0.94 ml). The mixture was stirred at RT for one h. The reaction mixture was quenched with HCl (2.0 M in water, 0.47 ml, 0.94 mmol) and diluted with EtOAc and water. The organic layer was separated, dried over MgSO$_4$, filtered, and concentrated under reduced pressure to afford (S)-4-(5-(3-((2-((S)-4-(tert-butoxy)-3-methyl-4-oxobutanoyl)-6-methoxybenzo[b]thiophen-5-yl)oxy)propoxy)-4-fluoro-6-methoxybenzo[b]thiophen-2-yl)-2-methyl-4-oxobutanoic acid. LCMS ($C_{35}H_{40}FO_{10}S_2$) (ES, m/z): 725 [M+Na]$^+$.

Step 3: (S)-4-(5-(3-((2-((S)-4-((N,N-Dimethylsulfamoyl)amino)-3-methyl-4-oxobutanoyl)-4-fluoro-6-methoxybenzo[b]thiophen-5-yl)oxy)propoxy)-6-methoxybenzo[b]thiophen-2-yl)-2-methyl-4-oxobutanoic acid benzo[b]thiophen-5-yl)oxy)propoxy)-4-fluoro-6-methoxy-benzo[b]thiophen-2-yl)-2-methyl-4-oxobutanoic acid (50 mg, 0.071 mmol) in DCM (0.7 ml). The mixture was stirred at RT for 30 min. N,N-dimethylsulfamide (11 mg, 0.085 mmol) was added and the mixture was stirred for an additional 4 h. TFA (0.055 ml, 0.71 mmol) was then added and the mixture was stirred and heated to 45° C. for 2 h. The mixture was cooled to RT and was concentrated under reduced pressure. The residue was purified by reverse phase HPLC (ACN/water with 0.1% TFA) to afford (S)-4-(5-(3-((2-((S)-4-((N,N-dimethyl sulfamoyl)amino)-3-methyl-4-oxobutanoyl)-4-fluoro-6-methoxy benzo[b]thiophen-5-yl) oxy)propoxy)-6-methoxybenzo[b]thiophen-2-yl)-2-methyl-4-oxobutanoic acid. LCMS ($C_{33}H_{38}FN_2O_{11}S_3$) (ES, m/z): 775 [M+Na]$^+$. $^1$H NMR (499 MHz, DMSO-d$_6$) δ 11.50 (s, 1H), 8.30 (s, 1H), 8.22 (s, 1H), 7.59 (s, 1H), 7.56 (s, 1H), 7.52 (s, 1H), 4.26 (q, J=5.9 Hz, 4H), 3.87 (s, 3H), 3.85 (s, 3H), 3.48 (dd, J=17.8, 9.8 Hz, 1H), 3.40 (dd, J=17.3, 8.4 Hz, 1H), 3.16 (dd, J=17.8, 4.4 Hz, 1H), 3.09 (dd, J=17.3, 5.3 Hz, 1H), 3.00-2.94 (m, 1H), 2.94-2.87 (m, 1H), 2.79 (s, 6H), 2.23-2.17 (m, 2H), 1.21-1.15 (m, 6H).

Example 179, as shown in Table 22 below, was or may be prepared according to procedures analogous to those out-

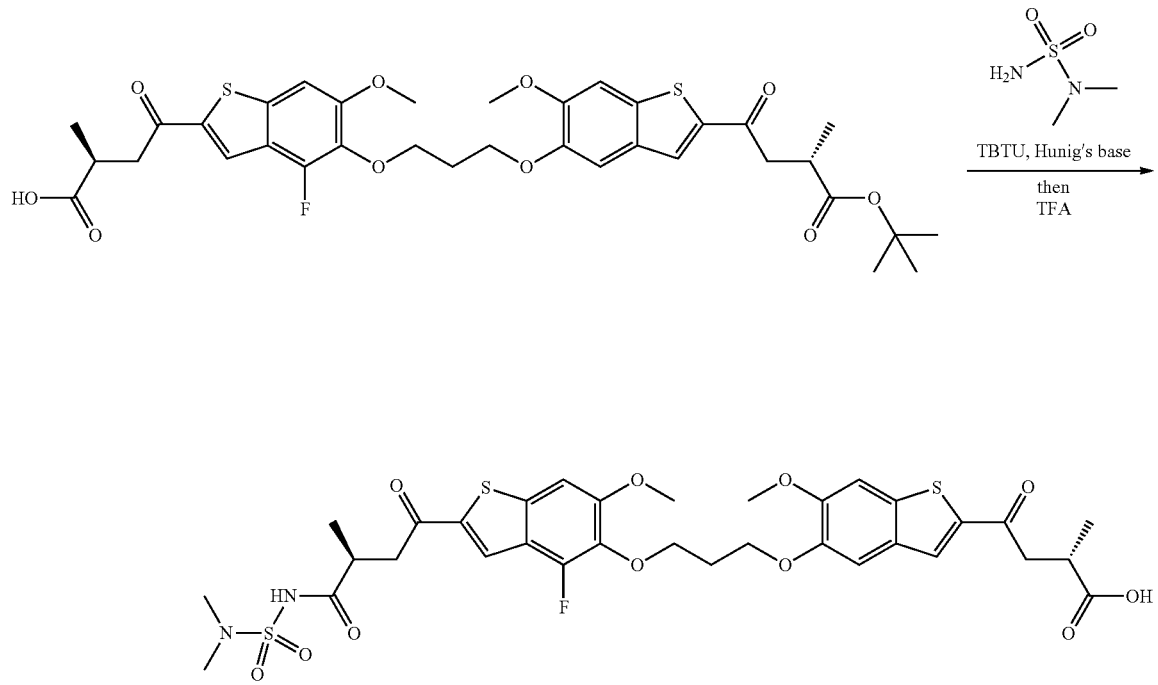

Hunig's base (0.062 ml, 0.36 mmol) and TBTU (23 mg, 0.071 mmol) were added to a mixture of (S)-4-(5-(3-((2-((S)-4-(tert-butoxy)-3-methyl-4-oxobutanoyl)-6-methoxylined in Example 178 above using the appropriate starting materials, described in the Preparations or Intermediates above, or as obtained from commercial sources.

TABLE 22

| Example | Structure | Name | Mass [M + H]+ |
|---|---|---|---|
| 179 | 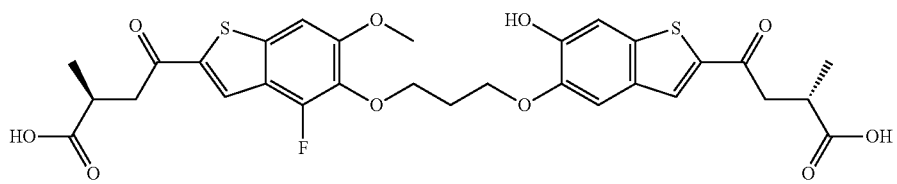 [SMILES: COc1cc2sc(C(=O)C[C@H](C)C(=O)O)cc2c(F)c1OCCCOc1cc2cc(C(=O)C[C@H](C)C(=O)O)sc2cc1O] | (S)-4-(5-(3-((4-fluoro-6-methoxy-2-((S)-3-methyl-4-(methylsulfonamido)-4-oxobutanoyl)-benzo[b]thiophen-5-yl)oxy)propoxy)-6-methoxybenzo[b]thiophen-2-yl)-2-methyl-4-oxobutanoic acid | 724 |

Example 180: (S)-4-(5-(3-((2-((S)-3-Carboxybutanoyl)-4-fluoro-6-methoxybenzo[b]thiophen-5-yl)oxy)propoxy)-6-hydroxybenzo[b]thiophen-2-yl)-2-methyl-4-oxobutanoic acid

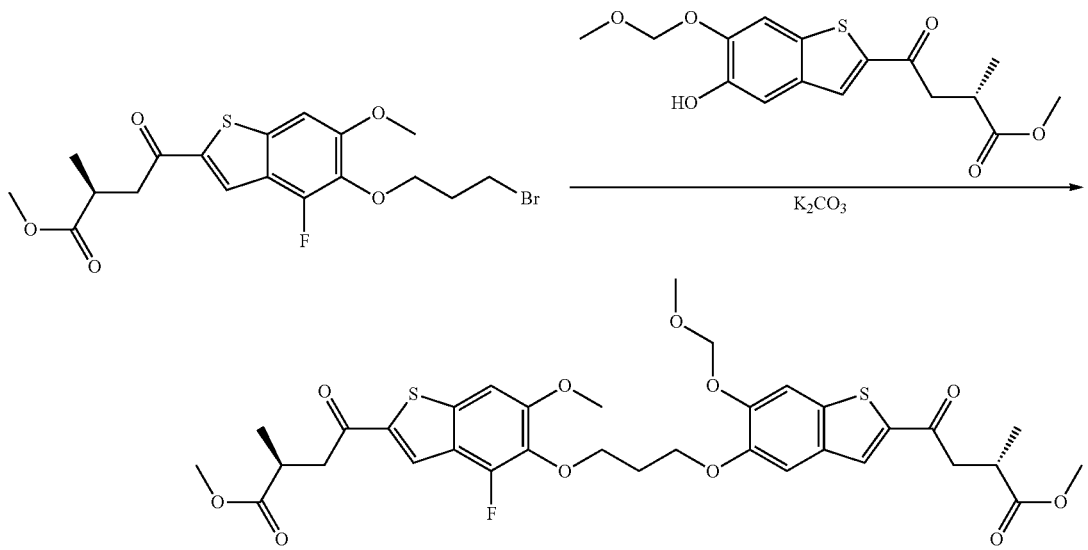

Step 1: Methyl (S)-4-(5-(3-((4-fluoro-6-methoxy-2-((S)-4-methoxy-3-methyl-4-oxobutanoyl)benzo[b]thiophen-5-yl)oxy)propoxy)-6-(methoxymethoxy)benzo[b]thiophen-2-yl)-2-methyl-4-oxobutanoate A mixture of methyl (S)-4-(5-(3-bromopropoxy)-4-fluoro-6-methoxybenzo[b]thiophen-2-yl)-2-methyl-4-oxobutanoate (30 mg, 0.068 mmol), methyl (S)-4-(5-hydroxy-6-(methoxymethoxy)benzo[b]thiophen-2-yl)-2-methyl-4-oxobutanoate (23 mg, 0.068 mmol), and potassium carbonate (38 mg, 0.27 mmol) was degassed with Ar. DMF (0.5 ml) was added to the mixture, and the reaction mixture was stirred and heated at 40° C. for 24 h. The reaction mixture was cooled to RT and then used without workup or purification in the subsequent reaction. LCMS ($C_{34}H_{38}FO_{11}S_2$) (ES, m/z): 705 [M+H]+.

Step 2: (S)-4-(5-(3-((2-((S)-3-carboxybutanoyl)-4-fluoro-6-methoxybenzo[b]thiophen-5-yl)oxy)propoxy)-6-hydroxybenzo[b]thiophen-2-yl)-2-methyl-4-oxobutanoic acid

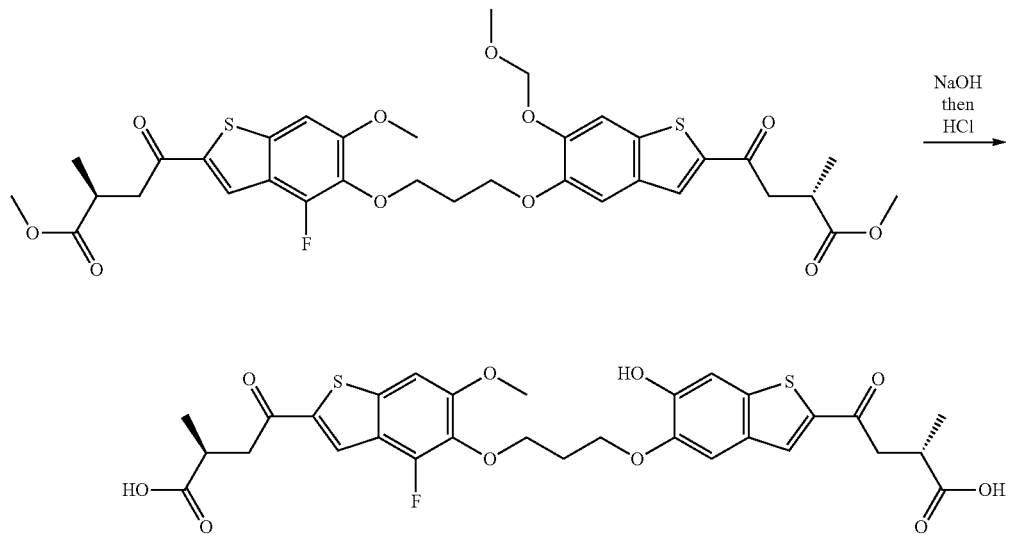

NaOH (0.55 ml, 1.0M in water, 0.55 mmol) was added to a solution of methyl (S)-4-(5-(3-((4-fluoro-6-methoxy-2-((S)-4-methoxy-3-methyl-4-oxobutanoyl)benzo[b]thiophen-5-yl)oxy)propoxy)-6-(methoxymethoxy)benzo[b]thiophen-2-yl)-2-methyl-4-oxobutanoate (48 mg, 0.068 mmol) in DMSO (2.5 ml) at 20° C. The reaction mixture was then stirred at 20° C. for 15 min. The reaction mixture was quenched with HCl (0.280 ml, 37% in water, 3.41 mmol). The reaction mixture was stirred at 20° C. for 20 h. The reaction mixture was filtered. The residue was purified by reverse phase HPLC (ACN/water with 0.1% TFA) to afford (S)-4-(5-(3-((2-((S)-3-carboxybutanoyl)-4-fluoro-6-methoxybenzo[b]thiophen-5-yl)oxy)propoxy)-6-hydroxybenzo[b]thiophen-2-yl)-2-methyl-4-oxobutanoic acid. LCMS ($C_{30}H_{30}FO_{10}S_2$) (ES, m/z): 633 [M+H]$^+$. $^1$H NMR (499 MHz, DMSO-$d_6$) δ 12.17 (s, 2H), 9.70 (s, 1H), 8.30 (s, 1H), 8.17 (s, 1H), 7.57 (s, 1H), 7.48 (s, 1H), 7.33 (s, 1H), 4.31-4.26 (m, 4H), 3.87 (s, 3H), 3.46 (dd, J=17.6, 8.6 Hz, 1H), 3.38 (dd, J=17.2, 8.4 Hz, 1H), 3.13 (dd, J=17.6, 5.1 Hz, 1H), 3.06 (dd, J=17.2, 5.3 Hz, 1H), 2.91-2.85 (m, 2H), 2.24-2.18 (m, 2H), 1.19 (d, J=7.2 Hz, 6H).

Examples 181 through 190, as shown in Table 23 below, were or may be prepared according to procedures analogous to those outlined in Example 180 above using the appropriate starting materials, described in the Preparations or Intermediates above, or as obtained from commercial sources.

TABLE 23

| Example | Structure | Name | Mass [M + H]$^+$ |
|---|---|---|---|
| 181 | 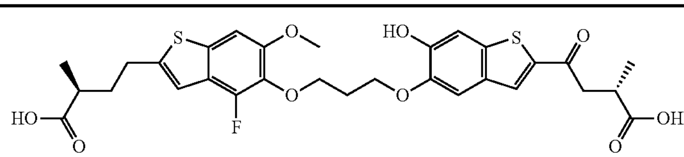 | (S)-4-(5-(3-((2-((S)-3-carboxybutyl)-4-fluoro-6-methoxybenzo[b]thiophen-5-yl)oxy)propoxy)-6-hydroxybenzo[b]thiophen-2-yl)-2-methyl-4-oxobutanoic acid | 619 |

TABLE 23-continued

| Example | Structure | Name | Mass [M + H]+ |
|---|---|---|---|
| 182 | 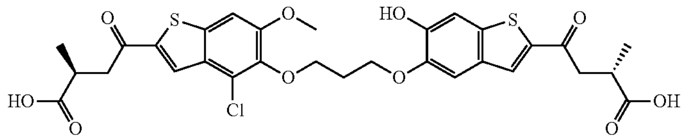 [SMILES: COc1cc2sc(C(=O)C[C@H](C)C(=O)O)cc2c(Cl)c1OCCCOc1cc2cc(C(=O)C[C@H](C)C(=O)O)sc2cc1O] | (S)-4-(5-(3-((2-((S)-3-carboxybutanoyl)-4-chloro-6-methoxybenzo[b]thiophen-5-yl)oxy)propoxy)-6-hydroxybenzo[b]thiophen-2-yl)-2-methyl-4-oxobutanoic acid | 649 |
| 183 | 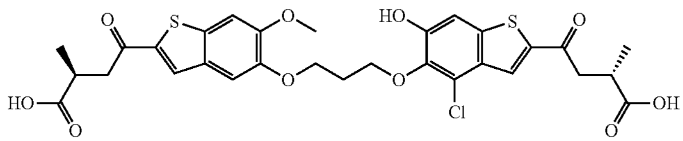 [SMILES: COc1cc2sc(C(=O)C[C@H](C)C(=O)O)cc2cc1OCCCOc1c(O)cc2sc(C(=O)C[C@H](C)C(=O)O)cc2c1Cl] | (S)-4-(5-(3-((2-((S)-3-carboxybutanoyl)-4-chloro-6-hydroxybenzo[b]thiophen-5-yl)oxy)propoxy)-6-methoxybenzo[b]thiophen-2-yl)-2-methyl-4-oxobutanoic acid | 649 |
| 184 | 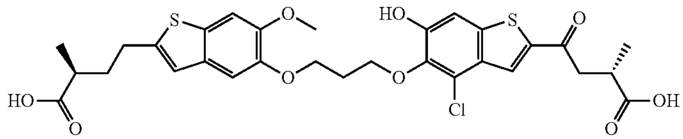 | (S)-4-(5-(3-((2-((S)-3-carboxybutyl)-6-methoxybenzo[b]thiophen-5-yl)oxy)propoxy)-4-chloro-6-hydroxybenzo[b]thiophen-2-yl)-2-methyl-4-oxobutanoic acid | 635 |
| 185 | 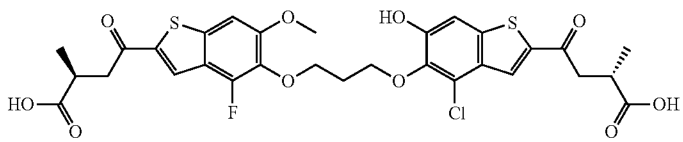 [SMILES: COc1cc2sc(C(=O)C[C@H](C)C(=O)O)cc2c(F)c1OCCCOc1c(O)cc2sc(C(=O)C[C@H](C)C(=O)O)cc2c1Cl] | (S)-4-(5-(3-((2-((S)-3-carboxybutanoyl)-4-chloro-6-hydroxybenzo[b]thiophen-5-yl)oxy)propoxy)-4-fluoro-6-methoxybenzo[b]thiophen-2-yl)-2-methyl-4-oxobutanoic acid | 649 (M − H$_2$O + H$^+$) |
| 186 | 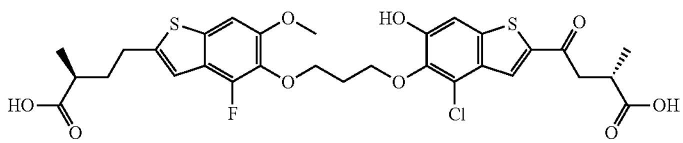 [SMILES: COc1cc2sc(CC[C@H](C)C(=O)O)cc2c(F)c1OCCCOc1c(O)cc2sc(C(=O)C[C@H](C)C(=O)O)cc2c1Cl] | (S)-4-(5-(3-((2-((S)-3-carboxybutyl)-4-fluoro-6-methoxybenzo[b]thiophen-5-yl)oxy)propoxy)-4-chloro-6-hydroxybenzo[b]thiophen-2-yl)-2-methyl-4-oxobutanoic acid | 653 |
| 187 | 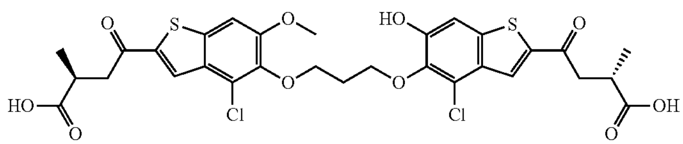 | (S)-4-(5-(3-((2-((S)-3-carboxybutanoyl)-4-chloro-6-hydroxybenzo[b]thiophen-5-yl)oxy)propoxy)-4-chloro-6-methoxybenzo[b]thiophen-2-yl)-2-methyl-4-oxobutanoic acid | 683, 685 |
| 188 | 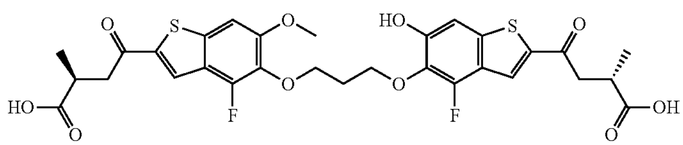 [SMILES: COc1cc2sc(C(=O)C[C@H](C)C(=O)O)cc2c(F)c1OCCCOc1c(O)cc2sc(C(=O)C[C@H](C)C(=O)O)cc2c1F] | (S)-4-(5-(3-((2-((S)-3-carboxybutanoyl)-4-fluoro-6-hydroxybenzo[b]thiophen-5-yl)oxy)propoxy)-4-fluoro-6-methoxybenzo[b]thiophen-2-yl)-2-methyl-4-oxobutanoic acid | 651 |
| 189 | 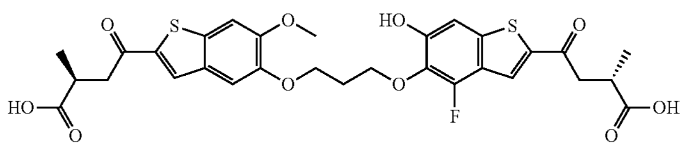 [SMILES: COc1cc2sc(C(=O)C[C@H](C)C(=O)O)cc2cc1OCCCOc1c(O)cc2sc(C(=O)C[C@H](C)C(=O)O)cc2c1F] | (S)-4-(5-(3-((2-((S)-3-carboxybutanoyl)-4-fluoro-6-hydroxybenzo[b]thiophen-5-yl)oxy)propoxy)-6-methoxybenzo[b]thiophen-2-yl)-2-methyl-4-oxobutanoic acid | 633 |
| 190 | 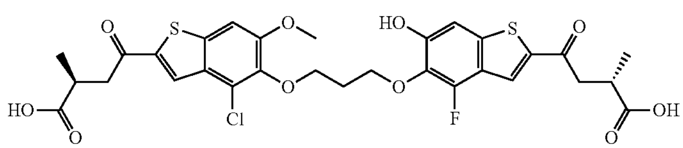 | (S)-4-(5-(3-((2-((S)-3-carboxybutanoyl)-4-chloro-6-methoxybenzo[b]thiophen-5-yl)oxy)propoxy)-4-fluoro-6-hydroxybenzo[b]thiophen-2-yl)-2-methyl-4-oxobutanoic acid | 667 |

Biological Evaluation

The individual compounds described in the Examples herein are defined as STING agonists by (i) binding to the STING protein as evidenced by a reduction in binding of tritiated cGAMP ligand to the STING protein by at least 20% at 20 uM (concentration of compound being tested) in a STING Biochemical [3H]cGAMP Competition Assay and (ii) demonstrating interferon production with a 6% or greater induction of IFN-3 secretion at 30 uM in the THP1 cell assay (where induction caused by cGAMP at 30 uM was set at 100%).

[$^3$H]-cGAMP Synthesis 2.3 mL of buffer solution containing 80 mM TrisCl, 200 mM MgCl$_2$, and 20 mM NaCl followed by 0.32 mL of a 10 mM aq solution of GTP was added to a plastic 50 mL AMICON tube. A solution of [$^3$H]ATP (21 Ci/mmol, 45 mCi) in 0.5 mL H$_2$O was then added followed by 1 mL of a 1 mg/mL solution of DNA (Herring testes activator DNA, Sigma, # D6898) and 53 uL of a 47 mM solution of cGAS enzyme. Additional H$_2$O was added to bring the total volume to 10 mL.

The reaction was stirred for 2 h at 37° C. and then added directly to an Amicon Ultra-15 10K centrifuge tube and spun for 1 h at 4,000 g. The collected solution was then purified on a semi-prep Mono Q column using the following mobile phases:

A: 0.05M TrisCl pH 8.5 adjusted with 1M NaOH
B: 0.05M TrisCl, 0.5M NaCl pH 8.5 adjusted with 1M NaOH Gradient: 100% A for 5 min followed by a linear gradient to 50:50 (A:B) over 25 min, 3 mL/min, 254 nm.

The collected product fractions were pooled and adjusted to a total volume of 30 mL with buffer A. A total yield of 15.5 mCi of [$^3$H]cGAMP was isolated at a radiochemical purity of 98.0% at a specific activity of 21.5 Ci/mmol.

cGAS Enzyme

A recombinant DNA vector was chemically synthesized to express the truncated human cGAS enzyme (residues 161-522). To aid in expression and purification, the amino terminus contains a hexahistidine tag, SUMO tag and TEV cleavage site. The recombinant enzyme was overexpressed in ROSETTA™ 2(DE3) Single Competent Cells (Novagen). Affinity purification was carried out using HIS-Select HF Nickel Affinity Gel (Sigma) followed by size exclusion chromatography using a Hi-Load 26/60 SUPERDEX200 prep grade column (GE Healthcare). Fractions were pooled, concentrated, flash-frozen in liquid nitrogen and stored at −80° C. until needed.

$^3$H-cGAMP Filtration Binding Assay (HAQ STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, www.expressionsystems.com) overexpressing full-length HAQ STING and tritiated cGAMP ligand.

The basic HAQ STING filtration assay protocol is as follows:

The compounds were serially titrated by the Hamilton STARPlus CORE in a 96-well plate (Greiner, #651201) using a 1:3 ten-point dose response format. After compound preparation, a 2.2 ug/ml working concentration of STING membrane (SEQ. ID. No. 1) was prepared by diluting concentrated membrane into assay buffer (1×PBS; Invitrogen # SH30028.02) and douncing 7× using a manual tissue homogenizer (Wheaton, #357546). 148 uL of prepared membrane was then manually added to each well of a 96-well deep-well polypropylene plate (Fisher Scientific, #12-566-121). Following membrane addition, 2 uL of either titrated test compound, DMSO control (Sigma #276855), or cold cGAMP control was added to the appropriate wells using a BIOMEK FX. Compound and membrane then preincubated for 60 min at RT to allow compound binding to equilibrate. Following equilibration, 8 nM of [$^3$H]c-GAMP ligand was prepared by diluting into assay buffer, and 50 uL of this working stock was then manually added to each well of the assay plate. Plates were then incubated at RT for 60 min, and the contents of each assay plate were then filtered through a 96-well GF/B filter plate (PerkinElmer, #6005250) using a TOMTEC MACH III Cell Harvester equipped with 20 mM HEPES buffer (Fisher Scientific, # BP299500). The filter plates were then dried at 55° C. for 30 min using a pressurized oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
|---|---|---|
| STING membrane | 148 | 1.5 ug/ml |
| $^3$H-cGAMP | 50 | 2.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 µM with 1.0% residual DMSO.

Full-Length STING (HAQ) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of HAQ STING [STING(1-379)R71H,G230A,H232R,R293Q-GG-AviTag-GS-HRV3C-HIS8/pBAC1] DNA (Genewiz custom synthesis) with 1 mL Sf-900II SFM media containing 10 µL Cellfectin® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA (SEQ. ID. No. 2) at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10$^5$ cells/mL to allow for one overnight doubling) in Sf-900II SFM media containing 5 µg/mL gentamicin (Invitrogen #15710072). The infected cells were then incubated at 27° C. for 3 days while shaking at 110 rpm (ATR Biotech Multitron Infors HT # AJ118). On day 3, P1 cultures were counted using a ViCell XR (Beckman Coulter Life Sciences #383556) to confirm infection had occurred (cell size ≥3 µm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryopreservation media containing Sf-900II SFM media with 10% heat inactivated FBS, 10% DMSO (Sigma # D2650), and 5 g/ml gentamicin was prepared and sterilized through 0.22 M filter immediately prior to use. P1 cell pellets were resuspended to a density of 2e7 cells/ml and aliquoted into cryovials (1 mL per vial). Cryovials were placed in Mr. Frosty™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of $5 \times 10^5$ cells/mL to allow for one overnight doubling) in Sf-900II SFM media containing 5 μg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (HAQ) Expression

To generate STING membranes, P1/P2 BIICs were amplified overnight by adding thawed BIICs to Sf21 cells seeded at a density of $1.0 \times 10^6$ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 μm larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of $1.0 \times 10^6$ in cell media (ESF921 SFM containing 5 μg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size ≥3 μm larger than uninfected cells and viability approximately 80-90%) prior to harvest.

Full-Length STING (HAQ) Membrane Generation

Buffer Stock Reagents:
1) 1M HEPES pH 7.5, Teknova, Cat # H1035
2) 5M NaCl, Sigma Aldrich, Cat # S5150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM $MgCl_2$, 20 mM KCl, (Benzonase 1:5000, Complete Protease Inhibitor tab/50 mL)] was added to the pellet of cells expressing full-length STING (HAQ) prepared above at 5 mL Lysis buffer per g of cell pellet. The pellet was resuspended and dounced twenty times using a Wheaton Dounce Homogenizer to disrupt the cell membrane. Homogenized lysate was then passed through the EMULSIFLEX-C5 microfluidizer at a pressure close to 5000 PSI. The resuspended pellet was centrifuged at 36,000 rpm (100,000×g) in a 45Ti rotor ultra-high speed centrifuge for 45 min, 4° C. The supernatant was removed. The pellet then was resuspended in wash buffer [(25 mM HEPES pH7.5, 1 mM $MgCl_2$, 20 mM KCl, 1M NaCl (Complete Protease Inhibitor tab/50 mL)] at a volume of 50 mL pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

Full-Length HAQ STING [STING(1-379)R71H, G230A, H232R, R293Q-GG-AviTag-GS-HRV3C-HIS8]Amino Acid Sequence:

(SEQ. ID. No. 1)

MPHSSLHPSIPCPRGHGAQKAALVLLSACLVTLWGLGEPPEHTLRYLVLHLASLQLGLL

LNGVCSLAEELHHIHSRYRGSYWRTVRACLGCPLRRGALLLLSIYFYYSLPNAVGPPFT

WMLALLGLSQALNILLGLKGLAPAEISAVCEKGNFNVAHGLAWSYYIGYLRLILPELQA

RIRTYNQHYNNLLRGAVSQRLYILLPLDCGVPDNLSMADPNIRFLDKLPQQTADRAGIK

DRVYSNSIYELLENGQRAGTCVLEYATPLQTLFAMSQYSQAGFSREDRLEQAKLFCQTL

EDILADAPESQNNCRLIAYQEPADDSSFSLSQEVLRHLRQEEKEEVTVGSLKTSAVPSTST

MSQEPELLISGMEKPLPLRTDFSGGGLNDIFEAQKIEWHEGSLEVLFQGPHHHHHHHH

Full-length HAQ [STING(1-379)R71H, G230A, H232R, R293Q-GG-AviTag-GS-HRV3C-HIS8/pBAC1] Plasmid DNA Sequence:

(SEQ. ID. No. 2)

GGAACGGCTCCGCCCACTATTAATGAAATTAAAAATTCCAATTTTAAAAAACGCAG

CAAGAGAAACATTTGTATGAAAGAATGCGTAGAAGGAAAGAAAAATGTCGTCGAC

ATGCTGAACAACAAGATTAATATGCCTCCGTGTATAAAAAAAATATTGAACGATTTG

AAAGAAAACAATGTACCGCGCGGCGGTATGTACAGGAAGAGGTTTATACTAAACTG

TTACATTGCAAACGTGGTTTCGTGTGCCAAGTGTGAAAACCGATGTTTAATCAAGGC

TCTGACGCATTTCTACAACCACGACTCCAAGTGTGTGGGTGAAGTCATGCATCTTTT

AATCAAATCCCAAGATGTGTATAAACCACCAAACTGCCAAAAAATGAAAACTGTCG

ACAAGCTCTGTCCGTTTGCTGGCAACTGCAAGGGTCTCAATCCTATTTGTAATTATTG

-continued

```
AATAATAAAACAATTATAAATGCTAAATTTGTTTTTTATTAACGATACAAACCAAAC

GCAACAAGAACATTTGTAGTATTATCTATAATTGAAAACGCGTAGTTATAATCGCTG

AGGTAATATTTAAAATCATTTTCAAATGATTCACAGTTAATTTGCGACAATATAATT

TTATTTTCACATAAACTAGACGCCTTGTCGTCTTCTTCTTCGTATTCCTTCTCTTTTTC

ATTTTTCTCTTCATAAAAATTAACATAGTTATTATCGTATCCATATATGTATCTATCG

TATAGAGTAAATTTTTTGTTGTCATAAATATATATGTCTTTTTTAATGGGGTGTATAG

TACCGCTGCGCATAGTTTTTCTGTAATTTACAACAGTGCTATTTTCTGGTAGTTCTTC

GGAGTGTGTTGCTTTAATTATTAAATTTATATAATCAATGAATTTGGGATCGTCGGTT

TTGTACAATATGTTGCCGGCATAGTACGCAGCTTCTTCTAGTTCAATTACACCATTTT

TTAGCAGCACCGGATTAACATAACTTTCCAAAATGTTGTACGAACCGTTAAACAAAA

ACAGTTCACCTCCCTTTTCTATACTATTGTCTGCGAGCAGTTGTTTGTTGTTAAAAAT

AACAGCCATTGTAATGAGACGCACAAACTAATATCACAAACTGGAAATGTCTATCA

ATATATAGTTGCTGATCAGATCTGATCATGGAGATAATTAAAATGATAACCATCTCG

CAAATAAATAAGTATTTTACTGTTTTCGTAACAGTTTTGTAATAAAAAAACCTATAA

ATATAGGATCCATGCCCCACTCCAGCCTGCATCCATCCATCCCGTGTCCCAGGGGTC

ACGGGGCCCAGAAGGCAGCCTTGGTTCTGCTGAGTGCCTGCCTGGTGACCCTTTGGG

GGCTAGGAGAGCCACCAGAGCACACTCTCCGGTACCTGGTGCTCCACCTAGCCTCCC

TGCAGCTGGGACTGCTGTTAAACGGGGTCTGCAGCCTGGCTGAGGAGCTGCACCAC

ATCCACTCCAGGTACCGGGGCAGCTACTGGAGGACTGTGCGGGCCTGCCTGGGCTG

CCCCCTCCGCCGTGGGGCCCTGTTGCTGCTGTCCATCTATTTCTACTACTCCCTCCCA

AATGCGGTCGGCCCGCCCTTCACTTGGATGCTTGCCCTCCTGGGCCTCTCGCAGGCA

CTGAACATCCTCCTGGGCCTCAAGGGCCTGGCCCCAGCTGAGATCTCTGCAGTGTGT

GAAAAAGGGAATTTCAACGTGGCCCATGGGCTGGCATGGTCATATTACATCGGATA

TCTGCGGCTGATCCTGCCAGAGCTCCAGGCCCGGATTCGAACTTACAATCAGCATTA

CAACAACCTGCTACGGGGTGCAGTGAGCCAGCGGCTGTATATTCTCCTCCCATTGGA

CTGTGGGGTGCCTGATAACCTGAGTATGGCTGACCCCAACATTCGCTTCCTGGATAA

ACTGCCCCAGCAGACCGCTGACCGTGCTGGCATCAAGGATCGGGTTTACAGCAACA

GCATCTATGAGCTTCTGGAGAACGGGCAGCGGGCGGGCACCTGTGTCCTGGAGTAC

GCCACCCCCTTGCAGACTTTGTTTGCCATGTCACAATACAGTCAAGCTGGCTTTAGC

CGGGAGGATAGGCTTGAGCAGGCCAAACTCTTCTGCCAGACACTTGAGGACATCCT

GGCAGATGCCCCTGAGTCTCAGAACAACTGCCGCCTCATTGCCTACCAGGAACCTGC

AGATGACAGCAGCTTCTCGCTGTCCCAGGAGGTTCTCCGGCACCTGCGGCAGGAGG

AAAAGGAAGAGGTTACTGTGGGCAGCTTGAAGACCTCAGCGGTGCCCAGTACCTCC

ACGATGTCCCAAGAGCCTGAGCTCCTCATCAGTGGAATGGAAAAGCCCCTCCCTCTC

CGCACGGATTTCTCTGGCGGTGGCCTGAACGACATCTTCGAAGCCCAGAAAATCGA

ATGGCATGAAGGCAGCCTGGAAGTGCTGTTCCAGGGCCCACACCACCATCATCACC

ATCACCATTAATGAGCGGCCGCACTCGAGCACCACCACCACCACCACTAACCTAGG

TAGCTGAGCGCATGCAAGCTGATCCGGGTTATTAGTACATTTATTAAGCGCTAGATT

CTGTGCGTTGTTGATTTACAGACAATTGTTGTACGTATTTTAATAATTCATTAAATTT

ATAATCTTTAGGGTGGTATGTTAGAGCGAAAATCAAATGATTTTCAGCGTCTTTATA

TCTGAATTTAAATATTAAATCCTCAATAGATTTGTAAAATAGGTTTCGATTAGTTTCA
```

-continued

```
AACAAGGGTTGTTTTTCCGAACCGATGGCTGGACTATCTAATGGATTTTCGCTCAAC
GCCACAAAACTTGCCAAATCTTGTAGCAGCAATCTAGCTTTGTCGATATTCGTTTGT
GTTTTGTTTTGTAATAAAGGTTCGACGTCGTTCAAAATATTATGCGCTTTTGTATTTC
TTTCATCACTGTCGTTAGTGTACAATTGACTCGACGTAAACACGTTAAATAGAGCTT
GGACATATTTAACATCGGGCGTGTTAGCTTTATTAGGCCGATTATCGTCGTCGTCCC
AACCCTCGTCGTTAGAAGTTGCTTCCGAAGACGATTTTGCCATAGCCACACGACGCC
TATTAATTGTGTCGGCTAACACGTCCGCGATCAAATTTGTAGTTGAGCTTTTTGGAAT
TATTTCTGATTGCGGGCGTTTTTGGGCGGGTTTCAATCTAACTGTGCCCGATTTTAAT
TCAGACAACACGTTAGAAAGCGATGGTGCAGGCGGTGGTAACATTTCAGACGGCAA
ATCTACTAATGGCGGCGGTGGTGGAGCTGATGATAAATCTACCATCGGTGGAGGCG
CAGGCGGGGCTGGCGGCGGAGGCGGAGGCGGAGGTGGTGGCGGTGATGCAGACGG
CGGTTTAGGCTCAAATGTCTCTTTAGGCAACACAGTCGGCACCTCAACTATTGTACT
GGTTTCGGGCGCCGTTTTTGGTTTGACCGGTCTGAGACGAGTGCGATTTTTTCGTTT
CTAATAGCTTCCAACAATTGTTGTCTGTCGTCTAAAGGTGCAGCGGGTTGAGGTTCC
GTCGGCATTGGTGGAGCGGGCGGCAATTCAGACATCGATGGTGGTGGTGGTGGTGG
AGGCGCTGGAATGTTAGGCACGGGAGAAGGTGGTGGCGGCGGTGCCGCCGGTATAA
TTTGTTCTGGTTTAGTTTGTTCGCGCACGATTGTGGGCACCGGCGCAGGCGCCGCTG
GCTGCACAACGGAAGGTCGTCTGCTTCGAGGCAGCGCTTGGGGTGGTGGCAATTCA
ATATTATAATTGGAATACAAATCGTAAAAATCTGCTATAAGCATTGTAATTTCGCTA
TCGTTTACCGTGCCGATATTTAACAACCGCTCAATGTAAGCAATTGTATTGTAAAGA
GATTGTCTCAAGCTCGGATCGATCCCGCACGCCGATAACAAGCCTTTTCATTTTTACT
ACAGCATTGTAGTGGCGAGACACTTCGCTGTCGTCGAGGTTTAAACGCTTCCTCGCT
CACTGACTCGCTGCGCTCGGTCGTTCGGCTGCGGCGAGCGGTATCAGCTCACTCAAA
GGCGGTAATACGGTTATCCACAGAATCAGGGGATAACGCAGGAAAGAACATGTGAG
CAAAAGGCCAGCAAAAGGCCAGGAACCGTAAAAAGGCCGCGTTGCTGGCGTTTTTC
CATAGGCTCCGCCCCCCTGACGAGCATCACAAAAATCGACGCTCAAGTCAGAGGTG
GCGAAACCCGACAGGACTATAAAGATACCAGGCGTTTCCCCCTGGAAGCTCCCTCG
TGCGCTCTCCTGTTCCGACCCTGCCGCTTACCGGATACCTGTCCGCCTTTCTCCCTTC
GGGAAGCGTGGCGCTTTCTCATAGCTCACGCTGTAGGTATCTCAGTTCGGTGTAGGT
CGTTCGCTCCAAGCTGGGCTGTGTGCACGAACCCCCCGTTCAGCCCGACCGCTGCGC
CTTATCCGGTAACTATCGTCTTGAGTCCAACCCGGTAAGACACGACTTATCGCCACT
GGCAGCAGCCACTGGTAACAGGATTAGCAGAGCGAGGTATGTAGGCGGTGCTACAG
AGTTCTTGAAGTGGTGGCCTAACTACGGCTACACTAGAAGGACAGTATTTGGTATCT
GCGCTCTGCTGAAGCCAGTTACCTTCGGAAAAAGAGTTGGTAGCTCTTGATCCGGCA
AACAAACCACCGCTGGTAGCGGTGGTTTTTTTGTTTGCAAGCAGCAGATTACGCGCA
GAAAAAAAGGATCTCAAGAAGATCCTTTGATCTTTTCTACGGGGTCTGACGCTCAGT
GGAACGAAAACTCACGTTAAGGGATTTTGGTCATGAGATTATCAAAAAGGATCTTC
ACCTAGATCCTTTTAAATTAAAAATGAAGTTTTAAATCAATCTAAAGTATATATGAG
TAAACTTGGTCTGACAGTTACCAATGCTTAATCAGTGAGGCACCTATCTCAGCGATC
TGTCTATTTCGTTCATCCATAGTTGCCTGACTCCCCGTCGTGTAGATAACTACGATAC
```

```
-continued
GGGAGGGCTTACCATCTGGCCCCAGTGCTGCAATGATACCGCGAGACCCACGCTCA

CCGGCTCCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGGAAGCTAG

AGTAAGTAGTTCGCCAGTTAATAGTTTGCGCAACGTTGTTGCCATTGCTACAGGCAT

CGTGGTGTCACGCTCGTCGTTTGGTATGGCTTCATTCAGCTCCGGTTCCCAACGATCA

AGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCA

CTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGG

CGTCAATACGGGATAATACCGCGCCACATAGCAGAACTTTAAAAGTGCTCATCATTG

GAAAACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAGCGT

TTCTGGGTGAGCAAAAACAGGAAGGCAAAATGCCGCAAAAAAGGGAATAAGGGCG

ACACGGAAATGTTGAATACTCATACTCTTCCTTTTTCAATATTATTGAAGCATTTATC

AGGGTTATTGTCTCATGAGCGGATACATATTTGAATGTATTTAGAAAAATAAACAAA

TAGGGGTTCCGCGCACATTTCCCCGAAAAGTGCCACCTGACGCGCCCTGTAGCGGCG

CATTAAGCGCGGCGGGTGTGGTGGTTACGCGCAGCGTGACCGCTACACTTGCCAGC

GCCCTAGCGCCCGCTCCTTTCGCTTTCTTCCCTTCCTTTCTCGCCACGTTCGCCGGCTT

TCCCCGTCAAGCTCTAAATCGGGGGCTCCCTTTAGGGTTCCGATTTAGTGCTTTACG

GCACCTCGACCCCAAAAAACTTGATTAGGGTGATGGTTCACGTAGTGGGCCATCGCC

CTGATAGACGGTTTTTCGCCCTTTGACGTTGGAGTCCACGTTCTTTAATAGTGGACTC

TTGTTCCAAACTGGAACAACACTCAACCCTATCTCGGTCTATTCTTTTGATTTATAAG

GGATTTTGCCGATTTCGGCCTATTGGTTAAAAAATGAGCTGATTTAACAAAAATTTA

ACGCGAATTTTAACAAAATATTAACGTTTACAATTTCCCATTCGCCATTCAGGCTGC

GCAACTGTTGGGAAGGGCGATCGGTGCGGGCCTCTTCGCTATTACGCCA
```

Certain compounds of the disclosure were evaluated in HAQ STING in vitro binding assay as described above. The following table tabulates the biological data for these compounds as $EC_{50}$ values.

TABLE 24

³H-cGAMP filtration binding assay for HAQ STING

| Example | $EC_{50}$ (nM) |
|---|---|
| 1 | 6 |
| 2 | 7 |
| 3 | 114 |
| 4 | 6 |
| 5 | 84 |
| 6 | 53 |
| 7 | 17 |
| 8 | 12 |
| 9 | 116 |
| 10 | 123 |
| 11 | 1762 |
| 12 | 2 |
| 13 | 158 |
| 14 | 3 |
| 15 | 107 |
| 16 | 22 |
| 17 | 52 |
| 18 | 2 |
| 19 | 2 |
| 20 | 7 |
| 21 | 1 |
| 22 | 1 |
| 23 | 1 |
| 24 | 17760 |
| 25 | 6 |
| 26 | 9 |
| 27 | 89 |
| 28 | 46 |
| 29 | 8 |
| 30 | 1001 |
| 31 | 3319 |
| 32 | 4 |
| 33 | 1 |
| 34 | 3 |
| 35 | 2 |
| 36 | 4 |
| 37 | 1 |
| 38 | 695 |
| 39 | 1 |
| 40 | 86 |

TABLE 24-continued $^3$H-cGAMP filtration binding assay for HAQ STING

| Example | EC$_{50}$ (nM) |
|---|---|
| 41 | 16 |
| 42 | 6 |
| 43 | 49 |
| 44 | 14 |
| 45 | 4328 |
| 46 | 133 |
| 47 | 14 |
| 48 | 12790 |
| 49 | 44% inhibition at 20,000 nM |
| 50 | 1 |
| 51 | 3 |
| 52 | 2 |
| 53 | 146 |
| 54 | 804 |
| 55 | 14 |
| 56 | 1068 |
| 57 | 92 |
| 58 | 1 |
| 59 | 1 |
| 60 | 19 |
| 61 | 33 |
| 62 | 2 |
| 63 | 1 |
| 64 | 2 |
| 65 | 1 |
| 66 | 4 |
| 67 | 40 |
| 68 | 50 |
| 69 | 1 |
| 70 | 1 |
| 71 | 3 |
| 72 | 1 |
| 73 | 1 |
| 74 | 4 |
| 75 | 139 |
| 76 | 22 |
| 77/78 (mixture) | 44 |
| 79 | 5 |
| 80 | 1305 |
| 81 | 2 |
| 82 | 1 |
| 83 | 2 |
| 84 | 50 |
| 85 | 360 |
| 86 | 1 |
| 87 | 167 |
| 88 | 3 |
| 89 | 2 |
| 90 | 58 |
| 91 | 7 |
| 92 | 3 |
| 93 | 1 |
| 94 | 6 |
| 95 | 237 |
| 96 | 18 |
| 97 | 20 |
| 98 | 1 |
| 99 | 1 |
| 100 | 277 |
| 101 | 1 |
| 102 | 15 |
| 103 | 22 |
| 104 | 467 |
| 105 | 39 |
| 106 | 10 |
| 107 | 1 |
| 108 | 35 |
| 109 | 10 |
| 110 | 18580 |
| 111 | 861 |
| 112 | 15540 |
| 113 | 2 |
| 114 | 21 |
| 115 | 20 |
| 116 | 623 |
| 117 | 340 |
| 118 | 60 |
| 119 | 1796 |
| 120 | 38 |
| 121 | 1551 |
| 122 | 1 |
| 123 | 1 |
| 124 | 263 |
| 125 | 1 |
| 126 | 2 |
| 127 | 16 |
| 128 | 1082 |
| 129 | 3496 |
| 130 | 3 |
| 131 | 25 |
| 132 | 3 |
| 133 | 15 |
| 134 | 22 |
| 135 | 1 |
| 136 | 314 |
| 137 | 40 |
| 138 | 2 |
| 139 | 3 |
| 140 | 2146 |
| 141 | 24 |
| 142 | 1 |
| 143 | 75 |
| 144 | 15 |
| 145 | 143 |
| 146 | 55% inhibition at 2,000 nM |
| 147 | 18 |
| 148 | 395 |
| 149 | 4 |
| 150 | 213 |
| 151 | 77 |
| 152 | 35% inhibition at 2,000 nM |
| 153 | 3 |
| 154 | 694 |
| 155 | 3 |
| 156 | 1 |
| 157 | 1 |
| 158 | 2 |
| 159 | 3 |
| 160 | 1 |
| 161 | 1 |
| 162 | 1 |
| 163 | 1 |
| 164 | 1 |
| 165 | 2 |
| 166 | 8 |
| 167 | 4 |
| 168 | 13 |
| 169 | 1 |
| 170 | 1 |
| 171 | 9 |
| 172 | 454 |
| 173 | 1 |
| 174 | 1 |
| 175 | 4016 |
| 176 | 1 |
| 177 | 68 |
| 178 | 4 |
| 179 | 1 |
| 180 | 1 |
| 181 | 5 |
| 182 | 1 |
| 183 | 1 |
| 184 | 353 |
| 185 | 1 |
| 186 | 133 |
| 187 | 4 |

TABLE 24-continued

³H-cGAMP filtration binding assay for HAQ STING

| Example | $EC_{50}$ (nM) |
|---|---|
| 188 | 1 |
| 189 | 1 |
| 190 | 1 |

³H-cGAMP Filtration Binding Assay (WT STING)

The ability of compounds to bind STING is quantified by their ability to compete with tritiated cGAMP ligand for human STING receptor membrane using a radioactive filter-binding assay. The binding assay employs STING receptor obtained from *Trichoplusia ni* cell membranes (*T. ni*; Expression Systems, cat #94-002F, www.expressionsystems.com) overexpressing full-length WT STING and tritiated cGAMP ligand.

The basic WT STING filtration assay protocol is as follows:

16 nM of [³H] c-GAMP ligand was prepared by diluting into assay buffer, and 50 uL of this working stock was manually added to each well of the assay plate. After ligand addition, 2 uL of either titrated test compound, DMSO control (Sigma #276855), or cold cGAMP control was added to the appropriate wells using a BIOMEK FX. The serially titrated compound was prepared on a Hamilton STARPlus CORE in a 96-well plate (Greiner, #651201) using a 1:3 ten-point dose response format. Following compound addition, a 2.2 ug/ml working concentration of STING membrane (SEQ. ID. No. 3) was prepared by diluting concentrated membrane into assay buffer (1×PBS; Invitrogen # SH30028.02) and douncing 7× using a manual tissue homogenizer (Wheaton, #357546). 148 uL of this prepared membrane was then manually added to each well of a 96-well deep-well polypropylene plate (Fisher Scientific, #12-566-121). Compound, ligand, and membrane then incubated for 60 min at RT before the contents of each assay plate were filtered through a 96-well GF/B filter plate (PerkinElmer, #6005250) using a TOMTEC MACH III Cell Harvester equipped with 20 mM HEPES buffer (Fisher Scientific, # BP299500). The filter plates were then dried at 55° C. for 30 min using a pressurized VWR oven before 30 uL of ULTIMA GOLD F scintillate was added to each well. Tritium levels for each reaction well were then measured using a PerkinElmer TopCount plate reader.

After normalization to controls, the percent activity for each compound concentration was calculated by measuring the amount of remaining radioactivity. The plot of percent activity versus the log of compound concentration was fit with a 4-parameter dose response equation to calculate $EC_{50}$ values.

The final reaction conditions were:

| Component | Volume (uL) | Final Concentration |
|---|---|---|
| STING membrane | 148 | 1.5 ug/ml |
| ³H-cGAMP | 50 | 4.0 nM |
| Low Control (cold cGAMP) | 2 | 10 uM |
| Test compound/DMSO | 2 | 10 uM |

Compound concentrations tested were 20.000, 637.00, 2.200, 0.740, 0.247, 0.082, 0.027, 0.009, 0.003, and 0.001 μM with 1.0% residual DMSO.

Full-Length STING (WT) Virus Generation

STING virus was generated using an insect cell baculovirus system. *Spodoptera frugiperda* Sf21 cells (Kempbio, Inc.) were diluted to 5e5 cells/ml in Sf-900II SFM media (LifeTechnologies #10902088) without antibiotics. The cell suspension was added to each well of a treated 6-well plate (2 mL per well, 1e6 cells total), and the cells were allowed to adhere for at least 30 min. Meanwhile, a 1 mL co-transfection mix was assembled by combining 500 ng of WT STING[STING(1-379)H232R-gg-AviTag-gs-HRV3C-HIS8/pBAC1] (Genewiz custom synthesis) with 1 mL Sf-900II SFM media containing 10 μL CELLFECTIN® II Reagent (Invitrogen #10362100) and 100 ng viral backbone BestBac 2.0, v-cath/chiA Deleted Linearized Baculovirus DNA (Expression Systems #91-002). The transfection mixtures were allowed to incubate for 30 min. After incubation, media was gently removed from the adhered cells in the 6-well plate, the 1 mL transfection mixtures were added (1 mL per well), and the plate was placed in a humidified incubator at 27° C. The following day, 1 mL Sf-900II SFM media (no antibiotics) was added to each well of the 6-well plate. After media addition, the cells were allowed to incubate with DNA [(SEQ. ID. No. 4) and linearized viral backbone BestBac 2.0] at 27° C. for 5-7 days to generate the P0 viral stock. To generate P1 viral stocks, 0.5 mL of P0 viral supernatant was added to 50 mL uninfected Sf21 cells (seeded the day prior to infection at a density of 5×10⁵ cells/mL to allow for one overnight doubling) in Sf-900II SFM media containing 5 μg/mL gentamicin (Invitrogen #15710072). The infected cells were then incubated at 27° C. for 3 days while shaking at 110 rpm (ATR Biotech Multitron Infors HT # AJ118). On day 3, P1 cultures were counted using a ViCell XR (Beckman Coulter Life Sciences #383556) to confirm infection had occurred (cell size ≥3 μm larger than uninfected cells and viability approximately 85-95%). Cultures were harvested in 50 mL conical tubes and centrifuged at 2000×g for 10 min at 4° C. The P1 viral supernatants were poured off into clean 50 ml centrifuge tubes, and the remaining P1 cell pellets were used to generate Baculovirus Infected Insect Cells (BIICs). Cryo-preservation media containing Sf-900II SFM media with 10% heat inactivated FBS, 10% DMSO (Sigma # D2650), and 5 g/ml gentamicin was prepared and sterilized through 0.22 M filter immediately prior to use. P1 cell pellets were resuspended to a density of 2e7 cells/ml and aliquoted into cryovials (1 mL per vial). Cryovials were placed in MR. FROSTY™ cell freezers O/N at −80° C. and transferred to liquid nitrogen for long term storage the following day. To generate P2 viral stock, 0.5 mL of the P1 viral supernatant was added to 50 mL uninfected Sf21 cells (seeded the day prior to infection at a density of 5×10⁵ cells/mL to allow for one overnight doubling) in Sf-900II SFM media containing 5 μg/mL gentamicin. These cells were incubated at 27° C. for 3 days while shaking at 110 rpm before harvesting P2 stock with centrifugation at 2000×g for 10 min at 4° C. The P2 viral supernatants were poured off and discarded, while the P2 cell pellets were used to generate P2 BIICs following the same protocol described above. The baculovirus generation protocol has been validated to consistently produce P1/P2 BIICs with titers of 2e9 pfu/mL (2e7 cells/mL×100 pfu/cell).

Full-Length STING (WT) Expression

To generate STING membranes, P1/P2 BIICs were amplified overnight by adding thawed BIICs to Sf21 cells seeded at a density of 1.0×10⁶ cells/mL. The volume of BIIC used to infect the culture was calculated using an assumed BIIC titer of 2e9 pfu/ml to achieve an MOI of 10 in the overnight amplification. After culturing overnight, the cells were counted on a ViCell XR to confirm infection had occurred (cell size ≥3 μm larger than uninfected cells and viability approximately 80-90%). The volume of infected Sf21 cells from the overnight amplification used to infect the large-scale expression of *Trichoplusia ni* (*T. ni*; Expression Systems, cat #94-002F, www.expressionsystems.com) seeded at a density of $1.0 \times 10^6$ in cell media (ESF921 SFM containing 5 μg/mL gentamicin) at MOI=2.0 was calculated based on (100 pfu/infected Sf21 cell). The cells were allowed to express for 48 h at 27° C. before harvesting the cell pellet, by centrifugation at 3,400×g for 10 min at 4° C. *T. ni* cells were counted on a ViCell XR to confirm infection had occurred (cell size ≥3 μm larger than uninfected cells and viability approximately 80-90%) prior to harvest.

Full-Length STING (WT) Membrane Generation
Buffer Stock Reagents:
1) 1 M HEPES pH 7.5, Teknova, Cat # H1035
2) 5 M NaCl, Sigma Aldrich, Cat # S5150-1L
3) KCl, Sigma Aldrich, Cat #319309-500ML
4) Complete EDTA-free protease inhibitor tablets, Roche Diagnostics, Cat #11873580001
5) Benzonase, Universal Nuclease, Pierce, Cat #88702

Lysis buffer [25 mM HEPES pH 7.5, 10 mM $MgCl_2$, 20 mM KCl, (Benzonase 1:5000, Complete Protease Inhibitor tab/50 mL)] was added to the pellet of cells expressing full-length STING (WT) prepared above at 5 mL Lysis buffer per g of cell pellet. The pellet was resuspended and dounced twenty times using a Wheaton Dounce Homogenizer to disrupt the cell membrane. Homogenized lysate was then passed through the emulsiflex-C5 microfluidizer at a pressure close to 5000 PSI. The resuspended pellet was centrifuged at 36,000 rpm (100,000×g) in a 45Ti rotor ultra-high speed centrifuge for 45 min, 4° C. The supernatant was removed. The pellet then was resuspended in wash buffer [(25 mM HEPES pH 7.5, 1 mM $MgCl_2$, 20 mM KCl, 1M NaCl (Complete Protease Inhibitor tab/50 mL)] at a volume of 50 mL/pellet/centrifuge tube. The pellet/wash buffer mixture was then homogenized, using a glass homogenizer on ice (20 strokes), followed by centrifugation at 36,000 rpm for 45 min at 4° C. The supernatant was removed. The wash step was repeated once more. The resulting membrane was resuspended in 20 mM HEPES pH 7.5, 500 mM NaCl, 10% glycerol, EDTA-free Protease Inhibitors (1 tablet/50 mL). The protein concentration was measured by Bradford assay (Bio-Rad Protein Assay, Cat #500-0006), and protein enrichment was determined by SDS-PAGE and confirmed by Western blot. The resuspended membranes were stored at −80° C.

```
Full-Length STING WT [STING(1-379)H232R-gg-AviTag-gs-HRV3C-HIS8]
Amino Acid Sequence:
                                                   (SEQ. ID. No. 3)
MPHSSLHPSIPCPRGHGAQKAALVLLSACLVTLWGLGEPPEHTLRYLVLHLASLQLGLL

LNGVCSLAEELRHIHSRYRGSYWRTVRACLGCPLRRGALLLLSIYFYYSLPNAVGPPFT

WMLALLGLSQALNILLGLKGLAPAEISAVCEKGNFNVAHGLAWSYYIGYLRLILPELQA

RIRTYNQHYNNLLRGAVSQRLYILLPLDCGVPDNLSMADPNIRFLDKLPQQTGDRAGIK

DRVYSNSIYELLENGQRAGTCVLEYATPLQTLFAMSQYSQAGFSREDRLEQAKLFCRTL

EDILADAPESQNNCRLIAYQEPADDSSFSLSQEVLRHLRQEEKEEVTVGSLKTSAVPSTST

MSQEPELLISGMEKPLPLRTDFSGGGLNDIFEAQKIEWHEGSLEVLFQGPHHHHHHHH

Full-length WT STING [STING(1-379)H232R-gg-AviTag-gs-HRV3C-HIS8/pBAC1]
plasmid sequence:
                                                   (SEQ. ID. No. 4)
GGAACGGCTCCGCCCACTATTAATGAAATTAAAAATTCCAATTTTAAAAAACGCAG

CAAGAGAAACATTTGTATGAAAGAATGCGTAGAAGGAAAGAAAAATGTCGTCGAC

ATGCTGAACAACAAGATTAATATGCCTCCGTGTATAAAAAAAATATTGAACGATTTG

AAAGAAAACAATGTACCGCGCGGCGGTATGTACAGGAAGAGGTTTATACTAAACTG

TTACATTGCAAACGTGGTTTCGTGTGCCAAGTGTGAAAACCGATGTTTAATCAAGGC

TCTGACGCATTTCTACAACCACGACTCCAAGTGTGTGGGTGAAGTCATGCATCTTTT

AATCAAATCCCAAGATGTGTATAAACCACCAAACTGCCAAAAAATGAAAACTGTCG

ACAAGCTCTGTCCGTTTGCTGGCAACTGCAAGGGTCTCAATCCTATTTGTAATTATTG

AATAATAAAACAATTATAAATGTCAAATTTGTTTTTTATTAACGATACAAACCAAAC

GCAACAAGAACATTTGTAGTATTATCTATAATTGAAAACGCGTAGTTATAATCGCTG

AGGTAATATTTAAAATCATTTTCAAATGATTCACAGTTAATTTGCGACAATATAATT

TTATTTTCACATAAACTAGACGCCTTGTCGTCTTCTTCTTCGTATTCCTTCTCTTTTTC

ATTTTTCTCTTCATAAAAATTAACATAGTTATTATCGTATCCATATATGTATCTATCG

TATAGAGTAAATTTTTTGTTGTCATAAATATATATGTCTTTTTTAATGGGGTGTATAG

TACCGCTGCGCATAGTTTTTCTGTAATTTACAACAGTGCTATTTTCTGGTAGTTCTTC
```

-continued

```
GGAGTGTGTTGCTTTAATTATTAAATTTATATAATCAATGAATTTGGGATCGTCGGTT

TTGTACAATATGTTGCCGGCATAGTACGCAGCTTCTTCTAGTTCAATTACACCATTTT

TTAGCAGCACCGGATTAACATAACTTTCCAAAATGTTGTACGAACCGTTAAACAAAA

ACAGTTCACCTCCCTTTTCTATACTATTGTCTGCGAGCAGTTGTTTGTTGTTAAAAAT

AACAGCCATTGTAATGAGACGCACAAACTAATATCACAAACTGGAAATGTCTATCA

ATATATAGTTGCTGATCAGATCTGATCATGGAGATAATTAAAATGATAACCATCTCG

CAAATAAATAAGTATTTTACTGTTTTCGTAACAGTTTTGTAATAAAAAAACCTATAA

ATATAGGATCCATGCCCCACTCCAGCCTGCATCCATCCCGTGTCCCAGGGGTC

ACGGGGCCCAGAAGGCAGCCTTGGTTCTGCTGAGTGCCTGCCTGGTGACCCTTTGGG

GGCTAGGAGAGCCACCAGAGCACACTCTCCGGTACCTGGTGCTCCACCTAGCCTCCC

TGCAGCTGGGACTGCTGTTAAACGGGGTCTGCAGCCTGGCTGAGGAGCTGCGCCAC

ATCCACTCCAGGTACCGGGGCAGCTACTGGAGGACTGTGCGGGCCTGCCTGGGCTG

CCCCCTCCGCCGTGGGCCCTGTTGCTGCTGTCCATCTATTTCTACTACTCCCTCCCA

AATGCGGTCGGCCCGCCCTTCACTTGGATGCTTGCCCTCCTGGGCCTCTCGCAGGCA

CTGAACATCCTCCTGGGCCTCAAGGGCCTGGCCCCAGCTGAGATCTCTGCAGTGTGT

GAAAAGGGAATTTCAACGTGGCCCATGGGCTGGCATGGTCATATTACATCGGATA

TCTGCGGCTGATCCTGCCAGAGCTCCAGGCCCGGATTCGAACTTACAATCAGCATTA

CAACAACCTGCTACGGGGTGCAGTGAGCCAGCGGCTGTATATTCTCCTCCCATTGGA

CTGTGGGGTGCCTGATAACCTGAGTATGGCTGACCCCAACATTCGCTTCCTGGATAA

ACTGCCCCAGCAGACCGGTGACCGTGCTGGCATCAAGGATCGGGTTTACAGCAACA

GCATCTATGAGCTTCTGGAGAACGGGCAGCGGGCGGGCACCTGTGTCCTGGAGTAC

GCCACCCCCTTGCAGACTTTGTTTGCCATGTCACAATACAGTCAAGCTGGCTTTAGC

CGGGAGGATAGGCTTGAGCAGGCCAAACTCTTCTGCCGGACACTTGAGGACATCCT

GGCAGATGCCCCTGAGTCTCAGAACAACTGCCGCCTCATTGCCTACCAGGAACCTGC

AGATGACAGCAGCTTCTCGCTGTCCCAGGAGGTTCTCCGGCACCTGCGGCAGGAGG

AAAAGGAAGAGGTTACTGTGGGCAGCTTGAAGACCTCAGCGGTGCCCAGTACCTCC

ACGATGTCCCAAGAGCCTGAGCTCCTCATCAGTGGAATGGAAAAGCCCCTCCCTCTC

CGCACGGATTTCTCTGGCGGTGGCCTGAACGACATCTTCGAAGCCCAGAAAATCGA

ATGGCATGAAGGCAGCCTGGAAGTGCTGTTCCAGGGCCCACACCACCATCATCACC

ATCACCATTAATGAGCGGCCGCACTCGAGCACCACCACCACCACCACTAACCTAGG

TAGCTGAGCGCATGCAAGCTGATCCGGGTTATTAGTACATTTATTAAGCGCTAGATT

CTGTGCGTTGTTGATTTACAGACAATTGTTGTACGTATTTTAATAATTCATTAAATTT

ATAATCTTTAGGGTGGTATGTTAGAGCGAAAATCAAATGATTTTCAGCGTCTTTATA

TCTGAATTTAAATATTAAATCCTCAATAGATTTGTAAAATAGGTTTCGATTAGTTTCA

AACAAGGGTTGTTTTTCCGAACCGATGGCTGGACTATCTAATGGATTTTCGCTCAAC

GCCACAAAACTTGCCAAATCTTGTAGCAGCAATCTAGCTTTGTCGATATTCGTTTGT

GTTTTGTTTTGTAATAAAGGTTCGACGTCGTTCAAAATATTATGCGCTTTTGTATTTC

TTTCATCACTGTCGTTAGTGTACAATTGACTCGACGTAAACACGTTAAATAGAGCTT

GGACATATTTAACATCGGGCGTGTTAGCTTTATTAGGCCGATTATCGTCGTCGTCCC

AACCCTCGTCGTTAGAAGTTGCTTCCGAAGACGATTTTGCCATAGCCACACGACGCC

TATTAATTGTGTCGGCTAACACGTCCGCGATCAAATTTGTAGTTGAGCTTTTTGGAAT
```

```
TATTTCTGATTGCGGGCGTTTTTGGGCGGGTTTCAATCTAACTGTGCCCGATTTTAAT

TCAGACAACACGTTAGAAAGCGATGGTGCAGGCGGTGGTAACATTTCAGACGGCAA

ATCTACTAATGGCGGCGGTGGTGGAGCTGATGATAAATCTACCATCGGTGGAGGCG

CAGGCGGGGCTGGCGGCGGAGGCGGAGGCGGAGGTGGTGGCGGTGATGCAGACGG

CGGTTTAGGCTCAAATGTCTCTTTAGGCAACACAGTCGGCACCTCAACTATTGTACT

GGTTTCGGGCGCCGTTTTTGGTTTGACCGGTCTGAGACGAGTGCGATTTTTTCGTTT

CTAATAGCTTCCAACAATTGTTGTCTGTCGTCTAAAGGTGCAGCGGGTTGAGGTTCC

GTCGGCATTGGTGGAGCGGGCGGCAATTCAGACATCGATGGTGGTGGTGGTGGTGG

AGGCGCTGGAATGTTAGGCACGGGAGAAGGTGGTGGCGGCGGTGCCGCCGGTATAA

TTTGTTCTGGTTTAGTTTGTTCGCGCACGATTGTGGGCACCGGCGCAGGCGCCGCTG

GCTGCACAACGGAAGGTCGTCTGCTTCGAGGCAGCGCTTGGGGTGGTGGCAATTCA

ATATTATAATTGGAATACAAATCGTAAAAATCTGCTATAAGCATTGTAATTTCGCTA

TCGTTTACCGTGCCGATATTTAACAACCGCTCAATGTAAGCAATTGTATTGTAAAGA

GATTGTCTCAAGCTCGGATCGATCCCGCACGCCGATAACAAGCCTTTTCATTTTTACT

ACAGCATTGTAGTGGCGAGACACTTCGCTGTCGTCGAGGTTTAAACGCTTCCTCGCT

CACTGACTCGCTGCGCTCGGTCGTTCGGCTGCGGCGAGCGGTATCAGCTCACTCAAA

GGCGGTAATACGGTTATCCACAGAATCAGGGGATAACGCAGGAAAGAACATGTGAG

CAAAAGGCCAGCAAAAGGCCAGGAACCGTAAAAAGGCCGCGTTGCTGGCGTTTTTC

CATAGGCTCCGCCCCCCTGACGAGCATCACAAAAATCGACGCTCAAGTCAGAGGTG

GCGAAACCCGACAGGACTATAAAGATACCAGGCGTTTCCCCCTGGAAGCTCCCTCG

TGCGCTCTCCTGTTCCGACCCTGCCGCTTACCGGATACCTGTCCGCCTTTCTCCCTTC

GGGAAGCGTGGCGCTTTCTCATAGCTCACGCTGTAGGTATCTCAGTTCGGTGTAGGT

CGTTCGCTCCAAGCTGGGCTGTGTGCACGAACCCCCCGTTCAGCCCGACCGCTGCGC

CTTATCCGGTAACTATCGTCTTGAGTCCAACCCGGTAAGACACGACTTATCGCCACT

GGCAGCAGCCACTGGTAACAGGATTAGCAGAGCGAGGTATGTAGGCGGTGCTACAG

AGTTCTTGAAGTGGTGGCCTAACTACGGCTACACTAGAAGGACAGTATTTGGTATCT

GCGCTCTGCTGAAGCCAGTTACCTTCGGAAAAAGAGTTGGTAGCTCTTGATCCGGCA

AACAAACCACCGCTGGTAGCGGTGGTTTTTTTGTTTGCAAGCAGCAGATTACGCGCA

GAAAAAAAGGATCTCAAGAAGATCCTTTGATCTTTTCTACGGGGTCTGACGCTCAGT

GGAACGAAAACTCACGTTAAGGGATTTTGGTCATGAGATTATCAAAAAGGATCTTC

ACCTAGATCCTTTTAAATTAAAAATGAAGTTTTAAATCAATCTAAAGTATATATGAG

TAAACTTGGTCTGACAGTTACCAATGCTTAATCAGTGAGGCACCTATCTCAGCGATC

TGTCTATTTCGTTCATCCATAGTTGCCTGACTCCCCGTCGTGTAGATAACTACGATAC

GGGAGGGCTTACCATCTGGCCCCAGTGCTGCAATGATACCGCGAGACCCACGCTCA

CCGGCTCCAGATTTATCAGCAATAAACCAGCCAGCCGGAAGGGCCGAGCGCAGAAG

TGGTCCTGCAACTTTATCCGCCTCCATCCAGTCTATTAATTGTTGCCGGGAAGCTAG

AGTAAGTAGTTCGCCAGTTAATAGTTTGCGCAACGTTGTTGCCATTGCTACAGGCAT

CGTGGTGTCACGCTCGTCGTTTGGTATGGCTTCATTCAGCTCCGGTTCCCAACGATCA

AGGCGAGTTACATGATCCCCCATGTTGTGCAAAAAAGCGGTTAGCTCCTTCGGTCCT

CCGATCGTTGTCAGAAGTAAGTTGGCCGCAGTGTTATCACTCATGGTTATGGCAGCA
```

```
-continued
CTGCATAATTCTCTTACTGTCATGCCATCCGTAAGATGCTTTTCTGTGACTGGTGAGT

ACTCAACCAAGTCATTCTGAGAATAGTGTATGCGGCGACCGAGTTGCTCTTGCCCGG

CGTCAATACGGGATAATACCGCGCCACATAGCAGAACTTTAAAAGTGCTCATCATTG

GAAAACGTTCTTCGGGGCGAAAACTCTCAAGGATCTTACCGCTGTTGAGATCCAGTT

CGATGTAACCCACTCGTGCACCCAACTGATCTTCAGCATCTTTTACTTTCACCAGCGT

TTCTGGGTGAGCAAAAACAGGAAGGCAAAATGCCGCAAAAAAGGGAATAAGGGCG

ACACGGAAATGTTGAATACTCATACTCTTCCTTTTTCAATATTATTGAAGCATTTATC

AGGGTTATTGTCTCATGAGCGGATACATATTTGAATGTATTTAGAAAAATAAACAAA

TAGGGGTTCCGCGCACATTTCCCCGAAAAGTGCCACCTGACGCGCCCTGTAGCGGCG

CATTAAGCGCGGCGGGTGTGGTGGTTACGCGCAGCGTGACCGCTACACTTGCCAGC

GCCCTAGCGCCCGCTCCTTTCGCTTTCTTCCCTTCCTTTCTCGCCACGTTCGCCGGCTT

TCCCCGTCAAGCTCTAAATCGGGGGCTCCCTTTAGGGTTCCGATTTAGTGCTTTACG

GCACCTCGACCCCAAAAAACTTGATTAGGGTGATGGTTCACGTAGTGGGCCATCGCC

CTGATAGACGGTTTTTCGCCCTTTGACGTTGGAGTCCACGTTCTTTAATAGTGGACTC

TTGTTCCAAACTGGAACAACACTCAACCCTATCTCGGTCTATTCTTTTGATTTATAAG

GGATTTTGCCGATTTCGGCCTATTGGTTAAAAAATGAGCTGATTTAACAAAAATTTA

ACGCGAATTTTAACAAAATATTAACGTTTACAATTTCCCATTCGCCATTCAGGCTGC

GCAACTGTTGGGAAGGGCGATCGGTGCGGGCCTCTTCGCTATTACGCCA
```

Certain compounds of the disclosure were evaluated in WT STING in vitro binding assay as described above. The following table tabulates the biological data for these compounds as $EC_{50}$ values.

TABLE 25

$^3$H-cGAMP filtration binding assay for WT STING

| Example | $EC_{50}$ (nM) |
| --- | --- |
| 1 | 117 |
| 2 | 14 |
| 3 | 273 |
| 4 | 33 |
| 5 | 381 |
| 6 | 206 |
| 7 | 71 |
| 8 | 76 |
| 9 | 322 |
| 10 | 421 |
| 11 | 4560 |
| 12 | 3 |
| 13 | 625 |
| 14 | 21 |
| 15 | 615 |
| 16 | 51 |
| 17 | 299 |
| 18 | 8 |
| 19 | 9 |
| 20 | 24 |
| 21 | 5 |
| 22 | 1 |
| 23 | 2 |
| 24 | 39% inhibition at 20,000 nM |
| 25 | 23 |
| 26 | 19 |
| 27 | 362 |
| 28 | 112 |
| 29 | 44 |
| 30 | 7520 |

TABLE 25-continued $^3$H-cGAMP filtration binding assay for WT STING

| Example | $EC_{50}$ (nM) |
| --- | --- |
| 31 | 9482 |
| 32 | 9 |
| 33 | 4 |
| 34 | 4 |
| 35 | 4 |
| 36 | 10 |
| 37 | 2 |
| 38 | 1039 |
| 39 | 2 |
| 40 | 1365 |
| 41 | 50 |
| 42 | 12 |
| 43 | 151 |
| 44 | 64 |
| 45 | 14760 |
| 46 | 394 |
| 47 | 81 |
| 48 | 43% inhibition at 20,000 nM |
| 49 | 34% inhibition at 20,000 nM |
| 50 | 1 |
| 51 | 8 |
| 52 | 4 |
| 53 | 713 |
| 54 | 3084 |
| 55 | 48 |
| 56 | 3127 |
| 57 | 398 |
| 58 | 1 |
| 59 | 2 |
| 60 | 67 |
| 61 | 327 |
| 62 | 2 |
| 63 | 4 |
| 64 | 4 |
| 65 | 1 |

TABLE 25-continued $^3$H-cGAMP filtration binding assay for WT STING

| Example | EC$_{50}$ (nM) |
| --- | --- |
| 66 | 20 |
| 67 | 45 |
| 68 | 443 |
| 69 | 2 |
| 70 | 1 |
| 71 | 2 |
| 72 | 2 |
| 73 | 4 |
| 74 | 6 |
| 75 | 691 |
| 76 | 56 |
| 77/78 (mixture) | 224 |
| 79 | 12 |
| 80 | 12650 |
| 81 | 23 |
| 82 | 2 |
| 83 | 9 |
| 84 | 1058 |
| 85 | 9008 |
| 86 | 9 |
| 87 | 1921 |
| 88 | 109 |
| 89 | 94 |
| 90 | 978 |
| 91 | 30 |
| 92 | 7 |
| 93 | 3 |
| 94 | 131 |
| 95 | 813 |
| 96 | 628 |
| 97 | 69 |
| 98 | 1 |
| 99 | 3 |
| 100 | 2240 |
| 101 | 2 |
| 102 | 213 |
| 103 | 371 |
| 104 | 8900 |
| 105 | 311 |
| 106 | 251 |
| 107 | 2 |
| 108 | 244 |
| 109 | 39 |
| 110 | 15% inhibition at 20,000 nM |
| 111 | 50% inhibition at 20,000 nM |
| 112 | 11% inhibition at 20,000 nM |
| 113 | 23 |
| 114 | 264 |
| 115 | 295 |
| 116 | 4241 |
| 117 | 2640 |
| 118 | 4996 |
| 119 | 32% inhibition at 20,000 nM |
| 120 | 698 |
| 121 | 43% inhibition at 20,000 nM |
| 122 | 1 |
| 123 | 2 |
| 124 | 3060 |
| 125 | 5 |
| 126 | 19 |
| 127 | 270 |
| 128 | 6314 |
| 129 | 17080 |
| 130 | 25 |
| 131 | 242 |
| 132 | 10 |
| 133 | 147 |
| 134 | 233 |
| 135 | 5 |
| 136 | 10310 |
| 137 | 319 |
| 138 | 2 |
| 139 | 12 |
| 140 | 28% inhibition at 7,000 nM |
| 141 | 219 |
| 142 | 1 |
| 143 | 1452 |
| 144 | 93 |
| 145 | 47% inhibition at 2,000 nM |
| 146 | 18% inhibition at 2,000 nM |
| 147 | 207 |
| 148 | 411 |
| 149 | 46 |
| 150 | 1035 |
| 151 | 1039 |
| 152 | 3% inhibition at 2,000 nM |
| 153 | 10 |
| 154 | 30% inhibition at 2,000 nM |
| 155 | 5 |
| 156 | 1 |
| 157 | 1 |
| 158 | 32 |
| 159 | 3 |
| 160 | 6 |
| 161 | 4 |
| 162 | 4 |
| 163 | 1 |
| 164 | 1 |
| 165 | 3 |
| 166 | 117 |
| 167 | 19 |
| 168 | 199 |
| 169 | 18 |
| 170 | 3 |
| 171 | 59 |
| 172 | 15060 |
| 173 | 3 |
| 174 | 1 |
| 175 | 46% inhibition at 20,000 nM |
| 176 | 2 |
| 177 | 720 |
| 178 | 31 |
| 179 | 1 |
| 180 | 1 |
| 181 | 177 |
| 182 | 2 |
| 183 | 3 |
| 184 | 29% inhibition at 2,000 nM |
| 185 | 1 |
| 186 | 756 |
| 187 | 46 |
| 188 | 1 |
| 189 | 2 |
| 190 | 2 |

IFN-β Secretion in THP1 Cell Culture (5 h)

The ability of compounds to stimulate the secretion of interferon-beta from THP1 cells was measured using a human IFN-β AlphaLISA kit (Perkin Elmer, Cat. No. AL265F). The basic protocol is as follows:

A Labcyte Echo 550 acoustic dispenser was used to transfer 120 nL of compound dissolved in DMSO into the wells of an empty, sterile 384-well microplate, (Corning, Cat. No. 3712). THP1 cells (American Type Culture Collection, Cat. No. TIB202) previously frozen in Recovery Medium (Life Technologies, Cat. No. 12648-010) were thawed and immediately diluted 10-fold into 37° C. assay medium (RPMI 1640+L-Glutamine & phenol red, Life Technologies, Cat. No. 11875-085; 0.5% heat inactivated fetal bovine serum, Sigma Aldrich, Cat. No. F4135; 1 mM Sodium Pyruvate, Life Technologies, Cat. No. 11360-070; 1× non-essential amino acids; Life Technologies, Cat. No. 11140-050). The cell viability and count was ascertained using a Beckman Coulter V-Cell XR cell counter. The cells suspension was centrifuged at 200×g for 5 min at RT. Cells were resuspended to a density of $0.8 \times 10^6$/mL in 37° C. assay medium. Subsequent liquid transfers were performed using either a Matrix electronic multichannel pipette or an Agilent Bravo Automated Liquid Handling Platform.

The assay was started by dispensing 40 μL of the previously prepared cell suspension into the wells of the plate containing compounds. After 5 h incubation at 37° C., 5% $CO_2$ in a humidified atmosphere, the plate of cells and compounds was centrifuged at 200×g for 5 min at RT. From each well, 5 μL of supernatant was transferred into corresponding wells of a white 384-well plate (Perkin Elmer, Cat. No. 6005620). To these supernatant-containing wells was added 10 μL of 5× Anti-Analyte Acceptor beads (50 μg/mL of AlphaLISA HiBlock Buffer) and incubated for 30 min at RT while shaking on an orbital plate shaker. To each well was added 10 μL of 5× Biotinylated Antibody Anti-analyte (5 nM in AlphaLISA HiBlock Buffer) and incubated on an orbital plate shaker for 60 min at RT or overnight at 4° C. To each well was added 25 μL of 2× SA-Donor beads (80 μg/mL in AlphaLISA HiBlock Buffer) and incubated for 30-45 min at RT in the dark while shaking on an orbital plate shaker. The plate was then read on a Perkin Elmer Envision ($\lambda_{ex}$=680 nm, $\lambda_{em}$=570 nm). The percent effect of the AlphaLISA signal at each compound concentration was calculated based on 30 uM cGAMP positive controls and 0.3% DMSO negative controls. The plot of percent effect versus the log of compound concentration was fit with a 4-parameter concentration response equation to calculate $EC_{50}$ values. The test compounds were tested at concentrations 30000, 10000, 3333, 1111, 370.4, 123.4, 41.2, 13.7, 4.6, and 1.5 nM with 0.3% residual DMSO. The control compound, cGAMP was tested at concentrations 100000, 33333, 11111, 3704, 1235, 412, 137, 46, and 15 nM with 0.3% residual DMSO.

Compounds of the disclosure were evaluated for IFN-β secretion in THP1 cell culture as described above. The following table tabulates the biological data for these compounds as percent activation relative to 2'3'-cGAMP at the 30 M concentration.

TABLE 26

| | IFN-β secretion in THP1 cell culture (5 h) |
|---|---|
| Example | % Effect at 30 μM relative to 2'3'-cGAMP |
| 1 | 26 |
| 2 | 192 |
| 3 | 151 |
| 4 | 93 |
| 5 | 96 |
| 6 | 106 |
| 7 | 97 |
| 8 | 99 |
| 9 | 48 |
| 10 | 134 |
| 11 | 7 |
| 12 | 74 |
| 13 | 67 |
| 14 | 77 |
| 15 | 114 |
| 16 | 70 |
| 17 | 38 |
| 18 | 62 |
| 19 | 30 |
| 20 | 63 |
| 21 | 59 |
| 22 | 48 |
| 23 | 83 |
| 24 | 150 |
| 25 | 136 |
| 26 | 129 |
| 27 | 113 |
| 28 | 116 |
| 29 | 107 |
| 30 | 103 |
| 31 | 117 |
| 32 | 117 |
| 33 | 104 |
| 34 | 72 |
| 35 | 80 |
| 36 | 102 |
| 37 | 76 |
| 38 | 17 |
| 39 | 75 |
| 40 | 27 |
| 41 | 117 |
| 42 | 67 |
| 43 | 69 |
| 44 | 108 |
| 45 | 8 |
| 46 | 60 |
| 47 | 62 |
| 48 | 22 |
| 49 | 17 |
| 50 | 44 |
| 51 | 43 |
| 52 | 53 |
| 53 | 23 |
| 54 | 9 |
| 55 | 53 |
| 56 | 30 |
| 57 | 15 |
| 58 | 46 |
| 59 | 18 |
| 60 | 106 |
| 61 | 62 |
| 62 | 106 |
| 63 | 62 |
| 64 | 58 |
| 65 | 105 |
| 66 | 103 |
| 67 | 92 |
| 68 | 24 |
| 69 | 46 |
| 70 | 47 |
| 71 | 15 |
| 72 | 77 |
| 73 | 67 |
| 74 | 16 |
| 75 | 63 |

TABLE 26-continued

IFN-β secretion in THP1 cell culture (5 h)

| Example | % Effect at 30 μM relative to 2'3'-cGAMP |
|---|---|
| 76 | 44 |
| 77/78 mixture | 43 |
| 79 | 49 |
| 80 | 12 |
| 81 | 120 |
| 82 | 158 |
| 83 | 107 |
| 84 | 148 |
| 85 | 145 |
| 86 | 131 |
| 87 | 120 |
| 88 | 152 |
| 89 | 112 |
| 90 | 125 |
| 91 | 109 |
| 92 | 62 |
| 93 | 87 |
| 94 | 100 |
| 95 | 72 |
| 96 | 43 |
| 97 | 54 |
| 98 | 92 |
| 99 | 82 |
| 100 | 33 (@ 3 uM) |
| 101 | 85 |
| 102 | 69 |
| 103 | 79 |
| 104 | 35 |
| 105 | 130 |
| 106 | 74 |
| 107 | 108 |
| 108 | 86 |
| 109 | 96 |
| 110 | 6 |
| 111 | 45 (@ 3 uM) |
| 112 | 23 |
| 113 | 93 |
| 114 | 57 |
| 115 | 110 |
| 116 | 8 |
| 117 | 123 |
| 118 | 117 |
| 119 | 13 |
| 120 | 45 (@ 3 uM) |
| 121 | 26 |
| 122 | 79 |
| 123 | 105 |
| 124 | 45 (@ 3 uM) |
| 125 | 156 |
| 126 | 91 |
| 127 | 120 |
| 128 | 83 |
| 129 | 50 |
| 130 | 61 |
| 131 | 38 (@ 3 uM) |
| 132 | 131 |
| 133 | 80 |
| 134 | 89 |
| 135 | 100 |
| 136 | 37 |
| 137 | 155 |
| 138 | 89 |
| 139 | 57 |
| 140 | 31 (@ 3 uM) |
| 141 | 143 |
| 142 | 81 |
| 143 | 26 (@ 3 uM) |
| 144 | 8 |
| 145 | 59 (@ 3 uM) |
| 146 | 27 (@ 3 uM) |
| 147 | 71 (@ 3 uM) |
| 148 | 41 (@ 3 uM) |
| 149 | 70 (@ 3 uM) |
| 150 | 52 (@ 3 uM) |
| 151 | 63 (@ 3 uM) |
| 152 | 7 (@ 3 uM) |
| 153 | 137 (@ 3 uM) |
| 154 | 76 (@ 3 uM) |
| 155 | 129 (@ 3 uM) |
| 156 | 118 (@ 3 uM) |
| 157 | 63% @ 3 uM |
| 158 | 43 |
| 159 | 99 |
| 160 | 18 |
| 161 | 106 |
| 162 | 98 |
| 163 | 135 |
| 164 | 131 |
| 165 | 21 |
| 166 | 34 |
| 167 | 66 |
| 168 | 102 |
| 169 | 64 |
| 170 | 86 |
| 171 | 97 |
| 172 | 16 (@ 3 uM) |
| 173 | 127 |
| 174 | 88 |
| 175 | 13 |
| 176 | 44 |
| 177 | 80 |
| 178 | 107 |
| 179 | 79 |
| 180 | 121 (@ 3 uM) |
| 181 | 104 (@ 3 uM) |
| 182 | 147 (@ 3 uM) |
| 183 | 127 (@ 3 uM) |
| 184 | 10 (@ 3 uM) |
| 185 | 122 (@ 3 uM) |
| 186 | 56 (@ 3 uM) |
| 187 | 128 (@ 3 uM) |
| 188 | 104 (@ 3 uM) |
| 189 | 111 (@ 3 uM) |
| 190 | 126 (@ 3 uM) |

It will be appreciated that various of the above-discussed and other features and functions, or alternatives thereof, may be desirably combined into many other different systems or applications. It also will be appreciated that various presently unforeseen or unanticipated alternatives, modifications, variations or improvements therein may be subsequently made by those skilled in the art and are also intended to be encompassed by the following claims.

What is claimed is:

1. A compound according to general formula (I):

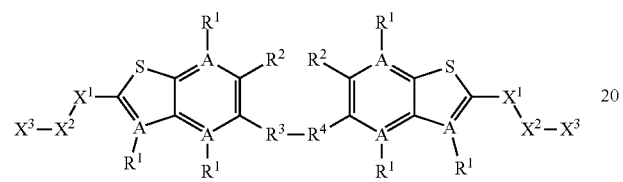
(I)

or a pharmaceutically acceptable salt thereof, wherein
- each A-$R^1$ is independently selected from the group consisting of C—$R^1$ and N;
- each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$;
- each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$;
- $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene);
- optionally $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl;
- each $R^6$ is independently selected from the group consisting of H, $C_1$-$C_6$ alkyl, and $C_1$-$C_6$ haloalkyl;
- each $X^1$ is independently selected from the group consisting of C=O, —$CH_2$—, —CHF—, and —$CF_2$—;
- each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$;
- optionally 2 $R^8$ on different carbon atoms may be taken together, along with the atoms to which they are attached, to form a 3- to 6-membered fused ring; and
- optionally 2 $R^8$ on a single carbon atom may be taken together, along with the atom to which they are attached, to form a 3- to 6-membered spirocycle;
- each $X^3$ is independently selected from the group consisting of $COOR^6$, $C(O)SR^6$, $C(S)OR^6$,

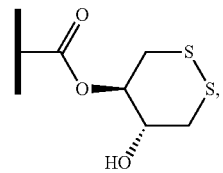

$SO_2R^6$, $C(O)N(R^9)_2$, and CN; and
- each $R^9$ is independently selected from the group consisting of H, $COOR^6$, and $SO_2R^6$.

2. The compound according to claim 1, or a pharmaceutically acceptable salt thereof, wherein each

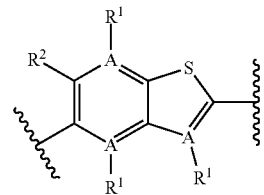

is independently selected from the group consisting of

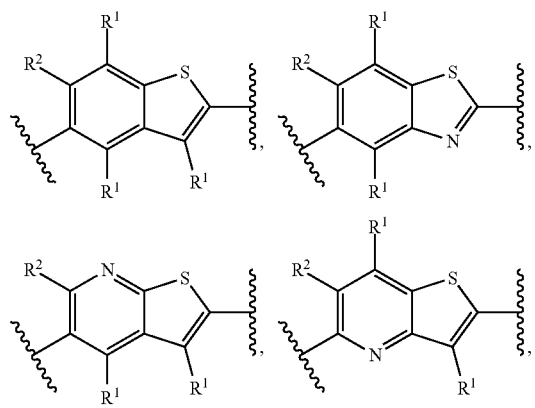

-continued

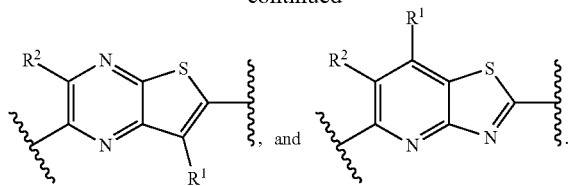, and

3. A compound of general formula (II):

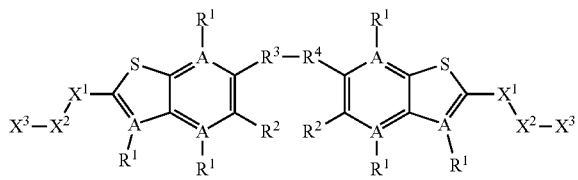

or a pharmaceutically acceptable salt thereof, wherein
each A-$R^1$ is independently selected from the group consisting of C—$R^1$ and N;
each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$;
each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$;
$R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene);
optionally $R^4$ may be taken together with an adjacent C—$R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^3$ from said ring E is from an atom on said ring E with an open valence for substitution and wherein said phenyl or heterocyclic ring is optionally substituted with one or more members of the group consisting of halogen, $C_1$-$C_3$ alkyl, and $C_1$-$C_3$ haloalkyl;
each $R^6$ is independently selected from the group consisting of H, $C_1$-$C_6$ alkyl, and $C_1$-$C_6$ haloalkyl;
each $X^1$ is independently selected from the group consisting of C=O, —$CH_2$—, —CHF—, and —$CF_2$—;
each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$;
optionally 2 $R^8$ on different carbon atoms may be taken together, along with the atoms to which they are attached, to form a 3- to 6-membered fused ring; and
optionally 2 $R^8$ on a single carbon atom may be taken together, along with the atom to which they are attached, to form a 3- to 6-membered spirocycle;
each $X^3$ is independently selected from the group consisting of $COOR^6$, $C(O)SR^6$, $C(S)OR^6$,

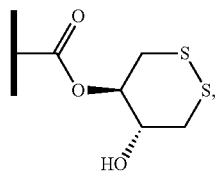

$SO_2R^6$, $C(O)N(R^9)_2$, and CN; and
each $R^9$ is independently selected from the group consisting of H, $COOR^6$, and $SO_2R^6$.

4. The compound according to claim 3, or a pharmaceutically acceptable salt thereof, wherein each

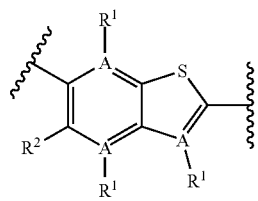

is independently selected from the group consisting of

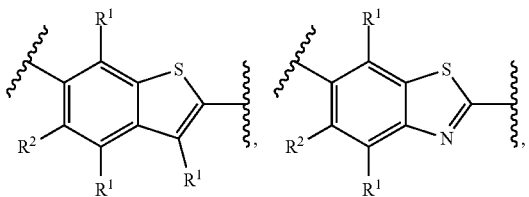

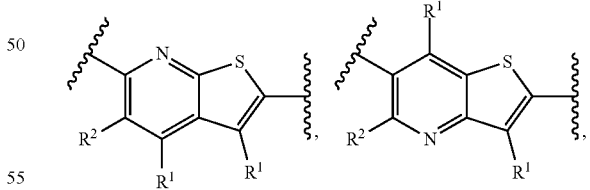

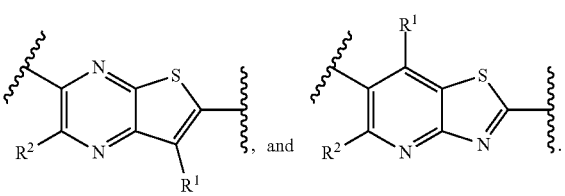

5. A compound of general formula (III):

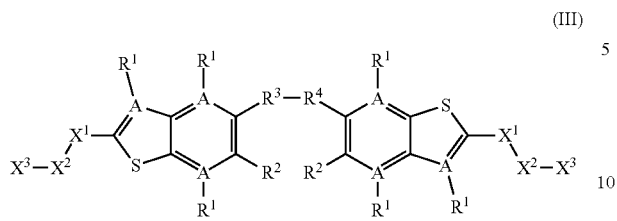

or a pharmaceutically acceptable salt thereof, wherein
  each $A-R^1$ is independently selected from the group consisting of $C-R^1$ and N;
  each $R^1$ is independently selected from the group consisting of H, halogen, $OR^6$, $N(R^6)_2$, $C_1-C_6$ alkyl, $C_1-C_6$ haloalkyl, $C_1-C_6$ alkyl substituted by $OR^6$, $C_1-C_6$ alkyl substituted by $N(R^6)_2$, $COOR^6$, and $C(O)N(R^6)_2$;
  each $R^2$ is independently selected from the group consisting of H, halogen, CN, $OR^6$, $N(R^6)_2$, $COOR^6$, $C(O)N(R^6)_2$, $SO_2R^6$, $C_1-C_6$ alkyl, $C_1-C_6$ haloalkyl, $C_1-C_6$ alkyl substituted by $OR^6$, $C_2-C_6$ alkenyl, $C_2-C_6$ haloalkenyl, $C_2-C_6$ alkenyl substituted by $OR^6$, $C_2-C_6$ alkynyl, $C_2-C_6$ haloalkynyl, $C_2-C_6$ alkynyl substituted by $OR^6$, $C_3-C_6$ cycloalkyl, and a 3- to 6-membered heterocyclic ring including 1 to 2 ring members selected from the group consisting of O, S, and $N(R^6)$;
  $R^3$ and $R^4$ are independently selected from the group consisting of O—($C_1-C_4$ alkylene or haloalkylene), $C_1-C_5$ alkylene or haloalkylene, and $N(R_6)$—($C_1-C_4$ alkylene or haloalkylene);
  optionally $R^3$ may be taken together with an adjacent $C-R^1$ and the atom to which they are attached to form fused ring G, which is selected from phenyl or a 5- or 6-membered heterocyclic ring including 1 to 2 ring members selected from the group consisting of O, S, N, and $N(R^6)$ wherein the bond to $R^3$ from said ring G is from an atom on said ring G with an open valence for substitution and wherein said phenyl or heterocyclic ring is optionally substituted with one or more members of the group consisting of halogen, $C_1-C_3$ alkyl, and $C_1-C_3$ haloalkyl;
  optionally $R^4$ may be taken together with an adjacent $C-R^1$ and the atom to which they are attached to form fused ring E, which is selected from phenyl or a 5- or 6-membered heterocyclic ring including 1 to 2 ring members selected from the group consisting of O, S, N, and $N(R^6)$ wherein the bond to $R^4$ from said ring E is from an atom on said ring E with an open valence for substitution and wherein said phenyl or heterocyclic ring is optionally substituted with one or more members of the group consisting of halogen, $C_1-C_3$ alkyl, and $C_1-C_3$ haloalkyl;
  each $R^6$ is independently selected from the group consisting of H, $C_1-C_6$ alkyl, and $C_1-C_6$ haloalkyl;
  each $X^1$ is independently selected from the group consisting of C=O, —$CH_2$—, —CHF—, and —$CF_2$—;
  each $X^2$ is independently selected from $(C(R^8)_2)_{(1-3)}$, wherein each $R^8$ is independently selected from the group consisting of H, halogen, $C_1-C_6$ alkyl, CN, $OR^6$, $N(R^6)_2$, $C_1-C_6$ haloalkyl, $C_3-C_6$ cycloalkyl, $C_1-C_6$ alkyl substituted by $OR^6$, and $C_1-C_6$ alkyl substituted by $N(R^6)_2$;
  optionally 2 $R^8$ on different carbon atoms may be taken together, along with the atoms to which they are attached, to form a 3- to 6-membered fused ring; and
  optionally 2 $R^8$ on a single carbon atom may be taken together, along with the atom to which they are attached, to form a 3- to 6-membered spirocycle;
  each $X^3$ is independently selected from the group consisting of $COOR^6$, $C(O)SR^6$, $C(S)OR^6$,

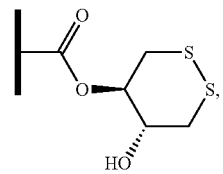

$SO_2R^6$, $C(O)N(R^9)_2$, and CN; and
  each $R^9$ is independently selected from the group consisting of H, $COOR^6$, and $SO_2R^6$.

6. The compound according to claim 5, or a pharmaceutically acceptable salt thereof, wherein

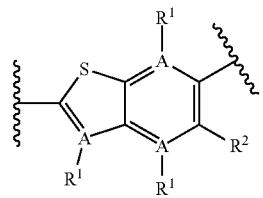

is independently selected from the group consisting of

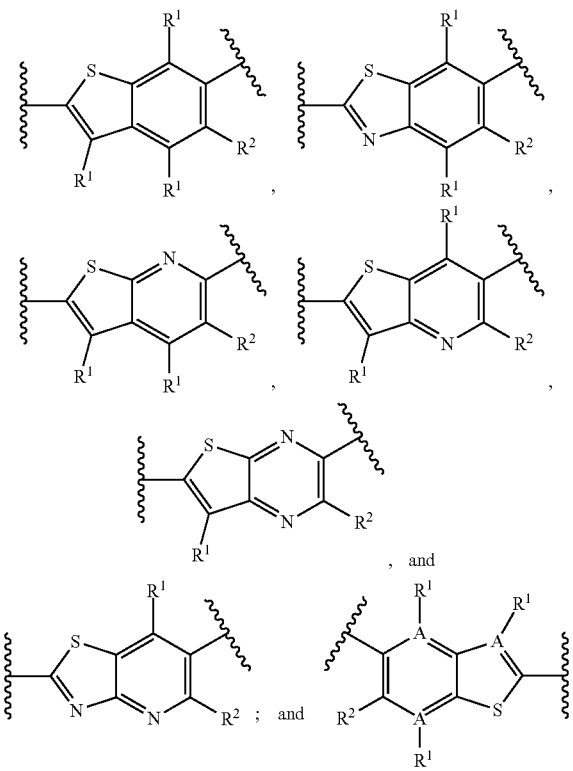

is selected from the group consisting of

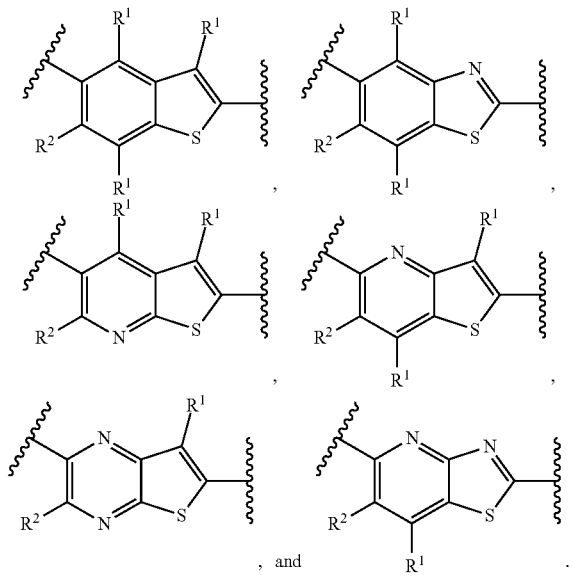

, and

7. A compound of general formula (IV):

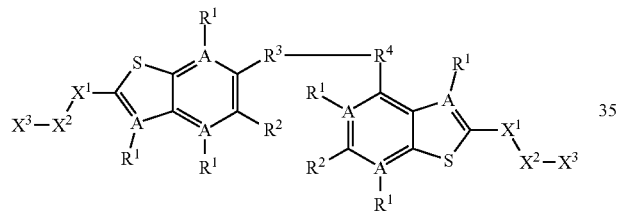

or a pharmaceutically acceptable salt thereof, wherein
each A-$R^1$ is independently selected from the group consisting of C—$R^1$ and N;
each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$;
each $R^2$ is independently selected from the group consisting of H, halogen, CN, $OR^6$, $N(R^6)_2$, $COOR^6$, $C(O)N(R^6)_2$, $SO_2R^6$, $C_1$-$C_6$ alkyl, $C_1$-$C_6$ haloalkyl, $C_1$-$C_6$ alkyl substituted by $OR^6$, $C_2$-$C_6$ alkenyl, $C_2$-$C_6$ haloalkenyl, $C_2$-$C_6$ alkenyl substituted by $OR^6$, $C_2$-$C_6$ alkynyl, $C_2$-$C_6$ haloalkynyl, $C_2$-$C_6$ alkynyl substituted by $OR^6$, $C_3$-$C_6$ cycloalkyl, and a 3- to 6-membered heterocyclic ring including 1 to 2 ring members selected from the group consisting of O, S, and $N(R^6)$;
$R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene);
each $R^6$ is independently selected from the group consisting of H, $C_1$-$C_6$ alkyl, and $C_1$-$C_6$ haloalkyl;
each $X^1$ is independently selected from the group consisting of C=O, —$CH_2$—, —CHF—, and —$CF_2$—;
each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$;
optionally 2 $R^8$ on different carbon atoms may be taken together, along with the atoms to which they are attached, to form a 3- to 6-membered fused ring; and
optionally 2 $R^8$ on a single carbon atom may be taken together, along with the atom to which they are attached, to form a 3- to 6-membered spirocycle;
each $X^3$ is independently selected from the group consisting of $COOR^6$, $C(O)SR^6$, $C(S)OR^6$,

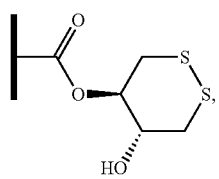

$SO_2R^6$, $C(O)N(R^9)_2$, and CN; and
each $R^9$ is independently selected from the group consisting of H, $COOR^6$, and $SO_2R^6$.

8. The compound according to claim 7, or a pharmaceutically acceptable salt thereof, wherein

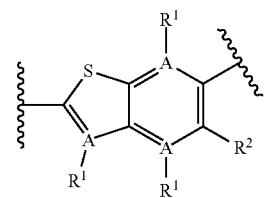

is independently selected from the group consisting of

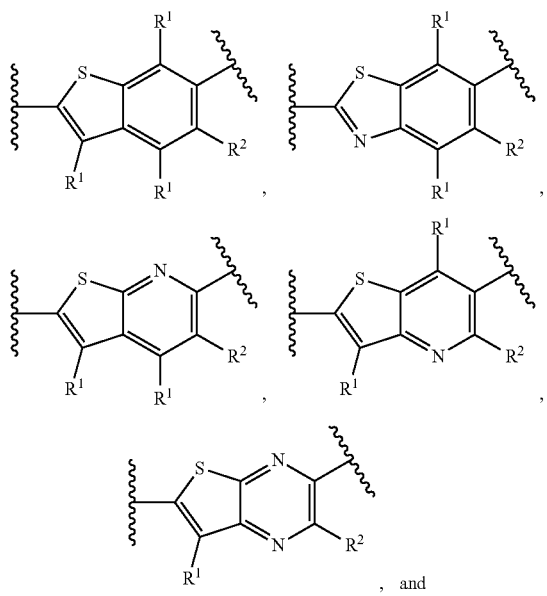

, and

-continued

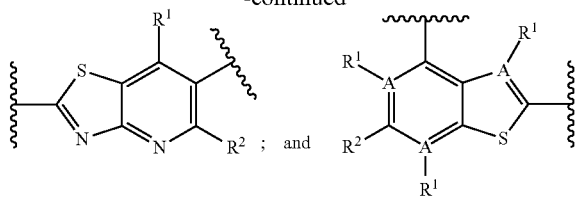

is selected from the group consisting of

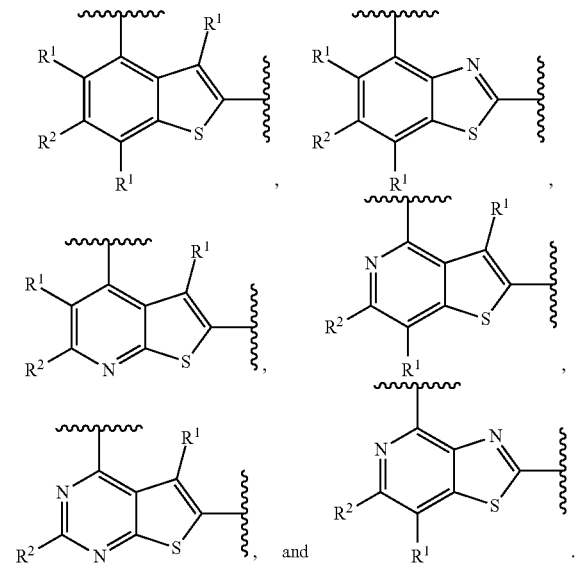

9. A compound of general formula (V):

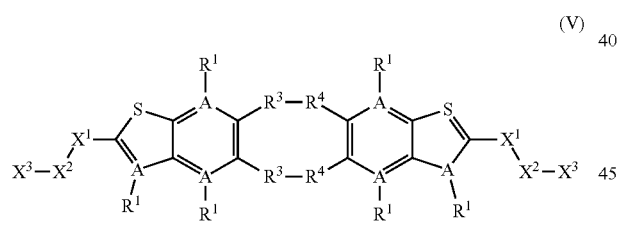

or a pharmaceutically acceptable salt thereof, wherein
each A-R¹ is independently selected from the group consisting of C—R¹ and N;
each R¹ is independently selected from the group consisting of H, halogen, OR⁶, N(R⁶)₂, C₁-C₆ alkyl, C₁-C₆ haloalkyl, C₁-C₆ alkyl substituted by OR⁶, C₁-C₆ alkyl substituted by N(R⁶)₂, COOR⁶, and C(O)N(R⁶)₂;
R³ and R⁴ are independently selected from the group consisting of O—(C₁-C₄ alkylene or haloalkylene), C₁-C₅ alkylene or haloalkylene, and N(R₆)—(C₁-C₄ alkylene or haloalkylene);
each X¹ is independently selected from the group consisting of C=O, —CH₂—, —CHF—, and —CF₂—;
each X² is independently selected from (C(R⁸)₂)₍₁₋₃₎, wherein each R⁸ is independently selected from the group consisting of H, halogen, C₁-C₆ alkyl, CN, OR⁶, N(R⁶)₂, C₁-C₆ haloalkyl, C₃-C₆ cycloalkyl, C₁-C₆ alkyl substituted by OR⁶, and C₁-C₆ alkyl substituted by N(R⁶)₂;

optionally 2 R⁸ on different carbon atoms may be taken together, along with the atoms to which they are attached, to form a 3- to 6-membered fused ring; and optionally 2 R⁸ on a single carbon atom may be taken together, along with the atom to which they are attached, to form a 3- to 6-membered spirocycle;

each X³ is independently selected from the group consisting of COOR⁶, C(O)SR⁶, C(S)OR⁶,

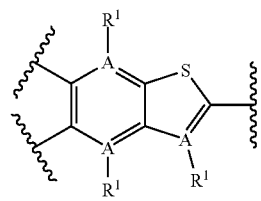

SO₂R⁶, C(O)N(R⁹)₂, and CN; and
each R⁹ is independently selected from the group consisting of H, COOR⁶, and SO₂R⁶.

10. The compound according to claim 9, or a pharmaceutically acceptable salt thereof, wherein each

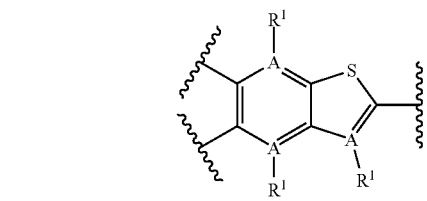

is independently selected from the group consisting of

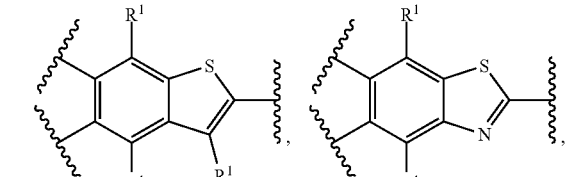

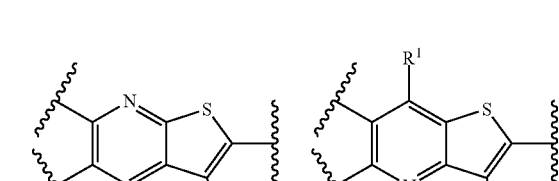

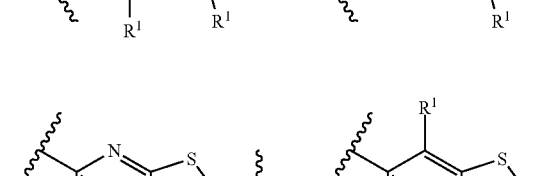

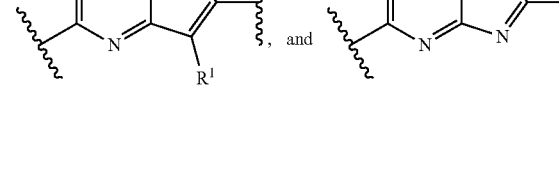

11. A compound of general formula (VI):

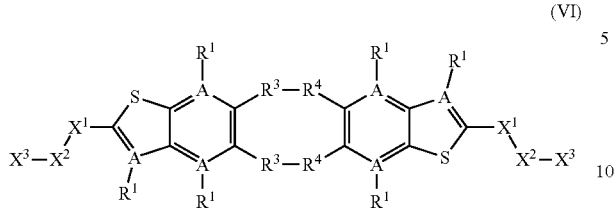

or a pharmaceutically acceptable salt thereof, wherein
- each A-$R^1$ is independently selected from the group consisting of C—$R^1$ and N;
- each $R^1$ is independently selected from the group consisting of H, halogen, $OR^6$, $N(R^6)_2$, $C_1$-$C_6$ alkyl, $C_1$-$C_6$ haloalkyl, $C_1$-$C_6$ alkyl substituted by $OR^6$, $C_1$-$C_6$ alkyl substituted by $N(R^6)_2$, $COOR^6$, and $C(O)N(R^6)_2$;
- $R^3$ and $R^4$ are independently selected from the group consisting of O—($C_1$-$C_4$ alkylene or haloalkylene), $C_1$-$C_5$ alkylene or haloalkylene, and $N(R_6)$—($C_1$-$C_4$ alkylene or haloalkylene);
- each $R^6$ is independently selected from the group consisting of H, $C_1$-$C_6$ alkyl, and $C_1$-$C_6$ haloalkyl;
- each $X^1$ is independently selected from the group consisting of C=O, —$CH_2$—, —CHF—, and —$CF_2$—;
- each $X^2$ is independently selected from $(C(R^8)_2)_{(1-3)}$, wherein each $R^8$ is independently selected from the group consisting of H, halogen, $C_1$-$C_6$ alkyl, CN, $OR^6$, $N(R^6)_2$, $C_1$-$C_6$ haloalkyl, $C_3$-$C_6$ cycloalkyl, $C_1$-$C_6$ alkyl substituted by $OR^6$, and $C_1$-$C_6$ alkyl substituted by $N(R^6)_2$;
  - optionally 2 $R^8$ on different carbon atoms may be taken together, along with the atoms to which they are attached, to form a 3- to 6-membered fused ring; and
  - optionally 2 $R^8$ on a single carbon atom may be taken together, along with the atom to which they are attached, to form a 3- to 6-membered spirocycle;
- each $X^3$ is independently selected from the group consisting of $COOR^6$, $C(O)SR^6$, $C(S)OR^6$,

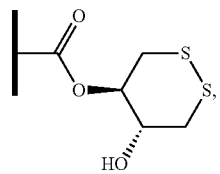

$SO_2R^6$, $C(O)N(R^9)_2$, and CN; and
- each $R^9$ is independently selected from the group consisting of H, $COOR^6$, and $SO_2R^6$.

12. The compound according to claim 11, or a pharmaceutically acceptable salt thereof, wherein each

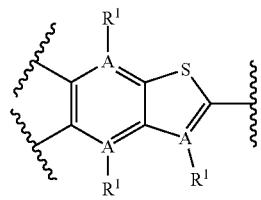

is independently selected from the group consisting of

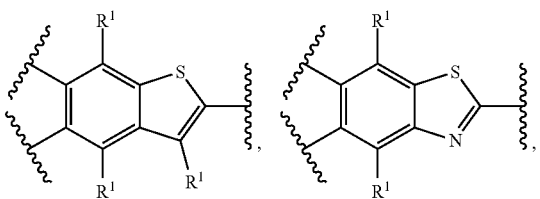

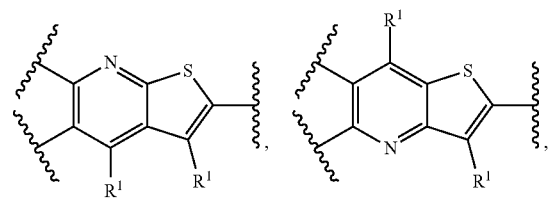

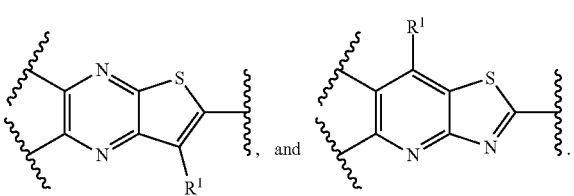

13. A compound selected from the group consisting of

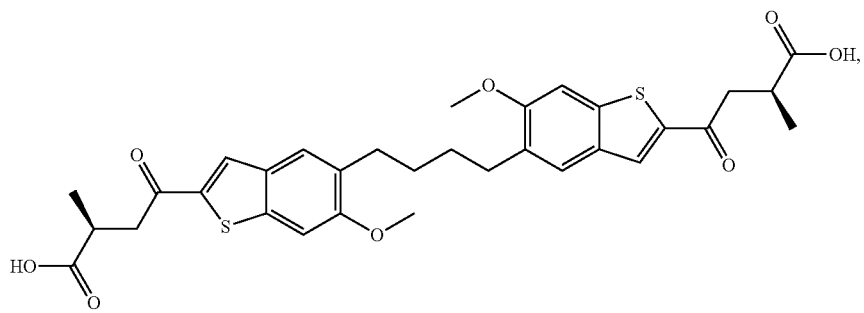

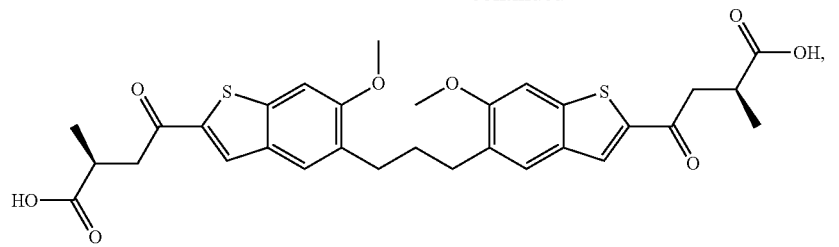
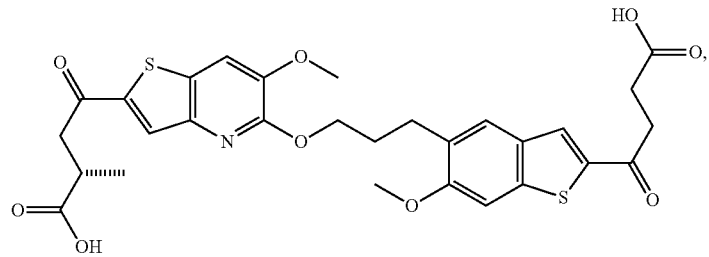
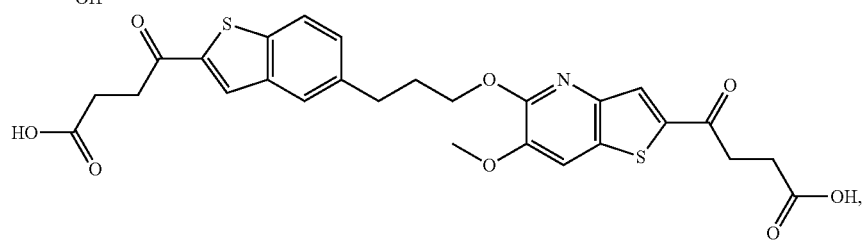
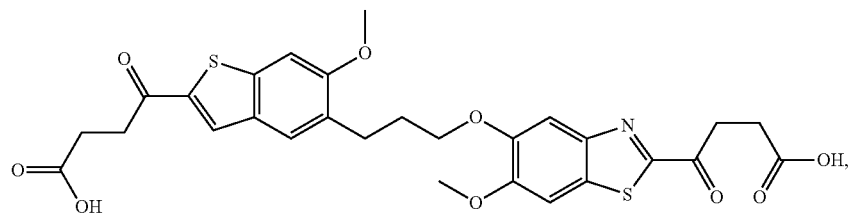
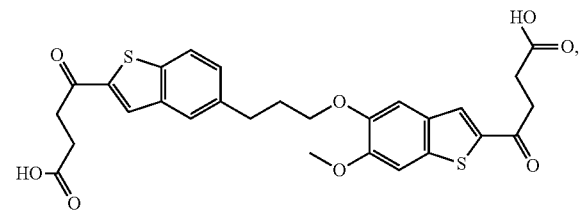
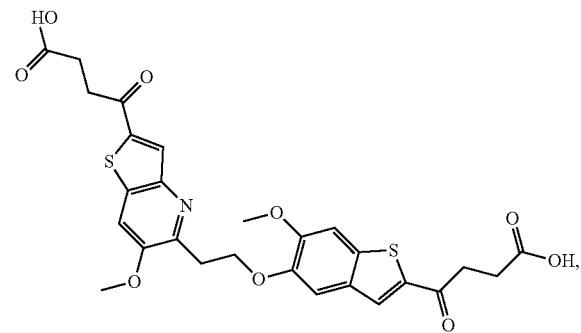

-continued
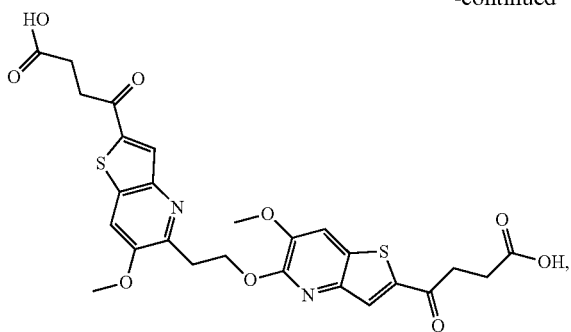
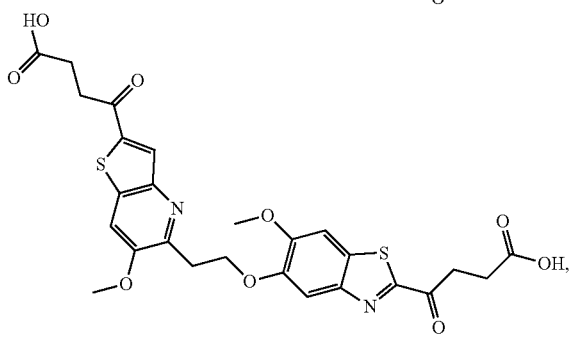
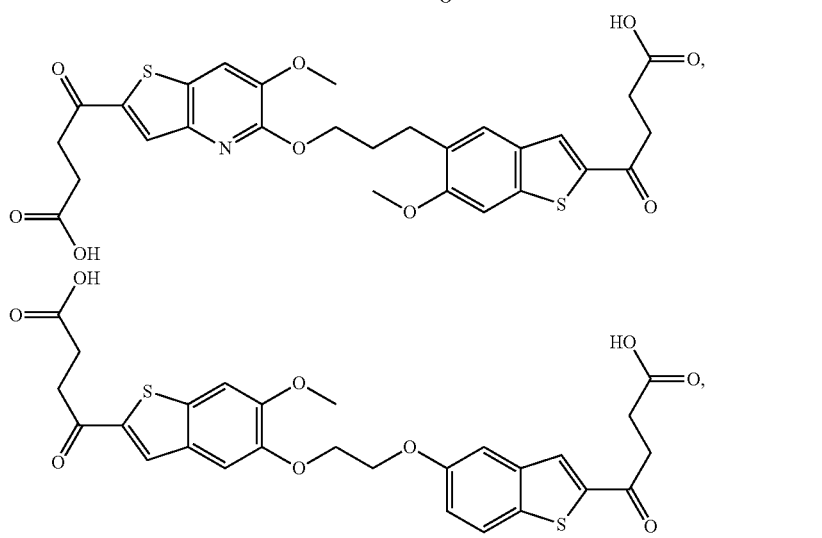
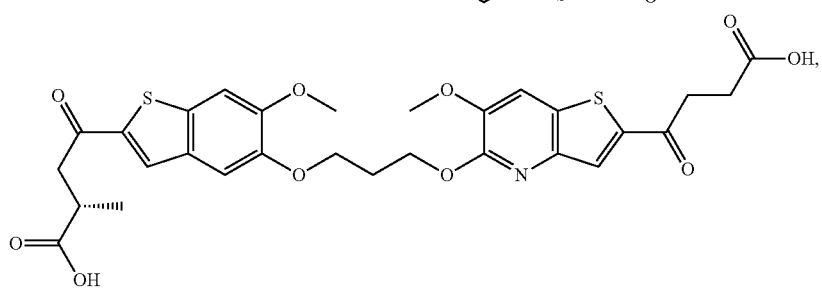
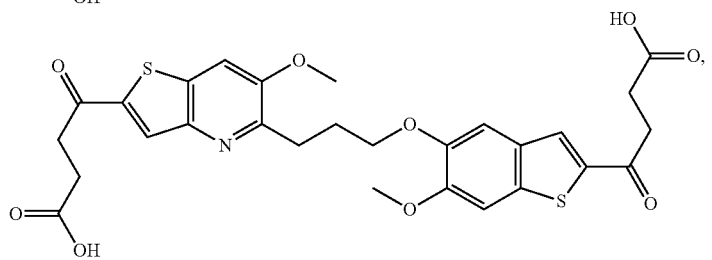

-continued
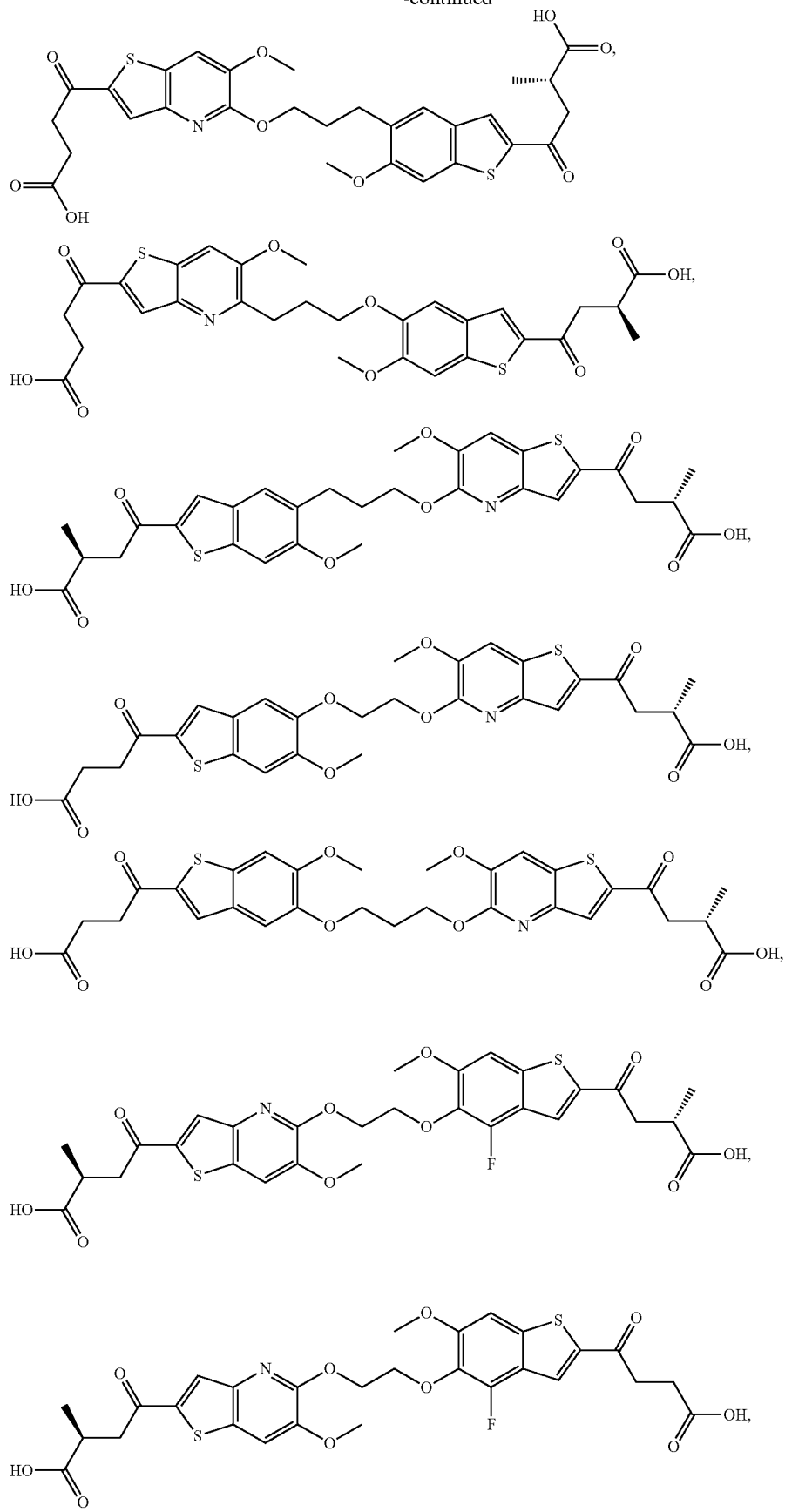

-continued
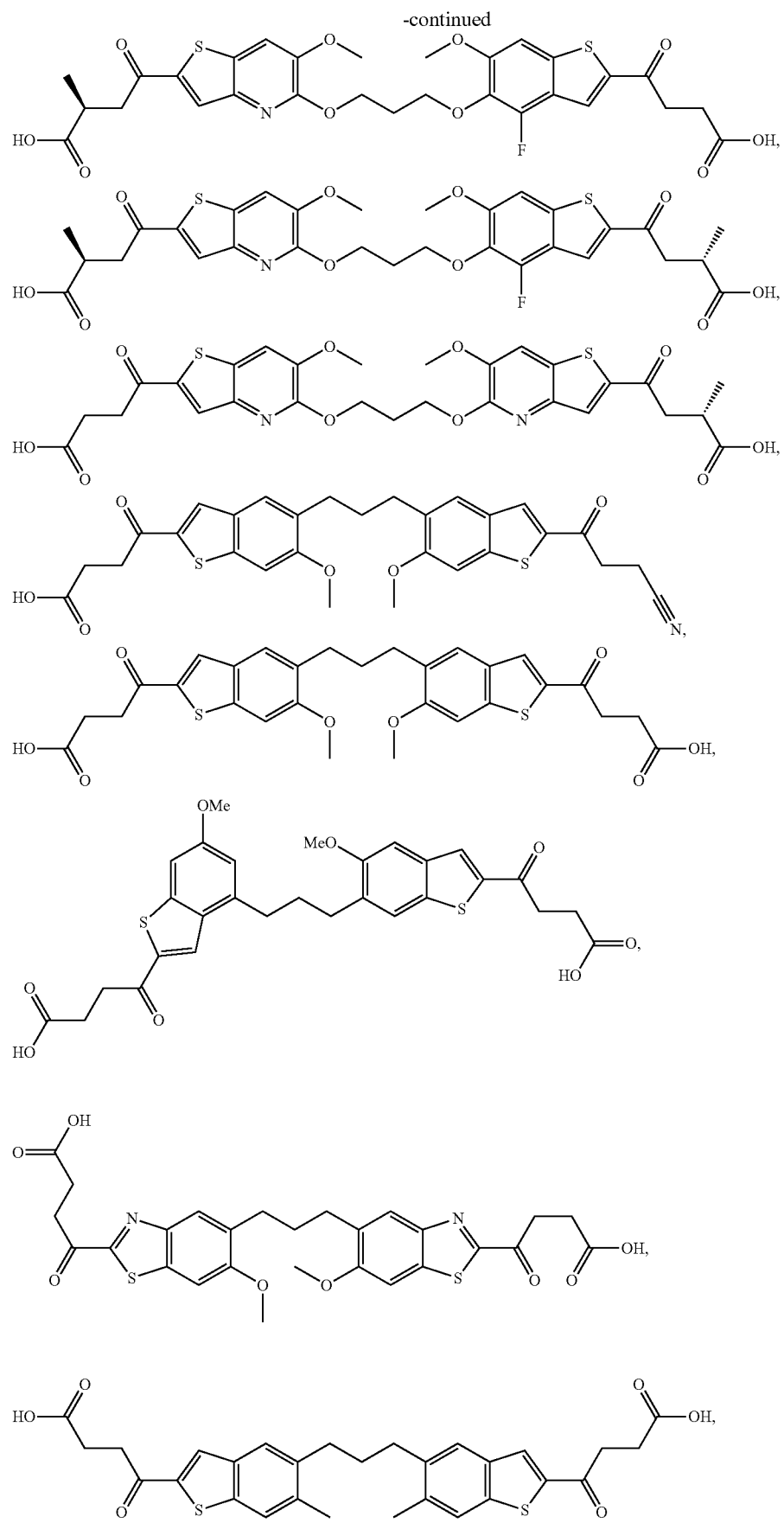

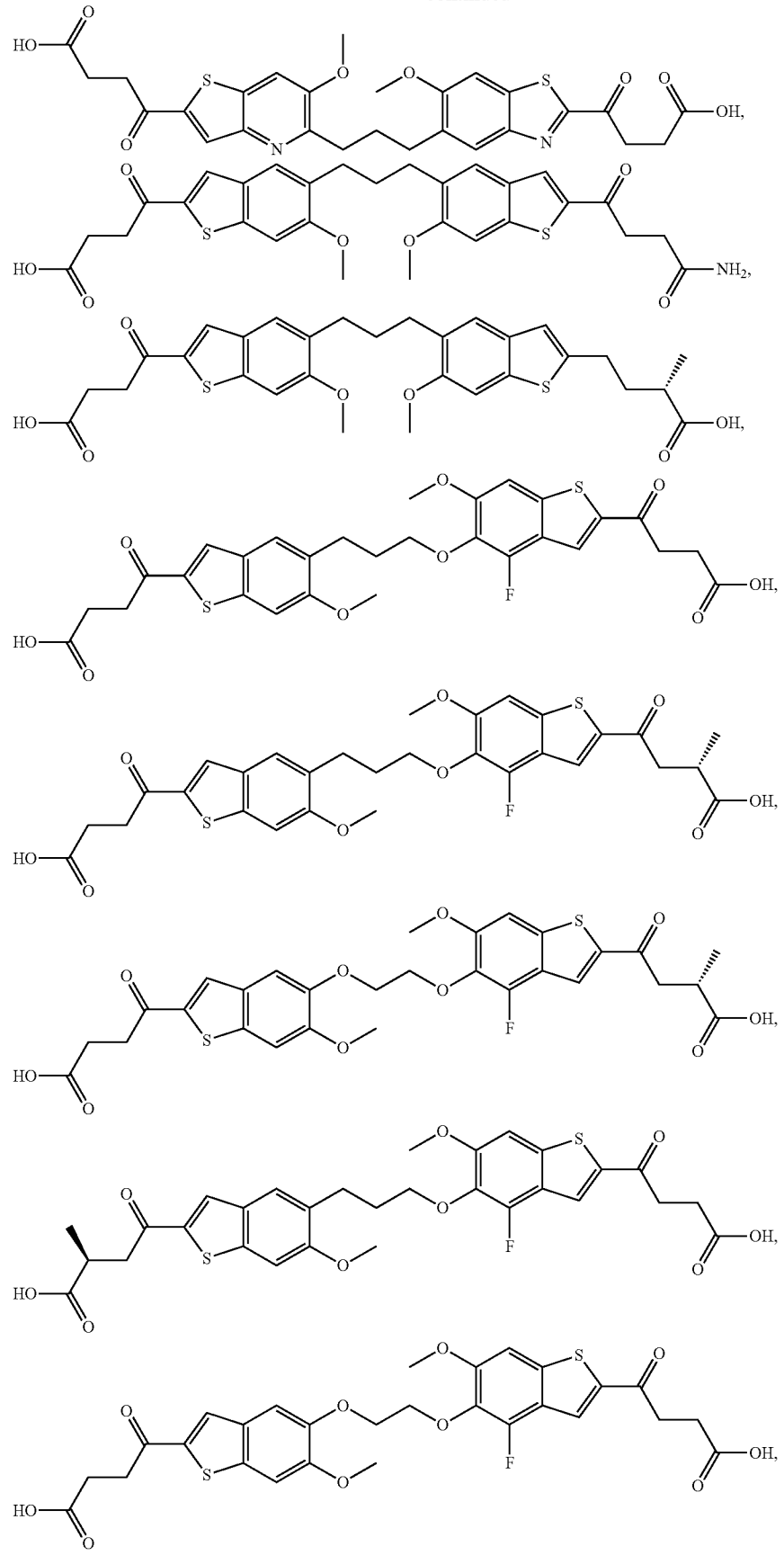

-continued
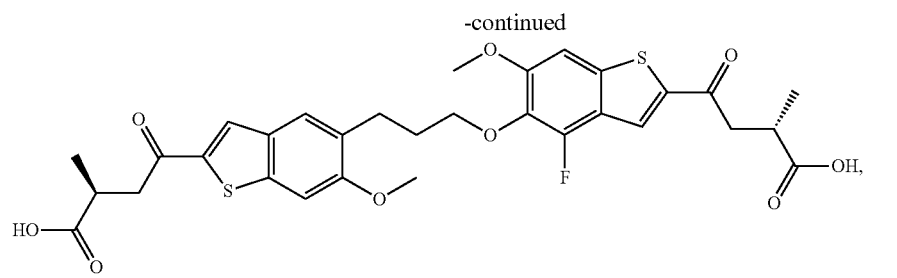
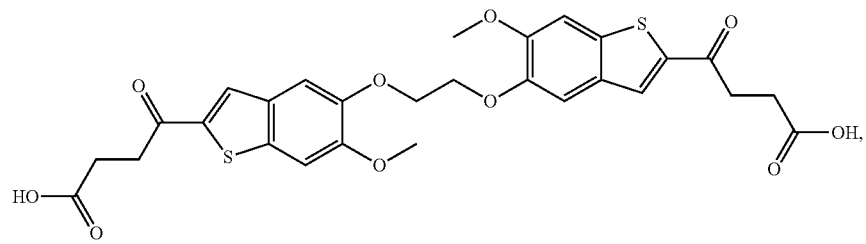
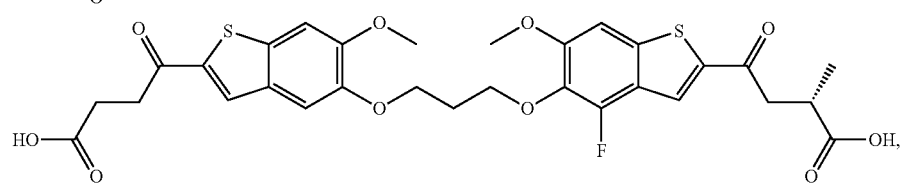
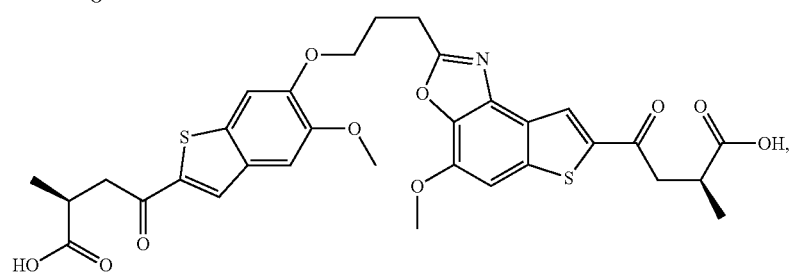
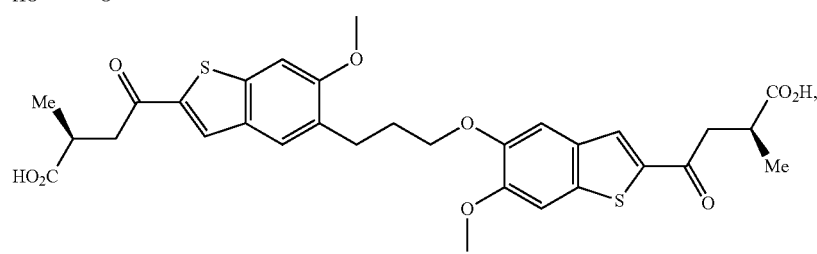
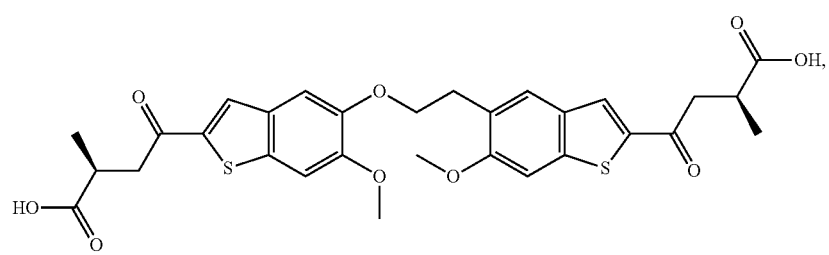
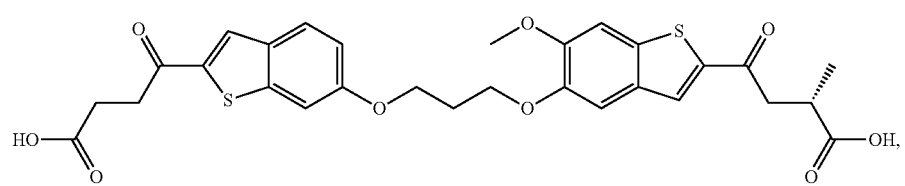

-continued
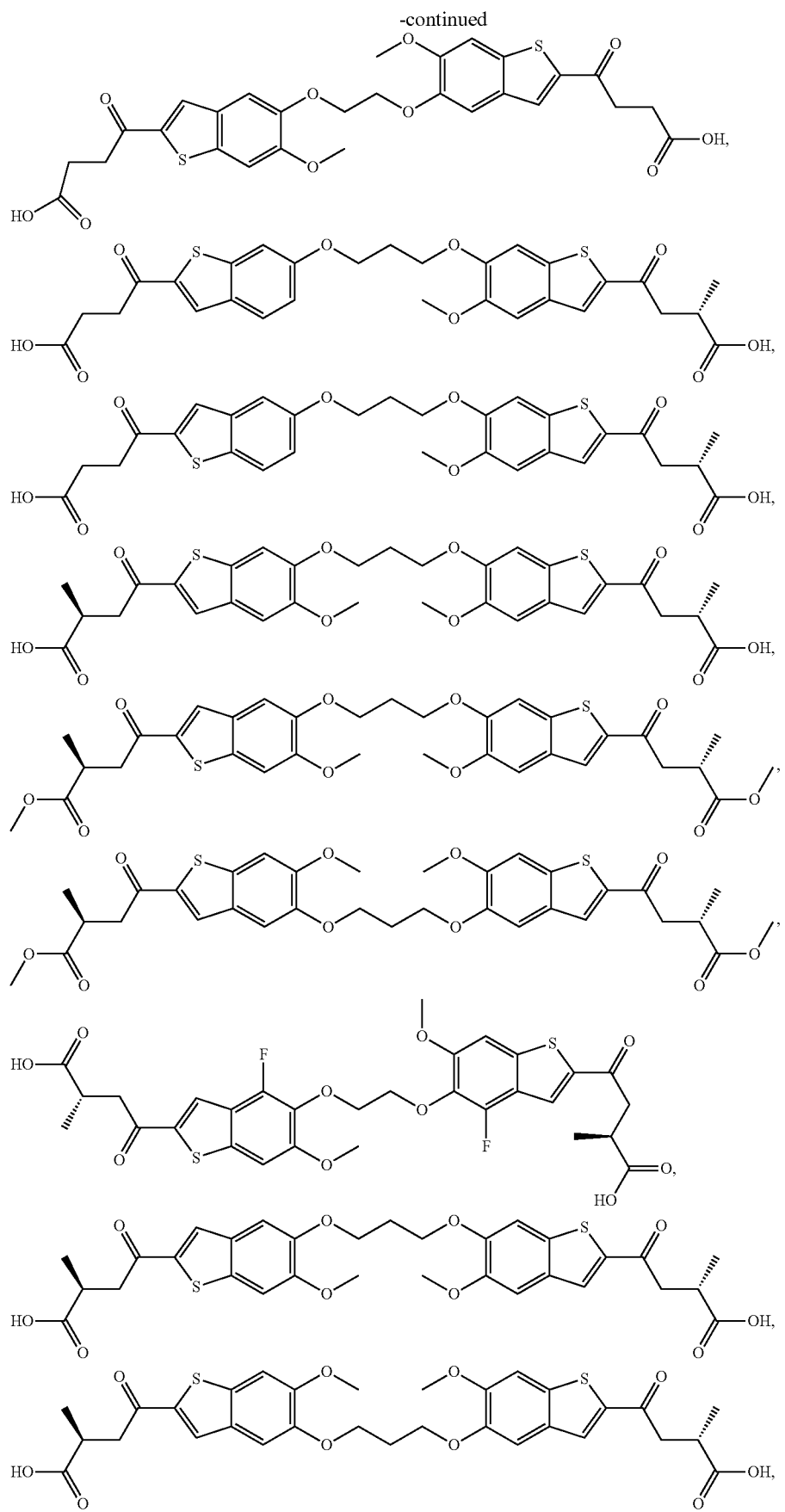

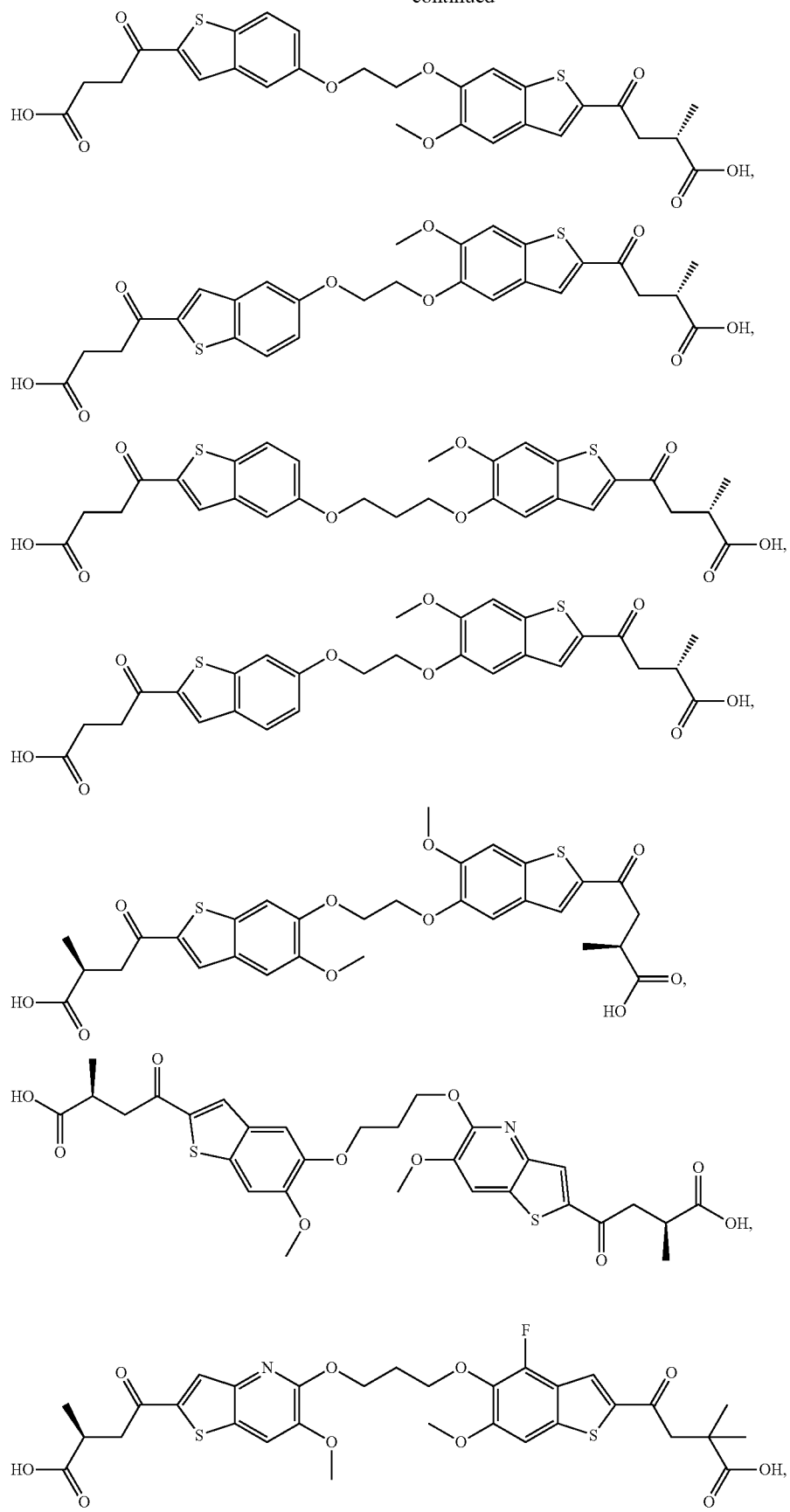

-continued
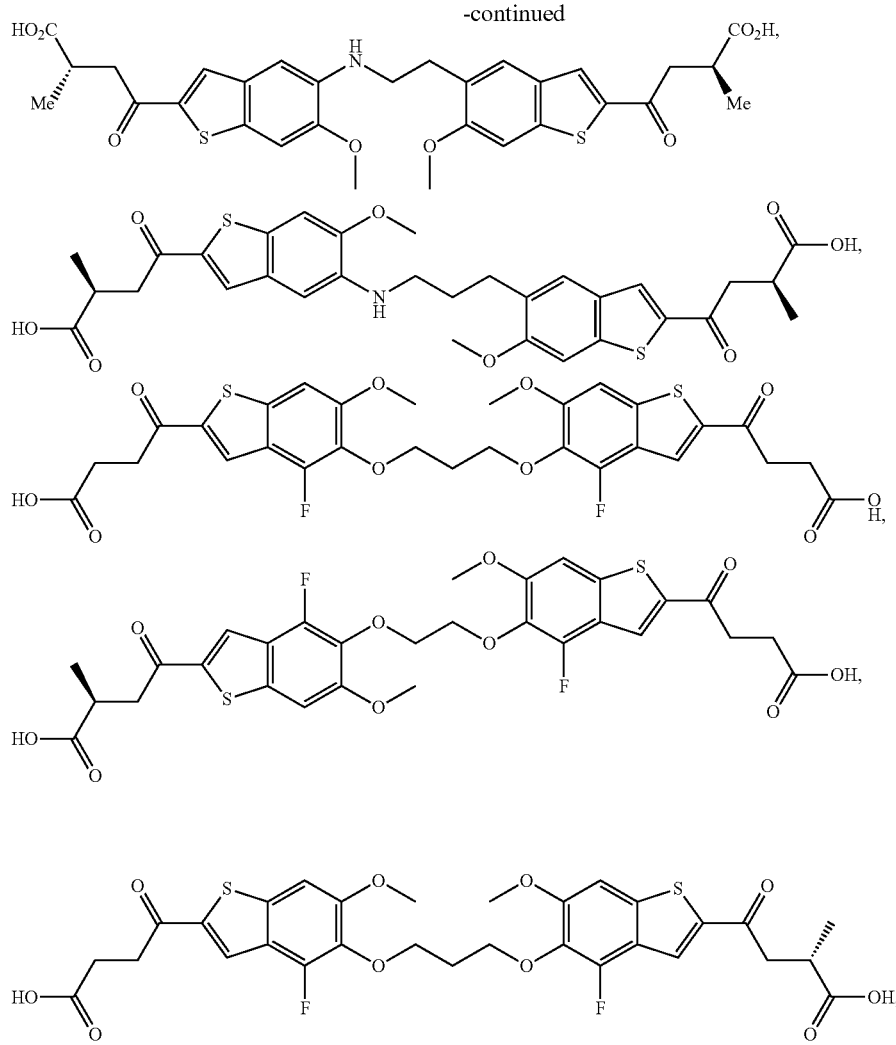
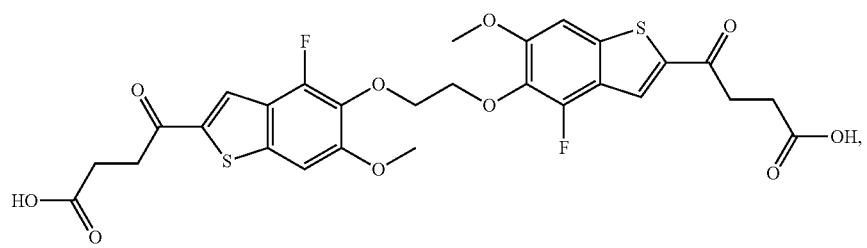
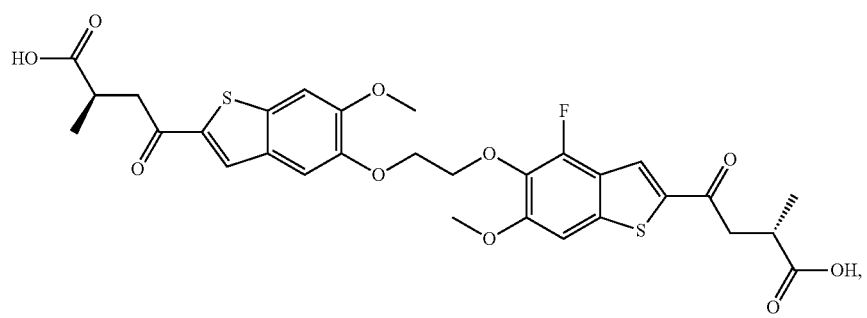

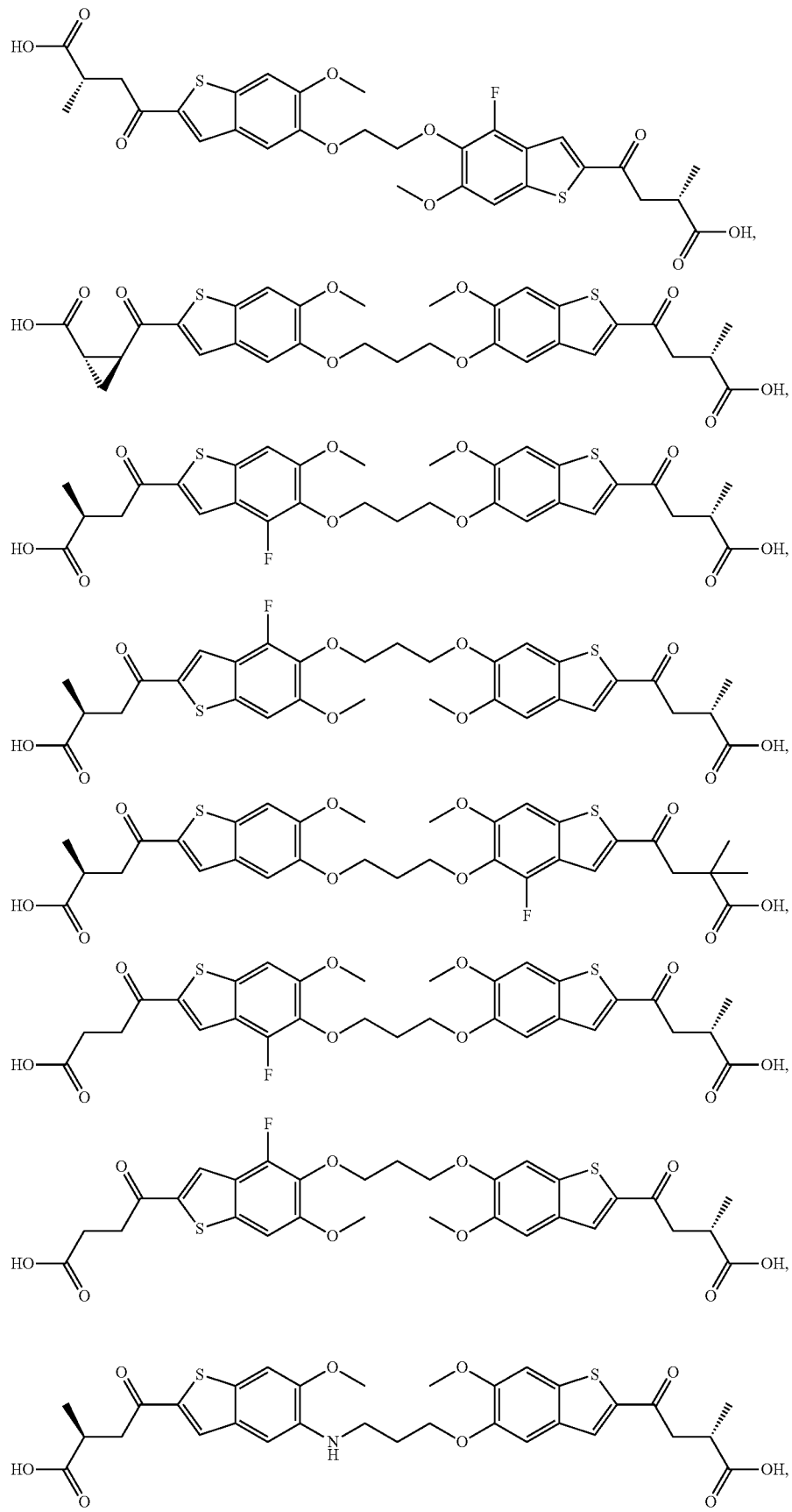

-continued
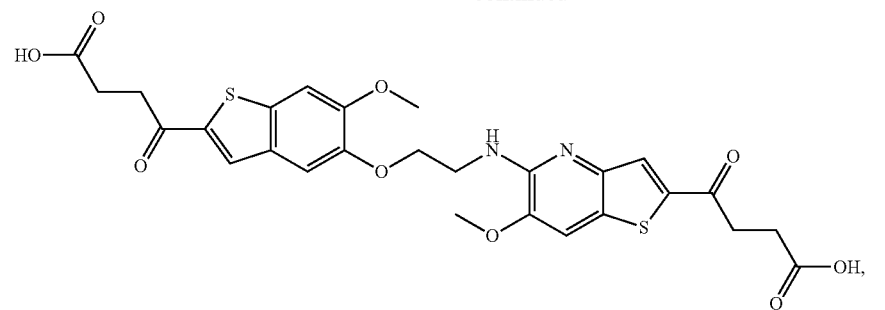
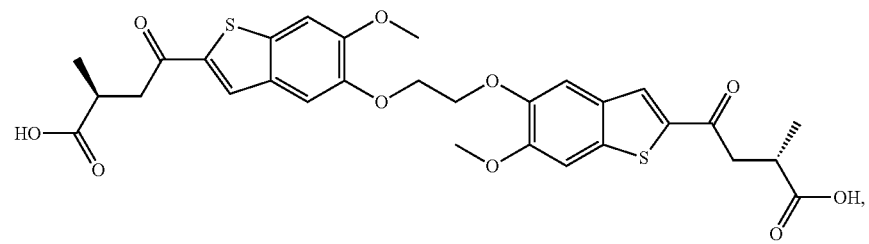
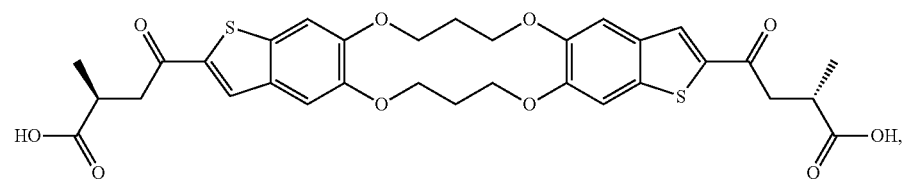
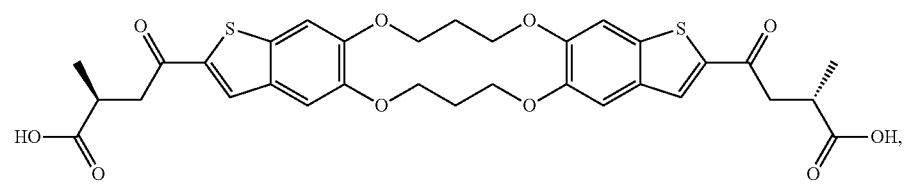
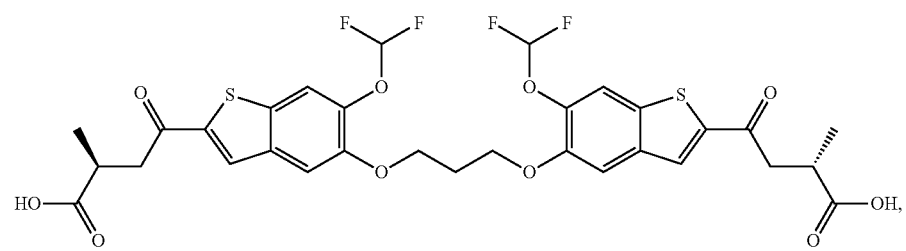
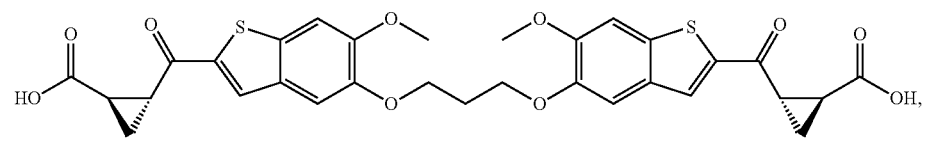
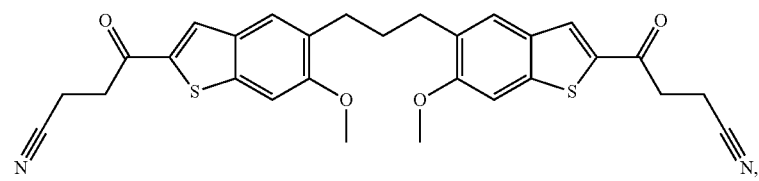
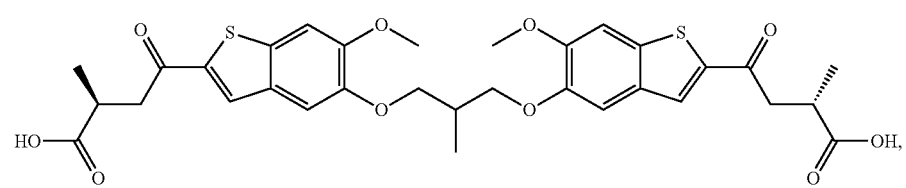

-continued
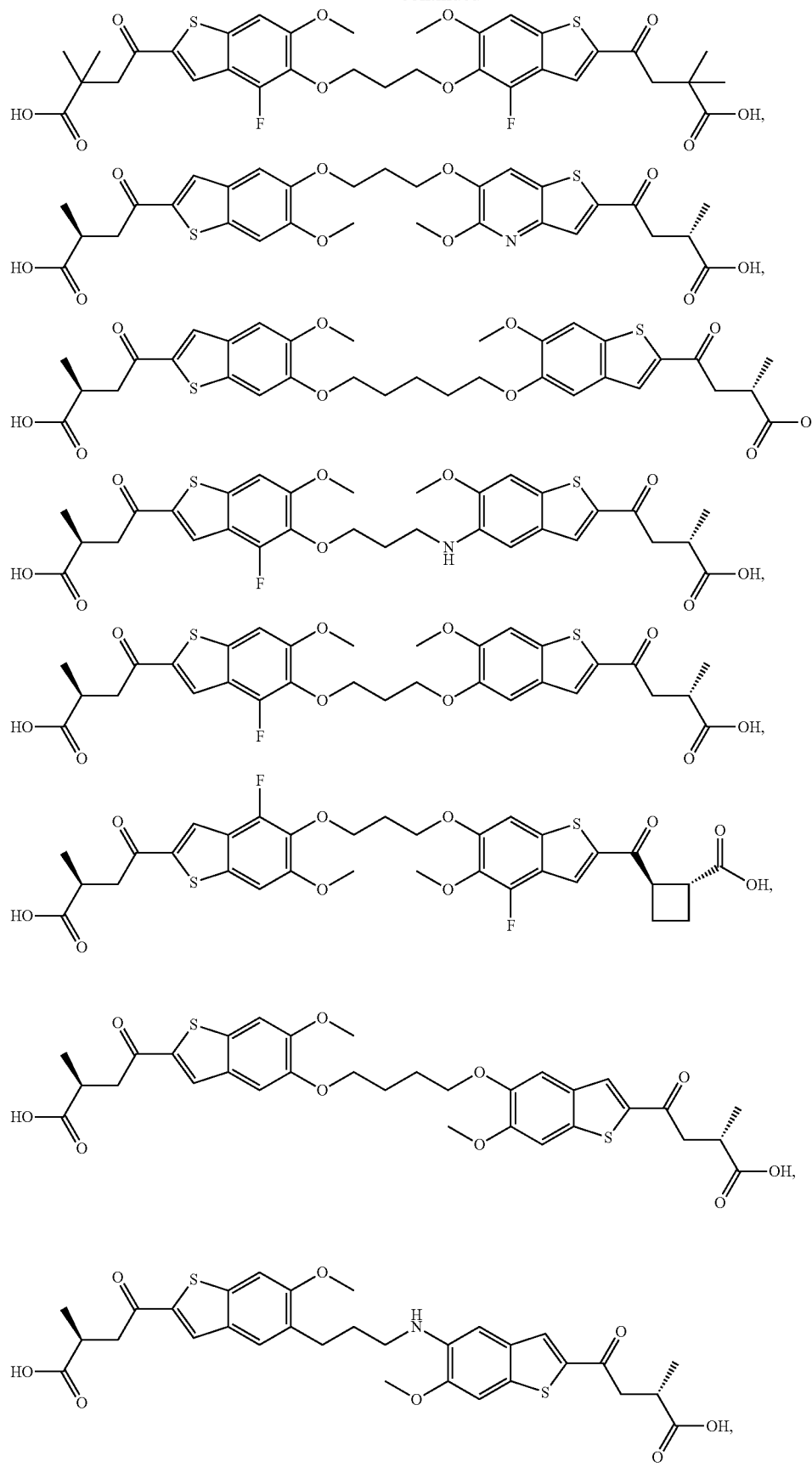

-continued
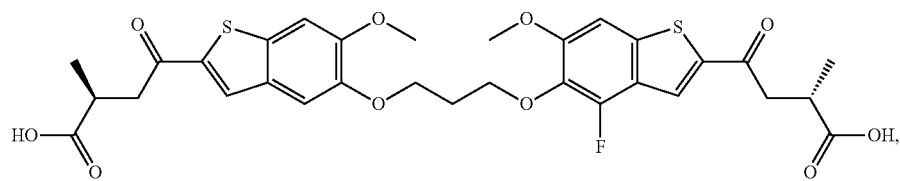
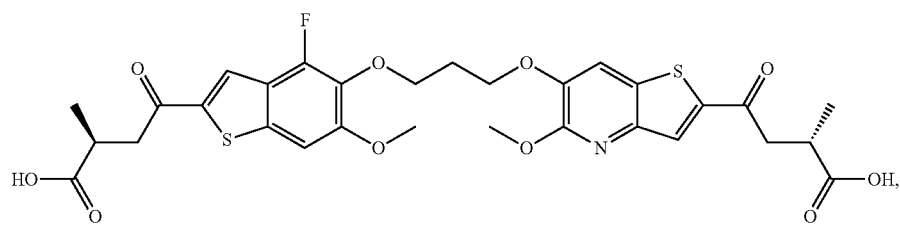
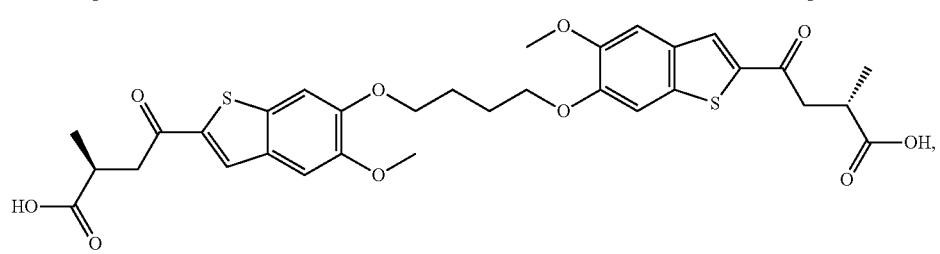
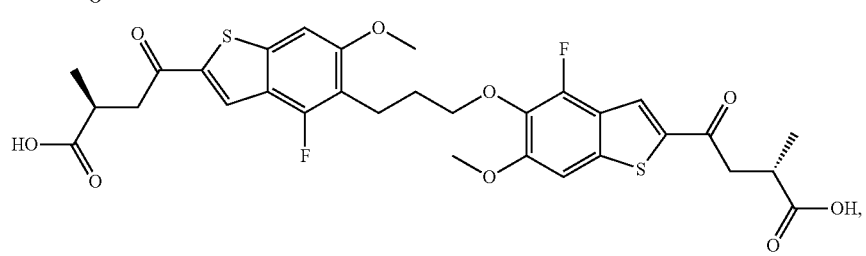
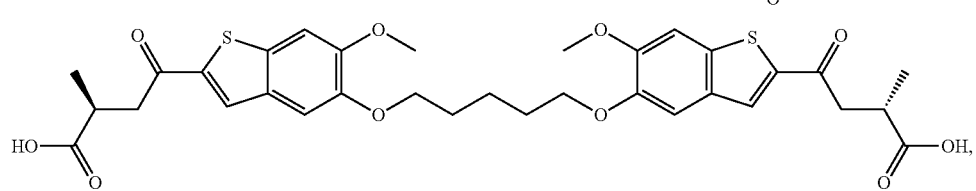
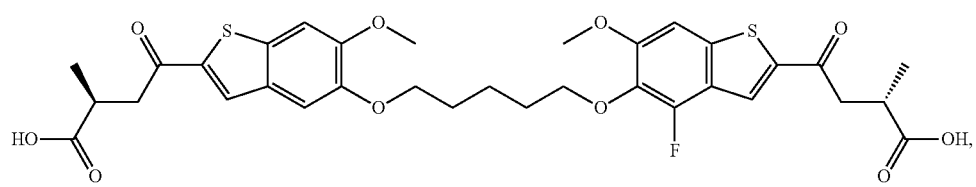
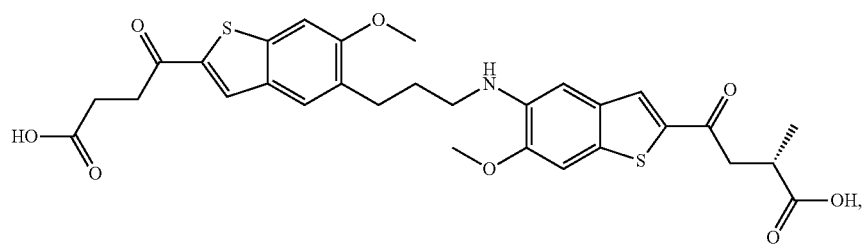
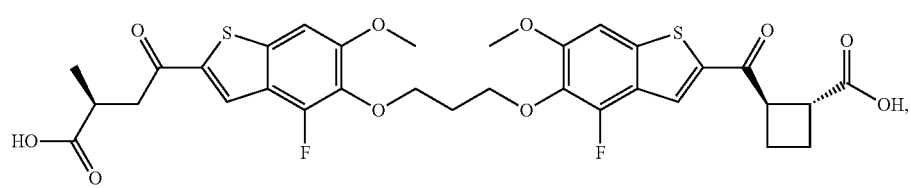

-continued
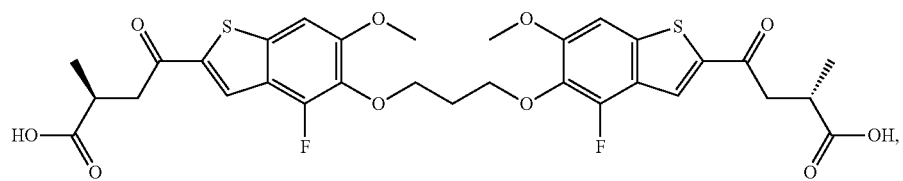
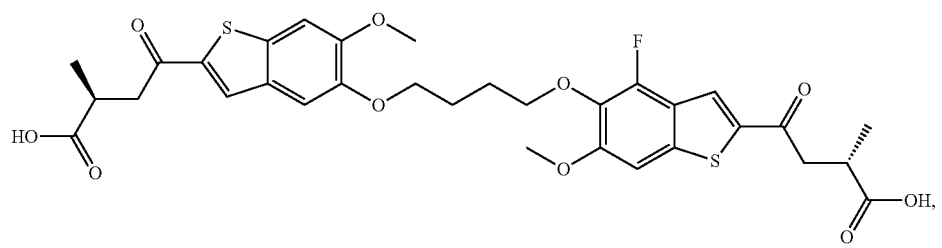
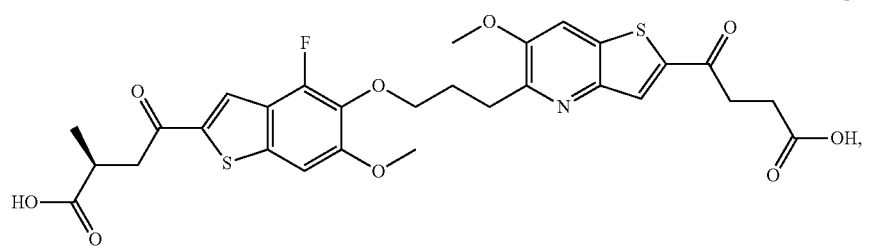
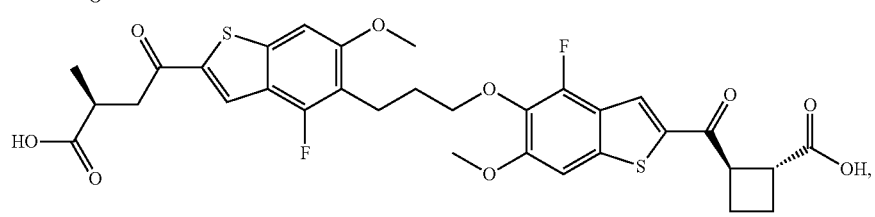
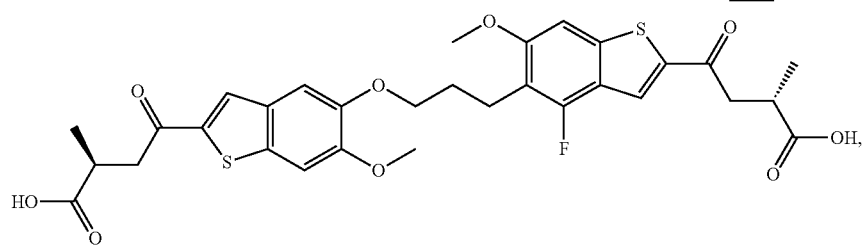
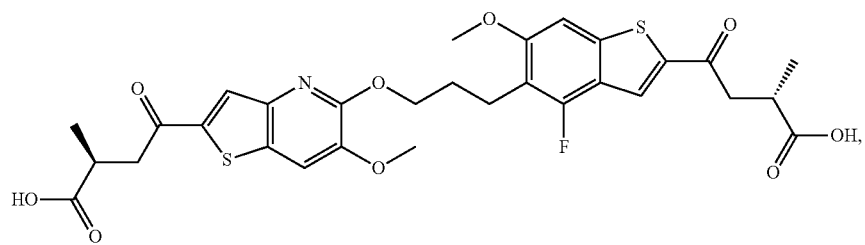
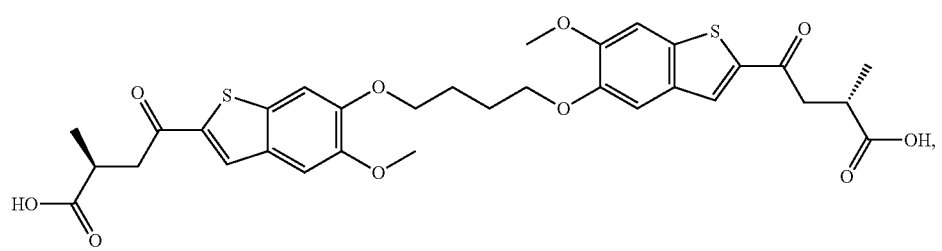

-continued
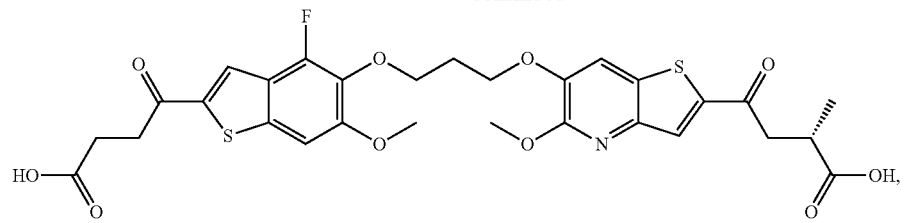
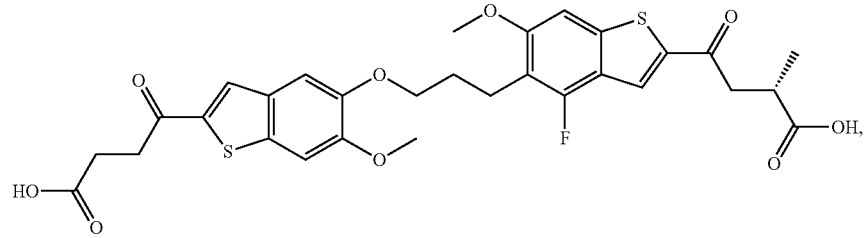
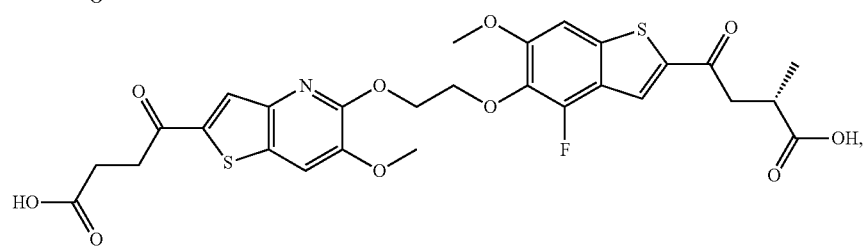
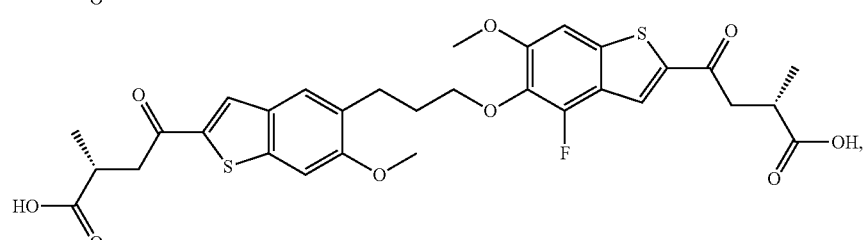
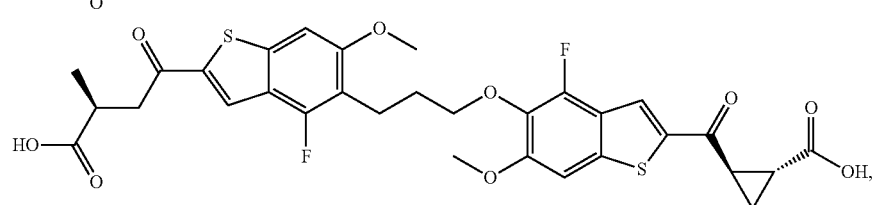
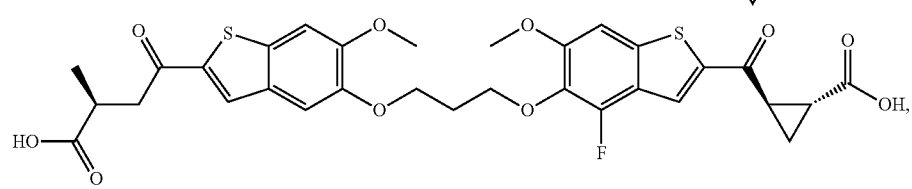
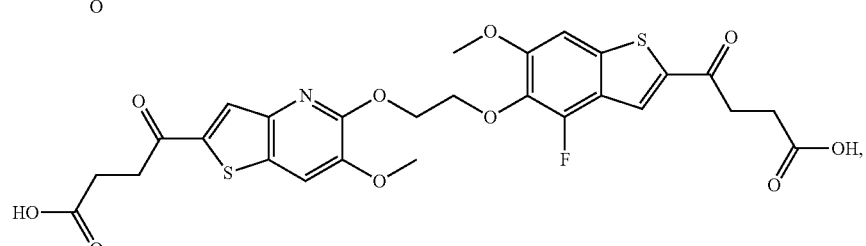
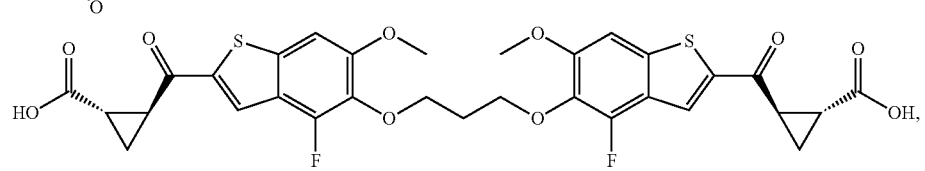

-continued
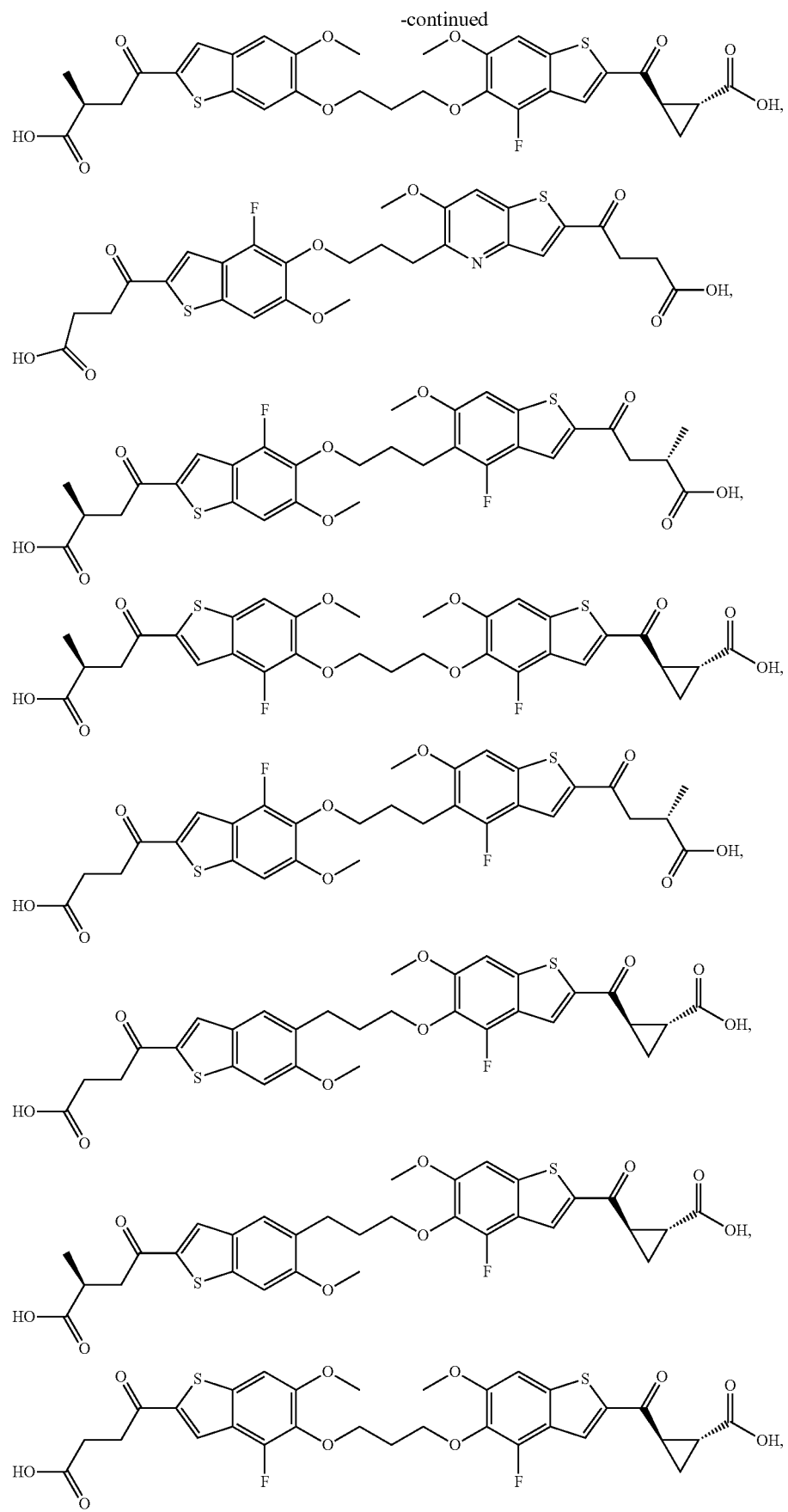

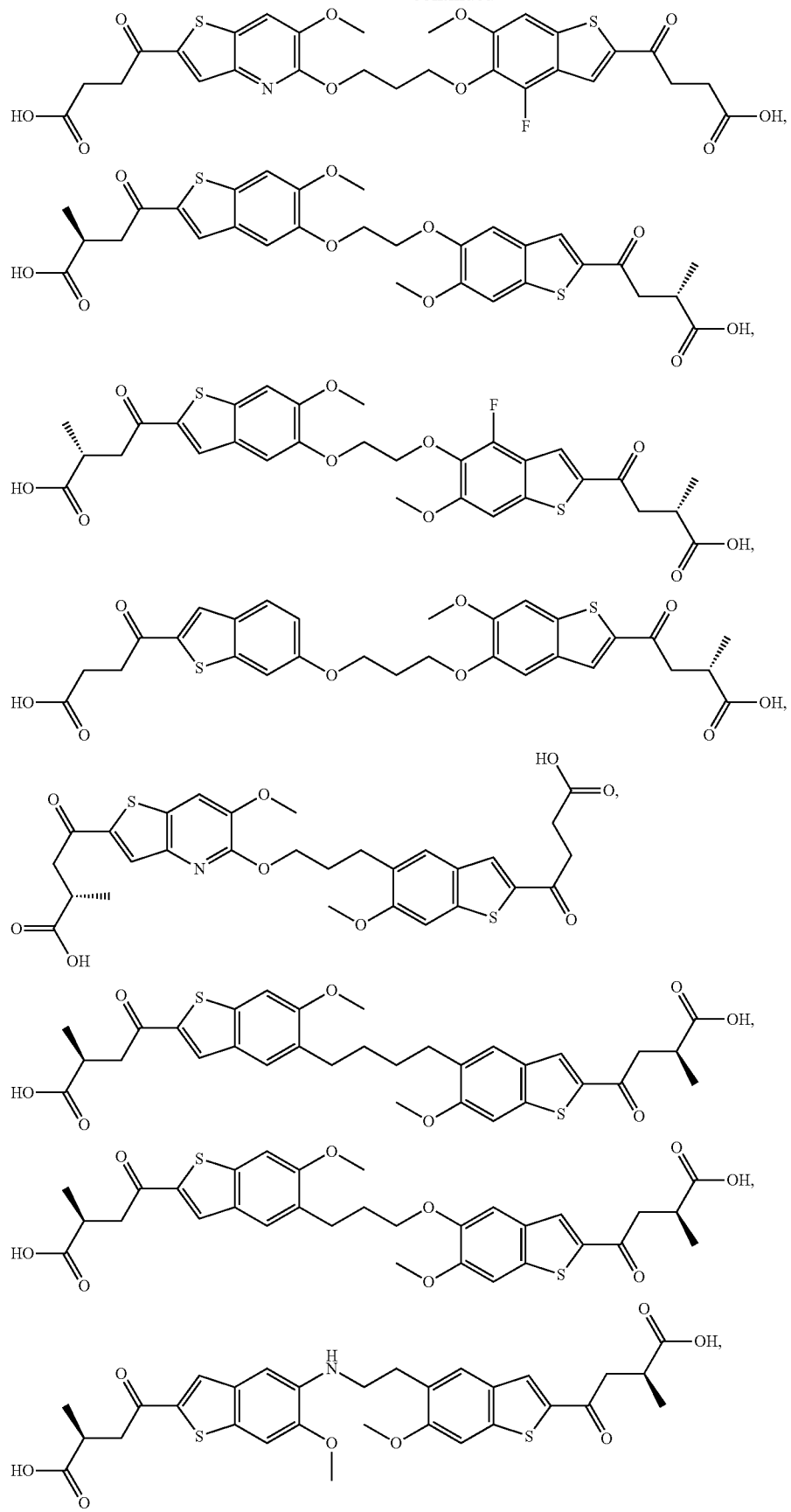

-continued
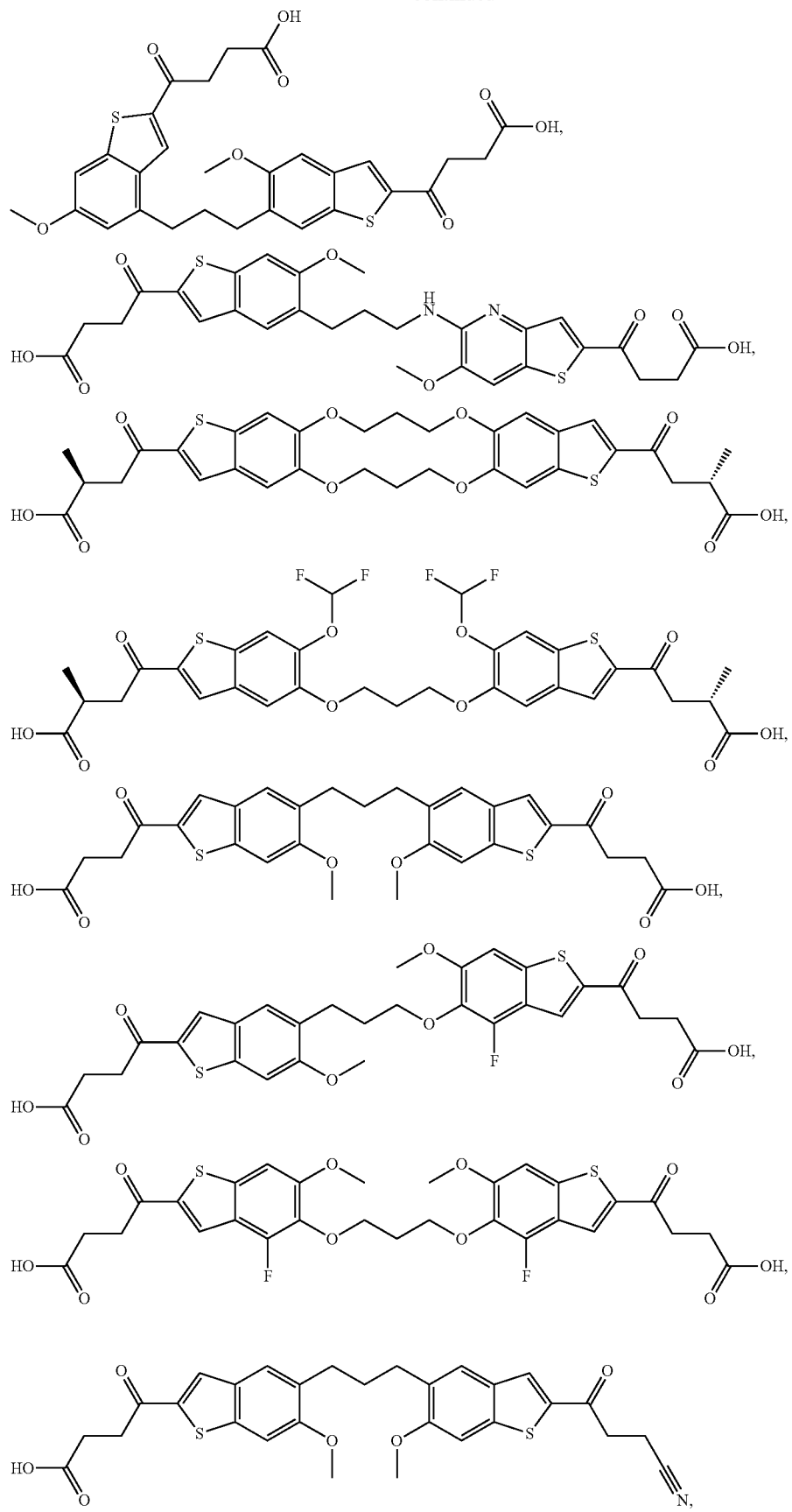

-continued
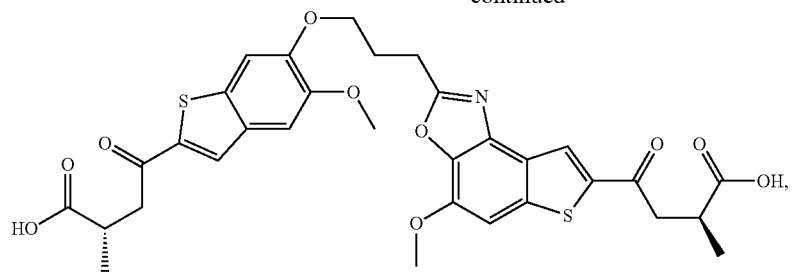
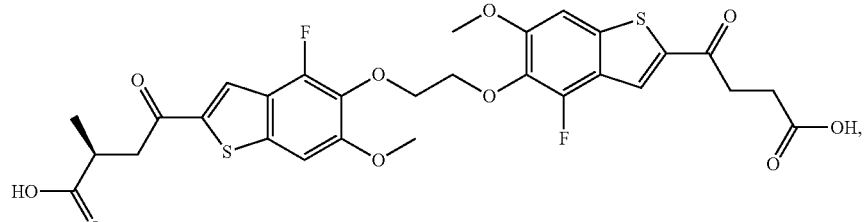
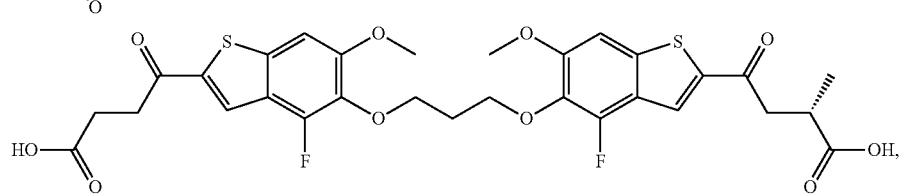
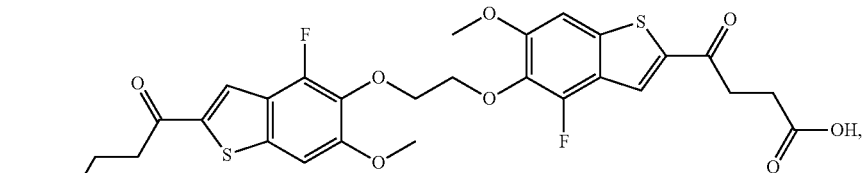
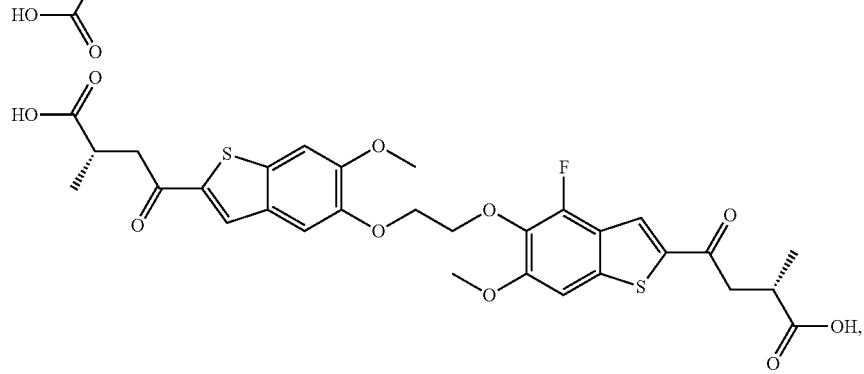
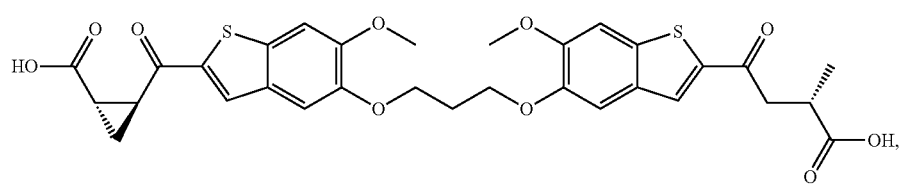
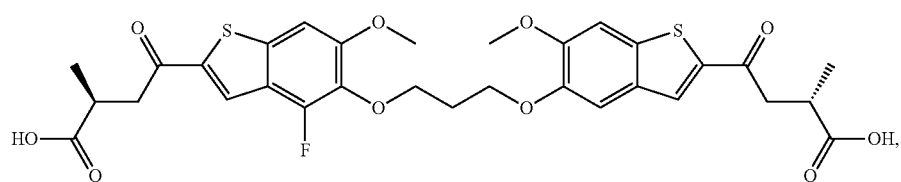

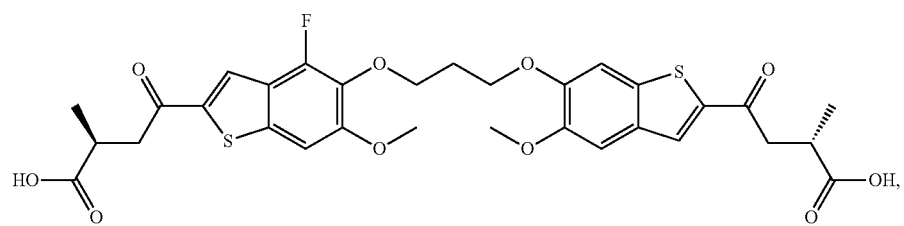
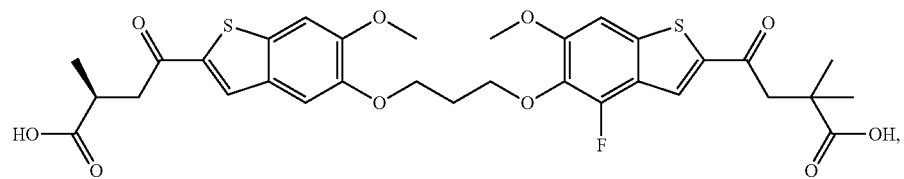
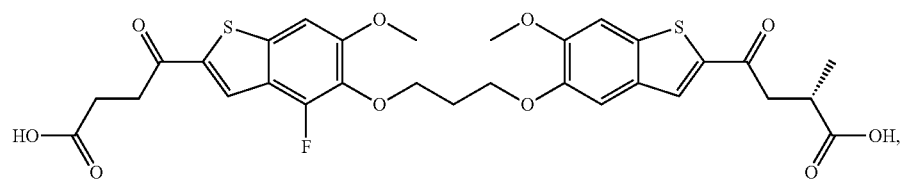
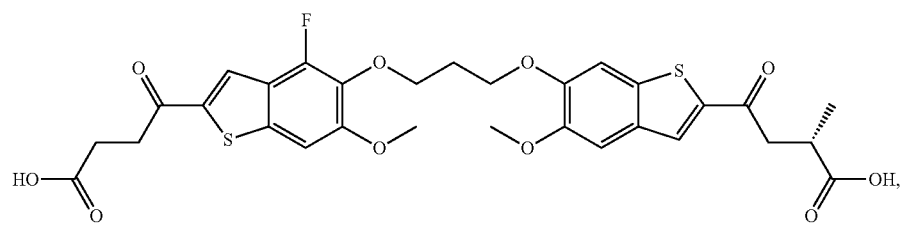
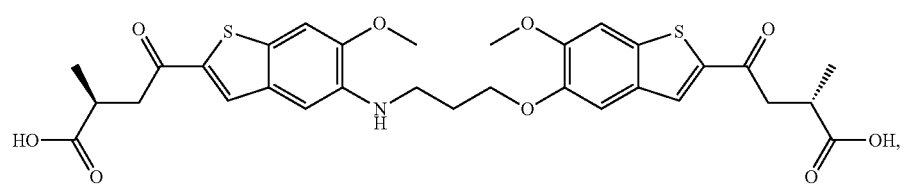
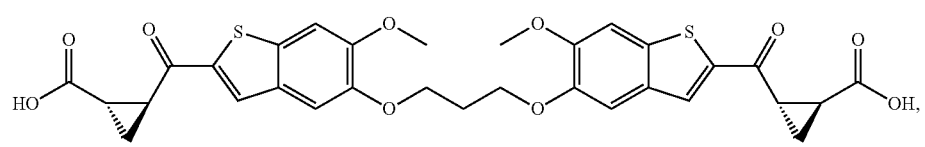
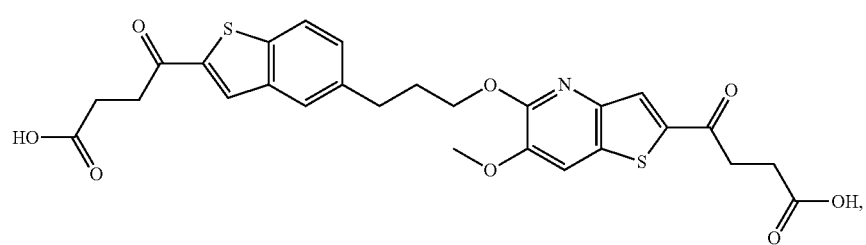
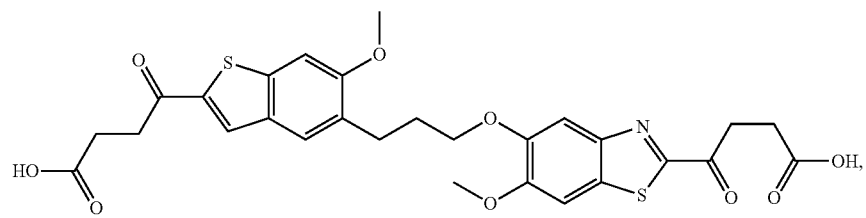

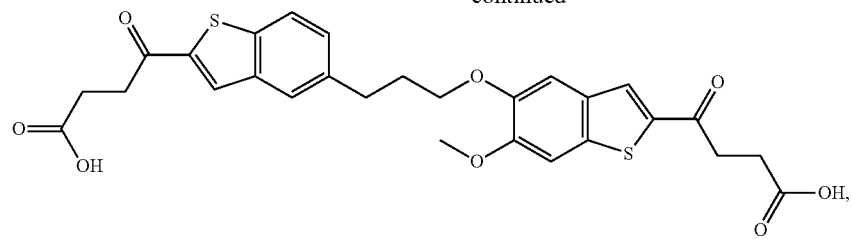
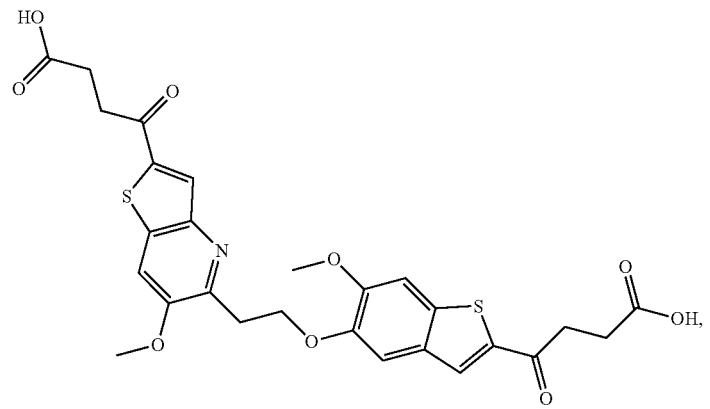
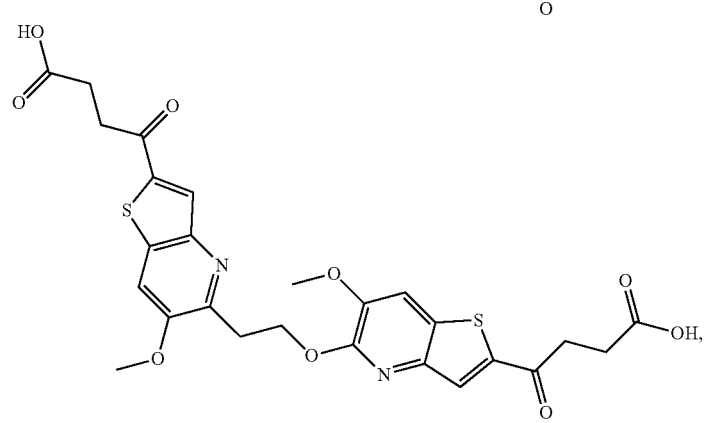
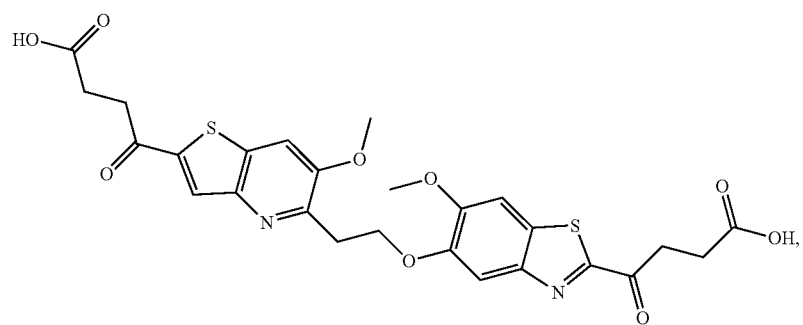
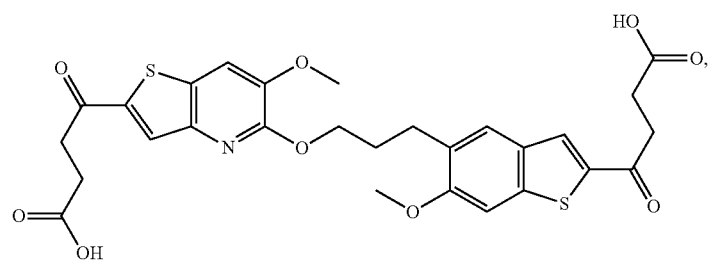

-continued
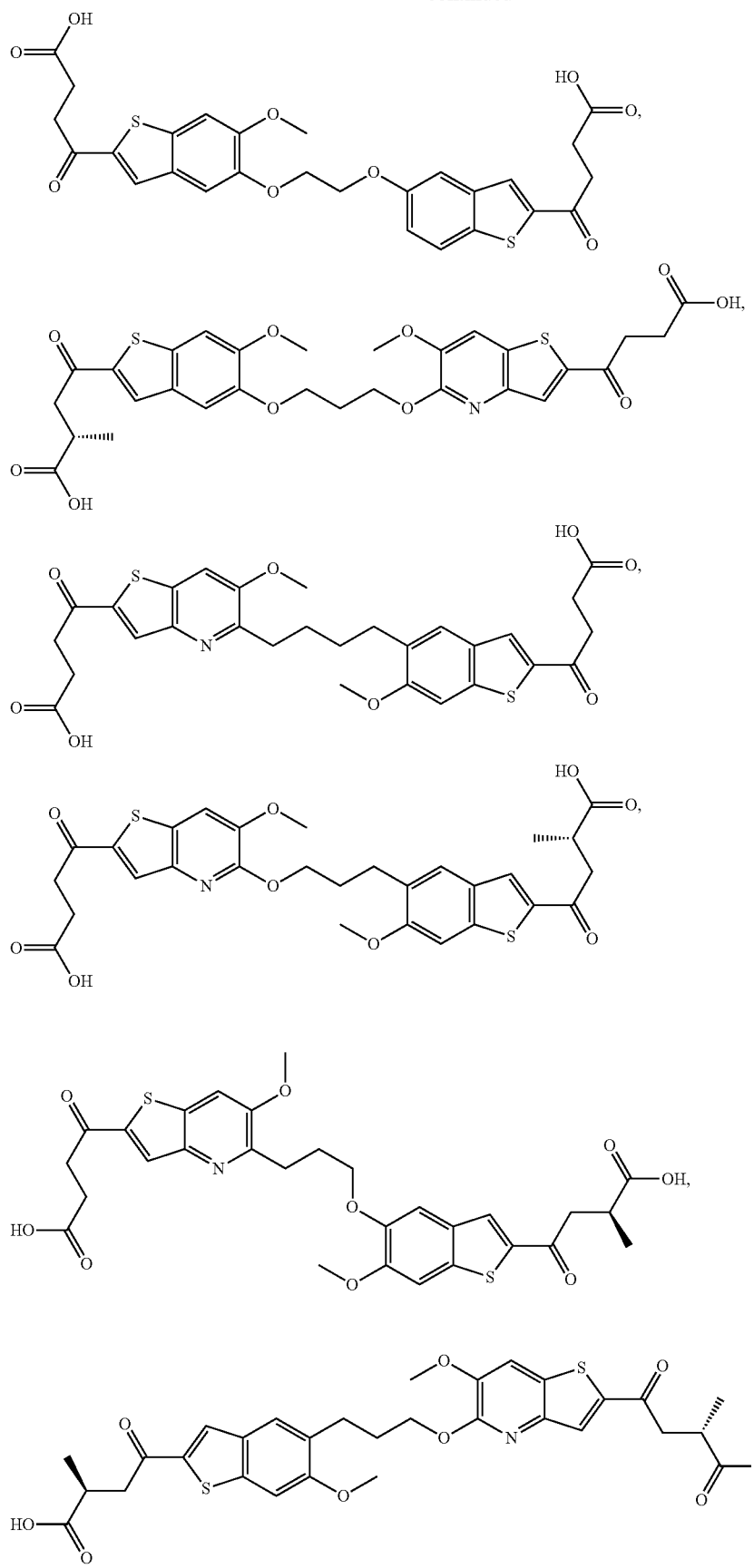

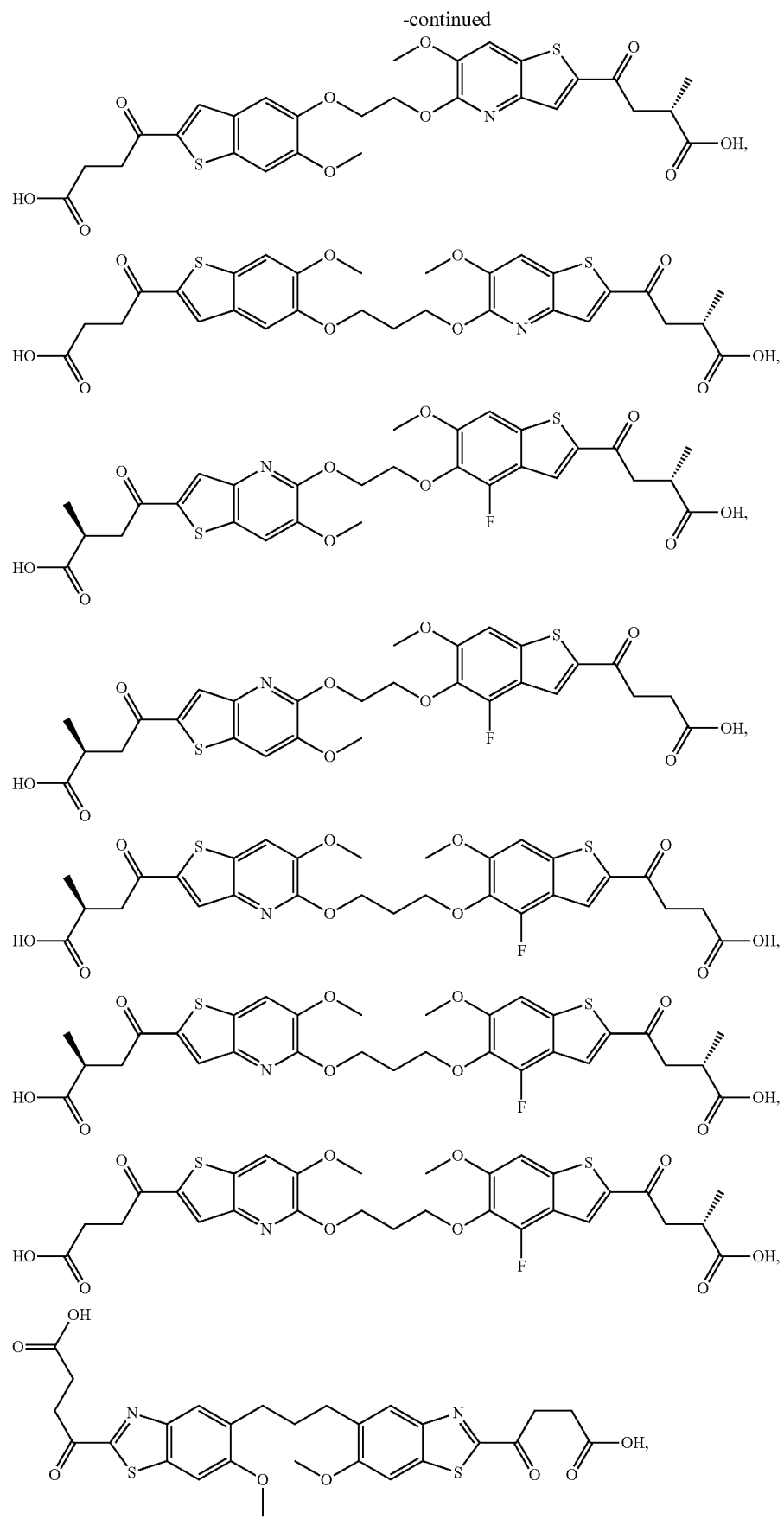

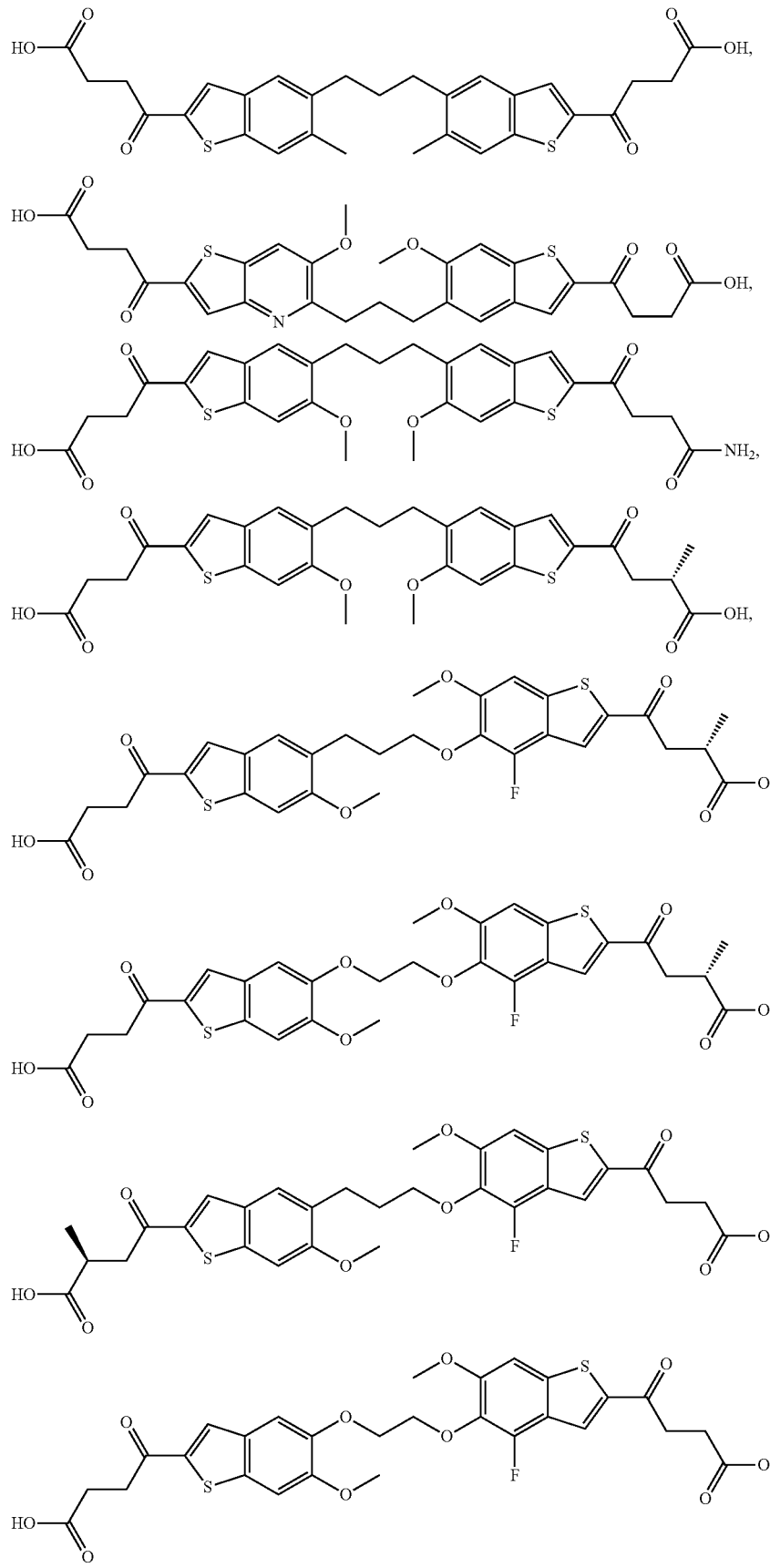

-continued
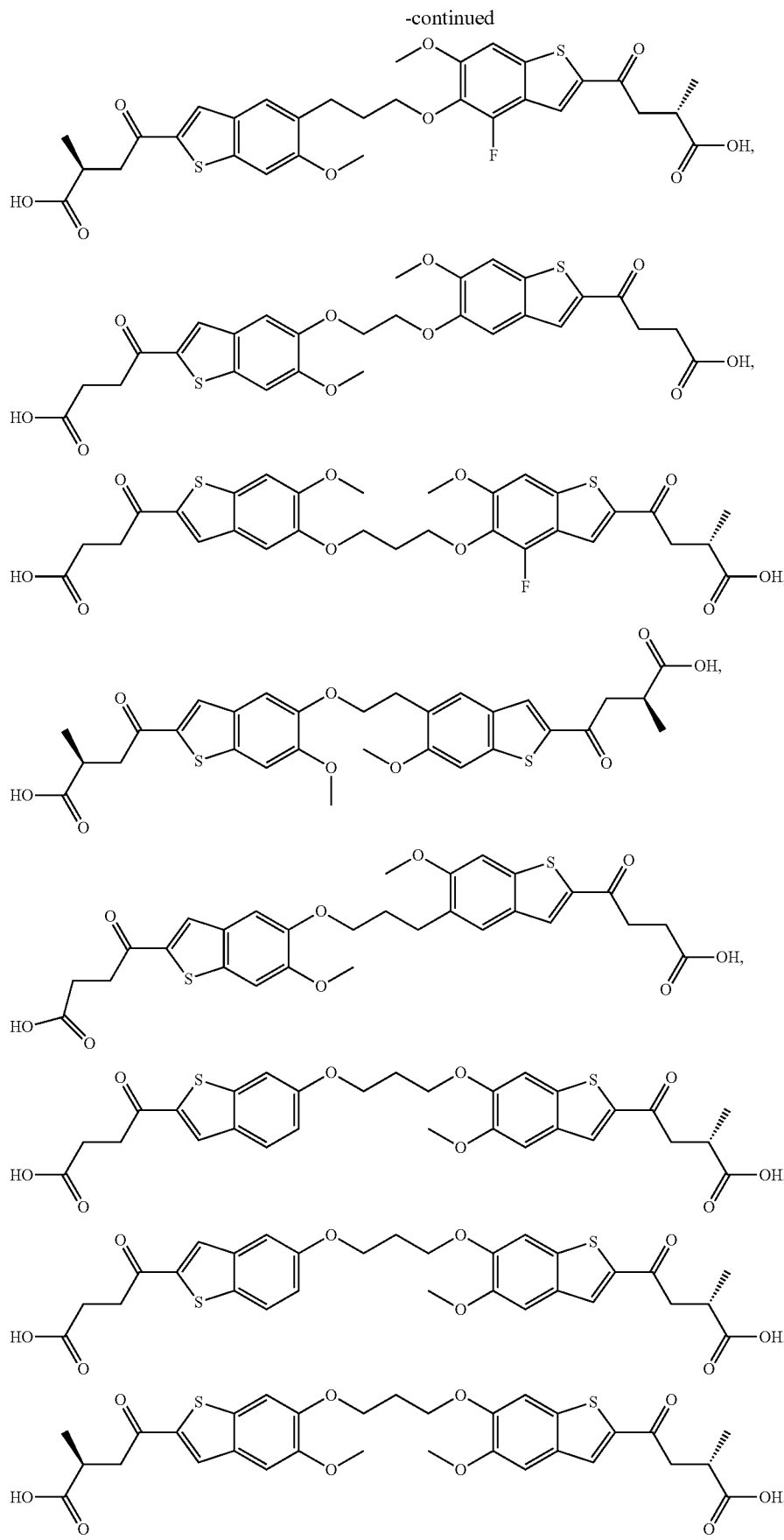

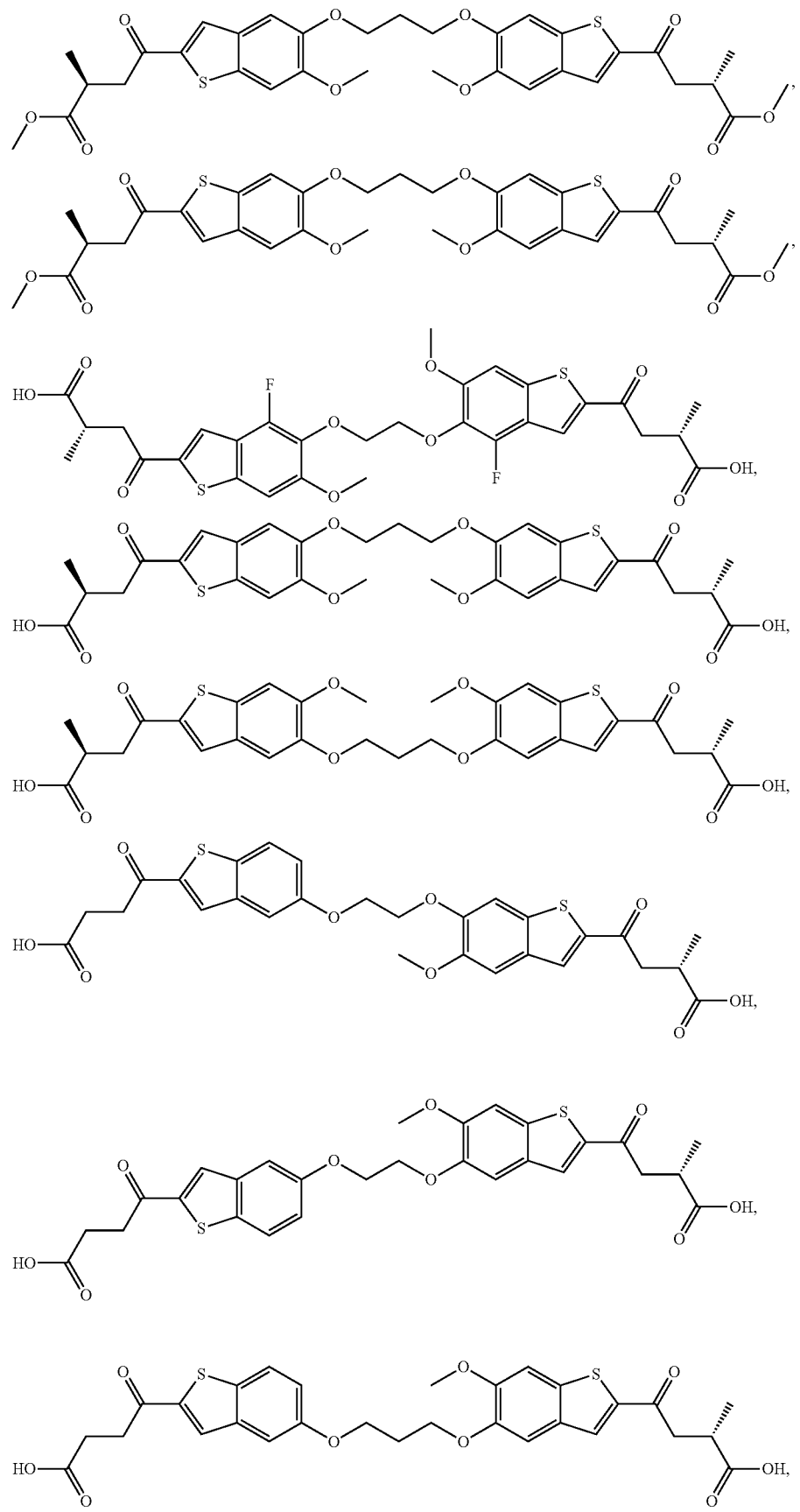

-continued
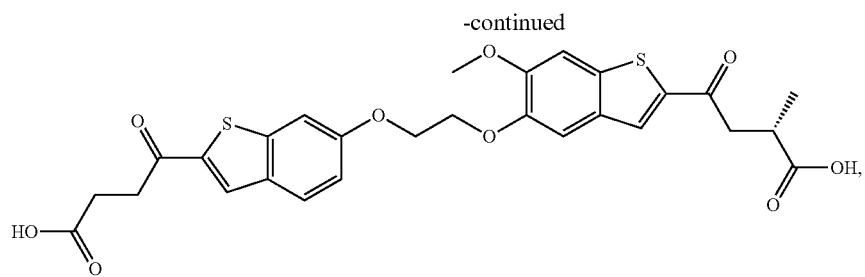
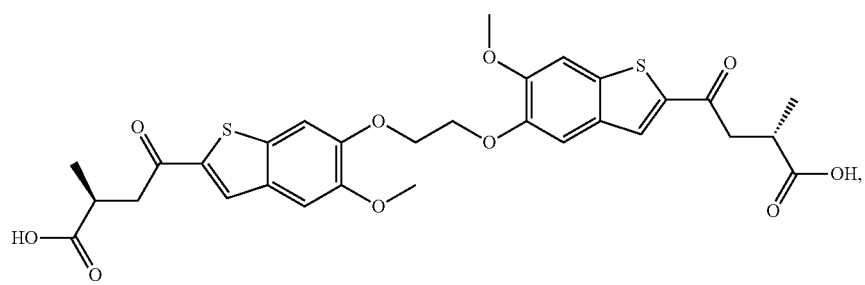
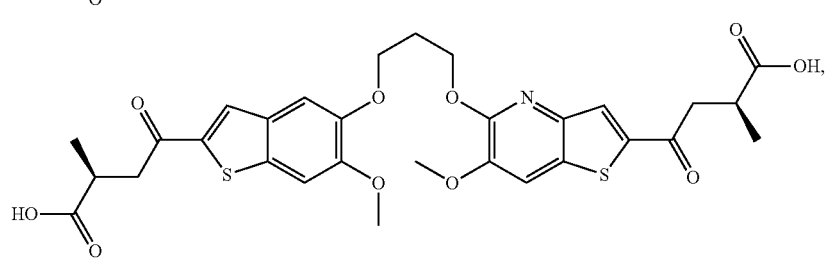
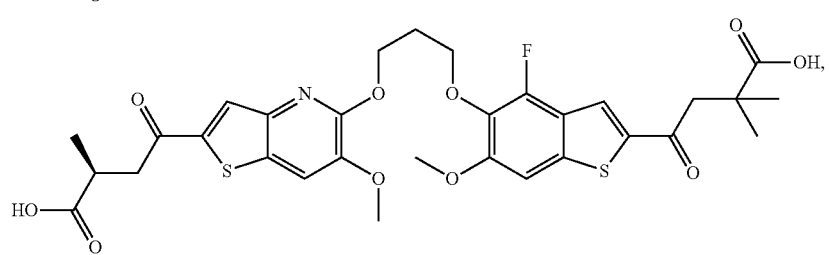
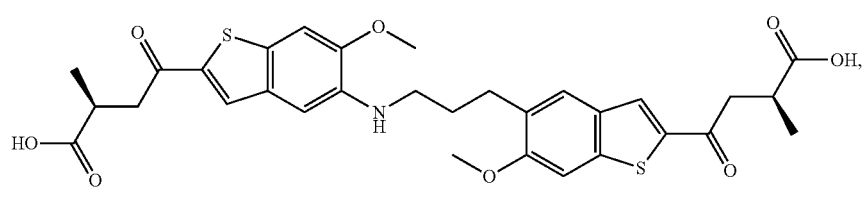
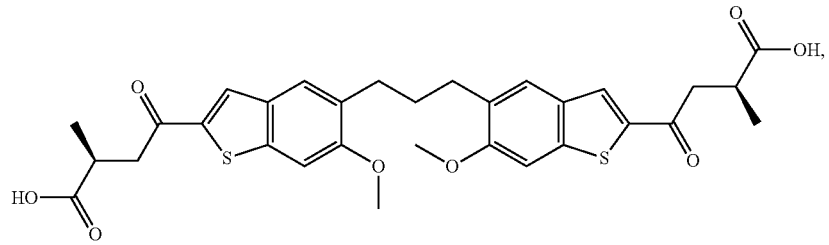
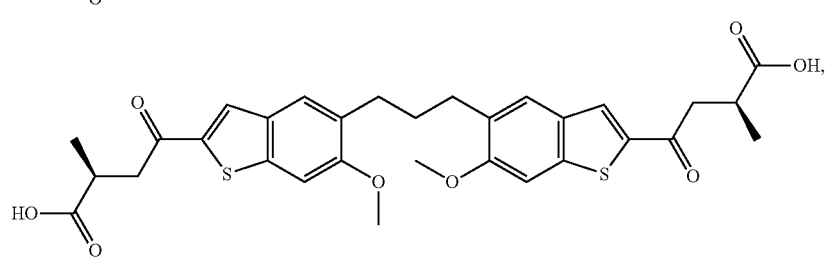

-continued
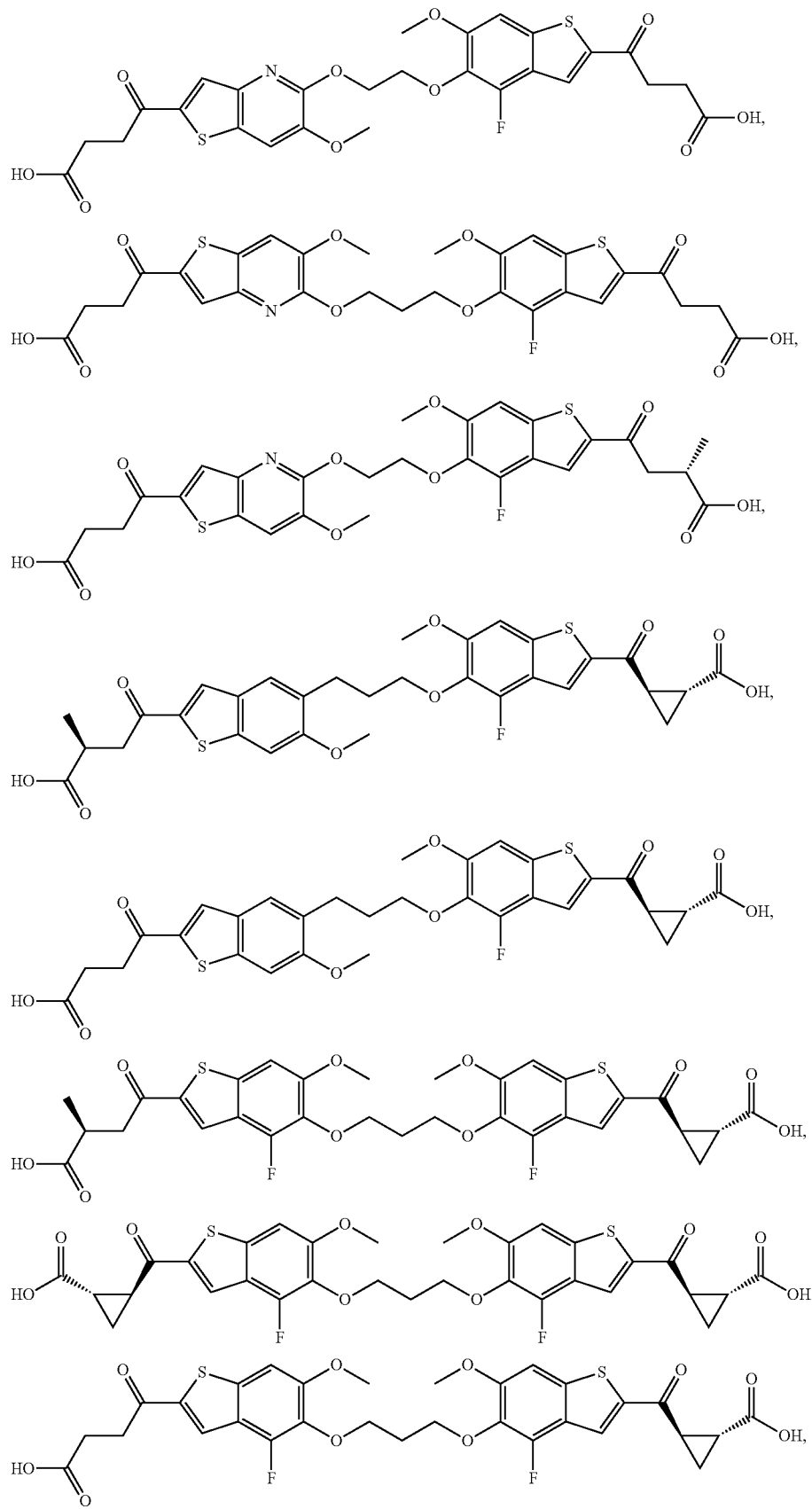

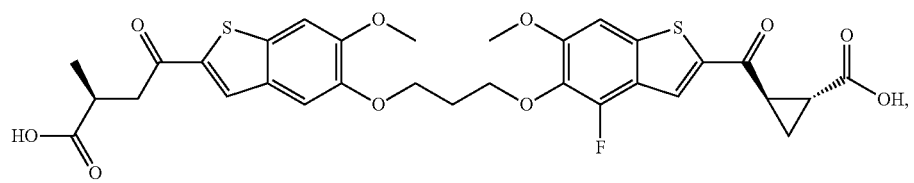
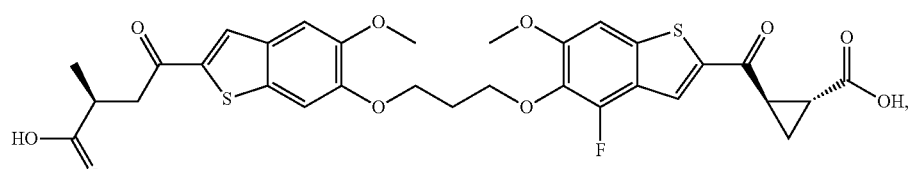
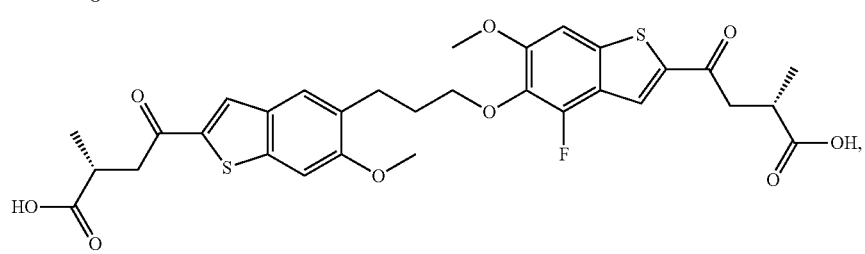
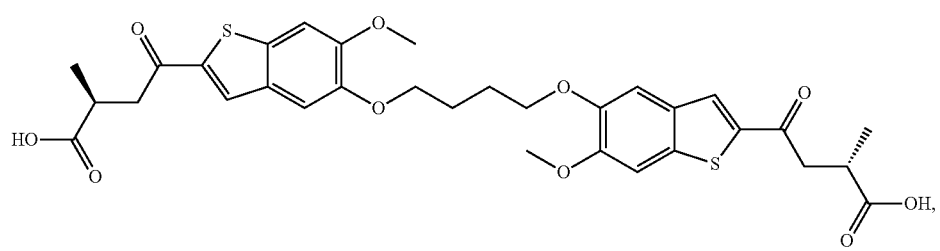
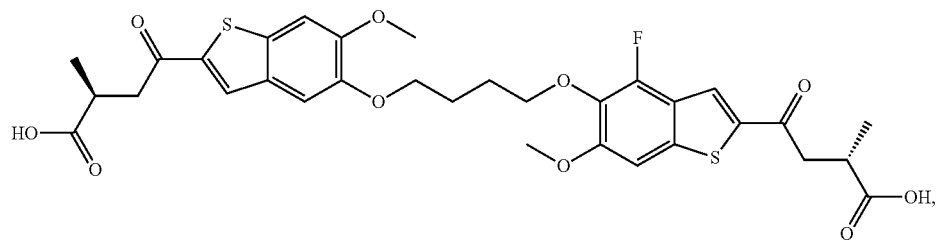
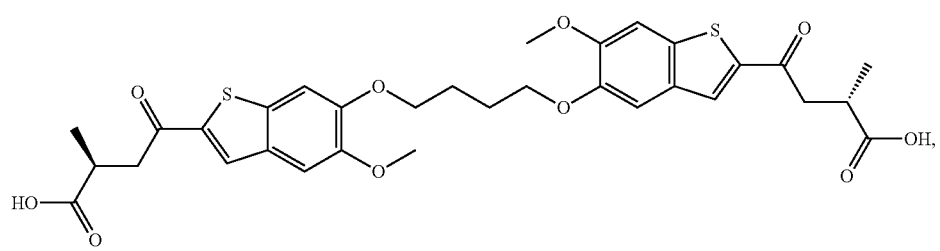
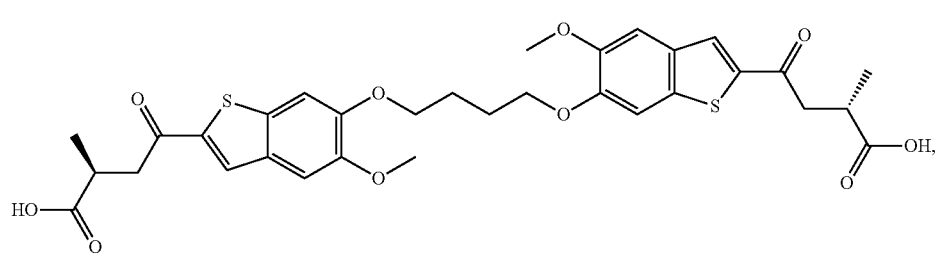

-continued
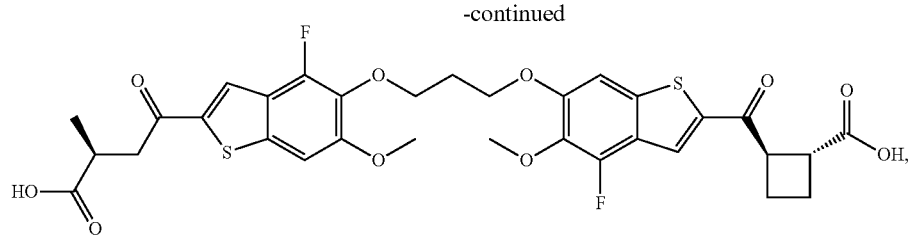
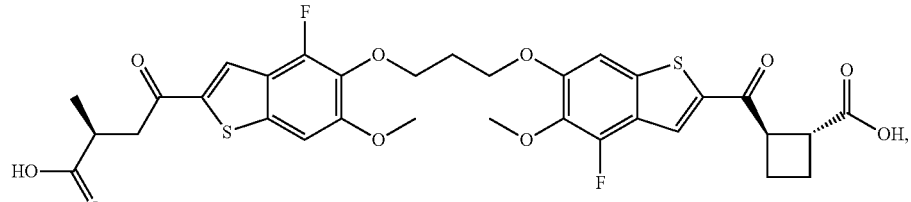
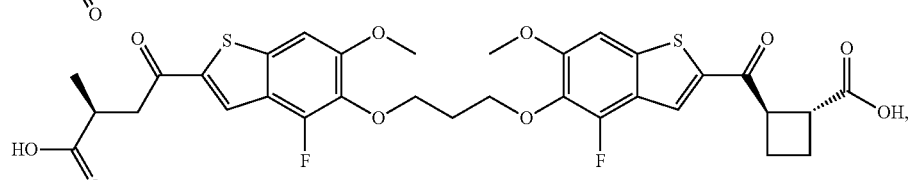
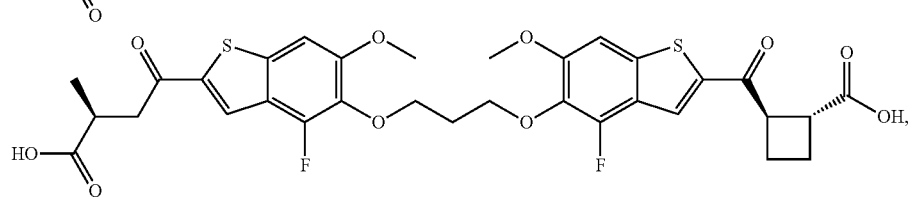
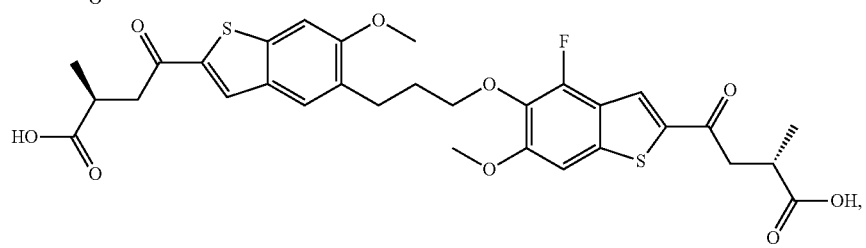
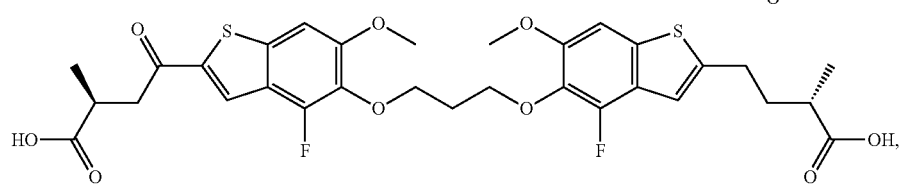
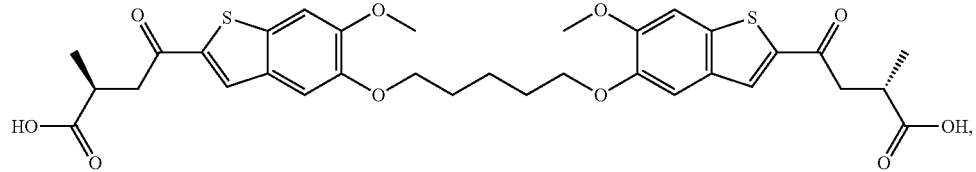
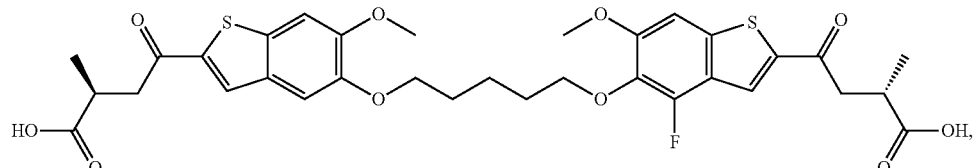
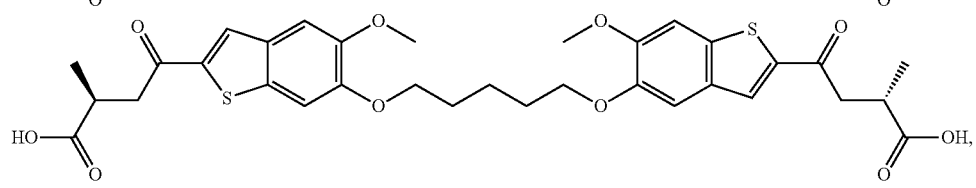

-continued
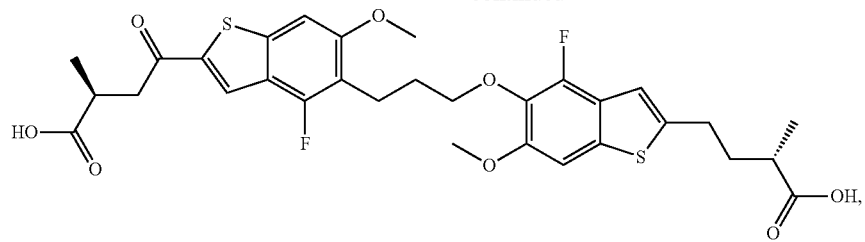
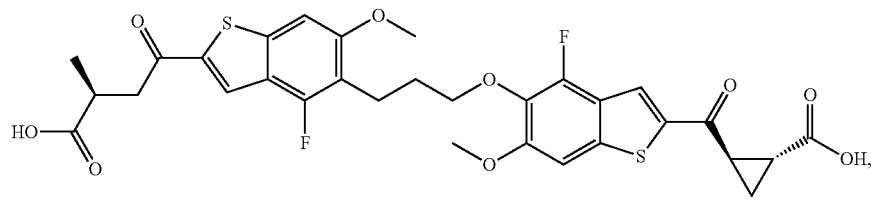
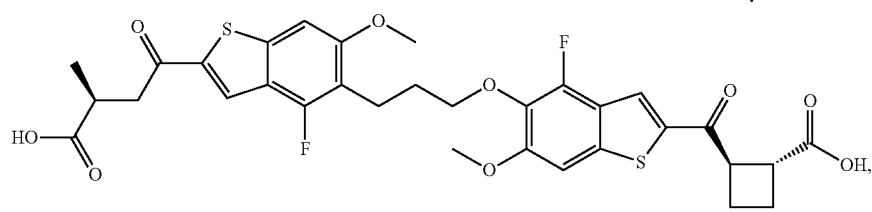
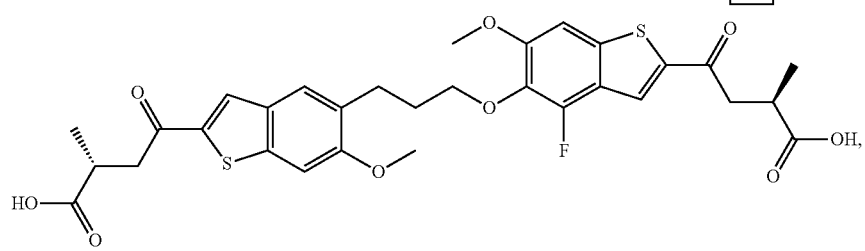
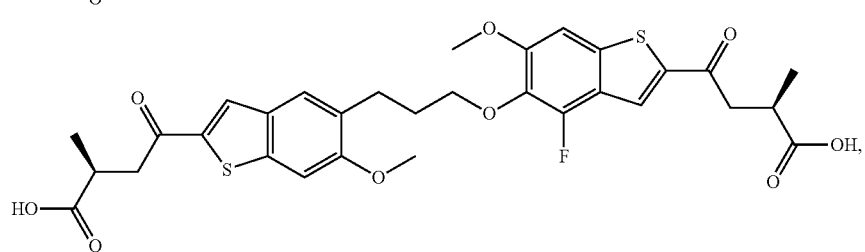
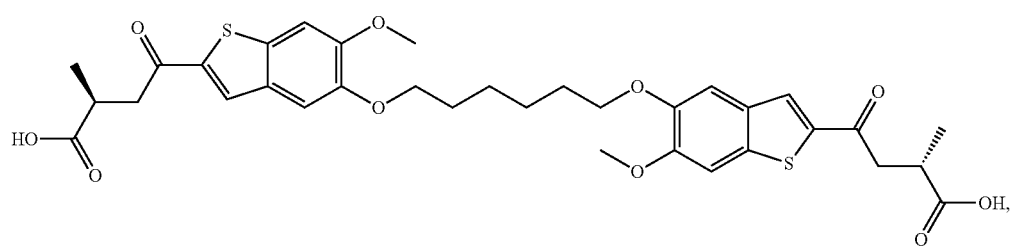
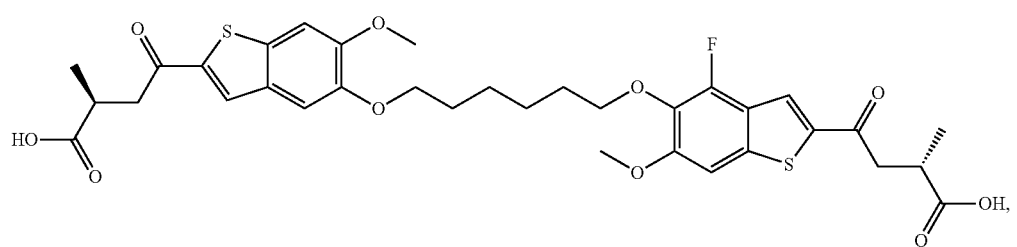

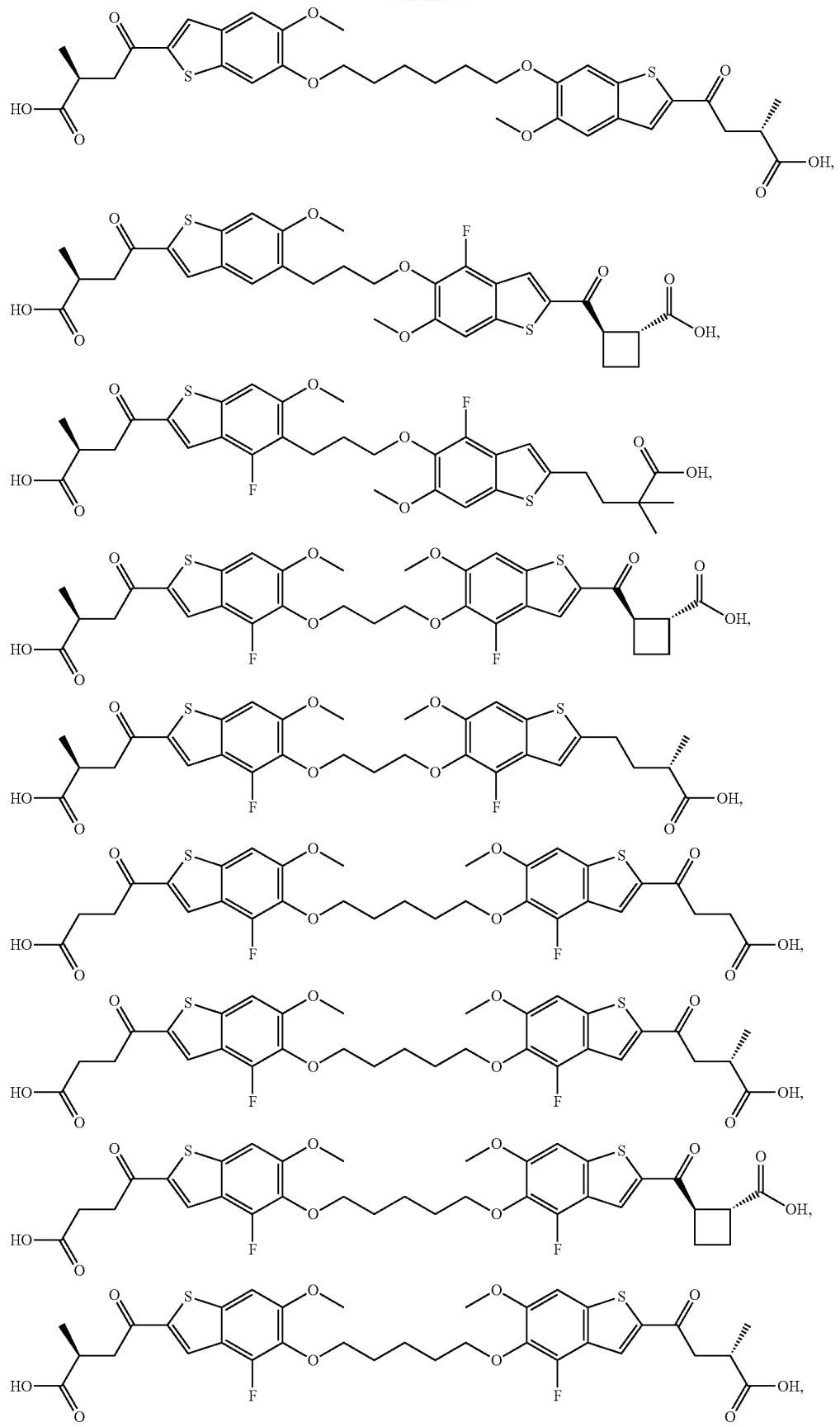

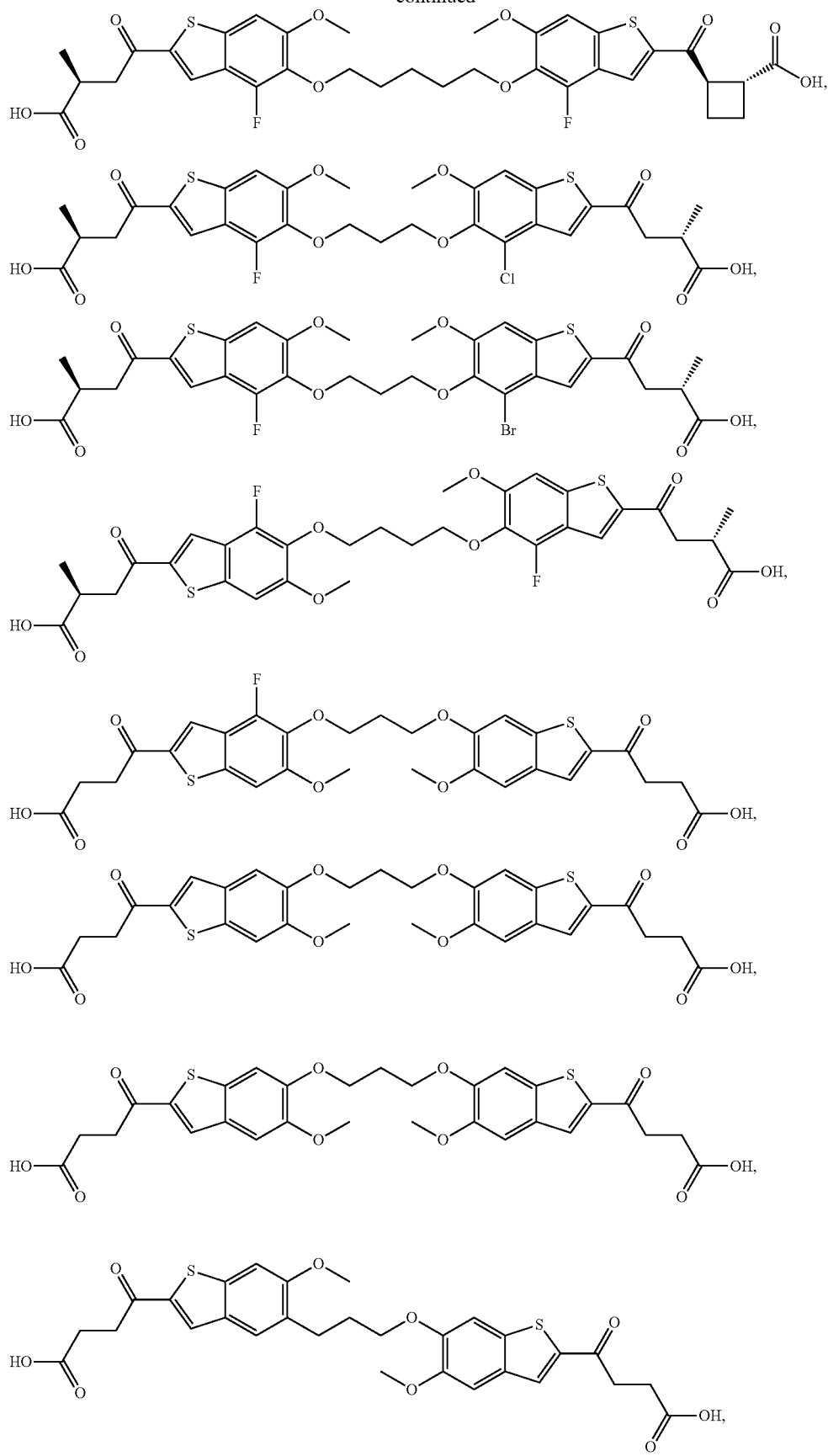

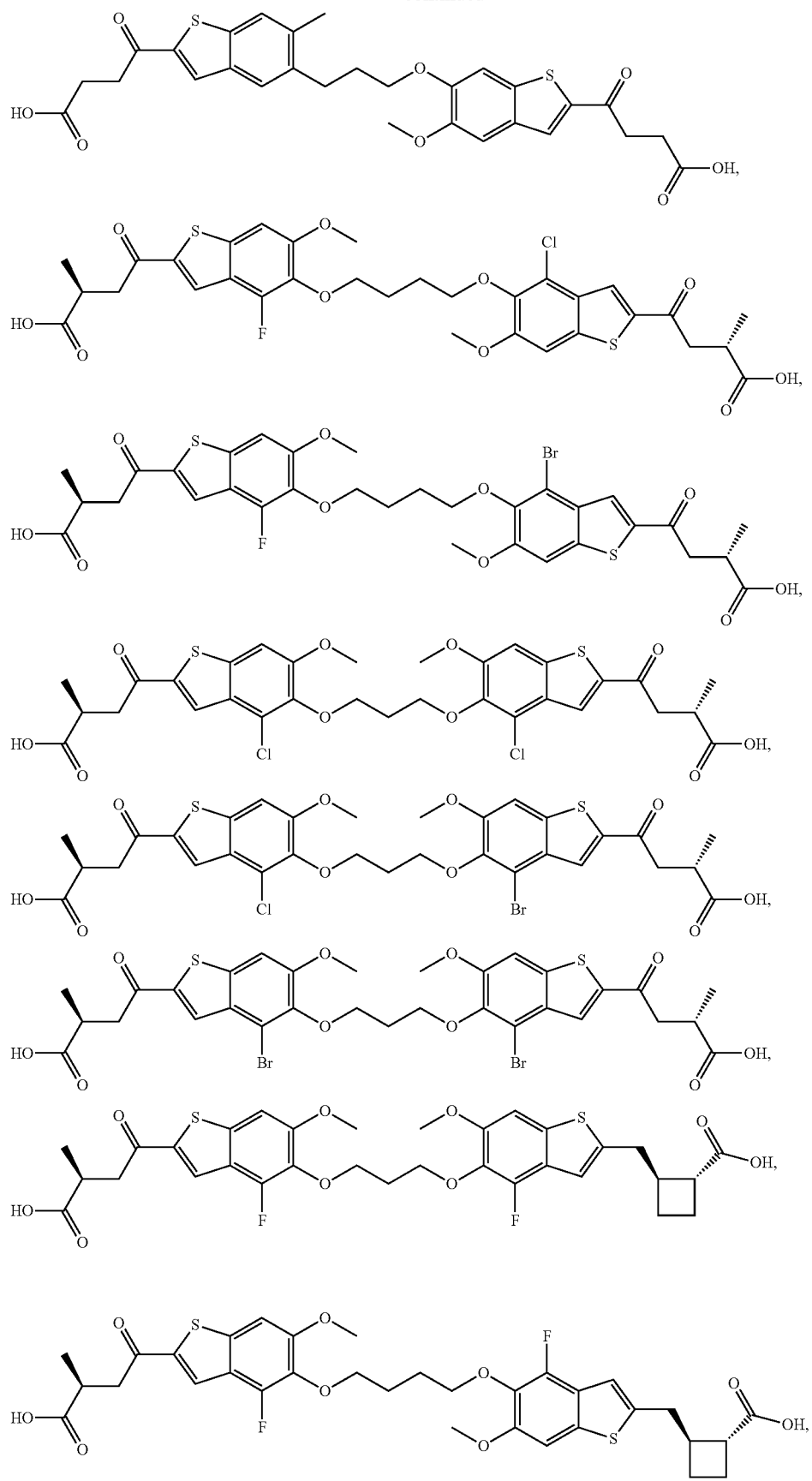

-continued
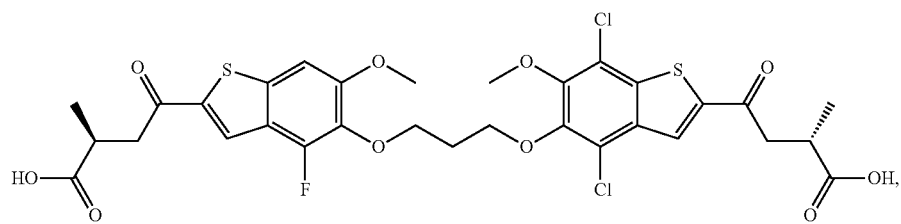
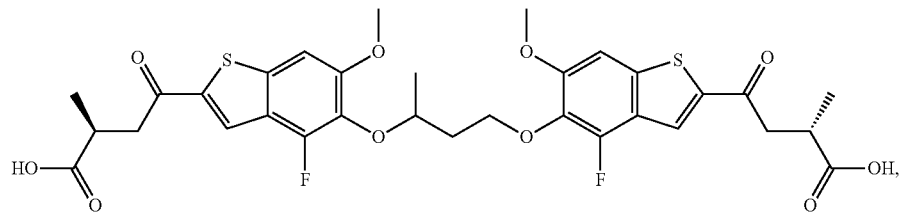
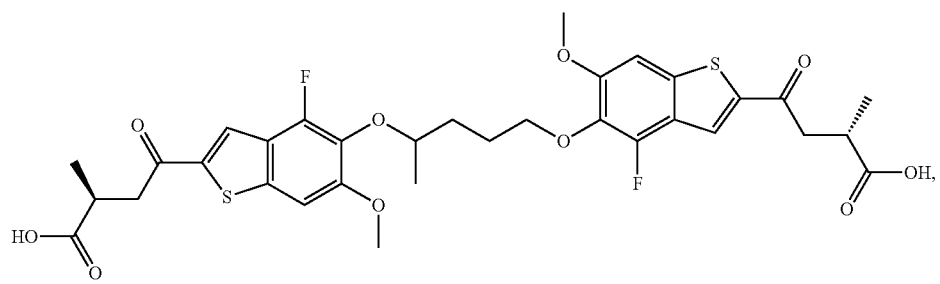
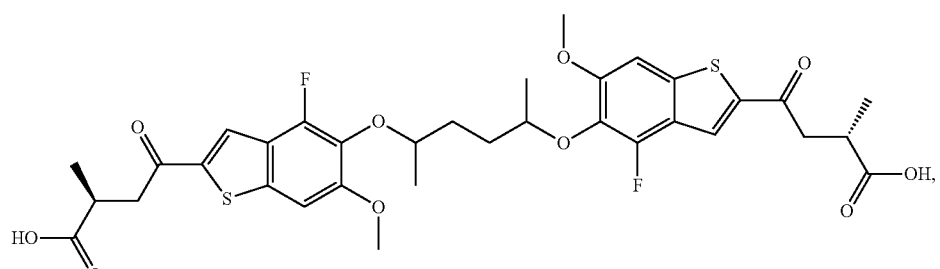
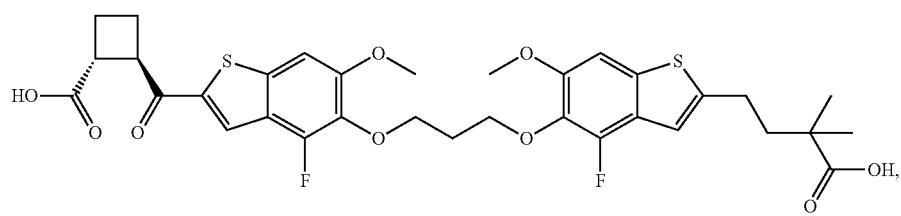
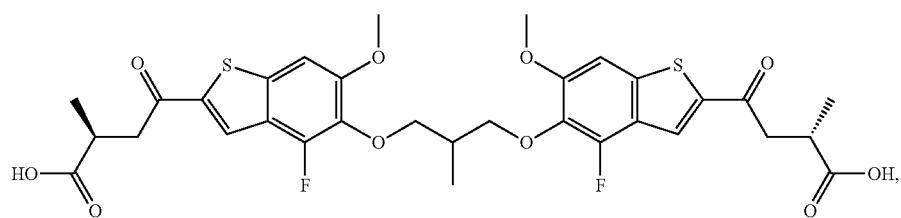
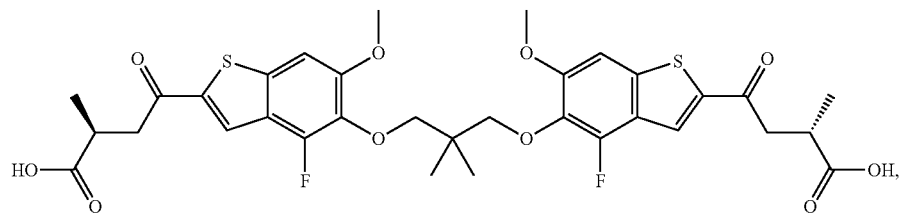

-continued
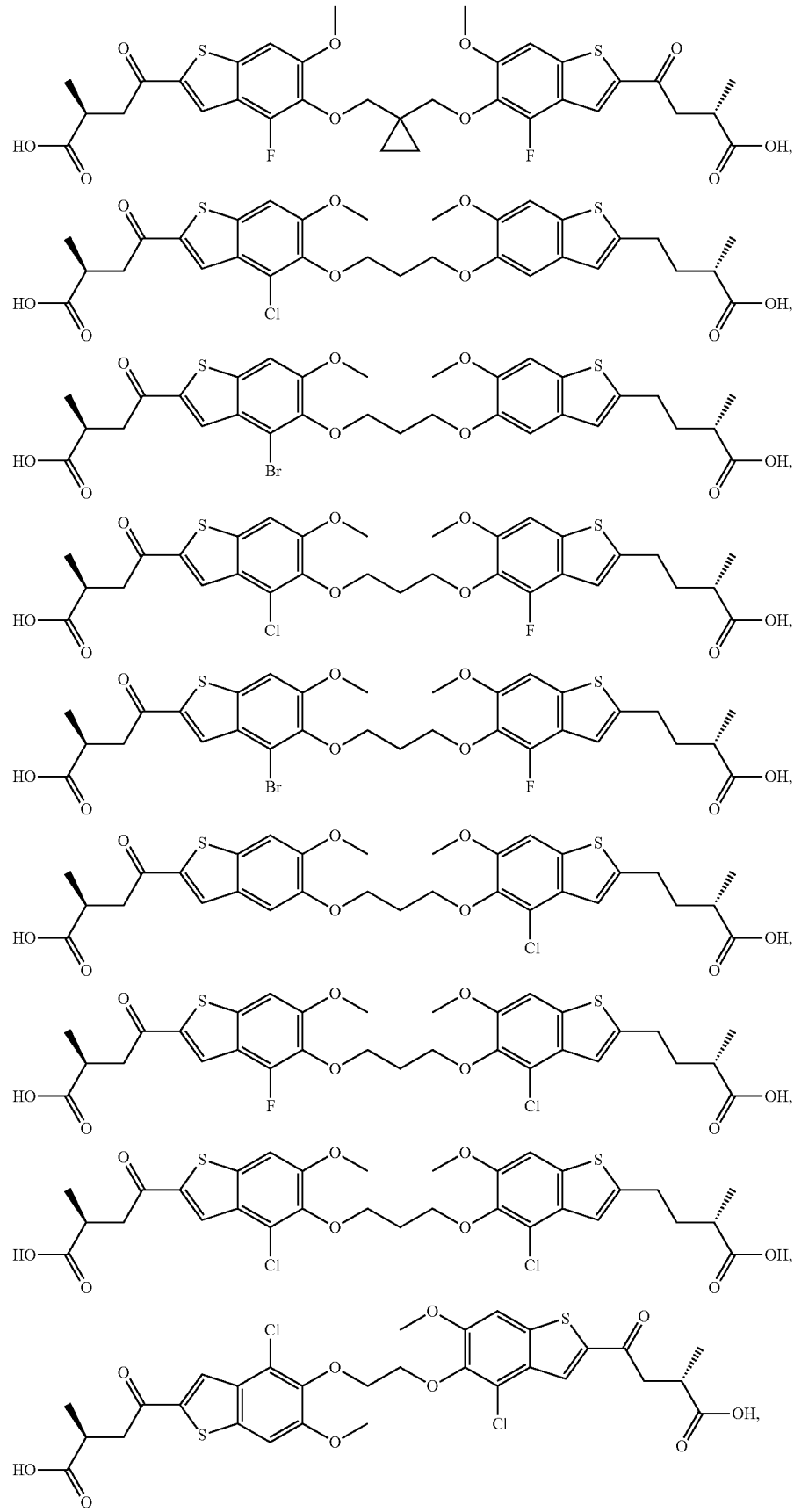

-continued
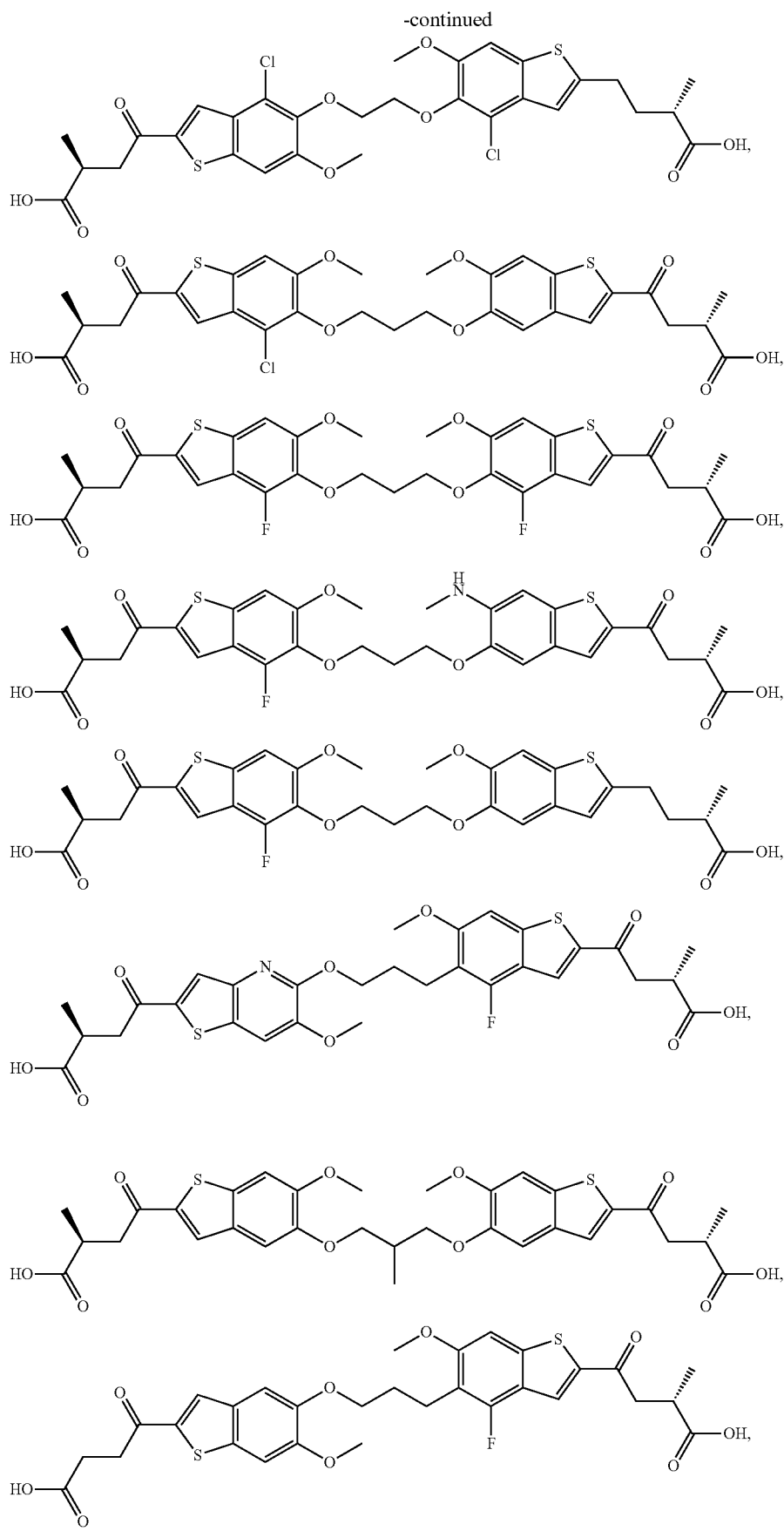

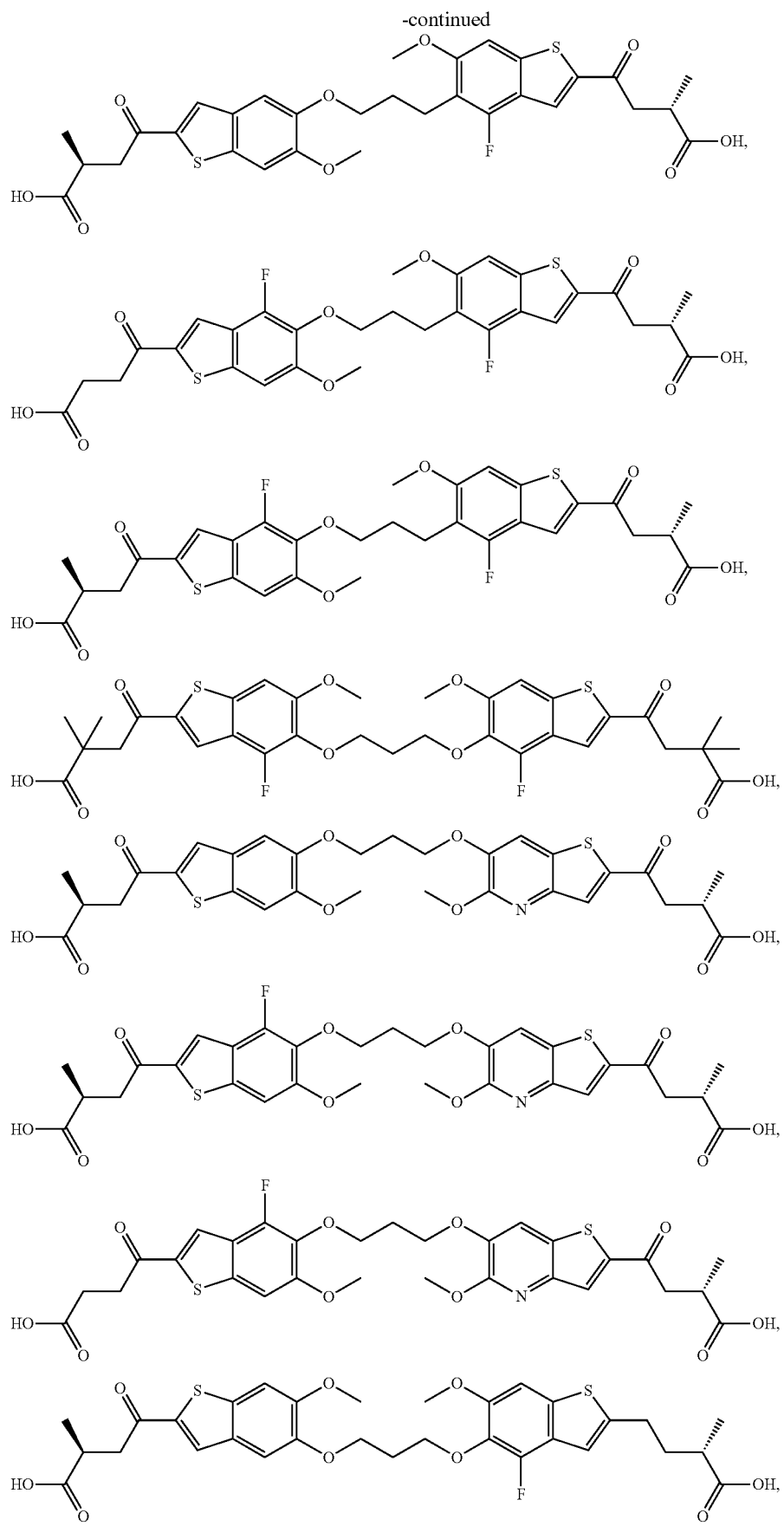

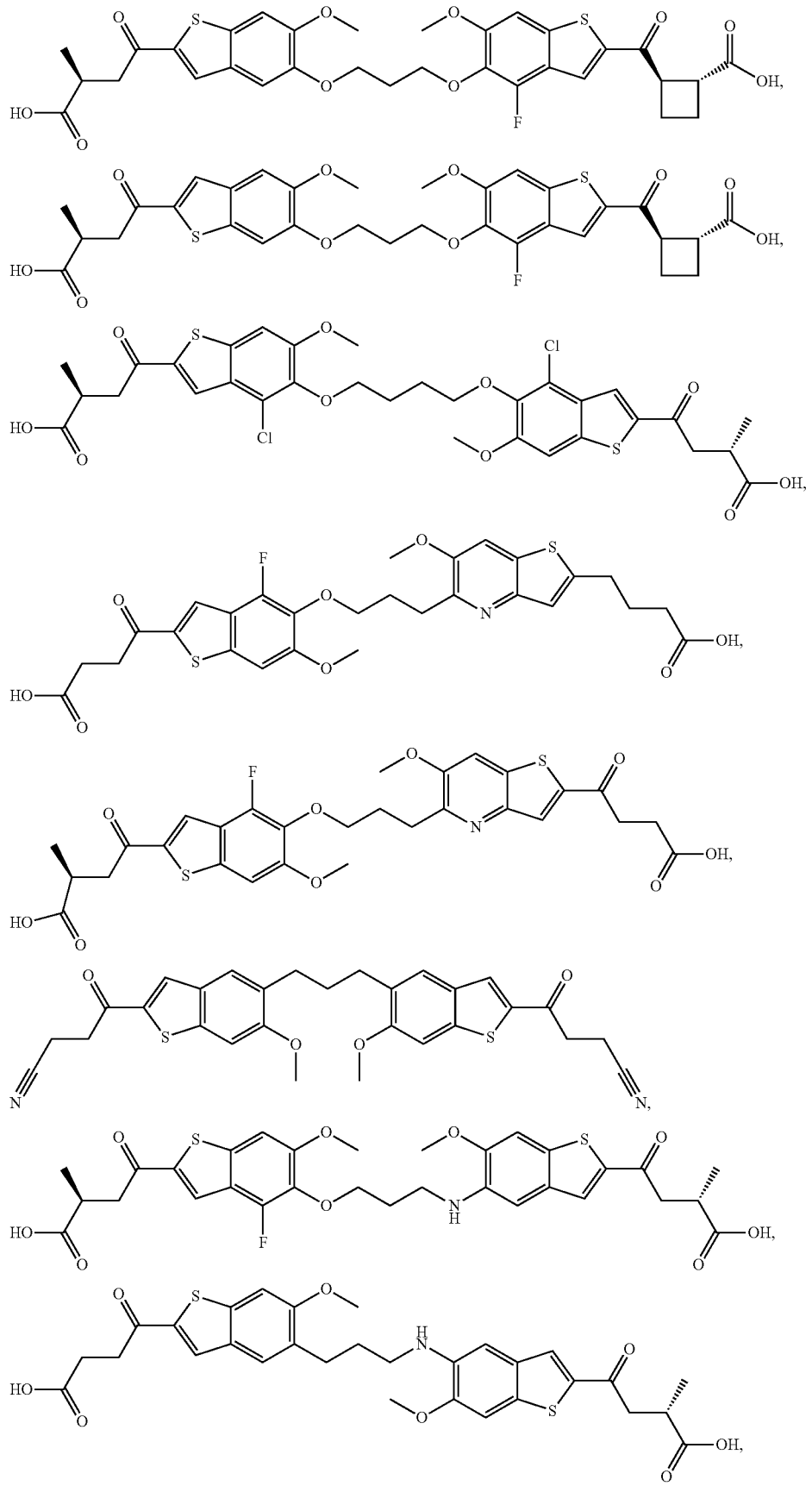

563
564
-continued
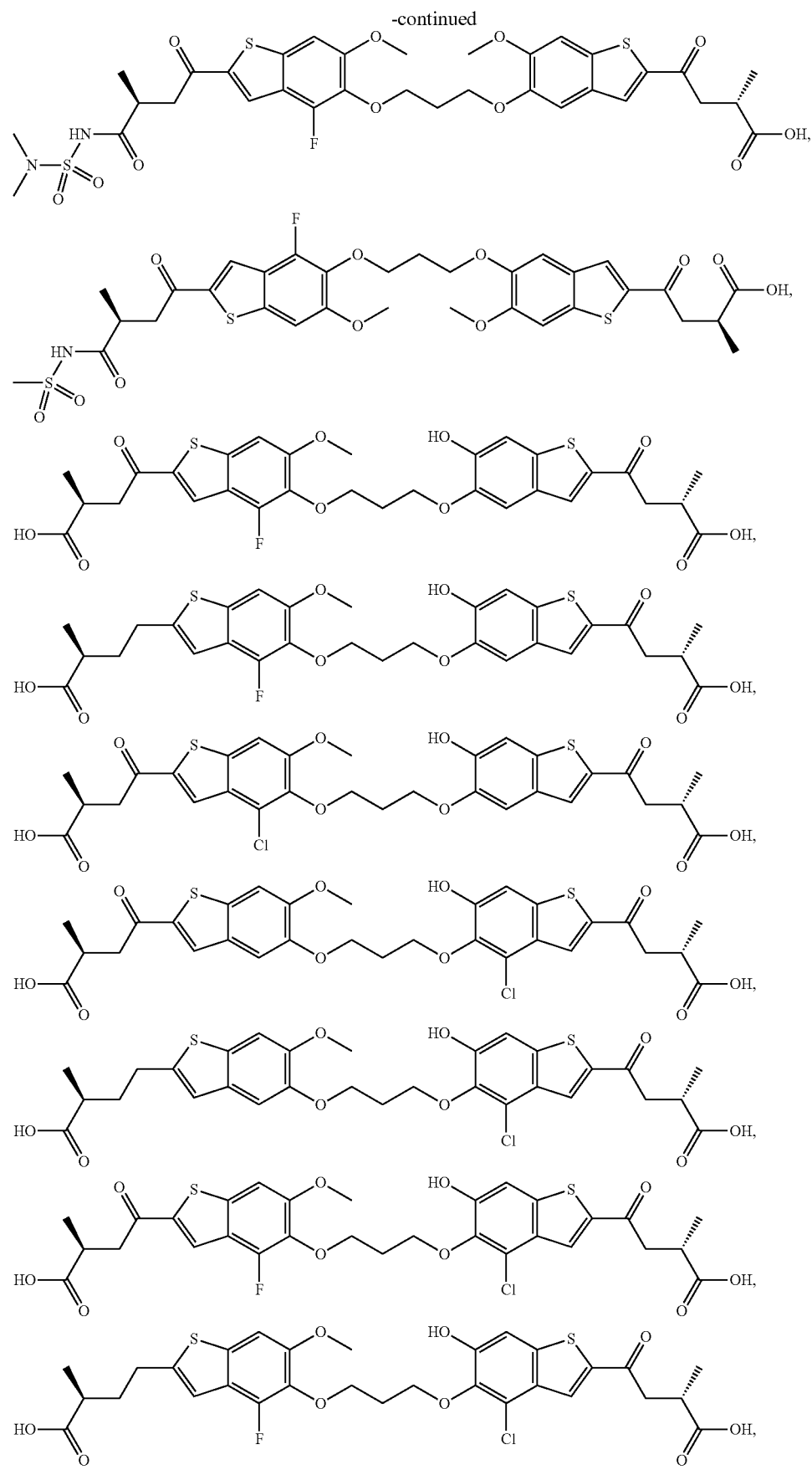

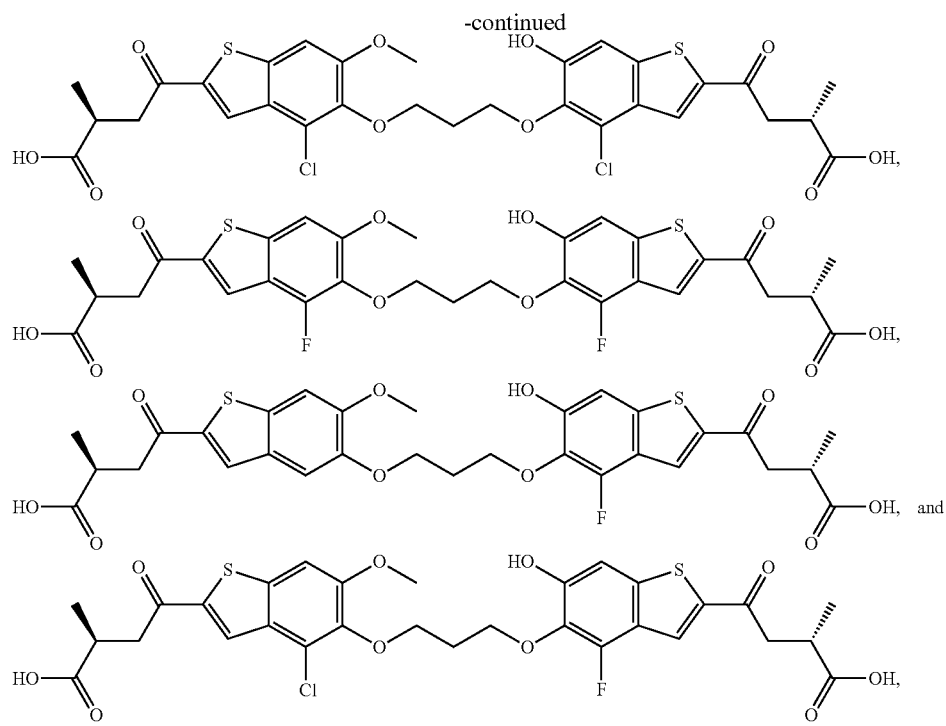
or a pharmaceutically acceptable salt thereof.
14. A compound selected from the group consisting of
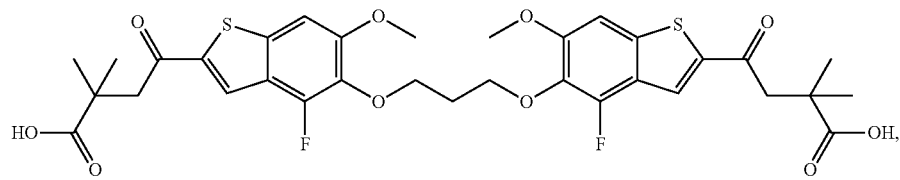
or a pharmaceutically acceptable salt thereof.
15. The compound according to claim 14, wherein the compound is a
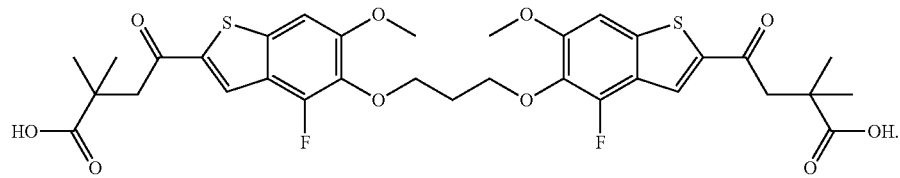
16. A compound selected from the group consisting of
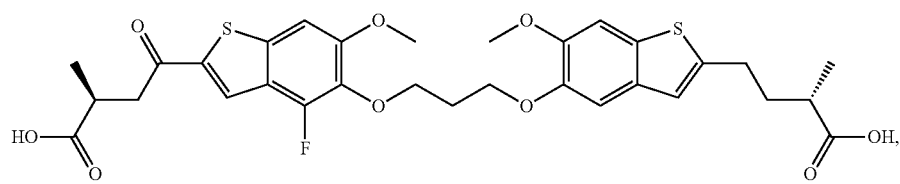 [SMILES: COc1cc2sc(CC[C@H](C)C(=O)O)cc2cc1OCCCOc1c(OC)cc2sc(C(=O)C[C@H](C)C(=O)O)cc2c1F]
or a pharmaceutically acceptable salt thereof.

17. The compound according to claim 16, wherein the compound is

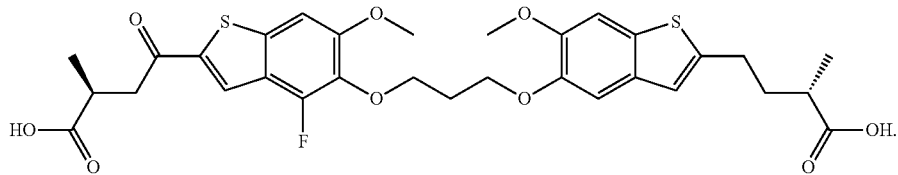 [SMILES: COc1cc2sc(CC[C@H](C)C(=O)O)cc2cc1OCCCOc1c(OC)cc2sc(C(=O)C[C@H](C)C(=O)O)cc2c1F]

18. A compound selected from the group consisting of

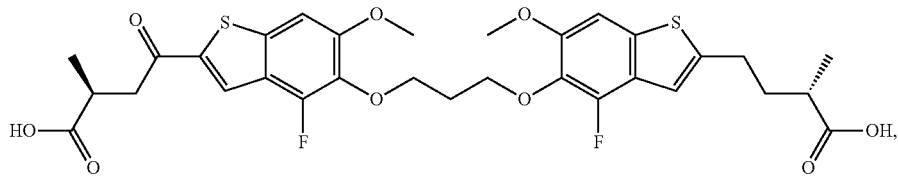 [SMILES: COc1cc2sc(CC[C@H](C)C(=O)O)cc2c(F)c1OCCCOc1c(OC)cc2sc(C(=O)C[C@H](C)C(=O)O)cc2c1F]

or a pharmaceutically acceptable salt thereof.

19. The compound according to claim 18, wherein the compound is

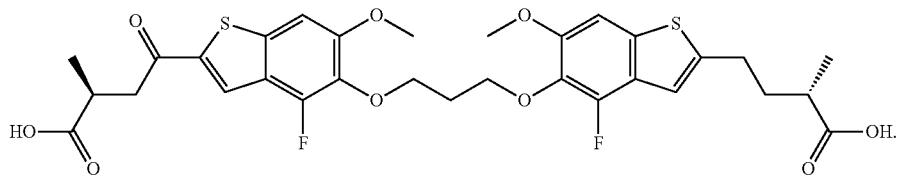 [SMILES: COc1cc2sc(CC[C@H](C)C(=O)O)cc2c(F)c1OCCCOc1c(OC)cc2sc(C(=O)C[C@H](C)C(=O)O)cc2c1F]

20. A compound selected from the group consisting of

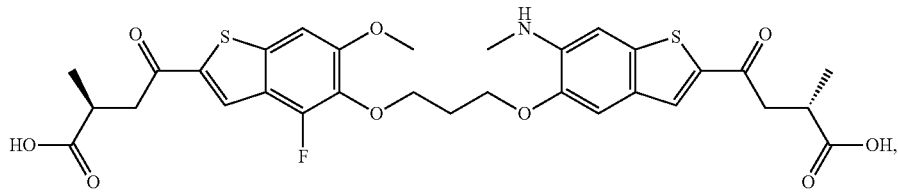 [SMILES: CNc1cc2sc(C(=O)C[C@H](C)C(=O)O)cc2cc1OCCCOc1c(OC)cc2sc(C(=O)C[C@H](C)C(=O)O)cc2c1F]

or a pharmaceutically acceptable salt thereof.

21. The compound according to claim 20, wherein the compound is

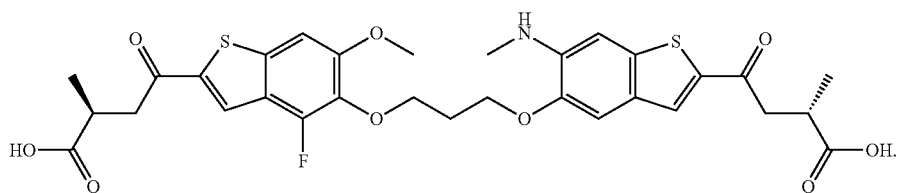 [SMILES: CNc1cc2sc(C(=O)C[C@H](C)C(=O)O)cc2cc1OCCCOc1c(OC)cc2sc(C(=O)C[C@H](C)C(=O)O)cc2c1F]

22. A compound selected from the group consisting of

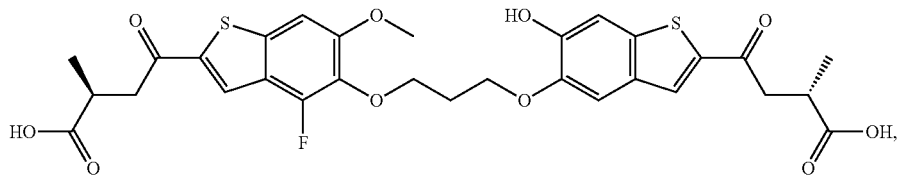 [SMILES: COc1cc2sc(C(=O)C[C@H](C)C(=O)O)cc2c(F)c1OCCCOc1cc2cc(C(=O)C[C@H](C)C(=O)O)sc2cc1O]

or a pharmaceutically acceptable salt thereof.

23. The compound according to claim 22, wherein the compound is

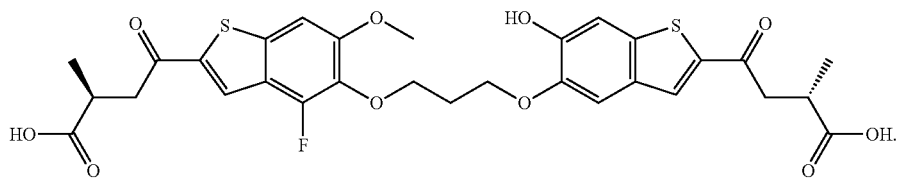 [SMILES: COc1cc2sc(C(=O)C[C@H](C)C(=O)O)cc2c(F)c1OCCCOc1cc2cc(C(=O)C[C@H](C)C(=O)O)sc2cc1O]

24. A compound selected from the group consisting of

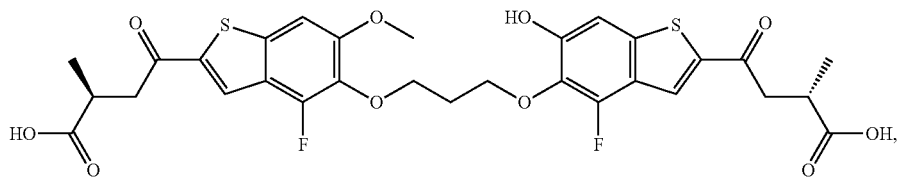 [SMILES: COc1cc2sc(C(=O)C[C@H](C)C(=O)O)cc2c(F)c1OCCCOc1c(O)cc2sc(C(=O)C[C@H](C)C(=O)O)cc2c1F]

or a pharmaceutically acceptable salt thereof.

25. The compound according to claim 24, wherein the compound is

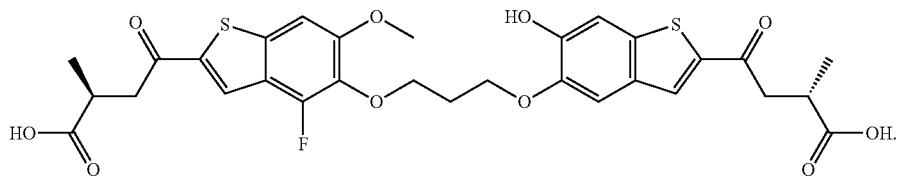 [SMILES: COc1cc2sc(C(=O)C[C@H](C)C(=O)O)cc2c(F)c1OCCCOc1cc2cc(C(=O)C[C@H](C)C(=O)O)sc2cc1O]

26. A pharmaceutical composition comprising a compound according to claim 1, or a pharmaceutically acceptable salt thereof, and a pharmaceutically acceptable carrier.

27. A pharmaceutical composition comprising a compound according to claim 13, or a pharmaceutically acceptable salt thereof, and a pharmaceutically acceptable carrier.

28. A method of inducing an immune response in a subject, said method comprising:
   (a) administering a therapeutically effective amount of a compound according to claim 1, or a pharmaceutically acceptable salt thereof, to the subject.

29. A method of inducing an immune response in a subject, said method comprising:
   (a) administering a therapeutically effective amount of a pharmaceutical composition according to claim 26 to the subject.

30. A method of inducing STING-dependent type I interferon production in a subject, said method comprising administering a therapeutically effective amount of a compound according to claim 1, or a pharmaceutically acceptable salt thereof, to the subject.

31. A method of inducing STING-dependent type I interferon production in a subject, said method comprising administering a therapeutically effective amount of a pharmaceutical composition according to claim 26 to the subject.

32. A method of treating a cell proliferation disorder in a subject, said method comprising administering a therapeutically effective amount of a compound according to claim 1, or a pharmaceutically acceptable salt thereof, to the subject.

33. The method of claim 32, wherein the cell proliferation disorder is cancer.

34. A method of treating a cell proliferation disorder in a subject, said method comprising administering a therapeutically effective amount of a pharmaceutical composition according to claim 26 to the subject.

35. The method of claim 34, wherein the cell proliferation disorder is cancer.

36. A method of inducing an immune response in a subject, said method comprising:
 (a) administering a therapeutically effective amount of a compound according to claim 13, or a pharmaceutically acceptable salt thereof, to the subject.

37. A method of inducing an immune response in a subject, said method comprising:
 (a) administering a therapeutically effective amount of a pharmaceutical composition according to claim 27 to the subject.

38. A method of inducing STING-dependent type I interferon production in a subject, said method comprising administering a therapeutically effective amount of a compound according to claim 13, or a pharmaceutically acceptable salt thereof, to the subject.

39. A method of inducing STING-dependent type I interferon production in a subject, said method comprising administering a therapeutically effective amount of a pharmaceutical composition according to claim 23 to the subject.

40. A method of treating a cell proliferation disorder in a subject, said method comprising administering a therapeutically effective amount of a compound according to claim 13, or a pharmaceutically acceptable salt thereof, to the subject.

41. The method of claim 40, wherein the cell proliferation disorder is cancer.

42. A method of treating a cell proliferation disorder in a subject, said method comprising administering a therapeutically effective amount of a pharmaceutical composition according to claim 27 to the subject.

43. The method of claim 42, wherein the cell proliferation disorder is cancer.

\* \* \* \* \*